US011293064B2

(12) United States Patent
Rigoutsos et al.

(10) Patent No.: US 11,293,064 B2
(45) Date of Patent: Apr. 5, 2022

(54) HUMAN MIRNAS FOR USE IN DIAGNOSIS, PROGNOSIS, AND THERAPY OF HUMAN CONDITIONS AND DISEASES

(71) Applicant: Thomas Jefferson University, Philadelphia, PA (US)

(72) Inventors: Isidore Rigoutsos, Astoria, NY (US); Phillipe Loher, Philadelphia, PA (US); Eric Londin, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 150 days.

(21) Appl. No.: 14/888,637

(22) PCT Filed: May 2, 2014

(86) PCT No.: PCT/US2014/036690
§ 371 (c)(1),
(2) Date: Nov. 2, 2015

(87) PCT Pub. No.: WO2014/179765
PCT Pub. Date: Nov. 6, 2014

(65) Prior Publication Data
US 2017/0009295 A1 Jan. 12, 2017

Related U.S. Application Data

(60) Provisional application No. 61/818,777, filed on May 2, 2013, provisional application No. 61/870,898, filed on Aug. 28, 2013, provisional application No. 61/901,989, filed on Nov. 8, 2013.

(51) Int. Cl.
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 7,625,699 B2 | 12/2009 | Devlin et al. |
| 8,574,838 B2 | 11/2013 | Zhang et al. |
| 2003/0194711 A1 | 10/2003 | Zapala et al. |
| 2007/0092882 A1* | 4/2007 | Wang ............ C12Q 1/6837 435/6.11 |
| 2011/0312520 A1 | 12/2011 | Kennedy et al. |
| 2013/0317083 A1* | 11/2013 | Rigoutsos ............ C12Q 1/6886 514/44 A |
| 2014/0213476 A1* | 7/2014 | Keller .................. C12Q 1/6886 506/9 |

FOREIGN PATENT DOCUMENTS

WO WO 2012/106586 8/2012

OTHER PUBLICATIONS

Landgraf, et al. (2007,Cell, v.129, No. 7: 1401-1414). (Year: 2007).*
MiRBase Accession No. MIMAT0000703 [online], [retrieved on Feb. 7, 2018]. Retrieved from the Internet: <http://www.mirbase.org/cgi-bin/mature.pl?mature_acc=MIMAT0000703>. (Year: 2007).*
MiRBase Accession No. MIMAT0001340 [online], [retrieved on Feb. 7, 2018]. Retrieved from the Internet: <http://www.mirbase.org/cgi-bin/mirna_entry.pl?acc=MIMAT0001340>. (Year: 2007).*
GEO accession No. GPL4867 [online], [retrieved on Feb. 7, 2018]. Retrieved from the Internet <https://www.ncbi.nlm.nih.gov/geo/query/acc.cgi?view=data&acc=GPL4867&id=39081&db=GeoDb_blob10>. (Year: 2007).*
MiRBase Accession No. MIMAT0000067 [online], [retrieved on Jan. 2, 2019], Retrieved from the Internet <http://www.mirbase.org/cgi-bin/mirna_entry.pl?acc=MIMAT0000067>. (Year: 2007).*
Motameny, et al. "Next Generation Sequencing of miRNAs—Strategies, Resources and Methods." Genes (2010) 1, 70-84. (Year: 2010).*
Hamfjord, et al. "Differential Expression of miRNAs in Colorectal Cancer: Comparison of Paired Tumor Tissue and Adjacent Normal Mucosa Using High-Throughput Sequencing." PLoS ONE (2012) 7(4): e34150. (Year: 2012).*
Guo, et al. "Global Expression Analysis of miRNA Gene Cluster and Family Based on isomiRs from Deep Sequencing Data." Computational Biology and Chemistry (2010) 34(3): 165-171. (Year: 2010).*
Bioconductor [online], [retrieved on Feb. 13, 2020], Retrieved from the Internet: <http://www.bioconductor.org/packages/release/bioc/html/DESeq2.html>. (Year: 2020).*
Abelson, J.F., et al., "Sequence variants in SLITRK1 are associated with Tourette's syndrome." Science, 2005. 310(5746): p. 317-320.
Allawi H. T. et al. "Quantitation of microRNAs using a modified Invader assay" RNA (2004) 10: 1153-1161.
Ambros, V., "A hierarchy of regulatory genes controls a larva-to-adult developmental switch in C. elegans." Cell, 1989. 57(1): p. 49-57.

(Continued)

*Primary Examiner* — Tracy Vivlemore
(74) *Attorney, Agent, or Firm* — Saul Ewing Arnstein & Lehr LLP; Kathryn Doyle; Justin Crotty

(57) ABSTRACT

Disclosed herein are novel compositions, methods, and systems for determining whether a subject has, or is at risk of developing, or is at a given stage of a condition afflicting a tissue of interest, or determining the tissue or cell provenance of a biological sample, based on expression level of one or more of the novel miRNA and isomiR sequences disclosed herein. The compositions, methods, and systems described herein can be used to diagnose a disease or disorder, or prognose a given stage and/or progression of the disease or disorder, or determine the identity of the tissue or cell in a sample. In some embodiments, the compositions, methods, and systems described herein can be used to develop a treatment for the disease or disorder. For example, in some embodiments, the novel miRNAs can be used as therapeutics for treatment of a disease or disorder.

3 Claims, 7 Drawing Sheets

Specification includes a Sequence Listing.

(56) References Cited

OTHER PUBLICATIONS

Ameres SL, Zamore PD. "Diversifying microRNA sequence and function." Nat Rev Mol Cell Biol (2013)14:475-488.
Arruda, M. et al. "Invader technology for DNA and RNA analysis: Principles and applications" Expert Rev. Mol. Diagn (2002) 2: 487-496.
Baek, D., et al., "The impact of microRNAs on protein output." Nature, 2008. 455(7209): p. 64-71.
Bartel, D.P., "MicroRNAs: genomics, biogenesis, mechanism, and function." Cell, 2004. 116(2): p. 281-297.
Bartel, D.P. "MicroRNAs: target recognition and regulatory functions." Cell, 2009. 136(2): p. 215-33.
Brennecke, J. and S.M. Cohen, "Towards a complete description of the microRNA complement of animal genomes." Genome Biol, 2003. 4(9): p. 228.
Brenner, S. et al. "Gene expression analysis by massively parallel signature sequencing (MPSS) on microbead arrays" Nature Biotechnology (2000) 18: 630-634.
Brodersen, P. and O. Voinnet, "Revisiting the principles of microRNA target recognition and mode of action." Nat Rev Mol Cell Biol, 2009. 10(2): p. 141-8.
Calin, G.A. and C.M. Croce, "Chronic lymphocytic leukemia: interplay between non-coding RNAs and protein-coding genes." Blood, 2009. 114(23): p. 4761-4770.
Calin, G.A. and C.M. Croce, "MicroRNA-cancer connection: the beginning of a new tale." Cancer Research, 2006. 66(15): p. 7390-7394.
Calin, G.A., et al., "Frequent deletions and down-regulation of micro-RNA genes miR15 and miR16 at 13q14 in chronic lymphocytic leukemia." Proc Natl Acad Sci U S A, 2002. 99(24): p. 15524-9.
Chang, S., et al., "MicroRNAs act sequentially and asymmetrically to control chemosensory laterality in the nematode." Nature, 2004. 430(7001): p. 785-9.
Chi, S.W., et al., "Argonaute HITS-CLIP decodes microRNA-mRNA interaction maps." Nature, 2009. 460(7254): p. 479-86.
Chi, S.W., G.J. Hannon, and R.B. Darnell, "An alternative mode of microRNA target recognition." Nat Struct Mol Biol, 2012. 19(3): p. 321-7.
Didiano, D. and O. Hobert, "Molecular architecture of a miRNA-regulated 3' UTR." RNA, 2008. 14(7): p. 1297-1317.
Didiano, D. and O. Hobert, "Perfect seed pairing is not a generally reliable predictor for miRNA-target interactions." Nat Struct Mol Biol, 2006. 13(9): p. 849-51.
Easow, G., A.A. Teleman, and S.M. Cohen, "Isolation of microRNA targets by miRNP immunopurification." RNA, 2007. 13(8): p. 1198-204.
Ebert and Shape. "MicroRNA sponges: Progress and possibilities" RNA (2010) 16:2043-2050.
Ebert et al. "MicroRNA sponges: Competitive inhibitors of small RNAs in mammalian cells" Nat. Methods (2007) 4: 721-726.
Eis, P.S. et al. "An invasive cleavage assay for direct quantitation of specific RNAs" Nat. Biotechnol. (2001)19: 673-676.
Esquela-Kerscher, A. and F.J. Slack, "Oncomirs—microRNAs with a role in cancer." Nature Reviews Cancer, 2006. 6(4): p. 259-269.
Fabian, M.R., N. Sonenberg, and W. Filipowicz, "Regulation of mRNA translation and stability by microRNAs." Annu Rev Biochem, 2010. 79: p. 351-79.
Farh, K.K., et al., "The widespread impact of mammalian MicroRNAs on mRNA repression and evolution". Science, 2005. 310(5755): p. 1817-21.
Friedländer, M.R., et al., "Discovering microRNAs from deep sequencing data using miRDeep." Nature Biotechnology, 2008, 26, 407-415.
Godshalk, S.E., et al., "A Variant in a MicroRNA complementary site in the 3' UTR of the KIT oncogene increases risk of acral melanoma." Oncogene, 2011, 30: 1542-50.
Griffiths-Jones, S., "miRBase: microRNA sequences, targets and gene nomenclature." Nucleic Acids Research, 2006. 34(90001): p. D140-D144.
Ha, I., B. Wightman, and G. Ruvkun, "A bulged lin-4/lin-14 RNA duplex is sufficient for Caenorhabditis elegans lin-14 temporal gradient formation." Genes Dev, 1996. 10(23): p. 3041-50.
Hafner, M., et al., "Transcriptome-wide identification of RNA-binding protein and microRNA target sites by PAR-CLIP." Cell, 2010. 141(1): p. 129-41.
Hammond, S.M. "MicroRNAs as tumor suppressors" Nature Genetics. 2007(39): p. 582-583.
Hebert, S.S. and B. De Strooper, "Alterations of the microRNA network cause neurodegenerative disease." Trends Neurosci, 2009. 32(4): p. 199-206.
Ibanez-Ventoso, C. and M. Driscoll, "MicroRNAs in C. elegans Aging: Molecular Insurance for Robustness?" Curr Genomics, 2009. 10(3): p. 144-53.
Johnston, R.J. and O. Hobert, "A microRNA controlling left/right neuronal asymmetry in Caenorhabditis elegans." Nature, 2003. 426(6968): p. 845-9.
Kodzius R. et al. "CAGE: cap analysis of gene expression" Nature Methods (2006) 3: 211-222.
Lagos Quintana et al, "Identification of Novel Genes Coding for Small Expressed RNAs" Science 294, 853-857 (2001).
Lagos-Quintana et al, "Identification of Tissue-Specific MicroRNAs from Mouse." Current Biology, 12, 735-739 (2002).
Lagos-Quintana et al, "New microRNAs from mouse and human" RNA, 9, 175-179 (2003).
Lal, A., et al., miR-24 Inhibits cell proliferation by targeting E2F2, MYC, and other cell-cycle genes via binding to "seedless" 3'UTR microRNA recognition elements. Mol Cell, 2009. 35(5): p. 610-25.
Lau et al., "An Abundant Class of Tiny RNAs with Probable Regulatory Roles in Caenorhabditis elegans" Science 294, 858-861 (2001).
Lee and Ambros "An Extensive Class of Small RNAs in Caenorhabditis elegans." Science, 294, 862 (2001).
Lee, R.C., R.L. Feinbaum, and V. Ambros, "The C. elegans heterochronic gene lin-4 encodes small RNAs with antisense complementarity to lin-14." Cell, 1993. 75(5): p. 843-854.
Lim, et al., The microRNAs of Caenorhabditis elegans Genes & Development, 17, p. 991-1008 (2003).
Lim, L.P., et al., "Vertebrate microRNA genes." Science 2003. 299(5612): p. 1540-1540.
Liu, X., K. Fortin, and Z. Mourelatos, "MicroRNAs: biogenesis and molecular functions." Brain Pathol, 2008. 18(1): p. 113-21.
Llorens et al., "A highly expressed miR-101 isomiR is a functional silencing small RNA" (2013) BMC Genomics 14: 104.
Lu, M., et al., "An analysis of human microRNA and disease associations." PLoS ONE, 2008. 3(10): p. e3420.
Ma, L.et al., "Tumour invasion and metastasis initiated by microRNA-10b in breast cancer." Nature, 2007. 449(7163): p. 682-688.
Mendell, J.T., "miRiad roles for the miR-17-92 cluster in development and disease." Cell, 2008. 133(2): p. 217-222.
Metzker M. L. "Sequencing technologies—the next generation" Nature Reviews (2010) 11: 31-46.
Miranda, K.C., et al., A pattern-based method for the identification of MicroRNA binding sites and their corresponding heteroduplexes. Cell, 2006. 126(6): p. 1203-1217.
Nelson, P.T., W.X. Wang, and B.W. Rajeev, MicroRNAs (miRNAs) in neurodegenerative diseases. Brain Pathol, 2008. 18(1): p. 130-8.
Pareek C. S. et al. "Sequencing technologies and genome sequencing" J. Appl Genetics (2011) 52: 413-435.
Perkel, J. "Making contact with Sequencing's Fourth Generation" BioTechniques (2011): 50:93-95.
Perkins, D.O., et al., "microRNA expression in the prefrontal cortex of individuals with schizophrenia and schizoaffective disorder." Genome Biology, 2007. 8(2): R27.
Poliseno, L., et al., "A coding-independent function of gene and pseudogene mRNAs regulates tumour biology"—Supplement. Nature, 2010. 465(7301): p. 1-19.
Reinhart, B.J., et al., "The 21-nucleotide let-7 RNA regulates developmental timing in Caenorhabditis elegans." Nature, 2000. 403(6772): p. 901-6.
Rigoutsos, I. and A. Tsirigos, in MicroRNAs in Development and Cancer Molecular Medicine and Medicinal Chemistry Ch.10, ed. F.J. Slack. vol. vol. 1. 2010: Imperial College Press.

(56) References Cited

OTHER PUBLICATIONS

Rigoutsos, I., et al., "Short blocks from the noncoding parts of the human genome have instances within nearly all known genes and relate to biological processes." Proceedings of the National Academy of Sciences of the United States of America, 2006. 103(17): p. 6605-6610.

Rigoutsos, I., "New tricks for animal microRNAS: targeting of amino acid coding regions at conserved and nonconserved sites." Cancer Research, 2009. 69(8): p. 3245-3248.

Ruvkun, G. and J. Giusto, "The Caenorhabditis elegans heterochronic gene lin-14 encodes a nuclear protein that forms a temporal developmental switch." Nature, 1989. 338(6213): p. 313-19.

Ryan, B.M., A.I. Robles, and C.C. Harris, "Genetic variation in microRNA networks: the implications for cancer research." Nature Reviews Cancer, 2010. 10(6): p. 389-402.

Saey, T., "Cancer's little helpers: Tiny pieces of RNA may turn cells to the dark side." Science News, 2010.

Saha S. et al. "Characterization of the yeast transcriptome" Cell (1997) 88: 243-251.

Selbach, M., et al., "Widespread changes in protein synthesis induced by microRNAs." Nature, 2008. 455(7209): p. 58-63.

Singh Y. et al. "Recent developments in oligonucleotide conjugation" Chem. Soc. Rev., 2010, 39, 2054-2070.

Skalsky, R.L., et al., "The viral and cellular microRNA targetome in lymphoblastoid cell lines." PLoS Pathog, 2012. 8(1): p. e1002484.

Small, E.M. and E.N. Olson, "Pervasive roles of microRNAs in cardiovascular biology." Nature, 2011. 469(7330): p. 336-342.

Small, E.M. et al., "MicroRNAs add a new dimension to cardiovascular disease." Circulation, 2010. 121(8): p. 1022-1032.

Somel, M., et al., "MicroRNA, mRNA, and protein expression link development and aging in human and macaque brain." Genome Res, 2010. 20(9): p. 1207-18.

Spizzo, R., et al., "SnapShot: MicroRNAs in Cancer." Cell, 2009. 137(3): p. 586.e1.

Stark, A., et al., "Animal MicroRNAs confer robustness to gene expression and have a significant impact on 3'UTR evolution." Cell, 2005. 123(6): p. 1133-46.

Swami M. "Small RNAs: Pseudogenes act as microRNA decoys." Nature Reviews Genetics (2010) 11: 530-531).

Taganov, K.D. et al. "MicroRNAs and immunity: tiny players in a big field." Immunity, 2007. 26(2): p. 133-137.

Tay, Y., et al., "MicroRNAs to Nanog, Oct4 and Sox2 coding regions modulate embryonic stem cell differentiation." Nature, 2008. 455(7216): p. 1124-1128.

Thomas, M., J. et al. "Desperately seeking microRNA targets." Nat Struct Mol Biol, 2010. 17(10): p. 1169-74.

Urquhart, et al., "Rate-Controlled Delivery Systems in Drug and Hormone Research" Ann. Rev. Pharmacol. Toxicol. 24: 199-236 (1984).

Vasilescu, C., et al., MicroRNA fingerprints identify miR-150 as a plasma prognostic marker in patients with sepsis. PLoS ONE, 2009. 4(10): p. e7405.

Velculescu, V. E. et al. "Serial Analysis of Gene Expression." Science (1995) 270: 484-487.

Vella, M.C., et al., "The C. elegans microRNA let-7 binds to imperfect let-7 complementary sites from the lin-41 3'UTR." Genes Dev, 2004. 18(2): p. 132-7.

Ventura, A. and T. Jacks, "MicroRNAs and Cancer: short RNAs go a long way." Cell, 2009. 136(4): p. 586-591.

Voelkerding K. V. et al. "Next-Generation Sequencing: From Basic Research to Diagnostics" Clinical Chemistry (2009) 55: 641-658.

Voorhoeve, P.M. and R. Agami, "Classifying microRNAs in cancer: The good, the bad and the ugly." Biochimica et Biophysica Acta (BBA)—Reviews on Cancer, 2007. 1775(2): p. 274-282.

Wang, W.-X., et al., "miR-107 regulates granulin/progranulin with implications for traumatic brain injury and neurodegenerative disease." The American Journal of Pathology, 2010. 177(1): p. 334-345.

Wang, W.-X., et al., "The expression of microRNA miR-107 decreases early in Alzheimer's disease and may accelerate disease progression through regulation of beta-site amyloid precursor protein-cleaving enzyme 1." Journal of Neuroscience, 2008. 28(5): p. 1213-1223.

Wang, Y., et al., MicroRNA: past and present. Front Biosci, 2007. 12: p. 2316-29.

Wightman, B., I. Ha, and G. Ruvkun, "Posttranscriptional regulation of the heterochronic gene lin-14 by lin-4 mediates temporal pattern formation in C. elegans." Cell, 1993. 75(5): p. 855-862.

Williams, A.H., et al., "MicroRNA-206 delays ALS progression and promotes regeneration of neuromuscular synapses in mice." Science 2009. 326(5959): p. 1549-1554.

Xia, Z., et al., "Molecular dynamics simulations of Ago silencing complexes reveal a large repertoire of admissible 'seed-less' targets." Sci Rep, 2012. 2: p. 569.

Zhang J. et al. "The impact of next-generation sequencing on genomics" J. Genet Genomics (2011) 38: 95-109.

Zisoulis, D.G., et al., "Comprehensive discovery of endogenous Argonaute binding sites in Caenorhabditis elegans." Nat Struct Mol Biol, 2010. 17(2): p. 173-9.

International Search Report for PCT/US14/36690 dated Feb. 4, 2015.

* cited by examiner

HUMAN MIRNAS FOR USE IN DIAGNOSIS, PROGNOSIS, AND THERAPY OF HUMAN CONDITIONS AND DISEASES

CROSS-REFERENCE TO RELATED APPLICATIONS

The present application is a 35 U.S.C. § 371 national phase application from, and claims priority to, International Application No. PCT/US2014/036690, filed May 2, 2014, and published under PCT Article 21(2) in English, which claims priority under 35 U.S.C. § 119(e) to U.S. Provisional Application No. 61/818,777, filed May 2, 2013, U.S. Provisional Application No. 61/870,898, filed Aug. 28, 2013, and U.S. Provisional Application No. 61/901,989, filed Nov. 8, 2013, all of which applications are incorporated herein by reference in their entireties.

GOVERNMENT SUPPORT

This invention was made with government support under grant No. 2U 19-AI056363-06/2030984, awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on May 2, 2014, is named 77983PCT.txt and is 8,071,491 bytes in size.

TECHNICAL FIELD

Provided herein relates to methods and compositions for determining a cellular state or a tissue state of a biological sample, or the tissue or cell provenance of a biological sample. Specifically, some embodiments of the methods described herein can be used to diagnose or prognose for a given stage of a disease, e.g., cancer, or disorder, in a subject. Other embodiments can be used to determine the tissue or cell type from which a biological sample was obtained.

BACKGROUND

MicroRNAs (miRNAs) are an abundant class of short non-coding RNAs (ncRNAs), ~22 nucleotides (nts) in length, which play a significant role in the regulation of gene expression. Bartel, D. P., Cell, 2004, 116(2): 281-97; Bartel, D. P., Cell, 2009, 136(2): 215-33. The first animal miRNA, lin-4, was discovered accidentally during a genetic screen in Caenorhabditis elegans (C. elegans) where it was previously reported to repress the expression of a protein-coding gene lin-14. Ambros, V., Cell, 1989, 57(1): 49-57; Ruvkun, G. and J. Giusto, Nature, 1989, 338(6213): 313-19. Downregulation of lin-14 led to a change in pattern formation in C. elegans larvae. In 2000, a second miRNA, let-7, was reported to be an important miRNA in C. elegans development. Reinhart, B. J., et al., Nature, 2000, 403(6772): 901-6. Other miRNAs have been previously reported in various species, including worms, flies, and mammals. See, e.g., Chang, S., et al., Nature, 2004, 430(7001): 785-89; Johnston, R. J. and O. Hobert, Nature, 2003, 426(6968): p. 845-49; Brennecke, J. and S. M. Cohen, Genome Biol, 2003, 4(9): 228. See also the miRNA database accessible online at www.mirbase.org. Currently, more than two thousand miRNAs are known for the human genome and contained in miRBase Release 19. Griffiths-Jones, S., Nucleic Acids Research, 2006, 34(90001): D140-D144.

MiRNAs interact with their target RNAs in a sequence-dependent manner. Miranda, K. C., et al., Cell, 2006, 126(6): 1203-1217; Bartel, D. P., Cell, 2004, 116(2): 281-297; Bartel, D. P., Cell, 2009, 136(2): 215-233; Rigoutsos, I., Cancer Research, 2009, 69(8): 3245-3248. MiRNAs can function as post-transcriptional regulators of gene expression. In mammals, over 90% of all protein-coding genes are generally believed to be regulated by miRNAs. Miranda, K. C., et al., Cell, 2006, 126(6): 1203-1217. Even though the entire miRNA sequence can bind to the mRNA target, the sequence spanning positions 2-7 inclusive from the 5' end of a miRNA, known as the "seed," is previously reported to be important for target determination and coupling. Bartel, D. P., Cell, 2004, 116(2): 281-97; Reinhart, B. J., et al., Nature, 2000, 403(6772): 901-06; Lee, R. C. et al., Cell, 1993, 75(5): 843-854; Wightman, B., et al., Cell, 1993, 75(5): 855-862; Tay, Y., et al., Nature, 2008, 455(7216): 1124-1128; Brodersen, P., Nat Rev Mol Cell Biol, 2009. 10(2): 141-48; Lal, A., et al., Mol Cell, 2009, 35(5): 610-25; Rigoutsos, I. and Tsirigos, A., in MicroRNAs in Development and Cancer Molecular Medicine and Medicinal Chemistry Ch. 10, ed. F. J. Slack. Vol. 1, 2010: Imperial College Press; Xia, Z., et al., Sci Rep, 2012, 2: 569. Originally it was assumed that the presence of the reverse complement of the seed in mRNAs was both a sufficient and necessary condition for targeting. Bartel, D. P., Cell, 2009, 136(2): 215-233. However, genetic studies and numerous subsequent efforts showed miRNA functionality in the presence of inexact matches and/or bulges in the seed region. Wightman, B., et al. Cell, 1993, 75(5): 855-862; Tay, Y., et al., Nature, 2008, 455(7216): 1124-1128; Lal, A., et al., Mol Cell, 2009, 35(5): 610-25; Ha, I. et al., Genes Dev, 1996. 10(23): p. 3041-50; Vella, M. C., et al., Genes Dev, 2004. 18(2): 132-37; Farh, K. K., et al., Science, 2005, 310(5755): 1817-21; Stark, A., et al., Cell, 2005, 123(6): 1133-46; Didiano, D. and Hobert O., Nat Struct Mol Biol, 2006. 13(9): 849-51; Easow, G. et al., RNA, 2007, 13(8): 1198-204; Baek, D., et al., Nature, 2008, 455(7209): 64-71; Selbach, M., et al., Nature, 2008. 455 (7209): 58-63; Chi, S. W., et al., Nature, 2009, 460(7254): 479-86; Fabian, M. R. et al., Annu Rev Biochem, 2010, 79: 351-79; Hafner, M., et al., Cell, 2010, 141(1): 129-41; Thomas, M., Nat Struct Mol Biol, 2010, 17(10): 1169-74; Zisoulis, D. G., et al., Nat Struct Mol Biol, 2010. 17(2): 173-79; Chi, S. W. et al., Nat Struct Mol Biol, 2012. 19(3): 321-27; Skalsky, R. L., et al., PLoS Pathog, 2012. 8(1): e1002484. The importance of such inexact matches has been previously reported to have direct relevance to answering the question of how many targets a miRNA can have.

The role of microRNAs was shown in previous reports where miR-15a and miR-16 are down-regulated or deleted in most patients with chronic lymphocytic leukemia (CLL). Calin, G. A., et al., Proc Natl Acad Sci USA, 2002, 99(24): 15524-9; Calin, G. A. and Croce, C. M., Blood, 2009, 114(23): 4761-4770. MiRNAs have also been reported to be involved in many fundamental biological processes. Lee, R. C. et al., Cell, 1993, 75(5): 843-854; Wightman, B. et al., Cell, 1993, 75(5): 855-862; Tay, Y., et al., Nature, 2008, 455(7216): 1124-1128; Ha, I. et al., Genes & Development, 1996, 10(23): 3041-3050; Ruvkun, G., et al., Nature, 2000. 403(6772): 901-906; Didiano, D. and Hobert, O., RNA, 2008. 14(7): 1297-1317. Previous reports have also showed miRNA connections to cardiovascular disease (Small, E. M. et al., Circulation, 2010. 121(8): 1022-1032; Small, E. M.

and Olson, E. N. Nature, 2011. 469(7330): 336-342), immunity (Taganov, K. D. et al., Immunity, 2007. 26(2): 133-137), schizophrenia (Perkins. D. O., et al., microRNA expression in the prefrontal cortex of individuals with schizophrenia and schizoaffective disorder. Genome Biology, 2007. 8(2): R27), brain processes (Liu, X., et al., Brain Pathol, 2008. 18(1): 113-21; Wang, Y., et al., Front Biosci, 2007. 12: 2316-29), neurodegeneration (Wang, W.-X., et al., Journal of Neuroscience, 2008. 28(5): 1213-1223; Wang, W.-X., et al., The American journal of pathology, 2010. 177(1): 334-345; Abelson, J. F., et al., Science, 2005. 310(5746): 317-320), Alzheimer's and brain aging (Nelson, P. T. et al., Brain Pathol, 2008, 18(1): p. 130-8; Hebert, S. S. and De Strooper, B., Trends Neurosci, 2009. 32(4): 199-206; Ibanez-Ventoso, C. and Driscoll, M. Curr Genomics, 2009. 10(3): 144-53; Somel, M., et al., Genome Res, 2010. 20(9): 1207-18), and other conditions (Small, E. M. and Olson, E. N., Nature, 2011, 469(7330): 336-342; Mendell, J. T., Cell, 2008. 133 (2): 217-222; Vasilescu, C., et al., PLoS ONE, 2009. 4(10): e7405; Williams, A. H., et al., Science, 2009. 326(5959): 1549-1554. Further, many miRNAs are also linked to cancers (Calin, G. A., et al., Proc Natl Acad Sci USA, 2002, 99(24): 15524-9; Calin, G. A. and Croce, C. M. Blood, 2009. 114(23): 4761-4770; Esquela-Kerscher, A. and Slack, F. J., Nature Reviews Cancer, 2006. 6(4): 259-269; Hammond, S. M., Nature Genetics. 2007, 39: 582-583; Poliseno, L., et al., Supplement. Nature, 2010. 465(7301): p. 1-19), invasion and metastasis (Ma, L., et al., Nature, 2007. 449(7163): 682-688), and exhibit tissue- and cell-state-dependent profiles (Calin, G. A. and Croce, C. M., Cancer Research, 2006. 66(15): 7390-7394; Lu, M., et al., PLoS ONE, 2008. 3(10): e3420; Godshalk, S. E., et al., Oncogene, 2011, 30: 1542-50; Ryan, B. M. et al., Nature Reviews Cancer, 2010, 10(6): 389-402; Saey, T., Science News, 2010, "Cancer's little helpers: Tiny pieces of RNA may turn cells to the dark side"; Spizzo, R., et al., Cell, 2009, 137(3): 586-586.e1; Ventura, A. and Jacks, T., Cell, 2009. 136(4): 586-591; Voorhoeve, P. M. and Agami, R., Cancer, 2007, 1775(2): 274-282). The prevalence of miRNA-driven regulatory interactions across a very wide spectrum of human conditions and diseases makes the question of how many miRNAs existing a very important one. Recent advances in next generation sequencing have further complicated the picture by revealing that multiple distinct mature miRNA species can arise from the same miRNA precursor arm: these mature miRNAs are termed "isomiRs." These isomiRs typically differ from the mature miRNA sequences currently in public databases such as miRBase (Griffiths-Jones S. 2006. Nucleic Acids Res 34(90001): D140-D144) on either their 5' or 3' ends thereby increasing the diversity and complexity of the miRNA-ome. While the biological relevance of isomiRs is not fully understood, they have been shown to associate with the Argonaute complex (Ameres S L, Zamore P D. 2013. Nat Rev Mol Cell Biol: 1-14) which in turn suggests a functional role. Recent studies of isomiR expression have either focused on isomiRs of a single miRNA or on the isomiR expression patterns within a specific tissue. For example, a 5'-isomiR of miR-101 was observed to be ubiquitously expressed in several human tissues and cell lines (Llorens et al., 2013. BMC Genomics 14: 104). There is a continuous demand for more accurate diagnostic and prognostic tools and improved therapies. As such, there is still a need to identify novel miRNA and isomiR sequences that can be used for diagnosis, prognosis, and therapy of human conditions or diseases or to identify the provenance (tissue or cell) of a biological sample.

SUMMARY

There is a need to identify novel miRNA sequences that provide more accurate or reliable diagnostic and/or prognostic tools and/or improved therapies or can be used to determine the origin of a biological sample. To this end, inventors analyzed about 1,367 next generation sequencing datasets (RNA-sequencing and Argonaute cross-linking and immunoprecipitation (CLIP)-sequencing) corresponding to human normal and disease states from 13 distinct tissue types (from a total of approximately 200 human tissue types) and discovered at least tens of thousands of novel miRNAs as disclosed herein: each of the novel miRNAs has an associated false discovery rate (FDR) of 0.05 or lower.

By analyzing a large collection of next generation sequencing datasets, the inventors have discovered numerous novel human miRNAs and variants thereof. For a large fraction of these novel miRNAs, the inventors have additional corroborating evidence, through the analysis of CLIP-sequencing datasets, that they are loaded on Argonaute, which provides further credence to their bona fide miRNA nature.

In addition, by analyzing short RNA sequence profiles of deep sequenced biological samples of various human tissues and/or cell types, the inventors have discovered that the actual instance of the mature miRNA product that arises from a given miRNA locus and is detected in a given cell or tissue context can be different from the instance of the mature miRNA product that arises from the same miRNA locus in a different cell or tissue context, and this finding has been observed for many of the miRNAs currently in miRBase, which is a public repository of miRNA sequences for vertebrates, invertebrates, viruses, and plants. Accordingly, these tissue and/or cell-type dependence correlation of the novel miRNAs described herein can be used to determine tissue of origin in samples of interest. Additionally or alternatively, the tissue/cell-type dependence of the novel miRNAs described herein can also be used to determine cell state, disease type, disease stage, etc.

Accordingly, these novel miRNAs described herein can be used in various applications, e.g., to generate novel molecular signatures for cell types, cell states, disease, disease stage, disease progression, etc. They can also be used to identify novel and unexpected molecular players in cellular contexts of interest and also to reveal unexpected molecular interplays that underlie the onset and progression of diseases. Further, the novel miRNAs described herein can provide novel and improved means for therapeutic interventions. Accordingly, provided herein relates to methods, compositions, assays and systems for determining a given state of a cell and/or a tissue, which can be used for diagnosing a disease or disorder, and/or prognosing a given stage and/or progression of a disease or disorder, and/or treating a disease or disorder.

In one aspect, provided herein relates to methods or assays of determining a given state of a cell and/or a tissue. The method or assay comprises detecting in a biological sample the presence or absence of one or more miRNAs described herein. In some embodiments, the biological sample can be derived from a subject suspected of being at risk of or having a given stage of a disease or disorder. Accordingly, methods or assays described herein can also be used to determine whether a subject has, or is at risk of developing, or is at a given stage of a disease or disorder, e.g., a condition afflicting a tissue of interest. In one embodiment, the condition afflicting a tissue of interest includes cancer.

In some embodiments, the method or assay described herein can comprise detecting in the biological sample the presence or absence of a plurality of the miRNAs described herein.

In some embodiments of the methods or assays described herein, detection of the presence or absence of at least one of the novel miRNAs described herein can include measuring an expression level of the miRNA of interest in the biological sample. The expression level of the miRNA of interest can be detected by any methods known in the art, including, but not limited to, sequencing, next-generation sequencing (e.g., deep sequencing), polymerase chain reaction (PCR), and real-time quantitative PCR, northern blot, microarray, in situ hybridization, serial analysis of gene expression (SAGE), cap analysis gene expression (CAGE), massively parallel signature sequencing (MPSS), direct multiplexed measurements of the type employed in the Nanostring platform, and any combinations thereof. In such embodiments, the methods or assays can further comprise comparing with a reference sample the determined expression level of the miRNA of interest in the biological sample. When there is a discrepancy in the expression level or amount of at least one miRNA molecule between the biological sample and the reference sample, the discrepancy can be indicative of the cell or the tissue in a state different from the reference sample. For example, in some embodiments, the discrepancy can be indicative of a subject either having, or being at risk of developing, or being at a given stage of a disease or disorder, e.g., a condition afflicting the tissue. In alternative embodiments, the discrepancy can be indicative of a subject lacking of a disease or disorder to be evaluated.

The reference sample used in the methods, assays and systems described herein can be a sample derived from the same type of cell or tissue with a known condition. For example, the reference sample can represent a normal condition of a cell or tissue to be detected. The normal reference sample can be obtained from the test subject or a different subject. Alternatively, the reference sample can represent a recognizable stage of a possibly abnormal condition of a cell or a tissue to be detected.

A biological sample for evaluation in the methods, assays, and systems described herein can include one or more cells derived from any tissue or fluid in a subject. In one embodiment, the biological sample can be a tissue suspected of being at risk of, or being afflicted with a given stage of a disease or a disorder. Non-limiting examples of sample origins can include, but are not limited to, breast, pancreas, blood, prostate, colon, lung, skin, brain, ovary, kidney, oral cavity, throat, cerebrospinal fluid, and liver.

Different embodiments of the methods, assays and systems described herein can be used for diagnosis and/or prognosis of a disease or disorder (including a given stage of a disease or disorder) in a subject, e.g., a disease or disorder afflicting a certain tissue in a subject. For example, the disease or disorder to be diagnosed and/or prognosed in a subject can be associated with breast, pancreas, blood, prostate, colon, lung, skin, brain, ovary, kidney, oral cavity, throat, cerebrospinal fluid, liver, and any combination thereof. In some embodiments, the disease or disorder to be diagnosed and/or prognosed with the methods, assays or systems described herein can be a blood disorder, e.g., associated with diseased or abnormal platelets. In other embodiments, the disease or disorder to be diagnosed and/or prognosed with the methods, assays or systems described herein can be any cancer, e.g., but not limited to breast cancer and pancreatic cancer.

For a subject who is determined to have, or is at risk of developing, or is at a given stage of the disease or disorder, the subject can be administered or prescribed with a specific treatment. For example, in some embodiments where the subject is diagnosed with cancer (e.g., breast carcinoma or pancreatic carcinoma) or progression thereof, the method can further comprise administering or prescribing the subject a treatment, e.g., chemotherapy, radiation therapy, surgery, engineered transcripts that can "sponge" various combinations of the novel miRNAs described herein, or any combinations thereof.

Another aspect provided herein relates to systems for analyzing a biological sample, e.g., to determine a given state of a cell or a tissue, and/or to diagnose and/or prognose a disease or disorder, or a given state of a disease or disorder in a subject. In one embodiment, the system comprises: (a) a determination module configured to receive a biological sample and to determine sequence information and, optionally quantity estimate information, wherein the sequence information comprises a sequence of one or more miRNAs described herein; and wherein the quantity estimate information comprises at least an estimate of the abundance of said sequence, with said abundance optionally scaled with regard to the abundance of a reference molecule; (b) a storage device configured to store sequence information and optionally the quantity estimate information from the determination module; (c) a comparison module adapted to compare the sequence information and optionally the quantity estimate information stored on the storage device with reference data, and to provide a comparison result, wherein the comparison result identifies the presence or absence of the miRNA molecule, and optionally how its quantity estimate is related to the reference data, wherein a discrepancy in a quantity estimate level is indicative of the biological sample having an increased likelihood of having, or being at a cellular or tissue state different from a state represented by the reference data; and (d) a display module for displaying a content based in part on the comparison result for the user, wherein the content is a signal indicative of a subject having, or being at risk of developing, or being at a given stage of a disease or disorder, or a signal indicative of lacking a disease or disorder.

A computer-readable physical medium for determination of a given state of a cell or a tissue, including diagnosis and/or prognosis of a disease or disorder, or a state of a disease or disorder in a subject, is also provided herein. The computer-readable physical medium having computer readable instructions recorded thereon to define software modules includes a comparison module and a display module for implementing a method on a computer, wherein the method comprises: (a) comparing with the comparison module the data stored on a storage device with reference data to provide a comparison result, wherein the comparison result captures the presence or absence of the miRNA molecule and/or the difference between its quantity estimate and the reference data, wherein a discrepancy in a quantity estimate level is indicative of a biological sample having an increased likelihood of having, or being at a cellular or tissue state different from a state represented by the reference data; and (b) a display module for displaying a content based in part on the comparison result for the user, wherein the content is a signal indicative of a subject having, or being at risk of developing, or being at a given stage of a disease or disorder, or a signal indicative of lack of a disease or disorder.

In some embodiments, kits and/or assays for expressing, silencing, and/or quantitating one or more of the novel miRNAs described herein from the model organism of choice (e.g., but not limited to, human, mouse, and rat) are also encompassed within the scope of various aspects described herein.

BRIEF DESCRIPTION OF THE FIGURES

FIG. 5A is based on male samples only. FIG. 5B is based on female samples only.

DETAILED DESCRIPTION OF THE INVENTION

Figure 1A:
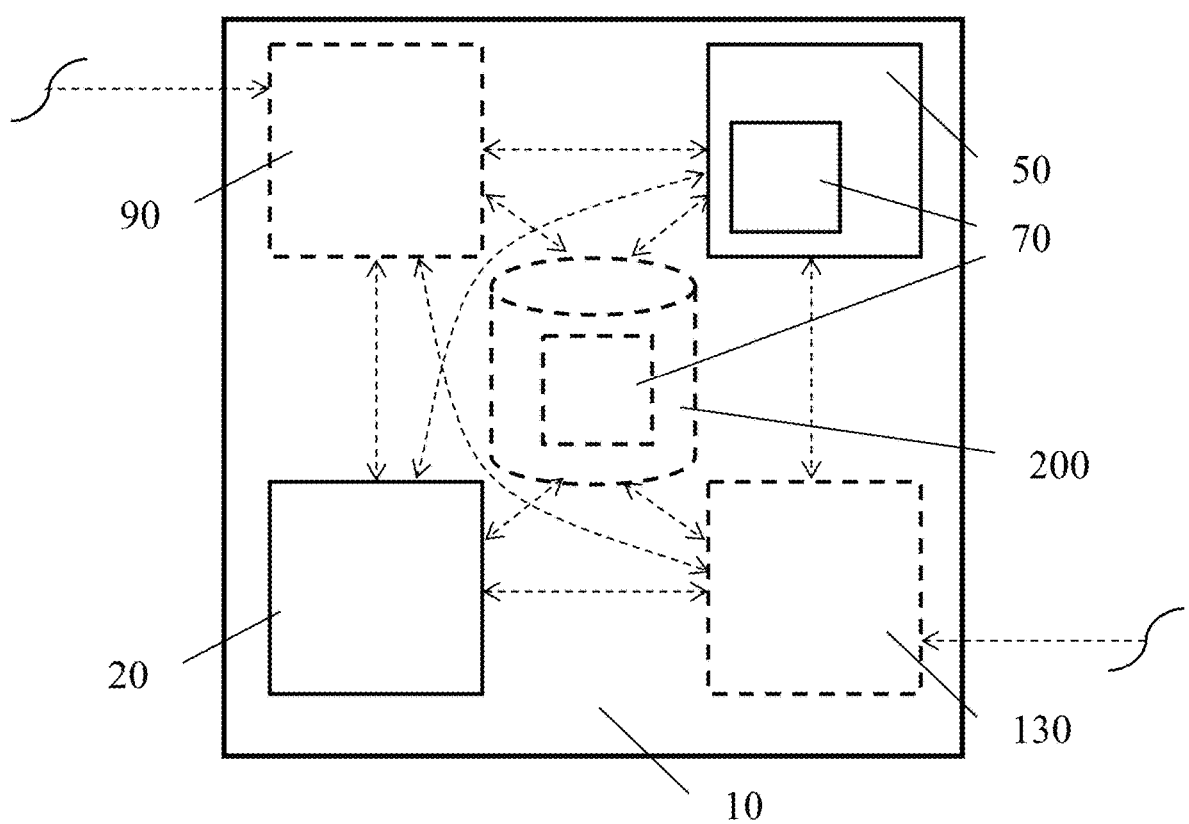
FIGS. 1A-1B are block diagrams showing an example of a system for determining a state of a cell or a tissue and/or for diagnosing or prognosing a disease or disorder, or a stage of a disease or disorder in a subject, based on expression level of one or more novel miRNAs described herein.

There is a need to identify novel miRNA sequences that provide more accurate or reliable diagnostic and/or prognostic tools and/or improved therapies or provide improved tissue of origin identification. To this end, inventors analyzed 1,367 next generation sequencing datasets (RNA-sequencing and Argonaute cross-linking and immunoprecipitation (CLIP)-sequencing) corresponding to human normal and disease states from 13 distinct tissue types (from a total of approximately 200 human tissue types)) and discovered at least tens of thousands of novel miRNAs as disclosed herein: each of the novel miRNAs has an associated FDR of 0.05 or lower.

By analyzing a large collection of next generation sequencing datasets, the inventors have discovered numerous novel human miRNAs and variants thereof. For a large fraction of these novel miRNAs, the inventors have additional corroborating evidence, through the analysis of CLIP-sequencing datasets, that they are loaded on Argonaute, which provides further credence to their bona fide miRNA nature.

In addition, by analyzing short RNA sequence profiles of deep sequenced biological samples of various human tissues and/or cell types, the inventors have discovered that the actual instance of the mature miRNA product that arises from a given miRNA locus and is detected in a given cell or tissue context can be different from the instance of the mature miRNA product that arises from the same miRNA locus in a different cell or tissue context, and this finding has been observed for many of the miRNAs currently in miR-Base, which is a public repository of miRNA sequences for vertebrates, invertebrates, viruses, and plants. Accordingly, these tissue and/or cell-type dependence correlation of the novel miRNAs described herein can be used to determine tissue of origin in samples of interest. Additionally or alternatively, the tissue/cell-type dependence of the novel miRNAs described herein can also be used to determine cell state, disease type, disease stage, etc.

Accordingly, these novel miRNAs described herein can be used in various applications, e.g., to generate novel molecular signatures for cell types, cell states, disease, disease stage, disease progression, etc. They can also be used to identify novel and unexpected molecular players in cellular contexts of interest and also to reveal unexpected molecular interplays that underlie the onset and progression of diseases. Further, the novel miRNAs described herein can provide novel and improved means for therapeutic interventions. Accordingly, provided herein relates to methods, compositions, assays and systems for determining a given state of a cell and/or a tissue, which can be used for diagnosing a disease or disorder, and/or prognosing a given stage and/or progression of a disease or disorder, and/or treating a disease or disorder.

Methods and Assays for Determining a Given State of a Cell or a Tissue, or for Determining Tissue of origin One aspect described herein provides methods and assays for determining a specific state or condition of a cell or a tissue. As the cell or tissue can be derived from a biological sample of a subject suspected of being at risk of or having a given stage of a disease or disorder, e.g., a condition afflicting a tissue, methods and assays for determining whether a subject has or is at risk of developing, or is at a given stage of a disease or disorder, e.g., a condition afflicting a tissue, are also provided herein. The methods or assays of any aspects described herein comprise measuring in a biological sample from a tissue of interest expression level of one or more miRNAs selected from SEQ ID NO: 1 to SEQ ID NO: 47,972 disclosed in Tables 1-3. In some embodiments, the methods or assays of any aspects described herein comprise measuring in a biological sample from a tissue of interest expression level of one or more miRNAs selected from SEQ ID NO: 1 to SEQ ID NO: 47,972 disclosed in Tables 1-3. An alteration of the level of one or more miRNAs as compared to the level of the same miRNA sequence(s) in a reference sample is indicative of the subject either having, or being at risk of developing, or being at a given stage of the condition.

As shown in the Examples, some of the novel miRNAs/isomiRs are preferentially present in some tissues but not in other tissues. This indicates that signatures of one or more miRNAs can be used to answer the question of tissue of origin. Thus, in some embodiments, the methods and/or assays described herein can also be used to determine tissue of origin by comparing the level(s) of one or more miRNAs in the biological sample to that of reference samples of different tissues.

As used herein, the term "alteration of the level of one or more miRNAs" refers to a change in the level of one or more miRNAs in a sample relative to the corresponding level(s) in a reference sample. In some embodiments, the alteration or change in the level of one or more miRNAs can refer to an increase in the level of one or more miRNAs in a sample relative to the corresponding level(s) in a reference sample. For example, in some embodiments where there is an alteration in the level of one or more miRNAs, the level of one or more miRNAs in a sample can be increased by at least about 10% or more, including, e.g., at least about 20%, at least about 30%, at least about 40%, at least about 50%, at least about 60%, at least about 70%, at least about 80%, at least about 90%, at least about 95%, at least about 97%, at least about 99% or more, relative to the corresponding level(s) in a reference sample. In some embodiments where there is an alteration in the level of one or more miRNAs, the level of one or more miRNAs in a sample can be increased by at least about 1.1-fold or more, including, e.g., at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or more, relative to the corresponding level(s) in a reference sample.

In some embodiments, the level(s) of one or more miRNAs are considered to be altered (or differentially expressed) relative to reference sample(s) if it has a mean expression of at least 25 or more sequenced reads, and a log 2-change in expression relative to the reference sample(s) of at least 0.5 or higher, or no more than −0.5 or lower.

In other embodiments, the alteration or change in the level of one or more miRNAs can refer to a decrease in the level of one or more miRNAs in a sample relative to the corresponding level(s) in a reference sample. For example, in some embodiments where there is an alteration in the level of one or more miRNAs, the level of one or more miRNAs in a sample can be decreased by at least about 10% or more, including, e.g., at least about 20%, at least about 30%, at least about 40%, at least about 50%, at least about 60%, at least about 70%, at least about 80%, at least about 90%, at least about 95%, at least about 97%, at least about 99% or more (including 100%), relative to the corresponding level(s) in a reference sample.

In some embodiments, the "alteration of the level of one or more miRNAs" can refer to the presence (e.g., a detectable level) of one or more miRNAs in a sample, as compared to the absence (e.g., no detectable level) of those miRNA(s) in a reference sample.

In alternative embodiments, the "alteration of the level of one or more miRNAs" can refer to the absence (e.g., no detectable level) of one or more miRNAs in a sample, as compared to the presence (e.g., a detectable level) of those miRNA(s) in a reference sample.

In some embodiments of any aspects described herein, the method or assay can comprise detecting in the biological sample the level of a plurality (e.g., at least 2, at least 3, at least 4, at least 5, at least 6, at least 7, at least 8, at least 9, at least 10, at least 15, at least 20, at least 25, at least 30, at least 40, at least 50, or more) of the miRNAs selected from SEQ ID NO: 1 to SEQ ID NO: 47,972 disclosed in Tables 1-3.

An amount of a miRNA sequence in the biological sample can be measured or quantified by any known RNA detection methods. By way of example only, the miRNA(s) in a biological sample can be detected or read by a sequencing method (including Sanger sequencing, next-generation sequencing or deep sequencing, direct multiplexing, and any art-recognized sequencing method) and a read count of each miRNA sequence can be generated to determine its amount present in the biological sample. Alternatively, where the miRNA sequence(s) in a biological sample are determined by PCR-based methods (e.g., real-time PCR), the amount of the miRNA sequence(s) present in the biological sample can be represented by a $C_t$ number, which can be compared to that of a reference sample. As a person having ordinary skill in the art would appreciate, a larger $C_t$ number generally indicates a lower amount of a nucleic acid sequence present in a sample. In some embodiments, the quantitative amount of the miRNA sequence(s) detected by PCR-based methods (e.g., real-time PCR) can also be determined from a calibration curve generated with known amounts of a nucleic acid sequence.

Any other art-recognized methods detecting or measuring the level of a miRNA sequence, e.g., but not limited to the methods and kits for miRNA isolation and quantitation as described in U.S. Pat. No. 8,574,838, can also be used herein. Additional information about measuring or quantifying one or more miRNA sequences is described in the section "Exemplary methods for detecting or measuring the level of a miRNA sequence" below.

As the amount of the miRNA sequence(s) is determined in the biological sample, in some embodiments, the methods or assays described herein can further comprise comparing with a reference sample the level of one or more miRNA sequences described herein in the biological sample. When there is a difference (e.g., at least about 10% difference or higher) or a statistically significant difference in an amount of at least one or more (e.g., at least 2 or more) or in the profile of miRNA sequences between the biological sample and the reference sample, the difference or significant difference can be indicative of the cell or the tissue in a state different from the reference sample. If the cell or the tissue is derived from a biological sample of a subject, the results of the comparison can be used for diagnosing or prognosing a disease or disorder, or a state of a disease or disorder. Depending on the choice of a reference sample, in some embodiments, the difference or significant difference can be indicative of a subject either having, or being at risk of developing, or being at a given stage of a disease or disorder, e.g., a condition afflicting the tissue; while in other embodiments, the difference or significant difference can be indicative of a subject free of a disease or disorder, e.g., a condition afflicting the tissue. For example, if a subject's miRNA sequence level or profile has no significant difference from that of a normal sample, it indicates that the subject is free of a condition or disease. Additionally or alternatively, if a subject's miRNA sequence level or profile is significantly different from that of a sample of a known disease or disorder to be diagnosed, it indicates that the subject does not likely have that disease or disorder.

If the miRNA sequence level or profile of a biological sample contain miRNA(s) that are preferentially present in a certain tissue but not in other tissues, the tissue origin of the biological sample can be determined based on the presence of those tissue-specific miRNA(s).

The threshold level selected to distinguish a given state of a cell or tissue from another, and/or to determine if a subject has, or is at risk of developing, or is at a given stage of a condition afflicting a tissue of interest can be determined experimentally. For example, by comparing the levels and/or profiles of one or more miRNA molecules detected in a number of references samples of known conditions in a specific tissue (e.g., a normal breast sample vs. a cancerous breast sample), e.g., by deep sequencing and/or quantitative RT-PCR, one of skill in the art can determine a threshold level for levels of one or more miRNA sequences required to distinguish one condition from another (e.g., to distinguish a normal breast sample from a cancerous breast sample).

In some embodiments, the threshold level needs not be pre-determined. For example, cluster analysis can be computationally performed to classify miRNA expression profiles of a biological sample and a set of reference samples into groups such that samples in the same group (called a cluster) have more similar miRNA expression profiling to each other than to those in other groups (clusters). Accordingly, when a biological sample is categorized into the same group with a subset of reference samples of similar miRNA expression profiles, the biological sample is considered to have similar properties (e.g., genotype or phenotype) as the subset of reference samples. For example, when a breast tissue sample from a subject is categorized into the same group representing cancerous breast tissue reference samples, or more specifically, into a sub-group representing invasive breast cancer, the subject is determined to likely to have breast cancer, or more specifically an invasive breast cancer. Various clustering algorithms for classification and clustering are known in the art and can be used for the purposes described herein. Examples of clustering algorithms and/or models include, but are not limited to connectivity-based clustering (e.g., hierarchical clustering), centroid-based clustering (e.g., k-means clustering), distribution-based clustering (e.g., multivariate normal distributions used by the expectation-maximization algorithm), density-based clustering (e.g., DBSCAN and OPTICS), subspace models (e.g., biclustering), and any combinations thereof.

The reference sample used in the methods and assays described herein can be a sample derived from the same type of cell or tissue as a biological sample, and with a known condition. For example, the reference sample can represent a normal condition of a cell or tissue in a biological sample to be analyzed. The normal reference sample can be collected from a subject whose biological sample is being analyzed or from a different subject. Alternatively, the reference sample can represent a recognizable stage of an abnormal condition of a cell or a tissue in a biological sample to be analyzed. By way of example only, if a disease or disorder to be diagnosed or prognosed in a subject is breast cancer, a reference sample can include a normal breast tissue, a ductal carcinoma in situ breast tissue sample, an invasive ductal carcinoma tissue sample or subtype, an invasive lobular carcinoma tissue sample, a lobular carcinoma in situ tissue sample, and any combinations thereof.

In some embodiments, the reference sample can present a known condition of a known tissue origin. Depending on applications, the reference sample can have the same or different tissue origin from the biological sample. For example, in order to determine the tissue origin of a biological sample, the level(s) and/or profile of one or more miRNAs described herein can be compared to reference samples of different tissues.

By way of example only, in some embodiments, the methods described herein can be used to determine a primary origin of an unknown tumor or cancer. Thus, in some embodiments, the methods described herein can be used to determine whether the tumor is a primary tumor or a secondary tumor (i.e., a metastasis). For example, a biopsy of an unknown tumor can be subjected to the methods or assays described herein to determine the tissue origin of the tumor, wherein if the tissue origin of the tumor is determined to be the same tissue type as from where the biopsy is collected, the tumor is diagnosed as a primary tumor, or if the tissue origin of the tumor is determined to be different from the type of the tissue from where the biopsy is collected, the tumor is diagnosed as a secondary tumor (i.e., a metastasis). Thus, the methods described herein can be used to fingerprint a biological sample, e.g., whether it is a normal sample or a diseased sample (e.g., a cancerous sample).

In some embodiments, more than one reference samples can be used, wherein the reference samples can represent a variety of different conditions (e.g., normal condition, different stages of a disease or disorder, different tissue origins). By way of example only, if a biological sample of a subject generates a similar or comparable miRNA expression profile (e.g., in terms of levels and/or locations of miRNA sequences) to that of a normal sample or a group of normal samples (reference samples), the subject can be considered normal with respect to the normal sample or the group normal samples. Similarly, if a biological sample of a subject generates a similar or comparable miRNA expression profile (e.g., in terms of levels and/or locations of miRNA sequences) to that of a sample or a group of samples derived from a given tissue (reference samples), the subject's biological sample can be considered to have the same tissue type as the reference samples.

The miRNA expression profile can be generated based on one or more genes. In some embodiments, the miRNA expression profile can be generated based on a specific gene, e.g., a gene that is associated with a condition or disorder. In some embodiments, miRNA sequences can be detected from at least two genes in a biological sample and compared to the corresponding reference sample to determine if similar conclusions are obtained.

For a subject who is determined to have, or is at risk of developing, or is at a given stage of the disease or disorder, the subject can be administered or prescribed with an appropriate treatment. For example, in some embodiments where the subject is diagnosed with cancer (e.g., breast carcinoma or pancreatic carcinoma) or progression thereof, the method can further comprise administering or prescribing the subject an anti-cancer treatment, e.g., chemotherapy, radiation therapy, surgery, immunotherapy, RNA therapeutics (e.g., siRNAs, miRNAs), or any combinations thereof.

In some embodiments, a subject in need thereof can be administered with an antagonist or a mimic of one or more (e.g., at least one, at least two, at least three, at least four, at least five, or more) of the miRNA sequences selected from SEQ ID NO: 1 to SEQ ID NO: 47,972 in Tables 1-3, depending on whether the subject is diagnosed to have an overexpression or a deficiency of one or more miRNA sequences determined to be associated with a condition or disorder. For example, in some embodiments where the level(s) of one or more miRNAs described herein are determined to represent a "causal event" for the disease or disorder, the level(s) of the miRNAs can be controlled in order to return their levels to what would be considered "normal" levels and thus alleviate the impact that can result from the changes in their amount. Examples of the techniques that can be used to control the level(s) of one or more miRNAs described herein include, but are not limited to, antisensing or sponging (e.g., microRNA sponges as described in Ebert and Shape. "MicroRNA sponges: Progress and possibilities" RNA (2010) 16:2043-2050; and Ebert et al. "MicroRNA sponges: Competitive inhibitors of small RNAs in mammalian cells" Nat. Methods (2007) 4: 721-726), decoying (e.g., as described in Swami M. "Small RNAs: Pseudogenes act as microRNA decoys." Nature Reviews Genetics (2010) 11: 530-531), overexpression, and/or any art-recognized techniques.

Additional information about antagonists or mimics of miRNAs described herein is described in the section "Pharmaceutical compositions" below.

Novel miRNA Sequences or Molecules Described Herein

The inventors have discovered a collection of novel microRNAs (miRNAs) of SEQ ID NO: 1 to SEQ ID NO: 47,972 in Tables 1-3 in a human genome, based on deep sequencing data using different tools and/or design methodology. The cardinality of the class of non-coding RNAs (ncRNAs) known as microRNAs or miRNAs has been a controversial issue for more than a decade. It was previously estimated that the number of human miRNAs would not exceed 300 (Lim et al. Science. 2003 Mar. 7; 299(5612): 1540). However, different methods that were used later provided higher, yet concordant, figures for the number of human miRNAs and their cardinality was estimated to be in the several tens of thousands. The miRBase repository has served as a widely-accepted public clearinghouse of miRNA sequences for vertebrates, invertebrates, viruses and plants. The database's latest release (Rel. 20) from 2013 contains ~2,600 human miRNA entries produced from ~1,800 miRNA precursors.

Tables 1-3 listing sequences of novel miRNAs of SEQ ID NO: 1 to SEQ ID NO: 47,972 are submitted and incorporated herein by reference in their entireties. Oligonucleotides comprising sequences complementary to the novel miRNAs listed in Tables 1-3 are also encompassed within the scope of the inventions described herein. By "complementary" is meant that an oligonucleotide can form hydrogen bond(s) with another oligonucleotide by either traditional Watson-Crick or other non-traditional types. The complementary oligonucleotides can be completely or partially complementary to the novel miRNA sequences listed in Tables 1-3. In some embodiments, partial complementarity is indicated by the percentage of contiguous residues in an oligonucleotide that can form hydrogen bonds (e.g., Watson-Crick base pairing) with a second oligonucleotide sequence (e.g., 5, 6, 7, 8, 9, 10 out of 10 being 50%, 60%, 70%, 80%, 90%, and 100% complementary). "Completely complementary" or 100% complementarity means that all the contiguous residues of an oligonucleotide sequence will form hydrogen bond with the same number of contiguous residues in a second oligonucleotide sequence. Less than perfect complementarity refers to the situation in which some, but not all, nucleotide units of two strands can hydrogen bond with each other.

Table 1 shows a listing of novel miRNAs of SEQ ID NO: 1 to SEQ ID NO: 19,754 that the inventors identified using their own designed methodology as described in Example 1. In Table 1, SEQ ID NO: 1 to SEQ ID NO: 9,877 contain miRNA sequences of mature form, while SEQ ID NO: 9,878 to SEQ ID NO: 19,754 contain sequences each having a hairpin sequence and a mature miRNA sequence.

Table 2 shows a listing of novel miRNAs of SEQ ID NO: 19,755 to SEQ ID NO: 27,168 that the inventors identified using a public tool called miRDeep2. MiRDeep2 (see Friedländer, M. R., et al., Nature Biotechnology, 2008, 26, 407-415, for methods of discovering microRNAs from deep sequencing data using miRDeep) follows a slightly different approach to finding miRNAs that is based on a multi-faceted scoring system. In an effort to be comprehensive, miRDeep2 was also used to discover miRNAs to complement the inventor's methodology (as described in Example 1). In Table 2, SEQ ID NO: 19,755 to SEQ ID NO: 23,461 contain miRNA sequences of mature form, while SEQ ID NO: 23,462 to SEQ ID NO: 27,168 contain sequences each having a hairpin sequence and a mature miRNA sequence.

Table 3 shows a listing of novel miRNAs of SEQ ID NO: 27,169 to SEQ ID NO: 47,972. These are variants or isomers of miRNAs, called isomiRs. The term "isomiR" generally refers to a miRNA who sequence is slightly different than the sequence of a known miRNA, e.g., a miRNA that is known in the public databases." However, this apparent difference could simply be because the "miRNA" is found in tissue X whereas the "isomiR" is found in tissue Y and it so happened that the tissue X was first studied. If tissue Y was first studied then what is called "isomiR" might have been called "miRNA" and vice versa.

In some instances, both the "miRNA" and the "isomiR" can be found in the same tissue but the isomiR has a lower expression than the miRNA. In some instances, tissues where what is commonly called as "miRNA" has lower expression than an "isomiR" from the same locus: in such examples, the labels of miRNA and isomiR can be used interchangeably. Accordingly, as used herein, the terms "miRNA" and "isomiR" are used herein interchangeably and will be making a distinction only if necessary to remove any ambiguities.

While the novel miRNA sequences listed in Tables 1-3 are from human genomes, many of these sequences are conserved in other species, e.g., but not limited to other primates such as Chimpanzee, Gorilla, Orangutan, and Macaque. Some human miRNA sequences as described herein are also conserved in mice, fruit-fly, and worms. See Example 2.

MicroRNAs (miRNAs) are small, non-coding RNA molecules that generally function as regulators of a genome. The terms "microRNA" or "miRNA" are used interchangeably herein, are generally endogenous RNAs, some of which are known to regulate the expression of protein-coding genes at the posttranscriptional level. As used herein, the term "microRNA" refers to any type of micro-interfering RNA, including but not limited to, endogenous microRNA and artificial or synthetic microRNA. Typically, endogenous microRNA are small RNAs encoded in the genome which are capable of modulating the productive utilization of mRNA. A mature miRNA is a single-stranded RNA molecule of about 21-23 nucleotides in length that is complementary to a target sequence and hybridizes to the target RNA sequence to inhibit expression of a (protein-coding or non-coding) gene which encodes a miRNA target sequence. miRNAs themselves are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression. MicroRNA sequences have been described in publications such as, Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into the precursor molecule.

A mature miRNA is produced as a result of a series of miRNA maturation steps; first a gene encoding the miRNA is transcribed. The gene encoding the miRNA is typically much longer than the processed mature miRNA molecule; miRNAs are first transcribed as primary transcripts or "pri-miRNA" with a cap and poly-A tail, which is subsequently processed to short, about 70-nucleotide "stem-loop structures" known as "pre-miRNA" in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). This complex is responsible for the gene silencing observed due to miRNA expression and RNA interference. The pathway is different for miRNAs derived from intronic stem-loops; these are processed by Drosha but not by Dicer. In some instances, a given region of DNA and its complementary strand can both function as templates to give rise to at least two miRNAs. Mature miRNAs can direct the cleavage of mRNA or they can interfere with translation of the mRNA, either of which results in reduced protein accumulation, rendering miRNAs capable of modulating gene expression and related cellular activities.

As discussed above, recent advances in next generation sequencing have complicated this picture by revealing that multiple distinct mature miRNA species, the isomiRs, can arise from the same miRNA precursor arm ("pre-miR"). The isomiRs typically differ from the mature miRNA sequences currently in public databases such as miRBase on either their 5' or 3' ends, thereby increasing the diversity and complexity of the miRNA-ome. IsomiRs, just like miRNAs, associate with the Argonaute complex. Accordingly, the terms "miRNA" and "isomiR" are used herein interchangeably and will be making a distinction only if necessary to remove any ambiguities.

The term "pri-miRNA" refers to a precursor to a mature miRNA molecule which comprises: (i) a microRNA sequence and (ii) stem-loop component which are both flanked (i.e. surrounded on each side) by "microRNA flanking sequences", where each flanking sequence typically ends in either a cap or poly-A tail. A pri-microRNA, (also referred to as large RNA precursors), are composed of any type of nucleic acid based molecule capable of accommodating the microRNA flanking sequences and the microRNA sequence. Examples of pri-miRNAs and the individual components of such precursors (flanking sequences and microRNA sequence) are provided herein. The nucleotide sequence of the pri-miRNA precursor and its stem-loop components can vary widely. In one embodiment, a pre-miRNA molecule can be an isolated nucleic acid; including microRNA flanking sequences and comprising a stem-loop structure and a microRNA sequence incorporated therein. A pri-miRNA molecule can be processed in vivo or in vitro to an intermediate species caller "pre-miRNA", which is further processed to produce a mature miRNA.

The term "pre-miRNA" refers to the intermediate miRNA species in the processing of a pri-miRNA to mature miRNA, where pri-miRNA is processed to pre-miRNA in the nucleus, whereupon pre-miRNA translocates to the cytoplasm where it undergoes additional processing in the cytoplasm to form mature miRNA. Pre-miRNAs are generally about 70 nucleotides long, but can be less than 70 nucleotides or more than 70 nucleotides.

The term "microRNA flanking sequence" as used herein refers to nucleotide sequences including microRNA processing elements. MicroRNA processing elements are the minimal nucleic acid sequences which contribute to the production of mature miRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure. Thus, in some embodiments the flanking sequences are 5-4,000 nucleotides in length. As a result, the length of the precursor molecule can be, in some instances at least about 150 nucleotides or 270 nucleotides in length. The total length of the precursor molecule, however, can be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

MicroRNA flanking sequences can be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. microRNA flanking sequences within the pri-miRNA molecule can flank one or both sides of the stem-loop structure encompassing the microRNA sequence. Thus, one end (i.e., 5') of the stem-loop structure can be adjacent to a single flanking sequence and the other end (i.e., 3) of the stem-loop structure cannot be adjacent to a flanking sequence. Preferred structures have flanking sequences on both ends of the stein-loop structure. The flanking sequences can be directly adjacent to one or both ends of the stem-loop structure or can be connected to the stem-loop structure through a linker, additional nucleotides or other molecules.

A "stem-loop structure" refers to a nucleic acid having a secondary structure that includes a region of nucleotides which are known or predicted to form a double strand (stein portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem can include one or more base mismatches. Alternatively, the base-pairing can be exact, i.e. not include any mismatches. In some instances the precursor microRNA molecule can include more than one stein-loop structure. The multiple stem-loop structures can be linked to one another through a linker, such as, for example, a nucleic acid linker or by a microRNA flanking sequence or other molecule or some combination thereof.

The hairpin sequences in Tables 1 and 2 can provide information about novel miRNAs and the pre-miRNA that are believed to be responsible for the miRNAs production. The hairpin sequences of Tables 1 and 2 can be used in the same manner that one would use a pre-miRNA (e.g., similar preparation methods, similar delivery methods, similar application settings, similar detection methods).

Furthermore, miRNA-like stem-loops can be expressed in cells as a vehicle to deliver artificial or synthetic miRNAs for the purpose of modulating the expression of endogenous genes through the miRNA and/or RNAi pathways.

In some embodiments, the miRNAs described herein are miRNA mimetic. As used herein, the term "miRNA mimetic" refers to an artificial miRNA which is flanked by the appropriate sequences that will allow it to form the stem-loop like structures that are typical of a pri-miRNA.

The term "artificial microRNA" includes any type of RNA sequence, other than endogenous microRNA, which is capable of modulating the productive utilization of mRNA. For instance, the term artificial microRNA also encompasses a nucleic acid sequence which would be previously identified as siRNA, where the siRNA is incorporated into a vector and surrounded by miRNA flanking sequences as described herein.

In some embodiments, the term "miRNA" as used herein can encompass an oligonucleotide having a hairpin sequence and a mature miRNA sequence. In some embodiments, the term "miRNA" can encompass isomiR.

In some embodiments, the novel miRNA sequences described herein can encompass at least one or more nucleotide modifications, e.g., addition, deletion and/or substitutions of nucleotides, and/or modifications to the side groups and/or backbone of the nucleotides. Unmodified miRNA sequences can be less than optimal in some applications, e.g., unmodified miRNA sequences can be prone to degradation by e.g., cellular nucleases. However, chemical modifications to one or more of the subunits of the miRNA sequences can confer improved properties, e.g., can render miRNA sequences more stable to nucleases. Typical miRNA sequence modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the 2' hydroxyl on the ribose sugar; (iii) wholesale replacement of the phosphate moiety with "dephospho" linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the oligonucleotide, e.g., removal, modification or replacement of a terminal phosphate group or conjugation of a moiety, e.g., conjugation of a ligand, to either the 3' or 5' end of oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

Diseases or Disorders that can be Diagnosed, Prognosed, and/or Treated Using One or More Novel miRNAs Described Herein or Complementary Sequences Thereof In some aspects, different embodiments of the methods, assays, compositions, and systems described herein can be used for diagnosis and/or prognosis of a disease or disorder, and/or the state of the disease or disorder in a subject, e.g., a condition afflicting a certain tissue in a subject. In other aspects, different compositions described herein can be used for treatment of a disease or disorder in a subject. For example, the disease or disorder in a subject can be associated with breast, pancreas, blood, prostate, colon, lung, skin, brain, ovary, kidney, oral cavity, throat, cerebrospinal fluid, liver, or other tissues, and any combination thereof. Examples 7-8 shows differential expression of some of the novel miRNA sequences listed in Tables 1-3 in tissues of different states (e.g., disease states or cell states).

In some embodiments, diseases or disorders that can be diagnosed, prognosed, and/or treated using one or more novel miRNAs described herein or complementary sequences thereof can include conditions that are not terminal but can cause an interruption, disturbance, or cessation of a bodily function, system, or organ. Such examples of diseases or disorders can include, e.g., but are not limited to, developmental disorders (e.g., autism), brain disorders (e.g., epilepsy), mental disorders (e.g., depression), endocrine disorders (e.g., diabetes), heart diseases (e.g., cardiomyopathy), or skin disorders (e.g., skin inflammation).

In some embodiments, diseases or disorders that can be diagnosed, prognosed, and/or treated using one or more novel miRNAs described herein or complementary sequences thereof can include breast diseases or disorders. Exemplary breast disease or disorder includes breast cancer.

In some embodiments, diseases or disorders that can be diagnosed, prognosed, and/or treated using one or more novel miRNAs described herein or complementary sequences thereof can include pancreatic diseases or disorders. Nonlimiting examples of pancreatic diseases or disorders include acute pancreatitis, chronic pancreatitis, hereditary pancreatitis, pancreatic cancer (e.g., endocrine or exocrine tumors), etc., and any combinations thereof.

In some embodiments, diseases or disorders that can be diagnosed, prognosed, and/or treated using one or more novel miRNAs described herein or complementary sequences thereof can include blood diseases or disorders. Examples of blood diseases or disorders include, but are not limited to, platelet disorders, von Willebrand diseases, deep vein thrombosis, pulmonary embolism, sickle cell anemia, thalassemia, anemia, aplastic anemia, fanconi anemia, hemochromatosis, hemolytic anemia, hemophilia, idiopathic thrombocytopenic purpura, iron deficiency anemia, pernicious anemia, polycythemia vera, thrombocythemia and thrombocytosis, thrombocytopenia, and any combinations thereof.

In some embodiments, diseases or disorders that can be diagnosed, prognosed, and/or treated using one or more novel miRNAs described herein or complementary sequences thereof can include prostate diseases or disorders. Non-limiting examples of prostate diseases or disorders can include prostatis, prostatic hyperplasia, prostate cancer, and any combinations thereof.

In some embodiments, diseases or disorders that can be diagnosed, prognosed, and/or treated using one or more novel miRNAs described herein or complementary sequences thereof can include colon diseases or disorders. Exemplary colon diseases or disorders can include, but are not limited to, colorectal cancer, colonic polyps, ulcerative colitis, diverticulitis, and any combinations thereof.

In some embodiments, diseases or disorders that can be diagnosed, prognosed, and/or treated using one or more novel miRNAs described herein or complementary sequences thereof can include lung diseases or disorders. Examples of lung diseases or disorders can include, but are not limited to, asthma, chronic obstructive pulmonary disease, infections, e.g., influenza, pneumonia and tuberculosis, and lung cancer.

In some embodiments, diseases or disorders that can be diagnosed, prognosed, and/or treated using one or more novel miRNAs described herein or complementary sequences thereof can include skin diseases or disorders, or skin conditions. An exemplary skin disease or disorder can include skin cancer, e.g., melanoma; and psoriasis.

In some embodiments, diseases or disorders that can be diagnosed, prognosed, and/or treated using one or more novel miRNAs described herein or complementary sequences thereof can include brain diseases or disorders. Examples of brain diseases or disorders can include, but are not limited to, brain infections (e.g., meningitis, encephalitis, brain abscess), brain tumor, glioblastoma, stroke, ischemic stroke, multiple sclerosis (MS), vasculitis, and neurodegenerative disorders (e.g., Parkinson's disease, Huntington's disease, Pick's disease, amyotrophic lateral sclerosis (ALS), dementia, and Alzheimer's disease), and any combinations thereof.

In some embodiments, diseases or disorders that can be diagnosed, prognosed, and/or treated using one or more novel miRNAs described herein or complementary sequences thereof can include liver diseases or disorders. Examples of liver diseases or disorders can include, but are not limited to, hepatitis, cirrhosis, liver cancer, billary cirrhosis, primary sclerosing cholangitis, Budd-Chiari syndrome, hemochromatosis, transthyretin-related hereditary amyloidosis, Gilbert's syndrome, and any combinations thereof.

In other embodiments, diseases or disorders that can be diagnosed, prognosed, and/or treated using one or more novel miRNAs described herein or complementary sequences thereof can include cancer. Examples of cancers can include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some embodiments, the methods, assays, kits, and systems described herein can be used for determining a given stage of cancer in a subject. The stage of a cancer generally describes the extent the cancer has progressed and/or spread. The stage usually takes into account the size of a tumor, how deeply the tumor has penetrated, whether the tumor has invaded adjacent organs, how many lymph nodes the tumor has metastasized to (if any), and whether the tumor has spread to distant organs. Staging of cancer is generally used to assess prognosis of cancer as a predictor of survival, and cancer treatment is primarily determined by staging. Thus, methods, systems, kits, and assays for determining a given stage of cancer in a subject are also provided herein. For example, such methods and assays can comprise detecting in a biological sample (e.g., a biopsy) the presence, absence or level of one or more miRNA sequences described herein.

In some embodiments, the cancer to be diagnosed or prognosed can be breast carcinoma. In such embodiments, the methods or assays described herein can be used to distinguish a cancerous breast tissue from a normal breast tissue, or identify a given stage of a cancerous breast tissue, e.g., ductal carcinoma in situ, lobular carcinoma in situ, invasive ductal carcinoma or a subtype, invasive lobular carcinoma, etc.

In some embodiments, the cancer to be diagnosed or prognosed can be pancreatic cancer. In such embodiments, the methods or assays described herein can be used to distinguish a cancerous pancreas tissue from a normal pancreas tissue, or identify a given state of a cancerous pancreas tissue, e.g., early-stage pancreatic cancer or late-stage pancreatic cancer.

In some embodiments, the methods, assays, kits, and systems described herein can be used for determining tissue origin of a biological sample from a subject. For example, the tissue origin of a biological sample from a subject can be determined based on comparison of the level(s) and/or profile of one or more miRNAs described herein in the biological sample with reference samples of different tissues. Example 3 shows tissue specificity of the novel miRNAs described herein that can be used to identify tissue origin of a biological sample.

By way of example only, in some embodiments, the methods, assays, kits, and systems described herein can be used to determine a primary origin of an unknown tumor or cancer. Thus, in some embodiments, the methods described herein can be used to determine whether the tumor is a primary tumor or a secondary tumor (i.e., a metastasis). For example, a biopsy of an unknown tumor can be subjected to the methods or assays described herein to determine the tissue origin of the tumor, wherein if the tissue origin of the tumor is determined to be the same tissue type as from where the biopsy is collected, the tumor is diagnosed as a primary tumor, or if the tissue origin of the tumor is determined to be different from the type of the tissue from where the biopsy is collected, the tumor is diagnosed as a secondary tumor (i.e., a metastasis). Thus, the methods described herein can be used to fingerprint a biological sample, e.g., whether it is a normal sample or a diseased sample (e.g., a cancerous sample).

For a subject who is determined to have, or is at risk of developing, or is at a given stage of cancer (e.g., breast carcinoma or pancreatic carcinoma), the subject can be administered or prescribed with an anti-cancer treatment, e.g., chemotherapy, radiation therapy, surgery, immunotherapy, RNA therapeutics (e.g., siRNAs, miRNAs), or any combinations thereof.

In some embodiments, a subject in need thereof can be administered with an antagonist or a mimic of one or more of the miRNA sequences selected from SEQ ID NO: 1 to SEQ ID NO: 47,972 in Tables 1-3, depending on whether the subject is diagnosed to have an overexpression or a deficiency of one or more miRNA sequences determined to be associated with a condition or disorder. Additional information about antagonists or mimics of miRNAs described herein is described in the section "Pharmaceutical compositions" below.

Exemplary Methods for Detecting One or More miRNA Sequences Described Herein

One or more miRNA sequence(s) can be detected by any methods known in the art, including, but not limited to, Sanger sequencing, nucleic acid amplification (e.g., polymerase chain reaction (PCR), and real-time quantitative PCR), northern blot, nucleic acid hybridization (e.g., microarray), in situ hybridization, serial analysis of gene expression (SAGE), cap analysis gene expression (CAGE) and massively parallel signature sequencing (MPSS), next generation sequencing (including deep sequencing, e.g., sequencing with deep coverage), direct multiplexing, etc., and any combinations thereof.

Methods for performing SAGE to detect RNAs have been previously described in Velculescu, V. E. et al. "Serial Analysis of Gene Expression." Science (1995) 270: 484-487; and Saha S. et al. "Characterization of the yeast transcriptome" Cell (1997) 88: 243-251, and exemplary SAGE protocols can be accessed at sagenet.org/protocol/index.htm. Methods for performing CAGE to detect RNAs has been previously described, e.g., in Kodzius R. et al. "CAGE: cap analysis of gene expression" Nature Methods (2006) 3: 211-222. Methods for performing MPSS to detect RNAs can be found, e.g., in Brenner, S. et al. "Gene expression analysis by massively parallel signature sequencing (MPSS) on microbead arrays" Nature Biotechnology (2000) 18: 630-634.

In some embodiments, the INVADER® assay (Third Wave Technologies Inc., Madison, Wis.) can be modified and used to detect miRNA sequences in a biological sample. The INVADER® assay is generally a homogeneous, isothermal, signal amplification system for the quantitative detection of nucleic acids. The assay can directly detect either DNA or RNA without target amplification or reverse transcription. It is based on the ability of Cleavase® enzymes to recognize as a substrate and cleave a specific nucleic acid structure generated through the hybridization of two oligonucleotides to the target sequence. Modification of the INVADER® assay for miRNA sequence detection has been previously described, e.g., in de Arruda, M. et al. "Invader technology for DNA and RNA analysis: Principles and applications" Expert Rev. Mol. Diagn (2002) 2: 487-496; Eis, P. S. et al. "An invasive cleavage assay for direct quantitation of specific RNAs" Nat. Biotechnol. (2001) 19: 673-676; and Allawi H. T. et al. "Quantitation of microRNAs using a modified Invader assay" RNA (2004) 10: 1153-1161.

Next-generation sequencing (NGS) is a novel approach for the detection and sequencing of DNA or RNA molecules as reviewed, e.g., in Voelkerding K. V. et al. "Next-Generation Sequencing: From Basic Research to Diagnostics" Clinical Chemistry (2009) 55: 641-658; Metzker M. L. "Sequencing technologies—the next generation" Nature Reviews (2010) 11: 31-46; Zhang J. et al. "The impact of next-generation sequencing on genomics" J. Genet Genomics (2011) 38: 95-109; and Pareek C. S. et al. "Sequencing technologies and genome sequencing" J. Appl Genetics (2011) 52: 413-435. Various commercial NGS instruments and reagent kits for high-throughput next-generation sequencing have been developed and used for RNA-sequencing. For example, exemplary NGS instruments that can be used for RNA-sequencing or deep sequencing of RNA can include, but are not limited to, the GS FLX sequencer (based on pyrosequencing) from 454 Life Sciences now part of ROCHE Diagnostics [http://www.454.com/], the Genome Analyzer (based on polymerase-based sequence-by-synthesis) from Illumina [http://www.illumina.com], the SOLiD™ System (based on ligation-based sequencing) from Applied Biosystems [http://www.appliedbiosystems.com/absite/us/en/home/applications-technologies/solid-next-generation-sequencing/next-generation-systems.html], and the HeliScope™ Single Molecule Sequencer from Helicos BioScience [http://www.helicosbio.com/].

Other NGS or higher-generation sequencing methods based on single-molecule sequencing (without PCR amplification) can also be used to detect miRNA sequences or molecules in some embodiments of the methods, assays, and systems described herein. Examples of single-molecule sequencing methods can include, but are not limited to, Ion Torrent (pH sensing), nanopore sequencing, and transmission electron microscope (TEM) for sequencing. See, e.g., Perkel, J. "Making contact with Sequencing's Fourth Generation" BioTechniques (2011): 50:93-95.

Systems and Computer Readable Media for Determination of a Given State of a Cell or Tissue Another aspect provided herein relates to systems (and non-transitory computer readable media for causing computer systems), e.g., to perform a method for determining a given state and/or condition of a cell or a tissue sample, and/or to perform the methods of various aspects described herein, based on determining presence and/or absence and/or level(s) of one or more miRNA sequence described herein. In some embodiments, the systems and computer readable media described herein can be used to diagnose and/or prognose a condition or a stage of the condition in a subject.

FIG. 1A depicts a device or a computer system 10 comprising one or more processors 20 and a memory 50 storing one or more programs 70 for execution by the one or more processors 20.

In some embodiments, the device or computer system 10 can further comprise a non-transitory computer-readable storage medium 200 storing the one or more programs 70 for execution by the one or more processors 20 of the device or computer system 10.

In some embodiments, the device or computer system 10 can further comprise one or more input devices 90, which can be configured to send or receive information to or from any one from the group consisting of: an external device (not shown), the one or more processors 20, the memory 50, the non-transitory computer-readable storage medium 200, and one or more output devices 130.

In some embodiments, the device or computer system 10 can further comprise one or more output devices 130, which can be configured to send or receive information to or from any one from the group consisting of: an external device (not shown), the one or more processors 20, the memory 50, and the non-transitory computer-readable storage medium 200.

In some embodiments, the device or computer system 10 for determining a given state and/or condition of a cell or tissue sample (biological sample) comprises:

one or more processors; and memory to store one or more programs, the one or more programs comprising instructions for:

(i) measuring in a biological sample the level(s) of one or more miRNA sequences selected from SEQ ID NO: 1 to SEQ ID NO: 47,972 listed in Tables 1-3; and (ii) comparing the measured level(s) of one or more miRNA sequences to that of at least one or more reference samples to determine any significant alteration or difference in the level(s) of the miRNAs between the biological sample and the reference sample(s); and (iii) displaying a content based in part on the data output from (ii), wherein the content comprises a signal indicative of a subject having, or being at risk of developing, or being at a given stage of a disease or disorder, or a signal indicative of no sign of the disease or disorder.

Figure 1B:
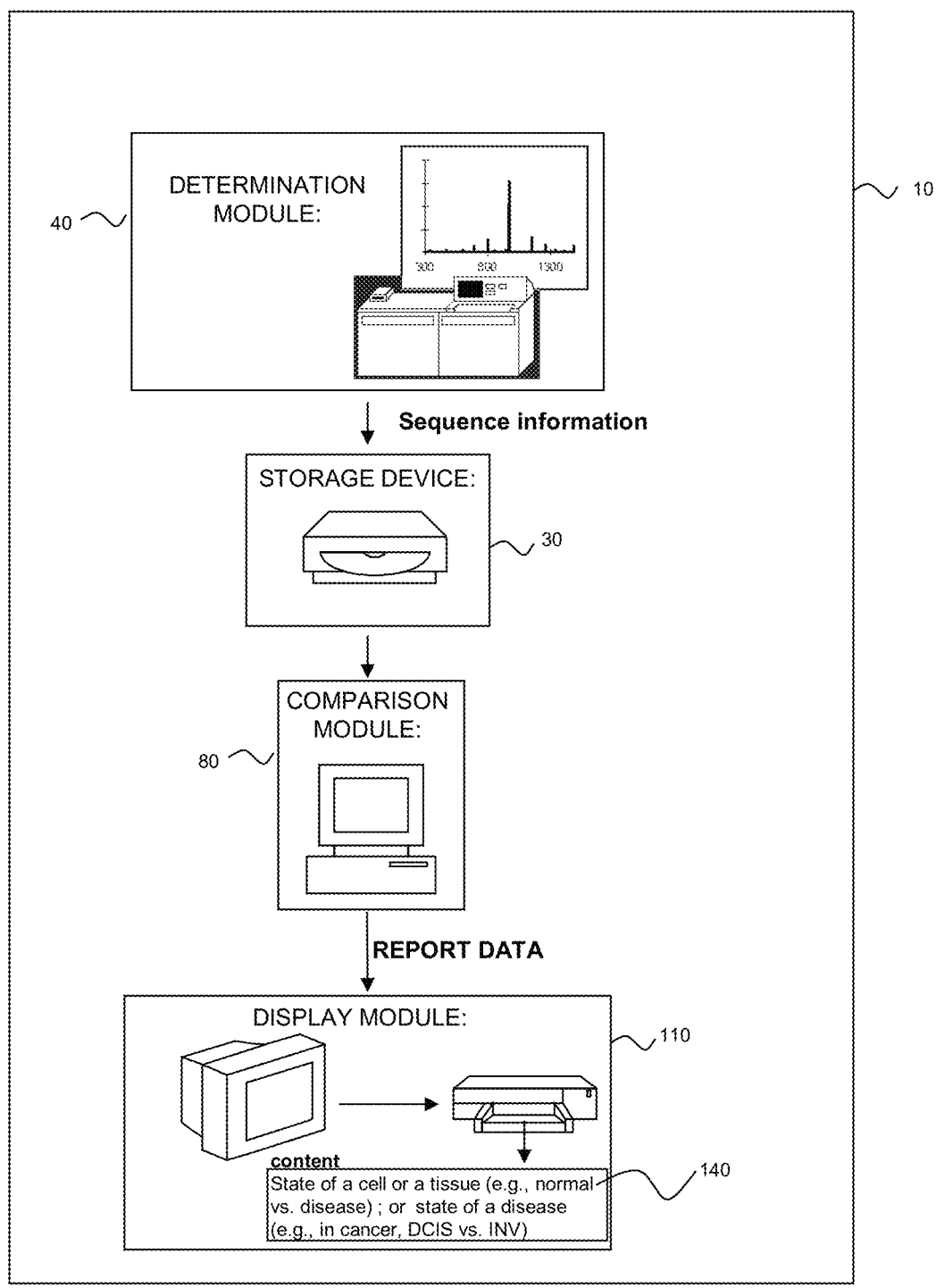
Figure 2:
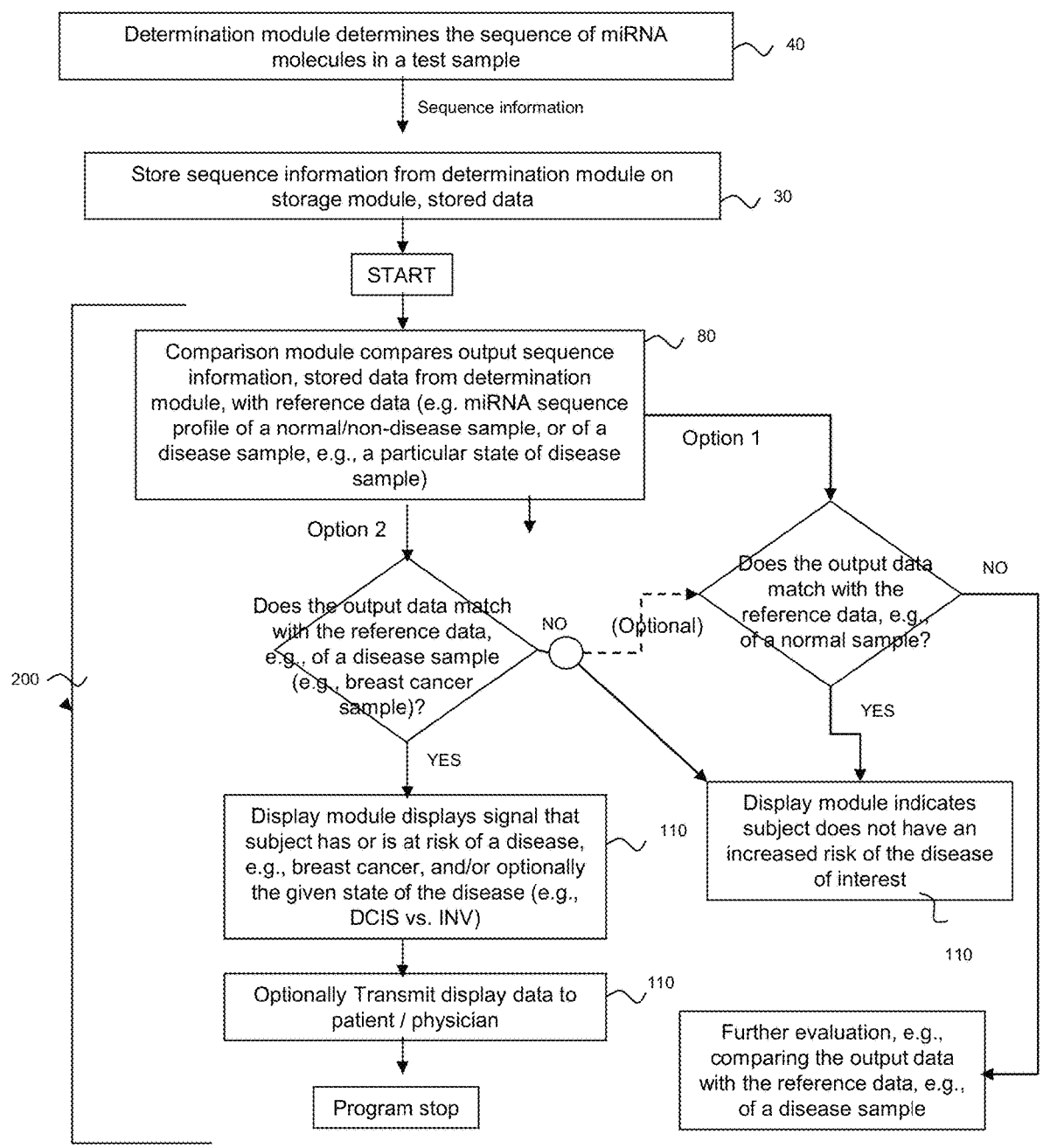
FIG. 2 is a block diagram showing exemplary instructions on a computer readable medium for determining a state of a cell or a tissue and/or for diagnosing or prognosing a disease or disorder, or a stage of a disease or disorder in a subject, based on expression level of one or more novel miRNAs described herein.

FIG. 1B depicts a device or a system (e.g., a computer system) for obtaining data from at least one biological sample obtained from one or more subjects. Accordingly, a system for analyzing a biological sample is provided herein. The system can be used to diagnose or prognose a condition or state of a condition in a subject. The system 10 comprises:

(a) a determination module 40 configured to receive a biological sample and to determine sequence information, wherein the sequence information comprises a sequence of at least one or more miRNA molecules from the biological sample; (b) a storage device 30 configured to store sequence information from the determination module 40; (c) a comparison module 80 adapted to compare the sequence information stored on the storage device with reference data, and to provide a comparison result, wherein the comparison result identifies the presence or absence or level(s) of the miRNA molecule(s), wherein a discrepancy in an expression level of the miRNA molecule(s) from the reference data is indicative of the biological sample having an increased likelihood of having or being at a cellular or tissue state different from a state represented by the reference data; and (d) a display module 110 for displaying a content based in part on the comparison result for the user, wherein the content is a signal indicative of a subject having, or being at risk of developing, or being at a given stage of a disease or disorder, or a signal indicative of lacking a disease or disorder.

A tangible and non-transitory (e.g., no transitory forms of signal transmission) computer readable medium 200 having computer readable instructions recorded thereon to define software modules for implementing a method on a computer is also provided herein. In some embodiments, the software modules can include a comparison module and a display module for implementing a method on a computer. In some embodiments, the computer-readable medium 200 stores one or more programs for determining a given state of a condition of a cell or tissue (a biological sample). In some embodiments, the computer-readable medium 200 stores one or more programs for determining a condition or state of a condition of a subject. The one or more programs for execution by one or more processors of a computer system comprises (a) instructions for comparing the measured miRNA data (from a biological sample) stored on a storage device with reference data to provide a comparison result, wherein the comparison result the comparison result identifies the presence or absence (or difference in levels) of the miRNA molecule(s), wherein a discrepancy in level(s) of the miRNA molecule(s) from the reference data is indicative of the biological sample having an increased likelihood of having or being at a cellular or tissue state different from a state represented by the reference data; and (b) instructions for displaying a content based in part on the comparison result for the user, wherein the content is a signal indicative of a subject having, or being at risk of developing, or being at a given stage of a disease or disorder, or a signal indicative of lacking a disease or disorder.

Embodiments provided herein have been described through functional modules, which are defined by computer executable instructions recorded on computer readable media and which cause a computer to perform method steps when executed. The modules have been segregated by function for the sake of clarity. However, it should be understood that the modules need not correspond to discrete blocks of code and the described functions can be carried out by the execution of various code portions stored on various media and executed at various times. Furthermore, it should be appreciated that the modules may perform other functions, thus the modules are not limited to having any particular functions or set of functions.

Computing devices typically include a variety of media, which can include computer-readable storage media and/or communications media, in which these two terms are used herein differently from one another as follows. Computer-readable storage media or computer readable media (e.g., 200) can be any available tangible media (e.g., tangible storage media) that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM (random access memory), ROM (read only memory), EEPROM (erasable programmable read only memory), flash memory or other memory technology, CD-ROM (compact disc read only memory), DVD (digital versatile disk) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In some embodiments, the computer readable storage media 200 can include the "cloud" system, in which a user can store data on a remote server, and later access the data or perform further analysis of the data from the remote server.

Computer-readable data embodied on one or more computer-readable media, or computer readable medium 200, can define instructions, for example, as part of one or more programs, that, as a result of being executed by a computer, instruct the computer to perform one or more of the functions described herein (e.g., in relation to system 10, or computer readable medium 200), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 10, or computer readable medium 200 described herein, can be distributed across one or more of such components, and may be in transition there between.

The computer-readable media can be transportable such that the instructions stored thereon can be loaded onto any computer resource to implement the aspects provided herein. In addition, it should be appreciated that the instructions stored on the computer readable media, or computer-readable medium 200, described above, are not limited to instructions embodied as part of an application program running on a host computer. Rather, the instructions can be embodied as any type of computer code (e.g., software or microcode) that can be employed to program a computer to implement various aspects described herein. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Baxevanis Bioinformatics: A Practical Guide for Analysis of Gene and Proteins (Wiley & Sons, Inc., 2nd ed., 2001).

The functional modules of certain embodiments provided herein include a determination module, a storage device, a comparison module and a display module. The functional modules can be executed on one, or multiple, computers, or by using one, or multiple, computer networks. The determination module 40 has computer executable instructions to provide sequence information in computer readable form. As used herein, "sequence information" refers to any nucleotide sequence, including but not limited to full-length sequence, partial sequence, or mutated sequences. Moreover, information "related to" the sequence information includes detection of the presence or absence of a miRNA sequence, determination of the expression level of a miRNA sequence in a biological sample, and the like. In some embodiments, the sequence information can include sequences of any miRNA molecules present in a biological sample. In some embodiments, the sequence information can include sequences of miRNA molecules. In other embodiments, the sequence information can include sequences of miRNA molecules described herein, miRNA molecules, piRNA molecules, mRNA molecules, or any combinations thereof. In some embodiments, the sequence information can include sequences of miRNA molecules present in a biological sample, and a genomic sequence of one or more protein-coding genes.

As an example, determination modules 40 for determining sequence information can include known systems for automated sequence analysis, including but not limited to, Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALF™ DNA Sequencer and Pharmacia ALFexpress™ (available from Amersham Biosciences UK Limited, Little Chalfont, Buckinghamshire, England); any next- or higher-generation sequencing instruments such as, but not limited to, GF GLX Titanium, G S Junior (available from 454 Life Sciences, part of Roche Diagnostic Corporation, Branford, Conn.); HiSeq 2000, Genome Analyzer IIX, Genome Analyzer IIE, iScan SQ (available from Illumina, San Diego, Calif.); ABI SOLiD™ system (e.g., SOLiD4 platform available from Life Technologies, Applied Biosystems, Carlsbad, Calif.); HeliScope™ Single Molecule Sequencer (available from Helicos Biosciences Corporation, Cambridge, Mass.); and PACBIO RS (available from Pacific Biosciences, Menlo Park, Calif.).

Alternative methods for determining sequence information, i.e., determination modules 40, include systems for nucleic acid analysis. For example, mass spectrometry systems including Matrix Assisted Laser Desorption Ionization-Time of Flight (MALDI-TOF) systems and SELDI-TOF-MS ProteinChip array profiling systems; systems for analyzing gene expression data (see, for example, published U.S. Patent Application, Pub. No. U.S. 2003/0194711); systems for array based expression analysis: e.g., HT array systems and cartridge array systems such as GeneChip® AutoLoader, Complete GeneChip® Instrument System, GeneChip® Fluidics Station 450, GeneChip® Hybridization Oven 645, GeneChip® QC Toolbox Software Kit, GeneChip® Scanner 3000 7G plus Targeted Genotyping System, GeneChip® Scanner 3000 7G Whole-Genome Association System, GeneTitan™ Instrument, and GeneChip® Array Station (each available from Affymetrix, Santa Clara, Calif.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence in situ hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACS-Vantage SE, (available from Becton Dickinson, Franklin Lakes, N.J.); and radio isotope analyzers (e.g. scintillation counters).

The sequence information determined in the determination module can be read by the storage device 30. As used herein the "storage device" 30 is intended to include any suitable computing or processing apparatus or other device configured or adapted for storing data or information. Examples of electronic apparatus suitable for use with various embodiments described herein can include stand-alone computing apparatus, data telecommunications networks, including local area networks (LAN), wide area networks (WAN), Internet, Intranet, and Extranet, and local and distributed computer processing systems. Storage devices 30 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device 30 is adapted or configured for having recorded thereon sequence information or expression level information. Such information may be provided in digital form that can be transmitted and read electronically, e.g., via the Internet, on diskette, via USB (universal serial bus) or via any other suitable mode of communication.

As used herein, "expression level information" refers to any nucleotide expression level information, including but not limited to full-length nucleotide sequences, partial nucleotide sequences, or mutated sequences. Moreover, information "related to" the expression level information includes detection of the presence or absence of a sequence (e.g., presence or absence of a nucleotide sequence), determination of the concentration of a sequence in the sample (e.g., nucleotide (RNA or DNA) expression levels), and the like.

As used herein, "stored" refers to a process for encoding information on the storage device 30. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information or expression level information in computer-readable form, one can use the sequence information or expression level information in readable form in the comparison module 80 to compare a specific sequence or expression profile with the reference data within the storage device 30. In some embodiments, the comparison module 80 can also include bioinformatics analysis tools for next-generation sequencing data (e.g., short-read sequence data). Examples of bioinformatics analysis tools for next-generation sequencing (NGS) data can include any commercial NGS analysis packages that are compatible with the sequenced reads obtained from the NGS instrument. The NGS analysis package can include a sequence mapping tool for mapping sequences (e.g., short-read sequences) to a reference genome, sequence assembly tool for de novo assembly of overlapping reads to form contiguous nucleic acid sequence, a genome browser, and any combinations thereof. Examples of short-read alignment tools for mapping miRNA sequences to a reference genome can include, without limitations, Bfast, BioScope, Bowtie, Burrows-Wheeler Aligner (BWA), CLC bio, CloudBurst, Eland/Eland2, Exonerate, GenomeMapper, GnuMap, Karma, MAQ, MOM, Mosaik, MrFAST/MrsFAST, NovoAlign, PASS, PerM, RazerS, RMAP, SSAHA2, Segemehl, SeqMap, SHRiMP, Slider/Sliderll, SOAP/SOAP2, Srprism, Stampy, vmatch, ZOOM and any art-recognized alignment tools that can be used to align short-read sequences to a reference genome. In one embodiment, Burrows-Wheeler Aligner (BWA) can be used to map miRNA sequences to a reference genome (e.g., a human genome). Examples of sequence assembly tools include, but are not limited to, ABySS, ALLPATHS, Edena, Euler-SR, SHARCGS, SHARP, SSAKE, Velvet and any other art-recognized assembly tools. Different genome browsers can be used to visualize genomic maps, e.g., generated after sequence alignment to a reference genome.

In one embodiment, the comparison module 80 uses sequence information alignment programs such as BLAST (Basic Local Alignment Search Tool) or FAST (using the Smith-Waterman algorithm) that may be employed individually or in combination. These algorithms determine the alignment between similar regions of sequences and a percent identity between sequences.

In some embodiments, the comparison module can include a pattern recognition pattern that can be pre-trained with different reference data sets such as data sets comprising profiles of miRNA sequences obtained from different state of a tissue (e.g., normal data set vs. diseased or abnormal data set; or data sets corresponding to different stages of a disease or disorder and a normal data set).

Accordingly, in some embodiments, the comparison module can compare a profile of miRNA sequences of a biological sample determined by the determination module 40 to reference data stored on the storage device 30, and classify the biological sample into a specific state (e.g., normal, diseased or abnormal, and/or a given stage of a disease or disorder). For example, comparison programs can be used to compare an expression level of a miRNA sequence in a biological sample to a reference data expression level (e.g., sequence data from a control/reference sample described herein) and/or profiles of miRNA sequences in a biological sample to reference data expression profiles (e.g., sequence data from a control/reference sample described herein). The comparison made in computer-readable form provides a computer readable comparison result, which can be processed by a variety of means. Content 140 based on the comparison result can be retrieved from the comparison module 80 to indicate a given state of a cell or a tissue, and/or whether a subject has, or is at risk of developing of a disease or disorder, or a given state of the disease or disorder.

In one embodiment, the reference data stored in the storage device 30 to be read by the comparison module 80 is sequence information data obtained from a reference sample described herein or a control biological sample of the same type as the biological sample to be tested. Alternatively, the reference data are a database, e.g., a collection of sequence information data obtained from a plurality of reference samples described herein and control biological samples of the same type as the biological sample to be tested. For example, reference data can include profiles of miRNA sequences that are indicative of a given state of a cell or tissue and/or a disease or disorder of interest or a given state of the disease or disorder. In one embodiment, the reference data can include sequence information of miRNA sequences and/or profiles of miRNA sequences that are indicative of a disease or disorder of interest, e.g., a disease or disorder afflicting a tissue, and or different stages of a disease or disorder of interest, e.g., different stages of cancer. By way of example only, reference data stored in a system for diagnosing and/or prognosing breast cancer can include, but not limited to, (a) profile(s) of miRNA sequences obtained from one or a group of normal subjects, (b) profile(s) of miRNA sequences obtained from one or a group of subjects having a given stage of breast cancer (e.g., DCIS, lobular carcinoma in situ, INV, etc.); (c) profile(s) of miRNA obtained from a normal tissue of the test subject, profile(s) of miRNA sequences obtained from a diseased or abnormal tissue of the test subject that was previously diagnosed, and any combinations thereof.

In one embodiment, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information can be stored in a relational database that may be employed to determine homologies between the reference data or genes or proteins within and among genomes.

The "comparison module" 80 can use a variety of available software programs and formats for the comparison operative to compare sequence information determined in the determination module 40 to reference data. In one embodiment, the comparison module 80 is configured to use pattern recognition techniques to compare sequence information from one or more entries to one or more reference data patterns. The comparison module 80 can be configured using existing commercially-available or freely-available software for comparing patterns, and may be optimized for particular data comparisons that are conducted. The comparison module 80 provides computer readable information related to the sequence information that can include, for example, detection of the presence or absence of a miRNA sequence; determination of the concentration of a miRNA sequence in the sample, or determination of an expression profile.

The comparison module 80, or any other module described herein, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file, which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment provided herein, users can directly access data (via Hypertext links for example) residing on Internet databases using a HTML interface provided by Web browsers and Web servers. In one embodiment, users can access data residing on Cloud storage.

Various algorithms or software packages are available which are useful for comparing and analyzing sequence information and/or expression data determined in the determination module 40. For example, various software packages for next-generation sequencing (NGS) analysis are available in the commercial and/or public domains. Exemplary software packages for NGS analysis can include, without limitations, sequence alignment tools as discussed above; de novo alignment and/or assembly tools as discussed above; integrated solutions, such as CLCbio Genomics Workbench, Galaxy, Genomatix, JMP Genomics, NExt-GENE, SeqMan Genome Analyzer, SHORE, SlimSearch; genome browser (including alignment viewer and/or assembly database) such as EagleView, LookSeq, MapView, Sequence Assembly Manager, STADEN, XMatchView; software packages for transciptomics such as ERANGE, S-Mo.R-Se, MapNext, QPalma, RSAT, TopHat; or any combinations thereof.

In some embodiments, when the sequence information is determined by microarray-based methods, various software packages for microarray analysis can be used, e.g., but not limited to, GeneChip® Sequence Analysis Software (GSEQ), GeneChip® Targeted Genotyping Analysis Software (GTGS) and Expression Console™ Software. Accordingly, depending on methods used to produce sequence information in the determination module 40, various sequence analysis software can be used.

In one embodiment described herein, pattern comparison software is used to compare an expression profile of miRNA sequences to a reference data for determining a given state of a cell or tissue, or whether the expression profiled obtained from a test subject is indicative of a disease or disorder, or a given state of a disease or disorder.

The comparison module 80 provides computer readable comparison result that can be processed in computer readable form by predefined criteria, or criteria defined by a user, to provide a content based in part on the comparison result that may be stored and output as requested by a user using a display module 110. The display module 110 enables display of a content 140 based in part on the comparison result for the user, wherein the content 140 is a signal indicative of a subject having, or being at risk of developing or being at a given stage of a disease or disorder, or a signal indicative of the subject having no risk of the disease or disorder. Such signal, can be for example, a display of content 140 indicative of the presence or absence of increased risk for a disease or disorder, or a given state of a disease or disorder on a computer monitor, a printed page of content 140 indicating the presence or absence of increased risk for a given state of a disease or disorder from a printer, or a light or sound indicative of the presence or absence of increased risk for a given state of a disease or disorder.

The content 140 based on the comparison result can include an expression profile of one or more miRNA sequences determined from the test subject. In one embodiment, the content 140 based on the comparison result can include a comparison of the miRNA expression profile between the test subject and one or more reference samples described herein. In one embodiment, the content 140 based on the comparison result is merely a signal indicative of the presence or absence of an increased risk of a given state of a disease or disorder.

In one embodiment provided herein, the content 140 based on the comparison result is displayed a on a computer monitor. In one embodiment, the content 140 based on the comparison result is displayed through printable media. The display module 110 can be any suitable device configured to receive from a computer and display computer readable information to a user. Non-limiting examples include, for example, general-purpose computers such as those based on INTEL® processor, QUALCOMM® processors, Sun Microsystems processors, Hewlett-Packard processors, any of a variety of processors available from Advanced Micro Devices (AMD) of Sunnyvale, Calif., or any other type of processors (including mobile processors), visual display devices such as tablet computers, flat panel displays, cathode ray tubes and the like, as well as computer printers of various types.

In one embodiment, a World Wide Web browser is used for providing a user interface for display of the content 140 based on the comparison result. It should be understood that other modules described herein can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests formulated with the user's Web browser are transmitted to a Web application which formats them to produce a query that can be employed to extract the pertinent information related to the sequence information, e.g., but not limited to, display of nucleotide (RNA or DNA) expression levels; or display of information based thereon.

In one embodiment, the sequence information of the reference sample data is also displayed.

In one embodiment, the display module 110 displays the comparison result based on sequence information and whether the comparison result is indicative of a disease or disorder, or a given stage of a disease or disorder. For example, in the case of diagnosis of breast cancer, the display module 110 can display the comparison result based on determined sequence information and whether the comparison results is indicative of breast cancer, or a particular stage of breast cancer (e.g., duct carcinoma in situ, lobular carcinoma in situ, invasive, etc.).

In one embodiment, the content 140 based on the comparison result that is displayed is a signal (e.g. positive or negative signal) indicative of the presence or absence of an increased risk for a disease or disorder, or a given stage of the disease or disorder, thus only a positive or negative indication may be displayed.

In any embodiments, the comparison module can be executed by a computer implemented software as discussed earlier. In such embodiments, a result from the comparison module can be displayed on an electronic display. The result can be displayed by graphs, numbers, characters or words. In additional embodiments, the results from the comparison module can be transmitted from one location to at least one other location. For example, the comparison results can be transmitted via any electronic media, e.g., internet, fax, phone, a "cloud" system, and any combinations thereof. Using the "cloud" system, users can store and access personal files and data or perform further analysis on a remote server rather than physically carrying around a storage medium such as a DVD or thumb drive.

Each of the above identified modules or programs corresponds to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments, memory may store a subset of the modules and data structures identified above. Furthermore, memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

Provided herein therefore relates to systems 10 (and computer readable medium 200 for causing computer systems) to perform methods for determining a given stage of a cell or a tissue, and/or whether a subject has, or is at risk of developing, or is at a given stage of a disease, e.g., cancer, or disorder, based on expression profiles of miRNA sequences.

System 10, and computer readable medium 200, are merely an illustrative embodiments provided herein for performing methods of determining whether an individual has a specific disease or disorder or a pre-disposition, for a specific disease or disorder based on expression profiles or sequence information, and are not intended to limit the scope described herein. Variations of system 10, and computer readable medium 200, are possible and are intended to fall within the scope described herein.

The modules of the machine, or used in the computer readable medium, may assume numerous configurations. For example, function may be provided on a single machine or distributed over multiple machines.

Reference Sample(s) or Reference Data

As used herein, a reference sample can include a normal or negative control, alternatively a disease (or disorder) or positive control, against which biological samples can be compared. Therefore, it can be determined whether the biological sample to be evaluated for a specific disease or disorder, or a stage of a disease or disorder, has measurable difference or substantially no difference, as compared to a reference sample. A normal or healthy sample or tissue refers to a sample or tissue that does not have a disease or disorder to be evaluated.

The reference sample can be obtained from the patient to be diagnosed or prognosed, or from a different subject, who is preferably of same age and/or race.

In one embodiment, the reference sample can be obtained from the same patient at the same time that the biological sample is taken. In one embodiment, the reference sample can be taken from a normal and/or healthy tissue of the same patient. In one embodiment, the reference sample can be taken from a normal and/or healthy tissue, for example tissue taken adjacent to the cancer, such as within 1 or 2 cm diameter from the leading front of the tumor. Alternatively, the reference sample can be taken from an equivalent position in the subject's body, for example in the case of breast cancer, a reference sample can be taken from any area of the breast which is not cancerous. In another embodiment, the reference sample can be a disease or abnormal sample taken previously from the same patient, against which a new biological sample can be compared to provide an evaluation of the therapeutic treatment efficacy.

In one embodiment, the reference sample can be a sample taken previously, e.g., a sample of the same or a different cancer/tumor, the comparison of which can, for example, provide characterization of the source of the new tumor, and/or progression or development of an existing cancer, such as before, during or after therapeutic treatment. For example, the reference sample can be obtained from a different patient, e.g., it can be a control sample, or a collection of control samples, representing different stages or different types of diseases or disorders. In one embodiment, the reference sample can be a control sample or a collection of control samples, representing different stages of a specific cancer (e.g., cancer staging samples) or different types of cancer, for example those listed herein (i.e., cancer reference samples). Comparison of the biological sample data with data obtained from such cancer staging or cancer reference samples can, for example, allow for the characterization of the assessed cancer to a specific stage and/or type of cancer.

Depending on various applications, the reference sample can comprise a sample derived from a tissue type that is same as or different from the tissue type of a biological sample. In some embodiments wherein the tissue origin of a biological sample is unknown, the level(s) and/or profile of the miRNA present in the biological sample can be compared to a set of reference samples of different tissue origins in order to identify the tissue origin of the biological sample. In some embodiments where the tissue origin of a biological sample is known or believed to be known (e.g., while a tissue biopsy is known to be collected from a lung tissue, the sample can comprise cells originated from breast due to metastasis), the reference sample(s) can comprise a sample of the same tissue type as the biological sample, and/or a sample of a different tissue type from the biological sample. By comparison between the biological sample and reference sample(s), tissue origin of the biological sample can be validated and/or identified.

As used herein, the term "reference data" refers to data obtained from a reference sample as described herein, or a collection of reference samples as described herein.

Biological Sample of a Subject and Preparation Thereof

A "biological sample" subjected to analysis using the methods, assays and systems described herein generally refers to a sample taken or isolated from a subject or a biological organism. In some embodiments, the biological sample contains one or more cells, e.g., tissue culture mammalian cells, cell lysate, a tissue sample from a subject, a homogenate of a tissue sample from a subject or a fluid sample from a subject. Exemplary biological samples include, but are not limited to, blood (including whole blood, serum, cord blood, and plasma), sputum, urine, spinal fluid, pleural fluid, nipple aspirates, lymph fluid, the external sections of the skin, respiratory, intestinal, and genitourinary tracts, tears, saliva, milk, feces, sperm, cells or cell cultures, serum, leukocyte fractions, smears, tissue samples of all kinds, embryos, etc. The term also includes both a mixture of the above-mentioned samples such as whole human blood containing a cell. The term "biological sample" also includes untreated or pretreated (or pre-processed) biological samples.

A "biological sample" can contain at least one cell or a plurality of cells from a subject. In some embodiments, the biological sample can contain one or more somatic cells from a subject. In other embodiments, the biological sample can contain one or more germ cells from a subject. In other embodiments, the biological sample can contain one or more stem cells from a subject.

In one embodiment, the biological sample can contain one or more cells from a subject's biological fluid sample. Examples of biological fluids include, but are not limited to, saliva, bone marrow, blood, serum, plasma, urine, sputum, cerebrospinal fluid, an aspirate, tears, and any combinations thereof.

For example, the biological sample can contain one or more circulating tumor cells from a subject's blood (including whole blood, serum, cord blood, and plasma). In some embodiments, the biological sample can contain at least one type of blood cells (e.g., red blood cells, white blood cells, platelets).

In one embodiment, the biological sample can contain one or more cells derived from any tissue of a subject, e.g., a tissue suspected of being at risk of, or being afflicted with a given stage of a disease or a disorder. Non-limiting examples of a tissue can include, but are not limited to, breast, pancreas, blood, prostate, colon, lung, skin, brain, ovary, kidney, oral cavity, throat, liver, and any combinations thereof. In some embodiments, the tissue can be obtained from a resection, biopsy, or core needle biopsy. In addition, fine needle aspirate samples can be used. Samples can be either paraffin-embedded or frozen tissue.

The biological sample can be obtained by removing a sample of cells from a subject, but can also be accomplished by using previously isolated cells (e.g. isolated by another person). In addition, the biological sample can be freshly collected or a previously collected sample.

In some embodiments, the biological sample is a frozen biological sample, e.g., a frozen tissue or fluid sample such as urine, blood, serum or plasma. The frozen sample can be thawed before employing methods, assays and systems described herein. After thawing, a frozen sample can be centrifuged before being subjected to methods, assays and systems described herein.

In some embodiments, a biological sample can be a nucleic acid product derived from a tissue (e.g., fresh/frozen and paraffin-embedded) or a fluid sample (e.g., blood) of a subject or cultured cells. The nucleic acid product can include DNA, RNA, mRNA, miRNA, piRNA, siRNA, snRNA, miRNA molecules described herein, and any combinations thereof. In some embodiments, the nucleic acid product can comprise one or more miRNA molecules described herein.

In some embodiments, a biological sample can include RNA isolated from a tissue (e.g., fresh or frozen or paraffin-embedded) or a fluid sample (e.g., blood) of a subject or cultured cells. Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In one embodiment, a biological sample can include RNA isolated from a tissue (e.g., fresh or frozen or paraffin-embedded) by any known methods in the art. When the RNA sample is deemed to be of good quality (according to one of skill in the art), the sample can be subjected to further treatment, following recommended instructions as provided by various commercial RNA preparation kits available for RNA sequencing (e.g., the kits from Life Technologies). Depending on the length of RNA molecules of interest, in some embodiments, the RNA sample can be subjected to miRNA sequencing. In other embodiments, the RNA sample can be subjected to long RNA sequencing.

In some embodiments, a biological sample can be an enriched RNA fraction derived from a tissue (e.g., fresh/frozen and paraffin-embedded) or a fluid sample (e.g., blood) of a subject or cultured cells, e.g., an RNA fraction enriched for non-coding RNAs. This can be achieved, for example, by removing mRNAs by use of affinity purification, e.g., using an oligodT column or any other art-recognized methods such as using commercial small RNA isolation kits.

In some embodiments, a biological sample can be a nucleic acid product or an RNA fraction amplified after polymerase chain reaction (PCR) or after reverse transcription-PCR. The nucleic acid product can include DNA (e.g., cDNA), RNA and mRNA and can be isolated from a particular biological sample using any of a number of procedures, which are well known in the art, the particular isolation procedure chosen being appropriate for the particular biological sample. Methods of isolating and analyzing nucleic acid variants as described above are well known to one skilled in the art and can be found, for example in the Molecular Cloning: A Laboratory Manual, 3rd Ed., Sambrook and Russel, Cold Spring Harbor Laboratory Press, 2001.

In some embodiments, the biological sample can be treated with a chemical and/or biological reagent. Chemical and/or biological reagents can be employed to protect and/or maintain the stability of the sample, including biomolecules (e.g., nucleic acids) therein, during processing. One exemplary reagent is an RNase inhibitor or RNA stabilizer, which is generally used to protect or maintain the stability of RNA during processing. In addition, or alternatively, chemical and/or biological reagents can be employed to release nucleic acid (e.g., miRNA molecules) from the biological sample.

The skilled artisan is well aware of methods and processes appropriate for pre-processing of biological samples required for determination of nucleic acid including miRNA molecules as described herein.

In some embodiments, a biological sample used for determining the level of one or more miRNAs can be a sample containing circulating miRNAs, e.g., extracellular miRNAs. Extracellular miRNAs freely circulate in a wide range of biological material, including bodily fluids, such as fluids from the circulatory system, e.g., a blood sample or a lymph sample, or from another bodily fluid such as cerebrospinal fluid (CSF), urine or saliva. Accordingly, in some embodiments, the biological sample used for determining the level of one or more miRNAs can be a bodily fluid, for example, blood, fractions thereof, serum, plasma, urine, saliva, tears, sweat, semen, vaginal secretions, lymph, bronchial secretions, CSF, etc. In some embodiments, the sample is a sample that is obtained non-invasively.

Circulating miRNAs include miRNAs in cells (cellular miRNA), extracellular miRNAs in microvesicles (microvesicle-associated miRNA), and extracellular miRNAs that are not associated with cells or microvesicles (extracellular, non-vesicular miRNA).

The biological sample is generally obtained from a subject who has or is suspected of having a disease or disorder, e.g., a condition afflicting a tissue, or who is suspected of having a risk of developing a disease or disorder, e.g., a condition afflicting a tissue. In some embodiments, the biological sample can be obtained from a subject who has or is suspected of having cancer, or who is suspected of having a risk of developing cancer. By way of example only, in one embodiment, the biological sample can be obtained from a subject who has or is suspected of having breast cancer, or who is suspected of having a risk of breast cancer. In another embodiment, the biological sample can be obtained from a subject who has or is suspected of having pancreatic cancer, or who is suspected of having a risk of pancreatic cancer.

In some embodiments, the biological sample can be obtained from a subject who is being treated for the disease or disorder, e.g., but not limited to, cancer such as breast cancer or pancreatic cancer. In other embodiments, the biological sample can be obtained from a subject whose previously-treated disease or disorder, e.g., but not limited to, cancer such as breast cancer or pancreatic cancer, is in remission. In other embodiments, the biological sample can be obtained from a subject who has a recurrence of a previously-treated disease or disorder, e.g., but not limited to, cancer such as breast cancer or pancreatic cancer.

As used herein, a "subject" can mean a human or an animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, and avian species, e.g., chicken, emu, ostrich. A patient or a subject includes any subset of the foregoing, e.g., all of the above, or includes one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. The term "patient" and "subject" does not denote a particular age. Thus, any mammalian subjects from adult to newborn subjects, as well as fetuses, are intended to be covered.

In one embodiment, the subject or patient is a mammal. The mammal can be a human, non-human primate, mouse, rat, dog, cat, horse, or cow, but are not limited to these examples. In one embodiment, the subject is a human being. In another embodiment, the subject can be a domesticated animal and/or pet. In some embodiments, the subject is a human.

Pharmaceutical Compositions and Administration Methods

In some embodiments, a subject in need thereof, e.g., whose level(s) of one or more miRNAs (as selected from SEQ ID NO: 1 to SEQ ID NO: 47,972 in Tables 1-3) in a biological sample are determined to be over-expressed or under-expressed, can be administered with a miRNA-related therapeutic. In some embodiments, the miRNA-related therapeutic is an antagonist against a target miRNA that inhibit the function of the target miRNA. As used herein, the term "antagonist" is used in the broadest sense, and includes any molecule that partially or fully blocks, inhibits, or neutralizes a biological activity of a microRNA disclosed herein. Suitable antagonist molecules specifically include, but are not limited to antisense oligonucleotides, small organic molecules, aptamers, etc. Methods for identifying antagonists of a microRNA can comprise contacting a target microRNA with a candidate antagonist molecule and measuring a detectable change in one or more biological activities normally associated with the microRNA. Accordingly, one aspect provides a pharmaceutical composition comprising an antagonist against one or more miRNAs selected from SEQ ID NO: 1 to SEQ ID NO: 47,972 in Tables 1-3.

In some embodiments, the miRNA-related therapeutic is a mimic of a target miRNA that induces or restores the function of the target miRNA. As used herein, the term "mimic" refers to a molecule (e.g., an oligonucleotide) that is capable of mimicking the activity of a miRNA molecule. In some embodiments, a miRNA mimic is a molecule (e.g., an oligonucleotide) that is capable of mimicking at least about 30% or above (including, e.g., at least about 40%, at least about 50%, at least about 60%, at least about 70%, at least about 80%, at least about 90%, at least about 95%, at least about 97%, at least about 99%, or up to 100%) of the activity of a miRNA molecule. Accordingly, a pharmaceutical composition comprising a mimic of one or more miRNAs selected from SEQ ID NO: 1 to SEQ ID NO: 47,972 in Tables 1-3 is also provided herein. In some embodiments, the pharmaceutical composition can comprise engineered transcripts that can "sponge" various combinations of the miRNAs described herein, or any combinations thereof.

In some embodiments, the miRNA mimics can be a double-stranded and/or blunt-ended oligonucleotide, which means the oligonucleotide is double-stranded throughout the molecule and/or blunt-ended on both ends. In some embodiments, the miRNA mimics can be a single-strand oligonucleotide. In some embodiments, the single-stranded oligonucleotide can comprise a hairpin structure. Methods of making miRNA mimics are known in the art, e.g., as described in the International Patent Publication No. WO 2012/106586, which is incorporated herein by reference.

In some embodiments where the miRNA antagonists or miRNA mimics comprise an oligonucleotide, the oligonucleotide can be modified. For example, in some embodiments, the backbone of the oligonucleotides described herein can be modified, e.g., to stabilize the oligonucleotides for in vivo delivery. For example, the modified backbone of the oligonucleotides can comprise morpholino subunits, phosphorothioate subunits, locked nucleic acid (LNA), peptide nucleic acid (PNC), hexitol nucleic acid (HNA), or any combinations thereof. See, e.g., Singh Y. et al. Chem. Soc. Rev., 2010, 39, 2054-2070 for additional information about various examples of oligonucleotide backbones.

Additionally or alternatively, the oligonucleotides can be modified for a desired property, e.g., improved cell delivery, cell-targeting delivery, and/or enhanced stability. By way of example only, the oligonucleotides can be modified by conjugating it to a delivery-targeting moiety. As used herein, the term "delivery-targeting moiety" refers to a moiety that can facilitate binding of an oligonucleotide to the outer surface of a cell and/or uptake or endocytosis of the oligonucleotide into the cell. Any art-recognized delivery-targeting moiety, e.g., but not limited to, antibodies, peptides, proteins, aptamers, dendrimers, and molecules, can be used. In some embodiments, the delivery-targeting moiety is a cell surface receptor ligand. As used herein, a "cell surface receptor ligand" refers to a molecule that can bind to the outer surface of a cell. Exemplary, cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug.

Cell surface receptor ligands include, but are not limited to, cytokines, growth factors, hormones, antibodies, and angiogenic factors.

In some embodiments, the delivery-targeting moiety can also refer to a molecule that binds to or interacts with a target molecule. Typically the nature of the interaction or binding is noncovalent, e.g., by hydrogen, electrostatic, or van der Waals interactions, however, binding may also be covalent.

In some embodiments, the delivery-targeting moiety can include an endosomolytic ligand. As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), Golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

In some embodiments, the delivery-targeting moiety can include a PK modulating ligand and/or PK modulator. As used herein, the terms "PK modulating ligand" and "PK modulator" refers to molecules which can modulate the pharmacokinetics (PK) of the composition described herein. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2, 4, 6-triiodophenol and flufenamic acid).

In some embodiments, the oligonucleotides described herein can be conjugated to a molecule in any methods known in the art. By way of example only, the oligonucleotides can be conjugated in the following methods: (i) peptide-oligonucleotide conjugates (POCs); (ii) carbohydrate-oligonucleotide conjugates (COCs); (iii) lipophilic oligonucleotide conjugates (LOCs); (iv) metal complex-oligonucleotide conjugates (MCOCs); (v) nanoparticle-oligonucleotide conjugates (NOCs); (vi) these can include bifunctional oligonucleotides, which have one domain that hybridizes to target RNA and a second domain that attracts activator proteins; (vii) peptide-conjugated oligonucleotides, which can be fused to a peptide domain consisting of cationic and hydrophobic residues that facilitates cell entry; (viii) cell penetrating peptide-oligonucleotide; and (ix) any combinations thereof. See, e.g., Singh Y. et al. Chem. Soc. Rev., 2010, 39, 2054-2070 for additional information about some conjugation methods of oligonucleotides to a molecule.

In some embodiments, the oligonucleotides can be conjugated to a carrier molecule. In some embodiments, a carrier molecule can be a natural or synthetic polymer. For example, a carrier molecule can be cholesterol or an RNA aptamer and the like. A carrier molecule can be conjugated to the oligonucleotides at the 5' and/or 3' end, or at the 5' and/or 3' end of one of the strands, or at an internal nucleotide position.

In some embodiments, one or two strands of the oligonucleotides can be encoded by or delivered with a viral vector. A variety of viral vectors know in the art can be modified to express or carry an oligonucleotide into a target cell, for example herpes simplex virus-1 or lentiviral vectors have been used to enhance the delivery of siRNA.

In some embodiments, an oligonucleotide can be associated with a non-viral vector. Non-viral vectors can be coupled to targeting and delivery enhancing moieties, such as antibodies, various polymers (e.g., PEG), fusogenic peptides, linkers, cell penetrating peptides and the like. Non-viral vectors include, but are not limited to liposomes and lipoplexes, polymers and peptides, synthetic particles and the like. In some embodiments, a liposome or lipoplex has a neutral, negative or positive charge and can comprise cardolipin, anisamide-conjugated polyethylene glycol, diolcoyl phosphatidylcholine, or a variety of other neutral, anionic, or cationic lipids or lipid conjugates. siRNAs can be complexed to cationic polymers (e.g., polyethylenimine (PEI)), biodegradable cationic polysaccharide (e.g., chitosan), or cationic polypeptides (e.g., atelocollagen, poly lysine, and protamine).

In some embodiments, oligonucleotide delivery can be enhanced by targeting the oligonucleotide to a cell. Targeting moieties can be conjugated to a variety of delivery compositions and provide selective or specific binding to a target cell(s). Targeting moieties can include, but are not limited to moieties that bind to cell surface receptors, cell specific extracellular polypeptide, saccharides or lipids, and the like. For example, small molecules such as folate, peptides such as RGD containing peptides, and antibodies such as antibodies to epidermal growth factor receptor can be used to target specific cell types.

In some embodiments, oligonucleotide delivery can be enhanced by moieties that interact with cellular mechanisms and machinery, such as uptake and intracellular trafficking. In certain aspects cell penetrating peptides (CPPs) (e.g., TAT and MPG from HIV-1, penetratin, polyarginine can be coupled with an siRNA or a delivery vector to enhance delivery into a cell. Fusogenic peptides (e.g., endodomain derivatives of HIV-1 envelope (HGP) or influenza fusogenic peptide (diINF-7)) can also be used to enhance cellular delivery.

A variety of delivery systems such as cholesterol-siRNA, RNA aptamers-siRNA, adenoviral vector, lentiviral vector, stable nucleic acid lipid particle (SNALP), cardiolipin analog-based liposome, DSPE-polyethylene glycol-DOTAP-cholesterol liposome, hyaluronan-DPPE liposome, neutral DOPC liposome, atelocollagen, chitosan, polyethylenimine, poly-lysine, protamine, RGD-polyethylene glycol-polyethylenimine, HER-2 liposome with histidine-lysine peptide, HIV antibody-protamine, arginine, oligoarginine(9R) conjugated water soluble lipopolymer (WSLP), oligoarginine (15R), TAT-PAMAM, cholesterol-MPG-8, DOPE-cationic liposome, GALA peptide-PEG-MMP-2 cleavable peptide-DOPE and the like have been used to enhance the delivery of siRNA.

As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; (9) nasally; or (10) intrathecally. Additionally, one or more REST E2- and/or E3-skipping modulating agents can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The amount of oligonucleotide which can be combined with a carrier material to produce a single dosage form will generally be that amount of the compound which produces a therapeutic effect. Generally out of one hundred percent, this amount will range from about 0.1% to 99% of oligonucleotide, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The dosage can be determined by a physician and adjusted, as necessary, to suit observed effects of the treatment. For example, a therapeutic dose range for the miRNA mimics can be 0.01-5.0 mg of miRNA per kg of patient body weight (mg/kg).

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the pharmaceutical composition further includes at least a second therapeutic agent (e.g., an agent other than a miRNA antagonist or mimic described herein). Exemplary therapeutic agents that can formulated with a miRNA antagonist or mimic described herein include, but are not limited to, those found in Harrison's Principles of Internal Medicine, 17th Edition, 2008, McGraw-Hill N.Y., NY; Physicians Desk Reference, 63rd Edition, 2008, Thomson Reuters, N.Y., N.Y.; Goodman & Gilman's The Pharmacological Basis of Therapeutics, 11th Edition, 2005, McGraw-Hill N.Y., NY; United States Pharmacopeia, The National Formulary, USP-32 NF-27, 2008, U.S. Pharmacopeia, Rockville, Md., the complete contents of all of which are incorporated herein by reference.

Kits

Based on the identification of novel miRNA sequences associated with a condition or disease, one aspect described herein also provides for the design and preparation of detection reagents needed to identify or detect one or more novel miRNAs disclosed herein in a biological sample of a subject. Examples of detection reagents that can be used to identify the disclosed miRNA sequences in a biological sample can include a primer and a probe, wherein the probe can selectively hybridize the miRNA of interest.

Accordingly, provided herein include kits for determining whether a subject has, or is at risk of developing, or is at a given stage of condition afflicting a tissue of interest. In some embodiments, the kits can be used for monitoring the response of a subject to a therapeutic treatment. The kits can include at least one reagent specific for detecting for the presence or absence of at least one novel miRNAs described herein, and instructions for use.

In one embodiment, a kit can comprise an oligonucleotide array affixed with a plurality of oligonucleotide probes that interrogate no more than 100 novel miRNAs described herein (including no more than 75 miRNAs, no more than 50 miRNAs, no more than 25 miRNAs, no more than 20 miRNAs, no more than 15 miRNAs, no more than 10 miRNAs, no more than 5 miRNAs or less), wherein the miRNAs comprise at least two or any combinations of the novel miRNAs disclosed in Tables 1-3 submitted herewith and incorporated herein by reference in their entireties, and an optional container containing a detectable label (e.g., comprising a fluorescent molecule) to be conjugated to a nucleotide molecule derived from a test sample of a human subject; and at least one reagent. Examples of a reagent that can be included in the kit can include, without limitations, a restriction enzyme, a universal adaptor to be conjugated to a nucleotide molecule, a primer complementary to the universal adaptor, a wash agent, and any combinations thereof.

In some embodiments, the plurality of oligonucleotide probes affixed to an oligonucleotide array can interrogate about 2-100 miRNAs, e.g., about 3-50 miRNAs, about 3-25 miRNAs, about 3-10 miRNAs, or about 3-5 miRNAs, wherein the miRNAs comprise at least two or any combinations of the novel miRNAs disclosed in Tables 1-3 submitted herewith and incorporated herein by reference in their entireties.

Additional reagents included in the kit can vary with the selection of a sequencing method described herein.

Embodiments of Various Aspects Described Herein can be Defined in any of the Following Numbered Paragraphs:
1. A method of determining whether a subject has, or is at risk of developing, or is at a given stage of a condition afflicting a tissue of interest, or a method of determining tissue origin comprising measuring in a biological sample from the tissue of interest expression level of one or more of the miRNAs, wherein the miRNAs comprise a sequence selected from SEQ ID NO: 1 to SEQ ID NO: 47,972, wherein the alteration of the level of said one or more miRNAs as compared to the level of the same one or more miRNA in a reference sample is indicative of the subject either having, or being at risk of developing, or is at a given stage of the condition.
2. The method of paragraph 1, wherein the reference sample represents a normal condition of the tissue.
3. The method of paragraph 1, wherein the reference sample represents a recognizable stage of an abnormal condition of the tissue.
4. The method of any of paragraphs 1-3, wherein the tissue of interest is breast.
5. The method of any of paragraphs 1-3, wherein the tissue of interest is pancreas.
6. The method of any of paragraphs 1-3, wherein the tissue of interest is blood.
7. The method of any of paragraphs 1-3, wherein the tissue of interest is prostate.
8. The method of any of paragraphs 1-3, wherein the tissue of interest is colon.
9. The method of any of paragraphs 1-3, wherein the tissue of interest is lung.
10. The method of any of paragraphs 1-3, wherein the tissue of interest is skin.
11. The method of any of paragraphs 1-3, wherein the tissue of interest is brain.
12. The method of any of paragraphs 1-3, wherein the tissue of interest is liver.
13. The method of any of paragraphs 1-3, wherein the tissue of interest is heart.
14. The method of any of paragraphs 1-3, wherein the tissue of interest is muscle.
15. The method of any of paragraphs 1-3, wherein the tissue of interest is ovary.
16. The method of any of paragraphs 1-3, wherein the tissue of interest is testicle.
17. The method of any of paragraphs 1-3, wherein the tissue of interest is bone marrow.
18. The method of paragraph 4, wherein the condition of interest is cancer of the breast.
19. The method of paragraph 5, wherein the condition of interest is cancer of the pancreas.
20. The method of paragraph 6, wherein the condition of interest is leukemia.
21. The method of paragraph 7, wherein the condition of interest is cancer of the prostate.
22. The method of paragraph 8, wherein the condition of interest is cancer of the colon.
23. The method of paragraph 9, wherein the condition of interest is cancer of the lung.
24. The method of paragraph 10, wherein the condition of interest is melanoma.
25. The method of paragraph 10, wherein the condition of interest is psoriasis.
26. The method of paragraph 10, wherein the condition of interest is scleroderma.
27. The method of paragraph 11, wherein the condition of interest is Alzheimer's disease.
28. The method of paragraph 11, wherein the condition of interest is Parkinson's disease.
29. The method of paragraph 11, wherein the condition of interest is Multiple Sclerosis.
30. The method of paragraph 11, wherein the condition of interest is cancer of the brain.
31. The method of paragraph 12, wherein the condition of interest is cancer of the liver.

32. The method of paragraph 13, wherein the condition of interest is cardiomyopathy.
33. The method of paragraph 14, wherein the condition of interest is a muscle disorder.
34. The method of paragraph 15, wherein the condition of interest is ovarian cancer.
35. The method of paragraph 16, wherein the condition of interest is testicular cancer.
36. The method of paragraph 17, wherein the condition of interest is myelodysplastic syndrome (MDS) or myeloproliferative disorders (MPD).
37. The method of any of paragraphs 1-36, wherein said one or more miRNAs are measured by a method comprising Sanger sequencing, polymerase chain reaction (PCR), and real-time quantitative PCR, northern blot, microarray, in situ hybridization, serial analysis of gene expression (SAGE), cap analysis gene expression (CAGE) and massively parallel signature sequencing (MPSS), next generation sequencing, deep sequencing, direct multiplexing, and any combinations thereof.
38. A computer implemented method for determining whether a subject has, or is at risk of developing, or is at a given stage of a condition afflicting a tissue of interest, comprising:
    on a device having one or more processors and a memory storing one or more programs for execution by one or more processors, the one or more programs including instructions for:
        measuring in a biological sample from the tissue of interest expression level of one or more of the miRNAs, wherein the miRNAs comprise a sequence selected from SEQ ID NO: 1 to SEQ ID NO: 47,972;
        comparing the measured level of one or more miRNAs to that of at least one or more reference samples to determine alteration in the level of the miRNAs between the biological sample and the reference samples, wherein the alteration in the level of said one or more miRNAs in the biological sample as compared to the level of the same one or more miRNAs in the reference samples is indicative of the subject either having, or being at risk of developing, or is at a given stage of the condition; and
        displaying a content based in part on the data output from (ii), wherein the content comprises a signal indicative of a subject having, or being at risk of developing, or being at a given stage of a disease or disorder, or a signal indicative of no sign of the disease or disorder.
39. The computer implemented method of paragraph 38, wherein said one or more miRNAs are measured by a method comprising Sanger sequencing, polymerase chain reaction (PCR), and real-time quantitative PCR, northern blot, microarray, in situ hybridization, serial analysis of gene expression (SAGE), cap analysis gene expression (CAGE) and massively parallel signature sequencing (MPSS), next generation sequencing, deep sequencing, direct multiplexing, and any combinations thereof.
40. The computer implemented method of paragraph 38 or 39, wherein the reference samples comprise a sample representing a normal condition of the tissue.
41. The computer implemented method of any of paragraphs 38-40, wherein the reference samples comprise a sample representing a recognizable stage of an abnormal condition of the tissue.
42. The computer implemented method of any of paragraphs 38-41, wherein the tissue of interest is breast.
43. The computer implemented method of any of paragraphs 38-41, wherein the tissue of interest is pancreas.
44. The computer implemented method of any of paragraphs 38-41, wherein the tissue of interest is blood.
45. The computer implemented method of any of paragraphs 38-41, wherein the tissue of interest is prostate.
46. The computer implemented method of any of paragraphs 38-41, wherein the tissue of interest is colon.
47. The computer implemented method of any of paragraphs 38-41, wherein the tissue of interest is lung.
48. The computer implemented method of any of paragraphs 38-41, wherein the tissue of interest is skin.
49. The computer implemented method of any of paragraphs 38-41, wherein the tissue of interest is brain.
50. The computer implemented method of any of paragraphs 38-41, wherein the tissue of interest is liver.
51. The computer implemented method of any of paragraphs 38-41, wherein the tissue of interest is heart.
52. The computer implemented method of any of paragraphs 38-41, wherein the tissue of interest is muscle.
53. The computer implemented method of any of paragraphs 38-41, wherein the tissue of interest is ovary.
54. The computer implemented method of any of paragraphs 38-41, wherein the tissue of interest is testicle.
55. The computer implemented method of any of paragraphs 38-41, wherein the tissue of interest is bone marrow.
56. The computer implemented method of paragraph 42, wherein the condition of interest is cancer of the breast.
57. The computer implemented method of paragraph 43, wherein the condition of interest is cancer of the pancreas.
58. The computer implemented method of paragraph 44, wherein the condition of interest is leukemia.
59. The computer implemented method of paragraph 45, wherein the condition of interest is cancer of the prostate.
60. The computer implemented method of paragraph 46, wherein the condition of interest is cancer of the colon.
61. The computer implemented method of paragraph 47, wherein the condition of interest is cancer of the lung.
62. The computer implemented method of paragraph 48, wherein the condition of interest is melanoma.
63. The computer implemented method of paragraph 48, wherein the condition of interest is psoriasis.
64. The computer implemented method of paragraph 48, wherein the condition of interest is scleroderma.
65. The computer implemented method of paragraph 49, wherein the condition of interest is Alzheimer's disease.
66. The computer implemented method of paragraph 49, wherein the condition of interest is Parkinson's disease.
67. The computer implemented method of paragraph 49, wherein the condition of interest is Multiple Sclerosis.
68. The computer implemented method of paragraph 49, wherein the condition of interest is cancer of the brain.
69. The computer implemented method of paragraph 50, wherein the condition of interest is cancer of the liver.
70. The computer implemented method of paragraph 51, wherein the condition of interest is cardiomyopathy.
71. The computer implemented method of paragraph 52, wherein the condition of interest is a muscle disorder.
72. The computer implemented method of paragraph 53, wherein the condition of interest is ovarian cancer.
73. The computer implemented method of paragraph 54, wherein the condition of interest is testicular cancer.
74. The computer implemented method of paragraph 55, wherein the condition of interest is myelodysplastic syndrome (MDS) or myeloproliferative disorders (MPD).
75. The computer implemented method of any of paragraphs 38-74, wherein the content is displayed on a computer display, a screen, a monitor, an email, a text message, a website, a physical printout (e.g., paper) or provided as stored information in a storage device.

76. A computer system for determining whether a subject has, or is at risk of developing, or is at a given stage of a condition afflicting a tissue of interest, comprising:
one or more processors and a memory to store one or more programs, the one or more programs comprising instructions for:
measuring in a biological sample from the tissue of interest expression level of one or more of the miRNAs, wherein the miRNAs comprise a sequence selected from SEQ ID NO: 1 to SEQ ID NO: 47,972;
comparing the measured level of one or more miRNAs to that of at least one or more reference samples to determine alteration in the level of the miRNAs between the biological sample and the reference samples, wherein the alteration in the level of said one or more miRNAs in the biological sample as compared to the level of the same one or more miRNAs in the reference samples is indicative of the subject either having, or being at risk of developing, or is at a given stage of the condition; and
displaying a content based in part on the data output from (ii), wherein the content comprises a signal indicative of a subject having, or being at risk of developing, or being at a given stage of a disease or disorder, or a signal indicative of no sign of the disease or disorder.

77. The computer system of paragraph 76, wherein said one or more miRNAs are measured by a method comprising Sanger sequencing, polymerase chain reaction (PCR), and real-time quantitative PCR, northern blot, microarray, in situ hybridization, serial analysis of gene expression (SAGE), cap analysis gene expression (CAGE) and massively parallel signature sequencing (MPSS), next generation sequencing, deep sequencing, direct multiplexing, and any combinations thereof.

78. The computer system of paragraph 76 or 77, wherein the reference samples comprise a sample representing a normal condition of the tissue.

79. The computer system of any of paragraphs 76-78, wherein the reference samples comprise a sample representing a recognizable stage of an abnormal condition of the tissue.

80. The computer system of any of paragraphs 76-79, wherein the tissue of interest is breast.

81. The computer system of any of paragraphs 76-79, wherein the tissue of interest is pancreas.

82. The computer system of any of paragraphs 76-79, wherein the tissue of interest is blood.

83. The computer system of any of paragraphs 76-79, wherein the tissue of interest is prostate.

84. The computer system of any of paragraphs 76-79, wherein the tissue of interest is colon.

85. The computer system of any of paragraphs 76-79, wherein the tissue of interest is lung.

86. The computer system of any of paragraphs 76-79, wherein the tissue of interest is skin.

87. The computer system of any of paragraphs 76-79, wherein the tissue of interest is brain.

88. The computer system of any of paragraphs 76-79, wherein the tissue of interest is liver.

89. The computer system of any of paragraphs 76-79, wherein the tissue of interest is heart.

90. The computer system of any of paragraphs 76-79, wherein the tissue of interest is muscle.

91. The computer system of any of paragraphs 76-79, wherein the tissue of interest is ovary.

92. The computer system of any of paragraphs 76-79, wherein the tissue of interest is testicle.

93. The computer system of any of paragraphs 76-79, wherein the tissue of interest is bone marrow.

94. The computer system of paragraph 80, wherein the condition of interest is cancer of the breast.

95. The computer system of paragraph 81, wherein the condition of interest is cancer of the pancreas.

96. The computer system of paragraph 82, wherein the condition of interest is leukemia.

97. The computer system of paragraph 83, wherein the condition of interest is cancer of the prostate.

98. The computer system of paragraph 84, wherein the condition of interest is cancer of the colon.

99. The computer system of paragraph 85, wherein the condition of interest is cancer of the lung.

100. The computer system of paragraph 86, wherein the condition of interest is melanoma.

101. The computer system of paragraph 86, wherein the condition of interest is psoriasis.

102. The computer system of paragraph 86, wherein the condition of interest is scleroderma.

103. The computer system of paragraph 87, wherein the condition of interest is Alzheimer's disease.

104. The computer system of paragraph 87, wherein the condition of interest is Parkinson's disease.

105. The computer system of paragraph 87, wherein the condition of interest is Multiple Sclerosis.

106. The computer system of paragraph 87, wherein the condition of interest is cancer of the brain.

107. The computer system of paragraph 88, wherein the condition of interest is cancer of the liver.

108. The computer system of paragraph 89, wherein the condition of interest is cardiomyopathy.

109. The computer system of paragraph 90, wherein the condition of interest is a muscle disorder.

110. The computer system of paragraph 91, wherein the condition of interest is ovarian cancer.

111. The computer system of paragraph 92, wherein the condition of interest is testicular cancer.

112. The computer system of paragraph 93, wherein the condition of interest is myelodysplastic syndrome (MDS) or myeloproliferative disorders (MPD).

113. The computer system of any of paragraphs 76-112, wherein the content is displayed on a computer display, a screen, a monitor, an email, a text message, a website, a physical printout (e.g., paper) or provided as stored information in a storage device.

114. A non-transitory computer-readable storage medium storing one or more programs for determining whether a subject has, or is at risk of developing, or is at a given stage of a condition afflicting a tissue of interest, the one or more programs for execution by one or more processors of a non-transitory computer-readable storage medium, the one or more programs comprising instructions for:
measuring in a biological sample from the tissue of interest expression level of one or more of the miRNAs, wherein the miRNAs comprise a sequence selected from SEQ ID NO: 1 to SEQ ID NO: 47,972;
comparing the measured level of one or more miRNAs to that of at least one or more reference samples to determine alteration in the level of the miRNAs between the biological sample and the reference samples, wherein the alteration in the level of said one or more miRNAs in the biological sample as compared to the level of the same one or more miRNAs in the reference samples is indicative of the subject either having, or being at risk of developing, or is at a given stage of the condition; and displaying a content based in part on the data output from (ii), wherein the content comprises a signal indicative of a subject having, or being at risk of developing, or being at a given stage of a disease or disorder, or a signal indicative of no sign of the disease or disorder.

115. The non-transitory computer-readable storage medium of paragraph 114, wherein said one or more miRNAs are measured by a method comprising Sanger sequencing, polymerase chain reaction (PCR), and real-time quantitative PCR, northern blot, microarray, in situ hybridization, serial analysis of gene expression (SAGE), cap analysis gene expression (CAGE) and massively parallel signature sequencing (MPSS), next generation sequencing, deep sequencing, direct multiplexing, and any combinations thereof.

116. The non-transitory computer-readable storage medium of paragraph 114 or 115, wherein the reference samples comprise a sample representing a normal condition of the tissue.

117. The non-transitory computer-readable storage medium of any of paragraphs 114-116, wherein the reference samples comprise a sample representing a recognizable stage of an abnormal condition of the tissue.

118. The non-transitory computer-readable storage medium of any of paragraphs 114-117, wherein the tissue of interest is breast.

119. The non-transitory computer-readable storage medium of any of paragraphs 114-117, wherein the tissue of interest is pancreas.

120. The non-transitory computer-readable storage medium of any of paragraphs 114-117, wherein the tissue of interest is blood.

121. The non-transitory computer-readable storage medium of any of paragraphs 114-117, wherein the tissue of interest is prostate.

122. The non-transitory computer-readable storage medium of any of paragraphs 114-117, wherein the tissue of interest is colon.

123. The non-transitory computer-readable storage medium of any of paragraphs 114-117, wherein the tissue of interest is lung.

124. The non-transitory computer-readable storage medium of any of paragraphs 114-117, wherein the tissue of interest is skin.

125. The non-transitory computer-readable storage medium of any of paragraphs 114-117, wherein the tissue of interest is brain.

126. The non-transitory computer-readable storage medium of any of paragraphs 114-117, wherein the tissue of interest is liver.

127. The non-transitory computer-readable storage medium of any of paragraphs 114-117, wherein the tissue of interest is heart.

128. The non-transitory computer-readable storage medium of any of paragraphs 114-117, wherein the tissue of interest is muscle.

129. The non-transitory computer-readable storage medium of any of paragraphs 114-117, wherein the tissue of interest is ovary.

130. The non-transitory computer-readable storage medium of any of paragraphs 114-117, wherein the tissue of interest is testicle.

131. The non-transitory computer-readable storage medium of any of paragraphs 114-117, wherein the tissue of interest is bone marrow.

132. The non-transitory computer-readable storage medium of paragraph 118, wherein the condition of interest is cancer of the breast.

133. The non-transitory computer-readable storage medium of paragraph 119, wherein the condition of interest is cancer of the pancreas.

134. The non-transitory computer-readable storage medium of paragraph 120, wherein the condition of interest is leukemia.

135. The non-transitory computer-readable storage medium of paragraph 121, wherein the condition of interest is cancer of the prostate.

136. The non-transitory computer-readable storage medium of paragraph 122, wherein the condition of interest is cancer of the colon.

137. The non-transitory computer-readable storage medium of paragraph 123, wherein the condition of interest is cancer of the lung.

138. The non-transitory computer-readable storage medium of paragraph 124, wherein the condition of interest is melanoma.

139. The non-transitory computer-readable storage medium of paragraph 124, wherein the condition of interest is psoriasis.

140. The non-transitory computer-readable storage medium of paragraph 124, wherein the condition of interest is scleroderma.

141. The non-transitory computer-readable storage medium of paragraph 125, wherein the condition of interest is Alzheimer's disease.

142. The non-transitory computer-readable storage medium of paragraph 125, wherein the condition of interest is Parkinson's disease.

143. The non-transitory computer-readable storage medium of paragraph 125, wherein the condition of interest is Multiple Sclerosis.

144. The non-transitory computer-readable storage medium of paragraph 125, wherein the condition of interest is cancer of the brain.

145. The non-transitory computer-readable storage medium of paragraph 126, wherein the condition of interest is cancer of the liver.

146. The non-transitory computer-readable storage medium of paragraph 127, wherein the condition of interest is cardiomyopathy.

147. The non-transitory computer-readable storage medium of paragraph 128, wherein the condition of interest is a muscle disorder.

148. The non-transitory computer-readable storage medium of paragraph 129, wherein the condition of interest is ovarian cancer.

149. The non-transitory computer-readable storage medium of paragraph 130, wherein the condition of interest is testicular cancer.

150. The non-transitory computer-readable storage medium of paragraph 131, wherein the condition of interest is myelodysplastic syndrome (MDS) or myeloproliferative disorders (MPD).

151. The non-transitory computer-readable storage medium of any of paragraphs 114-150, wherein the content is displayed on a computer display, a screen, a monitor, an email, a text message, a website, a physical printout (e.g., paper) or provided as stored information in a storage device.

152. The method, computer implemented method, computer system, or non-transitory computer-readable storage medium of any of the preceding claims, wherein isoforms of the miRNAs are used.
153. The method, computer implemented method, computer system, or non-transitory computer-readable storage medium of claim 152, wherein the isoforms can correspond to novel miRNAs.
154. The method, computer implemented method, computer system, or non-transitory computer-readable storage medium of claim 152, wherein the isoforms can correspond to known miRNAs.

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to describe the present invention, in connection with percentages means±1%.

In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventor is not entitled to antedate such disclosure by virtue of prior invention or for any other reason. All statements as to the date or representation as to the contents of these documents is based on the information available to the applicants and does not constitute any admission as to the correctness of the dates or contents of these documents.

The term "statistically significant" or "significantly" or "significant" refers to statistical significance and generally means a one standard deviation (1SD) above or below a reference level. Alternatively, statistical significance can be measured by means of a "false discovery rate" threshold, e.g. 0.05. The term refers to statistical evidence that there is a difference. It is defined as the probability of making a decision to reject the null hypothesis when the null hypothesis is actually true. The decision is often made using the p-value. Alternatively, the decision is made using the estimated false discovery rate.

The term "deep sequencing" as used herein generally refers to next- or higher-generation sequencing known to a skilled artisan.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G," a thymine "T" or a cytosine "C") or RNA (e.g. an A, a G, a uracil "U" or a C). The term "nucleic acid" encompasses the terms "oligonucleotide" and "polynucleotide," each as a subgenus of the term "nucleic acid." The term "oligonucleotide" refers to a molecule of between about 2 and about 100 nucleobases in length. The term "polynucleotide" refers to at least one molecule of greater than about 100 nucleobases in length.

The term "non-coding" refers to sequences of nucleic acid molecules that cannot be translated in a sequence-specific manner to produce into a particular polypeptide or peptide. In some embodiments, the term "non-coding" in reference to RNA can refer to a RNA sequence that is not translated in a sequence-specific manner to produce a particular polypeptide or peptide. In some embodiments, a non-coding RNA can comprise a sequence corresponding to a fragment of a protein-coding region, but which is not translated into a functional peptide or protein when it forms part of a non-coding RNA. Non-coding sequences include but are not limited to introns or parts thereof, promoter regions or parts thereof, 3' untranslated regions (3' UTR) or parts thereof, 5' untranslated regions (5' UTR) or parts thereof, as well as intergenic regions. In general, a 3' or 5' untranslated region is part of or spans one or more exons.

The term "coding region" or "protein-coding region" as used herein, refers to a portion of the nucleic acid sequence, which is transcribed and translated in a sequence-specific manner to produce a particular polypeptide or protein when placed under the control of appropriate regulatory sequences and appropriate molecular machinery. The coding region of a protein-coding gene is said to encode one, or more, such polypeptide or protein.

The term "oligonucleotide," as used herein is defined as a nucleic acid molecule, or its sequence representation, comprised of at least two or more ribo- or deoxyribonucleotides. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, an oligonucleotide probe typically contains 15-25 or more nucleotides, although it may contain fewer nucleotides. The probes as disclosed herein are selected to be "substantially complementary" to different strands of a particular target nucleic acid sequence. This means that the probes must be sufficiently complementary so as to be able to "specifically hybridize" or anneal with their respective target strands. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarily with the sequence of the target nucleic acid to anneal therewith specifically.

In the context of this disclosure, the term "probe" refers to a molecule that can detectably distinguish among target molecules differing in sequence composition and also in structure (e.g. nucleic acid or protein sequence). Detection can be accomplished in a variety of different ways depending on the type of probe used and the type of target molecule. Thus, for example, detection may be based on discrimination on detection of specific binding. Examples of such specific binding include antibody binding and nucleic acid, antibody binding to protein, nucleic acid binding to nucleic acid, or aptamer binding to protein or nucleic acid. Thus, for example, probes can include enzyme substrates, antibodies and antibody fragments, and preferably nucleic acid hybridization probes.

The term "specifically hybridize" refers to the association between two single-stranded nucleic acid molecules of sufficient complementary sequence to permit such hybridization under pre-determined conditions generally used in the art (sometimes the sequences are referred to as "substantially complementary"). In particular, the term specifically hybridize also refers to hybridization of an oligonucleotide with a substantially complementary sequence as compared to non-complementary sequence.

The term "specifically" as used herein with reference to a probe which is used to specifically detect a given sequence of contiguous nucleotides, refers to a probe that identifies the particular sequence based on preferential hybridization to the sequence under consideration stringent hybridization conditions and/or on exclusive amplification or replication of molecules of interest.

The term "specifically" as used herein with reference to a probe which is used to specifically detect a sequence difference, refers to a probe that identifies a particular sequence difference based on exclusive hybridization to the sequence difference under stringent hybridization conditions and/or on exclusive amplification or replication of the sequence difference.

In its broadest sense, the term "substantially" as used herein in respect to "substantially complementary", or when used herein with respect to a nucleotide sequence in relation to a reference or a target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons can be carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above), or any of the tools that have been used for this purpose by the skilled artisan. A nucleotide sequence "substantially complementary" to a reference nucleotide sequence hybridizes to the reference nucleotide sequence under low stringency conditions, preferably medium stringency conditions, most preferably high stringency conditions.

In its broadest sense, the term "substantially identical," when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-40 nucleotides, such as at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above), or similar tools, as mentioned above. A nucleotide sequence "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that is at least 24% identical, at least 35% identical, at least 50% identical, at least 65% identical to the reference sequence, as measured using the parameters described above, wherein the molecule represented by the homologous sequence is considered to have the same biological activity as the molecule encoded by the specific nucleotide sequence. The term "substantially non-identical" refers to a nucleotide sequence that does not hybridize to the nucleic acid sequence under stringent conditions.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length, but can be longer as needed. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

In some embodiments, the term "complementary" as used herein refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine (for DNA) or uracil (for RNA). Similarly, it is known that a cytosine residue of a first nucleic acid strand is capable of base pairing with a residue of a second nucleic acid strand which is anti-parallel to the first strand if the residue is guanine. A cytosine residue of a first nucleic acid strand is also capable of base pairing with a residue of a second nucleic acid strand which is anti-parallel to the first strand if the residue is uracil—such interactions are referred to as "non-Watson-Crick" or "G:U wobbles." A first region of a nucleic acid is complementary to a second region of the same or a different nucleic acid if at least one nucleotide residue of the first region is capable of base pairing with a residue of the second region, when the two regions are arranged in an anti-parallel fashion. Preferably, the first region comprises a first portion and the second region comprises a second portion, whereby, when the first and second portions are arranged in an anti-parallel fashion, such that at least about 50%, and preferably at least about 75%, at least about 90%, or at least about 95% or at least 100% of the nucleotide residues of the first portion are capable of base pairing with nucleotide residues in the second portion. More preferably, all nucleotide residues of the first portion are capable of base pairing with nucleotide residues in the second portion. A first region of a nucleic acid is "near-complementary" to a second region of the same or a different nucleic acid if, at least one nucleotide residue of the first region is capable of base pairing with a residue of the second region, when the two regions are arranged in an anti-parallel fashion, and not all of the nucleotides of the two regions are base-paired. Such interactions are exemplified by heteroduplexes of miRNAs with mRNAs where the typical interaction between the two molecules is effected by only a subset of the residues spanning each region. Additionally, the two interacting regions need not have the same length.

The term "antisense" generally refers to a nucleotide or a ribonucleotide sequence being complementary to the gene's messenger RNA (mRNA), which is called the "sense" sequence. For example, a sense segment of mRNA "5'-AAGGUC-3'" would be blocked by the anti-sense mRNA segment "3'-UUCCAG-5'").

The term "antisense oligonucleotide" refers to a nucleotide sequence including a "region of complementarity" that is substantially complementary to a sequence, for example a target sequence. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5' and/or 3' terminus.

As used herein, the term "antisense oligonucleotides comprising a nucleotide sequence" refers to an antisense oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured herein by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1. An Exemplary Methodology to Identify Novel miRNAs

Identification of Candidate Hairpin Precursors within a Dataset

To identify novel miRNAs the following three steps are carried out; candidates that satisfy the conditions of all these stages are labeled 'novel miRNAs':

(i) For each sample, only those short RNA sequence reads that mapped unambiguously on the human genome are considered. The sequence reads were expanded into putative "sequence islands", and only those islands ranging in length from 20-30 nts were retained. From these islands, only those overlapping sequence reads whose length ranged between 20 and 24 nts inclusive were considered for further analysis.

(ii) Each 20-24 nt sequence reads was expanded out into a putative precursor segment of 70-75 nts in length. To ensure that we tested all possible arrangements, the following 4 options were considered:

a. Addition of 45 nts to the 5'-end and of 5 nts to the 3'-end of the sequence island b. Addition of 35 nts to the 5'-end and 15 nts to the 3'-end of the sequence island c. Addition of 5 nts to the 5'-end and 45 nts to the 3'-end of the sequence island d. Addition of 15 nts to the 5'-end and 35 nts to the 3'-end of the sequence island For each of the four conditions, RNAfold from the 'Vienna package' (Hofacker et al. "Fast Folding and comparison of RNA secondary structures." Monatshefte fuer Chemie, Vol 125, 167-188, 1996) was used to predict the folding structure of the resulting sequence segment and to examine whether it folded into a hairpin with the miRNA product on either the hairpin's 5' (a. and b.) or 3' (c. and d.) arm. The two different sets of hairpin lengths that were tested (conditions a and b; and c and d above) allowed control for the offset of the mature miRNA from the loop within the hairpin structure, a distance that can be variable.

(iii) Only those candidate segments, and their associated miRNA candidates, which folded into a hairpin structure, had at least 15 base pairs between the two arms, and an energy value of −12 Kcal/mol or less were kept.

Identification of Mature miRNA and Precursor Sequence Boundaries

The boundaries of the mature miRNA candidates at each locus were determined by identifying the segment with the highest percentage of sequenced reads among the isomiRs. The most abundant segment with length between 20 and 24 nts was considered to be the representative mature miRNA from the locus at hand. The genomic locations of the hairpin were determined from the folded hairpin structures surrounding a potential miRNA. The hairpin with the highest folding energy was determined as the most likely candidate.

Determination of False Discovery Rate

Each one of the 962 datasets was considered in turn. Counts for unambiguously mapped reads were generated for each known and novel miRNA in the sample under consideration. Significant miRNAs (whether known or novel) were determined using a method adapted from CHIP-seq peak calling (Xu, J. & Zhang, Y. "A generalized linear model for peak calling in ChIP-Seq data." Journal of computational biology: a journal of computational molecular cell biology 19, 826-838, 2012.), maximum likelihood estimates of the parameters of the negative binomial distribution are calculated from the probability density function and subsequent p-values determined from the cumulative distribution function of the fitted data. P-values were corrected for multiple testing using the Benjamini-Hochberg procedure and an FDR calculated for each miRNA. Only those miRNAs (known or novel) with a FDR <=0.001 were kept. Sequences that were already contained in Rel. 20 of miRBase or the public mirtron repository were removed from further consideration. Additionally, any sequences that overlapped with tRNAs, rRNAs and snRNAs were removed from further consideration.

Example 2. Conservation Properties of the Novel miRNAs Described Herein in Other Species For about 9,877 novel miRNAs listed in Table 1 that were discovered by the inventors using the method that they developed as described in Example 1, it was sought to determine the extent to which the mature miRNA and the corresponding precursor miRNA are conserved across model organisms. In particular, the inventors performed a stringent search where they sought instances not only of the mature miRNA but also of the full-length precursor in several model organisms (referred to as "novel hairpin: mature miRNA combination" or "mature miRNA:novel hairpin combination"). For this purpose, the inventors used GLSEARCH (Pearson W R. 2000. "Flexible sequence similarity searching with the FASTA3 program package." *Methods in molecular biology* (Clifton, N.J.) 132: 185-219) to look for each of the identified novel miRNA precursors and their corresponding mature miRNA(s) in the chimpanzee, gorilla, orangutan, macaque, mouse, *drosophila* and worm genome assemblies. During these searches it was required that (a) at least 70% of the miRNA precursor positions be identically present in the searched genome; and, (b) at least 85% of the human mature miRNA positions be identically present in the identified orthologous precursor including an identically present seed. It was found that the vast majority of these miRNAs are conserved in primates with only a small fraction of them being present in rodents or invertebrates. Table 4 below summarizes the conservation properties of this collection of miRNAs:

TABLE 4

Number of novel hairpin:mature miRNA combinations conserved in genomes of various species for the novel miRNAs discovered using the inventors' method as described in Example 1

| Present in Which Genome | Number of Novel hairpins:Mature miRNA Combinations (n = 9,877) |
|---|---|
| Human (Hu) | 9,877 |
| Chimpanzee (Ch) | 8,536 |
| Gorilla (Go) | 8,303 |
| Orangutan (Or) | 7,013 |
| Macaque (Ma) | 5,434 |
| Mouse (Mo) | 160 |
| Drosophila (Dr) | 1 |
| Worm (Wo) | 1 |

Of the 9,877 cases, 499 miRNA:hairpin combinations (5.1%) are present exclusively in the human genome. This finding shows that these 499 instances could be involved in molecular mechanisms that may not be present in mouse models.

The following Table 5 shows in more detail the conservation properties of each of the 9,877 novel miRNA:hairpin combinations (discovered using the inventor's own method as described in Example 1) across the examined model organisms. The actual miRNA and hairpin sequences and corresponding SEQ ID NOs. can be identified in Table 1 according to the "Novel miRNA ID" and "Hairpin ID" listed in Table 5. In Table 5, "Hu" stands for Human; "Ch" stands for Chimpanzee; "Go" stands for Gorilla; "Or" stands for Orangutan or Pongo; "Ma" stands for "Macaque"; "Mo" stands for "Mouse"; "Dr" stands for Drosophia or fruit-fly; "Wo" stands for "worm."

Lengthy table referenced here

US11293064-20220405-T00001

Please refer to the end of the specification for access instructions.

The inventors also examined the 3,707 novel miRNAs that they discovered using the miRDeep2 method (as listed in Table 2) for conservation of the corresponding miRNA: hairpin combination across model organisms (using the above mentioned approach). As with the collection of the 9,877 novel miRNAs that the inventors discovered using their own method, they find that the vast majority of the miRNAs discovered using the miRDeep2 method are conserved in primates with only a small fraction of them being present in rodents or invertebrates. Table 6 below summarizes the conservation properties of this collection of miRNAs.

TABLE 6

Number of novel hairpin:mature miRNA combinations conserved in genomes of various species for the novel miRNAs discovered using the miRDeep2 method.

| Present in Which Genome | Number of Novel hairpins:Mature miRNA Combinations (n = 3,707) |
|---|---|
| Human (Hu) | 3,707 |
| Chimpanzee (Ch) | 1,242 |
| Gorilla (Go) | 1,273 |
| Orangutan (Or) | 999 |
| Macaque (Ma) | 661 |
| Mouse (Mo) | 109 |

TABLE 6-continued

Number of novel hairpin:mature miRNA combinations conserved in genomes of various species for the novel miRNAs discovered using the miRDeep2 method.

| Present in Which Genome | Number of Novel hairpins:Mature miRNA Combinations (n = 3,707) |
|---|---|
| Drosophila (Dr) | 1 |
| Worm (Wo) | 0 |

Of these 3,707 cases, 2,140 novel miRNA:hairpin combinations (57.7%) are present exclusively in the human genome. The following Table 7 shows in more detail the conservation properties of each of the 3,707 novel miRNA: hairpin combinations across the examined model organisms. The actual miRNA and hairpin sequences and corresponding SEQ ID NOs. can be identified in Table 2 according to the "Novel miRNA ID" and "Hairpin ID" listed in Table 7. In Table 7, "Hu" stands for Human; "Ch" stands for Chimpanzee; "Go" stands for Gorilla; "Or" stands for Orangutan or Pongo; "Ma" stands for "Macaque"; "Mo" stands for "Mouse"; "Dr" stands for Drosophia or fruit-fly; "Wo" stands for "worm."

TABLE 7

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00001.5p-miR | TJU_CMC_MD2.ID00001.hairpin | YES | NO | NO | NO | NO | NO | NO | NO |
| TJU_CMC_MD2.ID00002.5p-miR | TJU_CMC_MD2.ID00002.hairpin | YES | NO | NO | NO | YES | NO | NO | NO |
| TJU_CMC_MD2.ID00003.5p-miR | TJU_CMC_MD2.ID00003.hairpin | YES | YES | YES | YES | NO | NO | NO | NO |
| TJU_CMC_MD2.ID00004.3p-miR | TJU_CMC_MD2.ID00004.hairpin | YES | NO | NO | NO | NO | NO | NO | NO |
| TJU_CMC_MD2.ID00004.5p-miR | TJU_CMC_MD2.ID00004.hairpin | YES | YES | YES | YES | YES | YES | NO | NO |
| TJU_CMC_MD2.ID00005.5p-miR | TJU_CMC_MD2.ID00005.hairpin | YES | NO | YES | YES | YES | NO | NO | NO |
| TJU_CMC_MD2.ID00006.3p-miR | TJU_CMC_MD2.ID00006.hairpin | YES | NO | NO | NO | NO | NO | NO | NO |
| TJU_CMC_MD2.ID00007.3p-miR | TJU_CMC_MD2.ID00007.hairpin | YES | NO | NO | NO | NO | NO | NO | NO |
| TJU_CMC_MD2.ID00008.3p-miR | TJU_CMC_MD2.ID00008.hairpin | YES | NO | NO | NO | NO | NO | NO | NO |
| TJU_CMC_MD2.ID00009.3p-miR | TJU_CMC_MD2.ID00009.hairpin | YES | NO | NO | NO | NO | NO | NO | NO |
| TJU_CMC_MD2.ID00010.3p-miR | TJU_CMC_MD2.ID00010.hairpin | YES | NO | NO | NO | NO | NO | NO | NO |
| TJU_CMC_MD2.ID00011.3p-miR | TJU_CMC_MD2.ID00011.hairpin | YES | NO | YES | YES | NO | NO | NO | NO |
| TJU_CMC_MD2.ID00011.5p-miR | TJU_CMC_MD2.ID00011.hairpin | YES | NO | YES | YES | NO | NO | NO | NO |
| TJU_CMC_MD2.ID00012.3p-miR | TJU_CMC_MD2.ID00012.hairpin | YES | NO | NO | NO | NO | NO | NO | NO |
| TJU_CMC_MD2.ID00013.3p-miR | TJU_CMC_MD2.ID00013.hairpin | YES | NO | NO | NO | NO | NO | NO | NO |
| TJU_CMC_MD2.ID00014.3p-miR | TJU_CMC_MD2.ID00014.hairpin | YES | NO | NO | NO | NO | NO | NO | NO |
| TJU_CMC_MD2.ID00015.5p-miR | TJU_CMC_MD2.ID00015.hairpin | YES | YES | YES | YES | NO | NO | NO | NO |
| TJU_CMC_MD2.ID00016.5p-miR | TJU_CMC_MD2.ID00016.hairpin | YES | NO | YES | YES | NO | NO | NO | NO |
| TJU_CMC_MD2.ID00017.3p-miR | TJU_CMC_MD2.ID00017.hairpin | YES | NO | NO | NO | NO | NO | NO | NO |
| TJU_CMC_MD2.ID00018.5p-miR | TJU_CMC_MD2.ID00018.hairpin | YES | NO | YES | YES | NO | NO | NO | NO |
| TJU_CMC_MD2.ID00019.3p-miR | TJU_CMC_MD2.ID00019.hairpin | YES | NO | NO | NO | NO | NO | NO | NO |
| TJU_CMC_MD2.ID00020.5p-miR | TJU_CMC_MD2.ID00020.hairpin | YES | NO | NO | NO | NO | NO | NO | NO |
| TJU_CMC_MD2.ID00021.5p-miR | TJU_CMC_MD2.ID00021.hairpin | YES | NO | NO | NO | NO | NO | NO | NO |
| TJU_CMC_MD2.ID00022.3p-miR | TJU_CMC_MD2.ID00022.hairpin | YES | NO | NO | NO | NO | NO | NO | NO |
| TJU_CMC_MD2.ID00023.3p-miR | TJU_CMC_MD2.ID00023.hairpin | YES | NO | NO | NO | NO | NO | NO | NO |
| TJU_CMC_MD2.ID00024.5p-miR | TJU_CMC_MD2.ID00024.hairpin | YES | YES | YES | YES | NO | NO | NO | NO |
| TJU_CMC_MD2.ID00025.5p-miR | TJU_CMC_MD2.ID00025.hairpin | YES | YES | YES | YES | YES | NO | NO | NO |
| TJU_CMC_MD2.ID00026.3p-miR | TJU_CMC_MD2.ID00026.hairpin | YES | NO | NO | NO | NO | NO | NO | NO |
| TJU_CMC_MD2.ID00027.5p-miR | TJU_CMC_MD2.ID00027.hairpin | YES | YES | YES | YES | YES | NO | NO | NO |
| TJU_CMC_MD2.ID00028.3p-miR | TJU_CMC_MD2.ID00028.hairpin | YES | NO | NO | NO | NO | NO | NO | NO |
| TJU_CMC_MD2.ID00029.5p-miR | TJU_CMC_MD2.ID00029.hairpin | YES | YES | YES | YES | YES | NO | NO | NO |
| TJU_CMC_MD2.ID00030.3p-miR | TJU_CMC_MD2.ID00030.hairpin | YES | NO | NO | NO | NO | NO | NO | NO |
| TJU_CMC_MD2.ID00031.3p-miR | TJU_CMC_MD2.ID00031.hairpin | YES | NO | NO | NO | NO | NO | NO | NO |
| TJU_CMC_MD2.ID00032.5p-miR | TJU_CMC_MD2.ID00032.hairpin | YES | NO | YES | YES | NO | NO | NO | NO |
| TJU_CMC_MD2.ID00033.5p-miR | TJU_CMC_MD2.ID00033.hairpin | YES | NO | YES | NO | NO | NO | NO | NO |
| TJU_CMC_MD2.ID00034.3p-miR | TJU_CMC_MD2.ID00034.hairpin | YES | NO | NO | NO | NO | NO | NO | NO |
| TJU_CMC_MD2.ID00035.3p-miR | TJU_CMC_MD2.ID00035.hairpin | YES | NO | NO | NO | NO | NO | NO | NO |
| TJU_CMC_MD2.ID00036.3p-miR | TJU_CMC_MD2.ID00036.hairpin | YES | NO | NO | NO | NO | NO | NO | NO |
| TJU_CMC_MD2.ID00037.3p-miR | TJU_CMC_MD2.ID00037.hairpin | YES | NO | NO | NO | NO | NO | NO | NO |
| TJU_CMC_MD2.ID00038.3p-miR | TJU_CMC_MD2.ID00038.hairpin | YES | NO | NO | NO | NO | NO | NO | NO |
| TJU_CMC_MD2.ID00039.3p-miR | TJU_CMC_MD2.ID00039.hairpin | YES | NO | NO | NO | NO | NO | NO | NO |
| TJU_CMC_MD2.ID00040.5p-miR | TJU_CMC_MD2.ID00040.hairpin | YES | YES | YES | YES | NO | NO | NO | NO |
| TJU_CMC_MD2.ID00041.3p-miR | TJU_CMC_MD2.ID00041.hairpin | YES | NO | NO | NO | NO | NO | NO | NO |
| TJU_CMC_MD2.ID00041.5p-miR | TJU_CMC_MD2.ID00041.hairpin | YES | YES | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00042.3p-miR | TJU_CMC_MD2.ID00042.hairpin | YES | NO | NO | NO | NO | NO | NO | NO |
| TJU_CMC_MD2.ID00043.5p-miR | TJU_CMC_MD2.ID00043.hairpin | YES | NO | NO | YES | NO | NO | NO | NO |
| TJU_CMC_MD2.ID00044.3p-miR | TJU_CMC_MD2.ID00044.hairpin | YES | NO | NO | NO | NO | NO | NO | NO |
| TJU_CMC_MD2.ID00045.5p-miR | TJU_CMC_MD2.ID00045.hairpin | YES | NO | YES | YES | NO | NO | NO | NO |
| TJU_CMC_MD2.ID00046.3p-miR | TJU_CMC_MD2.ID00046.hairpin | YES | NO | NO | NO | NO | NO | NO | NO |
| TJU_CMC_MD2.ID00046.5p-miR | TJU_CMC_MD2.ID00046.hairpin | YES | YES | YES | YES | NO | NO | NO | NO |
| TJU_CMC_MD2.ID00047.3p-miR | TJU_CMC_MD2.ID00047.hairpin | YES | NO | NO | NO | NO | NO | NO | NO |
| TJU_CMC_MD2.ID00048.5p-miR | TJU_CMC_MD2.ID00048.hairpin | YES | YES | YES | YES | NO | NO | NO | NO |
| TJU_CMC_MD2.ID00049.5p-miR | TJU_CMC_MD2.ID00049.hairpin | YES | NO | NO | NO | NO | NO | NO | NO |
| TJU_CMC_MD2.ID00050.5p-miR | TJU_CMC_MD2.ID00050.hairpin | YES | NO | YES | NO | NO | NO | NO | NO |
| TJU_CMC_MD2.ID00051.3p-miR | TJU_CMC_MD2.ID00051.hairpin | YES | NO | NO | NO | NO | NO | NO | NO |
| TJU_CMC_MD2.ID00052.3p-miR | TJU_CMC_MD2.ID00052.hairpin | YES | NO | NO | NO | NO | NO | NO | NO |
| TJU_CMC_MD2.ID00053.5p-miR | TJU_CMC_MD2.ID00053.hairpin | YES | YES | NO | YES | YES | NO | NO | NO |
| TJU_CMC_MD2.ID00054.5p-miR | TJU_CMC_MD2.ID00054.hairpin | YES | YES | NO | YES | YES | NO | NO | NO |
| TJU_CMC_MD2.ID00055.5p-miR | TJU_CMC_MD2.ID00055.hairpin | YES | YES | YES | YES | YES | NO | NO | NO |
| TJU_CMC_MD2.ID00056.3p-miR | TJU_CMC_MD2.ID00056.hairpin | YES | NO | NO | NO | NO | NO | NO | NO |
| TJU_CMC_MD2.ID00057.3p-miR | TJU_CMC_MD2.ID00057.hairpin | YES | NO | NO | NO | NO | NO | NO | NO |
| TJU_CMC_MD2.ID00058.5p-miR | TJU_CMC_MD2.ID00058.hairpin | YES | YES | NO | YES | YES | NO | NO | NO |
| TJU_CMC_MD2.ID00059.5p-miR | TJU_CMC_MD2.ID00059.hairpin | YES | YES | YES | YES | NO | NO | NO | NO |
| TJU_CMC_MD2.ID00060.3p-miR | TJU_CMC_MD2.ID00060.hairpin | YES | NO | NO | NO | NO | NO | NO | NO |
| TJU_CMC_MD2.ID00061.3p-miR | TJU_CMC_MD2.ID00061.hairpin | YES | NO | NO | NO | NO | NO | NO | NO |
| TJU_CMC_MD2.ID00062.5p-miR | TJU_CMC_MD2.ID00062.hairpin | YES | YES | YES | NO | YES | NO | NO | NO |
| TJU_CMC_MD2.ID00063.5p-miR | TJU_CMC_MD2.ID00063.hairpin | YES | YES | YES | YES | NO | NO | NO | NO |
| TJU_CMC_MD2.ID00064.3p-miR | TJU_CMC_MD2.ID00064.hairpin | YES | NO | NO | NO | NO | NO | NO | NO |
| TJU_CMC_MD2.ID00065.3p-miR | TJU_CMC_MD2.ID00065.hairpin | YES | NO | NO | NO | NO | NO | NO | NO |
| TJU_CMC_MD2.ID00066.3p-miR | TJU_CMC_MD2.ID00066.hairpin | YES | NO | NO | NO | NO | NO | NO | NO |
| TJU_CMC_MD2.ID00067.3p-miR | TJU_CMC_MD2.ID00067.hairpin | YES | NO | NO | NO | NO | NO | NO | NO |
| TJU_CMC_MD2.ID00068.5p-miR | TJU_CMC_MD2.ID00068.hairpin | YES | NO | YES | YES | NO | NO | NO | NO |
| TJU_CMC_MD2.ID00069.3p-miR | TJU_CMC_MD2.ID00069.hairpin | YES | NO | NO | NO | NO | NO | NO | NO |
| TJU_CMC_MD2.ID00070.5p-miR | TJU_CMC_MD2.ID00070.hairpin | YES | YES | YES | YES | YES | NO | NO | NO |
| TJU_CMC_MD2.ID00071.3p-miR | TJU_CMC_MD2.ID00071.hairpin | YES | NO | NO | NO | NO | NO | NO | NO |
| TJU_CMC_MD2.ID00072.5p-miR | TJU_CMC_MD2.ID00072.hairpin | YES | YES | YES | YES | NO | NO | NO | NO |
| TJU_CMC_MD2.ID00073.3p-miR | TJU_CMC_MD2.ID00073.hairpin | YES | NO | NO | NO | NO | NO | NO | NO |
| TJU_CMC_MD2.ID00074.3p-miR | TJU_CMC_MD2.ID00074.hairpin | YES | NO | NO | NO | NO | NO | NO | NO |
| TJU_CMC_MD2.ID00075.5p-miR | TJU_CMC_MD2.ID00075.hairpin | YES | YES | YES | NO | YES | NO | NO | NO |
| TJU_CMC_MD2.ID00076.5p-miR | TJU_CMC_MD2.ID00076.hairpin | YES | YES | YES | YES | YES | NO | NO | NO |
| TJU_CMC_MD2.ID00077.3p-miR | TJU_CMC_MD2.ID00077.hairpin | YES | NO | NO | NO | NO | NO | NO | NO |
| TJU_CMC_MD2.ID00078.3p-miR | TJU_CMC_MD2.ID00078.hairpin | YES | NO | NO | NO | NO | NO | NO | NO |
| TJU_CMC_MD2.ID00079.3p-miR | TJU_CMC_MD2.ID00079.hairpin | YES | YES | YES | NO | NO | NO | NO | NO |
| TJU_CMC_MD2.ID00080.3p-miR | TJU_CMC_MD2.ID00080.hairpin | YES | NO | NO | NO | NO | NO | NO | NO |
| TJU_CMC_MD2.ID00081.3p-miR | TJU_CMC_MD2.ID00081.hairpin | YES | NO | NO | NO | NO | NO | NO | NO |
| TJU_CMC_MD2.ID00082.3p-miR | TJU_CMC_MD2.ID00082.hairpin | YES | NO | NO | NO | NO | NO | NO | NO |
| TJU_CMC_MD2.ID00083.3p-miR | TJU_CMC_MD2.ID00083.hairpin | YES | NO | NO | NO | NO | NO | NO | NO |
| TJU_CMC_MD2.ID00084.5p-miR | TJU_CMC_MD2.ID00084.hairpin | YES | YES | YES | NO | YES | NO | NO | NO |
| TJU_CMC_MD2.ID00085.3p-miR | TJU_CMC_MD2.ID00085.hairpin | YES | NO | NO | NO | NO | NO | NO | NO |
| TJU_CMC_MD2.ID00086.3p-miR | TJU_CMC_MD2.ID00086.hairpin | YES | NO | NO | NO | NO | NO | NO | NO |
| TJU_CMC_MD2.ID00087.3p-miR | TJU_CMC_MD2.ID00087.hairpin | YES | NO | NO | NO | NO | NO | NO | NO |
| TJU_CMC_MD2.ID00088.5p-miR | TJU_CMC_MD2.ID00088.hairpin | YES | YES | YES | YES | NO | NO | NO | NO |
| TJU_CMC_MD2.ID00089.3p-miR | TJU_CMC_MD2.ID00089.hairpin | YES | NO | NO | NO | NO | NO | NO | NO |
| TJU_CMC_MD2.ID00090.3p-miR | TJU_CMC_MD2.ID00090.hairpin | YES | NO | NO | NO | NO | NO | NO | NO |
| TJU_CMC_MD2.ID00091.5p-miR | TJU_CMC_MD2.ID00091.hairpin | YES | YES | YES | YES | YES | NO | NO | NO |
| TJU_CMC_MD2.ID00092.3p-miR | TJU_CMC_MD2.ID00092.hairpin | YES | NO | NO | NO | NO | NO | NO | NO |
| TJU_CMC_MD2.ID00093.5p-miR | TJU_CMC_MD2.ID00093.hairpin | YES | YES | YES | YES | NO | YES | NO | NO |
| TJU_CMC_MD2.ID00094.3p-miR | TJU_CMC_MD2.ID00094.hairpin | YES | NO | NO | NO | NO | NO | NO | NO |
| TJU_CMC_MD2.ID00095.5p-miR | TJU_CMC_MD2.ID00095.hairpin | YES | YES | YES | YES | YES | NO | NO | NO |
| TJU_CMC_MD2.ID00096.5p-miR | TJU_CMC_MD2.ID00096.hairpin | YES | NO | NO | NO | NO | NO | NO | NO |
| TJU_CMC_MD2.ID00097.5p-miR | TJU_CMC_MD2.ID00097.hairpin | YES | YES | NO | YES | NO | NO | NO | NO |
| TJU_CMC_MD2.ID00098.5p-miR | TJU_CMC_MD2.ID00098.hairpin | YES | YES | YES | YES | NO | NO | NO | NO |
| TJU_CMC_MD2.ID00099.3p-miR | TJU_CMC_MD2.ID00099.hairpin | YES | NO | NO | NO | NO | NO | NO | NO |
| TJU_CMC_MD2.ID00100.5p-miR | TJU_CMC_MD2.ID00100.hairpin | YES | YES | YES | YES | YES | NO | NO | NO |
| TJU_CMC_MD2.ID00101.3p-miR | TJU_CMC_MD2.ID00101.hairpin | YES | NO | NO | NO | NO | NO | NO | NO |
| TJU_CMC_MD2.ID00102.3p-miR | TJU_CMC_MD2.ID00102.hairpin | YES | NO | NO | NO | NO | NO | NO | NO |
| TJU_CMC_MD2.ID00103.5p-miR | TJU_CMC_MD2.ID00103.hairpin | YES | NO | NO | NO | NO | YES | NO | NO |
| TJU_CMC_MD2.ID00104.5p-miR | TJU_CMC_MD2.ID00104.hairpin | YES | YES | YES | YES | NO | NO | NO | NO |
| TJU_CMC_MD2.ID00105.5p-miR | TJU_CMC_MD2.ID00105.hairpin | YES | YES | YES | NO | YES | NO | NO | NO |
| TJU_CMC_MD2.ID00106.5p-miR | TJU_CMC_MD2.ID00106.hairpin | YES | NO | YES | NO | NO | NO | NO | NO |
| TJU_CMC_MD2.ID00107.3p-miR | TJU_CMC_MD2.ID00107.hairpin | YES | NO | NO | NO | NO | NO | NO | NO |
| TJU_CMC_MD2.ID00108.3p-miR | TJU_CMC_MD2.ID00108.hairpin | YES | NO | NO | NO | NO | NO | NO | NO |
| TJU_CMC_MD2.ID00109.3p-miR | TJU_CMC_MD2.ID00109.hairpin | YES | NO | NO | NO | NO | NO | NO | NO |
| TJU_CMC_MD2.ID00110.5p-miR | TJU_CMC_MD2.ID00110.hairpin | YES | YES | YES | YES | YES | NO | NO | NO |
| TJU_CMC_MD2.ID00111.3p-miR | TJU_CMC_MD2.ID00111.hairpin | YES | NO | NO | NO | NO | NO | NO | NO |
| TJU_CMC_MD2.ID00112.5p-miR | TJU_CMC_MD2.ID00112.hairpin | YES | NO | NO | NO | NO | NO | NO | NO |
| TJU_CMC_MD2.ID00113.5p-miR | TJU_CMC_MD2.ID00113.hairpin | YES | YES | YES | NO | YES | NO | NO | NO |
| TJU_CMC_MD2.ID00114.5p-miR | TJU_CMC_MD2.ID00114.hairpin | YES | YES | YES | YES | YES | NO | NO | NO |
| TJU_CMC_MD2.ID00115.5p-miR | TJU_CMC_MD2.ID00115.hairpin | YES | YES | YES | YES | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00116.3p-miR | TJU_CMC_MD2.ID00116.hairpin | YES | NO | NO | NO | NO | NO | NO | NO |
| TJU_CMC_MD2.ID00117.5p-miR | TJU_CMC_MD2.ID00117.hairpin | YES | YES | YES | YES | NO | YES | NO | NO |
| TJU_CMC_MD2.ID00118.5p-miR | TJU_CMC_MD2.ID00118.hairpin | YES | NO | YES | YES | YES | NO | NO | NO |
| TJU_CMC_MD2.ID00119.3p-miR | TJU_CMC_MD2.ID00119.hairpin | YES | NO | NO | NO | NO | NO | NO | NO |
| TJU_CMC_MD2.ID00120.3p-miR | TJU_CMC_MD2.ID00120.hairpin | YES | NO | NO | NO | NO | NO | NO | NO |
| TJU_CMC_MD2.ID00121.5p-miR | TJU_CMC_MD2.ID00121.hairpin | YES | NO | NO | NO | NO | NO | NO | NO |
| TJU_CMC_MD2.ID00122.3p-miR | TJU_CMC_MD2.ID00122.hairpin | YES | NO | NO | NO | NO | NO | NO | NO |
| TJU_CMC_MD2.ID00122.5p-miR | TJU_CMC_MD2.ID00122.hairpin | YES | YES | YES | NO | YES | NO | NO | NO |
| TJU_CMC_MD2.ID00123.5p-miR | TJU_CMC_MD2.ID00123.hairpin | YES | YES | YES | YES | YES | NO | NO | NO |
| TJU_CMC_MD2.ID00124.5p-miR | TJU_CMC_MD2.ID00124.hairpin | YES | YES | YES | YES | YES | NO | NO | NO |
| TJU_CMC_MD2.ID00125.3p-miR | TJU_CMC_MD2.ID00125.hairpin | YES | NO | NO | NO | NO | NO | NO | NO |
| TJU_CMC_MD2.ID00126.5p-miR | TJU_CMC_MD2.ID00126.hairpin | YES | YES | YES | NO | NO | NO | NO | NO |
| TJU_CMC_MD2.ID00127.3p-miR | TJU_CMC_MD2.ID00127.hairpin | YES | NO | NO | NO | NO | NO | NO | NO |
| TJU_CMC_MD2.ID00128.3p-miR | TJU_CMC_MD2.ID00128.hairpin | YES | NO | NO | NO | NO | NO | NO | NO |
| TJU_CMC_MD2.ID00129.5p-miR | TJU_CMC_MD2.ID00129.hairpin | YES | YES | YES | YES | YES | NO | NO | NO |
| TJU_CMC_MD2.ID00130.3p-miR | TJU_CMC_MD2.ID00130.hairpin | YES | NO | NO | NO | NO | NO | NO | NO |
| TJU_CMC_MD2.ID00131.5p-miR | TJU_CMC_MD2.ID00131.hairpin | YES | YES | YES | YES | YES | NO | NO | NO |
| TJU_CMC_MD2.ID00132.5p-miR | TJU_CMC_MD2.ID00132.hairpin | YES | YES | YES | YES | YES | NO | NO | NO |
| TJU_CMC_MD2.ID00133.3p-miR | TJU_CMC_MD2.ID00133.hairpin | YES | NO | NO | NO | NO | NO | NO | NO |
| TJU_CMC_MD2.ID00134.3p-miR | TJU_CMC_MD2.ID00134.hairpin | YES | NO | NO | NO | NO | NO | NO | NO |
| TJU_CMC_MD2.ID00135.5p-miR | TJU_CMC_MD2.ID00135.hairpin | YES | NO | NO | NO | NO | NO | NO | NO |
| TJU_CMC_MD2.ID00136.5p-miR | TJU_CMC_MD2.ID00136.hairpin | YES | YES | YES | YES | NO | NO | NO | NO |
| TJU_CMC_MD2.ID00137.3p-miR | TJU_CMC_MD2.ID00137.hairpin | YES | NO | NO | NO | NO | NO | NO | NO |
| TJU_CMC_MD2.ID00138.3p-miR | TJU_CMC_MD2.ID00138.hairpin | YES | NO | NO | NO | NO | NO | NO | NO |
| TJU_CMC_MD2.ID00139.5p-miR | TJU_CMC_MD2.ID00139.hairpin | YES | YES | YES | YES | NO | NO | NO | NO |
| TJU_CMC_MD2.ID00140.3p-miR | TJU_CMC_MD2.ID00140.hairpin | YES | NO | NO | NO | NO | NO | NO | NO |
| TJU_CMC_MD2.ID00141.3p-miR | TJU_CMC_MD2.ID00141.hairpin | YES | NO | NO | NO | NO | NO | NO | NO |
| TJU_CMC_MD2.ID00142.3p-miR | TJU_CMC_MD2.ID00142.hairpin | YES | NO | NO | NO | NO | NO | NO | NO |
| TJU_CMC_MD2.ID00143.3p-miR | TJU_CMC_MD2.ID00143.hairpin | YES | YES | YES | YES | NO | NO | NO | NO |
| TJU_CMC_MD2.ID00144.3p-miR | TJU_CMC_MD2.ID00144.hairpin | YES | NO | NO | NO | NO | NO | NO | NO |
| TJU_CMC_MD2.ID00145.3p-miR | TJU_CMC_MD2.ID00145.hairpin | YES | NO | NO | NO | NO | NO | NO | NO |
| TJU_CMC_MD2.ID00145.5p-miR | TJU_CMC_MD2.ID00145.hairpin | YES | YES | YES | YES | YES | NO | NO | NO |
| TJU_CMC_MD2.ID00146.3p-miR | TJU_CMC_MD2.ID00146.hairpin | YES | NO | NO | NO | NO | NO | NO | NO |
| TJU_CMC_MD2.ID00146.5p-miR | TJU_CMC_MD2.ID00146.hairpin | YES | YES | YES | NO | YES | NO | NO | NO |
| TJU_CMC_MD2.ID00147.5p-miR | TJU_CMC_MD2.ID00147.hairpin | YES | NO | NO | NO | YES | NO | NO | NO |
| TJU_CMC_MD2.ID00148.5p-miR | TJU_CMC_MD2.ID00148.hairpin | YES | NO | NO | NO | NO | NO | NO | NO |
| TJU_CMC_MD2.ID00149.3p-miR | TJU_CMC_MD2.ID00149.hairpin | YES | NO | NO | NO | NO | NO | NO | NO |
| TJU_CMC_MD2.ID00150.5p-miR | TJU_CMC_MD2.ID00150.hairpin | YES | YES | YES | NO | NO | NO | NO | NO |
| TJU_CMC_MD2.ID00151.3p-miR | TJU_CMC_MD2.ID00151.hairpin | YES | NO | NO | NO | NO | NO | NO | NO |
| TJU_CMC_MD2.ID00152.3p-miR | TJU_CMC_MD2.ID00152.hairpin | YES | NO | NO | NO | NO | NO | NO | NO |
| TJU_CMC_MD2.ID00153.3p-miR | TJU_CMC_MD2.ID00153.hairpin | YES | NO | NO | NO | NO | NO | NO | NO |
| TJU_CMC_MD2.ID00154.3p-miR | TJU_CMC_MD2.ID00154.hairpin | YES | NO | NO | NO | NO | NO | NO | NO |
| TJU_CMC_MD2.ID00155.5p-miR | TJU_CMC_MD2.ID00155.hairpin | YES | NO | NO | NO | NO | NO | NO | NO |
| TJU_CMC_MD2.ID00156.5p-miR | TJU_CMC_MD2.ID00156.hairpin | YES | YES | YES | YES | YES | NO | NO | NO |
| TJU_CMC_MD2.ID00157.3p-miR | TJU_CMC_MD2.ID00157.hairpin | YES | NO | NO | NO | NO | NO | NO | NO |
| TJU_CMC_MD2.ID00158.5p-miR | TJU_CMC_MD2.ID00158.hairpin | YES | YES | YES | YES | YES | NO | NO | NO |
| TJU_CMC_MD2.ID00159.5p-miR | TJU_CMC_MD2.ID00159.hairpin | YES | YES | YES | YES | NO | NO | NO | NO |
| TJU_CMC_MD2.ID00160.5p-miR | TJU_CMC_MD2.ID00160.hairpin | YES | YES | YES | YES | NO | NO | NO | NO |
| TJU_CMC_MD2.ID00161.3p-miR | TJU_CMC_MD2.ID00161.hairpin | YES | NO | NO | NO | NO | NO | NO | NO |
| TJU_CMC_MD2.ID00162.3p-miR | TJU_CMC_MD2.ID00162.hairpin | YES | NO | NO | NO | NO | NO | NO | NO |
| TJU_CMC_MD2.ID00163.5p-miR | TJU_CMC_MD2.ID00163.hairpin | YES | YES | YES | YES | NO | NO | NO | NO |
| TJU_CMC_MD2.ID00164.5p-miR | TJU_CMC_MD2.ID00164.hairpin | YES | YES | YES | YES | YES | NO | NO | NO |
| TJU_CMC_MD2.ID00165.3p-miR | TJU_CMC_MD2.ID00165.hairpin | YES | NO | NO | NO | NO | NO | NO | NO |
| TJU_CMC_MD2.ID00166.5p-miR | TJU_CMC_MD2.ID00166.hairpin | YES | YES | YES | YES | YES | YES | NO | NO |
| TJU_CMC_MD2.ID00167.5p-miR | TJU_CMC_MD2.ID00167.hairpin | YES | YES | YES | YES | YES | YES | NO | NO |
| TJU_CMC_MD2.ID00168.3p-miR | TJU_CMC_MD2.ID00168.hairpin | YES | NO | NO | NO | NO | NO | NO | NO |
| TJU_CMC_MD2.ID00169.3p-miR | TJU_CMC_MD2.ID00169.hairpin | YES | NO | NO | NO | NO | NO | NO | NO |
| TJU_CMC_MD2.ID00170.3p-miR | TJU_CMC_MD2.ID00170.hairpin | YES | NO | NO | NO | NO | NO | NO | NO |
| TJU_CMC_MD2.ID00171.3p-miR | TJU_CMC_MD2.ID00171.hairpin | YES | NO | NO | NO | NO | NO | NO | NO |
| TJU_CMC_MD2.ID00172.3p-miR | TJU_CMC_MD2.ID00172.hairpin | YES | NO | NO | NO | NO | NO | NO | NO |
| TJU_CMC_MD2.ID00173.3p-miR | TJU_CMC_MD2.ID00173.hairpin | YES | NO | NO | NO | NO | NO | NO | NO |
| TJU_CMC_MD2.ID00174.5p-miR | TJU_CMC_MD2.ID00174.hairpin | YES | YES | NO | YES | YES | YES | NO | NO |
| TJU_CMC_MD2.ID00175.3p-miR | TJU_CMC_MD2.ID00175.hairpin | YES | NO | NO | NO | NO | NO | NO | NO |
| TJU_CMC_MD2.ID00176.5p-miR | TJU_CMC_MD2.ID00176.hairpin | YES | YES | YES | YES | NO | NO | NO | NO |
| TJU_CMC_MD2.ID00177.5p-miR | TJU_CMC_MD2.ID00177.hairpin | YES | YES | YES | YES | NO | NO | NO | NO |
| TJU_CMC_MD2.ID00178.5p-miR | TJU_CMC_MD2.ID00178.hairpin | YES | YES | YES | YES | YES | NO | NO | NO |
| TJU_CMC_MD2.ID00179.3p-miR | TJU_CMC_MD2.ID00179.hairpin | YES | NO | NO | NO | NO | NO | NO | NO |
| TJU_CMC_MD2.ID00180.5p-miR | TJU_CMC_MD2.ID00180.hairpin | YES | YES | YES | YES | YES | NO | NO | NO |
| TJU_CMC_MD2.ID00181.5p-miR | TJU_CMC_MD2.ID00181.hairpin | YES | NO | YES | YES | NO | NO | NO | NO |
| TJU_CMC_MD2.ID00182.5p-miR | TJU_CMC_MD2.ID00182.hairpin | YES | YES | YES | YES | YES | NO | NO | NO |
| TJU_CMC_MD2.ID00183.3p-miR | TJU_CMC_MD2.ID00183.hairpin | YES | NO | NO | NO | NO | NO | NO | NO |
| TJU_CMC_MD2.ID00183.5p-miR | TJU_CMC_MD2.ID00183.hairpin | YES | NO | NO | YES | NO | NO | NO | NO |
| TJU_CMC_MD2.ID00184.3p-miR | TJU_CMC_MD2.ID00184.hairpin | YES | NO | NO | NO | NO | NO | NO | NO |
| TJU_CMC_MD2.ID00185.5p-miR | TJU_CMC_MD2.ID00185.hairpin | YES | YES | YES | YES | NO | NO | NO | NO |
| TJU_CMC_MD2.ID00186.5p-miR | TJU_CMC_MD2.ID00186.hairpin | YES | YES | YES | YES | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
| --- | --- | --- | --- | --- | --- | --- | --- | --- | --- |
| TJU_CMC_MD2.ID00187.3p-miR | TJU_CMC_MD2.ID00187.hairpin | YES | NO | NO | NO | NO | NO | NO | NO |
| TJU_CMC_MD2.ID00188.3p-miR | TJU_CMC_MD2.ID00188.hairpin | YES | NO | NO | NO | NO | NO | NO | NO |
| TJU_CMC_MD2.ID00189.5p-miR | TJU_CMC_MD2.ID00189.hairpin | YES | YES | NO | YES | YES | NO | NO | NO |
| TJU_CMC_MD2.ID00190.3p-miR | TJU_CMC_MD2.ID00190.hairpin | YES | NO | NO | NO | NO | NO | NO | NO |
| TJU_CMC_MD2.ID00191.5p-miR | TJU_CMC_MD2.ID00191.hairpin | YES | NO | YES | NO | YES | NO | NO | NO |
| TJU_CMC_MD2.ID00192.3p-miR | TJU_CMC_MD2.ID00192.hairpin | YES | NO | NO | NO | NO | NO | NO | NO |
| TJU_CMC_MD2.ID00193.5p-miR | TJU_CMC_MD2.ID00193.hairpin | YES | YES | YES | NO | NO | NO | NO | NO |
| TJU_CMC_MD2.ID00194.3p-miR | TJU_CMC_MD2.ID00194.hairpin | YES | NO | NO | NO | NO | NO | NO | NO |
| TJU_CMC_MD2.ID00195.3p-miR | TJU_CMC_MD2.ID00195.hairpin | YES | NO | NO | NO | NO | NO | NO | NO |
| TJU_CMC_MD2.ID00196.3p-miR | TJU_CMC_MD2.ID00196.hairpin | YES | NO | NO | NO | NO | NO | NO | NO |
| TJU_CMC_MD2.ID00197.5p-miR | TJU_CMC_MD2.ID00197.hairpin | YES | YES | YES | YES | NO | NO | NO | NO |
| TJU_CMC_MD2.ID00198.3p-miR | TJU_CMC_MD2.ID00198.hairpin | YES | NO | NO | NO | NO | NO | NO | NO |
| TJU_CMC_MD2.ID00199.3p-miR | TJU_CMC_MD2.ID00199.hairpin | YES | NO | NO | NO | NO | NO | NO | NO |
| TJU_CMC_MD2.ID00200.5p-miR | TJU_CMC_MD2.ID00200.hairpin | YES | NO | NO | NO | NO | NO | NO | NO |
| TJU_CMC_MD2.ID00201.3p-miR | TJU_CMC_MD2.ID00201.hairpin | YES | NO | NO | NO | NO | NO | NO | NO |
| TJU_CMC_MD2.ID00202.5p-miR | TJU_CMC_MD2.ID00202.hairpin | YES | YES | YES | YES | NO | YES | NO | NO |
| TJU_CMC_MD2.ID00203.3p-miR | TJU_CMC_MD2.ID00203.hairpin | YES | NO | NO | NO | NO | NO | NO | NO |
| TJU_CMC_MD2.ID00204.5p-miR | TJU_CMC_MD2.ID00204.hairpin | YES | YES | YES | YES | YES | NO | NO | NO |
| TJU_CMC_MD2.ID00205.3p-miR | TJU_CMC_MD2.ID00205.hairpin | YES | YES | YES | YES | YES | NO | NO | NO |
| TJU_CMC_MD2.ID00206.3p-miR | TJU_CMC_MD2.ID00206.hairpin | YES | NO | NO | NO | NO | NO | NO | NO |
| TJU_CMC_MD2.ID00207.5p-miR | TJU_CMC_MD2.ID00207.hairpin | YES | YES | YES | NO | YES | NO | NO | NO |
| TJU_CMC_MD2.ID00208.5p-miR | TJU_CMC_MD2.ID00208.hairpin | YES | YES | YES | YES | YES | NO | NO | NO |
| TJU_CMC_MD2.ID00209.3p-miR | TJU_CMC_MD2.ID00209.hairpin | YES | NO | NO | NO | NO | NO | NO | NO |
| TJU_CMC_MD2.ID00210.5p-miR | TJU_CMC_MD2.ID00210.hairpin | YES | YES | YES | NO | NO | NO | NO | NO |
| TJU_CMC_MD2.ID00211.3p-miR | TJU_CMC_MD2.ID00211.hairpin | YES | NO | NO | NO | NO | NO | NO | NO |
| TJU_CMC_MD2.ID00212.3p-miR | TJU_CMC_MD2.ID00212.hairpin | YES | NO | NO | NO | NO | NO | NO | NO |
| TJU_CMC_MD2.ID00213.3p-miR | TJU_CMC_MD2.ID00213.hairpin | YES | NO | NO | NO | NO | NO | NO | NO |
| TJU_CMC_MD2.ID00214.3p-miR | TJU_CMC_MD2.ID00214.hairpin | YES | NO | NO | NO | NO | NO | NO | NO |
| TJU_CMC_MD2.ID00215.3p-miR | TJU_CMC_MD2.ID00215.hairpin | YES | NO | NO | NO | NO | NO | NO | NO |
| TJU_CMC_MD2.ID00216.3p-miR | TJU_CMC_MD2.ID00216.hairpin | YES | NO | NO | NO | NO | NO | NO | NO |
| TJU_CMC_MD2.ID00217.3p-miR | TJU_CMC_MD2.ID00217.hairpin | YES | NO | NO | NO | NO | NO | NO | NO |
| TJU_CMC_MD2.ID00217.5p-miR | TJU_CMC_MD2.ID00217.hairpin | YES | NO | NO | NO | NO | NO | NO | NO |
| TJU_CMC_MD2.ID00218.3p-miR | TJU_CMC_MD2.ID00218.hairpin | YES | NO | NO | NO | NO | NO | NO | NO |
| TJU_CMC_MD2.ID00219.3p-miR | TJU_CMC_MD2.ID00219.hairpin | YES | NO | NO | NO | NO | NO | NO | NO |
| TJU_CMC_MD2.ID00220.3p-miR | TJU_CMC_MD2.ID00220.hairpin | YES | NO | NO | NO | NO | NO | NO | NO |
| TJU_CMC_MD2.ID00221.5p-miR | TJU_CMC_MD2.ID00221.hairpin | YES | YES | NO | YES | NO | NO | NO | NO |
| TJU_CMC_MD2.ID00222.3p-miR | TJU_CMC_MD2.ID00222.hairpin | YES | NO | NO | NO | NO | NO | NO | NO |
| TJU_CMC_MD2.ID00223.5p-miR | TJU_CMC_MD2.ID00223.hairpin | YES | YES | YES | YES | YES | NO | NO | NO |
| TJU_CMC_MD2.ID00224.5p-miR | TJU_CMC_MD2.ID00224.hairpin | YES | YES | NO | YES | YES | NO | NO | NO |
| TJU_CMC_MD2.ID00225.3p-miR | TJU_CMC_MD2.ID00225.hairpin | YES | NO | NO | NO | NO | NO | NO | NO |
| TJU_CMC_MD2.ID00226.5p-miR | TJU_CMC_MD2.ID00226.hairpin | YES | YES | YES | YES | YES | YES | NO | NO |
| TJU_CMC_MD2.ID00227.5p-miR | TJU_CMC_MD2.ID00227.hairpin | YES | YES | YES | NO | NO | NO | NO | NO |
| TJU_CMC_MD2.ID00228.5p-miR | TJU_CMC_MD2.ID00228.hairpin | YES | YES | YES | YES | NO | NO | NO | NO |
| TJU_CMC_MD2.ID00229.5p-miR | TJU_CMC_MD2.ID00229.hairpin | YES | YES | YES | YES | YES | NO | NO | NO |
| TJU_CMC_MD2.ID00230.5p-miR | TJU_CMC_MD2.ID00230.hairpin | YES | YES | YES | YES | NO | NO | NO | NO |
| TJU_CMC_MD2.ID00231.3p-miR | TJU_CMC_MD2.ID00231.hairpin | YES | YES | YES | NO | NO | NO | NO | NO |
| TJU_CMC_MD2.ID00231.5p-miR | TJU_CMC_MD2.ID00231.hairpin | YES | YES | YES | NO | NO | NO | NO | NO |
| TJU_CMC_MD2.ID00232.3p-miR | TJU_CMC_MD2.ID00232.hairpin | YES | NO | NO | NO | NO | NO | NO | NO |
| TJU_CMC_MD2.ID00233.5p-miR | TJU_CMC_MD2.ID00233.hairpin | YES | NO | YES | NO | YES | NO | NO | NO |
| TJU_CMC_MD2.ID00234.3p-miR | TJU_CMC_MD2.ID00234.hairpin | YES | NO | NO | NO | NO | NO | NO | NO |
| TJU_CMC_MD2.ID00235.5p-miR | TJU_CMC_MD2.ID00235.hairpin | YES | NO | NO | NO | NO | NO | NO | NO |
| TJU_CMC_MD2.ID00236.5p-miR | TJU_CMC_MD2.ID00236.hairpin | YES | NO | NO | NO | NO | NO | NO | NO |
| TJU_CMC_MD2.ID00237.5p-miR | TJU_CMC_MD2.ID00237.hairpin | YES | YES | YES | YES | YES | YES | NO | NO |
| TJU_CMC_MD2.ID00238.3p-miR | TJU_CMC_MD2.ID00238.hairpin | YES | NO | NO | NO | NO | NO | NO | NO |
| TJU_CMC_MD2.ID00239.3p-miR | TJU_CMC_MD2.ID00239.hairpin | YES | NO | NO | NO | NO | NO | NO | NO |
| TJU_CMC_MD2.ID00240.5p-miR | TJU_CMC_MD2.ID00240.hairpin | YES | YES | YES | YES | YES | NO | NO | NO |
| TJU_CMC_MD2.ID00241.3p-miR | TJU_CMC_MD2.ID00241.hairpin | YES | YES | YES | YES | NO | NO | NO | NO |
| TJU_CMC_MD2.ID00242.3p-miR | TJU_CMC_MD2.ID00242.hairpin | YES | NO | NO | NO | NO | NO | NO | NO |
| TJU_CMC_MD2.ID00243.3p-miR | TJU_CMC_MD2.ID00243.hairpin | YES | NO | NO | NO | NO | NO | NO | NO |
| TJU_CMC_MD2.ID00244.3p-miR | TJU_CMC_MD2.ID00244.hairpin | YES | NO | NO | NO | NO | NO | NO | NO |
| TJU_CMC_MD2.ID00245.3p-miR | TJU_CMC_MD2.ID00245.hairpin | YES | NO | NO | NO | NO | NO | NO | NO |
| TJU_CMC_MD2.ID00246.3p-miR | TJU_CMC_MD2.ID00246.hairpin | YES | NO | NO | NO | NO | NO | NO | NO |
| TJU_CMC_MD2.ID00247.3p-miR | TJU_CMC_MD2.ID00247.hairpin | YES | YES | YES | NO | NO | NO | NO | NO |
| TJU_CMC_MD2.ID00247.5p-miR | TJU_CMC_MD2.ID00247.hairpin | YES | YES | YES | YES | NO | NO | NO | NO |
| TJU_CMC_MD2.ID00248.5p-miR | TJU_CMC_MD2.ID00248.hairpin | YES | YES | NO | YES | NO | NO | NO | NO |
| TJU_CMC_MD2.ID00249.3p-miR | TJU_CMC_MD2.ID00249.hairpin | YES | NO | NO | NO | NO | NO | NO | NO |
| TJU_CMC_MD2.ID00250.5p-miR | TJU_CMC_MD2.ID00250.hairpin | YES | YES | YES | YES | NO | NO | NO | NO |
| TJU_CMC_MD2.ID00251.5p-miR | TJU_CMC_MD2.ID00251.hairpin | YES | YES | NO | YES | NO | NO | NO | NO |
| TJU_CMC_MD2.ID00252.5p-miR | TJU_CMC_MD2.ID00252.hairpin | YES | YES | YES | YES | NO | NO | NO | NO |
| TJU_CMC_MD2.ID00253.5p-miR | TJU_CMC_MD2.ID00253.hairpin | YES | YES | YES | YES | YES | NO | NO | NO |
| TJU_CMC_MD2.ID00254.3p-miR | TJU_CMC_MD2.ID00254.hairpin | YES | NO | NO | NO | NO | NO | NO | NO |
| TJU_CMC_MD2.ID00255.5p-miR | TJU_CMC_MD2.ID00255.hairpin | YES | YES | YES | NO | YES | NO | NO | NO |
| TJU_CMC_MD2.ID00256.3p-miR | TJU_CMC_MD2.ID00256.hairpin | YES | NO | YES | NO | NO | NO | NO | NO |
| TJU_CMC_MD2.ID00257.3p-miR | TJU_CMC_MD2.ID00257.hairpin | YES | NO | NO | NO | NO | NO | NO | NO |
| TJU_CMC_MD2.ID00258.5p-miR | TJU_CMC_MD2.ID00258.hairpin | YES | YES | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00259.5p-miR | TJU_CMC_MD2.ID00259.hairpin | YES | NO | YES | NO | NO | NO | NO | NO |
| TJU_CMC_MD2.ID00260.3p-miR | TJU_CMC_MD2.ID00260.hairpin | YES | NO | NO | NO | NO | NO | NO | NO |
| TJU_CMC_MD2.ID00261.3p-miR | TJU_CMC_MD2.ID00261.hairpin | YES | NO | NO | NO | NO | NO | NO | NO |
| TJU_CMC_MD2.ID00262.3p-miR | TJU_CMC_MD2.ID00262.hairpin | YES | NO | NO | NO | NO | NO | NO | NO |
| TJU_CMC_MD2.ID00263.3p-miR | TJU_CMC_MD2.ID00263.hairpin | YES | NO | NO | NO | NO | NO | NO | NO |
| TJU_CMC_MD2.ID00264.5p-miR | TJU_CMC_MD2.ID00264.hairpin | YES | YES | YES | YES | YES | NO | NO | NO |
| TJU_CMC_MD2.ID00265.3p-miR | TJU_CMC_MD2.ID00265.hairpin | YES | NO | NO | NO | NO | NO | NO | NO |
| TJU_CMC_MD2.ID00266.3p-miR | TJU_CMC_MD2.ID00266.hairpin | YES | NO | NO | NO | NO | NO | NO | NO |
| TJU_CMC_MD2.ID00267.3p-miR | TJU_CMC_MD2.ID00267.hairpin | YES | NO | NO | NO | NO | NO | NO | NO |
| TJU_CMC_MD2.ID00268.3p-miR | TJU_CMC_MD2.ID00268.hairpin | YES | NO | NO | NO | NO | NO | NO | NO |
| TJU_CMC_MD2.ID00269.3p-miR | TJU_CMC_MD2.ID00269.hairpin | YES | NO | NO | NO | NO | NO | NO | NO |
| TJU_CMC_MD2.ID00270.5p-miR | TJU_CMC_MD2.ID00270.hairpin | YES | YES | YES | YES | NO | NO | NO | NO |
| TJU_CMC_MD2.ID00271.5p-miR | TJU_CMC_MD2.ID00271.hairpin | YES | YES | YES | NO | NO | NO | NO | NO |
| TJU_CMC_MD2.ID00272.3p-miR | TJU_CMC_MD2.ID00272.hairpin | YES | NO | NO | NO | NO | NO | NO | NO |
| TJU_CMC_MD2.ID00273.3p-miR | TJU_CMC_MD2.ID00273.hairpin | YES | YES | YES | YES | YES | NO | NO | NO |
| TJU_CMC_MD2.ID00274.5p-miR | TJU_CMC_MD2.ID00274.hairpin | YES | YES | YES | YES | NO | NO | NO | NO |
| TJU_CMC_MD2.ID00275.3p-miR | TJU_CMC_MD2.ID00275.hairpin | YES | NO | NO | NO | NO | NO | NO | NO |
| TJU_CMC_MD2.ID00276.3p-miR | TJU_CMC_MD2.ID00276.hairpin | YES | NO | NO | NO | NO | NO | NO | NO |
| TJU_CMC_MD2.ID00277.3p-miR | TJU_CMC_MD2.ID00277.hairpin | YES | NO | NO | NO | NO | NO | NO | NO |
| TJU_CMC_MD2.ID00278.3p-miR | TJU_CMC_MD2.ID00278.hairpin | YES | NO | NO | NO | NO | NO | NO | NO |
| TJU_CMC_MD2.ID00279.5p-miR | TJU_CMC_MD2.ID00279.hairpin | YES | YES | YES | YES | YES | NO | NO | NO |
| TJU_CMC_MD2.ID00280.3p-miR | TJU_CMC_MD2.ID00280.hairpin | YES | NO | NO | NO | NO | NO | NO | NO |
| TJU_CMC_MD2.ID00281.5p-miR | TJU_CMC_MD2.ID00281.hairpin | YES | YES | NO | NO | NO | NO | NO | NO |
| TJU_CMC_MD2.ID00282.5p-miR | TJU_CMC_MD2.ID00282.hairpin | YES | YES | YES | NO | YES | NO | NO | NO |
| TJU_CMC_MD2.ID00283.3p-miR | TJU_CMC_MD2.ID00283.hairpin | YES | NO | NO | NO | NO | NO | NO | NO |
| TJU_CMC_MD2.ID00284.5p-miR | TJU_CMC_MD2.ID00284.hairpin | YES | YES | YES | NO | YES | NO | NO | NO |
| TJU_CMC_MD2.ID00285.3p-miR | TJU_CMC_MD2.ID00285.hairpin | YES | NO | NO | NO | NO | NO | NO | NO |
| TJU_CMC_MD2.ID00286.3p-miR | TJU_CMC_MD2.ID00286.hairpin | YES | NO | NO | NO | NO | NO | NO | NO |
| TJU_CMC_MD2.ID00287.3p-miR | TJU_CMC_MD2.ID00287.hairpin | YES | NO | NO | NO | NO | NO | NO | NO |
| TJU_CMC_MD2.ID00288.3p-miR | TJU_CMC_MD2.ID00288.hairpin | YES | NO | NO | NO | NO | NO | NO | NO |
| TJU_CMC_MD2.ID00288.5p-miR | TJU_CMC_MD2.ID00288.hairpin | YES | NO | YES | NO | NO | NO | NO | NO |
| TJU_CMC_MD2.ID00289.5p-miR | TJU_CMC_MD2.ID00289.hairpin | YES | YES | YES | NO | YES | NO | NO | NO |
| TJU_CMC_MD2.ID00290.5p-miR | TJU_CMC_MD2.ID00290.hairpin | YES | YES | NO | NO | NO | NO | NO | NO |
| TJU_CMC_MD2.ID00291.3p-miR | TJU_CMC_MD2.ID00291.hairpin | YES | NO | NO | NO | NO | NO | NO | NO |
| TJU_CMC_MD2.ID00292.3p-miR | TJU_CMC_MD2.ID00292.hairpin | YES | NO | NO | NO | NO | NO | NO | NO |
| TJU_CMC_MD2.ID00293.3p-miR | TJU_CMC_MD2.ID00293.hairpin | YES | YES | YES | YES | NO | NO | NO | NO |
| TJU_CMC_MD2.ID00293.5p-miR | TJU_CMC_MD2.ID00293.hairpin | YES | YES | YES | YES | YES | NO | NO | NO |
| TJU_CMC_MD2.ID00294.5p-miR | TJU_CMC_MD2.ID00294.hairpin | YES | YES | YES | YES | NO | NO | NO | NO |
| TJU_CMC_MD2.ID00295.3p-miR | TJU_CMC_MD2.ID00295.hairpin | YES | NO | NO | NO | NO | NO | NO | NO |
| TJU_CMC_MD2.ID00296.3p-miR | TJU_CMC_MD2.ID00296.hairpin | YES | NO | YES | NO | NO | NO | NO | NO |
| TJU_CMC_MD2.ID00297.5p-miR | TJU_CMC_MD2.ID00297.hairpin | YES | YES | YES | YES | YES | NO | NO | NO |
| TJU_CMC_MD2.ID00298.3p-miR | TJU_CMC_MD2.ID00298.hairpin | YES | NO | NO | NO | NO | NO | NO | NO |
| TJU_CMC_MD2.ID00299.3p-miR | TJU_CMC_MD2.ID00299.hairpin | YES | NO | NO | NO | NO | NO | NO | NO |
| TJU_CMC_MD2.ID00300.5p-miR | TJU_CMC_MD2.ID00300.hairpin | YES | YES | YES | YES | NO | YES | NO | NO |
| TJU_CMC_MD2.ID00301.3p-miR | TJU_CMC_MD2.ID00301.hairpin | YES | NO | NO | NO | NO | NO | NO | NO |
| TJU_CMC_MD2.ID00302.5p-miR | TJU_CMC_MD2.ID00302.hairpin | YES | YES | YES | NO | NO | NO | NO | NO |
| TJU_CMC_MD2.ID00303.5p-miR | TJU_CMC_MD2.ID00303.hairpin | YES | YES | NO | YES | NO | NO | NO | NO |
| TJU_CMC_MD2.ID00304.5p-miR | TJU_CMC_MD2.ID00304.hairpin | YES | NO | NO | NO | NO | NO | NO | NO |
| TJU_CMC_MD2.ID00305.3p-miR | TJU_CMC_MD2.ID00305.hairpin | YES | NO | NO | NO | NO | NO | NO | NO |
| TJU_CMC_MD2.ID00306.5p-miR | TJU_CMC_MD2.ID00306.hairpin | YES | NO | NO | NO | NO | NO | NO | NO |
| TJU_CMC_MD2.ID00307.5p-miR | TJU_CMC_MD2.ID00307.hairpin | YES | NO | NO | NO | NO | NO | NO | NO |
| TJU_CMC_MD2.ID00308.3p-miR | TJU_CMC_MD2.ID00308.hairpin | YES | NO | NO | NO | NO | NO | NO | NO |
| TJU_CMC_MD2.ID00309.5p-miR | TJU_CMC_MD2.ID00309.hairpin | YES | YES | YES | YES | NO | NO | NO | NO |
| TJU_CMC_MD2.ID00310.3p-miR | TJU_CMC_MD2.ID00310.hairpin | YES | NO | NO | NO | NO | NO | NO | NO |
| TJU_CMC_MD2.ID00311.5p-miR | TJU_CMC_MD2.ID00311.hairpin | YES | NO | NO | NO | NO | NO | NO | NO |
| TJU_CMC_MD2.ID00312.3p-miR | TJU_CMC_MD2.ID00312.hairpin | YES | NO | NO | NO | NO | NO | NO | NO |
| TJU_CMC_MD2.ID00313.3p-miR | TJU_CMC_MD2.ID00313.hairpin | YES | NO | NO | NO | NO | NO | NO | NO |
| TJU_CMC_MD2.ID00314.3p-miR | TJU_CMC_MD2.ID00314.hairpin | YES | NO | NO | NO | NO | NO | NO | NO |
| TJU_CMC_MD2.ID00314.5p-miR | TJU_CMC_MD2.ID00314.hairpin | YES | YES | NO | YES | YES | NO | NO | NO |
| TJU_CMC_MD2.ID00315.3p-miR | TJU_CMC_MD2.ID00315.hairpin | YES | NO | NO | NO | NO | NO | NO | NO |
| TJU_CMC_MD2.ID00315.5p-miR | TJU_CMC_MD2.ID00315.hairpin | YES | NO | NO | NO | NO | NO | NO | NO |
| TJU_CMC_MD2.ID00316.3p-miR | TJU_CMC_MD2.ID00316.hairpin | YES | NO | NO | NO | NO | NO | NO | NO |
| TJU_CMC_MD2.ID00317.5p-miR | TJU_CMC_MD2.ID00317.hairpin | YES | YES | YES | YES | YES | NO | NO | NO |
| TJU_CMC_MD2.ID00318.3p-miR | TJU_CMC_MD2.ID00318.hairpin | YES | NO | NO | NO | NO | NO | NO | NO |
| TJU_CMC_MD2.ID00319.3p-miR | TJU_CMC_MD2.ID00319.hairpin | YES | NO | NO | NO | NO | NO | NO | NO |
| TJU_CMC_MD2.ID00320.3p-miR | TJU_CMC_MD2.ID00320.hairpin | YES | NO | NO | NO | NO | NO | NO | NO |
| TJU_CMC_MD2.ID00321.5p-miR | TJU_CMC_MD2.ID00321.hairpin | YES | NO | YES | YES | YES | NO | NO | NO |
| TJU_CMC_MD2.ID00322.5p-miR | TJU_CMC_MD2.ID00322.hairpin | YES | YES | YES | YES | YES | NO | NO | NO |
| TJU_CMC_MD2.ID00323.3p-miR | TJU_CMC_MD2.ID00323.hairpin | YES | NO | NO | NO | NO | NO | NO | NO |
| TJU_CMC_MD2.ID00324.3p-miR | TJU_CMC_MD2.ID00324.hairpin | YES | NO | NO | NO | NO | NO | NO | NO |
| TJU_CMC_MD2.ID00325.3p-miR | TJU_CMC_MD2.ID00325.hairpin | YES | NO | NO | NO | NO | NO | NO | NO |
| TJU_CMC_MD2.ID00326.5p-miR | TJU_CMC_MD2.ID00326.hairpin | YES | NO | NO | YES | NO | NO | NO | NO |
| TJU_CMC_MD2.ID00327.3p-miR | TJU_CMC_MD2.ID00327.hairpin | YES | NO | NO | NO | NO | NO | NO | NO |
| TJU_CMC_MD2.ID00327.5p-miR | TJU_CMC_MD2.ID00327.hairpin | YES | NO | NO | YES | NO | NO | NO | NO |
| TJU_CMC_MD2.ID00328.3p-miR | TJU_CMC_MD2.ID00328.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00329.3p-miR | TJU_CMC_MD2.ID00329.hairpin | YES | NO | NO | NO | NO | NO | NO | NO |
| TJU_CMC_MD2.ID00330.5p-miR | TJU_CMC_MD2.ID00330.hairpin | YES | YES | NO | NO | YES | NO | NO | NO |
| TJU_CMC_MD2.ID00331.5p-miR | TJU_CMC_MD2.ID00331.hairpin | YES | YES | NO | NO | NO | NO | NO | NO |
| TJU_CMC_MD2.ID00332.3p-miR | TJU_CMC_MD2.ID00332.hairpin | YES | NO | NO | NO | NO | NO | NO | NO |
| TJU_CMC_MD2.ID00333.3p-miR | TJU_CMC_MD2.ID00333.hairpin | YES | NO | NO | NO | NO | NO | NO | NO |
| TJU_CMC_MD2.ID00334.3p-miR | TJU_CMC_MD2.ID00334.hairpin | YES | NO | NO | NO | NO | NO | NO | NO |
| TJU_CMC_MD2.ID00335.5p-miR | TJU_CMC_MD2.ID00335.hairpin | YES | YES | YES | YES | YES | NO | NO | NO |
| TJU_CMC_MD2.ID00336.3p-miR | TJU_CMC_MD2.ID00336.hairpin | YES | NO | NO | NO | NO | NO | NO | NO |
| TJU_CMC_MD2.ID00337.3p-miR | TJU_CMC_MD2.ID00337.hairpin | YES | NO | NO | NO | NO | NO | NO | NO |
| TJU_CMC_MD2.ID00338.3p-miR | TJU_CMC_MD2.ID00338.hairpin | YES | NO | NO | NO | NO | NO | NO | NO |
| TJU_CMC_MD2.ID00339.3p-miR | TJU_CMC_MD2.ID00339.hairpin | YES | NO | NO | NO | NO | NO | NO | NO |
| TJU_CMC_MD2.ID00340.5p-miR | TJU_CMC_MD2.ID00340.hairpin | YES | YES | YES | NO | NO | NO | NO | NO |
| TJU_CMC_MD2.ID00341.5p-miR | TJU_CMC_MD2.ID00341.hairpin | YES | YES | NO | YES | YES | NO | NO | NO |
| TJU_CMC_MD2.ID00342.5p-miR | TJU_CMC_MD2.ID00342.hairpin | YES | YES | YES | YES | NO | YES | NO | NO |
| TJU_CMC_MD2.ID00343.3p-miR | TJU_CMC_MD2.ID00343.hairpin | YES | YES | YES | YES | NO | NO | NO | NO |
| TJU_CMC_MD2.ID00344.5p-miR | TJU_CMC_MD2.ID00344.hairpin | YES | YES | NO | NO | NO | NO | NO | NO |
| TJU_CMC_MD2.ID00345.3p-miR | TJU_CMC_MD2.ID00345.hairpin | YES | NO | NO | NO | NO | NO | NO | NO |
| TJU_CMC_MD2.ID00346.3p-miR | TJU_CMC_MD2.ID00346.hairpin | YES | NO | NO | NO | NO | NO | NO | NO |
| TJU_CMC_MD2.ID00347.3p-miR | TJU_CMC_MD2.ID00347.hairpin | YES | NO | NO | NO | NO | NO | NO | NO |
| TJU_CMC_MD2.ID00348.3p-miR | TJU_CMC_MD2.ID00348.hairpin | YES | NO | NO | NO | NO | NO | NO | NO |
| TJU_CMC_MD2.ID00349.3p-miR | TJU_CMC_MD2.ID00349.hairpin | YES | NO | NO | NO | NO | NO | NO | NO |
| TJU_CMC_MD2.ID00350.3p-miR | TJU_CMC_MD2.ID00350.hairpin | YES | NO | NO | NO | NO | NO | NO | NO |
| TJU_CMC_MD2.ID00350.5p-miR | TJU_CMC_MD2.ID00350.hairpin | YES | NO | YES | NO | YES | NO | NO | NO |
| TJU_CMC_MD2.ID00351.3p-miR | TJU_CMC_MD2.ID00351.hairpin | YES | NO | NO | NO | NO | NO | NO | NO |
| TJU_CMC_MD2.ID00352.3p-miR | TJU_CMC_MD2.ID00352.hairpin | YES | NO | NO | NO | NO | NO | NO | NO |
| TJU_CMC_MD2.ID00353.5p-miR | TJU_CMC_MD2.ID00353.hairpin | YES | YES | NO | NO | NO | NO | NO | NO |
| TJU_CMC_MD2.ID00354.3p-miR | TJU_CMC_MD2.ID00354.hairpin | YES | NO | NO | NO | NO | NO | NO | NO |
| TJU_CMC_MD2.ID00355.5p-miR | TJU_CMC_MD2.ID00355.hairpin | YES | YES | YES | YES | NO | NO | NO | NO |
| TJU_CMC_MD2.ID00356.3p-miR | TJU_CMC_MD2.ID00356.hairpin | YES | NO | NO | NO | NO | NO | NO | NO |
| TJU_CMC_MD2.ID00357.3p-miR | TJU_CMC_MD2.ID00357.hairpin | YES | NO | NO | NO | NO | NO | NO | NO |
| TJU_CMC_MD2.ID00357.5p-miR | TJU_CMC_MD2.ID00357.hairpin | YES | NO | YES | YES | NO | NO | NO | NO |
| TJU_CMC_MD2.ID00358.3p-miR | TJU_CMC_MD2.ID00358.hairpin | YES | NO | YES | YES | YES | NO | NO | NO |
| TJU_CMC_MD2.ID00358.5p-miR | TJU_CMC_MD2.ID00358.hairpin | YES | NO | YES | NO | NO | NO | NO | NO |
| TJU_CMC_MD2.ID00359.5p-miR | TJU_CMC_MD2.ID00359.hairpin | YES | NO | YES | NO | NO | NO | NO | NO |
| TJU_CMC_MD2.ID00360.3p-miR | TJU_CMC_MD2.ID00360.hairpin | YES | NO | NO | NO | NO | NO | NO | NO |
| TJU_CMC_MD2.ID00361.3p-miR | TJU_CMC_MD2.ID00361.hairpin | YES | NO | NO | NO | NO | NO | NO | NO |
| TJU_CMC_MD2.ID00362.5p-miR | TJU_CMC_MD2.ID00362.hairpin | YES | YES | YES | YES | YES | NO | NO | NO |
| TJU_CMC_MD2.ID00363.3p-miR | TJU_CMC_MD2.ID00363.hairpin | YES | NO | NO | NO | NO | NO | NO | NO |
| TJU_CMC_MD2.ID00364.5p-miR | TJU_CMC_MD2.ID00364.hairpin | YES | YES | YES | YES | NO | YES | NO | NO |
| TJU_CMC_MD2.ID00365.3p-miR | TJU_CMC_MD2.ID00365.hairpin | YES | NO | NO | NO | NO | NO | NO | NO |
| TJU_CMC_MD2.ID00365.5p-miR | TJU_CMC_MD2.ID00365.hairpin | YES | YES | YES | NO | YES | NO | NO | NO |
| TJU_CMC_MD2.ID00366.3p-miR | TJU_CMC_MD2.ID00366.hairpin | YES | YES | YES | YES | YES | NO | NO | NO |
| TJU_CMC_MD2.ID00367.5p-miR | TJU_CMC_MD2.ID00367.hairpin | YES | YES | YES | NO | YES | NO | NO | NO |
| TJU_CMC_MD2.ID00368.3p-miR | TJU_CMC_MD2.ID00368.hairpin | YES | NO | NO | NO | NO | NO | NO | NO |
| TJU_CMC_MD2.ID00369.3p-miR | TJU_CMC_MD2.ID00369.hairpin | YES | NO | NO | NO | NO | NO | NO | NO |
| TJU_CMC_MD2.ID00370.3p-miR | TJU_CMC_MD2.ID00370.hairpin | YES | NO | NO | NO | NO | NO | NO | NO |
| TJU_CMC_MD2.ID00370.5p-miR | TJU_CMC_MD2.ID00370.hairpin | YES | YES | YES | YES | NO | NO | NO | NO |
| TJU_CMC_MD2.ID00371.5p-miR | TJU_CMC_MD2.ID00371.hairpin | YES | NO | YES | YES | NO | NO | NO | NO |
| TJU_CMC_MD2.ID00372.5p-miR | TJU_CMC_MD2.ID00372.hairpin | YES | YES | NO | YES | NO | NO | NO | NO |
| TJU_CMC_MD2.ID00373.3p-miR | TJU_CMC_MD2.ID00373.hairpin | YES | NO | NO | NO | NO | NO | NO | NO |
| TJU_CMC_MD2.ID00374.3p-miR | TJU_CMC_MD2.ID00374.hairpin | YES | NO | NO | NO | NO | NO | NO | NO |
| TJU_CMC_MD2.ID00375.3p-miR | TJU_CMC_MD2.ID00375.hairpin | YES | NO | NO | NO | NO | NO | NO | NO |
| TJU_CMC_MD2.ID00376.5p-miR | TJU_CMC_MD2.ID00376.hairpin | YES | YES | YES | YES | NO | NO | NO | NO |
| TJU_CMC_MD2.ID00377.3p-miR | TJU_CMC_MD2.ID00377.hairpin | YES | NO | NO | NO | NO | NO | NO | NO |
| TJU_CMC_MD2.ID00378.3p-miR | TJU_CMC_MD2.ID00378.hairpin | YES | NO | NO | NO | NO | NO | NO | NO |
| TJU_CMC_MD2.ID00379.3p-miR | TJU_CMC_MD2.ID00379.hairpin | YES | NO | NO | NO | NO | NO | NO | NO |
| TJU_CMC_MD2.ID00380.3p-miR | TJU_CMC_MD2.ID00380.hairpin | YES | NO | NO | NO | NO | NO | NO | NO |
| TJU_CMC_MD2.ID00381.3p-miR | TJU_CMC_MD2.ID00381.hairpin | YES | NO | NO | NO | NO | NO | NO | NO |
| TJU_CMC_MD2.ID00382.3p-miR | TJU_CMC_MD2.ID00382.hairpin | YES | NO | NO | NO | NO | NO | NO | NO |
| TJU_CMC_MD2.ID00382.5p-miR | TJU_CMC_MD2.ID00382.hairpin | YES | NO | NO | NO | NO | NO | NO | NO |
| TJU_CMC_MD2.ID00383.3p-miR | TJU_CMC_MD2.ID00383.hairpin | YES | NO | NO | NO | NO | NO | NO | NO |
| TJU_CMC_MD2.ID00383.5p-miR | TJU_CMC_MD2.ID00383.hairpin | YES | YES | YES | NO | NO | NO | NO | NO |
| TJU_CMC_MD2.ID00384.3p-miR | TJU_CMC_MD2.ID00384.hairpin | YES | NO | NO | NO | NO | NO | NO | NO |
| TJU_CMC_MD2.ID00385.5p-miR | TJU_CMC_MD2.ID00385.hairpin | YES | YES | YES | NO | NO | NO | NO | NO |
| TJU_CMC_MD2.ID00386.3p-miR | TJU_CMC_MD2.ID00386.hairpin | YES | YES | YES | YES | YES | NO | NO | NO |
| TJU_CMC_MD2.ID00387.3p-miR | TJU_CMC_MD2.ID00387.hairpin | YES | NO | NO | NO | NO | NO | NO | NO |
| TJU_CMC_MD2.ID00388.3p-miR | TJU_CMC_MD2.ID00388.hairpin | YES | NO | NO | NO | NO | NO | NO | NO |
| TJU_CMC_MD2.ID00389.5p-miR | TJU_CMC_MD2.ID00389.hairpin | YES | YES | YES | YES | NO | NO | NO | NO |
| TJU_CMC_MD2.ID00390.5p-miR | TJU_CMC_MD2.ID00390.hairpin | YES | YES | YES | YES | YES | NO | NO | NO |
| TJU_CMC_MD2.ID00391.5p-miR | TJU_CMC_MD2.ID00391.hairpin | YES | YES | YES | YES | YES | NO | NO | NO |
| TJU_CMC_MD2.ID00392.3p-miR | TJU_CMC_MD2.ID00392.hairpin | YES | YES | YES | NO | NO | NO | NO | NO |
| TJU_CMC_MD2.ID00392.5p-miR | TJU_CMC_MD2.ID00392.hairpin | YES | YES | NO | NO | NO | NO | NO | NO |
| TJU_CMC_MD2.ID00393.3p-miR | TJU_CMC_MD2.ID00393.hairpin | YES | NO | NO | NO | NO | NO | NO | NO |
| TJU_CMC_MD2.ID00394.3p-miR | TJU_CMC_MD2.ID00394.hairpin | YES | NO | NO | NO | NO | NO | NO | NO |
| TJU_CMC_MD2.ID00395.5p-miR | TJU_CMC_MD2.ID00395.hairpin | YES | YES | YES | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00396.3p-miR | TJU_CMC_MD2.ID00396.hairpin | YES | YES | YES | YES | NO | NO | NO | NO |
| TJU_CMC_MD2.ID00397.5p-miR | TJU_CMC_MD2.ID00397.hairpin | YES | YES | YES | YES | NO | NO | NO | NO |
| TJU_CMC_MD2.ID00398.3p-miR | TJU_CMC_MD2.ID00398.hairpin | YES | NO | NO | NO | NO | NO | NO | NO |
| TJU_CMC_MD2.ID00399.3p-miR | TJU_CMC_MD2.ID00399.hairpin | YES | NO | NO | NO | NO | NO | NO | NO |
| TJU_CMC_MD2.ID00400.5p-miR | TJU_CMC_MD2.ID00400.hairpin | YES | YES | YES | YES | YES | YES | NO | NO |
| TJU_CMC_MD2.ID00401.5p-miR | TJU_CMC_MD2.ID00401.hairpin | YES | NO | NO | NO | NO | NO | NO | NO |
| TJU_CMC_MD2.ID00402.5p-miR | TJU_CMC_MD2.ID00402.hairpin | YES | YES | YES | YES | NO | NO | NO | NO |
| TJU_CMC_MD2.ID00403.3p-miR | TJU_CMC_MD2.ID00403.hairpin | YES | NO | NO | NO | NO | NO | NO | NO |
| TJU_CMC_MD2.ID00404.3p-miR | TJU_CMC_MD2.ID00404.hairpin | YES | NO | NO | NO | NO | NO | NO | NO |
| TJU_CMC_MD2.ID00405.3p-miR | TJU_CMC_MD2.ID00405.hairpin | YES | NO | NO | NO | NO | NO | NO | NO |
| TJU_CMC_MD2.ID00406.3p-miR | TJU_CMC_MD2.ID00406.hairpin | YES | NO | NO | NO | NO | NO | NO | NO |
| TJU_CMC_MD2.ID00407.3p-miR | TJU_CMC_MD2.ID00407.hairpin | YES | NO | NO | NO | NO | NO | NO | NO |
| TJU_CMC_MD2.ID00408.5p-miR | TJU_CMC_MD2.ID00408.hairpin | YES | YES | YES | NO | YES | NO | NO | NO |
| TJU_CMC_MD2.ID00409.5p-miR | TJU_CMC_MD2.ID00409.hairpin | YES | YES | YES | YES | NO | NO | NO | NO |
| TJU_CMC_MD2.ID00410.3p-miR | TJU_CMC_MD2.ID00410.hairpin | YES | NO | NO | NO | NO | NO | NO | NO |
| TJU_CMC_MD2.ID00411.5p-miR | TJU_CMC_MD2.ID00411.hairpin | YES | YES | YES | YES | NO | NO | NO | NO |
| TJU_CMC_MD2.ID00412.3p-miR | TJU_CMC_MD2.ID00412.hairpin | YES | NO | NO | NO | NO | NO | NO | NO |
| TJU_CMC_MD2.ID00413.5p-miR | TJU_CMC_MD2.ID00413.hairpin | YES | YES | YES | YES | YES | NO | NO | NO |
| TJU_CMC_MD2.ID00414.3p-miR | TJU_CMC_MD2.ID00414.hairpin | YES | NO | NO | NO | NO | NO | NO | NO |
| TJU_CMC_MD2.ID00415.5p-miR | TJU_CMC_MD2.ID00415.hairpin | YES | YES | YES | YES | NO | NO | NO | NO |
| TJU_CMC_MD2.ID00416.5p-miR | TJU_CMC_MD2.ID00416.hairpin | YES | YES | YES | YES | YES | NO | NO | NO |
| TJU_CMC_MD2.ID00417.3p-miR | TJU_CMC_MD2.ID00417.hairpin | YES | NO | NO | NO | NO | NO | NO | NO |
| TJU_CMC_MD2.ID00418.5p-miR | TJU_CMC_MD2.ID00418.hairpin | YES | NO | YES | YES | YES | YES | NO | NO |
| TJU_CMC_MD2.ID00419.3p-miR | TJU_CMC_MD2.ID00419.hairpin | YES | NO | NO | NO | NO | NO | NO | NO |
| TJU_CMC_MD2.ID00420.3p-miR | TJU_CMC_MD2.ID00420.hairpin | YES | NO | NO | NO | NO | NO | NO | NO |
| TJU_CMC_MD2.ID00421.3p-miR | TJU_CMC_MD2.ID00421.hairpin | YES | NO | NO | NO | NO | NO | NO | NO |
| TJU_CMC_MD2.ID00422.3p-miR | TJU_CMC_MD2.ID00422.hairpin | YES | NO | NO | NO | NO | NO | NO | NO |
| TJU_CMC_MD2.ID00423.3p-miR | TJU_CMC_MD2.ID00423.hairpin | YES | NO | NO | NO | NO | NO | NO | NO |
| TJU_CMC_MD2.ID00424.5p-miR | TJU_CMC_MD2.ID00424.hairpin | YES | YES | YES | YES | NO | NO | NO | NO |
| TJU_CMC_MD2.ID00425.5p-miR | TJU_CMC_MD2.ID00425.hairpin | YES | YES | YES | YES | YES | NO | NO | NO |
| TJU_CMC_MD2.ID00426.3p-miR | TJU_CMC_MD2.ID00426.hairpin | YES | NO | NO | NO | NO | NO | NO | NO |
| TJU_CMC_MD2.ID00427.5p-miR | TJU_CMC_MD2.ID00427.hairpin | YES | YES | YES | YES | NO | NO | NO | NO |
| TJU_CMC_MD2.ID00428.3p-miR | TJU_CMC_MD2.ID00428.hairpin | YES | NO | NO | NO | NO | NO | NO | NO |
| TJU_CMC_MD2.ID00429.3p-miR | TJU_CMC_MD2.ID00429.hairpin | YES | NO | NO | NO | NO | NO | NO | NO |
| TJU_CMC_MD2.ID00430.3p-miR | TJU_CMC_MD2.ID00430.hairpin | YES | YES | YES | YES | YES | NO | NO | NO |
| TJU_CMC_MD2.ID00431.5p-miR | TJU_CMC_MD2.ID00431.hairpin | YES | NO | NO | YES | NO | NO | NO | NO |
| TJU_CMC_MD2.ID00432.3p-miR | TJU_CMC_MD2.ID00432.hairpin | YES | NO | NO | NO | NO | NO | NO | NO |
| TJU_CMC_MD2.ID00433.3p-miR | TJU_CMC_MD2.ID00433.hairpin | YES | NO | NO | NO | NO | NO | NO | NO |
| TJU_CMC_MD2.ID00434.3p-miR | TJU_CMC_MD2.ID00434.hairpin | YES | NO | NO | NO | NO | NO | NO | NO |
| TJU_CMC_MD2.ID00435.3p-miR | TJU_CMC_MD2.ID00435.hairpin | YES | NO | NO | NO | NO | NO | NO | NO |
| TJU_CMC_MD2.ID00435.5p-miR | TJU_CMC_MD2.ID00435.hairpin | YES | YES | YES | YES | NO | NO | NO | NO |
| TJU_CMC_MD2.ID00436.3p-miR | TJU_CMC_MD2.ID00436.hairpin | YES | NO | NO | NO | NO | NO | NO | NO |
| TJU_CMC_MD2.ID00437.3p-miR | TJU_CMC_MD2.ID00437.hairpin | YES | NO | NO | NO | NO | NO | NO | NO |
| TJU_CMC_MD2.ID00438.3p-miR | TJU_CMC_MD2.ID00438.hairpin | YES | NO | NO | NO | NO | NO | NO | NO |
| TJU_CMC_MD2.ID00439.3p-miR | TJU_CMC_MD2.ID00439.hairpin | YES | YES | YES | YES | YES | NO | NO | NO |
| TJU_CMC_MD2.ID00440.5p-miR | TJU_CMC_MD2.ID00440.hairpin | YES | YES | YES | YES | NO | NO | NO | NO |
| TJU_CMC_MD2.ID00441.3p-miR | TJU_CMC_MD2.ID00441.hairpin | YES | NO | NO | NO | NO | NO | NO | NO |
| TJU_CMC_MD2.ID00442.5p-miR | TJU_CMC_MD2.ID00442.hairpin | YES | YES | YES | YES | YES | NO | NO | NO |
| TJU_CMC_MD2.ID00443.5p-miR | TJU_CMC_MD2.ID00443.hairpin | YES | YES | YES | YES | YES | NO | NO | NO |
| TJU_CMC_MD2.ID00444.5p-miR | TJU_CMC_MD2.ID00444.hairpin | YES | YES | YES | YES | NO | NO | NO | NO |
| TJU_CMC_MD2.ID00445.3p-miR | TJU_CMC_MD2.ID00445.hairpin | YES | NO | NO | NO | NO | NO | NO | NO |
| TJU_CMC_MD2.ID00446.3p-miR | TJU_CMC_MD2.ID00446.hairpin | YES | NO | NO | NO | NO | NO | NO | NO |
| TJU_CMC_MD2.ID00447.5p-miR | TJU_CMC_MD2.ID00447.hairpin | YES | YES | NO | YES | NO | NO | NO | NO |
| TJU_CMC_MD2.ID00448.3p-miR | TJU_CMC_MD2.ID00448.hairpin | YES | NO | NO | NO | NO | NO | NO | NO |
| TJU_CMC_MD2.ID00448.5p-miR | TJU_CMC_MD2.ID00448.hairpin | YES | YES | YES | YES | YES | NO | NO | NO |
| TJU_CMC_MD2.ID00449.5p-miR | TJU_CMC_MD2.ID00449.hairpin | YES | YES | YES | YES | YES | NO | NO | NO |
| TJU_CMC_MD2.ID00450.3p-miR | TJU_CMC_MD2.ID00450.hairpin | YES | NO | NO | NO | NO | NO | NO | NO |
| TJU_CMC_MD2.ID00451.3p-miR | TJU_CMC_MD2.ID00451.hairpin | YES | NO | NO | NO | NO | NO | NO | NO |
| TJU_CMC_MD2.ID00452.3p-miR | TJU_CMC_MD2.ID00452.hairpin | YES | NO | NO | NO | NO | NO | NO | NO |
| TJU_CMC_MD2.ID00453.3p-miR | TJU_CMC_MD2.ID00453.hairpin | YES | NO | NO | NO | NO | NO | NO | NO |
| TJU_CMC_MD2.ID00454.3p-miR | TJU_CMC_MD2.ID00454.hairpin | YES | NO | NO | NO | NO | NO | NO | NO |
| TJU_CMC_MD2.ID00455.5p-miR | TJU_CMC_MD2.ID00455.hairpin | YES | NO | NO | NO | NO | NO | NO | NO |
| TJU_CMC_MD2.ID00456.5p-miR | TJU_CMC_MD2.ID00456.hairpin | YES | YES | YES | YES | NO | NO | NO | NO |
| TJU_CMC_MD2.ID00457.3p-miR | TJU_CMC_MD2.ID00457.hairpin | YES | NO | NO | NO | NO | NO | NO | NO |
| TJU_CMC_MD2.ID00458.5p-miR | TJU_CMC_MD2.ID00458.hairpin | YES | NO | NO | NO | NO | NO | NO | NO |
| TJU_CMC_MD2.ID00459.5p-miR | TJU_CMC_MD2.ID00459.hairpin | YES | YES | NO | YES | NO | NO | NO | NO |
| TJU_CMC_MD2.ID00460.5p-miR | TJU_CMC_MD2.ID00460.hairpin | YES | NO | YES | YES | YES | NO | NO | NO |
| TJU_CMC_MD2.ID00461.3p-miR | TJU_CMC_MD2.ID00461.hairpin | YES | YES | YES | YES | YES | NO | NO | NO |
| TJU_CMC_MD2.ID00462.3p-miR | TJU_CMC_MD2.ID00462.hairpin | YES | NO | NO | NO | NO | NO | NO | NO |
| TJU_CMC_MD2.ID00463.3p-miR | TJU_CMC_MD2.ID00463.hairpin | YES | NO | NO | NO | NO | NO | NO | NO |
| TJU_CMC_MD2.ID00464.3p-miR | TJU_CMC_MD2.ID00464.hairpin | YES | NO | NO | NO | NO | NO | NO | NO |
| TJU_CMC_MD2.ID00464.5p-miR | TJU_CMC_MD2.ID00464.hairpin | YES | YES | YES | NO | YES | NO | NO | NO |
| TJU_CMC_MD2.ID00465.5p-miR | TJU_CMC_MD2.ID00465.hairpin | YES | NO | NO | NO | NO | NO | NO | NO |
| TJU_CMC_MD2.ID00466.5p-miR | TJU_CMC_MD2.ID00466.hairpin | YES | YES | YES | YES | NO | NO | NO | NO |
| TJU_CMC_MD2.ID00467.5p-miR | TJU_CMC_MD2.ID00467.hairpin | YES | YES | NO | YES | YES | NO | NO | NO |

TABLE 7-continued

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00468.3p-miR | TJU_CMC_MD2.ID00468.hairpin | YES | NO | NO | NO | NO | NO | NO | NO |
| TJU_CMC_MD2.ID00469.3p-miR | TJU_CMC_MD2.ID00469.hairpin | YES | NO | NO | NO | NO | NO | NO | NO |
| TJU_CMC_MD2.ID00470.5p-miR | TJU_CMC_MD2.ID00470.hairpin | YES | YES | YES | NO | NO | NO | NO | NO |
| TJU_CMC_MD2.ID00471.3p-miR | TJU_CMC_MD2.ID00471.hairpin | YES | NO | NO | NO | NO | NO | NO | NO |
| TJU_CMC_MD2.ID00472.3p-miR | TJU_CMC_MD2.ID00472.hairpin | YES | YES | YES | NO | YES | NO | NO | NO |
| TJU_CMC_MD2.ID00472.5p-miR | TJU_CMC_MD2.ID00472.hairpin | YES | YES | YES | NO | YES | NO | NO | NO |
| TJU_CMC_MD2.ID00473.3p-miR | TJU_CMC_MD2.ID00473.hairpin | YES | NO | NO | NO | NO | NO | NO | NO |
| TJU_CMC_MD2.ID00474.3p-miR | TJU_CMC_MD2.ID00474.hairpin | YES | NO | NO | NO | NO | NO | NO | NO |
| TJU_CMC_MD2.ID00475.3p-miR | TJU_CMC_MD2.ID00475.hairpin | YES | NO | NO | NO | NO | NO | NO | NO |
| TJU_CMC_MD2.ID00476.3p-miR | TJU_CMC_MD2.ID00476.hairpin | YES | NO | NO | NO | NO | NO | NO | NO |
| TJU_CMC_MD2.ID00477.5p-miR | TJU_CMC_MD2.ID00477.hairpin | YES | YES | YES | NO | NO | NO | NO | NO |
| TJU_CMC_MD2.ID00478.3p-miR | TJU_CMC_MD2.ID00478.hairpin | YES | NO | NO | NO | NO | NO | NO | NO |
| TJU_CMC_MD2.ID00479.5p-miR | TJU_CMC_MD2.ID00479.hairpin | YES | YES | NO | NO | NO | NO | NO | NO |
| TJU_CMC_MD2.ID00480.3p-miR | TJU_CMC_MD2.ID00480.hairpin | YES | YES | YES | NO | NO | NO | NO | NO |
| TJU_CMC_MD2.ID00480.5p-miR | TJU_CMC_MD2.ID00480.hairpin | YES | YES | YES | NO | NO | NO | NO | NO |
| TJU_CMC_MD2.ID00481.5p-miR | TJU_CMC_MD2.ID00481.hairpin | YES | YES | YES | NO | YES | NO | NO | NO |
| TJU_CMC_MD2.ID00482.5p-miR | TJU_CMC_MD2.ID00482.hairpin | YES | NO | YES | YES | NO | NO | NO | NO |
| TJU_CMC_MD2.ID00483.3p-miR | TJU_CMC_MD2.ID00483.hairpin | YES | NO | NO | NO | NO | NO | NO | NO |
| TJU_CMC_MD2.ID00484.3p-miR | TJU_CMC_MD2.ID00484.hairpin | YES | NO | NO | NO | NO | NO | NO | NO |
| TJU_CMC_MD2.ID00485.5p-miR | TJU_CMC_MD2.ID00485.hairpin | YES | YES | YES | NO | NO | NO | NO | NO |
| TJU_CMC_MD2.ID00486.3p-miR | TJU_CMC_MD2.ID00486.hairpin | YES | NO | NO | NO | NO | NO | NO | NO |
| TJU_CMC_MD2.ID00487.3p-miR | TJU_CMC_MD2.ID00487.hairpin | YES | NO | NO | NO | NO | NO | NO | NO |
| TJU_CMC_MD2.ID00488.5p-miR | TJU_CMC_MD2.ID00488.hairpin | YES | YES | YES | YES | NO | NO | NO | NO |
| TJU_CMC_MD2.ID00489.3p-miR | TJU_CMC_MD2.ID00489.hairpin | YES | NO | NO | NO | NO | NO | NO | NO |
| TJU_CMC_MD2.ID00490.5p-miR | TJU_CMC_MD2.ID00490.hairpin | YES | YES | YES | YES | NO | NO | NO | NO |
| TJU_CMC_MD2.ID00491.5p-miR | TJU_CMC_MD2.ID00491.hairpin | YES | YES | YES | YES | NO | NO | NO | NO |
| TJU_CMC_MD2.ID00492.5p-miR | TJU_CMC_MD2.ID00492.hairpin | YES | YES | YES | YES | NO | NO | NO | NO |
| TJU_CMC_MD2.ID00493.3p-miR | TJU_CMC_MD2.ID00493.hairpin | YES | NO | NO | NO | NO | NO | NO | NO |
| TJU_CMC_MD2.ID00494.5p-miR | TJU_CMC_MD2.ID00494.hairpin | YES | YES | YES | NO | YES | NO | NO | NO |
| TJU_CMC_MD2.ID00495.5p-miR | TJU_CMC_MD2.ID00495.hairpin | YES | YES | YES | YES | NO | NO | NO | NO |
| TJU_CMC_MD2.ID00496.5p-miR | TJU_CMC_MD2.ID00496.hairpin | YES | YES | YES | YES | NO | NO | NO | NO |
| TJU_CMC_MD2.ID00497.3p-miR | TJU_CMC_MD2.ID00497.hairpin | YES | NO | NO | NO | NO | NO | NO | NO |
| TJU_CMC_MD2.ID00498.5p-miR | TJU_CMC_MD2.ID00498.hairpin | YES | YES | YES | YES | NO | NO | NO | NO |
| TJU_CMC_MD2.ID00499.3p-miR | TJU_CMC_MD2.ID00499.hairpin | YES | NO | NO | NO | NO | NO | NO | NO |
| TJU_CMC_MD2.ID00500.3p-miR | TJU_CMC_MD2.ID00500.hairpin | YES | NO | NO | NO | NO | NO | NO | NO |
| TJU_CMC_MD2.ID00501.5p-miR | TJU_CMC_MD2.ID00501.hairpin | YES | YES | YES | YES | YES | NO | NO | NO |
| TJU_CMC_MD2.ID00502.5p-miR | TJU_CMC_MD2.ID00502.hairpin | YES | YES | NO | YES | NO | NO | NO | NO |
| TJU_CMC_MD2.ID00503.5p-miR | TJU_CMC_MD2.ID00503.hairpin | YES | YES | NO | YES | NO | YES | NO | NO |
| TJU_CMC_MD2.ID00504.3p-miR | TJU_CMC_MD2.ID00504.hairpin | YES | NO | NO | NO | NO | NO | NO | NO |
| TJU_CMC_MD2.ID00505.3p-miR | TJU_CMC_MD2.ID00505.hairpin | YES | NO | NO | NO | NO | NO | NO | NO |
| TJU_CMC_MD2.ID00506.3p-miR | TJU_CMC_MD2.ID00506.hairpin | YES | NO | NO | NO | NO | NO | NO | NO |
| TJU_CMC_MD2.ID00507.3p-miR | TJU_CMC_MD2.ID00507.hairpin | YES | NO | NO | NO | NO | NO | NO | NO |
| TJU_CMC_MD2.ID00508.3p-miR | TJU_CMC_MD2.ID00508.hairpin | YES | NO | NO | NO | NO | NO | NO | NO |
| TJU_CMC_MD2.ID00509.3p-miR | TJU_CMC_MD2.ID00509.hairpin | YES | NO | NO | NO | NO | NO | NO | NO |
| TJU_CMC_MD2.ID00510.5p-miR | TJU_CMC_MD2.ID00510.hairpin | YES | NO | YES | YES | YES | NO | NO | NO |
| TJU_CMC_MD2.ID00511.5p-miR | TJU_CMC_MD2.ID00511.hairpin | YES | YES | YES | YES | NO | NO | NO | NO |
| TJU_CMC_MD2.ID00512.3p-miR | TJU_CMC_MD2.ID00512.hairpin | YES | NO | NO | NO | NO | NO | NO | NO |
| TJU_CMC_MD2.ID00513.3p-miR | TJU_CMC_MD2.ID00513.hairpin | YES | NO | NO | NO | NO | NO | NO | NO |
| TJU_CMC_MD2.ID00514.3p-miR | TJU_CMC_MD2.ID00514.hairpin | YES | NO | NO | NO | NO | NO | NO | NO |
| TJU_CMC_MD2.ID00515.5p-miR | TJU_CMC_MD2.ID00515.hairpin | YES | YES | NO | YES | NO | NO | NO | NO |
| TJU_CMC_MD2.ID00516.5p-miR | TJU_CMC_MD2.ID00516.hairpin | YES | YES | YES | NO | NO | NO | NO | NO |
| TJU_CMC_MD2.ID00517.5p-miR | TJU_CMC_MD2.ID00517.hairpin | YES | NO | NO | NO | NO | NO | NO | NO |
| TJU_CMC_MD2.ID00518.5p-miR | TJU_CMC_MD2.ID00518.hairpin | YES | YES | YES | YES | YES | NO | NO | NO |
| TJU_CMC_MD2.ID00519.3p-miR | TJU_CMC_MD2.ID00519.hairpin | YES | NO | NO | NO | NO | NO | NO | NO |
| TJU_CMC_MD2.ID00520.5p-miR | TJU_CMC_MD2.ID00520.hairpin | YES | YES | YES | YES | NO | NO | NO | NO |
| TJU_CMC_MD2.ID00521.5p-miR | TJU_CMC_MD2.ID00521.hairpin | YES | YES | YES | YES | YES | NO | NO | NO |
| TJU_CMC_MD2.ID00522.5p-miR | TJU_CMC_MD2.ID00522.hairpin | YES | YES | NO | YES | NO | NO | NO | NO |
| TJU_CMC_MD2.ID00523.3p-miR | TJU_CMC_MD2.ID00523.hairpin | YES | NO | NO | NO | NO | NO | NO | NO |
| TJU_CMC_MD2.ID00524.3p-miR | TJU_CMC_MD2.ID00524.hairpin | YES | NO | NO | NO | NO | NO | NO | NO |
| TJU_CMC_MD2.ID00525.3p-miR | TJU_CMC_MD2.ID00525.hairpin | YES | NO | NO | NO | NO | NO | NO | NO |
| TJU_CMC_MD2.ID00526.3p-miR | TJU_CMC_MD2.ID00526.hairpin | YES | YES | YES | NO | NO | NO | NO | NO |
| TJU_CMC_MD2.ID00526.5p-miR | TJU_CMC_MD2.ID00526.hairpin | YES | YES | YES | NO | NO | NO | NO | NO |
| TJU_CMC_MD2.ID00527.5p-miR | TJU_CMC_MD2.ID00527.hairpin | YES | NO | NO | NO | NO | NO | NO | NO |
| TJU_CMC_MD2.ID00528.3p-miR | TJU_CMC_MD2.ID00528.hairpin | YES | NO | NO | NO | NO | NO | NO | NO |
| TJU_CMC_MD2.ID00529.3p-miR | TJU_CMC_MD2.ID00529.hairpin | YES | NO | NO | NO | NO | NO | NO | NO |
| TJU_CMC_MD2.ID00529.5p-miR | TJU_CMC_MD2.ID00529.hairpin | YES | YES | YES | YES | YES | NO | NO | NO |
| TJU_CMC_MD2.ID00530.3p-miR | TJU_CMC_MD2.ID00530.hairpin | YES | YES | YES | YES | NO | NO | NO | NO |
| TJU_CMC_MD2.ID00531.5p-miR | TJU_CMC_MD2.ID00531.hairpin | YES | YES | YES | NO | NO | NO | NO | NO |
| TJU_CMC_MD2.ID00532.3p-miR | TJU_CMC_MD2.ID00532.hairpin | YES | NO | NO | NO | NO | NO | NO | NO |
| TJU_CMC_MD2.ID00532.5p-miR | TJU_CMC_MD2.ID00532.hairpin | YES | NO | YES | NO | NO | NO | NO | NO |
| TJU_CMC_MD2.ID00533.3p-miR | TJU_CMC_MD2.ID00533.hairpin | YES | NO | YES | YES | YES | NO | NO | NO |
| TJU_CMC_MD2.ID00533.5p-miR | TJU_CMC_MD2.ID00533.hairpin | YES | NO | YES | YES | YES | NO | NO | NO |
| TJU_CMC_MD2.ID00534.3p-miR | TJU_CMC_MD2.ID00534.hairpin | YES | NO | NO | NO | NO | NO | NO | NO |
| TJU_CMC_MD2.ID00535.3p-miR | TJU_CMC_MD2.ID00535.hairpin | YES | NO | NO | NO | NO | NO | NO | NO |
| TJU_CMC_MD2.ID00536.3p-miR | TJU_CMC_MD2.ID00536.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00537.3p-miR | TJU_CMC_MD2.ID00537.hairpin | YES | NO | NO | NO | NO | NO | NO | NO |
| TJU_CMC_MD2.ID00538.5p-miR | TJU_CMC_MD2.ID00538.hairpin | YES | YES | YES | YES | NO | NO | NO | NO |
| TJU_CMC_MD2.ID00539.3p-miR | TJU_CMC_MD2.ID00539.hairpin | YES | YES | NO | YES | YES | NO | NO | NO |
| TJU_CMC_MD2.ID00539.5p-miR | TJU_CMC_MD2.ID00539.hairpin | YES | NO | YES | YES | YES | NO | NO | NO |
| TJU_CMC_MD2.ID00540.3p-miR | TJU_CMC_MD2.ID00540.hairpin | YES | NO | NO | NO | NO | NO | NO | NO |
| TJU_CMC_MD2.ID00541.5p-miR | TJU_CMC_MD2.ID00541.hairpin | YES | YES | YES | YES | YES | NO | NO | NO |
| TJU_CMC_MD2.ID00542.3p-miR | TJU_CMC_MD2.ID00542.hairpin | YES | NO | NO | NO | NO | NO | NO | NO |
| TJU_CMC_MD2.ID00543.3p-miR | TJU_CMC_MD2.ID00543.hairpin | YES | NO | NO | NO | NO | NO | NO | NO |
| TJU_CMC_MD2.ID00544.3p-miR | TJU_CMC_MD2.ID00544.hairpin | YES | NO | NO | NO | NO | NO | NO | NO |
| TJU_CMC_MD2.ID00545.3p-miR | TJU_CMC_MD2.ID00545.hairpin | YES | NO | NO | NO | NO | NO | NO | NO |
| TJU_CMC_MD2.ID00546.5p-miR | TJU_CMC_MD2.ID00546.hairpin | YES | YES | YES | YES | NO | NO | NO | NO |
| TJU_CMC_MD2.ID00547.3p-miR | TJU_CMC_MD2.ID00547.hairpin | YES | NO | NO | NO | NO | NO | NO | NO |
| TJU_CMC_MD2.ID00548.3p-miR | TJU_CMC_MD2.ID00548.hairpin | YES | NO | NO | NO | NO | NO | NO | NO |
| TJU_CMC_MD2.ID00549.3p-miR | TJU_CMC_MD2.ID00549.hairpin | YES | NO | NO | NO | NO | NO | NO | NO |
| TJU_CMC_MD2.ID00550.3p-miR | TJU_CMC_MD2.ID00550.hairpin | YES | NO | NO | NO | NO | NO | NO | NO |
| TJU_CMC_MD2.ID00550.5p-miR | TJU_CMC_MD2.ID00550.hairpin | YES | YES | YES | YES | NO | NO | NO | NO |
| TJU_CMC_MD2.ID00551.3p-miR | TJU_CMC_MD2.ID00551.hairpin | YES | NO | NO | NO | NO | NO | NO | NO |
| TJU_CMC_MD2.ID00552.3p-miR | TJU_CMC_MD2.ID00552.hairpin | YES | NO | NO | NO | NO | NO | NO | NO |
| TJU_CMC_MD2.ID00553.3p-miR | TJU_CMC_MD2.ID00553.hairpin | YES | NO | NO | NO | NO | NO | NO | NO |
| TJU_CMC_MD2.ID00554.3p-miR | TJU_CMC_MD2.ID00554.hairpin | YES | NO | NO | NO | NO | NO | NO | NO |
| TJU_CMC_MD2.ID00555.3p-miR | TJU_CMC_MD2.ID00555.hairpin | YES | NO | NO | NO | NO | NO | NO | NO |
| TJU_CMC_MD2.ID00556.5p-miR | TJU_CMC_MD2.ID00556.hairpin | YES | NO | YES | NO | NO | NO | NO | NO |
| TJU_CMC_MD2.ID00557.3p-miR | TJU_CMC_MD2.ID00557.hairpin | YES | NO | NO | NO | NO | NO | NO | NO |
| TJU_CMC_MD2.ID00558.3p-miR | TJU_CMC_MD2.ID00558.hairpin | YES | YES | YES | YES | YES | NO | NO | NO |
| TJU_CMC_MD2.ID00558.5p-miR | TJU_CMC_MD2.ID00558.hairpin | YES | NO | YES | NO | YES | NO | NO | NO |
| TJU_CMC_MD2.ID00559.3p-miR | TJU_CMC_MD2.ID00559.hairpin | YES | NO | NO | NO | NO | NO | NO | NO |
| TJU_CMC_MD2.ID00560.3p-miR | TJU_CMC_MD2.ID00560.hairpin | YES | NO | NO | NO | NO | NO | NO | NO |
| TJU_CMC_MD2.ID00561.3p-miR | TJU_CMC_MD2.ID00561.hairpin | YES | NO | NO | NO | NO | NO | NO | NO |
| TJU_CMC_MD2.ID00562.3p-miR | TJU_CMC_MD2.ID00562.hairpin | YES | NO | NO | NO | NO | NO | NO | NO |
| TJU_CMC_MD2.ID00563.3p-miR | TJU_CMC_MD2.ID00563.hairpin | YES | NO | NO | NO | NO | NO | NO | NO |
| TJU_CMC_MD2.ID00564.5p-miR | TJU_CMC_MD2.ID00564.hairpin | YES | YES | YES | NO | NO | NO | NO | NO |
| TJU_CMC_MD2.ID00565.3p-miR | TJU_CMC_MD2.ID00565.hairpin | YES | NO | NO | NO | NO | NO | NO | NO |
| TJU_CMC_MD2.ID00566.5p-miR | TJU_CMC_MD2.ID00566.hairpin | YES | YES | NO | YES | NO | NO | NO | NO |
| TJU_CMC_MD2.ID00567.3p-miR | TJU_CMC_MD2.ID00567.hairpin | YES | NO | NO | NO | NO | NO | NO | NO |
| TJU_CMC_MD2.ID00568.3p-miR | TJU_CMC_MD2.ID00568.hairpin | YES | NO | NO | NO | NO | NO | NO | NO |
| TJU_CMC_MD2.ID00569.3p-miR | TJU_CMC_MD2.ID00569.hairpin | YES | NO | NO | NO | NO | NO | NO | NO |
| TJU_CMC_MD2.ID00570.3p-miR | TJU_CMC_MD2.ID00570.hairpin | YES | NO | NO | NO | NO | NO | NO | NO |
| TJU_CMC_MD2.ID00571.3p-miR | TJU_CMC_MD2.ID00571.hairpin | YES | NO | NO | NO | NO | NO | NO | NO |
| TJU_CMC_MD2.ID00572.5p-miR | TJU_CMC_MD2.ID00572.hairpin | YES | YES | YES | NO | NO | NO | NO | NO |
| TJU_CMC_MD2.ID00573.5p-miR | TJU_CMC_MD2.ID00573.hairpin | YES | YES | YES | YES | YES | NO | NO | NO |
| TJU_CMC_MD2.ID00574.3p-miR | TJU_CMC_MD2.ID00574.hairpin | YES | NO | NO | NO | NO | NO | NO | NO |
| TJU_CMC_MD2.ID00574.5p-miR | TJU_CMC_MD2.ID00574.hairpin | YES | YES | YES | YES | YES | NO | NO | NO |
| TJU_CMC_MD2.ID00575.5p-miR | TJU_CMC_MD2.ID00575.hairpin | YES | YES | YES | YES | YES | NO | NO | NO |
| TJU_CMC_MD2.ID00576.5p-miR | TJU_CMC_MD2.ID00576.hairpin | YES | YES | YES | YES | YES | NO | NO | NO |
| TJU_CMC_MD2.ID00577.3p-miR | TJU_CMC_MD2.ID00577.hairpin | YES | NO | NO | NO | NO | NO | NO | NO |
| TJU_CMC_MD2.ID00578.3p-miR | TJU_CMC_MD2.ID00578.hairpin | YES | NO | NO | NO | NO | NO | NO | NO |
| TJU_CMC_MD2.ID00579.3p-miR | TJU_CMC_MD2.ID00579.hairpin | YES | NO | NO | NO | NO | NO | NO | NO |
| TJU_CMC_MD2.ID00580.3p-miR | TJU_CMC_MD2.ID00580.hairpin | YES | NO | NO | NO | NO | NO | NO | NO |
| TJU_CMC_MD2.ID00581.3p-miR | TJU_CMC_MD2.ID00581.hairpin | YES | NO | NO | NO | NO | NO | NO | NO |
| TJU_CMC_MD2.ID00582.3p-miR | TJU_CMC_MD2.ID00582.hairpin | YES | NO | NO | NO | NO | NO | NO | NO |
| TJU_CMC_MD2.ID00583.3p-miR | TJU_CMC_MD2.ID00583.hairpin | YES | NO | NO | NO | NO | NO | NO | NO |
| TJU_CMC_MD2.ID00584.5p-miR | TJU_CMC_MD2.ID00584.hairpin | YES | NO | YES | NO | NO | NO | NO | NO |
| TJU_CMC_MD2.ID00585.5p-miR | TJU_CMC_MD2.ID00585.hairpin | YES | NO | YES | YES | NO | NO | NO | NO |
| TJU_CMC_MD2.ID00586.3p-miR | TJU_CMC_MD2.ID00586.hairpin | YES | NO | NO | NO | NO | NO | NO | NO |
| TJU_CMC_MD2.ID00587.3p-miR | TJU_CMC_MD2.ID00587.hairpin | YES | YES | NO | YES | YES | NO | NO | NO |
| TJU_CMC_MD2.ID00588.3p-miR | TJU_CMC_MD2.ID00588.hairpin | YES | YES | YES | YES | YES | NO | NO | NO |
| TJU_CMC_MD2.ID00589.3p-miR | TJU_CMC_MD2.ID00589.hairpin | YES | NO | NO | NO | NO | NO | NO | NO |
| TJU_CMC_MD2.ID00590.5p-miR | TJU_CMC_MD2.ID00590.hairpin | YES | YES | YES | YES | NO | NO | NO | NO |
| TJU_CMC_MD2.ID00591.3p-miR | TJU_CMC_MD2.ID00591.hairpin | YES | NO | NO | NO | NO | NO | NO | NO |
| TJU_CMC_MD2.ID00591.5p-miR | TJU_CMC_MD2.ID00591.hairpin | YES | YES | YES | YES | YES | NO | NO | NO |
| TJU_CMC_MD2.ID00592.3p-miR | TJU_CMC_MD2.ID00592.hairpin | YES | NO | NO | NO | NO | NO | NO | NO |
| TJU_CMC_MD2.ID00593.3p-miR | TJU_CMC_MD2.ID00593.hairpin | YES | NO | NO | NO | NO | NO | NO | NO |
| TJU_CMC_MD2.ID00594.3p-miR | TJU_CMC_MD2.ID00594.hairpin | YES | NO | NO | NO | NO | NO | NO | NO |
| TJU_CMC_MD2.ID00595.3p-miR | TJU_CMC_MD2.ID00595.hairpin | YES | NO | NO | NO | NO | NO | NO | NO |
| TJU_CMC_MD2.ID00596.5p-miR | TJU_CMC_MD2.ID00596.hairpin | YES | YES | YES | YES | YES | NO | NO | NO |
| TJU_CMC_MD2.ID00597.3p-miR | TJU_CMC_MD2.ID00597.hairpin | YES | NO | NO | NO | NO | NO | NO | NO |
| TJU_CMC_MD2.ID00598.3p-miR | TJU_CMC_MD2.ID00598.hairpin | YES | NO | NO | NO | NO | NO | NO | NO |
| TJU_CMC_MD2.ID00599.5p-miR | TJU_CMC_MD2.ID00599.hairpin | YES | YES | YES | YES | NO | NO | NO | NO |
| TJU_CMC_MD2.ID00600.3p-miR | TJU_CMC_MD2.ID00600.hairpin | YES | NO | NO | NO | NO | NO | NO | NO |
| TJU_CMC_MD2.ID00601.3p-miR | TJU_CMC_MD2.ID00601.hairpin | YES | NO | NO | NO | NO | NO | NO | NO |
| TJU_CMC_MD2.ID00602.3p-miR | TJU_CMC_MD2.ID00602.hairpin | YES | NO | NO | NO | NO | NO | NO | NO |
| TJU_CMC_MD2.ID00603.5p-miR | TJU_CMC_MD2.ID00603.hairpin | YES | YES | NO | NO | NO | NO | NO | NO |
| TJU_CMC_MD2.ID00604.3p-miR | TJU_CMC_MD2.ID00604.hairpin | YES | NO | NO | NO | NO | NO | NO | NO |
| TJU_CMC_MD2.ID00605.5p-miR | TJU_CMC_MD2.ID00605.hairpin | YES | YES | YES | YES | YES | NO | NO | NO |
| TJU_CMC_MD2.ID00606.5p-miR | TJU_CMC_MD2.ID00606.hairpin | YES | YES | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00607.3p-miR | TJU_CMC_MD2.ID00607.hairpin | YES | NO | NO | NO | NO | NO | NO | NO |
| TJU_CMC_MD2.ID00608.3p-miR | TJU_CMC_MD2.ID00608.hairpin | YES | NO | NO | NO | NO | NO | NO | NO |
| TJU_CMC_MD2.ID00609.5p-miR | TJU_CMC_MD2.ID00609.hairpin | YES | NO | YES | YES | NO | NO | NO | NO |
| TJU_CMC_MD2.ID00610.3p-miR | TJU_CMC_MD2.ID00610.hairpin | YES | NO | NO | NO | NO | NO | NO | NO |
| TJU_CMC_MD2.ID00611.5p-miR | TJU_CMC_MD2.ID00611.hairpin | YES | NO | YES | NO | NO | NO | NO | NO |
| TJU_CMC_MD2.ID00612.3p-miR | TJU_CMC_MD2.ID00612.hairpin | YES | NO | NO | NO | NO | NO | NO | NO |
| TJU_CMC_MD2.ID00613.3p-miR | TJU_CMC_MD2.ID00613.hairpin | YES | NO | NO | NO | NO | NO | NO | NO |
| TJU_CMC_MD2.ID00614.3p-miR | TJU_CMC_MD2.ID00614.hairpin | YES | NO | NO | NO | NO | NO | NO | NO |
| TJU_CMC_MD2.ID00615.5p-miR | TJU_CMC_MD2.ID00615.hairpin | YES | YES | YES | NO | NO | NO | NO | NO |
| TJU_CMC_MD2.ID00616.5p-miR | TJU_CMC_MD2.ID00616.hairpin | YES | YES | YES | YES | NO | NO | NO | NO |
| TJU_CMC_MD2.ID00617.3p-miR | TJU_CMC_MD2.ID00617.hairpin | YES | NO | NO | NO | NO | NO | NO | NO |
| TJU_CMC_MD2.ID00618.3p-miR | TJU_CMC_MD2.ID00618.hairpin | YES | YES | YES | NO | NO | NO | NO | NO |
| TJU_CMC_MD2.ID00619.5p-miR | TJU_CMC_MD2.ID00619.hairpin | YES | YES | YES | YES | NO | NO | NO | NO |
| TJU_CMC_MD2.ID00620.3p-miR | TJU_CMC_MD2.ID00620.hairpin | YES | NO | NO | NO | NO | NO | NO | NO |
| TJU_CMC_MD2.ID00621.3p-miR | TJU_CMC_MD2.ID00621.hairpin | YES | NO | NO | NO | NO | NO | NO | NO |
| TJU_CMC_MD2.ID00622.3p-miR | TJU_CMC_MD2.ID00622.hairpin | YES | NO | NO | NO | NO | NO | NO | NO |
| TJU_CMC_MD2.ID00623.3p-miR | TJU_CMC_MD2.ID00623.hairpin | YES | YES | YES | NO | YES | NO | NO | NO |
| TJU_CMC_MD2.ID00623.5p-miR | TJU_CMC_MD2.ID00623.hairpin | YES | YES | YES | YES | YES | NO | NO | NO |
| TJU_CMC_MD2.ID00624.3p-miR | TJU_CMC_MD2.ID00624.hairpin | YES | NO | NO | NO | NO | NO | NO | NO |
| TJU_CMC_MD2.ID00625.5p-miR | TJU_CMC_MD2.ID00625.hairpin | YES | YES | NO | YES | YES | NO | NO | NO |
| TJU_CMC_MD2.ID00626.5p-miR | TJU_CMC_MD2.ID00626.hairpin | YES | NO | NO | YES | NO | NO | NO | NO |
| TJU_CMC_MD2.ID00627.5p-miR | TJU_CMC_MD2.ID00627.hairpin | YES | YES | YES | YES | YES | NO | NO | NO |
| TJU_CMC_MD2.ID00628.5p-miR | TJU_CMC_MD2.ID00628.hairpin | YES | YES | YES | YES | NO | NO | NO | NO |
| TJU_CMC_MD2.ID00629.3p-miR | TJU_CMC_MD2.ID00629.hairpin | YES | NO | NO | NO | NO | NO | NO | NO |
| TJU_CMC_MD2.ID00630.3p-miR | TJU_CMC_MD2.ID00630.hairpin | YES | NO | NO | NO | NO | NO | NO | NO |
| TJU_CMC_MD2.ID00631.5p-miR | TJU_CMC_MD2.ID00631.hairpin | YES | YES | NO | YES | NO | NO | NO | NO |
| TJU_CMC_MD2.ID00632.3p-miR | TJU_CMC_MD2.ID00632.hairpin | YES | NO | NO | NO | NO | NO | NO | NO |
| TJU_CMC_MD2.ID00633.3p-miR | TJU_CMC_MD2.ID00633.hairpin | YES | NO | NO | NO | NO | NO | NO | NO |
| TJU_CMC_MD2.ID00634.5p-miR | TJU_CMC_MD2.ID00634.hairpin | YES | YES | YES | NO | NO | NO | NO | NO |
| TJU_CMC_MD2.ID00635.5p-miR | TJU_CMC_MD2.ID00635.hairpin | YES | YES | YES | YES | YES | NO | NO | NO |
| TJU_CMC_MD2.ID00636.3p-miR | TJU_CMC_MD2.ID00636.hairpin | YES | NO | NO | NO | NO | NO | NO | NO |
| TJU_CMC_MD2.ID00637.5p-miR | TJU_CMC_MD2.ID00637.hairpin | YES | NO | NO | YES | NO | NO | NO | NO |
| TJU_CMC_MD2.ID00638.5p-miR | TJU_CMC_MD2.ID00638.hairpin | YES | YES | YES | YES | YES | NO | NO | NO |
| TJU_CMC_MD2.ID00639.3p-miR | TJU_CMC_MD2.ID00639.hairpin | YES | YES | YES | NO | NO | NO | NO | NO |
| TJU_CMC_MD2.ID00639.5p-miR | TJU_CMC_MD2.ID00639.hairpin | YES | YES | YES | NO | NO | NO | NO | NO |
| TJU_CMC_MD2.ID00640.3p-miR | TJU_CMC_MD2.ID00640.hairpin | YES | NO | NO | NO | NO | NO | NO | NO |
| TJU_CMC_MD2.ID00640.5p-miR | TJU_CMC_MD2.ID00640.hairpin | YES | YES | YES | YES | NO | NO | NO | NO |
| TJU_CMC_MD2.ID00641.3p-miR | TJU_CMC_MD2.ID00641.hairpin | YES | NO | NO | NO | NO | NO | NO | NO |
| TJU_CMC_MD2.ID00642.3p-miR | TJU_CMC_MD2.ID00642.hairpin | YES | NO | NO | NO | NO | NO | NO | NO |
| TJU_CMC_MD2.ID00643.3p-miR | TJU_CMC_MD2.ID00643.hairpin | YES | NO | NO | NO | NO | NO | NO | NO |
| TJU_CMC_MD2.ID00644.5p-miR | TJU_CMC_MD2.ID00644.hairpin | YES | YES | YES | YES | YES | NO | NO | NO |
| TJU_CMC_MD2.ID00645.5p-miR | TJU_CMC_MD2.ID00645.hairpin | YES | YES | YES | NO | YES | NO | NO | NO |
| TJU_CMC_MD2.ID00646.5p-miR | TJU_CMC_MD2.ID00646.hairpin | YES | YES | YES | NO | YES | NO | NO | NO |
| TJU_CMC_MD2.ID00647.3p-miR | TJU_CMC_MD2.ID00647.hairpin | YES | NO | NO | NO | NO | NO | NO | NO |
| TJU_CMC_MD2.ID00648.5p-miR | TJU_CMC_MD2.ID00648.hairpin | YES | YES | NO | NO | YES | NO | NO | NO |
| TJU_CMC_MD2.ID00649.3p-miR | TJU_CMC_MD2.ID00649.hairpin | YES | NO | NO | NO | NO | NO | NO | NO |
| TJU_CMC_MD2.ID00649.5p-miR | TJU_CMC_MD2.ID00649.hairpin | YES | NO | YES | NO | NO | NO | NO | NO |
| TJU_CMC_MD2.ID00650.5p-miR | TJU_CMC_MD2.ID00650.hairpin | YES | NO | YES | NO | NO | NO | NO | NO |
| TJU_CMC_MD2.ID00651.3p-miR | TJU_CMC_MD2.ID00651.hairpin | YES | NO | NO | NO | NO | NO | NO | NO |
| TJU_CMC_MD2.ID00651.5p-miR | TJU_CMC_MD2.ID00651.hairpin | YES | YES | YES | YES | YES | NO | NO | NO |
| TJU_CMC_MD2.ID00652.5p-miR | TJU_CMC_MD2.ID00652.hairpin | YES | YES | YES | NO | YES | NO | NO | NO |
| TJU_CMC_MD2.ID00653.3p-miR | TJU_CMC_MD2.ID00653.hairpin | YES | NO | NO | NO | NO | NO | NO | NO |
| TJU_CMC_MD2.ID00654.3p-miR | TJU_CMC_MD2.ID00654.hairpin | YES | NO | NO | NO | NO | NO | NO | NO |
| TJU_CMC_MD2.ID00655.3p-miR | TJU_CMC_MD2.ID00655.hairpin | YES | NO | NO | NO | NO | NO | NO | NO |
| TJU_CMC_MD2.ID00656.5p-miR | TJU_CMC_MD2.ID00656.hairpin | YES | YES | YES | NO | YES | NO | NO | NO |
| TJU_CMC_MD2.ID00657.3p-miR | TJU_CMC_MD2.ID00657.hairpin | YES | YES | YES | NO | NO | NO | NO | NO |
| TJU_CMC_MD2.ID00657.5p-miR | TJU_CMC_MD2.ID00657.hairpin | YES | YES | YES | NO | NO | NO | NO | NO |
| TJU_CMC_MD2.ID00658.5p-miR | TJU_CMC_MD2.ID00658.hairpin | YES | YES | NO | NO | NO | NO | NO | NO |
| TJU_CMC_MD2.ID00659.3p-miR | TJU_CMC_MD2.ID00659.hairpin | YES | NO | NO | NO | NO | NO | NO | NO |
| TJU_CMC_MD2.ID00660.5p-miR | TJU_CMC_MD2.ID00660.hairpin | YES | YES | YES | NO | YES | NO | NO | NO |
| TJU_CMC_MD2.ID00661.5p-miR | TJU_CMC_MD2.ID00661.hairpin | YES | YES | YES | YES | YES | NO | NO | NO |
| TJU_CMC_MD2.ID00662.3p-miR | TJU_CMC_MD2.ID00662.hairpin | YES | NO | NO | NO | NO | NO | NO | NO |
| TJU_CMC_MD2.ID00663.5p-miR | TJU_CMC_MD2.ID00663.hairpin | YES | YES | YES | YES | NO | NO | NO | NO |
| TJU_CMC_MD2.ID00664.3p-miR | TJU_CMC_MD2.ID00664.hairpin | YES | NO | NO | NO | NO | NO | NO | NO |
| TJU_CMC_MD2.ID00665.3p-miR | TJU_CMC_MD2.ID00665.hairpin | YES | NO | NO | NO | NO | NO | NO | NO |
| TJU_CMC_MD2.ID00666.3p-miR | TJU_CMC_MD2.ID00666.hairpin | YES | NO | NO | NO | NO | NO | NO | NO |
| TJU_CMC_MD2.ID00667.5p-miR | TJU_CMC_MD2.ID00667.hairpin | YES | NO | NO | YES | NO | YES | NO | NO |
| TJU_CMC_MD2.ID00668.3p-miR | TJU_CMC_MD2.ID00668.hairpin | YES | NO | NO | NO | NO | NO | NO | NO |
| TJU_CMC_MD2.ID00669.3p-miR | TJU_CMC_MD2.ID00669.hairpin | YES | NO | NO | NO | NO | NO | NO | NO |
| TJU_CMC_MD2.ID00670.3p-miR | TJU_CMC_MD2.ID00670.hairpin | YES | NO | NO | NO | NO | NO | NO | NO |
| TJU_CMC_MD2.ID00671.5p-miR | TJU_CMC_MD2.ID00671.hairpin | YES | NO | YES | NO | NO | NO | NO | NO |
| TJU_CMC_MD2.ID00672.3p-miR | TJU_CMC_MD2.ID00672.hairpin | YES | NO | NO | NO | NO | NO | NO | NO |
| TJU_CMC_MD2.ID00672.5p-miR | TJU_CMC_MD2.ID00672.hairpin | YES | YES | YES | YES | NO | NO | NO | NO |
| TJU_CMC_MD2.ID00673.3p-miR | TJU_CMC_MD2.ID00673.hairpin | YES | NO | NO | NO | NO | NO | NO | NO |
| TJU_CMC_MD2.ID00674.3p-miR | TJU_CMC_MD2.ID00674.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00675.3p-miR | TJU_CMC_MD2.ID00675.hairpin | YES | NO | NO | NO | NO | NO | NO | NO |
| TJU_CMC_MD2.ID00676.3p-miR | TJU_CMC_MD2.ID00676.hairpin | YES | NO | NO | NO | NO | NO | NO | NO |
| TJU_CMC_MD2.ID00677.3p-miR | TJU_CMC_MD2.ID00677.hairpin | YES | NO | NO | NO | NO | NO | NO | NO |
| TJU_CMC_MD2.ID00678.3p-miR | TJU_CMC_MD2.ID00678.hairpin | YES | NO | NO | NO | NO | NO | NO | NO |
| TJU_CMC_MD2.ID00679.5p-miR | TJU_CMC_MD2.ID00679.hairpin | YES | YES | YES | YES | NO | NO | NO | NO |
| TJU_CMC_MD2.ID00680.5p-miR | TJU_CMC_MD2.ID00680.hairpin | YES | YES | YES | YES | NO | NO | NO | NO |
| TJU_CMC_MD2.ID00681.5p-miR | TJU_CMC_MD2.ID00681.hairpin | YES | YES | YES | YES | YES | NO | NO | NO |
| TJU_CMC_MD2.ID00682.3p-miR | TJU_CMC_MD2.ID00682.hairpin | YES | NO | NO | NO | NO | NO | NO | NO |
| TJU_CMC_MD2.ID00683.3p-miR | TJU_CMC_MD2.ID00683.hairpin | YES | NO | NO | NO | NO | NO | NO | NO |
| TJU_CMC_MD2.ID00684.3p-miR | TJU_CMC_MD2.ID00684.hairpin | YES | NO | NO | NO | NO | NO | NO | NO |
| TJU_CMC_MD2.ID00685.3p-miR | TJU_CMC_MD2.ID00685.hairpin | YES | NO | NO | NO | NO | NO | NO | NO |
| TJU_CMC_MD2.ID00685.5p-miR | TJU_CMC_MD2.ID00685.hairpin | YES | NO | YES | YES | YES | NO | NO | NO |
| TJU_CMC_MD2.ID00686.3p-miR | TJU_CMC_MD2.ID00686.hairpin | YES | NO | NO | NO | NO | NO | NO | NO |
| TJU_CMC_MD2.ID00687.3p-miR | TJU_CMC_MD2.ID00687.hairpin | YES | NO | NO | NO | NO | NO | NO | NO |
| TJU_CMC_MD2.ID00688.3p-miR | TJU_CMC_MD2.ID00688.hairpin | YES | NO | NO | NO | NO | NO | NO | NO |
| TJU_CMC_MD2.ID00689.3p-miR | TJU_CMC_MD2.ID00689.hairpin | YES | NO | NO | NO | NO | NO | NO | NO |
| TJU_CMC_MD2.ID00690.5p-miR | TJU_CMC_MD2.ID00690.hairpin | YES | YES | NO | NO | NO | YES | NO | NO |
| TJU_CMC_MD2.ID00691.3p-miR | TJU_CMC_MD2.ID00691.hairpin | YES | NO | NO | NO | NO | NO | NO | NO |
| TJU_CMC_MD2.ID00691.5p-miR | TJU_CMC_MD2.ID00691.hairpin | YES | YES | YES | YES | YES | NO | NO | NO |
| TJU_CMC_MD2.ID00692.3p-miR | TJU_CMC_MD2.ID00692.hairpin | YES | NO | NO | NO | NO | NO | NO | NO |
| TJU_CMC_MD2.ID00693.5p-miR | TJU_CMC_MD2.ID00693.hairpin | YES | YES | YES | NO | YES | NO | NO | NO |
| TJU_CMC_MD2.ID00694.5p-miR | TJU_CMC_MD2.ID00694.hairpin | YES | YES | YES | YES | NO | NO | NO | NO |
| TJU_CMC_MD2.ID00695.3p-miR | TJU_CMC_MD2.ID00695.hairpin | YES | NO | NO | NO | NO | NO | NO | NO |
| TJU_CMC_MD2.ID00696.5p-miR | TJU_CMC_MD2.ID00696.hairpin | YES | YES | YES | NO | NO | NO | NO | NO |
| TJU_CMC_MD2.ID00697.3p-miR | TJU_CMC_MD2.ID00697.hairpin | YES | NO | NO | NO | NO | NO | NO | NO |
| TJU_CMC_MD2.ID00698.3p-miR | TJU_CMC_MD2.ID00698.hairpin | YES | NO | NO | NO | NO | NO | NO | NO |
| TJU_CMC_MD2.ID00699.3p-miR | TJU_CMC_MD2.ID00699.hairpin | YES | YES | YES | NO | YES | NO | NO | NO |
| TJU_CMC_MD2.ID00700.5p-miR | TJU_CMC_MD2.ID00700.hairpin | YES | YES | YES | YES | NO | NO | NO | NO |
| TJU_CMC_MD2.ID00701.5p-miR | TJU_CMC_MD2.ID00701.hairpin | YES | YES | YES | YES | NO | NO | NO | NO |
| TJU_CMC_MD2.ID00702.5p-miR | TJU_CMC_MD2.ID00702.hairpin | YES | YES | YES | NO | NO | NO | NO | NO |
| TJU_CMC_MD2.ID00703.3p-miR | TJU_CMC_MD2.ID00703.hairpin | YES | NO | NO | NO | NO | NO | NO | NO |
| TJU_CMC_MD2.ID00704.5p-miR | TJU_CMC_MD2.ID00704.hairpin | YES | YES | NO | NO | NO | NO | NO | NO |
| TJU_CMC_MD2.ID00705.3p-miR | TJU_CMC_MD2.ID00705.hairpin | YES | NO | NO | NO | NO | NO | NO | NO |
| TJU_CMC_MD2.ID00706.5p-miR | TJU_CMC_MD2.ID00706.hairpin | YES | YES | NO | YES | YES | NO | NO | NO |
| TJU_CMC_MD2.ID00707.5p-miR | TJU_CMC_MD2.ID00707.hairpin | YES | YES | YES | YES | YES | NO | NO | NO |
| TJU_CMC_MD2.ID00708.5p-miR | TJU_CMC_MD2.ID00708.hairpin | YES | YES | YES | YES | YES | NO | NO | NO |
| TJU_CMC_MD2.ID00709.3p-miR | TJU_CMC_MD2.ID00709.hairpin | YES | NO | NO | NO | NO | NO | NO | NO |
| TJU_CMC_MD2.ID00710.3p-miR | TJU_CMC_MD2.ID00710.hairpin | YES | NO | NO | NO | NO | NO | NO | NO |
| TJU_CMC_MD2.ID00711.3p-miR | TJU_CMC_MD2.ID00711.hairpin | YES | NO | NO | NO | NO | NO | NO | NO |
| TJU_CMC_MD2.ID00712.3p-miR | TJU_CMC_MD2.ID00712.hairpin | YES | NO | NO | NO | NO | NO | NO | NO |
| TJU_CMC_MD2.ID00713.5p-miR | TJU_CMC_MD2.ID00713.hairpin | YES | YES | YES | YES | YES | YES | NO | NO |
| TJU_CMC_MD2.ID00714.3p-miR | TJU_CMC_MD2.ID00714.hairpin | YES | NO | NO | NO | NO | NO | NO | NO |
| TJU_CMC_MD2.ID00715.3p-miR | TJU_CMC_MD2.ID00715.hairpin | YES | NO | NO | NO | NO | NO | NO | NO |
| TJU_CMC_MD2.ID00716.3p-miR | TJU_CMC_MD2.ID00716.hairpin | YES | YES | YES | YES | YES | YES | NO | NO |
| TJU_CMC_MD2.ID00716.5p-miR | TJU_CMC_MD2.ID00716.hairpin | YES | YES | YES | YES | YES | NO | NO | NO |
| TJU_CMC_MD2.ID00717.3p-miR | TJU_CMC_MD2.ID00717.hairpin | YES | NO | NO | NO | NO | NO | NO | NO |
| TJU_CMC_MD2.ID00718.5p-miR | TJU_CMC_MD2.ID00718.hairpin | YES | YES | YES | YES | YES | NO | NO | NO |
| TJU_CMC_MD2.ID00719.5p-miR | TJU_CMC_MD2.ID00719.hairpin | YES | YES | YES | YES | YES | NO | NO | NO |
| TJU_CMC_MD2.ID00720.5p-miR | TJU_CMC_MD2.ID00720.hairpin | YES | YES | YES | YES | YES | NO | NO | NO |
| TJU_CMC_MD2.ID00721.5p-miR | TJU_CMC_MD2.ID00721.hairpin | YES | YES | YES | YES | YES | NO | NO | NO |
| TJU_CMC_MD2.ID00722.5p-miR | TJU_CMC_MD2.ID00722.hairpin | YES | YES | NO | YES | YES | NO | NO | NO |
| TJU_CMC_MD2.ID00723.5p-miR | TJU_CMC_MD2.ID00723.hairpin | YES | YES | YES | YES | NO | NO | NO | NO |
| TJU_CMC_MD2.ID00724.5p-miR | TJU_CMC_MD2.ID00724.hairpin | YES | YES | YES | NO | NO | NO | NO | NO |
| TJU_CMC_MD2.ID00725.3p-miR | TJU_CMC_MD2.ID00725.hairpin | YES | YES | YES | YES | YES | NO | NO | NO |
| TJU_CMC_MD2.ID00726.3p-miR | TJU_CMC_MD2.ID00726.hairpin | YES | YES | YES | YES | YES | YES | NO | NO |
| TJU_CMC_MD2.ID00726.5p-miR | TJU_CMC_MD2.ID00726.hairpin | YES | YES | YES | YES | YES | YES | NO | NO |
| TJU_CMC_MD2.ID00727.3p-miR | TJU_CMC_MD2.ID00727.hairpin | YES | NO | NO | NO | NO | NO | NO | NO |
| TJU_CMC_MD2.ID00728.3p-miR | TJU_CMC_MD2.ID00728.hairpin | YES | NO | NO | NO | NO | NO | NO | NO |
| TJU_CMC_MD2.ID00729.5p-miR | TJU_CMC_MD2.ID00729.hairpin | YES | YES | NO | YES | NO | NO | NO | NO |
| TJU_CMC_MD2.ID00730.3p-miR | TJU_CMC_MD2.ID00730.hairpin | YES | NO | NO | NO | NO | NO | NO | NO |
| TJU_CMC_MD2.ID00731.5p-miR | TJU_CMC_MD2.ID00731.hairpin | YES | YES | YES | YES | NO | NO | NO | NO |
| TJU_CMC_MD2.ID00732.3p-miR | TJU_CMC_MD2.ID00732.hairpin | YES | NO | NO | NO | NO | NO | NO | NO |
| TJU_CMC_MD2.ID00733.5p-miR | TJU_CMC_MD2.ID00733.hairpin | YES | NO | YES | NO | NO | NO | NO | NO |
| TJU_CMC_MD2.ID00734.5p-miR | TJU_CMC_MD2.ID00734.hairpin | YES | YES | YES | YES | YES | YES | NO | NO |
| TJU_CMC_MD2.ID00735.3p-miR | TJU_CMC_MD2.ID00735.hairpin | YES | NO | NO | NO | NO | NO | NO | NO |
| TJU_CMC_MD2.ID00736.5p-miR | TJU_CMC_MD2.ID00736.hairpin | YES | NO | YES | NO | NO | NO | NO | NO |
| TJU_CMC_MD2.ID00737.3p-miR | TJU_CMC_MD2.ID00737.hairpin | YES | YES | YES | YES | YES | YES | NO | NO |
| TJU_CMC_MD2.ID00738.5p-miR | TJU_CMC_MD2.ID00738.hairpin | YES | YES | YES | YES | NO | NO | NO | NO |
| TJU_CMC_MD2.ID00739.3p-miR | TJU_CMC_MD2.ID00739.hairpin | YES | NO | NO | NO | NO | NO | NO | NO |
| TJU_CMC_MD2.ID00740.3p-miR | TJU_CMC_MD2.ID00740.hairpin | YES | NO | NO | NO | NO | NO | NO | NO |
| TJU_CMC_MD2.ID00741.3p-miR | TJU_CMC_MD2.ID00741.hairpin | YES | NO | NO | NO | NO | NO | NO | NO |
| TJU_CMC_MD2.ID00742.3p-miR | TJU_CMC_MD2.ID00742.hairpin | YES | NO | NO | NO | NO | NO | NO | NO |
| TJU_CMC_MD2.ID00743.5p-miR | TJU_CMC_MD2.ID00743.hairpin | YES | YES | YES | YES | NO | NO | NO | NO |
| TJU_CMC_MD2.ID00744.3p-miR | TJU_CMC_MD2.ID00744.hairpin | YES | NO | NO | NO | NO | NO | NO | NO |
| TJU_CMC_MD2.ID00745.5p-miR | TJU_CMC_MD2.ID00745.hairpin | YES | YES | YES | YES | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00746.5p-miR | TJU_CMC_MD2.ID00746.hairpin | YES | YES | YES | NO | YES | NO | NO | NO |
| TJU_CMC_MD2.ID00747.3p-miR | TJU_CMC_MD2.ID00747.hairpin | YES | NO | NO | NO | NO | NO | NO | NO |
| TJU_CMC_MD2.ID00748.3p-miR | TJU_CMC_MD2.ID00748.hairpin | YES | NO | NO | NO | NO | NO | NO | NO |
| TJU_CMC_MD2.ID00749.3p-miR | TJU_CMC_MD2.ID00749.hairpin | YES | NO | NO | NO | NO | NO | NO | NO |
| TJU_CMC_MD2.ID00750.3p-miR | TJU_CMC_MD2.ID00750.hairpin | YES | NO | NO | NO | NO | NO | NO | NO |
| TJU_CMC_MD2.ID00751.3p-miR | TJU_CMC_MD2.ID00751.hairpin | YES | NO | NO | NO | NO | NO | NO | NO |
| TJU_CMC_MD2.ID00752.3p-miR | TJU_CMC_MD2.ID00752.hairpin | YES | NO | NO | NO | NO | NO | NO | NO |
| TJU_CMC_MD2.ID00753.3p-miR | TJU_CMC_MD2.ID00753.hairpin | YES | NO | NO | NO | NO | NO | NO | NO |
| TJU_CMC_MD2.ID00754.3p-miR | TJU_CMC_MD2.ID00754.hairpin | YES | NO | NO | NO | NO | NO | NO | NO |
| TJU_CMC_MD2.ID00755.3p-miR | TJU_CMC_MD2.ID00755.hairpin | YES | NO | NO | NO | NO | NO | NO | NO |
| TJU_CMC_MD2.ID00755.5p-miR | TJU_CMC_MD2.ID00755.hairpin | YES | YES | YES | YES | YES | NO | NO | NO |
| TJU_CMC_MD2.ID00756.3p-miR | TJU_CMC_MD2.ID00756.hairpin | YES | NO | NO | NO | NO | NO | NO | NO |
| TJU_CMC_MD2.ID00757.3p-miR | TJU_CMC_MD2.ID00757.hairpin | YES | YES | YES | YES | YES | NO | NO | NO |
| TJU_CMC_MD2.ID00757.5p-miR | TJU_CMC_MD2.ID00757.hairpin | YES | YES | YES | YES | NO | NO | NO | NO |
| TJU_CMC_MD2.ID00758.5p-miR | TJU_CMC_MD2.ID00758.hairpin | YES | YES | YES | YES | YES | NO | NO | NO |
| TJU_CMC_MD2.ID00759.5p-miR | TJU_CMC_MD2.ID00759.hairpin | YES | YES | YES | YES | NO | NO | NO | NO |
| TJU_CMC_MD2.ID00760.3p-miR | TJU_CMC_MD2.ID00760.hairpin | YES | NO | NO | NO | NO | NO | NO | NO |
| TJU_CMC_MD2.ID00761.3p-miR | TJU_CMC_MD2.ID00761.hairpin | YES | NO | NO | NO | NO | NO | NO | NO |
| TJU_CMC_MD2.ID00762.3p-miR | TJU_CMC_MD2.ID00762.hairpin | YES | NO | NO | NO | NO | NO | NO | NO |
| TJU_CMC_MD2.ID00763.3p-miR | TJU_CMC_MD2.ID00763.hairpin | YES | NO | NO | NO | NO | NO | NO | NO |
| TJU_CMC_MD2.ID00764.5p-miR | TJU_CMC_MD2.ID00764.hairpin | YES | YES | YES | YES | NO | NO | NO | NO |
| TJU_CMC_MD2.ID00765.5p-miR | TJU_CMC_MD2.ID00765.hairpin | YES | NO | YES | YES | NO | NO | NO | NO |
| TJU_CMC_MD2.ID00766.5p-miR | TJU_CMC_MD2.ID00766.hairpin | YES | YES | YES | NO | NO | NO | NO | NO |
| TJU_CMC_MD2.ID00767.3p-miR | TJU_CMC_MD2.ID00767.hairpin | YES | NO | NO | NO | NO | NO | NO | NO |
| TJU_CMC_MD2.ID00768.3p-miR | TJU_CMC_MD2.ID00768.hairpin | YES | NO | NO | NO | NO | NO | NO | NO |
| TJU_CMC_MD2.ID00769.5p-miR | TJU_CMC_MD2.ID00769.hairpin | YES | NO | YES | YES | YES | NO | NO | NO |
| TJU_CMC_MD2.ID00770.3p-miR | TJU_CMC_MD2.ID00770.hairpin | YES | NO | NO | NO | NO | NO | NO | NO |
| TJU_CMC_MD2.ID00771.3p-miR | TJU_CMC_MD2.ID00771.hairpin | YES | YES | YES | YES | NO | NO | NO | NO |
| TJU_CMC_MD2.ID00771.5p-miR | TJU_CMC_MD2.ID00771.hairpin | YES | YES | YES | YES | YES | NO | NO | NO |
| TJU_CMC_MD2.ID00772.3p-miR | TJU_CMC_MD2.ID00772.hairpin | YES | NO | NO | NO | NO | NO | NO | NO |
| TJU_CMC_MD2.ID00772.5p-miR | TJU_CMC_MD2.ID00772.hairpin | YES | NO | YES | YES | NO | NO | NO | NO |
| TJU_CMC_MD2.ID00773.3p-miR | TJU_CMC_MD2.ID00773.hairpin | YES | NO | NO | NO | NO | NO | NO | NO |
| TJU_CMC_MD2.ID00774.3p-miR | TJU_CMC_MD2.ID00774.hairpin | YES | NO | NO | NO | NO | NO | NO | NO |
| TJU_CMC_MD2.ID00775.3p-miR | TJU_CMC_MD2.ID00775.hairpin | YES | NO | NO | NO | NO | NO | NO | NO |
| TJU_CMC_MD2.ID00776.3p-miR | TJU_CMC_MD2.ID00776.hairpin | YES | NO | NO | NO | NO | NO | NO | NO |
| TJU_CMC_MD2.ID00776.5p-miR | TJU_CMC_MD2.ID00776.hairpin | YES | YES | YES | YES | NO | NO | NO | NO |
| TJU_CMC_MD2.ID00777.3p-miR | TJU_CMC_MD2.ID00777.hairpin | YES | NO | NO | NO | NO | NO | NO | NO |
| TJU_CMC_MD2.ID00778.3p-miR | TJU_CMC_MD2.ID00778.hairpin | YES | NO | NO | NO | NO | NO | NO | NO |
| TJU_CMC_MD2.ID00779.3p-miR | TJU_CMC_MD2.ID00779.hairpin | YES | NO | NO | NO | NO | NO | NO | NO |
| TJU_CMC_MD2.ID00780.3p-miR | TJU_CMC_MD2.ID00780.hairpin | YES | NO | NO | NO | NO | NO | NO | NO |
| TJU_CMC_MD2.ID00781.3p-miR | TJU_CMC_MD2.ID00781.hairpin | YES | NO | NO | NO | NO | NO | NO | NO |
| TJU_CMC_MD2.ID00782.3p-miR | TJU_CMC_MD2.ID00782.hairpin | YES | NO | NO | NO | NO | NO | NO | NO |
| TJU_CMC_MD2.ID00783.3p-miR | TJU_CMC_MD2.ID00783.hairpin | YES | NO | NO | NO | NO | NO | NO | NO |
| TJU_CMC_MD2.ID00784.3p-miR | TJU_CMC_MD2.ID00784.hairpin | YES | NO | NO | NO | NO | NO | NO | NO |
| TJU_CMC_MD2.ID00785.3p-miR | TJU_CMC_MD2.ID00785.hairpin | YES | NO | NO | NO | NO | NO | NO | NO |
| TJU_CMC_MD2.ID00785.5p-miR | TJU_CMC_MD2.ID00785.hairpin | YES | YES | YES | YES | NO | NO | NO | NO |
| TJU_CMC_MD2.ID00786.5p-miR | TJU_CMC_MD2.ID00786.hairpin | YES | YES | YES | NO | NO | NO | NO | NO |
| TJU_CMC_MD2.ID00787.3p-miR | TJU_CMC_MD2.ID00787.hairpin | YES | NO | NO | NO | NO | NO | NO | NO |
| TJU_CMC_MD2.ID00788.5p-miR | TJU_CMC_MD2.ID00788.hairpin | YES | YES | YES | NO | NO | NO | NO | NO |
| TJU_CMC_MD2.ID00789.5p-miR | TJU_CMC_MD2.ID00789.hairpin | YES | YES | YES | YES | YES | NO | NO | NO |
| TJU_CMC_MD2.ID00790.3p-miR | TJU_CMC_MD2.ID00790.hairpin | YES | NO | NO | NO | NO | NO | NO | NO |
| TJU_CMC_MD2.ID00791.5p-miR | TJU_CMC_MD2.ID00791.hairpin | YES | YES | YES | YES | YES | NO | NO | NO |
| TJU_CMC_MD2.ID00792.3p-miR | TJU_CMC_MD2.ID00792.hairpin | YES | NO | NO | NO | NO | NO | NO | NO |
| TJU_CMC_MD2.ID00793.5p-miR | TJU_CMC_MD2.ID00793.hairpin | YES | YES | YES | YES | NO | NO | NO | NO |
| TJU_CMC_MD2.ID00794.3p-miR | TJU_CMC_MD2.ID00794.hairpin | YES | NO | NO | NO | NO | NO | NO | NO |
| TJU_CMC_MD2.ID00795.5p-miR | TJU_CMC_MD2.ID00795.hairpin | YES | NO | NO | NO | NO | NO | NO | NO |
| TJU_CMC_MD2.ID00796.3p-miR | TJU_CMC_MD2.ID00796.hairpin | YES | NO | NO | NO | NO | NO | NO | NO |
| TJU_CMC_MD2.ID00797.3p-miR | TJU_CMC_MD2.ID00797.hairpin | YES | NO | NO | NO | NO | NO | NO | NO |
| TJU_CMC_MD2.ID00798.3p-miR | TJU_CMC_MD2.ID00798.hairpin | YES | NO | NO | NO | NO | NO | NO | NO |
| TJU_CMC_MD2.ID00799.3p-miR | TJU_CMC_MD2.ID00799.hairpin | YES | NO | NO | NO | NO | NO | NO | NO |
| TJU_CMC_MD2.ID00800.5p-miR | TJU_CMC_MD2.ID00800.hairpin | YES | YES | YES | YES | YES | NO | NO | NO |
| TJU_CMC_MD2.ID00801.5p-miR | TJU_CMC_MD2.ID00801.hairpin | YES | YES | YES | YES | YES | NO | NO | NO |
| TJU_CMC_MD2.ID00802.5p-miR | TJU_CMC_MD2.ID00802.hairpin | YES | NO | NO | NO | YES | NO | NO | NO |
| TJU_CMC_MD2.ID00803.5p-miR | TJU_CMC_MD2.ID00803.hairpin | YES | NO | NO | YES | NO | NO | NO | NO |
| TJU_CMC_MD2.ID00804.3p-miR | TJU_CMC_MD2.ID00804.hairpin | YES | NO | NO | NO | NO | NO | NO | NO |
| TJU_CMC_MD2.ID00805.3p-miR | TJU_CMC_MD2.ID00805.hairpin | YES | NO | NO | NO | NO | NO | NO | NO |
| TJU_CMC_MD2.ID00806.5p-miR | TJU_CMC_MD2.ID00806.hairpin | YES | YES | YES | YES | NO | NO | NO | NO |
| TJU_CMC_MD2.ID00807.5p-miR | TJU_CMC_MD2.ID00807.hairpin | YES | NO | NO | NO | NO | NO | NO | NO |
| TJU_CMC_MD2.ID00808.3p-miR | TJU_CMC_MD2.ID00808.hairpin | YES | NO | NO | NO | NO | NO | NO | NO |
| TJU_CMC_MD2.ID00809.3p-miR | TJU_CMC_MD2.ID00809.hairpin | YES | NO | NO | NO | NO | NO | NO | NO |
| TJU_CMC_MD2.ID00810.3p-miR | TJU_CMC_MD2.ID00810.hairpin | YES | NO | NO | NO | NO | NO | NO | NO |
| TJU_CMC_MD2.ID00810.5p-miR | TJU_CMC_MD2.ID00810.hairpin | YES | YES | YES | NO | YES | NO | NO | NO |
| TJU_CMC_MD2.ID00811.3p-miR | TJU_CMC_MD2.ID00811.hairpin | YES | NO | NO | NO | NO | NO | NO | NO |
| TJU_CMC_MD2.ID00812.5p-miR | TJU_CMC_MD2.ID00812.hairpin | YES | YES | YES | NO | NO | NO | NO | NO |
| TJU_CMC_MD2.ID00813.5p-miR | TJU_CMC_MD2.ID00813.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00814.5p-miR | TJU_CMC_MD2.ID00814.hairpin | YES | YES | NO | YES | NO | NO | NO | NO |
| TJU_CMC_MD2.ID00815.5p-miR | TJU_CMC_MD2.ID00815.hairpin | YES | NO | YES | NO | YES | NO | NO | NO |
| TJU_CMC_MD2.ID00816.3p-miR | TJU_CMC_MD2.ID00816.hairpin | YES | NO | NO | NO | NO | NO | NO | NO |
| TJU_CMC_MD2.ID00817.3p-miR | TJU_CMC_MD2.ID00817.hairpin | YES | NO | NO | NO | NO | NO | NO | NO |
| TJU_CMC_MD2.ID00818.3p-miR | TJU_CMC_MD2.ID00818.hairpin | YES | NO | NO | NO | NO | NO | NO | NO |
| TJU_CMC_MD2.ID00819.3p-miR | TJU_CMC_MD2.ID00819.hairpin | YES | NO | NO | NO | NO | NO | NO | NO |
| TJU_CMC_MD2.ID00820.5p-miR | TJU_CMC_MD2.ID00820.hairpin | YES | NO | YES | NO | NO | NO | NO | NO |
| TJU_CMC_MD2.ID00821.3p-miR | TJU_CMC_MD2.ID00821.hairpin | YES | NO | NO | NO | NO | NO | NO | NO |
| TJU_CMC_MD2.ID00822.5p-miR | TJU_CMC_MD2.ID00822.hairpin | YES | YES | YES | YES | NO | NO | NO | NO |
| TJU_CMC_MD2.ID00823.3p-miR | TJU_CMC_MD2.ID00823.hairpin | YES | NO | NO | NO | NO | NO | NO | NO |
| TJU_CMC_MD2.ID00824.5p-miR | TJU_CMC_MD2.ID00824.hairpin | YES | YES | YES | YES | YES | NO | NO | NO |
| TJU_CMC_MD2.ID00825.3p-miR | TJU_CMC_MD2.ID00825.hairpin | YES | NO | NO | NO | NO | NO | NO | NO |
| TJU_CMC_MD2.ID00826.5p-miR | TJU_CMC_MD2.ID00826.hairpin | YES | YES | NO | YES | NO | NO | NO | NO |
| TJU_CMC_MD2.ID00827.3p-miR | TJU_CMC_MD2.ID00827.hairpin | YES | NO | NO | NO | NO | NO | NO | NO |
| TJU_CMC_MD2.ID00828.5p-miR | TJU_CMC_MD2.ID00828.hairpin | YES | YES | YES | YES | NO | YES | NO | NO |
| TJU_CMC_MD2.ID00829.5p-miR | TJU_CMC_MD2.ID00829.hairpin | YES | YES | YES | NO | NO | NO | NO | NO |
| TJU_CMC_MD2.ID00830.5p-miR | TJU_CMC_MD2.ID00830.hairpin | YES | YES | NO | YES | YES | NO | NO | NO |
| TJU_CMC_MD2.ID00831.5p-miR | TJU_CMC_MD2.ID00831.hairpin | YES | YES | NO | NO | NO | NO | NO | NO |
| TJU_CMC_MD2.ID00832.5p-miR | TJU_CMC_MD2.ID00832.hairpin | YES | NO | YES | NO | YES | NO | NO | NO |
| TJU_CMC_MD2.ID00833.5p-miR | TJU_CMC_MD2.ID00833.hairpin | YES | NO | NO | YES | YES | NO | NO | NO |
| TJU_CMC_MD2.ID00834.3p-miR | TJU_CMC_MD2.ID00834.hairpin | YES | NO | NO | NO | NO | NO | NO | NO |
| TJU_CMC_MD2.ID00835.5p-miR | TJU_CMC_MD2.ID00835.hairpin | YES | YES | YES | NO | YES | NO | NO | NO |
| TJU_CMC_MD2.ID00836.5p-miR | TJU_CMC_MD2.ID00836.hairpin | YES | YES | YES | YES | YES | NO | NO | NO |
| TJU_CMC_MD2.ID00837.5p-miR | TJU_CMC_MD2.ID00837.hairpin | YES | YES | YES | YES | YES | NO | NO | NO |
| TJU_CMC_MD2.ID00838.3p-miR | TJU_CMC_MD2.ID00838.hairpin | YES | NO | NO | NO | NO | NO | NO | NO |
| TJU_CMC_MD2.ID00839.3p-miR | TJU_CMC_MD2.ID00839.hairpin | YES | NO | NO | NO | NO | NO | NO | NO |
| TJU_CMC_MD2.ID00840.3p-miR | TJU_CMC_MD2.ID00840.hairpin | YES | NO | NO | NO | NO | NO | NO | NO |
| TJU_CMC_MD2.ID00840.5p-miR | TJU_CMC_MD2.ID00840.hairpin | YES | YES | YES | YES | YES | NO | NO | NO |
| TJU_CMC_MD2.ID00841.3p-miR | TJU_CMC_MD2.ID00841.hairpin | YES | NO | NO | NO | NO | NO | NO | NO |
| TJU_CMC_MD2.ID00842.3p-miR | TJU_CMC_MD2.ID00842.hairpin | YES | NO | NO | NO | NO | NO | NO | NO |
| TJU_CMC_MD2.ID00843.5p-miR | TJU_CMC_MD2.ID00843.hairpin | YES | NO | NO | NO | NO | NO | NO | NO |
| TJU_CMC_MD2.ID00844.3p-miR | TJU_CMC_MD2.ID00844.hairpin | YES | NO | NO | NO | NO | NO | NO | NO |
| TJU_CMC_MD2.ID00845.3p-miR | TJU_CMC_MD2.ID00845.hairpin | YES | NO | NO | NO | NO | NO | NO | NO |
| TJU_CMC_MD2.ID00846.3p-miR | TJU_CMC_MD2.ID00846.hairpin | YES | NO | NO | NO | NO | NO | NO | NO |
| TJU_CMC_MD2.ID00847.3p-miR | TJU_CMC_MD2.ID00847.hairpin | YES | NO | NO | NO | NO | NO | NO | NO |
| TJU_CMC_MD2.ID00848.5p-miR | TJU_CMC_MD2.ID00848.hairpin | YES | YES | YES | YES | NO | NO | NO | NO |
| TJU_CMC_MD2.ID00849.3p-miR | TJU_CMC_MD2.ID00849.hairpin | YES | NO | NO | NO | NO | NO | NO | NO |
| TJU_CMC_MD2.ID00850.3p-miR | TJU_CMC_MD2.ID00850.hairpin | YES | NO | NO | NO | NO | NO | NO | NO |
| TJU_CMC_MD2.ID00851.5p-miR | TJU_CMC_MD2.ID00851.hairpin | YES | YES | YES | NO | NO | NO | NO | NO |
| TJU_CMC_MD2.ID00852.5p-miR | TJU_CMC_MD2.ID00852.hairpin | YES | NO | YES | YES | YES | NO | NO | NO |
| TJU_CMC_MD2.ID00853.5p-miR | TJU_CMC_MD2.ID00853.hairpin | YES | NO | NO | NO | NO | NO | NO | NO |
| TJU_CMC_MD2.ID00854.5p-miR | TJU_CMC_MD2.ID00854.hairpin | YES | YES | NO | NO | NO | NO | NO | NO |
| TJU_CMC_MD2.ID00855.5p-miR | TJU_CMC_MD2.ID00855.hairpin | YES | NO | NO | NO | NO | NO | NO | NO |
| TJU_CMC_MD2.ID00856.3p-miR | TJU_CMC_MD2.ID00856.hairpin | YES | NO | NO | NO | NO | NO | NO | NO |
| TJU_CMC_MD2.ID00857.5p-miR | TJU_CMC_MD2.ID00857.hairpin | YES | YES | NO | YES | NO | NO | NO | NO |
| TJU_CMC_MD2.ID00858.5p-miR | TJU_CMC_MD2.ID00858.hairpin | YES | YES | YES | YES | YES | NO | NO | NO |
| TJU_CMC_MD2.ID00859.5p-miR | TJU_CMC_MD2.ID00859.hairpin | YES | YES | YES | NO | YES | NO | NO | NO |
| TJU_CMC_MD2.ID00860.3p-miR | TJU_CMC_MD2.ID00860.hairpin | YES | NO | NO | NO | NO | NO | NO | NO |
| TJU_CMC_MD2.ID00861.3p-miR | TJU_CMC_MD2.ID00861.hairpin | YES | NO | NO | NO | NO | NO | NO | NO |
| TJU_CMC_MD2.ID00862.3p-miR | TJU_CMC_MD2.ID00862.hairpin | YES | NO | NO | NO | NO | NO | NO | NO |
| TJU_CMC_MD2.ID00863.5p-miR | TJU_CMC_MD2.ID00863.hairpin | YES | YES | YES | YES | NO | NO | NO | NO |
| TJU_CMC_MD2.ID00864.3p-miR | TJU_CMC_MD2.ID00864.hairpin | YES | NO | NO | NO | NO | NO | NO | NO |
| TJU_CMC_MD2.ID00865.5p-miR | TJU_CMC_MD2.ID00865.hairpin | YES | YES | YES | YES | NO | NO | NO | NO |
| TJU_CMC_MD2.ID00866.3p-miR | TJU_CMC_MD2.ID00866.hairpin | YES | NO | NO | NO | NO | NO | NO | NO |
| TJU_CMC_MD2.ID00867.3p-miR | TJU_CMC_MD2.ID00867.hairpin | YES | NO | NO | NO | NO | NO | NO | NO |
| TJU_CMC_MD2.ID00868.5p-miR | TJU_CMC_MD2.ID00868.hairpin | YES | NO | NO | NO | NO | NO | NO | NO |
| TJU_CMC_MD2.ID00869.3p-miR | TJU_CMC_MD2.ID00869.hairpin | YES | NO | NO | NO | NO | NO | NO | NO |
| TJU_CMC_MD2.ID00870.5p-miR | TJU_CMC_MD2.ID00870.hairpin | YES | NO | YES | NO | NO | NO | NO | NO |
| TJU_CMC_MD2.ID00871.3p-miR | TJU_CMC_MD2.ID00871.hairpin | YES | NO | NO | NO | NO | NO | NO | NO |
| TJU_CMC_MD2.ID00872.3p-miR | TJU_CMC_MD2.ID00872.hairpin | YES | NO | NO | NO | NO | NO | NO | NO |
| TJU_CMC_MD2.ID00873.5p-miR | TJU_CMC_MD2.ID00873.hairpin | YES | NO | YES | NO | YES | NO | NO | NO |
| TJU_CMC_MD2.ID00874.3p-miR | TJU_CMC_MD2.ID00874.hairpin | YES | NO | NO | NO | NO | NO | NO | NO |
| TJU_CMC_MD2.ID00875.3p-miR | TJU_CMC_MD2.ID00875.hairpin | YES | NO | NO | NO | NO | NO | NO | NO |
| TJU_CMC_MD2.ID00876.3p-miR | TJU_CMC_MD2.ID00876.hairpin | YES | NO | NO | NO | NO | NO | NO | NO |
| TJU_CMC_MD2.ID00876.5p-miR | TJU_CMC_MD2.ID00876.hairpin | YES | YES | YES | NO | YES | NO | NO | NO |
| TJU_CMC_MD2.ID00877.5p-miR | TJU_CMC_MD2.ID00877.hairpin | YES | YES | YES | NO | NO | NO | NO | NO |
| TJU_CMC_MD2.ID00878.3p-miR | TJU_CMC_MD2.ID00878.hairpin | YES | NO | NO | NO | NO | NO | NO | NO |
| TJU_CMC_MD2.ID00879.3p-miR | TJU_CMC_MD2.ID00879.hairpin | YES | NO | NO | NO | NO | NO | NO | NO |
| TJU_CMC_MD2.ID00880.3p-miR | TJU_CMC_MD2.ID00880.hairpin | YES | NO | NO | NO | NO | NO | NO | NO |
| TJU_CMC_MD2.ID00881.3p-miR | TJU_CMC_MD2.ID00881.hairpin | YES | NO | NO | NO | NO | NO | NO | NO |
| TJU_CMC_MD2.ID00882.3p-miR | TJU_CMC_MD2.ID00882.hairpin | YES | NO | NO | NO | NO | NO | NO | NO |
| TJU_CMC_MD2.ID00883.3p-miR | TJU_CMC_MD2.ID00883.hairpin | YES | NO | NO | NO | NO | NO | NO | NO |
| TJU_CMC_MD2.ID00884.3p-miR | TJU_CMC_MD2.ID00884.hairpin | YES | NO | NO | NO | NO | NO | NO | NO |
| TJU_CMC_MD2.ID00885.3p-miR | TJU_CMC_MD2.ID00885.hairpin | YES | NO | NO | NO | NO | NO | NO | NO |
| TJU_CMC_MD2.ID00886.5p-miR | TJU_CMC_MD2.ID00886.hairpin | YES | YES | YES | NO | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00887.5p-miR | TJU_CMC_MD2.ID00887.hairpin | YES | NO | YES | NO | NO | NO | NO | NO |
| TJU_CMC_MD2.ID00888.5p-miR | TJU_CMC_MD2.ID00888.hairpin | YES | YES | YES | NO | YES | NO | NO | NO |
| TJU_CMC_MD2.ID00889.3p-miR | TJU_CMC_MD2.ID00889.hairpin | YES | NO | NO | NO | NO | NO | NO | NO |
| TJU_CMC_MD2.ID00890.3p-miR | TJU_CMC_MD2.ID00890.hairpin | YES | NO | NO | NO | NO | NO | NO | NO |
| TJU_CMC_MD2.ID00891.5p-miR | TJU_CMC_MD2.ID00891.hairpin | YES | NO | YES | YES | NO | NO | NO | NO |
| TJU_CMC_MD2.ID00892.3p-miR | TJU_CMC_MD2.ID00892.hairpin | YES | NO | NO | NO | NO | NO | NO | NO |
| TJU_CMC_MD2.ID00893.3p-miR | TJU_CMC_MD2.ID00893.hairpin | YES | NO | NO | NO | NO | NO | NO | NO |
| TJU_CMC_MD2.ID00894.5p-miR | TJU_CMC_MD2.ID00894.hairpin | YES | NO | YES | NO | NO | NO | NO | NO |
| TJU_CMC_MD2.ID00895.3p-miR | TJU_CMC_MD2.ID00895.hairpin | YES | NO | NO | NO | NO | NO | NO | NO |
| TJU_CMC_MD2.ID00896.5p-miR | TJU_CMC_MD2.ID00896.hairpin | YES | NO | YES | NO | NO | NO | NO | NO |
| TJU_CMC_MD2.ID00897.3p-miR | TJU_CMC_MD2.ID00897.hairpin | YES | NO | NO | NO | NO | NO | NO | NO |
| TJU_CMC_MD2.ID00898.3p-miR | TJU_CMC_MD2.ID00898.hairpin | YES | NO | NO | NO | NO | NO | NO | NO |
| TJU_CMC_MD2.ID00898.5p-miR | TJU_CMC_MD2.ID00898.hairpin | YES | NO | NO | NO | NO | NO | NO | NO |
| TJU_CMC_MD2.ID00899.5p-miR | TJU_CMC_MD2.ID00899.hairpin | YES | YES | NO | NO | NO | NO | NO | NO |
| TJU_CMC_MD2.ID00900.5p-miR | TJU_CMC_MD2.ID00900.hairpin | YES | YES | YES | YES | NO | NO | NO | NO |
| TJU_CMC_MD2.ID00901.3p-miR | TJU_CMC_MD2.ID00901.hairpin | YES | NO | NO | NO | NO | NO | NO | NO |
| TJU_CMC_MD2.ID00902.5p-miR | TJU_CMC_MD2.ID00902.hairpin | YES | YES | YES | NO | NO | NO | NO | NO |
| TJU_CMC_MD2.ID00903.5p-miR | TJU_CMC_MD2.ID00903.hairpin | YES | YES | YES | YES | YES | NO | NO | NO |
| TJU_CMC_MD2.ID00904.3p-miR | TJU_CMC_MD2.ID00904.hairpin | YES | NO | NO | NO | NO | NO | NO | NO |
| TJU_CMC_MD2.ID00905.3p-miR | TJU_CMC_MD2.ID00905.hairpin | YES | NO | NO | NO | NO | NO | NO | NO |
| TJU_CMC_MD2.ID00906.3p-miR | TJU_CMC_MD2.ID00906.hairpin | YES | NO | NO | NO | NO | NO | NO | NO |
| TJU_CMC_MD2.ID00907.5p-miR | TJU_CMC_MD2.ID00907.hairpin | YES | YES | YES | YES | YES | NO | NO | NO |
| TJU_CMC_MD2.ID00908.5p-miR | TJU_CMC_MD2.ID00908.hairpin | YES | YES | NO | YES | NO | NO | NO | NO |
| TJU_CMC_MD2.ID00909.3p-miR | TJU_CMC_MD2.ID00909.hairpin | YES | NO | NO | NO | NO | NO | NO | NO |
| TJU_CMC_MD2.ID00910.3p-miR | TJU_CMC_MD2.ID00910.hairpin | YES | NO | NO | NO | NO | NO | NO | NO |
| TJU_CMC_MD2.ID00911.5p-miR | TJU_CMC_MD2.ID00911.hairpin | YES | NO | YES | NO | NO | NO | NO | NO |
| TJU_CMC_MD2.ID00912.5p-miR | TJU_CMC_MD2.ID00912.hairpin | YES | NO | NO | YES | NO | NO | NO | NO |
| TJU_CMC_MD2.ID00913.5p-miR | TJU_CMC_MD2.ID00913.hairpin | YES | YES | NO | YES | NO | NO | NO | NO |
| TJU_CMC_MD2.ID00914.3p-miR | TJU_CMC_MD2.ID00914.hairpin | YES | NO | NO | NO | NO | NO | NO | NO |
| TJU_CMC_MD2.ID00915.3p-miR | TJU_CMC_MD2.ID00915.hairpin | YES | NO | NO | NO | NO | NO | NO | NO |
| TJU_CMC_MD2.ID00916.5p-miR | TJU_CMC_MD2.ID00916.hairpin | YES | YES | YES | YES | YES | NO | NO | NO |
| TJU_CMC_MD2.ID00917.5p-miR | TJU_CMC_MD2.ID00917.hairpin | YES | NO | YES | NO | YES | NO | NO | NO |
| TJU_CMC_MD2.ID00918.5p-miR | TJU_CMC_MD2.ID00918.hairpin | YES | NO | YES | YES | NO | NO | NO | NO |
| TJU_CMC_MD2.ID00919.3p-miR | TJU_CMC_MD2.ID00919.hairpin | YES | NO | NO | NO | NO | NO | NO | NO |
| TJU_CMC_MD2.ID00919.5p-miR | TJU_CMC_MD2.ID00919.hairpin | YES | YES | YES | NO | NO | NO | NO | NO |
| TJU_CMC_MD2.ID00920.5p-miR | TJU_CMC_MD2.ID00920.hairpin | YES | NO | NO | YES | NO | NO | NO | NO |
| TJU_CMC_MD2.ID00921.3p-miR | TJU_CMC_MD2.ID00921.hairpin | YES | NO | NO | NO | NO | NO | NO | NO |
| TJU_CMC_MD2.ID00922.3p-miR | TJU_CMC_MD2.ID00922.hairpin | YES | NO | NO | NO | NO | NO | NO | NO |
| TJU_CMC_MD2.ID00923.3p-miR | TJU_CMC_MD2.ID00923.hairpin | YES | NO | NO | NO | NO | NO | NO | NO |
| TJU_CMC_MD2.ID00924.3p-miR | TJU_CMC_MD2.ID00924.hairpin | YES | NO | NO | NO | NO | NO | NO | NO |
| TJU_CMC_MD2.ID00925.5p-miR | TJU_CMC_MD2.ID00925.hairpin | YES | YES | YES | YES | YES | NO | NO | NO |
| TJU_CMC_MD2.ID00926.5p-miR | TJU_CMC_MD2.ID00926.hairpin | YES | YES | YES | NO | YES | NO | NO | NO |
| TJU_CMC_MD2.ID00927.3p-miR | TJU_CMC_MD2.ID00927.hairpin | YES | NO | NO | NO | NO | NO | NO | NO |
| TJU_CMC_MD2.ID00928.3p-miR | TJU_CMC_MD2.ID00928.hairpin | YES | NO | NO | NO | NO | NO | NO | NO |
| TJU_CMC_MD2.ID00928.5p-miR | TJU_CMC_MD2.ID00928.hairpin | YES | YES | YES | YES | YES | YES | NO | NO |
| TJU_CMC_MD2.ID00929.5p-miR | TJU_CMC_MD2.ID00929.hairpin | YES | NO | YES | YES | YES | YES | NO | NO |
| TJU_CMC_MD2.ID00930.3p-miR | TJU_CMC_MD2.ID00930.hairpin | YES | NO | NO | NO | NO | NO | NO | NO |
| TJU_CMC_MD2.ID00931.3p-miR | TJU_CMC_MD2.ID00931.hairpin | YES | NO | NO | NO | NO | NO | NO | NO |
| TJU_CMC_MD2.ID00932.3p-miR | TJU_CMC_MD2.ID00932.hairpin | YES | NO | NO | NO | NO | NO | NO | NO |
| TJU_CMC_MD2.ID00933.3p-miR | TJU_CMC_MD2.ID00933.hairpin | YES | NO | NO | NO | NO | NO | NO | NO |
| TJU_CMC_MD2.ID00934.3p-miR | TJU_CMC_MD2.ID00934.hairpin | YES | YES | YES | YES | YES | NO | NO | NO |
| TJU_CMC_MD2.ID00935.5p-miR | TJU_CMC_MD2.ID00935.hairpin | YES | YES | YES | YES | YES | YES | NO | NO |
| TJU_CMC_MD2.ID00936.5p-miR | TJU_CMC_MD2.ID00936.hairpin | YES | YES | YES | YES | YES | YES | NO | NO |
| TJU_CMC_MD2.ID00937.5p-miR | TJU_CMC_MD2.ID00937.hairpin | YES | YES | YES | YES | YES | NO | NO | NO |
| TJU_CMC_MD2.ID00938.5p-miR | TJU_CMC_MD2.ID00938.hairpin | YES | YES | YES | YES | YES | YES | NO | NO |
| TJU_CMC_MD2.ID00939.5p-miR | TJU_CMC_MD2.ID00939.hairpin | YES | YES | YES | YES | YES | NO | NO | NO |
| TJU_CMC_MD2.ID00940.3p-miR | TJU_CMC_MD2.ID00940.hairpin | YES | NO | NO | NO | NO | NO | NO | NO |
| TJU_CMC_MD2.ID00941.3p-miR | TJU_CMC_MD2.ID00941.hairpin | YES | NO | NO | NO | NO | NO | NO | NO |
| TJU_CMC_MD2.ID00942.3p-miR | TJU_CMC_MD2.ID00942.hairpin | YES | NO | NO | NO | NO | NO | NO | NO |
| TJU_CMC_MD2.ID00942.5p-miR | TJU_CMC_MD2.ID00942.hairpin | YES | NO | YES | YES | YES | NO | NO | NO |
| TJU_CMC_MD2.ID00943.3p-miR | TJU_CMC_MD2.ID00943.hairpin | YES | NO | NO | NO | NO | NO | NO | NO |
| TJU_CMC_MD2.ID00944.5p-miR | TJU_CMC_MD2.ID00944.hairpin | YES | YES | YES | NO | NO | NO | NO | NO |
| TJU_CMC_MD2.ID00945.3p-miR | TJU_CMC_MD2.ID00945.hairpin | YES | NO | NO | NO | NO | NO | NO | NO |
| TJU_CMC_MD2.ID00946.5p-miR | TJU_CMC_MD2.ID00946.hairpin | YES | NO | YES | NO | NO | NO | NO | NO |
| TJU_CMC_MD2.ID00947.3p-miR | TJU_CMC_MD2.ID00947.hairpin | YES | NO | NO | NO | NO | NO | NO | NO |
| TJU_CMC_MD2.ID00948.5p-miR | TJU_CMC_MD2.ID00948.hairpin | YES | YES | NO | YES | NO | NO | NO | NO |
| TJU_CMC_MD2.ID00949.3p-miR | TJU_CMC_MD2.ID00949.hairpin | YES | NO | NO | NO | NO | NO | NO | NO |
| TJU_CMC_MD2.ID00950.3p-miR | TJU_CMC_MD2.ID00950.hairpin | YES | NO | NO | NO | NO | NO | NO | NO |
| TJU_CMC_MD2.ID00951.5p-miR | TJU_CMC_MD2.ID00951.hairpin | YES | NO | YES | NO | NO | NO | NO | NO |
| TJU_CMC_MD2.ID00952.5p-miR | TJU_CMC_MD2.ID00952.hairpin | YES | YES | YES | NO | YES | NO | NO | NO |
| TJU_CMC_MD2.ID00953.5p-miR | TJU_CMC_MD2.ID00953.hairpin | YES | YES | YES | YES | NO | NO | NO | NO |
| TJU_CMC_MD2.ID00954.3p-miR | TJU_CMC_MD2.ID00954.hairpin | YES | NO | NO | NO | NO | NO | NO | NO |
| TJU_CMC_MD2.ID00955.3p-miR | TJU_CMC_MD2.ID00955.hairpin | YES | NO | NO | NO | NO | NO | NO | NO |
| TJU_CMC_MD2.ID00956.5p-miR | TJU_CMC_MD2.ID00956.hairpin | YES | NO | YES | NO | YES | NO | NO | NO |
| TJU_CMC_MD2.ID00957.5p-miR | TJU_CMC_MD2.ID00957.hairpin | YES | YES | YES | NO | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID00958.3p-miR | TJU_CMC_MD2.ID00958.hairpin | YES | NO | NO | NO | NO | NO | NO | NO |
| TJU_CMC_MD2.ID00959.3p-miR | TJU_CMC_MD2.ID00959.hairpin | YES | NO | NO | NO | NO | NO | NO | NO |
| TJU_CMC_MD2.ID00960.5p-miR | TJU_CMC_MD2.ID00960.hairpin | YES | YES | YES | NO | NO | NO | NO | NO |
| TJU_CMC_MD2.ID00961.3p-miR | TJU_CMC_MD2.ID00961.hairpin | YES | NO | NO | NO | NO | NO | NO | NO |
| TJU_CMC_MD2.ID00962.3p-miR | TJU_CMC_MD2.ID00962.hairpin | YES | NO | NO | NO | NO | NO | NO | NO |
| TJU_CMC_MD2.ID00963.3p-miR | TJU_CMC_MD2.ID00963.hairpin | YES | NO | NO | NO | NO | NO | NO | NO |
| TJU_CMC_MD2.ID00964.5p-miR | TJU_CMC_MD2.ID00964.hairpin | YES | NO | YES | NO | YES | NO | NO | NO |
| TJU_CMC_MD2.ID00965.3p-miR | TJU_CMC_MD2.ID00965.hairpin | YES | NO | NO | NO | NO | NO | NO | NO |
| TJU_CMC_MD2.ID00966.5p-miR | TJU_CMC_MD2.ID00966.hairpin | YES | YES | YES | YES | NO | NO | NO | NO |
| TJU_CMC_MD2.ID00967.5p-miR | TJU_CMC_MD2.ID00967.hairpin | YES | YES | YES | NO | NO | NO | NO | NO |
| TJU_CMC_MD2.ID00968.3p-miR | TJU_CMC_MD2.ID00968.hairpin | YES | NO | NO | NO | NO | NO | NO | NO |
| TJU_CMC_MD2.ID00969.3p-miR | TJU_CMC_MD2.ID00969.hairpin | YES | NO | NO | NO | NO | NO | NO | NO |
| TJU_CMC_MD2.ID00970.3p-miR | TJU_CMC_MD2.ID00970.hairpin | YES | NO | NO | NO | NO | NO | NO | NO |
| TJU_CMC_MD2.ID00971.3p-miR | TJU_CMC_MD2.ID00971.hairpin | YES | NO | NO | NO | NO | NO | NO | NO |
| TJU_CMC_MD2.ID00971.5p-miR | TJU_CMC_MD2.ID00971.hairpin | YES | NO | YES | NO | NO | NO | NO | NO |
| TJU_CMC_MD2.ID00972.5p-miR | TJU_CMC_MD2.ID00972.hairpin | YES | YES | NO | NO | YES | NO | NO | NO |
| TJU_CMC_MD2.ID00973.3p-miR | TJU_CMC_MD2.ID00973.hairpin | YES | NO | NO | NO | NO | NO | NO | NO |
| TJU_CMC_MD2.ID00974.3p-miR | TJU_CMC_MD2.ID00974.hairpin | YES | NO | NO | NO | NO | NO | NO | NO |
| TJU_CMC_MD2.ID00975.5p-miR | TJU_CMC_MD2.ID00975.hairpin | YES | YES | YES | YES | NO | NO | NO | NO |
| TJU_CMC_MD2.ID00976.3p-miR | TJU_CMC_MD2.ID00976.hairpin | YES | NO | NO | NO | NO | NO | NO | NO |
| TJU_CMC_MD2.ID00977.3p-miR | TJU_CMC_MD2.ID00977.hairpin | YES | NO | NO | NO | NO | NO | NO | NO |
| TJU_CMC_MD2.ID00978.5p-miR | TJU_CMC_MD2.ID00978.hairpin | YES | YES | NO | NO | NO | NO | NO | NO |
| TJU_CMC_MD2.ID00979.5p-miR | TJU_CMC_MD2.ID00979.hairpin | YES | YES | YES | YES | YES | NO | NO | NO |
| TJU_CMC_MD2.ID00980.3p-miR | TJU_CMC_MD2.ID00980.hairpin | YES | NO | NO | NO | NO | NO | NO | NO |
| TJU_CMC_MD2.ID00981.3p-miR | TJU_CMC_MD2.ID00981.hairpin | YES | NO | NO | NO | NO | NO | NO | NO |
| TJU_CMC_MD2.ID00982.3p-miR | TJU_CMC_MD2.ID00982.hairpin | YES | NO | NO | NO | NO | NO | NO | NO |
| TJU_CMC_MD2.ID00983.3p-miR | TJU_CMC_MD2.ID00983.hairpin | YES | NO | NO | NO | NO | NO | NO | NO |
| TJU_CMC_MD2.ID00984.5p-miR | TJU_CMC_MD2.ID00984.hairpin | YES | YES | YES | NO | YES | NO | NO | NO |
| TJU_CMC_MD2.ID00985.3p-miR | TJU_CMC_MD2.ID00985.hairpin | YES | NO | NO | NO | NO | NO | NO | NO |
| TJU_CMC_MD2.ID00986.5p-miR | TJU_CMC_MD2.ID00986.hairpin | YES | NO | YES | NO | YES | NO | NO | NO |
| TJU_CMC_MD2.ID00987.3p-miR | TJU_CMC_MD2.ID00987.hairpin | YES | NO | NO | NO | NO | NO | NO | NO |
| TJU_CMC_MD2.ID00988.3p-miR | TJU_CMC_MD2.ID00988.hairpin | YES | NO | NO | NO | NO | NO | NO | NO |
| TJU_CMC_MD2.ID00989.5p-miR | TJU_CMC_MD2.ID00989.hairpin | YES | YES | YES | YES | NO | NO | NO | NO |
| TJU_CMC_MD2.ID00990.5p-miR | TJU_CMC_MD2.ID00990.hairpin | YES | YES | YES | YES | YES | NO | NO | NO |
| TJU_CMC_MD2.ID00991.5p-miR | TJU_CMC_MD2.ID00991.hairpin | YES | YES | YES | YES | YES | YES | NO | NO |
| TJU_CMC_MD2.ID00992.5p-miR | TJU_CMC_MD2.ID00992.hairpin | YES | YES | YES | YES | NO | NO | NO | NO |
| TJU_CMC_MD2.ID00993.5p-miR | TJU_CMC_MD2.ID00993.hairpin | YES | NO | YES | NO | YES | NO | NO | NO |
| TJU_CMC_MD2.ID00994.3p-miR | TJU_CMC_MD2.ID00994.hairpin | YES | NO | NO | NO | NO | NO | NO | NO |
| TJU_CMC_MD2.ID00995.5p-miR | TJU_CMC_MD2.ID00995.hairpin | YES | YES | YES | YES | NO | NO | NO | NO |
| TJU_CMC_MD2.ID00996.5p-miR | TJU_CMC_MD2.ID00996.hairpin | YES | YES | YES | NO | YES | NO | NO | NO |
| TJU_CMC_MD2.ID00997.3p-miR | TJU_CMC_MD2.ID00997.hairpin | YES | NO | NO | NO | NO | NO | NO | NO |
| TJU_CMC_MD2.ID00998.3p-miR | TJU_CMC_MD2.ID00998.hairpin | YES | NO | NO | NO | NO | NO | NO | NO |
| TJU_CMC_MD2.ID00999.3p-miR | TJU_CMC_MD2.ID00999.hairpin | YES | NO | NO | NO | NO | NO | NO | NO |
| TJU_CMC_MD2.ID01000.3p-miR | TJU_CMC_MD2.ID01000.hairpin | YES | NO | NO | NO | NO | NO | NO | NO |
| TJU_CMC_MD2.ID01001.3p-miR | TJU_CMC_MD2.ID01001.hairpin | YES | NO | NO | NO | NO | NO | NO | NO |
| TJU_CMC_MD2.ID01002.3p-miR | TJU_CMC_MD2.ID01002.hairpin | YES | NO | NO | NO | NO | NO | NO | NO |
| TJU_CMC_MD2.ID01003.3p-miR | TJU_CMC_MD2.ID01003.hairpin | YES | NO | NO | NO | NO | NO | NO | NO |
| TJU_CMC_MD2.ID01004.3p-miR | TJU_CMC_MD2.ID01004.hairpin | YES | NO | NO | NO | NO | NO | NO | NO |
| TJU_CMC_MD2.ID01005.5p-miR | TJU_CMC_MD2.ID01005.hairpin | YES | NO | NO | NO | NO | NO | NO | NO |
| TJU_CMC_MD2.ID01006.3p-miR | TJU_CMC_MD2.ID01006.hairpin | YES | NO | NO | NO | NO | NO | NO | NO |
| TJU_CMC_MD2.ID01007.5p-miR | TJU_CMC_MD2.ID01007.hairpin | YES | NO | YES | YES | YES | NO | NO | NO |
| TJU_CMC_MD2.ID01008.3p-miR | TJU_CMC_MD2.ID01008.hairpin | YES | NO | NO | NO | NO | NO | NO | NO |
| TJU_CMC_MD2.ID01009.5p-miR | TJU_CMC_MD2.ID01009.hairpin | YES | YES | YES | NO | NO | NO | NO | NO |
| TJU_CMC_MD2.ID01010.5p-miR | TJU_CMC_MD2.ID01010.hairpin | YES | YES | YES | YES | YES | YES | NO | NO |
| TJU_CMC_MD2.ID01011.5p-miR | TJU_CMC_MD2.ID01011.hairpin | YES | NO | YES | YES | YES | NO | NO | NO |
| TJU_CMC_MD2.ID01012.3p-miR | TJU_CMC_MD2.ID01012.hairpin | YES | NO | NO | NO | NO | NO | NO | NO |
| TJU_CMC_MD2.ID01013.3p-miR | TJU_CMC_MD2.ID01013.hairpin | YES | NO | NO | NO | NO | NO | NO | NO |
| TJU_CMC_MD2.ID01014.3p-miR | TJU_CMC_MD2.ID01014.hairpin | YES | NO | NO | NO | NO | NO | NO | NO |
| TJU_CMC_MD2.ID01015.3p-miR | TJU_CMC_MD2.ID01015.hairpin | YES | NO | NO | NO | NO | NO | NO | NO |
| TJU_CMC_MD2.ID01016.5p-miR | TJU_CMC_MD2.ID01016.hairpin | YES | NO | YES | YES | NO | NO | NO | NO |
| TJU_CMC_MD2.ID01017.3p-miR | TJU_CMC_MD2.ID01017.hairpin | YES | NO | NO | NO | NO | NO | NO | NO |
| TJU_CMC_MD2.ID01018.3p-miR | TJU_CMC_MD2.ID01018.hairpin | YES | NO | NO | NO | NO | NO | NO | NO |
| TJU_CMC_MD2.ID01019.3p-miR | TJU_CMC_MD2.ID01019.hairpin | YES | NO | NO | NO | NO | NO | NO | NO |
| TJU_CMC_MD2.ID01020.5p-miR | TJU_CMC_MD2.ID01020.hairpin | YES | YES | NO | YES | NO | NO | NO | NO |
| TJU_CMC_MD2.ID01021.3p-miR | TJU_CMC_MD2.ID01021.hairpin | YES | NO | NO | NO | NO | NO | NO | NO |
| TJU_CMC_MD2.ID01022.5p-miR | TJU_CMC_MD2.ID01022.hairpin | YES | YES | NO | NO | NO | NO | NO | NO |
| TJU_CMC_MD2.ID01023.3p-miR | TJU_CMC_MD2.ID01023.hairpin | YES | NO | NO | NO | NO | NO | NO | NO |
| TJU_CMC_MD2.ID01023.5p-miR | TJU_CMC_MD2.ID01023.hairpin | YES | NO | YES | NO | YES | NO | NO | NO |
| TJU_CMC_MD2.ID01024.5p-miR | TJU_CMC_MD2.ID01024.hairpin | YES | YES | YES | YES | YES | NO | NO | NO |
| TJU_CMC_MD2.ID01025.3p-miR | TJU_CMC_MD2.ID01025.hairpin | YES | NO | YES | NO | NO | NO | NO | NO |
| TJU_CMC_MD2.ID01025.5p-miR | TJU_CMC_MD2.ID01025.hairpin | YES | NO | YES | NO | NO | NO | NO | NO |
| TJU_CMC_MD2.ID01026.3p-miR | TJU_CMC_MD2.ID01026.hairpin | YES | NO | NO | NO | NO | NO | NO | NO |
| TJU_CMC_MD2.ID01027.5p-miR | TJU_CMC_MD2.ID01027.hairpin | YES | NO | YES | NO | NO | NO | NO | NO |
| TJU_CMC_MD2.ID01028.3p-miR | TJU_CMC_MD2.ID01028.hairpin | YES | NO | NO | NO | NO | NO | NO | NO |
| TJU_CMC_MD2.ID01028.5p-miR | TJU_CMC_MD2.ID01028.hairpin | YES | NO | YES | NO | YES | NO | NO | NO |

TABLE 7-continued

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01029.5p-miR | TJU_CMC_MD2.ID01029.hairpin | YES | NO | NO | YES | NO | NO | NO | NO |
| TJU_CMC_MD2.ID01030.3p-miR | TJU_CMC_MD2.ID01030.hairpin | YES | NO | NO | NO | NO | NO | NO | NO |
| TJU_CMC_MD2.ID01031.5p-miR | TJU_CMC_MD2.ID01031.hairpin | YES | YES | YES | NO | NO | NO | NO | NO |
| TJU_CMC_MD2.ID01032.3p-miR | TJU_CMC_MD2.ID01032.hairpin | YES | NO | NO | NO | NO | NO | NO | NO |
| TJU_CMC_MD2.ID01033.5p-miR | TJU_CMC_MD2.ID01033.hairpin | YES | YES | YES | YES | NO | YES | NO | NO |
| TJU_CMC_MD2.ID01034.5p-miR | TJU_CMC_MD2.ID01034.hairpin | YES | NO | YES | NO | NO | YES | NO | NO |
| TJU_CMC_MD2.ID01035.3p-miR | TJU_CMC_MD2.ID01035.hairpin | YES | NO | NO | NO | NO | NO | NO | NO |
| TJU_CMC_MD2.ID01036.3p-miR | TJU_CMC_MD2.ID01036.hairpin | YES | NO | NO | NO | NO | NO | NO | NO |
| TJU_CMC_MD2.ID01037.5p-miR | TJU_CMC_MD2.ID01037.hairpin | YES | NO | YES | NO | NO | NO | NO | NO |
| TJU_CMC_MD2.ID01038.3p-miR | TJU_CMC_MD2.ID01038.hairpin | YES | NO | YES | NO | YES | NO | NO | NO |
| TJU_CMC_MD2.ID01038.5p-miR | TJU_CMC_MD2.ID01038.hairpin | YES | NO | YES | NO | YES | NO | NO | NO |
| TJU_CMC_MD2.ID01039.5p-miR | TJU_CMC_MD2.ID01039.hairpin | YES | YES | NO | NO | NO | NO | NO | NO |
| TJU_CMC_MD2.ID01040.5p-miR | TJU_CMC_MD2.ID01040.hairpin | YES | YES | YES | YES | NO | NO | NO | NO |
| TJU_CMC_MD2.ID01041.5p-miR | TJU_CMC_MD2.ID01041.hairpin | YES | NO | NO | NO | NO | NO | NO | NO |
| TJU_CMC_MD2.ID01042.5p-miR | TJU_CMC_MD2.ID01042.hairpin | YES | NO | NO | NO | NO | NO | NO | NO |
| TJU_CMC_MD2.ID01043.5p-miR | TJU_CMC_MD2.ID01043.hairpin | YES | YES | NO | YES | YES | YES | NO | NO |
| TJU_CMC_MD2.ID01044.5p-miR | TJU_CMC_MD2.ID01044.hairpin | YES | NO | NO | NO | NO | NO | NO | NO |
| TJU_CMC_MD2.ID01045.5p-miR | TJU_CMC_MD2.ID01045.hairpin | YES | YES | YES | YES | YES | NO | NO | NO |
| TJU_CMC_MD2.ID01046.3p-miR | TJU_CMC_MD2.ID01046.hairpin | YES | NO | NO | NO | NO | NO | NO | NO |
| TJU_CMC_MD2.ID01046.5p-miR | TJU_CMC_MD2.ID01046.hairpin | YES | YES | YES | YES | YES | NO | NO | NO |
| TJU_CMC_MD2.ID01047.3p-miR | TJU_CMC_MD2.ID01047.hairpin | YES | NO | NO | NO | NO | NO | NO | NO |
| TJU_CMC_MD2.ID01048.5p-miR | TJU_CMC_MD2.ID01048.hairpin | YES | NO | YES | NO | NO | NO | NO | NO |
| TJU_CMC_MD2.ID01049.5p-miR | TJU_CMC_MD2.ID01049.hairpin | YES | YES | YES | YES | YES | NO | NO | NO |
| TJU_CMC_MD2.ID01050.3p-miR | TJU_CMC_MD2.ID01050.hairpin | YES | YES | YES | YES | YES | NO | NO | NO |
| TJU_CMC_MD2.ID01051.5p-miR | TJU_CMC_MD2.ID01051.hairpin | YES | NO | YES | NO | NO | NO | NO | NO |
| TJU_CMC_MD2.ID01052.3p-miR | TJU_CMC_MD2.ID01052.hairpin | YES | NO | NO | NO | NO | NO | NO | NO |
| TJU_CMC_MD2.ID01053.3p-miR | TJU_CMC_MD2.ID01053.hairpin | YES | NO | NO | NO | NO | NO | NO | NO |
| TJU_CMC_MD2.ID01054.5p-miR | TJU_CMC_MD2.ID01054.hairpin | YES | YES | YES | YES | YES | NO | NO | NO |
| TJU_CMC_MD2.ID01055.3p-miR | TJU_CMC_MD2.ID01055.hairpin | YES | NO | NO | NO | NO | NO | NO | NO |
| TJU_CMC_MD2.ID01056.5p-miR | TJU_CMC_MD2.ID01056.hairpin | YES | YES | YES | NO | YES | NO | NO | NO |
| TJU_CMC_MD2.ID01057.5p-miR | TJU_CMC_MD2.ID01057.hairpin | YES | NO | YES | YES | YES | NO | NO | NO |
| TJU_CMC_MD2.ID01058.5p-miR | TJU_CMC_MD2.ID01058.hairpin | YES | YES | YES | YES | NO | NO | NO | NO |
| TJU_CMC_MD2.ID01059.3p-miR | TJU_CMC_MD2.ID01059.hairpin | YES | NO | NO | NO | NO | NO | NO | NO |
| TJU_CMC_MD2.ID01060.3p-miR | TJU_CMC_MD2.ID01060.hairpin | YES | NO | NO | NO | NO | NO | NO | NO |
| TJU_CMC_MD2.ID01061.5p-miR | TJU_CMC_MD2.ID01061.hairpin | YES | YES | YES | YES | YES | YES | NO | NO |
| TJU_CMC_MD2.ID01062.3p-miR | TJU_CMC_MD2.ID01062.hairpin | YES | NO | NO | NO | NO | NO | NO | NO |
| TJU_CMC_MD2.ID01063.5p-miR | TJU_CMC_MD2.ID01063.hairpin | YES | YES | YES | YES | YES | NO | NO | NO |
| TJU_CMC_MD2.ID01064.5p-miR | TJU_CMC_MD2.ID01064.hairpin | YES | YES | YES | YES | YES | NO | NO | NO |
| TJU_CMC_MD2.ID01065.5p-miR | TJU_CMC_MD2.ID01065.hairpin | YES | YES | NO | NO | NO | NO | NO | NO |
| TJU_CMC_MD2.ID01066.3p-miR | TJU_CMC_MD2.ID01066.hairpin | YES | NO | NO | NO | NO | NO | NO | NO |
| TJU_CMC_MD2.ID01067.5p-miR | TJU_CMC_MD2.ID01067.hairpin | YES | YES | NO | NO | NO | NO | NO | NO |
| TJU_CMC_MD2.ID01068.3p-miR | TJU_CMC_MD2.ID01068.hairpin | YES | NO | NO | NO | NO | NO | NO | NO |
| TJU_CMC_MD2.ID01069.3p-miR | TJU_CMC_MD2.ID01069.hairpin | YES | NO | NO | NO | NO | NO | NO | NO |
| TJU_CMC_MD2.ID01070.3p-miR | TJU_CMC_MD2.ID01070.hairpin | YES | NO | NO | NO | NO | NO | NO | NO |
| TJU_CMC_MD2.ID01071.5p-miR | TJU_CMC_MD2.ID01071.hairpin | YES | NO | NO | YES | NO | NO | NO | NO |
| TJU_CMC_MD2.ID01072.5p-miR | TJU_CMC_MD2.ID01072.hairpin | YES | YES | NO | NO | NO | NO | NO | NO |
| TJU_CMC_MD2.ID01073.3p-miR | TJU_CMC_MD2.ID01073.hairpin | YES | NO | NO | NO | NO | NO | NO | NO |
| TJU_CMC_MD2.ID01074.3p-miR | TJU_CMC_MD2.ID01074.hairpin | YES | NO | NO | NO | NO | NO | NO | NO |
| TJU_CMC_MD2.ID01075.3p-miR | TJU_CMC_MD2.ID01075.hairpin | YES | NO | NO | NO | NO | NO | NO | NO |
| TJU_CMC_MD2.ID01076.5p-miR | TJU_CMC_MD2.ID01076.hairpin | YES | YES | YES | YES | NO | NO | NO | NO |
| TJU_CMC_MD2.ID01077.3p-miR | TJU_CMC_MD2.ID01077.hairpin | YES | NO | NO | NO | NO | NO | NO | NO |
| TJU_CMC_MD2.ID01078.3p-miR | TJU_CMC_MD2.ID01078.hairpin | YES | NO | NO | NO | NO | NO | NO | NO |
| TJU_CMC_MD2.ID01079.5p-miR | TJU_CMC_MD2.ID01079.hairpin | YES | NO | NO | YES | NO | NO | NO | NO |
| TJU_CMC_MD2.ID01080.3p-miR | TJU_CMC_MD2.ID01080.hairpin | YES | NO | NO | NO | NO | NO | NO | NO |
| TJU_CMC_MD2.ID01081.3p-miR | TJU_CMC_MD2.ID01081.hairpin | YES | NO | NO | NO | NO | NO | NO | NO |
| TJU_CMC_MD2.ID01082.3p-miR | TJU_CMC_MD2.ID01082.hairpin | YES | NO | NO | NO | NO | NO | NO | NO |
| TJU_CMC_MD2.ID01083.3p-miR | TJU_CMC_MD2.ID01083.hairpin | YES | NO | NO | NO | NO | NO | NO | NO |
| TJU_CMC_MD2.ID01084.3p-miR | TJU_CMC_MD2.ID01084.hairpin | YES | NO | NO | NO | NO | NO | NO | NO |
| TJU_CMC_MD2.ID01085.3p-miR | TJU_CMC_MD2.ID01085.hairpin | YES | NO | NO | NO | NO | NO | NO | NO |
| TJU_CMC_MD2.ID01086.3p-miR | TJU_CMC_MD2.ID01086.hairpin | YES | NO | NO | NO | NO | NO | NO | NO |
| TJU_CMC_MD2.ID01087.3p-miR | TJU_CMC_MD2.ID01087.hairpin | YES | NO | NO | NO | NO | NO | NO | NO |
| TJU_CMC_MD2.ID01088.3p-miR | TJU_CMC_MD2.ID01088.hairpin | YES | NO | NO | NO | NO | NO | NO | NO |
| TJU_CMC_MD2.ID01089.3p-miR | TJU_CMC_MD2.ID01089.hairpin | YES | NO | NO | NO | NO | NO | NO | NO |
| TJU_CMC_MD2.ID01090.3p-miR | TJU_CMC_MD2.ID01090.hairpin | YES | NO | NO | NO | NO | NO | NO | NO |
| TJU_CMC_MD2.ID01091.3p-miR | TJU_CMC_MD2.ID01091.hairpin | YES | NO | NO | NO | NO | NO | NO | NO |
| TJU_CMC_MD2.ID01092.5p-miR | TJU_CMC_MD2.ID01092.hairpin | YES | NO | YES | YES | NO | NO | NO | NO |
| TJU_CMC_MD2.ID01093.5p-miR | TJU_CMC_MD2.ID01093.hairpin | YES | YES | NO | YES | NO | NO | NO | NO |
| TJU_CMC_MD2.ID01094.3p-miR | TJU_CMC_MD2.ID01094.hairpin | YES | NO | NO | NO | NO | NO | NO | NO |
| TJU_CMC_MD2.ID01095.5p-miR | TJU_CMC_MD2.ID01095.hairpin | YES | YES | YES | YES | YES | NO | NO | NO |
| TJU_CMC_MD2.ID01096.3p-miR | TJU_CMC_MD2.ID01096.hairpin | YES | NO | NO | NO | NO | NO | NO | NO |
| TJU_CMC_MD2.ID01097.3p-miR | TJU_CMC_MD2.ID01097.hairpin | YES | NO | NO | NO | NO | NO | NO | NO |
| TJU_CMC_MD2.ID01098.3p-miR | TJU_CMC_MD2.ID01098.hairpin | YES | NO | NO | NO | NO | NO | NO | NO |
| TJU_CMC_MD2.ID01099.5p-miR | TJU_CMC_MD2.ID01099.hairpin | YES | YES | NO | NO | NO | NO | NO | NO |
| TJU_CMC_MD2.ID01100.5p-miR | TJU_CMC_MD2.ID01100.hairpin | YES | YES | YES | NO | YES | NO | NO | NO |
| TJU_CMC_MD2.ID01101.3p-miR | TJU_CMC_MD2.ID01101.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01102.5p-miR | TJU_CMC_MD2.ID01102.hairpin | YES | YES | YES | YES | YES | YES | NO | NO |
| TJU_CMC_MD2.ID01103.3p-miR | TJU_CMC_MD2.ID01103.hairpin | YES | NO | NO | NO | NO | NO | NO | NO |
| TJU_CMC_MD2.ID01104.3p-miR | TJU_CMC_MD2.ID01104.hairpin | YES | NO | NO | NO | NO | NO | NO | NO |
| TJU_CMC_MD2.ID01104.5p-miR | TJU_CMC_MD2.ID01104.hairpin | YES | YES | YES | YES | YES | NO | NO | NO |
| TJU_CMC_MD2.ID01105.5p-miR | TJU_CMC_MD2.ID01105.hairpin | YES | YES | YES | YES | YES | YES | NO | NO |
| TJU_CMC_MD2.ID01106.5p-miR | TJU_CMC_MD2.ID01106.hairpin | YES | YES | YES | YES | NO | NO | NO | NO |
| TJU_CMC_MD2.ID01107.3p-miR | TJU_CMC_MD2.ID01107.hairpin | YES | NO | NO | NO | NO | NO | NO | NO |
| TJU_CMC_MD2.ID01108.3p-miR | TJU_CMC_MD2.ID01108.hairpin | YES | NO | NO | NO | NO | NO | NO | NO |
| TJU_CMC_MD2.ID01109.5p-miR | TJU_CMC_MD2.ID01109.hairpin | YES | YES | YES | NO | YES | NO | NO | NO |
| TJU_CMC_MD2.ID01110.3p-miR | TJU_CMC_MD2.ID01110.hairpin | YES | NO | NO | NO | NO | NO | NO | NO |
| TJU_CMC_MD2.ID01111.3p-miR | TJU_CMC_MD2.ID01111.hairpin | YES | NO | NO | NO | NO | NO | NO | NO |
| TJU_CMC_MD2.ID01112.3p-miR | TJU_CMC_MD2.ID01112.hairpin | YES | NO | NO | NO | NO | NO | NO | NO |
| TJU_CMC_MD2.ID01113.3p-miR | TJU_CMC_MD2.ID01113.hairpin | YES | NO | NO | NO | NO | NO | NO | NO |
| TJU_CMC_MD2.ID01114.3p-miR | TJU_CMC_MD2.ID01114.hairpin | YES | NO | NO | NO | NO | NO | NO | NO |
| TJU_CMC_MD2.ID01115.3p-miR | TJU_CMC_MD2.ID01115.hairpin | YES | NO | NO | NO | NO | NO | NO | NO |
| TJU_CMC_MD2.ID01116.3p-miR | TJU_CMC_MD2.ID01116.hairpin | YES | NO | NO | NO | NO | NO | NO | NO |
| TJU_CMC_MD2.ID01117.5p-miR | TJU_CMC_MD2.ID01117.hairpin | YES | YES | NO | NO | NO | NO | NO | NO |
| TJU_CMC_MD2.ID01118.3p-miR | TJU_CMC_MD2.ID01118.hairpin | YES | NO | NO | NO | NO | NO | NO | NO |
| TJU_CMC_MD2.ID01119.3p-miR | TJU_CMC_MD2.ID01119.hairpin | YES | NO | NO | NO | NO | NO | NO | NO |
| TJU_CMC_MD2.ID01120.5p-miR | TJU_CMC_MD2.ID01120.hairpin | YES | NO | YES | YES | NO | NO | NO | NO |
| TJU_CMC_MD2.ID01121.5p-miR | TJU_CMC_MD2.ID01121.hairpin | YES | YES | NO | YES | NO | NO | NO | NO |
| TJU_CMC_MD2.ID01122.5p-miR | TJU_CMC_MD2.ID01122.hairpin | YES | YES | YES | YES | NO | NO | NO | NO |
| TJU_CMC_MD2.ID01123.3p-miR | TJU_CMC_MD2.ID01123.hairpin | YES | NO | NO | NO | NO | NO | NO | NO |
| TJU_CMC_MD2.ID01124.3p-miR | TJU_CMC_MD2.ID01124.hairpin | YES | NO | NO | NO | NO | NO | NO | NO |
| TJU_CMC_MD2.ID01125.3p-miR | TJU_CMC_MD2.ID01125.hairpin | YES | NO | NO | NO | NO | NO | NO | NO |
| TJU_CMC_MD2.ID01126.3p-miR | TJU_CMC_MD2.ID01126.hairpin | YES | NO | NO | NO | NO | NO | NO | NO |
| TJU_CMC_MD2.ID01127.3p-miR | TJU_CMC_MD2.ID01127.hairpin | YES | NO | NO | NO | NO | NO | NO | NO |
| TJU_CMC_MD2.ID01128.5p-miR | TJU_CMC_MD2.ID01128.hairpin | YES | YES | YES | YES | NO | NO | NO | NO |
| TJU_CMC_MD2.ID01129.5p-miR | TJU_CMC_MD2.ID01129.hairpin | YES | YES | YES | YES | NO | NO | NO | NO |
| TJU_CMC_MD2.ID01130.5p-miR | TJU_CMC_MD2.ID01130.hairpin | YES | YES | YES | YES | NO | NO | NO | NO |
| TJU_CMC_MD2.ID01131.5p-miR | TJU_CMC_MD2.ID01131.hairpin | YES | YES | YES | YES | YES | NO | NO | NO |
| TJU_CMC_MD2.ID01132.3p-miR | TJU_CMC_MD2.ID01132.hairpin | YES | NO | NO | NO | NO | NO | NO | NO |
| TJU_CMC_MD2.ID01133.3p-miR | TJU_CMC_MD2.ID01133.hairpin | YES | NO | NO | NO | NO | NO | NO | NO |
| TJU_CMC_MD2.ID01134.3p-miR | TJU_CMC_MD2.ID01134.hairpin | YES | NO | NO | NO | NO | NO | NO | NO |
| TJU_CMC_MD2.ID01135.5p-miR | TJU_CMC_MD2.ID01135.hairpin | YES | YES | YES | YES | YES | NO | NO | NO |
| TJU_CMC_MD2.ID01136.3p-miR | TJU_CMC_MD2.ID01136.hairpin | YES | NO | NO | NO | NO | NO | NO | NO |
| TJU_CMC_MD2.ID01137.5p-miR | TJU_CMC_MD2.ID01137.hairpin | YES | NO | NO | YES | YES | NO | NO | NO |
| TJU_CMC_MD2.ID01138.3p-miR | TJU_CMC_MD2.ID01138.hairpin | YES | NO | NO | NO | NO | NO | NO | NO |
| TJU_CMC_MD2.ID01139.3p-miR | TJU_CMC_MD2.ID01139.hairpin | YES | NO | NO | NO | NO | NO | NO | NO |
| TJU_CMC_MD2.ID01140.3p-miR | TJU_CMC_MD2.ID01140.hairpin | YES | NO | NO | NO | NO | NO | NO | NO |
| TJU_CMC_MD2.ID01141.5p-miR | TJU_CMC_MD2.ID01141.hairpin | YES | YES | NO | NO | YES | NO | NO | NO |
| TJU_CMC_MD2.ID01142.3p-miR | TJU_CMC_MD2.ID01142.hairpin | YES | NO | NO | NO | NO | NO | NO | NO |
| TJU_CMC_MD2.ID01143.3p-miR | TJU_CMC_MD2.ID01143.hairpin | YES | NO | NO | NO | NO | NO | NO | NO |
| TJU_CMC_MD2.ID01144.3p-miR | TJU_CMC_MD2.ID01144.hairpin | YES | NO | NO | NO | NO | NO | NO | NO |
| TJU_CMC_MD2.ID01145.3p-miR | TJU_CMC_MD2.ID01145.hairpin | YES | NO | NO | NO | NO | NO | NO | NO |
| TJU_CMC_MD2.ID01145.5p-miR | TJU_CMC_MD2.ID01145.hairpin | YES | YES | YES | YES | YES | NO | NO | NO |
| TJU_CMC_MD2.ID01146.5p-miR | TJU_CMC_MD2.ID01146.hairpin | YES | YES | NO | YES | NO | YES | NO | NO |
| TJU_CMC_MD2.ID01147.3p-miR | TJU_CMC_MD2.ID01147.hairpin | YES | NO | NO | NO | NO | NO | NO | NO |
| TJU_CMC_MD2.ID01148.5p-miR | TJU_CMC_MD2.ID01148.hairpin | YES | YES | NO | YES | YES | NO | NO | NO |
| TJU_CMC_MD2.ID01149.3p-miR | TJU_CMC_MD2.ID01149.hairpin | YES | NO | NO | NO | NO | NO | NO | NO |
| TJU_CMC_MD2.ID01150.3p-miR | TJU_CMC_MD2.ID01150.hairpin | YES | YES | NO | YES | NO | NO | NO | NO |
| TJU_CMC_MD2.ID01151.3p-miR | TJU_CMC_MD2.ID01151.hairpin | YES | NO | NO | NO | NO | NO | NO | NO |
| TJU_CMC_MD2.ID01152.3p-miR | TJU_CMC_MD2.ID01152.hairpin | YES | NO | NO | NO | NO | NO | NO | NO |
| TJU_CMC_MD2.ID01153.3p-miR | TJU_CMC_MD2.ID01153.hairpin | YES | NO | NO | NO | NO | NO | NO | NO |
| TJU_CMC_MD2.ID01154.5p-miR | TJU_CMC_MD2.ID01154.hairpin | YES | NO | YES | NO | NO | NO | NO | NO |
| TJU_CMC_MD2.ID01155.5p-miR | TJU_CMC_MD2.ID01155.hairpin | YES | NO | YES | NO | NO | NO | NO | NO |
| TJU_CMC_MD2.ID01156.3p-miR | TJU_CMC_MD2.ID01156.hairpin | YES | NO | NO | NO | NO | NO | NO | NO |
| TJU_CMC_MD2.ID01157.5p-miR | TJU_CMC_MD2.ID01157.hairpin | YES | YES | NO | NO | NO | YES | NO | NO |
| TJU_CMC_MD2.ID01158.3p-miR | TJU_CMC_MD2.ID01158.hairpin | YES | NO | NO | NO | NO | NO | NO | NO |
| TJU_CMC_MD2.ID01159.5p-miR | TJU_CMC_MD2.ID01159.hairpin | YES | NO | NO | NO | NO | YES | NO | NO |
| TJU_CMC_MD2.ID01160.3p-miR | TJU_CMC_MD2.ID01160.hairpin | YES | NO | NO | NO | NO | NO | NO | NO |
| TJU_CMC_MD2.ID01161.5p-miR | TJU_CMC_MD2.ID01161.hairpin | YES | YES | YES | YES | YES | NO | NO | NO |
| TJU_CMC_MD2.ID01162.3p-miR | TJU_CMC_MD2.ID01162.hairpin | YES | NO | NO | NO | NO | NO | NO | NO |
| TJU_CMC_MD2.ID01163.3p-miR | TJU_CMC_MD2.ID01163.hairpin | YES | NO | NO | NO | NO | NO | NO | NO |
| TJU_CMC_MD2.ID01164.3p-miR | TJU_CMC_MD2.ID01164.hairpin | YES | NO | NO | NO | NO | NO | NO | NO |
| TJU_CMC_MD2.ID01165.3p-miR | TJU_CMC_MD2.ID01165.hairpin | YES | NO | NO | NO | NO | NO | NO | NO |
| TJU_CMC_MD2.ID01166.3p-miR | TJU_CMC_MD2.ID01166.hairpin | YES | NO | NO | NO | NO | NO | NO | NO |
| TJU_CMC_MD2.ID01167.3p-miR | TJU_CMC_MD2.ID01167.hairpin | YES | YES | YES | YES | YES | NO | NO | NO |
| TJU_CMC_MD2.ID01167.5p-miR | TJU_CMC_MD2.ID01167.hairpin | YES | YES | YES | YES | YES | NO | NO | NO |
| TJU_CMC_MD2.ID01168.5p-miR | TJU_CMC_MD2.ID01168.hairpin | YES | NO | NO | NO | NO | NO | NO | NO |
| TJU_CMC_MD2.ID01169.5p-miR | TJU_CMC_MD2.ID01169.hairpin | YES | YES | YES | YES | YES | NO | NO | NO |
| TJU_CMC_MD2.ID01170.3p-miR | TJU_CMC_MD2.ID01170.hairpin | YES | NO | NO | NO | NO | NO | NO | NO |
| TJU_CMC_MD2.ID01171.3p-miR | TJU_CMC_MD2.ID01171.hairpin | YES | NO | NO | NO | NO | NO | NO | NO |
| TJU_CMC_MD2.ID01172.3p-miR | TJU_CMC_MD2.ID01172.hairpin | YES | NO | NO | NO | NO | NO | NO | NO |
| TJU_CMC_MD2.ID01173.3p-miR | TJU_CMC_MD2.ID01173.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01174.5p-miR | TJU_CMC_MD2.ID01174.hairpin | YES | YES | YES | YES | NO | NO | NO | NO |
| TJU_CMC_MD2.ID01175.3p-miR | TJU_CMC_MD2.ID01175.hairpin | YES | NO | NO | NO | NO | NO | NO | NO |
| TJU_CMC_MD2.ID01176.5p-miR | TJU_CMC_MD2.ID01176.hairpin | YES | YES | NO | YES | NO | NO | NO | NO |
| TJU_CMC_MD2.ID01177.5p-miR | TJU_CMC_MD2.ID01177.hairpin | YES | YES | NO | YES | NO | NO | NO | NO |
| TJU_CMC_MD2.ID01178.5p-miR | TJU_CMC_MD2.ID01178.hairpin | YES | YES | YES | YES | NO | NO | NO | NO |
| TJU_CMC_MD2.ID01179.3p-miR | TJU_CMC_MD2.ID01179.hairpin | YES | NO | NO | NO | NO | NO | NO | NO |
| TJU_CMC_MD2.ID01180.3p-miR | TJU_CMC_MD2.ID01180.hairpin | YES | NO | NO | NO | NO | NO | NO | NO |
| TJU_CMC_MD2.ID01181.3p-miR | TJU_CMC_MD2.ID01181.hairpin | YES | NO | NO | NO | NO | NO | NO | NO |
| TJU_CMC_MD2.ID01181.5p-miR | TJU_CMC_MD2.ID01181.hairpin | YES | YES | YES | YES | NO | NO | NO | NO |
| TJU_CMC_MD2.ID01182.5p-miR | TJU_CMC_MD2.ID01182.hairpin | YES | YES | YES | YES | NO | NO | NO | NO |
| TJU_CMC_MD2.ID01183.3p-miR | TJU_CMC_MD2.ID01183.hairpin | YES | NO | NO | NO | NO | NO | NO | NO |
| TJU_CMC_MD2.ID01184.3p-miR | TJU_CMC_MD2.ID01184.hairpin | YES | NO | NO | NO | NO | NO | NO | NO |
| TJU_CMC_MD2.ID01185.3p-miR | TJU_CMC_MD2.ID01185.hairpin | YES | NO | YES | NO | NO | NO | NO | NO |
| TJU_CMC_MD2.ID01186.3p-miR | TJU_CMC_MD2.ID01186.hairpin | YES | NO | NO | NO | NO | NO | NO | NO |
| TJU_CMC_MD2.ID01187.3p-miR | TJU_CMC_MD2.ID01187.hairpin | YES | NO | NO | NO | NO | NO | NO | NO |
| TJU_CMC_MD2.ID01188.3p-miR | TJU_CMC_MD2.ID01188.hairpin | YES | NO | NO | NO | NO | NO | NO | NO |
| TJU_CMC_MD2.ID01188.5p-miR | TJU_CMC_MD2.ID01188.hairpin | YES | YES | NO | NO | NO | NO | NO | NO |
| TJU_CMC_MD2.ID01189.5p-miR | TJU_CMC_MD2.ID01189.hairpin | YES | NO | NO | NO | NO | NO | NO | NO |
| TJU_CMC_MD2.ID01190.5p-miR | TJU_CMC_MD2.ID01190.hairpin | YES | NO | NO | NO | NO | NO | NO | NO |
| TJU_CMC_MD2.ID01191.5p-miR | TJU_CMC_MD2.ID01191.hairpin | YES | YES | YES | YES | NO | NO | NO | NO |
| TJU_CMC_MD2.ID01192.5p-miR | TJU_CMC_MD2.ID01192.hairpin | YES | YES | YES | YES | YES | NO | NO | NO |
| TJU_CMC_MD2.ID01193.3p-miR | TJU_CMC_MD2.ID01193.hairpin | YES | NO | NO | NO | NO | NO | NO | NO |
| TJU_CMC_MD2.ID01194.3p-miR | TJU_CMC_MD2.ID01194.hairpin | YES | NO | NO | NO | NO | NO | NO | NO |
| TJU_CMC_MD2.ID01194.5p-miR | TJU_CMC_MD2.ID01194.hairpin | YES | NO | NO | YES | NO | NO | NO | NO |
| TJU_CMC_MD2.ID01195.3p-miR | TJU_CMC_MD2.ID01195.hairpin | YES | NO | NO | NO | NO | NO | NO | NO |
| TJU_CMC_MD2.ID01196.3p-miR | TJU_CMC_MD2.ID01196.hairpin | YES | NO | NO | NO | NO | NO | NO | NO |
| TJU_CMC_MD2.ID01197.3p-miR | TJU_CMC_MD2.ID01197.hairpin | YES | NO | NO | NO | NO | NO | NO | NO |
| TJU_CMC_MD2.ID01198.3p-miR | TJU_CMC_MD2.ID01198.hairpin | YES | NO | NO | NO | NO | NO | NO | NO |
| TJU_CMC_MD2.ID01198.5p-miR | TJU_CMC_MD2.ID01198.hairpin | YES | YES | YES | NO | NO | NO | NO | NO |
| TJU_CMC_MD2.ID01199.5p-miR | TJU_CMC_MD2.ID01199.hairpin | YES | NO | NO | YES | NO | NO | NO | NO |
| TJU_CMC_MD2.ID01200.3p-miR | TJU_CMC_MD2.ID01200.hairpin | YES | NO | NO | NO | NO | NO | NO | NO |
| TJU_CMC_MD2.ID01201.5p-miR | TJU_CMC_MD2.ID01201.hairpin | YES | NO | NO | NO | NO | NO | NO | NO |
| TJU_CMC_MD2.ID01202.5p-miR | TJU_CMC_MD2.ID01202.hairpin | YES | YES | NO | NO | NO | NO | NO | NO |
| TJU_CMC_MD2.ID01203.3p-miR | TJU_CMC_MD2.ID01203.hairpin | YES | NO | NO | NO | NO | NO | NO | NO |
| TJU_CMC_MD2.ID01204.3p-miR | TJU_CMC_MD2.ID01204.hairpin | YES | NO | NO | NO | NO | NO | NO | NO |
| TJU_CMC_MD2.ID01205.5p-miR | TJU_CMC_MD2.ID01205.hairpin | YES | YES | YES | YES | YES | NO | NO | NO |
| TJU_CMC_MD2.ID01206.3p-miR | TJU_CMC_MD2.ID01206.hairpin | YES | NO | NO | NO | NO | NO | NO | NO |
| TJU_CMC_MD2.ID01207.3p-miR | TJU_CMC_MD2.ID01207.hairpin | YES | NO | NO | NO | NO | NO | NO | NO |
| TJU_CMC_MD2.ID01208.3p-miR | TJU_CMC_MD2.ID01208.hairpin | YES | NO | NO | NO | NO | NO | NO | NO |
| TJU_CMC_MD2.ID01208.5p-miR | TJU_CMC_MD2.ID01208.hairpin | YES | YES | NO | NO | NO | NO | NO | NO |
| TJU_CMC_MD2.ID01209.3p-miR | TJU_CMC_MD2.ID01209.hairpin | YES | NO | NO | NO | NO | NO | NO | NO |
| TJU_CMC_MD2.ID01210.3p-miR | TJU_CMC_MD2.ID01210.hairpin | YES | NO | NO | NO | NO | NO | NO | NO |
| TJU_CMC_MD2.ID01211.3p-miR | TJU_CMC_MD2.ID01211.hairpin | YES | NO | NO | NO | NO | NO | NO | NO |
| TJU_CMC_MD2.ID01212.5p-miR | TJU_CMC_MD2.ID01212.hairpin | YES | YES | YES | YES | YES | NO | NO | NO |
| TJU_CMC_MD2.ID01213.5p-miR | TJU_CMC_MD2.ID01213.hairpin | YES | YES | YES | YES | NO | NO | NO | NO |
| TJU_CMC_MD2.ID01214.5p-miR | TJU_CMC_MD2.ID01214.hairpin | YES | YES | YES | NO | NO | NO | NO | NO |
| TJU_CMC_MD2.ID01215.5p-miR | TJU_CMC_MD2.ID01215.hairpin | YES | YES | YES | YES | NO | NO | NO | NO |
| TJU_CMC_MD2.ID01216.3p-miR | TJU_CMC_MD2.ID01216.hairpin | YES | NO | NO | NO | NO | NO | NO | NO |
| TJU_CMC_MD2.ID01217.5p-miR | TJU_CMC_MD2.ID01217.hairpin | YES | YES | NO | NO | NO | NO | NO | NO |
| TJU_CMC_MD2.ID01218.3p-miR | TJU_CMC_MD2.ID01218.hairpin | YES | NO | NO | NO | NO | NO | NO | NO |
| TJU_CMC_MD2.ID01219.3p-miR | TJU_CMC_MD2.ID01219.hairpin | YES | NO | NO | NO | NO | NO | NO | NO |
| TJU_CMC_MD2.ID01220.5p-miR | TJU_CMC_MD2.ID01220.hairpin | YES | YES | YES | NO | YES | NO | NO | NO |
| TJU_CMC_MD2.ID01221.3p-miR | TJU_CMC_MD2.ID01221.hairpin | YES | NO | NO | NO | NO | NO | NO | NO |
| TJU_CMC_MD2.ID01222.3p-miR | TJU_CMC_MD2.ID01222.hairpin | YES | NO | NO | NO | NO | NO | NO | NO |
| TJU_CMC_MD2.ID01223.5p-miR | TJU_CMC_MD2.ID01223.hairpin | YES | NO | NO | NO | NO | NO | NO | NO |
| TJU_CMC_MD2.ID01224.5p-miR | TJU_CMC_MD2.ID01224.hairpin | YES | NO | NO | NO | NO | NO | NO | NO |
| TJU_CMC_MD2.ID01225.3p-miR | TJU_CMC_MD2.ID01225.hairpin | YES | NO | NO | NO | NO | NO | NO | NO |
| TJU_CMC_MD2.ID01226.5p-miR | TJU_CMC_MD2.ID01226.hairpin | YES | YES | YES | YES | NO | NO | NO | NO |
| TJU_CMC_MD2.ID01227.5p-miR | TJU_CMC_MD2.ID01227.hairpin | YES | YES | YES | YES | NO | NO | NO | NO |
| TJU_CMC_MD2.ID01228.3p-miR | TJU_CMC_MD2.ID01228.hairpin | YES | NO | NO | NO | NO | NO | NO | NO |
| TJU_CMC_MD2.ID01229.3p-miR | TJU_CMC_MD2.ID01229.hairpin | YES | NO | NO | NO | NO | NO | NO | NO |
| TJU_CMC_MD2.ID01230.3p-miR | TJU_CMC_MD2.ID01230.hairpin | YES | NO | NO | NO | NO | NO | NO | NO |
| TJU_CMC_MD2.ID01231.3p-miR | TJU_CMC_MD2.ID01231.hairpin | YES | NO | NO | NO | NO | NO | NO | NO |
| TJU_CMC_MD2.ID01232.3p-miR | TJU_CMC_MD2.ID01232.hairpin | YES | NO | NO | NO | NO | NO | NO | NO |
| TJU_CMC_MD2.ID01233.3p-miR | TJU_CMC_MD2.ID01233.hairpin | YES | NO | NO | NO | NO | NO | NO | NO |
| TJU_CMC_MD2.ID01234.3p-miR | TJU_CMC_MD2.ID01234.hairpin | YES | NO | NO | NO | NO | NO | NO | NO |
| TJU_CMC_MD2.ID01235.3p-miR | TJU_CMC_MD2.ID01235.hairpin | YES | NO | NO | NO | NO | NO | NO | NO |
| TJU_CMC_MD2.ID01236.5p-miR | TJU_CMC_MD2.ID01236.hairpin | YES | NO | YES | NO | NO | NO | NO | NO |
| TJU_CMC_MD2.ID01237.3p-miR | TJU_CMC_MD2.ID01237.hairpin | YES | NO | NO | NO | NO | NO | NO | NO |
| TJU_CMC_MD2.ID01238.5p-miR | TJU_CMC_MD2.ID01238.hairpin | YES | YES | YES | YES | NO | NO | NO | NO |
| TJU_CMC_MD2.ID01239.3p-miR | TJU_CMC_MD2.ID01239.hairpin | YES | NO | NO | NO | NO | NO | NO | NO |
| TJU_CMC_MD2.ID01240.5p-miR | TJU_CMC_MD2.ID01240.hairpin | YES | YES | YES | NO | NO | NO | NO | NO |
| TJU_CMC_MD2.ID01241.3p-miR | TJU_CMC_MD2.ID01241.hairpin | YES | NO | NO | NO | NO | NO | NO | NO |
| TJU_CMC_MD2.ID01242.3p-miR | TJU_CMC_MD2.ID01242.hairpin | YES | NO | NO | NO | NO | NO | NO | NO |
| TJU_CMC_MD2.ID01243.3p-miR | TJU_CMC_MD2.ID01243.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01244.3p-miR | TJU_CMC_MD2.ID01244.hairpin | YES | NO | NO | NO | NO | NO | NO | NO |
| TJU_CMC_MD2.ID01245.3p-miR | TJU_CMC_MD2.ID01245.hairpin | YES | NO | NO | NO | NO | NO | NO | NO |
| TJU_CMC_MD2.ID01246.3p-miR | TJU_CMC_MD2.ID01246.hairpin | YES | NO | NO | NO | NO | NO | NO | NO |
| TJU_CMC_MD2.ID01247.3p-miR | TJU_CMC_MD2.ID01247.hairpin | YES | NO | NO | NO | NO | NO | NO | NO |
| TJU_CMC_MD2.ID01248.3p-miR | TJU_CMC_MD2.ID01248.hairpin | YES | NO | NO | NO | NO | NO | NO | NO |
| TJU_CMC_MD2.ID01249.5p-miR | TJU_CMC_MD2.ID01249.hairpin | YES | YES | YES | YES | YES | YES | NO | NO |
| TJU_CMC_MD2.ID01250.3p-miR | TJU_CMC_MD2.ID01250.hairpin | YES | YES | YES | YES | YES | NO | NO | NO |
| TJU_CMC_MD2.ID01250.5p-miR | TJU_CMC_MD2.ID01250.hairpin | YES | NO | YES | NO | NO | NO | NO | NO |
| TJU_CMC_MD2.ID01251.3p-miR | TJU_CMC_MD2.ID01251.hairpin | YES | NO | NO | NO | NO | NO | NO | NO |
| TJU_CMC_MD2.ID01252.3p-miR | TJU_CMC_MD2.ID01252.hairpin | YES | NO | NO | NO | NO | NO | NO | NO |
| TJU_CMC_MD2.ID01253.3p-miR | TJU_CMC_MD2.ID01253.hairpin | YES | NO | NO | NO | NO | NO | NO | NO |
| TJU_CMC_MD2.ID01254.5p-miR | TJU_CMC_MD2.ID01254.hairpin | YES | YES | YES | NO | NO | NO | NO | NO |
| TJU_CMC_MD2.ID01255.5p-miR | TJU_CMC_MD2.ID01255.hairpin | YES | YES | NO | NO | NO | NO | NO | NO |
| TJU_CMC_MD2.ID01256.3p-miR | TJU_CMC_MD2.ID01256.hairpin | YES | NO | NO | NO | NO | NO | NO | NO |
| TJU_CMC_MD2.ID01257.3p-miR | TJU_CMC_MD2.ID01257.hairpin | YES | NO | NO | NO | NO | NO | NO | NO |
| TJU_CMC_MD2.ID01258.3p-miR | TJU_CMC_MD2.ID01258.hairpin | YES | NO | NO | NO | NO | NO | NO | NO |
| TJU_CMC_MD2.ID01259.3p-miR | TJU_CMC_MD2.ID01259.hairpin | YES | NO | NO | NO | NO | NO | NO | NO |
| TJU_CMC_MD2.ID01260.3p-miR | TJU_CMC_MD2.ID01260.hairpin | YES | NO | NO | NO | NO | NO | NO | NO |
| TJU_CMC_MD2.ID01261.5p-miR | TJU_CMC_MD2.ID01261.hairpin | YES | YES | YES | YES | YES | NO | NO | NO |
| TJU_CMC_MD2.ID01262.3p-miR | TJU_CMC_MD2.ID01262.hairpin | YES | NO | NO | NO | NO | NO | NO | NO |
| TJU_CMC_MD2.ID01263.5p-miR | TJU_CMC_MD2.ID01263.hairpin | YES | NO | YES | YES | NO | NO | NO | NO |
| TJU_CMC_MD2.ID01264.3p-miR | TJU_CMC_MD2.ID01264.hairpin | YES | NO | NO | NO | NO | NO | NO | NO |
| TJU_CMC_MD2.ID01265.3p-miR | TJU_CMC_MD2.ID01265.hairpin | YES | NO | NO | NO | NO | NO | NO | NO |
| TJU_CMC_MD2.ID01266.3p-miR | TJU_CMC_MD2.ID01266.hairpin | YES | NO | NO | NO | NO | NO | NO | NO |
| TJU_CMC_MD2.ID01267.3p-miR | TJU_CMC_MD2.ID01267.hairpin | YES | NO | NO | NO | NO | NO | NO | NO |
| TJU_CMC_MD2.ID01268.3p-miR | TJU_CMC_MD2.ID01268.hairpin | YES | NO | NO | NO | NO | NO | NO | NO |
| TJU_CMC_MD2.ID01269.3p-miR | TJU_CMC_MD2.ID01269.hairpin | YES | NO | NO | NO | NO | NO | NO | NO |
| TJU_CMC_MD2.ID01270.3p-miR | TJU_CMC_MD2.ID01270.hairpin | YES | NO | NO | NO | NO | NO | NO | NO |
| TJU_CMC_MD2.ID01271.3p-miR | TJU_CMC_MD2.ID01271.hairpin | YES | NO | NO | NO | NO | NO | NO | NO |
| TJU_CMC_MD2.ID01272.3p-miR | TJU_CMC_MD2.ID01272.hairpin | YES | NO | NO | NO | NO | NO | NO | NO |
| TJU_CMC_MD2.ID01273.3p-miR | TJU_CMC_MD2.ID01273.hairpin | YES | NO | NO | NO | NO | NO | NO | NO |
| TJU_CMC_MD2.ID01273.5p-miR | TJU_CMC_MD2.ID01273.hairpin | YES | NO | YES | NO | NO | NO | NO | NO |
| TJU_CMC_MD2.ID01274.5p-miR | TJU_CMC_MD2.ID01274.hairpin | YES | NO | YES | YES | NO | NO | NO | NO |
| TJU_CMC_MD2.ID01275.5p-miR | TJU_CMC_MD2.ID01275.hairpin | YES | NO | YES | YES | NO | NO | NO | NO |
| TJU_CMC_MD2.ID01276.5p-miR | TJU_CMC_MD2.ID01276.hairpin | YES | YES | YES | NO | NO | NO | NO | NO |
| TJU_CMC_MD2.ID01277.5p-miR | TJU_CMC_MD2.ID01277.hairpin | YES | YES | YES | YES | NO | NO | NO | NO |
| TJU_CMC_MD2.ID01278.3p-miR | TJU_CMC_MD2.ID01278.hairpin | YES | NO | YES | NO | NO | YES | NO | NO |
| TJU_CMC_MD2.ID01278.5p-miR | TJU_CMC_MD2.ID01278.hairpin | YES | NO | YES | NO | NO | YES | NO | NO |
| TJU_CMC_MD2.ID01279.5p-miR | TJU_CMC_MD2.ID01279.hairpin | YES | YES | YES | YES | NO | NO | NO | NO |
| TJU_CMC_MD2.ID01280.3p-miR | TJU_CMC_MD2.ID01280.hairpin | YES | NO | NO | NO | NO | NO | NO | NO |
| TJU_CMC_MD2.ID01281.3p-miR | TJU_CMC_MD2.ID01281.hairpin | YES | NO | NO | NO | NO | NO | NO | NO |
| TJU_CMC_MD2.ID01282.3p-miR | TJU_CMC_MD2.ID01282.hairpin | YES | NO | NO | NO | NO | NO | NO | NO |
| TJU_CMC_MD2.ID01283.3p-miR | TJU_CMC_MD2.ID01283.hairpin | YES | NO | NO | NO | NO | NO | NO | NO |
| TJU_CMC_MD2.ID01284.3p-miR | TJU_CMC_MD2.ID01284.hairpin | YES | NO | NO | NO | NO | NO | NO | NO |
| TJU_CMC_MD2.ID01285.3p-miR | TJU_CMC_MD2.ID01285.hairpin | YES | NO | NO | NO | NO | NO | NO | NO |
| TJU_CMC_MD2.ID01286.3p-miR | TJU_CMC_MD2.ID01286.hairpin | YES | NO | NO | NO | NO | NO | NO | NO |
| TJU_CMC_MD2.ID01287.5p-miR | TJU_CMC_MD2.ID01287.hairpin | YES | NO | NO | NO | NO | NO | NO | NO |
| TJU_CMC_MD2.ID01288.3p-miR | TJU_CMC_MD2.ID01288.hairpin | YES | NO | NO | NO | NO | NO | NO | NO |
| TJU_CMC_MD2.ID01289.5p-miR | TJU_CMC_MD2.ID01289.hairpin | YES | YES | YES | YES | YES | NO | NO | NO |
| TJU_CMC_MD2.ID01290.3p-miR | TJU_CMC_MD2.ID01290.hairpin | YES | NO | NO | NO | NO | NO | NO | NO |
| TJU_CMC_MD2.ID01291.3p-miR | TJU_CMC_MD2.ID01291.hairpin | YES | YES | YES | YES | NO | NO | NO | NO |
| TJU_CMC_MD2.ID01292.5p-miR | TJU_CMC_MD2.ID01292.hairpin | YES | YES | NO | YES | NO | NO | NO | NO |
| TJU_CMC_MD2.ID01293.5p-miR | TJU_CMC_MD2.ID01293.hairpin | YES | NO | YES | NO | NO | NO | NO | NO |
| TJU_CMC_MD2.ID01294.3p-miR | TJU_CMC_MD2.ID01294.hairpin | YES | NO | NO | NO | NO | NO | NO | NO |
| TJU_CMC_MD2.ID01295.3p-miR | TJU_CMC_MD2.ID01295.hairpin | YES | NO | NO | NO | NO | NO | NO | NO |
| TJU_CMC_MD2.ID01296.5p-miR | TJU_CMC_MD2.ID01296.hairpin | YES | YES | YES | NO | YES | NO | NO | NO |
| TJU_CMC_MD2.ID01297.5p-miR | TJU_CMC_MD2.ID01297.hairpin | YES | YES | YES | NO | NO | NO | NO | NO |
| TJU_CMC_MD2.ID01298.5p-miR | TJU_CMC_MD2.ID01298.hairpin | YES | NO | YES | NO | YES | YES | NO | NO |
| TJU_CMC_MD2.ID01299.3p-miR | TJU_CMC_MD2.ID01299.hairpin | YES | NO | NO | NO | NO | NO | NO | NO |
| TJU_CMC_MD2.ID01300.3p-miR | TJU_CMC_MD2.ID01300.hairpin | YES | NO | NO | NO | NO | NO | NO | NO |
| TJU_CMC_MD2.ID01301.3p-miR | TJU_CMC_MD2.ID01301.hairpin | YES | NO | NO | NO | NO | NO | NO | NO |
| TJU_CMC_MD2.ID01302.5p-miR | TJU_CMC_MD2.ID01302.hairpin | YES | YES | YES | YES | YES | NO | NO | NO |
| TJU_CMC_MD2.ID01303.5p-miR | TJU_CMC_MD2.ID01303.hairpin | YES | YES | YES | YES | YES | NO | NO | NO |
| TJU_CMC_MD2.ID01304.5p-miR | TJU_CMC_MD2.ID01304.hairpin | YES | YES | YES | YES | NO | NO | NO | NO |
| TJU_CMC_MD2.ID01305.3p-miR | TJU_CMC_MD2.ID01305.hairpin | YES | NO | NO | NO | NO | NO | NO | NO |
| TJU_CMC_MD2.ID01306.5p-miR | TJU_CMC_MD2.ID01306.hairpin | YES | YES | YES | YES | YES | NO | NO | NO |
| TJU_CMC_MD2.ID01307.3p-miR | TJU_CMC_MD2.ID01307.hairpin | YES | NO | NO | NO | NO | NO | NO | NO |
| TJU_CMC_MD2.ID01308.3p-miR | TJU_CMC_MD2.ID01308.hairpin | YES | NO | NO | NO | NO | NO | NO | NO |
| TJU_CMC_MD2.ID01309.3p-miR | TJU_CMC_MD2.ID01309.hairpin | YES | NO | NO | NO | NO | NO | NO | NO |
| TJU_CMC_MD2.ID01310.3p-miR | TJU_CMC_MD2.ID01310.hairpin | YES | NO | NO | NO | NO | NO | NO | NO |
| TJU_CMC_MD2.ID01310.5p-miR | TJU_CMC_MD2.ID01310.hairpin | YES | NO | NO | NO | NO | YES | NO | NO |
| TJU_CMC_MD2.ID01311.3p-miR | TJU_CMC_MD2.ID01311.hairpin | YES | NO | NO | NO | NO | NO | NO | NO |
| TJU_CMC_MD2.ID01312.5p-miR | TJU_CMC_MD2.ID01312.hairpin | YES | YES | YES | YES | YES | NO | NO | NO |
| TJU_CMC_MD2.ID01313.3p-miR | TJU_CMC_MD2.ID01313.hairpin | YES | NO | NO | NO | NO | NO | NO | NO |
| TJU_CMC_MD2.ID01314.5p-miR | TJU_CMC_MD2.ID01314.hairpin | YES | YES | YES | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01315.3p-miR | TJU_CMC_MD2.ID01315.hairpin | YES | NO | NO | NO | NO | NO | NO | NO |
| TJU_CMC_MD2.ID01316.5p-miR | TJU_CMC_MD2.ID01316.hairpin | YES | YES | YES | YES | NO | YES | NO | NO |
| TJU_CMC_MD2.ID01317.5p-miR | TJU_CMC_MD2.ID01317.hairpin | YES | YES | NO | NO | YES | NO | NO | NO |
| TJU_CMC_MD2.ID01318.3p-miR | TJU_CMC_MD2.ID01318.hairpin | YES | YES | NO | YES | NO | NO | NO | NO |
| TJU_CMC_MD2.ID01319.5p-miR | TJU_CMC_MD2.ID01319.hairpin | YES | NO | NO | NO | NO | NO | NO | NO |
| TJU_CMC_MD2.ID01320.3p-miR | TJU_CMC_MD2.ID01320.hairpin | YES | NO | NO | NO | NO | NO | NO | NO |
| TJU_CMC_MD2.ID01321.5p-miR | TJU_CMC_MD2.ID01321.hairpin | YES | NO | NO | YES | NO | NO | NO | NO |
| TJU_CMC_MD2.ID01322.3p-miR | TJU_CMC_MD2.ID01322.hairpin | YES | NO | NO | NO | NO | NO | NO | NO |
| TJU_CMC_MD2.ID01322.5p-miR | TJU_CMC_MD2.ID01322.hairpin | YES | NO | YES | YES | NO | NO | NO | NO |
| TJU_CMC_MD2.ID01323.3p-miR | TJU_CMC_MD2.ID01323.hairpin | YES | NO | NO | NO | NO | NO | NO | NO |
| TJU_CMC_MD2.ID01324.5p-miR | TJU_CMC_MD2.ID01324.hairpin | YES | NO | NO | YES | NO | YES | NO | NO |
| TJU_CMC_MD2.ID01325.3p-miR | TJU_CMC_MD2.ID01325.hairpin | YES | NO | NO | NO | NO | NO | NO | NO |
| TJU_CMC_MD2.ID01326.3p-miR | TJU_CMC_MD2.ID01326.hairpin | YES | YES | YES | YES | NO | NO | NO | NO |
| TJU_CMC_MD2.ID01326.5p-miR | TJU_CMC_MD2.ID01326.hairpin | YES | YES | YES | YES | YES | NO | NO | NO |
| TJU_CMC_MD2.ID01327.3p-miR | TJU_CMC_MD2.ID01327.hairpin | YES | NO | NO | NO | NO | NO | NO | NO |
| TJU_CMC_MD2.ID01328.3p-miR | TJU_CMC_MD2.ID01328.hairpin | YES | NO | NO | NO | NO | NO | NO | NO |
| TJU_CMC_MD2.ID01329.3p-miR | TJU_CMC_MD2.ID01329.hairpin | YES | NO | NO | NO | NO | NO | NO | NO |
| TJU_CMC_MD2.ID01330.3p-miR | TJU_CMC_MD2.ID01330.hairpin | YES | NO | NO | NO | NO | NO | NO | NO |
| TJU_CMC_MD2.ID01331.3p-miR | TJU_CMC_MD2.ID01331.hairpin | YES | NO | NO | NO | NO | NO | NO | NO |
| TJU_CMC_MD2.ID01332.3p-miR | TJU_CMC_MD2.ID01332.hairpin | YES | NO | NO | NO | NO | NO | NO | NO |
| TJU_CMC_MD2.ID01333.3p-miR | TJU_CMC_MD2.ID01333.hairpin | YES | NO | NO | NO | NO | NO | NO | NO |
| TJU_CMC_MD2.ID01334.3p-miR | TJU_CMC_MD2.ID01334.hairpin | YES | NO | NO | NO | NO | NO | NO | NO |
| TJU_CMC_MD2.ID01334.5p-miR | TJU_CMC_MD2.ID01334.hairpin | YES | NO | NO | NO | NO | NO | NO | NO |
| TJU_CMC_MD2.ID01335.3p-miR | TJU_CMC_MD2.ID01335.hairpin | YES | NO | NO | NO | NO | NO | NO | NO |
| TJU_CMC_MD2.ID01336.3p-miR | TJU_CMC_MD2.ID01336.hairpin | YES | NO | NO | NO | NO | NO | NO | NO |
| TJU_CMC_MD2.ID01337.3p-miR | TJU_CMC_MD2.ID01337.hairpin | YES | NO | NO | NO | NO | NO | NO | NO |
| TJU_CMC_MD2.ID01338.5p-miR | TJU_CMC_MD2.ID01338.hairpin | YES | NO | YES | YES | NO | NO | NO | NO |
| TJU_CMC_MD2.ID01339.3p-miR | TJU_CMC_MD2.ID01339.hairpin | YES | YES | NO | NO | NO | NO | NO | NO |
| TJU_CMC_MD2.ID01340.5p-miR | TJU_CMC_MD2.ID01340.hairpin | YES | NO | YES | YES | NO | NO | NO | NO |
| TJU_CMC_MD2.ID01341.5p-miR | TJU_CMC_MD2.ID01341.hairpin | YES | YES | YES | NO | NO | NO | NO | NO |
| TJU_CMC_MD2.ID01342.5p-miR | TJU_CMC_MD2.ID01342.hairpin | YES | YES | YES | NO | NO | NO | NO | NO |
| TJU_CMC_MD2.ID01343.5p-miR | TJU_CMC_MD2.ID01343.hairpin | YES | YES | YES | NO | YES | NO | NO | NO |
| TJU_CMC_MD2.ID01344.3p-miR | TJU_CMC_MD2.ID01344.hairpin | YES | NO | NO | NO | NO | NO | NO | NO |
| TJU_CMC_MD2.ID01345.3p-miR | TJU_CMC_MD2.ID01345.hairpin | YES | NO | NO | NO | NO | NO | NO | NO |
| TJU_CMC_MD2.ID01346.3p-miR | TJU_CMC_MD2.ID01346.hairpin | YES | NO | NO | NO | NO | NO | NO | NO |
| TJU_CMC_MD2.ID01347.3p-miR | TJU_CMC_MD2.ID01347.hairpin | YES | NO | NO | NO | NO | NO | NO | NO |
| TJU_CMC_MD2.ID01348.3p-miR | TJU_CMC_MD2.ID01348.hairpin | YES | NO | NO | NO | NO | NO | NO | NO |
| TJU_CMC_MD2.ID01349.3p-miR | TJU_CMC_MD2.ID01349.hairpin | YES | NO | YES | NO | NO | NO | NO | NO |
| TJU_CMC_MD2.ID01349.5p-miR | TJU_CMC_MD2.ID01349.hairpin | YES | YES | YES | NO | NO | NO | NO | NO |
| TJU_CMC_MD2.ID01350.3p-miR | TJU_CMC_MD2.ID01350.hairpin | YES | YES | YES | NO | YES | NO | NO | NO |
| TJU_CMC_MD2.ID01351.3p-miR | TJU_CMC_MD2.ID01351.hairpin | YES | NO | NO | NO | NO | NO | NO | NO |
| TJU_CMC_MD2.ID01351.5p-miR | TJU_CMC_MD2.ID01351.hairpin | YES | NO | YES | NO | NO | NO | NO | NO |
| TJU_CMC_MD2.ID01352.3p-miR | TJU_CMC_MD2.ID01352.hairpin | YES | NO | NO | NO | NO | NO | NO | NO |
| TJU_CMC_MD2.ID01353.3p-miR | TJU_CMC_MD2.ID01353.hairpin | YES | NO | NO | NO | NO | NO | NO | NO |
| TJU_CMC_MD2.ID01354.3p-miR | TJU_CMC_MD2.ID01354.hairpin | YES | NO | NO | NO | NO | NO | NO | NO |
| TJU_CMC_MD2.ID01355.3p-miR | TJU_CMC_MD2.ID01355.hairpin | YES | NO | NO | NO | NO | NO | NO | NO |
| TJU_CMC_MD2.ID01356.3p-miR | TJU_CMC_MD2.ID01356.hairpin | YES | NO | NO | NO | NO | NO | NO | NO |
| TJU_CMC_MD2.ID01357.5p-miR | TJU_CMC_MD2.ID01357.hairpin | YES | YES | YES | YES | NO | NO | NO | NO |
| TJU_CMC_MD2.ID01358.5p-miR | TJU_CMC_MD2.ID01358.hairpin | YES | YES | YES | NO | NO | YES | NO | NO |
| TJU_CMC_MD2.ID01359.5p-miR | TJU_CMC_MD2.ID01359.hairpin | YES | NO | YES | YES | YES | NO | NO | NO |
| TJU_CMC_MD2.ID01360.3p-miR | TJU_CMC_MD2.ID01360.hairpin | YES | NO | NO | NO | NO | NO | NO | NO |
| TJU_CMC_MD2.ID01361.5p-miR | TJU_CMC_MD2.ID01361.hairpin | YES | NO | NO | YES | NO | NO | NO | NO |
| TJU_CMC_MD2.ID01362.5p-miR | TJU_CMC_MD2.ID01362.hairpin | YES | YES | YES | YES | YES | NO | NO | NO |
| TJU_CMC_MD2.ID01363.3p-miR | TJU_CMC_MD2.ID01363.hairpin | YES | NO | NO | NO | NO | NO | NO | NO |
| TJU_CMC_MD2.ID01364.3p-miR | TJU_CMC_MD2.ID01364.hairpin | YES | NO | NO | NO | NO | NO | NO | NO |
| TJU_CMC_MD2.ID01365.3p-miR | TJU_CMC_MD2.ID01365.hairpin | YES | NO | NO | NO | NO | NO | NO | NO |
| TJU_CMC_MD2.ID01366.5p-miR | TJU_CMC_MD2.ID01366.hairpin | YES | YES | NO | NO | NO | NO | NO | NO |
| TJU_CMC_MD2.ID01367.5p-miR | TJU_CMC_MD2.ID01367.hairpin | YES | YES | NO | NO | NO | NO | NO | NO |
| TJU_CMC_MD2.ID01368.3p-miR | TJU_CMC_MD2.ID01368.hairpin | YES | YES | YES | NO | YES | NO | NO | NO |
| TJU_CMC_MD2.ID01369.3p-miR | TJU_CMC_MD2.ID01369.hairpin | YES | NO | NO | NO | NO | NO | NO | NO |
| TJU_CMC_MD2.ID01370.5p-miR | TJU_CMC_MD2.ID01370.hairpin | YES | YES | YES | YES | NO | NO | NO | NO |
| TJU_CMC_MD2.ID01371.3p-miR | TJU_CMC_MD2.ID01371.hairpin | YES | NO | NO | NO | NO | NO | NO | NO |
| TJU_CMC_MD2.ID01371.5p-miR | TJU_CMC_MD2.ID01371.hairpin | YES | NO | NO | NO | NO | YES | NO | NO |
| TJU_CMC_MD2.ID01372.3p-miR | TJU_CMC_MD2.ID01372.hairpin | YES | NO | NO | NO | NO | NO | NO | NO |
| TJU_CMC_MD2.ID01373.3p-miR | TJU_CMC_MD2.ID01373.hairpin | YES | NO | NO | NO | NO | NO | NO | NO |
| TJU_CMC_MD2.ID01374.3p-miR | TJU_CMC_MD2.ID01374.hairpin | YES | NO | NO | NO | NO | NO | NO | NO |
| TJU_CMC_MD2.ID01375.5p-miR | TJU_CMC_MD2.ID01375.hairpin | YES | YES | NO | NO | YES | NO | NO | NO |
| TJU_CMC_MD2.ID01376.5p-miR | TJU_CMC_MD2.ID01376.hairpin | YES | YES | YES | YES | NO | NO | NO | NO |
| TJU_CMC_MD2.ID01377.3p-miR | TJU_CMC_MD2.ID01377.hairpin | YES | NO | NO | NO | NO | NO | NO | NO |
| TJU_CMC_MD2.ID01378.5p-miR | TJU_CMC_MD2.ID01378.hairpin | YES | YES | YES | YES | NO | NO | NO | NO |
| TJU_CMC_MD2.ID01379.3p-miR | TJU_CMC_MD2.ID01379.hairpin | YES | NO | NO | NO | NO | NO | NO | NO |
| TJU_CMC_MD2.ID01380.3p-miR | TJU_CMC_MD2.ID01380.hairpin | YES | NO | NO | NO | NO | NO | NO | NO |
| TJU_CMC_MD2.ID01381.3p-miR | TJU_CMC_MD2.ID01381.hairpin | YES | NO | NO | NO | NO | NO | NO | NO |
| TJU_CMC_MD2.ID01382.3p-miR | TJU_CMC_MD2.ID01382.hairpin | YES | NO | NO | NO | NO | NO | NO | NO |
| TJU_CMC_MD2.ID01383.3p-miR | TJU_CMC_MD2.ID01383.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01384.5p-miR | TJU_CMC_MD2.ID01384.hairpin | YES | YES | YES | NO | NO | NO | NO | NO |
| TJU_CMC_MD2.ID01385.5p-miR | TJU_CMC_MD2.ID01385.hairpin | YES | YES | NO | NO | NO | NO | NO | NO |
| TJU_CMC_MD2.ID01386.5p-miR | TJU_CMC_MD2.ID01386.hairpin | YES | NO | NO | YES | YES | NO | NO | NO |
| TJU_CMC_MD2.ID01387.3p-miR | TJU_CMC_MD2.ID01387.hairpin | YES | NO | NO | NO | NO | NO | NO | NO |
| TJU_CMC_MD2.ID01388.5p-miR | TJU_CMC_MD2.ID01388.hairpin | YES | NO | YES | NO | YES | NO | NO | NO |
| TJU_CMC_MD2.ID01389.5p-miR | TJU_CMC_MD2.ID01389.hairpin | YES | YES | NO | NO | YES | NO | NO | NO |
| TJU_CMC_MD2.ID01390.3p-miR | TJU_CMC_MD2.ID01390.hairpin | YES | NO | NO | NO | NO | NO | NO | NO |
| TJU_CMC_MD2.ID01391.3p-miR | TJU_CMC_MD2.ID01391.hairpin | YES | NO | NO | NO | NO | NO | NO | NO |
| TJU_CMC_MD2.ID01392.3p-miR | TJU_CMC_MD2.ID01392.hairpin | YES | NO | NO | NO | NO | NO | NO | NO |
| TJU_CMC_MD2.ID01393.3p-miR | TJU_CMC_MD2.ID01393.hairpin | YES | NO | NO | NO | NO | NO | NO | NO |
| TJU_CMC_MD2.ID01394.5p-miR | TJU_CMC_MD2.ID01394.hairpin | YES | YES | YES | YES | NO | NO | NO | NO |
| TJU_CMC_MD2.ID01395.5p-miR | TJU_CMC_MD2.ID01395.hairpin | YES | YES | YES | YES | YES | NO | NO | NO |
| TJU_CMC_MD2.ID01396.3p-miR | TJU_CMC_MD2.ID01396.hairpin | YES | NO | NO | NO | NO | NO | NO | NO |
| TJU_CMC_MD2.ID01397.5p-miR | TJU_CMC_MD2.ID01397.hairpin | YES | YES | YES | NO | NO | NO | NO | NO |
| TJU_CMC_MD2.ID01398.3p-miR | TJU_CMC_MD2.ID01398.hairpin | YES | NO | NO | NO | NO | NO | NO | NO |
| TJU_CMC_MD2.ID01399.3p-miR | TJU_CMC_MD2.ID01399.hairpin | YES | NO | NO | NO | NO | NO | NO | NO |
| TJU_CMC_MD2.ID01400.3p-miR | TJU_CMC_MD2.ID01400.hairpin | YES | NO | NO | NO | NO | NO | NO | NO |
| TJU_CMC_MD2.ID01401.3p-miR | TJU_CMC_MD2.ID01401.hairpin | YES | NO | NO | NO | NO | NO | NO | NO |
| TJU_CMC_MD2.ID01402.5p-miR | TJU_CMC_MD2.ID01402.hairpin | YES | YES | YES | YES | YES | NO | NO | NO |
| TJU_CMC_MD2.ID01403.5p-miR | TJU_CMC_MD2.ID01403.hairpin | YES | YES | YES | NO | NO | NO | NO | NO |
| TJU_CMC_MD2.ID01404.5p-miR | TJU_CMC_MD2.ID01404.hairpin | YES | YES | NO | YES | NO | NO | NO | NO |
| TJU_CMC_MD2.ID01405.5p-miR | TJU_CMC_MD2.ID01405.hairpin | YES | YES | YES | YES | NO | NO | NO | NO |
| TJU_CMC_MD2.ID01406.5p-miR | TJU_CMC_MD2.ID01406.hairpin | YES | YES | YES | NO | NO | NO | NO | NO |
| TJU_CMC_MD2.ID01407.3p-miR | TJU_CMC_MD2.ID01407.hairpin | YES | NO | NO | NO | NO | NO | NO | NO |
| TJU_CMC_MD2.ID01408.3p-miR | TJU_CMC_MD2.ID01408.hairpin | YES | NO | NO | NO | NO | NO | NO | NO |
| TJU_CMC_MD2.ID01408.5p-miR | TJU_CMC_MD2.ID01408.hairpin | YES | YES | YES | YES | YES | NO | NO | NO |
| TJU_CMC_MD2.ID01409.3p-miR | TJU_CMC_MD2.ID01409.hairpin | YES | NO | NO | NO | NO | NO | NO | NO |
| TJU_CMC_MD2.ID01410.5p-miR | TJU_CMC_MD2.ID01410.hairpin | YES | YES | YES | YES | NO | NO | NO | NO |
| TJU_CMC_MD2.ID01411.3p-miR | TJU_CMC_MD2.ID01411.hairpin | YES | NO | NO | NO | NO | NO | NO | NO |
| TJU_CMC_MD2.ID01412.5p-miR | TJU_CMC_MD2.ID01412.hairpin | YES | YES | YES | YES | YES | NO | NO | NO |
| TJU_CMC_MD2.ID01413.3p-miR | TJU_CMC_MD2.ID01413.hairpin | YES | NO | NO | NO | NO | NO | NO | NO |
| TJU_CMC_MD2.ID01414.3p-miR | TJU_CMC_MD2.ID01414.hairpin | YES | NO | NO | NO | NO | NO | NO | NO |
| TJU_CMC_MD2.ID01415.3p-miR | TJU_CMC_MD2.ID01415.hairpin | YES | NO | NO | NO | NO | NO | NO | NO |
| TJU_CMC_MD2.ID01415.5p-miR | TJU_CMC_MD2.ID01415.hairpin | YES | YES | YES | YES | NO | NO | NO | NO |
| TJU_CMC_MD2.ID01416.3p-miR | TJU_CMC_MD2.ID01416.hairpin | YES | NO | NO | NO | NO | NO | NO | NO |
| TJU_CMC_MD2.ID01417.3p-miR | TJU_CMC_MD2.ID01417.hairpin | YES | NO | NO | NO | NO | NO | NO | NO |
| TJU_CMC_MD2.ID01418.3p-miR | TJU_CMC_MD2.ID01418.hairpin | YES | NO | NO | NO | NO | NO | NO | NO |
| TJU_CMC_MD2.ID01419.3p-miR | TJU_CMC_MD2.ID01419.hairpin | YES | NO | NO | NO | NO | NO | NO | NO |
| TJU_CMC_MD2.ID01420.3p-miR | TJU_CMC_MD2.ID01420.hairpin | YES | NO | NO | NO | NO | NO | NO | NO |
| TJU_CMC_MD2.ID01421.3p-miR | TJU_CMC_MD2.ID01421.hairpin | YES | NO | NO | NO | NO | NO | NO | NO |
| TJU_CMC_MD2.ID01422.3p-miR | TJU_CMC_MD2.ID01422.hairpin | YES | NO | YES | NO | YES | NO | NO | NO |
| TJU_CMC_MD2.ID01423.3p-miR | TJU_CMC_MD2.ID01423.hairpin | YES | YES | YES | NO | NO | NO | NO | NO |
| TJU_CMC_MD2.ID01424.5p-miR | TJU_CMC_MD2.ID01424.hairpin | YES | YES | NO | NO | NO | YES | NO | NO |
| TJU_CMC_MD2.ID01425.3p-miR | TJU_CMC_MD2.ID01425.hairpin | YES | NO | NO | NO | NO | NO | NO | NO |
| TJU_CMC_MD2.ID01426.5p-miR | TJU_CMC_MD2.ID01426.hairpin | YES | YES | YES | YES | NO | NO | NO | NO |
| TJU_CMC_MD2.ID01427.3p-miR | TJU_CMC_MD2.ID01427.hairpin | YES | NO | NO | NO | NO | NO | NO | NO |
| TJU_CMC_MD2.ID01428.3p-miR | TJU_CMC_MD2.ID01428.hairpin | YES | NO | NO | NO | NO | NO | NO | NO |
| TJU_CMC_MD2.ID01429.5p-miR | TJU_CMC_MD2.ID01429.hairpin | YES | YES | YES | YES | YES | NO | NO | NO |
| TJU_CMC_MD2.ID01430.3p-miR | TJU_CMC_MD2.ID01430.hairpin | YES | NO | NO | NO | NO | NO | NO | NO |
| TJU_CMC_MD2.ID01431.3p-miR | TJU_CMC_MD2.ID01431.hairpin | YES | NO | NO | NO | NO | NO | NO | NO |
| TJU_CMC_MD2.ID01432.3p-miR | TJU_CMC_MD2.ID01432.hairpin | YES | NO | NO | NO | NO | NO | NO | NO |
| TJU_CMC_MD2.ID01433.5p-miR | TJU_CMC_MD2.ID01433.hairpin | YES | YES | NO | NO | YES | NO | NO | NO |
| TJU_CMC_MD2.ID01434.5p-miR | TJU_CMC_MD2.ID01434.hairpin | YES | YES | YES | NO | NO | NO | NO | NO |
| TJU_CMC_MD2.ID01435.3p-miR | TJU_CMC_MD2.ID01435.hairpin | YES | NO | NO | NO | NO | NO | NO | NO |
| TJU_CMC_MD2.ID01436.3p-miR | TJU_CMC_MD2.ID01436.hairpin | YES | YES | NO | NO | YES | NO | NO | NO |
| TJU_CMC_MD2.ID01436.5p-miR | TJU_CMC_MD2.ID01436.hairpin | YES | YES | NO | YES | YES | NO | NO | NO |
| TJU_CMC_MD2.ID01437.5p-miR | TJU_CMC_MD2.ID01437.hairpin | YES | NO | NO | NO | NO | NO | NO | NO |
| TJU_CMC_MD2.ID01438.3p-miR | TJU_CMC_MD2.ID01438.hairpin | YES | NO | NO | NO | NO | NO | NO | NO |
| TJU_CMC_MD2.ID01439.3p-miR | TJU_CMC_MD2.ID01439.hairpin | YES | NO | NO | NO | NO | NO | NO | NO |
| TJU_CMC_MD2.ID01440.3p-miR | TJU_CMC_MD2.ID01440.hairpin | YES | NO | NO | NO | NO | NO | NO | NO |
| TJU_CMC_MD2.ID01441.5p-miR | TJU_CMC_MD2.ID01441.hairpin | YES | YES | NO | YES | NO | NO | NO | NO |
| TJU_CMC_MD2.ID01442.3p-miR | TJU_CMC_MD2.ID01442.hairpin | YES | NO | NO | NO | NO | NO | NO | NO |
| TJU_CMC_MD2.ID01443.3p-miR | TJU_CMC_MD2.ID01443.hairpin | YES | NO | NO | NO | NO | NO | NO | NO |
| TJU_CMC_MD2.ID01444.5p-miR | TJU_CMC_MD2.ID01444.hairpin | YES | YES | YES | NO | YES | NO | NO | NO |
| TJU_CMC_MD2.ID01445.3p-miR | TJU_CMC_MD2.ID01445.hairpin | YES | NO | NO | NO | NO | NO | NO | NO |
| TJU_CMC_MD2.ID01446.5p-miR | TJU_CMC_MD2.ID01446.hairpin | YES | YES | YES | YES | YES | NO | NO | NO |
| TJU_CMC_MD2.ID01447.5p-miR | TJU_CMC_MD2.ID01447.hairpin | YES | YES | NO | YES | NO | NO | NO | NO |
| TJU_CMC_MD2.ID01448.5p-miR | TJU_CMC_MD2.ID01448.hairpin | YES | NO | YES | YES | NO | NO | NO | NO |
| TJU_CMC_MD2.ID01449.3p-miR | TJU_CMC_MD2.ID01449.hairpin | YES | NO | NO | NO | NO | NO | NO | NO |
| TJU_CMC_MD2.ID01450.5p-miR | TJU_CMC_MD2.ID01450.hairpin | YES | YES | YES | NO | YES | NO | NO | NO |
| TJU_CMC_MD2.ID01451.3p-miR | TJU_CMC_MD2.ID01451.hairpin | YES | NO | NO | NO | NO | NO | NO | NO |
| TJU_CMC_MD2.ID01452.3p-miR | TJU_CMC_MD2.ID01452.hairpin | YES | NO | NO | NO | NO | NO | NO | NO |
| TJU_CMC_MD2.ID01453.3p-miR | TJU_CMC_MD2.ID01453.hairpin | YES | NO | NO | NO | NO | NO | NO | NO |
| TJU_CMC_MD2.ID01454.3p-miR | TJU_CMC_MD2.ID01454.hairpin | YES | YES | NO | NO | NO | NO | NO | NO |
| TJU_CMC_MD2.ID01455.5p-miR | TJU_CMC_MD2.ID01455.hairpin | YES | YES | NO | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01456.3p-miR | TJU_CMC_MD2.ID01456.hairpin | YES | NO | NO | NO | NO | NO | NO | NO |
| TJU_CMC_MD2.ID01457.3p-miR | TJU_CMC_MD2.ID01457.hairpin | YES | NO | NO | NO | NO | NO | NO | NO |
| TJU_CMC_MD2.ID01458.5p-miR | TJU_CMC_MD2.ID01458.hairpin | YES | NO | NO | NO | NO | NO | NO | NO |
| TJU_CMC_MD2.ID01459.3p-miR | TJU_CMC_MD2.ID01459.hairpin | YES | NO | NO | NO | NO | NO | NO | NO |
| TJU_CMC_MD2.ID01460.3p-miR | TJU_CMC_MD2.ID01460.hairpin | YES | NO | NO | NO | NO | NO | NO | NO |
| TJU_CMC_MD2.ID01461.3p-miR | TJU_CMC_MD2.ID01461.hairpin | YES | NO | NO | NO | NO | NO | NO | NO |
| TJU_CMC_MD2.ID01462.3p-miR | TJU_CMC_MD2.ID01462.hairpin | YES | NO | NO | NO | NO | NO | NO | NO |
| TJU_CMC_MD2.ID01463.3p-miR | TJU_CMC_MD2.ID01463.hairpin | YES | NO | NO | NO | NO | NO | NO | NO |
| TJU_CMC_MD2.ID01464.5p-miR | TJU_CMC_MD2.ID01464.hairpin | YES | YES | YES | YES | NO | NO | NO | NO |
| TJU_CMC_MD2.ID01465.5p-miR | TJU_CMC_MD2.ID01465.hairpin | YES | YES | YES | YES | YES | NO | NO | NO |
| TJU_CMC_MD2.ID01466.3p-miR | TJU_CMC_MD2.ID01466.hairpin | YES | YES | YES | YES | YES | NO | NO | NO |
| TJU_CMC_MD2.ID01467.3p-miR | TJU_CMC_MD2.ID01467.hairpin | YES | NO | NO | NO | NO | NO | NO | NO |
| TJU_CMC_MD2.ID01468.3p-miR | TJU_CMC_MD2.ID01468.hairpin | YES | NO | NO | NO | NO | NO | NO | NO |
| TJU_CMC_MD2.ID01469.5p-miR | TJU_CMC_MD2.ID01469.hairpin | YES | NO | NO | NO | NO | NO | NO | NO |
| TJU_CMC_MD2.ID01470.3p-miR | TJU_CMC_MD2.ID01470.hairpin | YES | NO | NO | NO | NO | NO | NO | NO |
| TJU_CMC_MD2.ID01471.5p-miR | TJU_CMC_MD2.ID01471.hairpin | YES | NO | YES | YES | NO | NO | NO | NO |
| TJU_CMC_MD2.ID01472.3p-miR | TJU_CMC_MD2.ID01472.hairpin | YES | NO | NO | NO | NO | NO | NO | NO |
| TJU_CMC_MD2.ID01473.3p-miR | TJU_CMC_MD2.ID01473.hairpin | YES | NO | NO | NO | NO | NO | NO | NO |
| TJU_CMC_MD2.ID01474.3p-miR | TJU_CMC_MD2.ID01474.hairpin | YES | NO | NO | NO | NO | NO | NO | NO |
| TJU_CMC_MD2.ID01475.5p-miR | TJU_CMC_MD2.ID01475.hairpin | YES | NO | NO | YES | YES | NO | NO | NO |
| TJU_CMC_MD2.ID01476.3p-miR | TJU_CMC_MD2.ID01476.hairpin | YES | NO | NO | NO | NO | NO | NO | NO |
| TJU_CMC_MD2.ID01477.5p-miR | TJU_CMC_MD2.ID01477.hairpin | YES | YES | NO | YES | YES | NO | NO | NO |
| TJU_CMC_MD2.ID01478.3p-miR | TJU_CMC_MD2.ID01478.hairpin | YES | NO | NO | NO | NO | NO | NO | NO |
| TJU_CMC_MD2.ID01479.5p-miR | TJU_CMC_MD2.ID01479.hairpin | YES | YES | YES | NO | NO | NO | NO | NO |
| TJU_CMC_MD2.ID01480.5p-miR | TJU_CMC_MD2.ID01480.hairpin | YES | YES | YES | YES | NO | NO | NO | NO |
| TJU_CMC_MD2.ID01481.5p-miR | TJU_CMC_MD2.ID01481.hairpin | YES | YES | YES | NO | YES | NO | NO | NO |
| TJU_CMC_MD2.ID01482.5p-miR | TJU_CMC_MD2.ID01482.hairpin | YES | YES | NO | YES | NO | NO | NO | NO |
| TJU_CMC_MD2.ID01483.5p-miR | TJU_CMC_MD2.ID01483.hairpin | YES | YES | YES | NO | YES | YES | NO | NO |
| TJU_CMC_MD2.ID01484.3p-miR | TJU_CMC_MD2.ID01484.hairpin | YES | NO | NO | NO | NO | NO | NO | NO |
| TJU_CMC_MD2.ID01485.5p-miR | TJU_CMC_MD2.ID01485.hairpin | YES | YES | NO | YES | YES | NO | NO | NO |
| TJU_CMC_MD2.ID01486.3p-miR | TJU_CMC_MD2.ID01486.hairpin | YES | NO | NO | NO | NO | NO | NO | NO |
| TJU_CMC_MD2.ID01487.3p-miR | TJU_CMC_MD2.ID01487.hairpin | YES | NO | NO | NO | NO | NO | NO | NO |
| TJU_CMC_MD2.ID01488.5p-miR | TJU_CMC_MD2.ID01488.hairpin | YES | YES | YES | YES | YES | YES | NO | NO |
| TJU_CMC_MD2.ID01489.3p-miR | TJU_CMC_MD2.ID01489.hairpin | YES | NO | NO | NO | NO | NO | NO | NO |
| TJU_CMC_MD2.ID01490.3p-miR | TJU_CMC_MD2.ID01490.hairpin | YES | NO | NO | NO | NO | NO | NO | NO |
| TJU_CMC_MD2.ID01491.3p-miR | TJU_CMC_MD2.ID01491.hairpin | YES | NO | NO | NO | NO | NO | NO | NO |
| TJU_CMC_MD2.ID01492.3p-miR | TJU_CMC_MD2.ID01492.hairpin | YES | NO | NO | NO | NO | NO | NO | NO |
| TJU_CMC_MD2.ID01493.3p-miR | TJU_CMC_MD2.ID01493.hairpin | YES | NO | NO | NO | NO | NO | NO | NO |
| TJU_CMC_MD2.ID01494.5p-miR | TJU_CMC_MD2.ID01494.hairpin | YES | YES | YES | YES | NO | NO | NO | NO |
| TJU_CMC_MD2.ID01495.3p-miR | TJU_CMC_MD2.ID01495.hairpin | YES | NO | NO | NO | NO | NO | NO | NO |
| TJU_CMC_MD2.ID01496.3p-miR | TJU_CMC_MD2.ID01496.hairpin | YES | NO | NO | NO | NO | NO | NO | NO |
| TJU_CMC_MD2.ID01497.5p-miR | TJU_CMC_MD2.ID01497.hairpin | YES | NO | YES | NO | NO | NO | NO | NO |
| TJU_CMC_MD2.ID01498.3p-miR | TJU_CMC_MD2.ID01498.hairpin | YES | NO | NO | NO | NO | NO | NO | NO |
| TJU_CMC_MD2.ID01499.5p-miR | TJU_CMC_MD2.ID01499.hairpin | YES | YES | YES | NO | YES | NO | NO | NO |
| TJU_CMC_MD2.ID01500.3p-miR | TJU_CMC_MD2.ID01500.hairpin | YES | NO | NO | NO | NO | NO | NO | NO |
| TJU_CMC_MD2.ID01501.5p-miR | TJU_CMC_MD2.ID01501.hairpin | YES | YES | YES | NO | NO | NO | NO | NO |
| TJU_CMC_MD2.ID01502.3p-miR | TJU_CMC_MD2.ID01502.hairpin | YES | NO | NO | NO | NO | NO | NO | NO |
| TJU_CMC_MD2.ID01503.3p-miR | TJU_CMC_MD2.ID01503.hairpin | YES | NO | NO | NO | NO | NO | NO | NO |
| TJU_CMC_MD2.ID01504.3p-miR | TJU_CMC_MD2.ID01504.hairpin | YES | NO | NO | NO | NO | NO | NO | NO |
| TJU_CMC_MD2.ID01505.3p-miR | TJU_CMC_MD2.ID01505.hairpin | YES | NO | NO | NO | NO | NO | NO | NO |
| TJU_CMC_MD2.ID01505.5p-miR | TJU_CMC_MD2.ID01505.hairpin | YES | NO | NO | NO | NO | NO | NO | NO |
| TJU_CMC_MD2.ID01506.3p-miR | TJU_CMC_MD2.ID01506.hairpin | YES | NO | NO | NO | NO | NO | NO | NO |
| TJU_CMC_MD2.ID01507.3p-miR | TJU_CMC_MD2.ID01507.hairpin | YES | YES | YES | NO | YES | NO | NO | NO |
| TJU_CMC_MD2.ID01508.5p-miR | TJU_CMC_MD2.ID01508.hairpin | YES | NO | YES | NO | NO | NO | NO | NO |
| TJU_CMC_MD2.ID01509.3p-miR | TJU_CMC_MD2.ID01509.hairpin | YES | NO | NO | NO | NO | NO | NO | NO |
| TJU_CMC_MD2.ID01510.3p-miR | TJU_CMC_MD2.ID01510.hairpin | YES | NO | NO | NO | NO | NO | NO | NO |
| TJU_CMC_MD2.ID01511.5p-miR | TJU_CMC_MD2.ID01511.hairpin | YES | YES | YES | YES | NO | NO | NO | NO |
| TJU_CMC_MD2.ID01512.3p-miR | TJU_CMC_MD2.ID01512.hairpin | YES | NO | NO | NO | NO | NO | NO | NO |
| TJU_CMC_MD2.ID01513.5p-miR | TJU_CMC_MD2.ID01513.hairpin | YES | YES | YES | NO | NO | NO | NO | NO |
| TJU_CMC_MD2.ID01514.3p-miR | TJU_CMC_MD2.ID01514.hairpin | YES | YES | NO | NO | NO | NO | NO | NO |
| TJU_CMC_MD2.ID01515.3p-miR | TJU_CMC_MD2.ID01515.hairpin | YES | NO | NO | NO | NO | NO | NO | NO |
| TJU_CMC_MD2.ID01516.3p-miR | TJU_CMC_MD2.ID01516.hairpin | YES | NO | NO | NO | NO | NO | NO | NO |
| TJU_CMC_MD2.ID01517.3p-miR | TJU_CMC_MD2.ID01517.hairpin | YES | NO | NO | NO | NO | NO | NO | NO |
| TJU_CMC_MD2.ID01518.3p-miR | TJU_CMC_MD2.ID01518.hairpin | YES | NO | NO | NO | NO | NO | NO | NO |
| TJU_CMC_MD2.ID01519.5p-miR | TJU_CMC_MD2.ID01519.hairpin | YES | YES | YES | YES | NO | NO | NO | NO |
| TJU_CMC_MD2.ID01520.3p-miR | TJU_CMC_MD2.ID01520.hairpin | YES | NO | NO | NO | NO | NO | NO | NO |
| TJU_CMC_MD2.ID01521.3p-miR | TJU_CMC_MD2.ID01521.hairpin | YES | NO | NO | NO | NO | NO | NO | NO |
| TJU_CMC_MD2.ID01522.3p-miR | TJU_CMC_MD2.ID01522.hairpin | YES | NO | NO | NO | NO | NO | NO | NO |
| TJU_CMC_MD2.ID01523.3p-miR | TJU_CMC_MD2.ID01523.hairpin | YES | NO | NO | NO | NO | NO | NO | NO |
| TJU_CMC_MD2.ID01524.3p-miR | TJU_CMC_MD2.ID01524.hairpin | YES | NO | NO | NO | NO | NO | NO | NO |
| TJU_CMC_MD2.ID01525.3p-miR | TJU_CMC_MD2.ID01525.hairpin | YES | NO | NO | NO | NO | NO | NO | NO |
| TJU_CMC_MD2.ID01526.3p-miR | TJU_CMC_MD2.ID01526.hairpin | YES | NO | NO | NO | NO | NO | NO | NO |
| TJU_CMC_MD2.ID01527.3p-miR | TJU_CMC_MD2.ID01527.hairpin | YES | YES | YES | YES | NO | NO | NO | NO |
| TJU_CMC_MD2.ID01528.3p-miR | TJU_CMC_MD2.ID01528.hairpin | YES | NO | NO | NO | NO | NO | NO | NO |
| TJU_CMC_MD2.ID01529.5p-miR | TJU_CMC_MD2.ID01529.hairpin | YES | NO | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01530.5p-miR | TJU_CMC_MD2.ID01530.hairpin | YES | YES | YES | NO | NO | YES | NO | NO |
| TJU_CMC_MD2.ID01531.3p-miR | TJU_CMC_MD2.ID01531.hairpin | YES | NO | NO | NO | NO | NO | NO | NO |
| TJU_CMC_MD2.ID01532.3p-miR | TJU_CMC_MD2.ID01532.hairpin | YES | NO | NO | NO | NO | NO | NO | NO |
| TJU_CMC_MD2.ID01533.3p-miR | TJU_CMC_MD2.ID01533.hairpin | YES | NO | NO | NO | NO | NO | NO | NO |
| TJU_CMC_MD2.ID01534.3p-miR | TJU_CMC_MD2.ID01534.hairpin | YES | NO | NO | NO | NO | NO | NO | NO |
| TJU_CMC_MD2.ID01535.3p-miR | TJU_CMC_MD2.ID01535.hairpin | YES | NO | NO | NO | NO | NO | NO | NO |
| TJU_CMC_MD2.ID01536.3p-miR | TJU_CMC_MD2.ID01536.hairpin | YES | NO | NO | NO | NO | NO | NO | NO |
| TJU_CMC_MD2.ID01537.3p-miR | TJU_CMC_MD2.ID01537.hairpin | YES | NO | NO | NO | NO | NO | NO | NO |
| TJU_CMC_MD2.ID01538.3p-miR | TJU_CMC_MD2.ID01538.hairpin | YES | NO | NO | NO | NO | NO | NO | NO |
| TJU_CMC_MD2.ID01539.3p-miR | TJU_CMC_MD2.ID01539.hairpin | YES | NO | NO | NO | NO | NO | NO | NO |
| TJU_CMC_MD2.ID01540.3p-miR | TJU_CMC_MD2.ID01540.hairpin | YES | NO | NO | NO | NO | NO | NO | NO |
| TJU_CMC_MD2.ID01541.3p-miR | TJU_CMC_MD2.ID01541.hairpin | YES | NO | NO | NO | NO | NO | NO | NO |
| TJU_CMC_MD2.ID01542.3p-miR | TJU_CMC_MD2.ID01542.hairpin | YES | NO | NO | NO | NO | NO | NO | NO |
| TJU_CMC_MD2.ID01543.3p-miR | TJU_CMC_MD2.ID01543.hairpin | YES | NO | NO | NO | NO | NO | NO | NO |
| TJU_CMC_MD2.ID01544.3p-miR | TJU_CMC_MD2.ID01544.hairpin | YES | NO | NO | NO | NO | NO | NO | NO |
| TJU_CMC_MD2.ID01545.3p-miR | TJU_CMC_MD2.ID01545.hairpin | YES | NO | NO | NO | NO | NO | NO | NO |
| TJU_CMC_MD2.ID01546.5p-miR | TJU_CMC_MD2.ID01546.hairpin | YES | YES | YES | NO | NO | NO | NO | NO |
| TJU_CMC_MD2.ID01547.3p-miR | TJU_CMC_MD2.ID01547.hairpin | YES | NO | NO | NO | NO | NO | NO | NO |
| TJU_CMC_MD2.ID01548.5p-miR | TJU_CMC_MD2.ID01548.hairpin | YES | YES | NO | YES | NO | NO | NO | NO |
| TJU_CMC_MD2.ID01549.5p-miR | TJU_CMC_MD2.ID01549.hairpin | YES | YES | YES | NO | NO | NO | NO | NO |
| TJU_CMC_MD2.ID01550.3p-miR | TJU_CMC_MD2.ID01550.hairpin | YES | NO | NO | NO | NO | NO | NO | NO |
| TJU_CMC_MD2.ID01551.3p-miR | TJU_CMC_MD2.ID01551.hairpin | YES | NO | NO | NO | NO | NO | NO | NO |
| TJU_CMC_MD2.ID01552.5p-miR | TJU_CMC_MD2.ID01552.hairpin | YES | YES | NO | YES | YES | NO | NO | NO |
| TJU_CMC_MD2.ID01553.3p-miR | TJU_CMC_MD2.ID01553.hairpin | YES | NO | NO | NO | NO | NO | NO | NO |
| TJU_CMC_MD2.ID01554.3p-miR | TJU_CMC_MD2.ID01554.hairpin | YES | NO | NO | NO | NO | NO | NO | NO |
| TJU_CMC_MD2.ID01555.5p-miR | TJU_CMC_MD2.ID01555.hairpin | YES | YES | YES | YES | YES | NO | NO | NO |
| TJU_CMC_MD2.ID01556.3p-miR | TJU_CMC_MD2.ID01556.hairpin | YES | NO | YES | NO | YES | NO | NO | NO |
| TJU_CMC_MD2.ID01557.5p-miR | TJU_CMC_MD2.ID01557.hairpin | YES | NO | YES | YES | NO | NO | NO | NO |
| TJU_CMC_MD2.ID01558.3p-miR | TJU_CMC_MD2.ID01558.hairpin | YES | NO | NO | NO | NO | NO | NO | NO |
| TJU_CMC_MD2.ID01559.3p-miR | TJU_CMC_MD2.ID01559.hairpin | YES | NO | NO | NO | NO | NO | NO | NO |
| TJU_CMC_MD2.ID01560.3p-miR | TJU_CMC_MD2.ID01560.hairpin | YES | NO | NO | NO | NO | NO | NO | NO |
| TJU_CMC_MD2.ID01561.3p-miR | TJU_CMC_MD2.ID01561.hairpin | YES | NO | NO | NO | NO | NO | NO | NO |
| TJU_CMC_MD2.ID01562.3p-miR | TJU_CMC_MD2.ID01562.hairpin | YES | NO | NO | NO | NO | NO | NO | NO |
| TJU_CMC_MD2.ID01563.5p-miR | TJU_CMC_MD2.ID01563.hairpin | YES | YES | YES | YES | NO | NO | NO | NO |
| TJU_CMC_MD2.ID01564.3p-miR | TJU_CMC_MD2.ID01564.hairpin | YES | NO | NO | NO | NO | NO | NO | NO |
| TJU_CMC_MD2.ID01565.5p-miR | TJU_CMC_MD2.ID01565.hairpin | YES | YES | NO | YES | NO | NO | NO | NO |
| TJU_CMC_MD2.ID01566.3p-miR | TJU_CMC_MD2.ID01566.hairpin | YES | NO | NO | NO | NO | NO | NO | NO |
| TJU_CMC_MD2.ID01567.5p-miR | TJU_CMC_MD2.ID01567.hairpin | YES | NO | NO | YES | NO | NO | NO | NO |
| TJU_CMC_MD2.ID01568.3p-miR | TJU_CMC_MD2.ID01568.hairpin | YES | NO | NO | NO | NO | NO | NO | NO |
| TJU_CMC_MD2.ID01569.3p-miR | TJU_CMC_MD2.ID01569.hairpin | YES | NO | NO | NO | NO | NO | NO | NO |
| TJU_CMC_MD2.ID01570.3p-miR | TJU_CMC_MD2.ID01570.hairpin | YES | NO | NO | NO | NO | NO | NO | NO |
| TJU_CMC_MD2.ID01571.3p-miR | TJU_CMC_MD2.ID01571.hairpin | YES | NO | NO | NO | NO | NO | NO | NO |
| TJU_CMC_MD2.ID01572.5p-miR | TJU_CMC_MD2.ID01572.hairpin | YES | NO | YES | NO | NO | NO | NO | NO |
| TJU_CMC_MD2.ID01573.5p-miR | TJU_CMC_MD2.ID01573.hairpin | YES | YES | NO | NO | NO | NO | NO | NO |
| TJU_CMC_MD2.ID01574.5p-miR | TJU_CMC_MD2.ID01574.hairpin | YES | YES | YES | YES | NO | NO | NO | NO |
| TJU_CMC_MD2.ID01575.5p-miR | TJU_CMC_MD2.ID01575.hairpin | YES | YES | YES | NO | NO | NO | NO | NO |
| TJU_CMC_MD2.ID01576.3p-miR | TJU_CMC_MD2.ID01576.hairpin | YES | NO | NO | NO | NO | NO | NO | NO |
| TJU_CMC_MD2.ID01577.3p-miR | TJU_CMC_MD2.ID01577.hairpin | YES | YES | NO | YES | YES | NO | NO | NO |
| TJU_CMC_MD2.ID01578.5p-miR | TJU_CMC_MD2.ID01578.hairpin | YES | NO | YES | NO | NO | NO | NO | NO |
| TJU_CMC_MD2.ID01579.5p-miR | TJU_CMC_MD2.ID01579.hairpin | YES | NO | YES | YES | NO | NO | NO | NO |
| TJU_CMC_MD2.ID01580.3p-miR | TJU_CMC_MD2.ID01580.hairpin | YES | NO | NO | NO | NO | NO | NO | NO |
| TJU_CMC_MD2.ID01581.5p-miR | TJU_CMC_MD2.ID01581.hairpin | YES | YES | YES | YES | NO | NO | NO | NO |
| TJU_CMC_MD2.ID01582.3p-miR | TJU_CMC_MD2.ID01582.hairpin | YES | NO | NO | NO | NO | NO | NO | NO |
| TJU_CMC_MD2.ID01583.3p-miR | TJU_CMC_MD2.ID01583.hairpin | YES | NO | NO | NO | NO | NO | NO | NO |
| TJU_CMC_MD2.ID01584.3p-miR | TJU_CMC_MD2.ID01584.hairpin | YES | NO | NO | NO | NO | NO | NO | NO |
| TJU_CMC_MD2.ID01585.3p-miR | TJU_CMC_MD2.ID01585.hairpin | YES | NO | NO | NO | NO | NO | NO | NO |
| TJU_CMC_MD2.ID01586.3p-miR | TJU_CMC_MD2.ID01586.hairpin | YES | NO | NO | NO | NO | NO | NO | NO |
| TJU_CMC_MD2.ID01587.3p-miR | TJU_CMC_MD2.ID01587.hairpin | YES | NO | NO | NO | NO | NO | NO | NO |
| TJU_CMC_MD2.ID01587.5p-miR | TJU_CMC_MD2.ID01587.hairpin | YES | YES | YES | NO | NO | NO | NO | NO |
| TJU_CMC_MD2.ID01588.3p-miR | TJU_CMC_MD2.ID01588.hairpin | YES | NO | NO | NO | NO | NO | NO | NO |
| TJU_CMC_MD2.ID01589.3p-miR | TJU_CMC_MD2.ID01589.hairpin | YES | NO | NO | NO | NO | NO | NO | NO |
| TJU_CMC_MD2.ID01590.3p-miR | TJU_CMC_MD2.ID01590.hairpin | YES | NO | NO | NO | NO | NO | NO | NO |
| TJU_CMC_MD2.ID01591.3p-miR | TJU_CMC_MD2.ID01591.hairpin | YES | NO | NO | NO | NO | NO | NO | NO |
| TJU_CMC_MD2.ID01592.3p-miR | TJU_CMC_MD2.ID01592.hairpin | YES | NO | NO | NO | NO | NO | NO | NO |
| TJU_CMC_MD2.ID01593.5p-miR | TJU_CMC_MD2.ID01593.hairpin | YES | NO | YES | YES | NO | NO | NO | NO |
| TJU_CMC_MD2.ID01594.3p-miR | TJU_CMC_MD2.ID01594.hairpin | YES | NO | NO | NO | NO | NO | NO | NO |
| TJU_CMC_MD2.ID01595.3p-miR | TJU_CMC_MD2.ID01595.hairpin | YES | NO | NO | NO | NO | NO | NO | NO |
| TJU_CMC_MD2.ID01596.5p-miR | TJU_CMC_MD2.ID01596.hairpin | YES | YES | NO | YES | NO | NO | NO | NO |
| TJU_CMC_MD2.ID01597.3p-miR | TJU_CMC_MD2.ID01597.hairpin | YES | NO | NO | NO | NO | NO | NO | NO |
| TJU_CMC_MD2.ID01598.3p-miR | TJU_CMC_MD2.ID01598.hairpin | YES | NO | NO | NO | NO | NO | NO | NO |
| TJU_CMC_MD2.ID01599.3p-miR | TJU_CMC_MD2.ID01599.hairpin | YES | NO | NO | NO | NO | NO | NO | NO |
| TJU_CMC_MD2.ID01600.3p-miR | TJU_CMC_MD2.ID01600.hairpin | YES | NO | NO | NO | NO | NO | NO | NO |
| TJU_CMC_MD2.ID01601.3p-miR | TJU_CMC_MD2.ID01601.hairpin | YES | NO | NO | NO | NO | NO | NO | NO |
| TJU_CMC_MD2.ID01602.5p-miR | TJU_CMC_MD2.ID01602.hairpin | YES | YES | YES | YES | NO | NO | NO | NO |
| TJU_CMC_MD2.ID01603.3p-miR | TJU_CMC_MD2.ID01603.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01604.3p-miR | TJU_CMC_MD2.ID01604.hairpin | YES | NO | NO | NO | NO | NO | NO | NO |
| TJU_CMC_MD2.ID01605.3p-miR | TJU_CMC_MD2.ID01605.hairpin | YES | YES | YES | NO | YES | NO | NO | NO |
| TJU_CMC_MD2.ID01606.3p-miR | TJU_CMC_MD2.ID01606.hairpin | YES | NO | NO | NO | NO | NO | NO | NO |
| TJU_CMC_MD2.ID01607.3p-miR | TJU_CMC_MD2.ID01607.hairpin | YES | YES | YES | YES | YES | NO | NO | NO |
| TJU_CMC_MD2.ID01607.5p-miR | TJU_CMC_MD2.ID01607.hairpin | YES | YES | YES | YES | YES | NO | NO | NO |
| TJU_CMC_MD2.ID01608.3p-miR | TJU_CMC_MD2.ID01608.hairpin | YES | NO | NO | NO | NO | NO | NO | NO |
| TJU_CMC_MD2.ID01609.5p-miR | TJU_CMC_MD2.ID01609.hairpin | YES | YES | YES | YES | NO | NO | NO | NO |
| TJU_CMC_MD2.ID01610.5p-miR | TJU_CMC_MD2.ID01610.hairpin | YES | YES | YES | YES | YES | NO | NO | NO |
| TJU_CMC_MD2.ID01611.5p-miR | TJU_CMC_MD2.ID01611.hairpin | YES | YES | YES | YES | YES | NO | NO | NO |
| TJU_CMC_MD2.ID01612.3p-miR | TJU_CMC_MD2.ID01612.hairpin | YES | NO | NO | NO | NO | NO | NO | NO |
| TJU_CMC_MD2.ID01613.3p-miR | TJU_CMC_MD2.ID01613.hairpin | YES | NO | NO | NO | NO | NO | NO | NO |
| TJU_CMC_MD2.ID01613.5p-miR | TJU_CMC_MD2.ID01613.hairpin | YES | YES | YES | YES | YES | NO | NO | NO |
| TJU_CMC_MD2.ID01614.5p-miR | TJU_CMC_MD2.ID01614.hairpin | YES | YES | YES | NO | YES | NO | NO | NO |
| TJU_CMC_MD2.ID01615.3p-miR | TJU_CMC_MD2.ID01615.hairpin | YES | NO | NO | NO | NO | NO | NO | NO |
| TJU_CMC_MD2.ID01616.3p-miR | TJU_CMC_MD2.ID01616.hairpin | YES | NO | NO | NO | NO | NO | NO | NO |
| TJU_CMC_MD2.ID01617.3p-miR | TJU_CMC_MD2.ID01617.hairpin | YES | NO | NO | NO | NO | NO | NO | NO |
| TJU_CMC_MD2.ID01618.3p-miR | TJU_CMC_MD2.ID01618.hairpin | YES | NO | NO | NO | NO | NO | NO | NO |
| TJU_CMC_MD2.ID01619.3p-miR | TJU_CMC_MD2.ID01619.hairpin | YES | NO | NO | NO | NO | NO | NO | NO |
| TJU_CMC_MD2.ID01620.3p-miR | TJU_CMC_MD2.ID01620.hairpin | YES | NO | NO | NO | NO | NO | NO | NO |
| TJU_CMC_MD2.ID01621.3p-miR | TJU_CMC_MD2.ID01621.hairpin | YES | NO | NO | NO | NO | NO | NO | NO |
| TJU_CMC_MD2.ID01622.3p-miR | TJU_CMC_MD2.ID01622.hairpin | YES | NO | NO | NO | NO | NO | NO | NO |
| TJU_CMC_MD2.ID01623.3p-miR | TJU_CMC_MD2.ID01623.hairpin | YES | NO | NO | NO | NO | NO | NO | NO |
| TJU_CMC_MD2.ID01624.5p-miR | TJU_CMC_MD2.ID01624.hairpin | YES | NO | NO | YES | YES | NO | NO | NO |
| TJU_CMC_MD2.ID01625.3p-miR | TJU_CMC_MD2.ID01625.hairpin | YES | NO | NO | NO | NO | NO | NO | NO |
| TJU_CMC_MD2.ID01626.3p-miR | TJU_CMC_MD2.ID01626.hairpin | YES | NO | NO | NO | NO | NO | NO | NO |
| TJU_CMC_MD2.ID01627.5p-miR | TJU_CMC_MD2.ID01627.hairpin | YES | YES | YES | YES | YES | NO | NO | NO |
| TJU_CMC_MD2.ID01628.5p-miR | TJU_CMC_MD2.ID01628.hairpin | YES | YES | NO | NO | NO | NO | NO | NO |
| TJU_CMC_MD2.ID01629.5p-miR | TJU_CMC_MD2.ID01629.hairpin | YES | YES | YES | NO | NO | NO | NO | NO |
| TJU_CMC_MD2.ID01630.5p-miR | TJU_CMC_MD2.ID01630.hairpin | YES | NO | YES | NO | NO | NO | NO | NO |
| TJU_CMC_MD2.ID01631.3p-miR | TJU_CMC_MD2.ID01631.hairpin | YES | YES | NO | NO | NO | NO | NO | NO |
| TJU_CMC_MD2.ID01632.5p-miR | TJU_CMC_MD2.ID01632.hairpin | YES | YES | YES | YES | NO | NO | NO | NO |
| TJU_CMC_MD2.ID01633.3p-miR | TJU_CMC_MD2.ID01633.hairpin | YES | NO | NO | NO | NO | NO | NO | NO |
| TJU_CMC_MD2.ID01634.3p-miR | TJU_CMC_MD2.ID01634.hairpin | YES | NO | NO | NO | NO | NO | NO | NO |
| TJU_CMC_MD2.ID01635.3p-miR | TJU_CMC_MD2.ID01635.hairpin | YES | NO | NO | NO | NO | NO | NO | NO |
| TJU_CMC_MD2.ID01636.5p-miR | TJU_CMC_MD2.ID01636.hairpin | YES | YES | YES | YES | NO | NO | NO | NO |
| TJU_CMC_MD2.ID01637.3p-miR | TJU_CMC_MD2.ID01637.hairpin | YES | NO | NO | NO | NO | NO | NO | NO |
| TJU_CMC_MD2.ID01638.3p-miR | TJU_CMC_MD2.ID01638.hairpin | YES | NO | NO | NO | NO | NO | NO | NO |
| TJU_CMC_MD2.ID01639.5p-miR | TJU_CMC_MD2.ID01639.hairpin | YES | YES | NO | YES | NO | NO | NO | NO |
| TJU_CMC_MD2.ID01640.5p-miR | TJU_CMC_MD2.ID01640.hairpin | YES | YES | NO | NO | NO | NO | NO | NO |
| TJU_CMC_MD2.ID01641.3p-miR | TJU_CMC_MD2.ID01641.hairpin | YES | NO | NO | NO | NO | NO | NO | NO |
| TJU_CMC_MD2.ID01642.3p-miR | TJU_CMC_MD2.ID01642.hairpin | YES | NO | NO | NO | NO | NO | NO | NO |
| TJU_CMC_MD2.ID01642.5p-miR | TJU_CMC_MD2.ID01642.hairpin | YES | YES | YES | YES | YES | NO | NO | NO |
| TJU_CMC_MD2.ID01643.3p-miR | TJU_CMC_MD2.ID01643.hairpin | YES | NO | NO | NO | NO | NO | NO | NO |
| TJU_CMC_MD2.ID01644.3p-miR | TJU_CMC_MD2.ID01644.hairpin | YES | NO | NO | NO | NO | NO | NO | NO |
| TJU_CMC_MD2.ID01645.5p-miR | TJU_CMC_MD2.ID01645.hairpin | YES | YES | YES | YES | NO | NO | NO | NO |
| TJU_CMC_MD2.ID01646.3p-miR | TJU_CMC_MD2.ID01646.hairpin | YES | NO | YES | NO | NO | NO | NO | NO |
| TJU_CMC_MD2.ID01646.5p-miR | TJU_CMC_MD2.ID01646.hairpin | YES | NO | YES | NO | NO | NO | NO | NO |
| TJU_CMC_MD2.ID01647.5p-miR | TJU_CMC_MD2.ID01647.hairpin | YES | NO | YES | NO | NO | NO | NO | NO |
| TJU_CMC_MD2.ID01648.3p-miR | TJU_CMC_MD2.ID01648.hairpin | YES | NO | NO | NO | NO | NO | NO | NO |
| TJU_CMC_MD2.ID01648.5p-miR | TJU_CMC_MD2.ID01648.hairpin | YES | YES | NO | YES | NO | NO | NO | NO |
| TJU_CMC_MD2.ID01649.5p-miR | TJU_CMC_MD2.ID01649.hairpin | YES | YES | YES | YES | NO | NO | NO | NO |
| TJU_CMC_MD2.ID01650.3p-miR | TJU_CMC_MD2.ID01650.hairpin | YES | NO | NO | NO | NO | NO | NO | NO |
| TJU_CMC_MD2.ID01651.5p-miR | TJU_CMC_MD2.ID01651.hairpin | YES | YES | NO | NO | NO | NO | NO | NO |
| TJU_CMC_MD2.ID01652.3p-miR | TJU_CMC_MD2.ID01652.hairpin | YES | NO | NO | NO | NO | NO | NO | NO |
| TJU_CMC_MD2.ID01653.5p-miR | TJU_CMC_MD2.ID01653.hairpin | YES | NO | NO | NO | NO | NO | NO | NO |
| TJU_CMC_MD2.ID01654.3p-miR | TJU_CMC_MD2.ID01654.hairpin | YES | NO | NO | NO | NO | NO | NO | NO |
| TJU_CMC_MD2.ID01655.3p-miR | TJU_CMC_MD2.ID01655.hairpin | YES | NO | NO | NO | NO | NO | NO | NO |
| TJU_CMC_MD2.ID01656.3p-miR | TJU_CMC_MD2.ID01656.hairpin | YES | NO | NO | NO | NO | NO | NO | NO |
| TJU_CMC_MD2.ID01657.5p-miR | TJU_CMC_MD2.ID01657.hairpin | YES | YES | YES | NO | NO | NO | NO | NO |
| TJU_CMC_MD2.ID01658.3p-miR | TJU_CMC_MD2.ID01658.hairpin | YES | NO | NO | NO | NO | NO | NO | NO |
| TJU_CMC_MD2.ID01659.3p-miR | TJU_CMC_MD2.ID01659.hairpin | YES | NO | NO | NO | NO | NO | NO | NO |
| TJU_CMC_MD2.ID01660.3p-miR | TJU_CMC_MD2.ID01660.hairpin | YES | NO | NO | NO | NO | NO | NO | NO |
| TJU_CMC_MD2.ID01661.3p-miR | TJU_CMC_MD2.ID01661.hairpin | YES | NO | NO | NO | NO | NO | NO | NO |
| TJU_CMC_MD2.ID01662.3p-miR | TJU_CMC_MD2.ID01662.hairpin | YES | NO | NO | NO | NO | NO | NO | NO |
| TJU_CMC_MD2.ID01663.3p-miR | TJU_CMC_MD2.ID01663.hairpin | YES | NO | NO | NO | NO | NO | NO | NO |
| TJU_CMC_MD2.ID01664.3p-miR | TJU_CMC_MD2.ID01664.hairpin | YES | NO | NO | NO | NO | NO | NO | NO |
| TJU_CMC_MD2.ID01664.5p-miR | TJU_CMC_MD2.ID01664.hairpin | YES | YES | YES | YES | NO | NO | NO | NO |
| TJU_CMC_MD2.ID01665.3p-miR | TJU_CMC_MD2.ID01665.hairpin | YES | NO | NO | NO | NO | NO | NO | NO |
| TJU_CMC_MD2.ID01666.3p-miR | TJU_CMC_MD2.ID01666.hairpin | YES | NO | YES | YES | NO | NO | NO | NO |
| TJU_CMC_MD2.ID01666.5p-miR | TJU_CMC_MD2.ID01666.hairpin | YES | NO | YES | YES | NO | NO | NO | NO |
| TJU_CMC_MD2.ID01667.3p-miR | TJU_CMC_MD2.ID01667.hairpin | YES | NO | NO | NO | NO | NO | NO | NO |
| TJU_CMC_MD2.ID01668.5p-miR | TJU_CMC_MD2.ID01668.hairpin | YES | YES | YES | YES | NO | NO | NO | NO |
| TJU_CMC_MD2.ID01669.3p-miR | TJU_CMC_MD2.ID01669.hairpin | YES | NO | NO | NO | NO | NO | NO | NO |
| TJU_CMC_MD2.ID01670.5p-miR | TJU_CMC_MD2.ID01670.hairpin | YES | NO | NO | NO | NO | NO | NO | NO |
| TJU_CMC_MD2.ID01671.3p-miR | TJU_CMC_MD2.ID01671.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01672.5p-miR | TJU_CMC_MD2.ID01672.hairpin | YES | YES | YES | NO | NO | NO | NO | NO |
| TJU_CMC_MD2.ID01673.3p-miR | TJU_CMC_MD2.ID01673.hairpin | YES | NO | NO | NO | NO | NO | NO | NO |
| TJU_CMC_MD2.ID01674.3p-miR | TJU_CMC_MD2.ID01674.hairpin | YES | NO | NO | NO | NO | NO | NO | NO |
| TJU_CMC_MD2.ID01674.5p-miR | TJU_CMC_MD2.ID01674.hairpin | YES | YES | YES | YES | YES | NO | NO | NO |
| TJU_CMC_MD2.ID01675.5p-miR | TJU_CMC_MD2.ID01675.hairpin | YES | YES | YES | NO | NO | YES | NO | NO |
| TJU_CMC_MD2.ID01676.3p-miR | TJU_CMC_MD2.ID01676.hairpin | YES | NO | NO | NO | NO | NO | NO | NO |
| TJU_CMC_MD2.ID01677.3p-miR | TJU_CMC_MD2.ID01677.hairpin | YES | NO | NO | NO | NO | NO | NO | NO |
| TJU_CMC_MD2.ID01678.3p-miR | TJU_CMC_MD2.ID01678.hairpin | YES | YES | YES | YES | NO | NO | NO | NO |
| TJU_CMC_MD2.ID01679.5p-miR | TJU_CMC_MD2.ID01679.hairpin | YES | YES | YES | YES | NO | NO | NO | NO |
| TJU_CMC_MD2.ID01680.3p-miR | TJU_CMC_MD2.ID01680.hairpin | YES | YES | YES | NO | YES | NO | NO | NO |
| TJU_CMC_MD2.ID01680.5p-miR | TJU_CMC_MD2.ID01680.hairpin | YES | NO | NO | NO | YES | NO | NO | NO |
| TJU_CMC_MD2.ID01681.3p-miR | TJU_CMC_MD2.ID01681.hairpin | YES | NO | NO | NO | NO | NO | NO | NO |
| TJU_CMC_MD2.ID01682.3p-miR | TJU_CMC_MD2.ID01682.hairpin | YES | NO | NO | NO | NO | NO | NO | NO |
| TJU_CMC_MD2.ID01683.5p-miR | TJU_CMC_MD2.ID01683.hairpin | YES | YES | NO | NO | NO | NO | NO | NO |
| TJU_CMC_MD2.ID01684.3p-miR | TJU_CMC_MD2.ID01684.hairpin | YES | NO | NO | NO | NO | NO | NO | NO |
| TJU_CMC_MD2.ID01685.5p-miR | TJU_CMC_MD2.ID01685.hairpin | YES | YES | YES | YES | NO | NO | NO | NO |
| TJU_CMC_MD2.ID01686.5p-miR | TJU_CMC_MD2.ID01686.hairpin | YES | NO | NO | NO | NO | YES | NO | NO |
| TJU_CMC_MD2.ID01687.3p-miR | TJU_CMC_MD2.ID01687.hairpin | YES | NO | NO | NO | NO | NO | NO | NO |
| TJU_CMC_MD2.ID01688.3p-miR | TJU_CMC_MD2.ID01688.hairpin | YES | NO | NO | NO | NO | NO | NO | NO |
| TJU_CMC_MD2.ID01689.3p-miR | TJU_CMC_MD2.ID01689.hairpin | YES | NO | NO | NO | NO | NO | NO | NO |
| TJU_CMC_MD2.ID01690.3p-miR | TJU_CMC_MD2.ID01690.hairpin | YES | NO | NO | NO | NO | NO | NO | NO |
| TJU_CMC_MD2.ID01691.5p-miR | TJU_CMC_MD2.ID01691.hairpin | YES | YES | NO | YES | NO | YES | NO | NO |
| TJU_CMC_MD2.ID01692.3p-miR | TJU_CMC_MD2.ID01692.hairpin | YES | NO | NO | NO | NO | NO | NO | NO |
| TJU_CMC_MD2.ID01692.5p-miR | TJU_CMC_MD2.ID01692.hairpin | YES | YES | YES | YES | YES | NO | NO | NO |
| TJU_CMC_MD2.ID01693.5p-miR | TJU_CMC_MD2.ID01693.hairpin | YES | YES | YES | YES | YES | NO | NO | NO |
| TJU_CMC_MD2.ID01694.5p-miR | TJU_CMC_MD2.ID01694.hairpin | YES | NO | YES | NO | NO | NO | NO | NO |
| TJU_CMC_MD2.ID01695.3p-miR | TJU_CMC_MD2.ID01695.hairpin | YES | NO | NO | NO | NO | NO | NO | NO |
| TJU_CMC_MD2.ID01696.3p-miR | TJU_CMC_MD2.ID01696.hairpin | YES | NO | NO | NO | NO | NO | NO | NO |
| TJU_CMC_MD2.ID01697.5p-miR | TJU_CMC_MD2.ID01697.hairpin | YES | NO | NO | NO | NO | NO | NO | NO |
| TJU_CMC_MD2.ID01698.3p-miR | TJU_CMC_MD2.ID01698.hairpin | YES | NO | NO | NO | NO | NO | NO | NO |
| TJU_CMC_MD2.ID01699.5p-miR | TJU_CMC_MD2.ID01699.hairpin | YES | YES | YES | YES | YES | NO | NO | NO |
| TJU_CMC_MD2.ID01700.3p-miR | TJU_CMC_MD2.ID01700.hairpin | YES | NO | NO | NO | NO | NO | NO | NO |
| TJU_CMC_MD2.ID01701.3p-miR | TJU_CMC_MD2.ID01701.hairpin | YES | NO | NO | NO | NO | NO | NO | NO |
| TJU_CMC_MD2.ID01702.3p-miR | TJU_CMC_MD2.ID01702.hairpin | YES | NO | NO | NO | NO | NO | NO | NO |
| TJU_CMC_MD2.ID01703.3p-miR | TJU_CMC_MD2.ID01703.hairpin | YES | NO | NO | NO | NO | NO | NO | NO |
| TJU_CMC_MD2.ID01704.5p-miR | TJU_CMC_MD2.ID01704.hairpin | YES | NO | NO | NO | NO | NO | NO | NO |
| TJU_CMC_MD2.ID01705.3p-miR | TJU_CMC_MD2.ID01705.hairpin | YES | NO | NO | NO | NO | NO | NO | NO |
| TJU_CMC_MD2.ID01706.3p-miR | TJU_CMC_MD2.ID01706.hairpin | YES | NO | NO | NO | NO | NO | NO | NO |
| TJU_CMC_MD2.ID01707.5p-miR | TJU_CMC_MD2.ID01707.hairpin | YES | YES | YES | YES | NO | NO | NO | NO |
| TJU_CMC_MD2.ID01708.5p-miR | TJU_CMC_MD2.ID01708.hairpin | YES | YES | YES | NO | NO | NO | NO | NO |
| TJU_CMC_MD2.ID01709.3p-miR | TJU_CMC_MD2.ID01709.hairpin | YES | NO | NO | NO | NO | NO | NO | NO |
| TJU_CMC_MD2.ID01710.3p-miR | TJU_CMC_MD2.ID01710.hairpin | YES | NO | NO | NO | NO | NO | NO | NO |
| TJU_CMC_MD2.ID01711.3p-miR | TJU_CMC_MD2.ID01711.hairpin | YES | NO | NO | NO | NO | NO | NO | NO |
| TJU_CMC_MD2.ID01712.5p-miR | TJU_CMC_MD2.ID01712.hairpin | YES | YES | NO | YES | NO | NO | NO | NO |
| TJU_CMC_MD2.ID01713.5p-miR | TJU_CMC_MD2.ID01713.hairpin | YES | YES | YES | YES | NO | NO | NO | NO |
| TJU_CMC_MD2.ID01714.3p-miR | TJU_CMC_MD2.ID01714.hairpin | YES | NO | NO | NO | NO | NO | NO | NO |
| TJU_CMC_MD2.ID01715.3p-miR | TJU_CMC_MD2.ID01715.hairpin | YES | YES | YES | NO | NO | NO | NO | NO |
| TJU_CMC_MD2.ID01716.3p-miR | TJU_CMC_MD2.ID01716.hairpin | YES | NO | NO | NO | NO | NO | NO | NO |
| TJU_CMC_MD2.ID01717.3p-miR | TJU_CMC_MD2.ID01717.hairpin | YES | NO | NO | NO | NO | NO | NO | NO |
| TJU_CMC_MD2.ID01718.3p-miR | TJU_CMC_MD2.ID01718.hairpin | YES | NO | NO | NO | NO | NO | NO | NO |
| TJU_CMC_MD2.ID01719.3p-miR | TJU_CMC_MD2.ID01719.hairpin | YES | NO | NO | NO | NO | NO | NO | NO |
| TJU_CMC_MD2.ID01720.5p-miR | TJU_CMC_MD2.ID01720.hairpin | YES | NO | NO | NO | NO | NO | NO | NO |
| TJU_CMC_MD2.ID01721.3p-miR | TJU_CMC_MD2.ID01721.hairpin | YES | NO | NO | NO | NO | NO | NO | NO |
| TJU_CMC_MD2.ID01722.3p-miR | TJU_CMC_MD2.ID01722.hairpin | YES | NO | NO | NO | NO | NO | NO | NO |
| TJU_CMC_MD2.ID01723.5p-miR | TJU_CMC_MD2.ID01723.hairpin | YES | NO | YES | YES | NO | NO | NO | NO |
| TJU_CMC_MD2.ID01724.3p-miR | TJU_CMC_MD2.ID01724.hairpin | YES | NO | NO | NO | NO | NO | NO | NO |
| TJU_CMC_MD2.ID01725.3p-miR | TJU_CMC_MD2.ID01725.hairpin | YES | NO | NO | NO | NO | NO | NO | NO |
| TJU_CMC_MD2.ID01726.3p-miR | TJU_CMC_MD2.ID01726.hairpin | YES | NO | NO | NO | NO | NO | NO | NO |
| TJU_CMC_MD2.ID01727.5p-miR | TJU_CMC_MD2.ID01727.hairpin | YES | NO | NO | YES | NO | NO | NO | NO |
| TJU_CMC_MD2.ID01728.3p-miR | TJU_CMC_MD2.ID01728.hairpin | YES | NO | NO | NO | NO | NO | NO | NO |
| TJU_CMC_MD2.ID01729.3p-miR | TJU_CMC_MD2.ID01729.hairpin | YES | NO | NO | NO | NO | NO | NO | NO |
| TJU_CMC_MD2.ID01730.3p-miR | TJU_CMC_MD2.ID01730.hairpin | YES | NO | NO | NO | NO | NO | NO | NO |
| TJU_CMC_MD2.ID01731.5p-miR | TJU_CMC_MD2.ID01731.hairpin | YES | YES | YES | YES | NO | NO | NO | NO |
| TJU_CMC_MD2.ID01732.3p-miR | TJU_CMC_MD2.ID01732.hairpin | YES | NO | NO | NO | NO | NO | NO | NO |
| TJU_CMC_MD2.ID01733.3p-miR | TJU_CMC_MD2.ID01733.hairpin | YES | NO | NO | NO | NO | NO | NO | NO |
| TJU_CMC_MD2.ID01734.5p-miR | TJU_CMC_MD2.ID01734.hairpin | YES | YES | YES | YES | NO | NO | NO | NO |
| TJU_CMC_MD2.ID01735.3p-miR | TJU_CMC_MD2.ID01735.hairpin | YES | NO | NO | NO | NO | NO | NO | NO |
| TJU_CMC_MD2.ID01736.3p-miR | TJU_CMC_MD2.ID01736.hairpin | YES | NO | NO | NO | NO | NO | NO | NO |
| TJU_CMC_MD2.ID01737.3p-miR | TJU_CMC_MD2.ID01737.hairpin | YES | NO | NO | NO | NO | NO | NO | NO |
| TJU_CMC_MD2.ID01738.5p-miR | TJU_CMC_MD2.ID01738.hairpin | YES | YES | NO | YES | NO | NO | NO | NO |
| TJU_CMC_MD2.ID01739.3p-miR | TJU_CMC_MD2.ID01739.hairpin | YES | NO | NO | NO | NO | NO | NO | NO |
| TJU_CMC_MD2.ID01740.5p-miR | TJU_CMC_MD2.ID01740.hairpin | YES | NO | NO | NO | NO | NO | NO | NO |
| TJU_CMC_MD2.ID01741.5p-miR | TJU_CMC_MD2.ID01741.hairpin | YES | NO | NO | NO | NO | NO | NO | NO |
| TJU_CMC_MD2.ID01742.3p-miR | TJU_CMC_MD2.ID01742.hairpin | YES | NO | NO | NO | NO | NO | NO | NO |
| TJU_CMC_MD2.ID01743.5p-miR | TJU_CMC_MD2.ID01743.hairpin | YES | YES | YES | YES | YES | NO | NO | NO |

TABLE 7-continued

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01744.3p-miR | TJU_CMC_MD2.ID01744.hairpin | YES | NO | NO | NO | NO | NO | NO | NO |
| TJU_CMC_MD2.ID01745.3p-miR | TJU_CMC_MD2.ID01745.hairpin | YES | NO | NO | NO | NO | NO | NO | NO |
| TJU_CMC_MD2.ID01746.3p-miR | TJU_CMC_MD2.ID01746.hairpin | YES | NO | NO | NO | NO | NO | NO | NO |
| TJU_CMC_MD2.ID01747.5p-miR | TJU_CMC_MD2.ID01747.hairpin | YES | NO | NO | YES | NO | NO | NO | NO |
| TJU_CMC_MD2.ID01748.3p-miR | TJU_CMC_MD2.ID01748.hairpin | YES | NO | NO | NO | NO | NO | NO | NO |
| TJU_CMC_MD2.ID01749.3p-miR | TJU_CMC_MD2.ID01749.hairpin | YES | NO | NO | NO | NO | NO | NO | NO |
| TJU_CMC_MD2.ID01750.5p-miR | TJU_CMC_MD2.ID01750.hairpin | YES | NO | NO | YES | NO | NO | NO | NO |
| TJU_CMC_MD2.ID01751.5p-miR | TJU_CMC_MD2.ID01751.hairpin | YES | YES | YES | NO | NO | NO | NO | NO |
| TJU_CMC_MD2.ID01752.5p-miR | TJU_CMC_MD2.ID01752.hairpin | YES | NO | YES | NO | NO | NO | NO | NO |
| TJU_CMC_MD2.ID01753.3p-miR | TJU_CMC_MD2.ID01753.hairpin | YES | NO | NO | NO | NO | NO | NO | NO |
| TJU_CMC_MD2.ID01754.3p-miR | TJU_CMC_MD2.ID01754.hairpin | YES | NO | NO | NO | NO | NO | NO | NO |
| TJU_CMC_MD2.ID01755.3p-miR | TJU_CMC_MD2.ID01755.hairpin | YES | NO | NO | NO | NO | NO | NO | NO |
| TJU_CMC_MD2.ID01756.5p-miR | TJU_CMC_MD2.ID01756.hairpin | YES | NO | NO | NO | NO | NO | NO | NO |
| TJU_CMC_MD2.ID01757.3p-miR | TJU_CMC_MD2.ID01757.hairpin | YES | NO | NO | NO | NO | NO | NO | NO |
| TJU_CMC_MD2.ID01758.3p-miR | TJU_CMC_MD2.ID01758.hairpin | YES | NO | NO | NO | NO | NO | NO | NO |
| TJU_CMC_MD2.ID01759.3p-miR | TJU_CMC_MD2.ID01759.hairpin | YES | NO | NO | NO | NO | NO | NO | NO |
| TJU_CMC_MD2.ID01760.3p-miR | TJU_CMC_MD2.ID01760.hairpin | YES | NO | NO | NO | NO | NO | NO | NO |
| TJU_CMC_MD2.ID01761.3p-miR | TJU_CMC_MD2.ID01761.hairpin | YES | YES | YES | YES | NO | NO | NO | NO |
| TJU_CMC_MD2.ID01762.5p-miR | TJU_CMC_MD2.ID01762.hairpin | YES | YES | NO | NO | YES | NO | NO | NO |
| TJU_CMC_MD2.ID01763.5p-miR | TJU_CMC_MD2.ID01763.hairpin | YES | NO | NO | NO | NO | NO | NO | NO |
| TJU_CMC_MD2.ID01764.5p-miR | TJU_CMC_MD2.ID01764.hairpin | YES | YES | YES | NO | YES | NO | NO | NO |
| TJU_CMC_MD2.ID01765.3p-miR | TJU_CMC_MD2.ID01765.hairpin | YES | NO | NO | NO | NO | NO | NO | NO |
| TJU_CMC_MD2.ID01766.5p-miR | TJU_CMC_MD2.ID01766.hairpin | YES | YES | NO | NO | NO | NO | NO | NO |
| TJU_CMC_MD2.ID01767.5p-miR | TJU_CMC_MD2.ID01767.hairpin | YES | NO | YES | YES | NO | NO | NO | NO |
| TJU_CMC_MD2.ID01768.3p-miR | TJU_CMC_MD2.ID01768.hairpin | YES | NO | NO | NO | NO | NO | NO | NO |
| TJU_CMC_MD2.ID01769.5p-miR | TJU_CMC_MD2.ID01769.hairpin | YES | YES | YES | YES | NO | YES | NO | NO |
| TJU_CMC_MD2.ID01770.3p-miR | TJU_CMC_MD2.ID01770.hairpin | YES | YES | YES | NO | NO | NO | NO | NO |
| TJU_CMC_MD2.ID01771.5p-miR | TJU_CMC_MD2.ID01771.hairpin | YES | YES | NO | YES | NO | NO | NO | NO |
| TJU_CMC_MD2.ID01772.3p-miR | TJU_CMC_MD2.ID01772.hairpin | YES | NO | NO | NO | NO | NO | NO | NO |
| TJU_CMC_MD2.ID01772.5p-miR | TJU_CMC_MD2.ID01772.hairpin | YES | YES | YES | YES | NO | NO | NO | NO |
| TJU_CMC_MD2.ID01773.3p-miR | TJU_CMC_MD2.ID01773.hairpin | YES | NO | NO | NO | NO | NO | NO | NO |
| TJU_CMC_MD2.ID01774.5p-miR | TJU_CMC_MD2.ID01774.hairpin | YES | YES | YES | NO | NO | NO | NO | NO |
| TJU_CMC_MD2.ID01775.3p-miR | TJU_CMC_MD2.ID01775.hairpin | YES | NO | NO | NO | NO | NO | NO | NO |
| TJU_CMC_MD2.ID01776.3p-miR | TJU_CMC_MD2.ID01776.hairpin | YES | NO | NO | NO | NO | NO | NO | NO |
| TJU_CMC_MD2.ID01777.3p-miR | TJU_CMC_MD2.ID01777.hairpin | YES | NO | NO | NO | NO | NO | NO | NO |
| TJU_CMC_MD2.ID01778.3p-miR | TJU_CMC_MD2.ID01778.hairpin | YES | NO | NO | NO | NO | NO | NO | NO |
| TJU_CMC_MD2.ID01779.3p-miR | TJU_CMC_MD2.ID01779.hairpin | YES | NO | NO | NO | NO | NO | NO | NO |
| TJU_CMC_MD2.ID01780.5p-miR | TJU_CMC_MD2.ID01780.hairpin | YES | NO | YES | NO | NO | NO | NO | NO |
| TJU_CMC_MD2.ID01781.5p-miR | TJU_CMC_MD2.ID01781.hairpin | YES | YES | YES | YES | NO | NO | NO | NO |
| TJU_CMC_MD2.ID01782.3p-miR | TJU_CMC_MD2.ID01782.hairpin | YES | NO | NO | NO | NO | NO | NO | NO |
| TJU_CMC_MD2.ID01783.3p-miR | TJU_CMC_MD2.ID01783.hairpin | YES | NO | NO | NO | NO | NO | NO | NO |
| TJU_CMC_MD2.ID01784.5p-miR | TJU_CMC_MD2.ID01784.hairpin | YES | YES | YES | YES | NO | NO | NO | NO |
| TJU_CMC_MD2.ID01785.3p-miR | TJU_CMC_MD2.ID01785.hairpin | YES | NO | NO | NO | NO | NO | NO | NO |
| TJU_CMC_MD2.ID01786.5p-miR | TJU_CMC_MD2.ID01786.hairpin | YES | YES | YES | NO | NO | NO | NO | NO |
| TJU_CMC_MD2.ID01787.3p-miR | TJU_CMC_MD2.ID01787.hairpin | YES | NO | NO | NO | NO | NO | NO | NO |
| TJU_CMC_MD2.ID01788.3p-miR | TJU_CMC_MD2.ID01788.hairpin | YES | NO | NO | NO | NO | NO | NO | NO |
| TJU_CMC_MD2.ID01789.3p-miR | TJU_CMC_MD2.ID01789.hairpin | YES | NO | NO | NO | NO | NO | NO | NO |
| TJU_CMC_MD2.ID01790.5p-miR | TJU_CMC_MD2.ID01790.hairpin | YES | YES | YES | YES | YES | NO | NO | NO |
| TJU_CMC_MD2.ID01791.3p-miR | TJU_CMC_MD2.ID01791.hairpin | YES | NO | NO | NO | NO | NO | NO | NO |
| TJU_CMC_MD2.ID01792.5p-miR | TJU_CMC_MD2.ID01792.hairpin | YES | YES | YES | YES | YES | NO | NO | NO |
| TJU_CMC_MD2.ID01793.3p-miR | TJU_CMC_MD2.ID01793.hairpin | YES | YES | YES | NO | YES | NO | NO | NO |
| TJU_CMC_MD2.ID01793.5p-miR | TJU_CMC_MD2.ID01793.hairpin | YES | YES | YES | YES | YES | NO | NO | NO |
| TJU_CMC_MD2.ID01794.5p-miR | TJU_CMC_MD2.ID01794.hairpin | YES | YES | YES | YES | NO | NO | NO | NO |
| TJU_CMC_MD2.ID01795.5p-miR | TJU_CMC_MD2.ID01795.hairpin | YES | YES | NO | NO | YES | NO | NO | NO |
| TJU_CMC_MD2.ID01796.3p-miR | TJU_CMC_MD2.ID01796.hairpin | YES | NO | NO | NO | NO | NO | NO | NO |
| TJU_CMC_MD2.ID01797.3p-miR | TJU_CMC_MD2.ID01797.hairpin | YES | NO | NO | NO | NO | NO | NO | NO |
| TJU_CMC_MD2.ID01798.3p-miR | TJU_CMC_MD2.ID01798.hairpin | YES | NO | NO | NO | NO | NO | NO | NO |
| TJU_CMC_MD2.ID01799.5p-miR | TJU_CMC_MD2.ID01799.hairpin | YES | YES | NO | NO | NO | NO | NO | NO |
| TJU_CMC_MD2.ID01800.5p-miR | TJU_CMC_MD2.ID01800.hairpin | YES | NO | NO | NO | NO | NO | NO | NO |
| TJU_CMC_MD2.ID01801.3p-miR | TJU_CMC_MD2.ID01801.hairpin | YES | NO | NO | NO | NO | NO | NO | NO |
| TJU_CMC_MD2.ID01801.5p-miR | TJU_CMC_MD2.ID01801.hairpin | YES | YES | NO | NO | YES | NO | NO | NO |
| TJU_CMC_MD2.ID01802.5p-miR | TJU_CMC_MD2.ID01802.hairpin | YES | NO | YES | YES | YES | NO | NO | NO |
| TJU_CMC_MD2.ID01803.5p-miR | TJU_CMC_MD2.ID01803.hairpin | YES | YES | YES | YES | YES | NO | NO | NO |
| TJU_CMC_MD2.ID01804.3p-miR | TJU_CMC_MD2.ID01804.hairpin | YES | NO | NO | NO | NO | NO | NO | NO |
| TJU_CMC_MD2.ID01805.3p-miR | TJU_CMC_MD2.ID01805.hairpin | YES | NO | NO | NO | NO | NO | NO | NO |
| TJU_CMC_MD2.ID01805.5p-miR | TJU_CMC_MD2.ID01805.hairpin | YES | NO | YES | YES | NO | NO | NO | NO |
| TJU_CMC_MD2.ID01806.3p-miR | TJU_CMC_MD2.ID01806.hairpin | YES | NO | NO | NO | NO | NO | NO | NO |
| TJU_CMC_MD2.ID01807.3p-miR | TJU_CMC_MD2.ID01807.hairpin | YES | NO | NO | NO | NO | NO | NO | NO |
| TJU_CMC_MD2.ID01808.5p-miR | TJU_CMC_MD2.ID01808.hairpin | YES | YES | YES | YES | YES | NO | NO | NO |
| TJU_CMC_MD2.ID01809.3p-miR | TJU_CMC_MD2.ID01809.hairpin | YES | NO | NO | NO | NO | NO | NO | NO |
| TJU_CMC_MD2.ID01810.3p-miR | TJU_CMC_MD2.ID01810.hairpin | YES | NO | NO | NO | NO | NO | NO | NO |
| TJU_CMC_MD2.ID01811.5p-miR | TJU_CMC_MD2.ID01811.hairpin | YES | YES | YES | NO | NO | NO | NO | NO |
| TJU_CMC_MD2.ID01812.5p-miR | TJU_CMC_MD2.ID01812.hairpin | YES | YES | YES | NO | YES | NO | NO | NO |
| TJU_CMC_MD2.ID01813.3p-miR | TJU_CMC_MD2.ID01813.hairpin | YES | NO | NO | NO | NO | NO | NO | NO |
| TJU_CMC_MD2.ID01813.5p-miR | TJU_CMC_MD2.ID01813.hairpin | YES | NO | YES | YES | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01814.3p-miR | TJU_CMC_MD2.ID01814.hairpin | YES | NO | NO | NO | NO | NO | NO | NO |
| TJU_CMC_MD2.ID01815.5p-miR | TJU_CMC_MD2.ID01815.hairpin | YES | YES | YES | NO | NO | NO | NO | NO |
| TJU_CMC_MD2.ID01816.3p-miR | TJU_CMC_MD2.ID01816.hairpin | YES | NO | NO | NO | NO | NO | NO | NO |
| TJU_CMC_MD2.ID01817.3p-miR | TJU_CMC_MD2.ID01817.hairpin | YES | NO | NO | NO | NO | NO | NO | NO |
| TJU_CMC_MD2.ID01818.3p-miR | TJU_CMC_MD2.ID01818.hairpin | YES | NO | NO | NO | NO | NO | NO | NO |
| TJU_CMC_MD2.ID01819.5p-miR | TJU_CMC_MD2.ID01819.hairpin | YES | YES | YES | YES | NO | NO | NO | NO |
| TJU_CMC_MD2.ID01820.3p-miR | TJU_CMC_MD2.ID01820.hairpin | YES | NO | NO | NO | NO | NO | NO | NO |
| TJU_CMC_MD2.ID01821.3p-miR | TJU_CMC_MD2.ID01821.hairpin | YES | NO | NO | NO | NO | NO | NO | NO |
| TJU_CMC_MD2.ID01822.3p-miR | TJU_CMC_MD2.ID01822.hairpin | YES | NO | NO | NO | NO | NO | NO | NO |
| TJU_CMC_MD2.ID01822.5p-miR | TJU_CMC_MD2.ID01822.hairpin | YES | YES | NO | YES | YES | NO | NO | NO |
| TJU_CMC_MD2.ID01823.5p-miR | TJU_CMC_MD2.ID01823.hairpin | YES | NO | YES | YES | NO | NO | NO | NO |
| TJU_CMC_MD2.ID01824.3p-miR | TJU_CMC_MD2.ID01824.hairpin | YES | NO | NO | NO | NO | NO | NO | NO |
| TJU_CMC_MD2.ID01825.3p-miR | TJU_CMC_MD2.ID01825.hairpin | YES | NO | NO | NO | NO | NO | NO | NO |
| TJU_CMC_MD2.ID01826.3p-miR | TJU_CMC_MD2.ID01826.hairpin | YES | NO | NO | NO | NO | NO | NO | NO |
| TJU_CMC_MD2.ID01826.5p-miR | TJU_CMC_MD2.ID01826.hairpin | YES | NO | NO | NO | NO | NO | NO | NO |
| TJU_CMC_MD2.ID01827.3p-miR | TJU_CMC_MD2.ID01827.hairpin | YES | NO | NO | NO | NO | NO | NO | NO |
| TJU_CMC_MD2.ID01828.3p-miR | TJU_CMC_MD2.ID01828.hairpin | YES | YES | YES | YES | YES | NO | NO | NO |
| TJU_CMC_MD2.ID01829.5p-miR | TJU_CMC_MD2.ID01829.hairpin | YES | YES | YES | YES | YES | NO | NO | NO |
| TJU_CMC_MD2.ID01830.5p-miR | TJU_CMC_MD2.ID01830.hairpin | YES | YES | YES | YES | YES | NO | NO | NO |
| TJU_CMC_MD2.ID01831.3p-miR | TJU_CMC_MD2.ID01831.hairpin | YES | NO | NO | NO | NO | NO | NO | NO |
| TJU_CMC_MD2.ID01832.5p-miR | TJU_CMC_MD2.ID01832.hairpin | YES | YES | YES | NO | NO | NO | NO | NO |
| TJU_CMC_MD2.ID01833.3p-miR | TJU_CMC_MD2.ID01833.hairpin | YES | YES | YES | YES | YES | YES | NO | NO |
| TJU_CMC_MD2.ID01834.5p-miR | TJU_CMC_MD2.ID01834.hairpin | YES | YES | YES | YES | NO | NO | NO | NO |
| TJU_CMC_MD2.ID01835.3p-miR | TJU_CMC_MD2.ID01835.hairpin | YES | NO | NO | NO | NO | NO | NO | NO |
| TJU_CMC_MD2.ID01836.5p-miR | TJU_CMC_MD2.ID01836.hairpin | YES | YES | NO | NO | YES | NO | NO | NO |
| TJU_CMC_MD2.ID01837.3p-miR | TJU_CMC_MD2.ID01837.hairpin | YES | NO | NO | NO | NO | NO | NO | NO |
| TJU_CMC_MD2.ID01838.5p-miR | TJU_CMC_MD2.ID01838.hairpin | YES | YES | YES | NO | NO | NO | NO | NO |
| TJU_CMC_MD2.ID01839.3p-miR | TJU_CMC_MD2.ID01839.hairpin | YES | NO | NO | NO | NO | NO | NO | NO |
| TJU_CMC_MD2.ID01840.5p-miR | TJU_CMC_MD2.ID01840.hairpin | YES | YES | YES | YES | NO | NO | NO | NO |
| TJU_CMC_MD2.ID01841.3p-miR | TJU_CMC_MD2.ID01841.hairpin | YES | NO | NO | NO | NO | NO | NO | NO |
| TJU_CMC_MD2.ID01842.3p-miR | TJU_CMC_MD2.ID01842.hairpin | YES | NO | NO | NO | NO | NO | NO | NO |
| TJU_CMC_MD2.ID01842.5p-miR | TJU_CMC_MD2.ID01842.hairpin | YES | YES | YES | YES | NO | NO | NO | NO |
| TJU_CMC_MD2.ID01843.3p-miR | TJU_CMC_MD2.ID01843.hairpin | YES | NO | NO | NO | NO | NO | NO | NO |
| TJU_CMC_MD2.ID01844.5p-miR | TJU_CMC_MD2.ID01844.hairpin | YES | YES | YES | NO | NO | NO | NO | NO |
| TJU_CMC_MD2.ID01845.5p-miR | TJU_CMC_MD2.ID01845.hairpin | YES | YES | YES | YES | NO | NO | NO | NO |
| TJU_CMC_MD2.ID01846.5p-miR | TJU_CMC_MD2.ID01846.hairpin | YES | NO | NO | YES | NO | NO | NO | NO |
| TJU_CMC_MD2.ID01847.5p-miR | TJU_CMC_MD2.ID01847.hairpin | YES | YES | YES | YES | NO | YES | NO | NO |
| TJU_CMC_MD2.ID01848.5p-miR | TJU_CMC_MD2.ID01848.hairpin | YES | YES | YES | YES | YES | NO | NO | NO |
| TJU_CMC_MD2.ID01849.5p-miR | TJU_CMC_MD2.ID01849.hairpin | YES | YES | YES | NO | YES | NO | NO | NO |
| TJU_CMC_MD2.ID01850.5p-miR | TJU_CMC_MD2.ID01850.hairpin | YES | YES | YES | NO | NO | NO | NO | NO |
| TJU_CMC_MD2.ID01851.5p-miR | TJU_CMC_MD2.ID01851.hairpin | YES | YES | YES | YES | YES | NO | NO | NO |
| TJU_CMC_MD2.ID01852.3p-miR | TJU_CMC_MD2.ID01852.hairpin | YES | NO | NO | NO | NO | NO | NO | NO |
| TJU_CMC_MD2.ID01853.3p-miR | TJU_CMC_MD2.ID01853.hairpin | YES | NO | NO | NO | NO | NO | NO | NO |
| TJU_CMC_MD2.ID01854.5p-miR | TJU_CMC_MD2.ID01854.hairpin | YES | YES | YES | YES | NO | NO | NO | NO |
| TJU_CMC_MD2.ID01855.3p-miR | TJU_CMC_MD2.ID01855.hairpin | YES | NO | NO | NO | NO | NO | NO | NO |
| TJU_CMC_MD2.ID01856.3p-miR | TJU_CMC_MD2.ID01856.hairpin | YES | NO | NO | NO | NO | NO | NO | NO |
| TJU_CMC_MD2.ID01857.3p-miR | TJU_CMC_MD2.ID01857.hairpin | YES | NO | NO | NO | NO | NO | NO | NO |
| TJU_CMC_MD2.ID01858.3p-miR | TJU_CMC_MD2.ID01858.hairpin | YES | NO | NO | NO | NO | NO | NO | NO |
| TJU_CMC_MD2.ID01859.5p-miR | TJU_CMC_MD2.ID01859.hairpin | YES | YES | NO | YES | YES | NO | NO | NO |
| TJU_CMC_MD2.ID01860.3p-miR | TJU_CMC_MD2.ID01860.hairpin | YES | NO | NO | NO | NO | NO | NO | NO |
| TJU_CMC_MD2.ID01860.5p-miR | TJU_CMC_MD2.ID01860.hairpin | YES | YES | YES | YES | NO | NO | NO | NO |
| TJU_CMC_MD2.ID01861.3p-miR | TJU_CMC_MD2.ID01861.hairpin | YES | NO | NO | NO | NO | NO | NO | NO |
| TJU_CMC_MD2.ID01862.5p-miR | TJU_CMC_MD2.ID01862.hairpin | YES | NO | NO | NO | NO | NO | NO | NO |
| TJU_CMC_MD2.ID01863.5p-miR | TJU_CMC_MD2.ID01863.hairpin | YES | YES | YES | YES | NO | NO | NO | NO |
| TJU_CMC_MD2.ID01864.5p-miR | TJU_CMC_MD2.ID01864.hairpin | YES | YES | YES | NO | NO | NO | NO | NO |
| TJU_CMC_MD2.ID01865.3p-miR | TJU_CMC_MD2.ID01865.hairpin | YES | NO | NO | NO | NO | NO | NO | NO |
| TJU_CMC_MD2.ID01866.5p-miR | TJU_CMC_MD2.ID01866.hairpin | YES | YES | NO | NO | NO | NO | NO | NO |
| TJU_CMC_MD2.ID01867.3p-miR | TJU_CMC_MD2.ID01867.hairpin | YES | NO | NO | NO | NO | NO | NO | NO |
| TJU_CMC_MD2.ID01868.3p-miR | TJU_CMC_MD2.ID01868.hairpin | YES | NO | NO | NO | NO | NO | NO | NO |
| TJU_CMC_MD2.ID01869.3p-miR | TJU_CMC_MD2.ID01869.hairpin | YES | NO | NO | NO | NO | NO | NO | NO |
| TJU_CMC_MD2.ID01870.5p-miR | TJU_CMC_MD2.ID01870.hairpin | YES | NO | NO | NO | NO | NO | NO | NO |
| TJU_CMC_MD2.ID01871.3p-miR | TJU_CMC_MD2.ID01871.hairpin | YES | NO | NO | NO | NO | NO | NO | NO |
| TJU_CMC_MD2.ID01872.3p-miR | TJU_CMC_MD2.ID01872.hairpin | YES | NO | NO | NO | NO | NO | NO | NO |
| TJU_CMC_MD2.ID01873.3p-miR | TJU_CMC_MD2.ID01873.hairpin | YES | NO | NO | NO | NO | NO | NO | NO |
| TJU_CMC_MD2.ID01874.3p-miR | TJU_CMC_MD2.ID01874.hairpin | YES | NO | NO | NO | NO | NO | NO | NO |
| TJU_CMC_MD2.ID01875.3p-miR | TJU_CMC_MD2.ID01875.hairpin | YES | YES | YES | YES | NO | NO | NO | NO |
| TJU_CMC_MD2.ID01876.3p-miR | TJU_CMC_MD2.ID01876.hairpin | YES | NO | NO | NO | NO | NO | NO | NO |
| TJU_CMC_MD2.ID01877.3p-miR | TJU_CMC_MD2.ID01877.hairpin | YES | NO | NO | NO | NO | NO | NO | NO |
| TJU_CMC_MD2.ID01878.5p-miR | TJU_CMC_MD2.ID01878.hairpin | YES | YES | YES | YES | YES | NO | NO | NO |
| TJU_CMC_MD2.ID01879.5p-miR | TJU_CMC_MD2.ID01879.hairpin | YES | NO | NO | NO | NO | NO | NO | NO |
| TJU_CMC_MD2.ID01880.5p-miR | TJU_CMC_MD2.ID01880.hairpin | YES | NO | YES | YES | YES | NO | NO | NO |
| TJU_CMC_MD2.ID01881.5p-miR | TJU_CMC_MD2.ID01881.hairpin | YES | YES | YES | YES | NO | NO | NO | NO |
| TJU_CMC_MD2.ID01882.5p-miR | TJU_CMC_MD2.ID01882.hairpin | YES | NO | NO | NO | NO | NO | NO | NO |
| TJU_CMC_MD2.ID01883.5p-miR | TJU_CMC_MD2.ID01883.hairpin | YES | YES | NO | NO | NO | NO | NO | NO |
| TJU_CMC_MD2.ID01884.5p-miR | TJU_CMC_MD2.ID01884.hairpin | YES | YES | YES | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01885.5p-miR | TJU_CMC_MD2.ID01885.hairpin | YES | NO | NO | NO | NO | NO | NO | NO |
| TJU_CMC_MD2.ID01886.3p-miR | TJU_CMC_MD2.ID01886.hairpin | YES | NO | NO | NO | NO | NO | NO | NO |
| TJU_CMC_MD2.ID01887.5p-miR | TJU_CMC_MD2.ID01887.hairpin | YES | YES | YES | YES | YES | NO | NO | NO |
| TJU_CMC_MD2.ID01888.3p-miR | TJU_CMC_MD2.ID01888.hairpin | YES | NO | NO | NO | NO | NO | NO | NO |
| TJU_CMC_MD2.ID01889.3p-miR | TJU_CMC_MD2.ID01889.hairpin | YES | NO | NO | NO | NO | NO | NO | NO |
| TJU_CMC_MD2.ID01890.5p-miR | TJU_CMC_MD2.ID01890.hairpin | YES | NO | NO | NO | NO | NO | NO | NO |
| TJU_CMC_MD2.ID01891.3p-miR | TJU_CMC_MD2.ID01891.hairpin | YES | NO | NO | NO | NO | NO | NO | NO |
| TJU_CMC_MD2.ID01892.3p-miR | TJU_CMC_MD2.ID01892.hairpin | YES | NO | NO | NO | NO | NO | NO | NO |
| TJU_CMC_MD2.ID01893.3p-miR | TJU_CMC_MD2.ID01893.hairpin | YES | YES | YES | YES | NO | NO | NO | NO |
| TJU_CMC_MD2.ID01893.5p-miR | TJU_CMC_MD2.ID01893.hairpin | YES | YES | YES | NO | NO | NO | NO | NO |
| TJU_CMC_MD2.ID01894.3p-miR | TJU_CMC_MD2.ID01894.hairpin | YES | NO | NO | NO | NO | NO | NO | NO |
| TJU_CMC_MD2.ID01895.5p-miR | TJU_CMC_MD2.ID01895.hairpin | YES | NO | NO | NO | NO | NO | NO | NO |
| TJU_CMC_MD2.ID01896.3p-miR | TJU_CMC_MD2.ID01896.hairpin | YES | NO | NO | NO | NO | NO | NO | NO |
| TJU_CMC_MD2.ID01897.3p-miR | TJU_CMC_MD2.ID01897.hairpin | YES | NO | NO | NO | NO | NO | NO | NO |
| TJU_CMC_MD2.ID01898.3p-miR | TJU_CMC_MD2.ID01898.hairpin | YES | NO | NO | NO | NO | NO | NO | NO |
| TJU_CMC_MD2.ID01899.5p-miR | TJU_CMC_MD2.ID01899.hairpin | YES | NO | NO | NO | NO | NO | NO | NO |
| TJU_CMC_MD2.ID01900.5p-miR | TJU_CMC_MD2.ID01900.hairpin | YES | YES | YES | YES | NO | NO | NO | NO |
| TJU_CMC_MD2.ID01901.5p-miR | TJU_CMC_MD2.ID01901.hairpin | YES | NO | YES | NO | NO | NO | NO | NO |
| TJU_CMC_MD2.ID01902.5p-miR | TJU_CMC_MD2.ID01902.hairpin | YES | NO | YES | YES | YES | NO | NO | NO |
| TJU_CMC_MD2.ID01903.3p-miR | TJU_CMC_MD2.ID01903.hairpin | YES | NO | NO | NO | NO | NO | NO | NO |
| TJU_CMC_MD2.ID01904.3p-miR | TJU_CMC_MD2.ID01904.hairpin | YES | NO | NO | NO | NO | NO | NO | NO |
| TJU_CMC_MD2.ID01905.5p-miR | TJU_CMC_MD2.ID01905.hairpin | YES | YES | YES | NO | NO | NO | NO | NO |
| TJU_CMC_MD2.ID01906.3p-miR | TJU_CMC_MD2.ID01906.hairpin | YES | NO | NO | NO | NO | NO | NO | NO |
| TJU_CMC_MD2.ID01907.5p-miR | TJU_CMC_MD2.ID01907.hairpin | YES | YES | YES | NO | YES | NO | NO | NO |
| TJU_CMC_MD2.ID01908.3p-miR | TJU_CMC_MD2.ID01908.hairpin | YES | NO | NO | NO | NO | NO | NO | NO |
| TJU_CMC_MD2.ID01909.3p-miR | TJU_CMC_MD2.ID01909.hairpin | YES | NO | NO | NO | NO | NO | NO | NO |
| TJU_CMC_MD2.ID01910.3p-miR | TJU_CMC_MD2.ID01910.hairpin | YES | NO | NO | NO | NO | NO | NO | NO |
| TJU_CMC_MD2.ID01911.5p-miR | TJU_CMC_MD2.ID01911.hairpin | YES | NO | YES | YES | NO | NO | NO | NO |
| TJU_CMC_MD2.ID01912.5p-miR | TJU_CMC_MD2.ID01912.hairpin | YES | YES | YES | YES | NO | NO | NO | NO |
| TJU_CMC_MD2.ID01913.3p-miR | TJU_CMC_MD2.ID01913.hairpin | YES | NO | NO | NO | NO | NO | NO | NO |
| TJU_CMC_MD2.ID01914.5p-miR | TJU_CMC_MD2.ID01914.hairpin | YES | NO | YES | YES | NO | NO | NO | NO |
| TJU_CMC_MD2.ID01915.5p-miR | TJU_CMC_MD2.ID01915.hairpin | YES | NO | YES | NO | NO | NO | NO | NO |
| TJU_CMC_MD2.ID01916.5p-miR | TJU_CMC_MD2.ID01916.hairpin | YES | NO | NO | NO | NO | NO | NO | NO |
| TJU_CMC_MD2.ID01917.3p-miR | TJU_CMC_MD2.ID01917.hairpin | YES | NO | NO | NO | NO | NO | NO | NO |
| TJU_CMC_MD2.ID01918.5p-miR | TJU_CMC_MD2.ID01918.hairpin | YES | YES | YES | YES | YES | NO | NO | NO |
| TJU_CMC_MD2.ID01919.5p-miR | TJU_CMC_MD2.ID01919.hairpin | YES | YES | YES | YES | YES | YES | NO | NO |
| TJU_CMC_MD2.ID01920.3p-miR | TJU_CMC_MD2.ID01920.hairpin | YES | NO | NO | NO | NO | NO | NO | NO |
| TJU_CMC_MD2.ID01921.5p-miR | TJU_CMC_MD2.ID01921.hairpin | YES | NO | NO | NO | NO | YES | NO | NO |
| TJU_CMC_MD2.ID01922.3p-miR | TJU_CMC_MD2.ID01922.hairpin | YES | NO | NO | NO | NO | NO | NO | NO |
| TJU_CMC_MD2.ID01923.3p-miR | TJU_CMC_MD2.ID01923.hairpin | YES | NO | NO | NO | NO | NO | NO | NO |
| TJU_CMC_MD2.ID01924.5p-miR | TJU_CMC_MD2.ID01924.hairpin | YES | YES | YES | YES | YES | NO | NO | NO |
| TJU_CMC_MD2.ID01925.5p-miR | TJU_CMC_MD2.ID01925.hairpin | YES | YES | YES | YES | YES | NO | NO | NO |
| TJU_CMC_MD2.ID01926.3p-miR | TJU_CMC_MD2.ID01926.hairpin | YES | NO | NO | NO | NO | NO | NO | NO |
| TJU_CMC_MD2.ID01927.5p-miR | TJU_CMC_MD2.ID01927.hairpin | YES | YES | YES | NO | NO | NO | NO | NO |
| TJU_CMC_MD2.ID01928.3p-miR | TJU_CMC_MD2.ID01928.hairpin | YES | NO | NO | NO | NO | NO | NO | NO |
| TJU_CMC_MD2.ID01929.3p-miR | TJU_CMC_MD2.ID01929.hairpin | YES | NO | NO | NO | NO | NO | NO | NO |
| TJU_CMC_MD2.ID01930.3p-miR | TJU_CMC_MD2.ID01930.hairpin | YES | NO | NO | NO | NO | NO | NO | NO |
| TJU_CMC_MD2.ID01931.5p-miR | TJU_CMC_MD2.ID01931.hairpin | YES | NO | YES | NO | NO | NO | NO | NO |
| TJU_CMC_MD2.ID01932.5p-miR | TJU_CMC_MD2.ID01932.hairpin | YES | NO | YES | NO | NO | NO | NO | NO |
| TJU_CMC_MD2.ID01933.3p-miR | TJU_CMC_MD2.ID01933.hairpin | YES | NO | NO | NO | NO | NO | NO | NO |
| TJU_CMC_MD2.ID01934.5p-miR | TJU_CMC_MD2.ID01934.hairpin | YES | YES | YES | NO | NO | NO | NO | NO |
| TJU_CMC_MD2.ID01935.5p-miR | TJU_CMC_MD2.ID01935.hairpin | YES | NO | YES | YES | NO | NO | NO | NO |
| TJU_CMC_MD2.ID01936.5p-miR | TJU_CMC_MD2.ID01936.hairpin | YES | YES | YES | YES | NO | NO | NO | NO |
| TJU_CMC_MD2.ID01937.3p-miR | TJU_CMC_MD2.ID01937.hairpin | YES | NO | NO | NO | NO | NO | NO | NO |
| TJU_CMC_MD2.ID01938.5p-miR | TJU_CMC_MD2.ID01938.hairpin | YES | YES | YES | YES | NO | NO | NO | NO |
| TJU_CMC_MD2.ID01939.5p-miR | TJU_CMC_MD2.ID01939.hairpin | YES | YES | YES | YES | NO | NO | NO | NO |
| TJU_CMC_MD2.ID01940.3p-miR | TJU_CMC_MD2.ID01940.hairpin | YES | NO | NO | NO | NO | NO | NO | NO |
| TJU_CMC_MD2.ID01941.5p-miR | TJU_CMC_MD2.ID01941.hairpin | YES | NO | YES | NO | NO | NO | NO | NO |
| TJU_CMC_MD2.ID01942.3p-miR | TJU_CMC_MD2.ID01942.hairpin | YES | NO | NO | NO | NO | NO | NO | NO |
| TJU_CMC_MD2.ID01943.5p-miR | TJU_CMC_MD2.ID01943.hairpin | YES | NO | NO | YES | YES | NO | NO | NO |
| TJU_CMC_MD2.ID01944.5p-miR | TJU_CMC_MD2.ID01944.hairpin | YES | NO | YES | YES | NO | NO | NO | NO |
| TJU_CMC_MD2.ID01945.3p-miR | TJU_CMC_MD2.ID01945.hairpin | YES | NO | NO | NO | NO | NO | NO | NO |
| TJU_CMC_MD2.ID01946.3p-miR | TJU_CMC_MD2.ID01946.hairpin | YES | NO | NO | NO | NO | NO | NO | NO |
| TJU_CMC_MD2.ID01947.5p-miR | TJU_CMC_MD2.ID01947.hairpin | YES | YES | YES | NO | NO | NO | NO | NO |
| TJU_CMC_MD2.ID01948.5p-miR | TJU_CMC_MD2.ID01948.hairpin | YES | NO | NO | YES | NO | NO | NO | NO |
| TJU_CMC_MD2.ID01949.3p-miR | TJU_CMC_MD2.ID01949.hairpin | YES | NO | NO | NO | NO | NO | NO | NO |
| TJU_CMC_MD2.ID01950.3p-miR | TJU_CMC_MD2.ID01950.hairpin | YES | NO | NO | NO | NO | NO | NO | NO |
| TJU_CMC_MD2.ID01950.5p-miR | TJU_CMC_MD2.ID01950.hairpin | YES | NO | YES | YES | YES | NO | NO | NO |
| TJU_CMC_MD2.ID01951.3p-miR | TJU_CMC_MD2.ID01951.hairpin | YES | NO | NO | NO | NO | NO | NO | NO |
| TJU_CMC_MD2.ID01952.5p-miR | TJU_CMC_MD2.ID01952.hairpin | YES | NO | YES | YES | NO | NO | NO | NO |
| TJU_CMC_MD2.ID01953.5p-miR | TJU_CMC_MD2.ID01953.hairpin | YES | YES | YES | NO | NO | NO | NO | NO |
| TJU_CMC_MD2.ID01954.3p-miR | TJU_CMC_MD2.ID01954.hairpin | YES | NO | NO | NO | NO | NO | NO | NO |
| TJU_CMC_MD2.ID01955.3p-miR | TJU_CMC_MD2.ID01955.hairpin | YES | NO | NO | NO | NO | NO | NO | NO |
| TJU_CMC_MD2.ID01956.5p-miR | TJU_CMC_MD2.ID01956.hairpin | YES | NO | YES | NO | NO | NO | NO | NO |
| TJU_CMC_MD2.ID01957.3p-miR | TJU_CMC_MD2.ID01957.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID01958.3p-miR | TJU_CMC_MD2.ID01958.hairpin | YES | NO | NO | NO | NO | NO | NO | NO |
| TJU_CMC_MD2.ID01959.3p-miR | TJU_CMC_MD2.ID01959.hairpin | YES | NO | NO | NO | NO | NO | NO | NO |
| TJU_CMC_MD2.ID01959.5p-miR | TJU_CMC_MD2.ID01959.hairpin | YES | NO | NO | YES | NO | NO | NO | NO |
| TJU_CMC_MD2.ID01960.3p-miR | TJU_CMC_MD2.ID01960.hairpin | YES | NO | NO | NO | NO | NO | NO | NO |
| TJU_CMC_MD2.ID01961.5p-miR | TJU_CMC_MD2.ID01961.hairpin | YES | YES | YES | YES | NO | NO | NO | NO |
| TJU_CMC_MD2.ID01962.3p-miR | TJU_CMC_MD2.ID01962.hairpin | YES | NO | NO | NO | NO | NO | NO | NO |
| TJU_CMC_MD2.ID01963.3p-miR | TJU_CMC_MD2.ID01963.hairpin | YES | NO | NO | NO | NO | NO | NO | NO |
| TJU_CMC_MD2.ID01963.5p-miR | TJU_CMC_MD2.ID01963.hairpin | YES | NO | NO | NO | NO | NO | NO | NO |
| TJU_CMC_MD2.ID01964.3p-miR | TJU_CMC_MD2.ID01964.hairpin | YES | NO | NO | NO | NO | NO | NO | NO |
| TJU_CMC_MD2.ID01965.5p-miR | TJU_CMC_MD2.ID01965.hairpin | YES | NO | NO | NO | NO | NO | NO | NO |
| TJU_CMC_MD2.ID01966.5p-miR | TJU_CMC_MD2.ID01966.hairpin | YES | YES | YES | YES | YES | YES | NO | NO |
| TJU_CMC_MD2.ID01967.5p-miR | TJU_CMC_MD2.ID01967.hairpin | YES | NO | YES | YES | YES | NO | NO | NO |
| TJU_CMC_MD2.ID01968.3p-miR | TJU_CMC_MD2.ID01968.hairpin | YES | NO | NO | NO | NO | NO | NO | NO |
| TJU_CMC_MD2.ID01969.3p-miR | TJU_CMC_MD2.ID01969.hairpin | YES | NO | NO | NO | NO | NO | NO | NO |
| TJU_CMC_MD2.ID01970.3p-miR | TJU_CMC_MD2.ID01970.hairpin | YES | NO | NO | NO | NO | NO | NO | NO |
| TJU_CMC_MD2.ID01971.3p-miR | TJU_CMC_MD2.ID01971.hairpin | YES | YES | YES | NO | NO | NO | NO | NO |
| TJU_CMC_MD2.ID01972.5p-miR | TJU_CMC_MD2.ID01972.hairpin | YES | YES | YES | YES | NO | NO | NO | NO |
| TJU_CMC_MD2.ID01973.3p-miR | TJU_CMC_MD2.ID01973.hairpin | YES | NO | NO | NO | NO | NO | NO | NO |
| TJU_CMC_MD2.ID01974.5p-miR | TJU_CMC_MD2.ID01974.hairpin | YES | NO | YES | YES | YES | NO | NO | NO |
| TJU_CMC_MD2.ID01975.3p-miR | TJU_CMC_MD2.ID01975.hairpin | YES | NO | NO | NO | NO | NO | NO | NO |
| TJU_CMC_MD2.ID01976.5p-miR | TJU_CMC_MD2.ID01976.hairpin | YES | YES | YES | YES | NO | NO | NO | NO |
| TJU_CMC_MD2.ID01977.3p-miR | TJU_CMC_MD2.ID01977.hairpin | YES | NO | NO | NO | NO | NO | NO | NO |
| TJU_CMC_MD2.ID01978.5p-miR | TJU_CMC_MD2.ID01978.hairpin | YES | NO | NO | NO | NO | NO | NO | NO |
| TJU_CMC_MD2.ID01979.3p-miR | TJU_CMC_MD2.ID01979.hairpin | YES | NO | NO | NO | NO | NO | NO | NO |
| TJU_CMC_MD2.ID01980.5p-miR | TJU_CMC_MD2.ID01980.hairpin | YES | YES | YES | NO | YES | NO | NO | NO |
| TJU_CMC_MD2.ID01981.3p-miR | TJU_CMC_MD2.ID01981.hairpin | YES | NO | NO | NO | NO | NO | NO | NO |
| TJU_CMC_MD2.ID01982.5p-miR | TJU_CMC_MD2.ID01982.hairpin | YES | YES | YES | YES | NO | NO | NO | NO |
| TJU_CMC_MD2.ID01983.3p-miR | TJU_CMC_MD2.ID01983.hairpin | YES | NO | NO | NO | NO | NO | NO | NO |
| TJU_CMC_MD2.ID01984.3p-miR | TJU_CMC_MD2.ID01984.hairpin | YES | NO | NO | NO | NO | NO | NO | NO |
| TJU_CMC_MD2.ID01985.5p-miR | TJU_CMC_MD2.ID01985.hairpin | YES | NO | NO | NO | NO | NO | NO | NO |
| TJU_CMC_MD2.ID01986.5p-miR | TJU_CMC_MD2.ID01986.hairpin | YES | NO | YES | YES | NO | NO | NO | NO |
| TJU_CMC_MD2.ID01987.3p-miR | TJU_CMC_MD2.ID01987.hairpin | YES | NO | NO | NO | NO | NO | NO | NO |
| TJU_CMC_MD2.ID01988.5p-miR | TJU_CMC_MD2.ID01988.hairpin | YES | NO | YES | YES | NO | NO | NO | NO |
| TJU_CMC_MD2.ID01989.5p-miR | TJU_CMC_MD2.ID01989.hairpin | YES | NO | NO | YES | NO | NO | NO | NO |
| TJU_CMC_MD2.ID01990.3p-miR | TJU_CMC_MD2.ID01990.hairpin | YES | NO | NO | NO | NO | NO | NO | NO |
| TJU_CMC_MD2.ID01991.5p-miR | TJU_CMC_MD2.ID01991.hairpin | YES | NO | YES | NO | YES | NO | NO | NO |
| TJU_CMC_MD2.ID01992.3p-miR | TJU_CMC_MD2.ID01992.hairpin | YES | NO | NO | NO | NO | NO | NO | NO |
| TJU_CMC_MD2.ID01993.3p-miR | TJU_CMC_MD2.ID01993.hairpin | YES | NO | NO | NO | NO | NO | NO | NO |
| TJU_CMC_MD2.ID01994.3p-miR | TJU_CMC_MD2.ID01994.hairpin | YES | NO | NO | NO | NO | NO | NO | NO |
| TJU_CMC_MD2.ID01995.3p-miR | TJU_CMC_MD2.ID01995.hairpin | YES | NO | NO | NO | NO | NO | NO | NO |
| TJU_CMC_MD2.ID01996.3p-miR | TJU_CMC_MD2.ID01996.hairpin | YES | NO | NO | NO | NO | NO | NO | NO |
| TJU_CMC_MD2.ID01997.5p-miR | TJU_CMC_MD2.ID01997.hairpin | YES | YES | YES | NO | NO | NO | NO | NO |
| TJU_CMC_MD2.ID01998.3p-miR | TJU_CMC_MD2.ID01998.hairpin | YES | NO | NO | NO | NO | NO | NO | NO |
| TJU_CMC_MD2.ID01999.3p-miR | TJU_CMC_MD2.ID01999.hairpin | YES | NO | NO | NO | NO | NO | NO | NO |
| TJU_CMC_MD2.ID01999.5p-miR | TJU_CMC_MD2.ID01999.hairpin | YES | NO | YES | YES | YES | NO | NO | NO |
| TJU_CMC_MD2.ID02000.3p-miR | TJU_CMC_MD2.ID02000.hairpin | YES | NO | NO | NO | NO | NO | NO | NO |
| TJU_CMC_MD2.ID02001.5p-miR | TJU_CMC_MD2.ID02001.hairpin | YES | NO | YES | YES | YES | NO | NO | NO |
| TJU_CMC_MD2.ID02002.5p-miR | TJU_CMC_MD2.ID02002.hairpin | YES | YES | NO | NO | NO | NO | NO | NO |
| TJU_CMC_MD2.ID02003.3p-miR | TJU_CMC_MD2.ID02003.hairpin | YES | NO | NO | NO | NO | NO | NO | NO |
| TJU_CMC_MD2.ID02004.3p-miR | TJU_CMC_MD2.ID02004.hairpin | YES | NO | NO | NO | NO | NO | NO | NO |
| TJU_CMC_MD2.ID02005.5p-miR | TJU_CMC_MD2.ID02005.hairpin | YES | NO | NO | NO | NO | NO | NO | NO |
| TJU_CMC_MD2.ID02006.3p-miR | TJU_CMC_MD2.ID02006.hairpin | YES | NO | NO | NO | NO | NO | NO | NO |
| TJU_CMC_MD2.ID02007.3p-miR | TJU_CMC_MD2.ID02007.hairpin | YES | NO | NO | NO | NO | NO | NO | NO |
| TJU_CMC_MD2.ID02008.5p-miR | TJU_CMC_MD2.ID02008.hairpin | YES | NO | YES | YES | YES | NO | NO | NO |
| TJU_CMC_MD2.ID02009.5p-miR | TJU_CMC_MD2.ID02009.hairpin | YES | YES | NO | YES | NO | NO | NO | NO |
| TJU_CMC_MD2.ID02010.3p-miR | TJU_CMC_MD2.ID02010.hairpin | YES | NO | NO | NO | NO | NO | NO | NO |
| TJU_CMC_MD2.ID02011.3p-miR | TJU_CMC_MD2.ID02011.hairpin | YES | NO | NO | NO | NO | NO | NO | NO |
| TJU_CMC_MD2.ID02012.5p-miR | TJU_CMC_MD2.ID02012.hairpin | YES | YES | NO | YES | NO | NO | NO | NO |
| TJU_CMC_MD2.ID02013.3p-miR | TJU_CMC_MD2.ID02013.hairpin | YES | NO | NO | NO | NO | NO | NO | NO |
| TJU_CMC_MD2.ID02014.5p-miR | TJU_CMC_MD2.ID02014.hairpin | YES | NO | NO | NO | NO | NO | NO | NO |
| TJU_CMC_MD2.ID02015.5p-miR | TJU_CMC_MD2.ID02015.hairpin | YES | NO | YES | NO | NO | NO | NO | NO |
| TJU_CMC_MD2.ID02016.3p-miR | TJU_CMC_MD2.ID02016.hairpin | YES | NO | NO | NO | NO | NO | NO | NO |
| TJU_CMC_MD2.ID02017.3p-miR | TJU_CMC_MD2.ID02017.hairpin | YES | NO | NO | NO | NO | NO | NO | NO |
| TJU_CMC_MD2.ID02018.3p-miR | TJU_CMC_MD2.ID02018.hairpin | YES | NO | NO | NO | NO | NO | NO | NO |
| TJU_CMC_MD2.ID02019.3p-miR | TJU_CMC_MD2.ID02019.hairpin | YES | NO | NO | NO | NO | NO | NO | NO |
| TJU_CMC_MD2.ID02020.3p-miR | TJU_CMC_MD2.ID02020.hairpin | YES | NO | NO | NO | NO | NO | NO | NO |
| TJU_CMC_MD2.ID02021.3p-miR | TJU_CMC_MD2.ID02021.hairpin | YES | NO | NO | NO | NO | NO | NO | NO |
| TJU_CMC_MD2.ID02022.5p-miR | TJU_CMC_MD2.ID02022.hairpin | YES | YES | YES | NO | YES | NO | NO | NO |
| TJU_CMC_MD2.ID02023.5p-miR | TJU_CMC_MD2.ID02023.hairpin | YES | YES | YES | YES | NO | NO | NO | NO |
| TJU_CMC_MD2.ID02024.3p-miR | TJU_CMC_MD2.ID02024.hairpin | YES | NO | NO | NO | NO | NO | NO | NO |
| TJU_CMC_MD2.ID02025.5p-miR | TJU_CMC_MD2.ID02025.hairpin | YES | YES | YES | YES | YES | NO | NO | NO |
| TJU_CMC_MD2.ID02026.5p-miR | TJU_CMC_MD2.ID02026.hairpin | YES | YES | YES | YES | YES | NO | NO | NO |
| TJU_CMC_MD2.ID02027.3p-miR | TJU_CMC_MD2.ID02027.hairpin | YES | NO | NO | NO | NO | NO | NO | NO |
| TJU_CMC_MD2.ID02028.3p-miR | TJU_CMC_MD2.ID02028.hairpin | YES | NO | NO | NO | NO | NO | NO | NO |
| TJU_CMC_MD2.ID02029.5p-miR | TJU_CMC_MD2.ID02029.hairpin | YES | YES | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02030.3p-miR | TJU_CMC_MD2.ID02030.hairpin | YES | NO | NO | NO | NO | NO | NO | NO |
| TJU_CMC_MD2.ID02031.5p-miR | TJU_CMC_MD2.ID02031.hairpin | YES | YES | YES | YES | YES | NO | NO | NO |
| TJU_CMC_MD2.ID02032.5p-miR | TJU_CMC_MD2.ID02032.hairpin | YES | NO | NO | NO | NO | NO | NO | NO |
| TJU_CMC_MD2.ID02033.5p-miR | TJU_CMC_MD2.ID02033.hairpin | YES | YES | YES | YES | NO | NO | NO | NO |
| TJU_CMC_MD2.ID02034.5p-miR | TJU_CMC_MD2.ID02034.hairpin | YES | YES | YES | YES | YES | NO | NO | NO |
| TJU_CMC_MD2.ID02035.5p-miR | TJU_CMC_MD2.ID02035.hairpin | YES | YES | YES | YES | YES | NO | NO | NO |
| TJU_CMC_MD2.ID02036.3p-miR | TJU_CMC_MD2.ID02036.hairpin | YES | NO | NO | NO | NO | NO | NO | NO |
| TJU_CMC_MD2.ID02037.5p-miR | TJU_CMC_MD2.ID02037.hairpin | YES | NO | NO | NO | NO | NO | NO | NO |
| TJU_CMC_MD2.ID02038.5p-miR | TJU_CMC_MD2.ID02038.hairpin | YES | YES | YES | YES | NO | NO | NO | NO |
| TJU_CMC_MD2.ID02039.3p-miR | TJU_CMC_MD2.ID02039.hairpin | YES | NO | NO | NO | NO | NO | NO | NO |
| TJU_CMC_MD2.ID02040.5p-miR | TJU_CMC_MD2.ID02040.hairpin | YES | YES | YES | YES | NO | NO | NO | NO |
| TJU_CMC_MD2.ID02041.3p-miR | TJU_CMC_MD2.ID02041.hairpin | YES | NO | NO | NO | NO | NO | NO | NO |
| TJU_CMC_MD2.ID02042.5p-miR | TJU_CMC_MD2.ID02042.hairpin | YES | NO | YES | NO | NO | NO | NO | NO |
| TJU_CMC_MD2.ID02043.3p-miR | TJU_CMC_MD2.ID02043.hairpin | YES | NO | YES | NO | NO | NO | NO | NO |
| TJU_CMC_MD2.ID02043.5p-miR | TJU_CMC_MD2.ID02043.hairpin | YES | NO | YES | NO | NO | NO | NO | NO |
| TJU_CMC_MD2.ID02044.3p-miR | TJU_CMC_MD2.ID02044.hairpin | YES | NO | NO | NO | NO | NO | NO | NO |
| TJU_CMC_MD2.ID02045.3p-miR | TJU_CMC_MD2.ID02045.hairpin | YES | NO | NO | NO | NO | NO | NO | NO |
| TJU_CMC_MD2.ID02046.3p-miR | TJU_CMC_MD2.ID02046.hairpin | YES | NO | NO | NO | NO | NO | NO | NO |
| TJU_CMC_MD2.ID02047.5p-miR | TJU_CMC_MD2.ID02047.hairpin | YES | NO | NO | NO | NO | NO | NO | NO |
| TJU_CMC_MD2.ID02048.3p-miR | TJU_CMC_MD2.ID02048.hairpin | YES | NO | NO | NO | NO | NO | NO | NO |
| TJU_CMC_MD2.ID02049.3p-miR | TJU_CMC_MD2.ID02049.hairpin | YES | NO | NO | NO | NO | NO | NO | NO |
| TJU_CMC_MD2.ID02050.3p-miR | TJU_CMC_MD2.ID02050.hairpin | YES | NO | NO | NO | NO | NO | NO | NO |
| TJU_CMC_MD2.ID02050.5p-miR | TJU_CMC_MD2.ID02050.hairpin | YES | YES | YES | YES | YES | NO | NO | NO |
| TJU_CMC_MD2.ID02051.3p-miR | TJU_CMC_MD2.ID02051.hairpin | YES | NO | NO | NO | NO | NO | NO | NO |
| TJU_CMC_MD2.ID02052.5p-miR | TJU_CMC_MD2.ID02052.hairpin | YES | NO | NO | NO | NO | YES | NO | NO |
| TJU_CMC_MD2.ID02053.5p-miR | TJU_CMC_MD2.ID02053.hairpin | YES | NO | YES | NO | NO | NO | NO | NO |
| TJU_CMC_MD2.ID02054.3p-miR | TJU_CMC_MD2.ID02054.hairpin | YES | NO | NO | NO | NO | NO | NO | NO |
| TJU_CMC_MD2.ID02055.5p-miR | TJU_CMC_MD2.ID02055.hairpin | YES | YES | YES | YES | YES | NO | NO | NO |
| TJU_CMC_MD2.ID02056.3p-miR | TJU_CMC_MD2.ID02056.hairpin | YES | NO | NO | NO | NO | NO | NO | NO |
| TJU_CMC_MD2.ID02057.3p-miR | TJU_CMC_MD2.ID02057.hairpin | YES | NO | NO | NO | NO | NO | NO | NO |
| TJU_CMC_MD2.ID02058.5p-miR | TJU_CMC_MD2.ID02058.hairpin | YES | NO | YES | NO | NO | NO | NO | NO |
| TJU_CMC_MD2.ID02059.3p-miR | TJU_CMC_MD2.ID02059.hairpin | YES | NO | YES | NO | YES | NO | NO | NO |
| TJU_CMC_MD2.ID02059.5p-miR | TJU_CMC_MD2.ID02059.hairpin | YES | NO | YES | NO | YES | NO | NO | NO |
| TJU_CMC_MD2.ID02060.3p-miR | TJU_CMC_MD2.ID02060.hairpin | YES | NO | NO | NO | NO | NO | NO | NO |
| TJU_CMC_MD2.ID02061.3p-miR | TJU_CMC_MD2.ID02061.hairpin | YES | NO | NO | NO | NO | NO | NO | NO |
| TJU_CMC_MD2.ID02062.3p-miR | TJU_CMC_MD2.ID02062.hairpin | YES | NO | NO | NO | NO | NO | NO | NO |
| TJU_CMC_MD2.ID02063.5p-miR | TJU_CMC_MD2.ID02063.hairpin | YES | YES | YES | YES | YES | NO | NO | NO |
| TJU_CMC_MD2.ID02064.5p-miR | TJU_CMC_MD2.ID02064.hairpin | YES | YES | NO | YES | NO | NO | NO | NO |
| TJU_CMC_MD2.ID02065.5p-miR | TJU_CMC_MD2.ID02065.hairpin | YES | NO | NO | NO | NO | NO | NO | NO |
| TJU_CMC_MD2.ID02066.5p-miR | TJU_CMC_MD2.ID02066.hairpin | YES | YES | NO | NO | NO | NO | NO | NO |
| TJU_CMC_MD2.ID02067.3p-miR | TJU_CMC_MD2.ID02067.hairpin | YES | NO | NO | NO | NO | NO | NO | NO |
| TJU_CMC_MD2.ID02068.5p-miR | TJU_CMC_MD2.ID02068.hairpin | YES | YES | NO | NO | NO | NO | NO | NO |
| TJU_CMC_MD2.ID02069.5p-miR | TJU_CMC_MD2.ID02069.hairpin | YES | YES | NO | YES | YES | NO | NO | NO |
| TJU_CMC_MD2.ID02070.5p-miR | TJU_CMC_MD2.ID02070.hairpin | YES | YES | YES | YES | YES | NO | NO | NO |
| TJU_CMC_MD2.ID02071.3p-miR | TJU_CMC_MD2.ID02071.hairpin | YES | NO | NO | NO | NO | NO | NO | NO |
| TJU_CMC_MD2.ID02072.3p-miR | TJU_CMC_MD2.ID02072.hairpin | YES | NO | NO | NO | NO | NO | NO | NO |
| TJU_CMC_MD2.ID02073.5p-miR | TJU_CMC_MD2.ID02073.hairpin | YES | YES | YES | YES | YES | NO | NO | NO |
| TJU_CMC_MD2.ID02074.3p-miR | TJU_CMC_MD2.ID02074.hairpin | YES | NO | NO | NO | NO | NO | NO | NO |
| TJU_CMC_MD2.ID02074.5p-miR | TJU_CMC_MD2.ID02074.hairpin | YES | YES | YES | YES | YES | NO | NO | NO |
| TJU_CMC_MD2.ID02075.3p-miR | TJU_CMC_MD2.ID02075.hairpin | YES | NO | NO | NO | NO | NO | NO | NO |
| TJU_CMC_MD2.ID02076.5p-miR | TJU_CMC_MD2.ID02076.hairpin | YES | YES | YES | YES | NO | YES | NO | NO |
| TJU_CMC_MD2.ID02077.3p-miR | TJU_CMC_MD2.ID02077.hairpin | YES | NO | NO | NO | NO | NO | NO | NO |
| TJU_CMC_MD2.ID02078.5p-miR | TJU_CMC_MD2.ID02078.hairpin | YES | YES | YES | YES | YES | NO | NO | NO |
| TJU_CMC_MD2.ID02079.5p-miR | TJU_CMC_MD2.ID02079.hairpin | YES | YES | NO | NO | NO | NO | NO | NO |
| TJU_CMC_MD2.ID02080.3p-miR | TJU_CMC_MD2.ID02080.hairpin | YES | NO | NO | NO | NO | NO | NO | NO |
| TJU_CMC_MD2.ID02081.5p-miR | TJU_CMC_MD2.ID02081.hairpin | YES | YES | YES | NO | YES | NO | NO | NO |
| TJU_CMC_MD2.ID02082.3p-miR | TJU_CMC_MD2.ID02082.hairpin | YES | NO | NO | NO | NO | NO | NO | NO |
| TJU_CMC_MD2.ID02083.3p-miR | TJU_CMC_MD2.ID02083.hairpin | YES | NO | NO | NO | NO | NO | NO | NO |
| TJU_CMC_MD2.ID02084.3p-miR | TJU_CMC_MD2.ID02084.hairpin | YES | NO | NO | NO | NO | NO | NO | NO |
| TJU_CMC_MD2.ID02085.3p-miR | TJU_CMC_MD2.ID02085.hairpin | YES | NO | NO | NO | NO | NO | NO | NO |
| TJU_CMC_MD2.ID02085.5p-miR | TJU_CMC_MD2.ID02085.hairpin | YES | YES | YES | YES | YES | NO | NO | NO |
| TJU_CMC_MD2.ID02086.5p-miR | TJU_CMC_MD2.ID02086.hairpin | YES | NO | NO | NO | NO | NO | NO | NO |
| TJU_CMC_MD2.ID02087.5p-miR | TJU_CMC_MD2.ID02087.hairpin | YES | NO | YES | NO | NO | NO | NO | NO |
| TJU_CMC_MD2.ID02088.3p-miR | TJU_CMC_MD2.ID02088.hairpin | YES | NO | NO | NO | NO | NO | NO | NO |
| TJU_CMC_MD2.ID02088.5p-miR | TJU_CMC_MD2.ID02088.hairpin | YES | NO | YES | NO | YES | NO | NO | NO |
| TJU_CMC_MD2.ID02089.3p-miR | TJU_CMC_MD2.ID02089.hairpin | YES | NO | NO | NO | NO | NO | NO | NO |
| TJU_CMC_MD2.ID02090.3p-miR | TJU_CMC_MD2.ID02090.hairpin | YES | NO | NO | NO | NO | NO | NO | NO |
| TJU_CMC_MD2.ID02091.5p-miR | TJU_CMC_MD2.ID02091.hairpin | YES | YES | YES | YES | NO | NO | NO | NO |
| TJU_CMC_MD2.ID02092.5p-miR | TJU_CMC_MD2.ID02092.hairpin | YES | YES | YES | NO | NO | NO | NO | NO |
| TJU_CMC_MD2.ID02093.5p-miR | TJU_CMC_MD2.ID02093.hairpin | YES | YES | YES | NO | NO | NO | NO | NO |
| TJU_CMC_MD2.ID02094.3p-miR | TJU_CMC_MD2.ID02094.hairpin | YES | NO | NO | NO | NO | NO | NO | NO |
| TJU_CMC_MD2.ID02095.3p-miR | TJU_CMC_MD2.ID02095.hairpin | YES | NO | NO | NO | NO | NO | NO | NO |
| TJU_CMC_MD2.ID02096.3p-miR | TJU_CMC_MD2.ID02096.hairpin | YES | NO | NO | NO | NO | NO | NO | NO |
| TJU_CMC_MD2.ID02096.5p-miR | TJU_CMC_MD2.ID02096.hairpin | YES | YES | YES | YES | YES | NO | NO | NO |
| TJU_CMC_MD2.ID02097.3p-miR | TJU_CMC_MD2.ID02097.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02098.3p-miR | TJU_CMC_MD2.ID02098.hairpin | YES | NO | NO | NO | NO | NO | NO | NO |
| TJU_CMC_MD2.ID02099.5p-miR | TJU_CMC_MD2.ID02099.hairpin | YES | YES | NO | YES | NO | NO | NO | NO |
| TJU_CMC_MD2.ID02100.3p-miR | TJU_CMC_MD2.ID02100.hairpin | YES | NO | NO | NO | NO | NO | NO | NO |
| TJU_CMC_MD2.ID02101.3p-miR | TJU_CMC_MD2.ID02101.hairpin | YES | NO | NO | NO | NO | NO | NO | NO |
| TJU_CMC_MD2.ID02102.5p-miR | TJU_CMC_MD2.ID02102.hairpin | YES | YES | YES | YES | YES | NO | NO | NO |
| TJU_CMC_MD2.ID02103.5p-miR | TJU_CMC_MD2.ID02103.hairpin | YES | YES | YES | YES | NO | NO | NO | NO |
| TJU_CMC_MD2.ID02104.5p-miR | TJU_CMC_MD2.ID02104.hairpin | YES | YES | NO | YES | YES | YES | NO | NO |
| TJU_CMC_MD2.ID02105.3p-miR | TJU_CMC_MD2.ID02105.hairpin | YES | NO | NO | NO | NO | NO | NO | NO |
| TJU_CMC_MD2.ID02106.3p-miR | TJU_CMC_MD2.ID02106.hairpin | YES | NO | NO | NO | NO | NO | NO | NO |
| TJU_CMC_MD2.ID02107.5p-miR | TJU_CMC_MD2.ID02107.hairpin | YES | YES | YES | YES | NO | NO | NO | NO |
| TJU_CMC_MD2.ID02108.3p-miR | TJU_CMC_MD2.ID02108.hairpin | YES | NO | NO | NO | NO | NO | NO | NO |
| TJU_CMC_MD2.ID02109.5p-miR | TJU_CMC_MD2.ID02109.hairpin | YES | NO | YES | NO | NO | NO | NO | NO |
| TJU_CMC_MD2.ID02110.5p-miR | TJU_CMC_MD2.ID02110.hairpin | YES | YES | YES | YES | YES | NO | NO | NO |
| TJU_CMC_MD2.ID02111.3p-miR | TJU_CMC_MD2.ID02111.hairpin | YES | NO | NO | NO | NO | NO | NO | NO |
| TJU_CMC_MD2.ID02112.3p-miR | TJU_CMC_MD2.ID02112.hairpin | YES | NO | NO | NO | NO | NO | NO | NO |
| TJU_CMC_MD2.ID02113.5p-miR | TJU_CMC_MD2.ID02113.hairpin | YES | YES | YES | NO | NO | NO | NO | NO |
| TJU_CMC_MD2.ID02114.3p-miR | TJU_CMC_MD2.ID02114.hairpin | YES | NO | NO | NO | NO | NO | NO | NO |
| TJU_CMC_MD2.ID02115.5p-miR | TJU_CMC_MD2.ID02115.hairpin | YES | NO | NO | NO | NO | NO | NO | NO |
| TJU_CMC_MD2.ID02116.3p-miR | TJU_CMC_MD2.ID02116.hairpin | YES | NO | NO | NO | NO | NO | NO | NO |
| TJU_CMC_MD2.ID02117.3p-miR | TJU_CMC_MD2.ID02117.hairpin | YES | NO | YES | NO | NO | NO | NO | NO |
| TJU_CMC_MD2.ID02118.3p-miR | TJU_CMC_MD2.ID02118.hairpin | YES | NO | NO | NO | NO | NO | NO | NO |
| TJU_CMC_MD2.ID02119.3p-miR | TJU_CMC_MD2.ID02119.hairpin | YES | NO | NO | NO | NO | NO | NO | NO |
| TJU_CMC_MD2.ID02120.3p-miR | TJU_CMC_MD2.ID02120.hairpin | YES | NO | NO | NO | NO | NO | NO | NO |
| TJU_CMC_MD2.ID02121.3p-miR | TJU_CMC_MD2.ID02121.hairpin | YES | NO | NO | NO | NO | NO | NO | NO |
| TJU_CMC_MD2.ID02122.5p-miR | TJU_CMC_MD2.ID02122.hairpin | YES | NO | NO | NO | NO | NO | NO | NO |
| TJU_CMC_MD2.ID02123.3p-miR | TJU_CMC_MD2.ID02123.hairpin | YES | NO | NO | NO | NO | NO | NO | NO |
| TJU_CMC_MD2.ID02124.5p-miR | TJU_CMC_MD2.ID02124.hairpin | YES | NO | NO | NO | NO | NO | NO | NO |
| TJU_CMC_MD2.ID02125.3p-miR | TJU_CMC_MD2.ID02125.hairpin | YES | NO | NO | NO | NO | NO | NO | NO |
| TJU_CMC_MD2.ID02125.5p-miR | TJU_CMC_MD2.ID02125.hairpin | YES | NO | NO | NO | NO | NO | NO | NO |
| TJU_CMC_MD2.ID02126.3p-miR | TJU_CMC_MD2.ID02126.hairpin | YES | NO | NO | NO | NO | NO | NO | NO |
| TJU_CMC_MD2.ID02126.5p-miR | TJU_CMC_MD2.ID02126.hairpin | YES | NO | YES | NO | NO | NO | NO | NO |
| TJU_CMC_MD2.ID02127.5p-miR | TJU_CMC_MD2.ID02127.hairpin | YES | NO | YES | NO | NO | NO | NO | NO |
| TJU_CMC_MD2.ID02128.5p-miR | TJU_CMC_MD2.ID02128.hairpin | YES | NO | YES | NO | NO | NO | NO | NO |
| TJU_CMC_MD2.ID02129.5p-miR | TJU_CMC_MD2.ID02129.hairpin | YES | NO | YES | NO | YES | NO | NO | NO |
| TJU_CMC_MD2.ID02130.3p-miR | TJU_CMC_MD2.ID02130.hairpin | YES | NO | NO | NO | NO | NO | NO | NO |
| TJU_CMC_MD2.ID02131.5p-miR | TJU_CMC_MD2.ID02131.hairpin | YES | NO | NO | NO | NO | NO | NO | NO |
| TJU_CMC_MD2.ID02132.3p-miR | TJU_CMC_MD2.ID02132.hairpin | YES | NO | NO | NO | NO | NO | NO | NO |
| TJU_CMC_MD2.ID02133.5p-miR | TJU_CMC_MD2.ID02133.hairpin | YES | YES | YES | YES | NO | NO | NO | NO |
| TJU_CMC_MD2.ID02134.5p-miR | TJU_CMC_MD2.ID02134.hairpin | YES | YES | YES | YES | NO | NO | NO | NO |
| TJU_CMC_MD2.ID02135.5p-miR | TJU_CMC_MD2.ID02135.hairpin | YES | YES | YES | YES | NO | NO | NO | NO |
| TJU_CMC_MD2.ID02136.5p-miR | TJU_CMC_MD2.ID02136.hairpin | YES | NO | NO | NO | NO | NO | NO | NO |
| TJU_CMC_MD2.ID02137.5p-miR | TJU_CMC_MD2.ID02137.hairpin | YES | NO | NO | YES | NO | NO | NO | NO |
| TJU_CMC_MD2.ID02138.5p-miR | TJU_CMC_MD2.ID02138.hairpin | YES | YES | YES | NO | YES | NO | NO | NO |
| TJU_CMC_MD2.ID02139.3p-miR | TJU_CMC_MD2.ID02139.hairpin | YES | NO | NO | NO | NO | NO | NO | NO |
| TJU_CMC_MD2.ID02140.5p-miR | TJU_CMC_MD2.ID02140.hairpin | YES | YES | YES | YES | YES | YES | NO | NO |
| TJU_CMC_MD2.ID02141.5p-miR | TJU_CMC_MD2.ID02141.hairpin | YES | NO | YES | YES | YES | YES | NO | NO |
| TJU_CMC_MD2.ID02142.3p-miR | TJU_CMC_MD2.ID02142.hairpin | YES | NO | NO | NO | NO | NO | NO | NO |
| TJU_CMC_MD2.ID02143.3p-miR | TJU_CMC_MD2.ID02143.hairpin | YES | YES | YES | YES | YES | NO | NO | NO |
| TJU_CMC_MD2.ID02143.5p-miR | TJU_CMC_MD2.ID02143.hairpin | YES | YES | YES | YES | YES | NO | NO | NO |
| TJU_CMC_MD2.ID02144.5p-miR | TJU_CMC_MD2.ID02144.hairpin | YES | NO | YES | NO | YES | NO | NO | NO |
| TJU_CMC_MD2.ID02145.5p-miR | TJU_CMC_MD2.ID02145.hairpin | YES | YES | NO | NO | NO | NO | NO | NO |
| TJU_CMC_MD2.ID02146.5p-miR | TJU_CMC_MD2.ID02146.hairpin | YES | NO | NO | NO | NO | NO | NO | NO |
| TJU_CMC_MD2.ID02147.5p-miR | TJU_CMC_MD2.ID02147.hairpin | YES | NO | YES | NO | NO | NO | NO | NO |
| TJU_CMC_MD2.ID02148.3p-miR | TJU_CMC_MD2.ID02148.hairpin | YES | NO | NO | NO | NO | NO | NO | NO |
| TJU_CMC_MD2.ID02149.3p-miR | TJU_CMC_MD2.ID02149.hairpin | YES | NO | NO | NO | NO | NO | NO | NO |
| TJU_CMC_MD2.ID02150.5p-miR | TJU_CMC_MD2.ID02150.hairpin | YES | YES | YES | NO | NO | NO | NO | NO |
| TJU_CMC_MD2.ID02151.5p-miR | TJU_CMC_MD2.ID02151.hairpin | YES | YES | YES | NO | NO | NO | NO | NO |
| TJU_CMC_MD2.ID02152.3p-miR | TJU_CMC_MD2.ID02152.hairpin | YES | NO | NO | NO | NO | NO | NO | NO |
| TJU_CMC_MD2.ID02153.5p-miR | TJU_CMC_MD2.ID02153.hairpin | YES | NO | YES | NO | NO | NO | NO | NO |
| TJU_CMC_MD2.ID02154.3p-miR | TJU_CMC_MD2.ID02154.hairpin | YES | NO | NO | NO | NO | NO | NO | NO |
| TJU_CMC_MD2.ID02155.3p-miR | TJU_CMC_MD2.ID02155.hairpin | YES | NO | NO | NO | NO | NO | NO | NO |
| TJU_CMC_MD2.ID02156.3p-miR | TJU_CMC_MD2.ID02156.hairpin | YES | NO | NO | NO | NO | NO | NO | NO |
| TJU_CMC_MD2.ID02157.5p-miR | TJU_CMC_MD2.ID02157.hairpin | YES | YES | YES | NO | NO | NO | NO | NO |
| TJU_CMC_MD2.ID02158.5p-miR | TJU_CMC_MD2.ID02158.hairpin | YES | YES | NO | NO | NO | NO | NO | NO |
| TJU_CMC_MD2.ID02159.3p-miR | TJU_CMC_MD2.ID02159.hairpin | YES | NO | NO | NO | NO | NO | NO | NO |
| TJU_CMC_MD2.ID02160.3p-miR | TJU_CMC_MD2.ID02160.hairpin | YES | NO | NO | NO | NO | NO | NO | NO |
| TJU_CMC_MD2.ID02161.3p-miR | TJU_CMC_MD2.ID02161.hairpin | YES | NO | NO | NO | NO | NO | NO | NO |
| TJU_CMC_MD2.ID02162.5p-miR | TJU_CMC_MD2.ID02162.hairpin | YES | NO | YES | NO | YES | NO | NO | NO |
| TJU_CMC_MD2.ID02163.3p-miR | TJU_CMC_MD2.ID02163.hairpin | YES | NO | NO | NO | NO | NO | NO | NO |
| TJU_CMC_MD2.ID02164.3p-miR | TJU_CMC_MD2.ID02164.hairpin | YES | NO | NO | NO | NO | NO | NO | NO |
| TJU_CMC_MD2.ID02165.3p-miR | TJU_CMC_MD2.ID02165.hairpin | YES | NO | NO | NO | NO | NO | NO | NO |
| TJU_CMC_MD2.ID02165.5p-miR | TJU_CMC_MD2.ID02165.hairpin | YES | YES | YES | NO | YES | NO | NO | NO |
| TJU_CMC_MD2.ID02166.3p-miR | TJU_CMC_MD2.ID02166.hairpin | YES | NO | NO | NO | NO | NO | NO | NO |
| TJU_CMC_MD2.ID02167.3p-miR | TJU_CMC_MD2.ID02167.hairpin | YES | NO | NO | NO | NO | NO | NO | NO |
| TJU_CMC_MD2.ID02168.5p-miR | TJU_CMC_MD2.ID02168.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02169.3p-miR | TJU_CMC_MD2.ID02169.hairpin | YES | NO | NO | NO | NO | NO | NO | NO |
| TJU_CMC_MD2.ID02169.5p-miR | TJU_CMC_MD2.ID02169.hairpin | YES | NO | YES | NO | YES | NO | NO | NO |
| TJU_CMC_MD2.ID02170.3p-miR | TJU_CMC_MD2.ID02170.hairpin | YES | NO | NO | NO | NO | NO | NO | NO |
| TJU_CMC_MD2.ID02171.5p-miR | TJU_CMC_MD2.ID02171.hairpin | YES | YES | YES | YES | NO | YES | NO | NO |
| TJU_CMC_MD2.ID02172.5p-miR | TJU_CMC_MD2.ID02172.hairpin | YES | NO | YES | NO | YES | NO | NO | NO |
| TJU_CMC_MD2.ID02173.3p-miR | TJU_CMC_MD2.ID02173.hairpin | YES | NO | NO | NO | NO | NO | NO | NO |
| TJU_CMC_MD2.ID02174.5p-miR | TJU_CMC_MD2.ID02174.hairpin | YES | YES | YES | NO | NO | NO | NO | NO |
| TJU_CMC_MD2.ID02175.5p-miR | TJU_CMC_MD2.ID02175.hairpin | YES | NO | NO | NO | NO | NO | NO | NO |
| TJU_CMC_MD2.ID02176.3p-miR | TJU_CMC_MD2.ID02176.hairpin | YES | NO | NO | NO | NO | NO | NO | NO |
| TJU_CMC_MD2.ID02176.5p-miR | TJU_CMC_MD2.ID02176.hairpin | YES | YES | YES | YES | NO | NO | NO | NO |
| TJU_CMC_MD2.ID02177.5p-miR | TJU_CMC_MD2.ID02177.hairpin | YES | NO | NO | NO | NO | NO | NO | NO |
| TJU_CMC_MD2.ID02178.5p-miR | TJU_CMC_MD2.ID02178.hairpin | YES | YES | YES | NO | NO | NO | NO | NO |
| TJU_CMC_MD2.ID02179.3p-miR | TJU_CMC_MD2.ID02179.hairpin | YES | NO | NO | NO | NO | NO | NO | NO |
| TJU_CMC_MD2.ID02180.3p-miR | TJU_CMC_MD2.ID02180.hairpin | YES | NO | NO | NO | NO | NO | NO | NO |
| TJU_CMC_MD2.ID02181.3p-miR | TJU_CMC_MD2.ID02181.hairpin | YES | NO | NO | NO | NO | NO | NO | NO |
| TJU_CMC_MD2.ID02182.5p-miR | TJU_CMC_MD2.ID02182.hairpin | YES | NO | NO | NO | YES | NO | NO | NO |
| TJU_CMC_MD2.ID02183.5p-miR | TJU_CMC_MD2.ID02183.hairpin | YES | YES | YES | YES | YES | YES | NO | NO |
| TJU_CMC_MD2.ID02184.3p-miR | TJU_CMC_MD2.ID02184.hairpin | YES | NO | NO | NO | NO | NO | NO | NO |
| TJU_CMC_MD2.ID02185.5p-miR | TJU_CMC_MD2.ID02185.hairpin | YES | NO | YES | NO | YES | NO | NO | NO |
| TJU_CMC_MD2.ID02186.5p-miR | TJU_CMC_MD2.ID02186.hairpin | YES | YES | YES | YES | YES | NO | NO | NO |
| TJU_CMC_MD2.ID02187.5p-miR | TJU_CMC_MD2.ID02187.hairpin | YES | NO | NO | NO | NO | NO | NO | NO |
| TJU_CMC_MD2.ID02188.3p-miR | TJU_CMC_MD2.ID02188.hairpin | YES | NO | NO | NO | NO | NO | NO | NO |
| TJU_CMC_MD2.ID02188.5p-miR | TJU_CMC_MD2.ID02188.hairpin | YES | NO | YES | NO | YES | NO | NO | NO |
| TJU_CMC_MD2.ID02189.5p-miR | TJU_CMC_MD2.ID02189.hairpin | YES | YES | YES | NO | YES | NO | NO | NO |
| TJU_CMC_MD2.ID02190.5p-miR | TJU_CMC_MD2.ID02190.hairpin | YES | NO | NO | NO | NO | NO | NO | NO |
| TJU_CMC_MD2.ID02191.5p-miR | TJU_CMC_MD2.ID02191.hairpin | YES | NO | YES | NO | YES | NO | NO | NO |
| TJU_CMC_MD2.ID02192.5p-miR | TJU_CMC_MD2.ID02192.hairpin | YES | NO | NO | NO | NO | NO | NO | NO |
| TJU_CMC_MD2.ID02193.3p-miR | TJU_CMC_MD2.ID02193.hairpin | YES | NO | NO | NO | NO | NO | NO | NO |
| TJU_CMC_MD2.ID02194.3p-miR | TJU_CMC_MD2.ID02194.hairpin | YES | NO | NO | NO | NO | NO | NO | NO |
| TJU_CMC_MD2.ID02195.3p-miR | TJU_CMC_MD2.ID02195.hairpin | YES | NO | NO | NO | NO | NO | NO | NO |
| TJU_CMC_MD2.ID02196.5p-miR | TJU_CMC_MD2.ID02196.hairpin | YES | NO | NO | NO | YES | NO | NO | NO |
| TJU_CMC_MD2.ID02197.3p-miR | TJU_CMC_MD2.ID02197.hairpin | YES | NO | NO | NO | NO | NO | NO | NO |
| TJU_CMC_MD2.ID02198.3p-miR | TJU_CMC_MD2.ID02198.hairpin | YES | NO | NO | NO | NO | NO | NO | NO |
| TJU_CMC_MD2.ID02199.5p-miR | TJU_CMC_MD2.ID02199.hairpin | YES | YES | YES | YES | YES | NO | NO | NO |
| TJU_CMC_MD2.ID02200.3p-miR | TJU_CMC_MD2.ID02200.hairpin | YES | NO | NO | NO | NO | NO | NO | NO |
| TJU_CMC_MD2.ID02201.3p-miR | TJU_CMC_MD2.ID02201.hairpin | YES | NO | NO | NO | NO | NO | NO | NO |
| TJU_CMC_MD2.ID02202.5p-miR | TJU_CMC_MD2.ID02202.hairpin | YES | NO | YES | NO | NO | NO | NO | NO |
| TJU_CMC_MD2.ID02203.5p-miR | TJU_CMC_MD2.ID02203.hairpin | YES | YES | YES | YES | NO | NO | NO | NO |
| TJU_CMC_MD2.ID02204.5p-miR | TJU_CMC_MD2.ID02204.hairpin | YES | YES | YES | YES | NO | NO | NO | NO |
| TJU_CMC_MD2.ID02205.5p-miR | TJU_CMC_MD2.ID02205.hairpin | YES | YES | YES | YES | YES | NO | NO | NO |
| TJU_CMC_MD2.ID02206.5p-miR | TJU_CMC_MD2.ID02206.hairpin | YES | NO | YES | NO | YES | NO | NO | NO |
| TJU_CMC_MD2.ID02207.5p-miR | TJU_CMC_MD2.ID02207.hairpin | YES | YES | YES | YES | YES | NO | NO | NO |
| TJU_CMC_MD2.ID02208.5p-miR | TJU_CMC_MD2.ID02208.hairpin | YES | YES | YES | NO | NO | NO | NO | NO |
| TJU_CMC_MD2.ID02209.3p-miR | TJU_CMC_MD2.ID02209.hairpin | YES | NO | NO | NO | NO | NO | NO | NO |
| TJU_CMC_MD2.ID02210.5p-miR | TJU_CMC_MD2.ID02210.hairpin | YES | NO | NO | NO | NO | NO | NO | NO |
| TJU_CMC_MD2.ID02211.5p-miR | TJU_CMC_MD2.ID02211.hairpin | YES | YES | YES | YES | YES | NO | NO | NO |
| TJU_CMC_MD2.ID02212.5p-miR | TJU_CMC_MD2.ID02212.hairpin | YES | NO | YES | NO | YES | NO | NO | NO |
| TJU_CMC_MD2.ID02213.3p-miR | TJU_CMC_MD2.ID02213.hairpin | YES | NO | NO | NO | NO | NO | NO | NO |
| TJU_CMC_MD2.ID02214.3p-miR | TJU_CMC_MD2.ID02214.hairpin | YES | NO | NO | NO | NO | NO | NO | NO |
| TJU_CMC_MD2.ID02215.5p-miR | TJU_CMC_MD2.ID02215.hairpin | YES | NO | YES | NO | YES | NO | NO | NO |
| TJU_CMC_MD2.ID02216.3p-miR | TJU_CMC_MD2.ID02216.hairpin | YES | NO | NO | NO | NO | NO | NO | NO |
| TJU_CMC_MD2.ID02217.5p-miR | TJU_CMC_MD2.ID02217.hairpin | YES | NO | YES | NO | NO | NO | NO | NO |
| TJU_CMC_MD2.ID02218.3p-miR | TJU_CMC_MD2.ID02218.hairpin | YES | NO | NO | NO | NO | NO | NO | NO |
| TJU_CMC_MD2.ID02219.3p-miR | TJU_CMC_MD2.ID02219.hairpin | YES | NO | NO | NO | NO | NO | NO | NO |
| TJU_CMC_MD2.ID02220.5p-miR | TJU_CMC_MD2.ID02220.hairpin | YES | YES | YES | YES | YES | NO | NO | NO |
| TJU_CMC_MD2.ID02221.3p-miR | TJU_CMC_MD2.ID02221.hairpin | YES | NO | NO | NO | NO | NO | NO | NO |
| TJU_CMC_MD2.ID02222.3p-miR | TJU_CMC_MD2.ID02222.hairpin | YES | NO | NO | NO | NO | NO | NO | NO |
| TJU_CMC_MD2.ID02223.3p-miR | TJU_CMC_MD2.ID02223.hairpin | YES | NO | NO | NO | NO | NO | NO | NO |
| TJU_CMC_MD2.ID02224.3p-miR | TJU_CMC_MD2.ID02224.hairpin | YES | NO | NO | NO | NO | NO | NO | NO |
| TJU_CMC_MD2.ID02224.5p-miR | TJU_CMC_MD2.ID02224.hairpin | YES | YES | YES | YES | YES | NO | NO | NO |
| TJU_CMC_MD2.ID02225.5p-miR | TJU_CMC_MD2.ID02225.hairpin | YES | YES | YES | YES | NO | NO | NO | NO |
| TJU_CMC_MD2.ID02226.3p-miR | TJU_CMC_MD2.ID02226.hairpin | YES | NO | NO | NO | NO | NO | NO | NO |
| TJU_CMC_MD2.ID02227.3p-miR | TJU_CMC_MD2.ID02227.hairpin | YES | NO | NO | NO | NO | NO | NO | NO |
| TJU_CMC_MD2.ID02228.3p-miR | TJU_CMC_MD2.ID02228.hairpin | YES | NO | NO | NO | NO | NO | NO | NO |
| TJU_CMC_MD2.ID02229.3p-miR | TJU_CMC_MD2.ID02229.hairpin | YES | NO | NO | NO | NO | NO | NO | NO |
| TJU_CMC_MD2.ID02230.3p-miR | TJU_CMC_MD2.ID02230.hairpin | YES | NO | NO | NO | NO | NO | NO | NO |
| TJU_CMC_MD2.ID02231.3p-miR | TJU_CMC_MD2.ID02231.hairpin | YES | NO | NO | NO | NO | NO | NO | NO |
| TJU_CMC_MD2.ID02232.3p-miR | TJU_CMC_MD2.ID02232.hairpin | YES | NO | NO | NO | NO | NO | NO | NO |
| TJU_CMC_MD2.ID02233.3p-miR | TJU_CMC_MD2.ID02233.hairpin | YES | NO | NO | NO | NO | NO | NO | NO |
| TJU_CMC_MD2.ID02234.5p-miR | TJU_CMC_MD2.ID02234.hairpin | YES | NO | YES | NO | YES | NO | NO | NO |
| TJU_CMC_MD2.ID02235.5p-miR | TJU_CMC_MD2.ID02235.hairpin | YES | NO | NO | NO | NO | NO | NO | NO |
| TJU_CMC_MD2.ID02236.3p-miR | TJU_CMC_MD2.ID02236.hairpin | YES | NO | NO | NO | NO | NO | NO | NO |
| TJU_CMC_MD2.ID02236.5p-miR | TJU_CMC_MD2.ID02236.hairpin | YES | YES | YES | YES | YES | NO | NO | NO |
| TJU_CMC_MD2.ID02237.3p-miR | TJU_CMC_MD2.ID02237.hairpin | YES | NO | NO | NO | NO | NO | NO | NO |
| TJU_CMC_MD2.ID02237.5p-miR | TJU_CMC_MD2.ID02237.hairpin | YES | NO | YES | NO | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02238.5p-miR | TJU_CMC_MD2.ID02238.hairpin | YES | NO | YES | NO | NO | NO | NO | NO |
| TJU_CMC_MD2.ID02239.3p-miR | TJU_CMC_MD2.ID02239.hairpin | YES | NO | NO | NO | NO | NO | NO | NO |
| TJU_CMC_MD2.ID02240.3p-miR | TJU_CMC_MD2.ID02240.hairpin | YES | NO | NO | NO | NO | NO | NO | NO |
| TJU_CMC_MD2.ID02241.3p-miR | TJU_CMC_MD2.ID02241.hairpin | YES | NO | NO | NO | NO | NO | NO | NO |
| TJU_CMC_MD2.ID02242.3p-miR | TJU_CMC_MD2.ID02242.hairpin | YES | NO | NO | NO | NO | NO | NO | NO |
| TJU_CMC_MD2.ID02243.5p-miR | TJU_CMC_MD2.ID02243.hairpin | YES | YES | YES | YES | YES | YES | NO | NO |
| TJU_CMC_MD2.ID02244.3p-miR | TJU_CMC_MD2.ID02244.hairpin | YES | NO | NO | NO | NO | NO | NO | NO |
| TJU_CMC_MD2.ID02245.5p-miR | TJU_CMC_MD2.ID02245.hairpin | YES | NO | YES | NO | NO | NO | NO | NO |
| TJU_CMC_MD2.ID02246.3p-miR | TJU_CMC_MD2.ID02246.hairpin | YES | NO | NO | NO | NO | NO | NO | NO |
| TJU_CMC_MD2.ID02247.3p-miR | TJU_CMC_MD2.ID02247.hairpin | YES | NO | NO | NO | NO | NO | NO | NO |
| TJU_CMC_MD2.ID02248.5p-miR | TJU_CMC_MD2.ID02248.hairpin | YES | NO | YES | NO | YES | NO | NO | NO |
| TJU_CMC_MD2.ID02249.3p-miR | TJU_CMC_MD2.ID02249.hairpin | YES | NO | NO | NO | NO | NO | NO | NO |
| TJU_CMC_MD2.ID02250.3p-miR | TJU_CMC_MD2.ID02250.hairpin | YES | NO | NO | NO | NO | NO | NO | NO |
| TJU_CMC_MD2.ID02251.5p-miR | TJU_CMC_MD2.ID02251.hairpin | YES | NO | NO | NO | NO | NO | NO | NO |
| TJU_CMC_MD2.ID02252.3p-miR | TJU_CMC_MD2.ID02252.hairpin | YES | NO | NO | NO | NO | NO | NO | NO |
| TJU_CMC_MD2.ID02253.3p-miR | TJU_CMC_MD2.ID02253.hairpin | YES | NO | NO | NO | NO | NO | NO | NO |
| TJU_CMC_MD2.ID02254.5p-miR | TJU_CMC_MD2.ID02254.hairpin | YES | NO | NO | NO | NO | NO | NO | NO |
| TJU_CMC_MD2.ID02255.5p-miR | TJU_CMC_MD2.ID02255.hairpin | YES | NO | NO | NO | NO | NO | NO | NO |
| TJU_CMC_MD2.ID02256.3p-miR | TJU_CMC_MD2.ID02256.hairpin | YES | NO | NO | NO | NO | NO | NO | NO |
| TJU_CMC_MD2.ID02257.3p-miR | TJU_CMC_MD2.ID02257.hairpin | YES | NO | NO | NO | NO | NO | NO | NO |
| TJU_CMC_MD2.ID02258.3p-miR | TJU_CMC_MD2.ID02258.hairpin | YES | NO | NO | NO | NO | NO | NO | NO |
| TJU_CMC_MD2.ID02259.5p-miR | TJU_CMC_MD2.ID02259.hairpin | YES | NO | YES | NO | NO | NO | NO | NO |
| TJU_CMC_MD2.ID02260.5p-miR | TJU_CMC_MD2.ID02260.hairpin | YES | NO | NO | NO | NO | NO | NO | NO |
| TJU_CMC_MD2.ID02261.5p-miR | TJU_CMC_MD2.ID02261.hairpin | YES | YES | YES | NO | YES | NO | NO | NO |
| TJU_CMC_MD2.ID02262.3p-miR | TJU_CMC_MD2.ID02262.hairpin | YES | NO | NO | NO | NO | NO | NO | NO |
| TJU_CMC_MD2.ID02263.3p-miR | TJU_CMC_MD2.ID02263.hairpin | YES | NO | NO | NO | NO | NO | NO | NO |
| TJU_CMC_MD2.ID02264.3p-miR | TJU_CMC_MD2.ID02264.hairpin | YES | NO | NO | NO | NO | NO | NO | NO |
| TJU_CMC_MD2.ID02264.5p-miR | TJU_CMC_MD2.ID02264.hairpin | YES | NO | YES | NO | YES | NO | NO | NO |
| TJU_CMC_MD2.ID02265.5p-miR | TJU_CMC_MD2.ID02265.hairpin | YES | NO | YES | NO | YES | NO | NO | NO |
| TJU_CMC_MD2.ID02266.5p-miR | TJU_CMC_MD2.ID02266.hairpin | YES | NO | YES | NO | NO | NO | NO | NO |
| TJU_CMC_MD2.ID02267.3p-miR | TJU_CMC_MD2.ID02267.hairpin | YES | NO | NO | NO | NO | NO | NO | NO |
| TJU_CMC_MD2.ID02268.3p-miR | TJU_CMC_MD2.ID02268.hairpin | YES | NO | NO | NO | NO | NO | NO | NO |
| TJU_CMC_MD2.ID02269.3p-miR | TJU_CMC_MD2.ID02269.hairpin | YES | NO | NO | NO | NO | NO | NO | NO |
| TJU_CMC_MD2.ID02270.3p-miR | TJU_CMC_MD2.ID02270.hairpin | YES | NO | NO | NO | NO | NO | NO | NO |
| TJU_CMC_MD2.ID02271.3p-miR | TJU_CMC_MD2.ID02271.hairpin | YES | NO | NO | NO | NO | NO | NO | NO |
| TJU_CMC_MD2.ID02272.5p-miR | TJU_CMC_MD2.ID02272.hairpin | YES | YES | YES | YES | NO | NO | NO | NO |
| TJU_CMC_MD2.ID02273.3p-miR | TJU_CMC_MD2.ID02273.hairpin | YES | NO | NO | NO | NO | NO | NO | NO |
| TJU_CMC_MD2.ID02274.3p-miR | TJU_CMC_MD2.ID02274.hairpin | YES | NO | NO | NO | NO | NO | NO | NO |
| TJU_CMC_MD2.ID02275.5p-miR | TJU_CMC_MD2.ID02275.hairpin | YES | YES | YES | YES | YES | NO | NO | NO |
| TJU_CMC_MD2.ID02276.3p-miR | TJU_CMC_MD2.ID02276.hairpin | YES | NO | NO | NO | NO | NO | NO | NO |
| TJU_CMC_MD2.ID02276.5p-miR | TJU_CMC_MD2.ID02276.hairpin | YES | NO | YES | NO | NO | NO | NO | NO |
| TJU_CMC_MD2.ID02277.3p-miR | TJU_CMC_MD2.ID02277.hairpin | YES | NO | NO | NO | NO | NO | NO | NO |
| TJU_CMC_MD2.ID02277.5p-miR | TJU_CMC_MD2.ID02277.hairpin | YES | YES | YES | YES | NO | NO | NO | NO |
| TJU_CMC_MD2.ID02278.5p-miR | TJU_CMC_MD2.ID02278.hairpin | YES | NO | NO | NO | NO | NO | NO | NO |
| TJU_CMC_MD2.ID02279.3p-miR | TJU_CMC_MD2.ID02279.hairpin | YES | YES | YES | NO | NO | NO | NO | NO |
| TJU_CMC_MD2.ID02280.3p-miR | TJU_CMC_MD2.ID02280.hairpin | YES | NO | NO | NO | NO | NO | NO | NO |
| TJU_CMC_MD2.ID02280.5p-miR | TJU_CMC_MD2.ID02280.hairpin | YES | YES | YES | YES | NO | NO | NO | NO |
| TJU_CMC_MD2.ID02281.5p-miR | TJU_CMC_MD2.ID02281.hairpin | YES | YES | YES | YES | YES | NO | NO | NO |
| TJU_CMC_MD2.ID02282.5p-miR | TJU_CMC_MD2.ID02282.hairpin | YES | YES | NO | YES | NO | NO | NO | NO |
| TJU_CMC_MD2.ID02283.3p-miR | TJU_CMC_MD2.ID02283.hairpin | YES | NO | NO | NO | NO | NO | NO | NO |
| TJU_CMC_MD2.ID02284.3p-miR | TJU_CMC_MD2.ID02284.hairpin | YES | NO | NO | NO | NO | NO | NO | NO |
| TJU_CMC_MD2.ID02285.5p-miR | TJU_CMC_MD2.ID02285.hairpin | YES | NO | YES | NO | NO | NO | NO | NO |
| TJU_CMC_MD2.ID02286.3p-miR | TJU_CMC_MD2.ID02286.hairpin | YES | NO | NO | NO | NO | NO | NO | NO |
| TJU_CMC_MD2.ID02287.5p-miR | TJU_CMC_MD2.ID02287.hairpin | YES | YES | YES | NO | NO | NO | NO | NO |
| TJU_CMC_MD2.ID02288.5p-miR | TJU_CMC_MD2.ID02288.hairpin | YES | YES | YES | YES | YES | NO | NO | NO |
| TJU_CMC_MD2.ID02289.3p-miR | TJU_CMC_MD2.ID02289.hairpin | YES | NO | NO | NO | NO | NO | NO | NO |
| TJU_CMC_MD2.ID02289.5p-miR | TJU_CMC_MD2.ID02289.hairpin | YES | YES | YES | NO | NO | NO | NO | NO |
| TJU_CMC_MD2.ID02290.3p-miR | TJU_CMC_MD2.ID02290.hairpin | YES | YES | YES | NO | YES | NO | NO | NO |
| TJU_CMC_MD2.ID02290.5p-miR | TJU_CMC_MD2.ID02290.hairpin | YES | YES | YES | NO | YES | NO | NO | NO |
| TJU_CMC_MD2.ID02291.3p-miR | TJU_CMC_MD2.ID02291.hairpin | YES | NO | NO | NO | NO | NO | NO | NO |
| TJU_CMC_MD2.ID02291.5p-miR | TJU_CMC_MD2.ID02291.hairpin | YES | YES | YES | YES | YES | NO | NO | NO |
| TJU_CMC_MD2.ID02292.5p-miR | TJU_CMC_MD2.ID02292.hairpin | YES | YES | NO | NO | NO | NO | NO | NO |
| TJU_CMC_MD2.ID02293.3p-miR | TJU_CMC_MD2.ID02293.hairpin | YES | NO | NO | NO | NO | NO | NO | NO |
| TJU_CMC_MD2.ID02294.5p-miR | TJU_CMC_MD2.ID02294.hairpin | YES | NO | NO | NO | NO | NO | NO | NO |
| TJU_CMC_MD2.ID02295.3p-miR | TJU_CMC_MD2.ID02295.hairpin | YES | NO | NO | NO | NO | NO | NO | NO |
| TJU_CMC_MD2.ID02295.5p-miR | TJU_CMC_MD2.ID02295.hairpin | YES | YES | NO | YES | NO | NO | NO | NO |
| TJU_CMC_MD2.ID02296.5p-miR | TJU_CMC_MD2.ID02296.hairpin | YES | YES | NO | YES | NO | NO | NO | NO |
| TJU_CMC_MD2.ID02297.3p-miR | TJU_CMC_MD2.ID02297.hairpin | YES | NO | NO | NO | NO | NO | NO | NO |
| TJU_CMC_MD2.ID02298.3p-miR | TJU_CMC_MD2.ID02298.hairpin | YES | NO | NO | NO | NO | NO | NO | NO |
| TJU_CMC_MD2.ID02299.5p-miR | TJU_CMC_MD2.ID02299.hairpin | YES | NO | YES | NO | NO | NO | NO | NO |
| TJU_CMC_MD2.ID02300.3p-miR | TJU_CMC_MD2.ID02300.hairpin | YES | NO | NO | NO | NO | NO | NO | NO |
| TJU_CMC_MD2.ID02301.5p-miR | TJU_CMC_MD2.ID02301.hairpin | YES | YES | YES | NO | NO | NO | NO | NO |
| TJU_CMC_MD2.ID02302.3p-miR | TJU_CMC_MD2.ID02302.hairpin | YES | NO | NO | NO | NO | NO | NO | NO |
| TJU_CMC_MD2.ID02303.5p-miR | TJU_CMC_MD2.ID02303.hairpin | YES | YES | YES | YES | NO | NO | NO | NO |
| TJU_CMC_MD2.ID02304.5p-miR | TJU_CMC_MD2.ID02304.hairpin | YES | YES | NO | YES | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02305.3p-miR | TJU_CMC_MD2.ID02305.hairpin | YES | NO | NO | NO | NO | NO | NO | NO |
| TJU_CMC_MD2.ID02306.3p-miR | TJU_CMC_MD2.ID02306.hairpin | YES | NO | NO | NO | NO | NO | NO | NO |
| TJU_CMC_MD2.ID02307.3p-miR | TJU_CMC_MD2.ID02307.hairpin | YES | NO | NO | NO | NO | NO | NO | NO |
| TJU_CMC_MD2.ID02308.3p-miR | TJU_CMC_MD2.ID02308.hairpin | YES | NO | NO | NO | NO | NO | NO | NO |
| TJU_CMC_MD2.ID02309.3p-miR | TJU_CMC_MD2.ID02309.hairpin | YES | NO | NO | NO | NO | NO | NO | NO |
| TJU_CMC_MD2.ID02310.3p-miR | TJU_CMC_MD2.ID02310.hairpin | YES | NO | NO | NO | NO | NO | NO | NO |
| TJU_CMC_MD2.ID02311.3p-miR | TJU_CMC_MD2.ID02311.hairpin | YES | NO | NO | NO | NO | NO | NO | NO |
| TJU_CMC_MD2.ID02312.5p-miR | TJU_CMC_MD2.ID02312.hairpin | YES | YES | YES | YES | YES | NO | NO | NO |
| TJU_CMC_MD2.ID02313.3p-miR | TJU_CMC_MD2.ID02313.hairpin | YES | NO | NO | NO | NO | NO | NO | NO |
| TJU_CMC_MD2.ID02314.3p-miR | TJU_CMC_MD2.ID02314.hairpin | YES | NO | NO | NO | NO | NO | NO | NO |
| TJU_CMC_MD2.ID02315.3p-miR | TJU_CMC_MD2.ID02315.hairpin | YES | NO | NO | NO | NO | NO | NO | NO |
| TJU_CMC_MD2.ID02316.3p-miR | TJU_CMC_MD2.ID02316.hairpin | YES | NO | NO | NO | NO | NO | NO | NO |
| TJU_CMC_MD2.ID02317.3p-miR | TJU_CMC_MD2.ID02317.hairpin | YES | NO | NO | NO | NO | NO | NO | NO |
| TJU_CMC_MD2.ID02318.5p-miR | TJU_CMC_MD2.ID02318.hairpin | YES | YES | YES | YES | YES | NO | NO | NO |
| TJU_CMC_MD2.ID02319.3p-miR | TJU_CMC_MD2.ID02319.hairpin | YES | NO | NO | NO | NO | NO | NO | NO |
| TJU_CMC_MD2.ID02320.3p-miR | TJU_CMC_MD2.ID02320.hairpin | YES | NO | NO | NO | NO | NO | NO | NO |
| TJU_CMC_MD2.ID02321.5p-miR | TJU_CMC_MD2.ID02321.hairpin | YES | YES | YES | YES | YES | NO | NO | NO |
| TJU_CMC_MD2.ID02322.5p-miR | TJU_CMC_MD2.ID02322.hairpin | YES | YES | NO | YES | NO | NO | NO | NO |
| TJU_CMC_MD2.ID02323.3p-miR | TJU_CMC_MD2.ID02323.hairpin | YES | NO | NO | NO | NO | NO | NO | NO |
| TJU_CMC_MD2.ID02324.3p-miR | TJU_CMC_MD2.ID02324.hairpin | YES | NO | NO | NO | NO | NO | NO | NO |
| TJU_CMC_MD2.ID02325.3p-miR | TJU_CMC_MD2.ID02325.hairpin | YES | NO | NO | NO | NO | NO | NO | NO |
| TJU_CMC_MD2.ID02325.5p-miR | TJU_CMC_MD2.ID02325.hairpin | YES | YES | YES | YES | YES | NO | NO | NO |
| TJU_CMC_MD2.ID02326.5p-miR | TJU_CMC_MD2.ID02326.hairpin | YES | YES | NO | NO | NO | NO | NO | NO |
| TJU_CMC_MD2.ID02327.5p-miR | TJU_CMC_MD2.ID02327.hairpin | YES | YES | YES | YES | YES | YES | NO | NO |
| TJU_CMC_MD2.ID02328.5p-miR | TJU_CMC_MD2.ID02328.hairpin | YES | YES | YES | NO | YES | NO | NO | NO |
| TJU_CMC_MD2.ID02329.3p-miR | TJU_CMC_MD2.ID02329.hairpin | YES | NO | NO | NO | NO | NO | NO | NO |
| TJU_CMC_MD2.ID02330.3p-miR | TJU_CMC_MD2.ID02330.hairpin | YES | NO | NO | NO | NO | NO | NO | NO |
| TJU_CMC_MD2.ID02331.3p-miR | TJU_CMC_MD2.ID02331.hairpin | YES | NO | NO | NO | NO | NO | NO | NO |
| TJU_CMC_MD2.ID02332.3p-miR | TJU_CMC_MD2.ID02332.hairpin | YES | NO | NO | NO | NO | NO | NO | NO |
| TJU_CMC_MD2.ID02333.3p-miR | TJU_CMC_MD2.ID02333.hairpin | YES | NO | NO | NO | NO | NO | NO | NO |
| TJU_CMC_MD2.ID02334.5p-miR | TJU_CMC_MD2.ID02334.hairpin | YES | YES | YES | YES | NO | NO | NO | NO |
| TJU_CMC_MD2.ID02335.5p-miR | TJU_CMC_MD2.ID02335.hairpin | YES | YES | YES | NO | YES | NO | NO | NO |
| TJU_CMC_MD2.ID02336.3p-miR | TJU_CMC_MD2.ID02336.hairpin | YES | NO | NO | NO | NO | NO | NO | NO |
| TJU_CMC_MD2.ID02337.3p-miR | TJU_CMC_MD2.ID02337.hairpin | YES | NO | NO | NO | NO | NO | NO | NO |
| TJU_CMC_MD2.ID02338.3p-miR | TJU_CMC_MD2.ID02338.hairpin | YES | NO | NO | NO | NO | NO | NO | NO |
| TJU_CMC_MD2.ID02338.5p-miR | TJU_CMC_MD2.ID02338.hairpin | YES | YES | YES | YES | YES | NO | NO | NO |
| TJU_CMC_MD2.ID02339.5p-miR | TJU_CMC_MD2.ID02339.hairpin | YES | NO | YES | YES | YES | NO | NO | NO |
| TJU_CMC_MD2.ID02340.3p-miR | TJU_CMC_MD2.ID02340.hairpin | YES | NO | NO | NO | NO | NO | NO | NO |
| TJU_CMC_MD2.ID02341.3p-miR | TJU_CMC_MD2.ID02341.hairpin | YES | NO | NO | NO | NO | NO | NO | NO |
| TJU_CMC_MD2.ID02342.5p-miR | TJU_CMC_MD2.ID02342.hairpin | YES | NO | NO | YES | NO | NO | NO | NO |
| TJU_CMC_MD2.ID02343.3p-miR | TJU_CMC_MD2.ID02343.hairpin | YES | NO | NO | NO | NO | NO | NO | NO |
| TJU_CMC_MD2.ID02344.3p-miR | TJU_CMC_MD2.ID02344.hairpin | YES | NO | NO | NO | NO | NO | NO | NO |
| TJU_CMC_MD2.ID02345.3p-miR | TJU_CMC_MD2.ID02345.hairpin | YES | NO | NO | NO | NO | NO | NO | NO |
| TJU_CMC_MD2.ID02346.3p-miR | TJU_CMC_MD2.ID02346.hairpin | YES | NO | NO | NO | NO | NO | NO | NO |
| TJU_CMC_MD2.ID02347.5p-miR | TJU_CMC_MD2.ID02347.hairpin | YES | YES | YES | YES | NO | NO | NO | NO |
| TJU_CMC_MD2.ID02348.3p-miR | TJU_CMC_MD2.ID02348.hairpin | YES | NO | NO | NO | NO | NO | NO | NO |
| TJU_CMC_MD2.ID02348.5p-miR | TJU_CMC_MD2.ID02348.hairpin | YES | YES | YES | YES | YES | NO | NO | NO |
| TJU_CMC_MD2.ID02349.3p-miR | TJU_CMC_MD2.ID02349.hairpin | YES | NO | NO | NO | NO | NO | NO | NO |
| TJU_CMC_MD2.ID02350.5p-miR | TJU_CMC_MD2.ID02350.hairpin | YES | YES | YES | YES | NO | NO | NO | NO |
| TJU_CMC_MD2.ID02351.5p-miR | TJU_CMC_MD2.ID02351.hairpin | YES | YES | YES | YES | NO | NO | NO | NO |
| TJU_CMC_MD2.ID02352.5p-miR | TJU_CMC_MD2.ID02352.hairpin | YES | YES | YES | YES | YES | NO | NO | NO |
| TJU_CMC_MD2.ID02353.3p-miR | TJU_CMC_MD2.ID02353.hairpin | YES | NO | NO | NO | NO | NO | NO | NO |
| TJU_CMC_MD2.ID02354.3p-miR | TJU_CMC_MD2.ID02354.hairpin | YES | YES | YES | YES | YES | NO | NO | NO |
| TJU_CMC_MD2.ID02355.3p-miR | TJU_CMC_MD2.ID02355.hairpin | YES | NO | NO | NO | NO | NO | NO | NO |
| TJU_CMC_MD2.ID02355.5p-miR | TJU_CMC_MD2.ID02355.hairpin | YES | YES | YES | YES | NO | NO | NO | NO |
| TJU_CMC_MD2.ID02356.3p-miR | TJU_CMC_MD2.ID02356.hairpin | YES | NO | NO | NO | NO | NO | NO | NO |
| TJU_CMC_MD2.ID02357.3p-miR | TJU_CMC_MD2.ID02357.hairpin | YES | NO | NO | NO | NO | NO | NO | NO |
| TJU_CMC_MD2.ID02358.3p-miR | TJU_CMC_MD2.ID02358.hairpin | YES | NO | NO | NO | NO | NO | NO | NO |
| TJU_CMC_MD2.ID02359.5p-miR | TJU_CMC_MD2.ID02359.hairpin | YES | YES | YES | NO | NO | NO | NO | NO |
| TJU_CMC_MD2.ID02360.5p-miR | TJU_CMC_MD2.ID02360.hairpin | YES | YES | NO | YES | NO | NO | NO | NO |
| TJU_CMC_MD2.ID02361.3p-miR | TJU_CMC_MD2.ID02361.hairpin | YES | NO | NO | NO | NO | NO | NO | NO |
| TJU_CMC_MD2.ID02362.5p-miR | TJU_CMC_MD2.ID02362.hairpin | YES | YES | YES | YES | NO | NO | NO | NO |
| TJU_CMC_MD2.ID02363.5p-miR | TJU_CMC_MD2.ID02363.hairpin | YES | YES | NO | YES | NO | NO | NO | NO |
| TJU_CMC_MD2.ID02364.3p-miR | TJU_CMC_MD2.ID02364.hairpin | YES | NO | NO | NO | NO | NO | NO | NO |
| TJU_CMC_MD2.ID02365.5p-miR | TJU_CMC_MD2.ID02365.hairpin | YES | YES | YES | YES | NO | NO | NO | NO |
| TJU_CMC_MD2.ID02366.3p-miR | TJU_CMC_MD2.ID02366.hairpin | YES | NO | NO | NO | NO | NO | NO | NO |
| TJU_CMC_MD2.ID02367.3p-miR | TJU_CMC_MD2.ID02367.hairpin | YES | NO | NO | NO | NO | NO | NO | NO |
| TJU_CMC_MD2.ID02367.5p-miR | TJU_CMC_MD2.ID02367.hairpin | YES | YES | YES | NO | YES | NO | NO | NO |
| TJU_CMC_MD2.ID02368.3p-miR | TJU_CMC_MD2.ID02368.hairpin | YES | NO | NO | NO | NO | NO | NO | NO |
| TJU_CMC_MD2.ID02369.5p-miR | TJU_CMC_MD2.ID02369.hairpin | YES | YES | YES | YES | YES | NO | NO | NO |
| TJU_CMC_MD2.ID02370.3p-miR | TJU_CMC_MD2.ID02370.hairpin | YES | NO | NO | NO | NO | NO | NO | NO |
| TJU_CMC_MD2.ID02371.5p-miR | TJU_CMC_MD2.ID02371.hairpin | YES | YES | YES | NO | YES | NO | NO | NO |
| TJU_CMC_MD2.ID02372.3p-miR | TJU_CMC_MD2.ID02372.hairpin | YES | NO | NO | NO | NO | NO | NO | NO |
| TJU_CMC_MD2.ID02373.5p-miR | TJU_CMC_MD2.ID02373.hairpin | YES | YES | YES | YES | NO | NO | NO | NO |
| TJU_CMC_MD2.ID02374.3p-miR | TJU_CMC_MD2.ID02374.hairpin | YES | NO | NO | NO | NO | NO | NO | NO |

TABLE 7-continued

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02375.3p-miR | TJU_CMC_MD2.ID02375.hairpin | YES | NO | NO | NO | NO | NO | NO | NO |
| TJU_CMC_MD2.ID02376.3p-miR | TJU_CMC_MD2.ID02376.hairpin | YES | YES | YES | YES | YES | NO | NO | NO |
| TJU_CMC_MD2.ID02376.5p-miR | TJU_CMC_MD2.ID02376.hairpin | YES | YES | YES | YES | NO | NO | NO | NO |
| TJU_CMC_MD2.ID02377.5p-miR | TJU_CMC_MD2.ID02377.hairpin | YES | NO | YES | YES | YES | NO | NO | NO |
| TJU_CMC_MD2.ID02378.5p-miR | TJU_CMC_MD2.ID02378.hairpin | YES | YES | NO | NO | NO | NO | NO | NO |
| TJU_CMC_MD2.ID02379.3p-miR | TJU_CMC_MD2.ID02379.hairpin | YES | NO | NO | NO | NO | NO | NO | NO |
| TJU_CMC_MD2.ID02380.5p-miR | TJU_CMC_MD2.ID02380.hairpin | YES | YES | YES | YES | NO | NO | NO | NO |
| TJU_CMC_MD2.ID02381.3p-miR | TJU_CMC_MD2.ID02381.hairpin | YES | YES | YES | NO | NO | NO | NO | NO |
| TJU_CMC_MD2.ID02382.3p-miR | TJU_CMC_MD2.ID02382.hairpin | YES | NO | NO | NO | NO | NO | NO | NO |
| TJU_CMC_MD2.ID02383.5p-miR | TJU_CMC_MD2.ID02383.hairpin | YES | YES | YES | NO | NO | NO | NO | NO |
| TJU_CMC_MD2.ID02384.5p-miR | TJU_CMC_MD2.ID02384.hairpin | YES | YES | YES | YES | NO | NO | NO | NO |
| TJU_CMC_MD2.ID02385.3p-miR | TJU_CMC_MD2.ID02385.hairpin | YES | NO | NO | NO | NO | NO | NO | NO |
| TJU_CMC_MD2.ID02386.3p-miR | TJU_CMC_MD2.ID02386.hairpin | YES | NO | NO | NO | NO | NO | NO | NO |
| TJU_CMC_MD2.ID02387.5p-miR | TJU_CMC_MD2.ID02387.hairpin | YES | YES | YES | YES | YES | NO | NO | NO |
| TJU_CMC_MD2.ID02388.3p-miR | TJU_CMC_MD2.ID02388.hairpin | YES | NO | NO | NO | NO | NO | NO | NO |
| TJU_CMC_MD2.ID02389.3p-miR | TJU_CMC_MD2.ID02389.hairpin | YES | NO | NO | NO | NO | NO | NO | NO |
| TJU_CMC_MD2.ID02390.3p-miR | TJU_CMC_MD2.ID02390.hairpin | YES | NO | NO | NO | NO | NO | NO | NO |
| TJU_CMC_MD2.ID02391.3p-miR | TJU_CMC_MD2.ID02391.hairpin | YES | YES | NO | YES | YES | NO | NO | NO |
| TJU_CMC_MD2.ID02392.3p-miR | TJU_CMC_MD2.ID02392.hairpin | YES | NO | NO | NO | NO | NO | NO | NO |
| TJU_CMC_MD2.ID02393.5p-miR | TJU_CMC_MD2.ID02393.hairpin | YES | YES | YES | YES | YES | NO | NO | NO |
| TJU_CMC_MD2.ID02394.5p-miR | TJU_CMC_MD2.ID02394.hairpin | YES | NO | NO | NO | NO | NO | NO | NO |
| TJU_CMC_MD2.ID02395.3p-miR | TJU_CMC_MD2.ID02395.hairpin | YES | NO | NO | NO | NO | NO | NO | NO |
| TJU_CMC_MD2.ID02396.3p-miR | TJU_CMC_MD2.ID02396.hairpin | YES | NO | NO | NO | NO | NO | NO | NO |
| TJU_CMC_MD2.ID02396.5p-miR | TJU_CMC_MD2.ID02396.hairpin | YES | NO | YES | NO | NO | NO | NO | NO |
| TJU_CMC_MD2.ID02397.3p-miR | TJU_CMC_MD2.ID02397.hairpin | YES | NO | NO | NO | NO | NO | NO | NO |
| TJU_CMC_MD2.ID02398.3p-miR | TJU_CMC_MD2.ID02398.hairpin | YES | NO | NO | NO | NO | NO | NO | NO |
| TJU_CMC_MD2.ID02399.3p-miR | TJU_CMC_MD2.ID02399.hairpin | YES | NO | NO | NO | NO | NO | NO | NO |
| TJU_CMC_MD2.ID02400.5p-miR | TJU_CMC_MD2.ID02400.hairpin | YES | YES | YES | YES | YES | NO | NO | NO |
| TJU_CMC_MD2.ID02401.3p-miR | TJU_CMC_MD2.ID02401.hairpin | YES | NO | NO | NO | NO | NO | NO | NO |
| TJU_CMC_MD2.ID02402.3p-miR | TJU_CMC_MD2.ID02402.hairpin | YES | YES | YES | YES | YES | NO | NO | NO |
| TJU_CMC_MD2.ID02403.3p-miR | TJU_CMC_MD2.ID02403.hairpin | YES | NO | NO | NO | NO | NO | NO | NO |
| TJU_CMC_MD2.ID02404.3p-miR | TJU_CMC_MD2.ID02404.hairpin | YES | NO | NO | NO | NO | NO | NO | NO |
| TJU_CMC_MD2.ID02405.5p-miR | TJU_CMC_MD2.ID02405.hairpin | YES | YES | YES | YES | YES | NO | NO | NO |
| TJU_CMC_MD2.ID02406.5p-miR | TJU_CMC_MD2.ID02406.hairpin | YES | YES | YES | YES | YES | NO | NO | NO |
| TJU_CMC_MD2.ID02407.3p-miR | TJU_CMC_MD2.ID02407.hairpin | YES | NO | NO | NO | NO | NO | NO | NO |
| TJU_CMC_MD2.ID02408.3p-miR | TJU_CMC_MD2.ID02408.hairpin | YES | NO | NO | NO | NO | NO | NO | NO |
| TJU_CMC_MD2.ID02409.3p-miR | TJU_CMC_MD2.ID02409.hairpin | YES | NO | NO | NO | NO | NO | NO | NO |
| TJU_CMC_MD2.ID02410.3p-miR | TJU_CMC_MD2.ID02410.hairpin | YES | NO | NO | NO | NO | NO | NO | NO |
| TJU_CMC_MD2.ID02410.5p-miR | TJU_CMC_MD2.ID02410.hairpin | YES | YES | YES | NO | NO | NO | NO | NO |
| TJU_CMC_MD2.ID02411.3p-miR | TJU_CMC_MD2.ID02411.hairpin | YES | YES | YES | YES | YES | NO | NO | NO |
| TJU_CMC_MD2.ID02411.5p-miR | TJU_CMC_MD2.ID02411.hairpin | YES | YES | YES | YES | NO | NO | NO | NO |
| TJU_CMC_MD2.ID02412.3p-miR | TJU_CMC_MD2.ID02412.hairpin | YES | NO | NO | NO | NO | NO | NO | NO |
| TJU_CMC_MD2.ID02413.5p-miR | TJU_CMC_MD2.ID02413.hairpin | YES | NO | NO | NO | NO | NO | NO | NO |
| TJU_CMC_MD2.ID02414.3p-miR | TJU_CMC_MD2.ID02414.hairpin | YES | NO | NO | NO | NO | NO | NO | NO |
| TJU_CMC_MD2.ID02415.3p-miR | TJU_CMC_MD2.ID02415.hairpin | YES | NO | NO | NO | NO | NO | NO | NO |
| TJU_CMC_MD2.ID02416.5p-miR | TJU_CMC_MD2.ID02416.hairpin | YES | YES | YES | YES | NO | NO | NO | NO |
| TJU_CMC_MD2.ID02417.5p-miR | TJU_CMC_MD2.ID02417.hairpin | YES | YES | YES | YES | YES | NO | NO | NO |
| TJU_CMC_MD2.ID02418.3p-miR | TJU_CMC_MD2.ID02418.hairpin | YES | NO | NO | NO | NO | NO | NO | NO |
| TJU_CMC_MD2.ID02419.3p-miR | TJU_CMC_MD2.ID02419.hairpin | YES | NO | NO | NO | NO | NO | NO | NO |
| TJU_CMC_MD2.ID02420.5p-miR | TJU_CMC_MD2.ID02420.hairpin | YES | NO | YES | NO | NO | NO | NO | NO |
| TJU_CMC_MD2.ID02421.5p-miR | TJU_CMC_MD2.ID02421.hairpin | YES | NO | YES | NO | YES | NO | NO | NO |
| TJU_CMC_MD2.ID02422.3p-miR | TJU_CMC_MD2.ID02422.hairpin | YES | NO | NO | NO | NO | NO | NO | NO |
| TJU_CMC_MD2.ID02422.5p-miR | TJU_CMC_MD2.ID02422.hairpin | YES | YES | YES | NO | NO | NO | NO | NO |
| TJU_CMC_MD2.ID02423.5p-miR | TJU_CMC_MD2.ID02423.hairpin | YES | YES | YES | YES | NO | YES | NO | NO |
| TJU_CMC_MD2.ID02424.3p-miR | TJU_CMC_MD2.ID02424.hairpin | YES | NO | NO | NO | NO | NO | NO | NO |
| TJU_CMC_MD2.ID02425.3p-miR | TJU_CMC_MD2.ID02425.hairpin | YES | NO | NO | NO | NO | NO | NO | NO |
| TJU_CMC_MD2.ID02426.5p-miR | TJU_CMC_MD2.ID02426.hairpin | YES | YES | YES | YES | YES | NO | NO | NO |
| TJU_CMC_MD2.ID02427.3p-miR | TJU_CMC_MD2.ID02427.hairpin | YES | YES | NO | YES | NO | NO | NO | NO |
| TJU_CMC_MD2.ID02428.3p-miR | TJU_CMC_MD2.ID02428.hairpin | YES | NO | NO | NO | NO | NO | NO | NO |
| TJU_CMC_MD2.ID02429.3p-miR | TJU_CMC_MD2.ID02429.hairpin | YES | NO | NO | NO | NO | NO | NO | NO |
| TJU_CMC_MD2.ID02430.3p-miR | TJU_CMC_MD2.ID02430.hairpin | YES | NO | NO | NO | NO | NO | NO | NO |
| TJU_CMC_MD2.ID02431.3p-miR | TJU_CMC_MD2.ID02431.hairpin | YES | NO | NO | NO | NO | NO | NO | NO |
| TJU_CMC_MD2.ID02432.3p-miR | TJU_CMC_MD2.ID02432.hairpin | YES | NO | NO | NO | NO | NO | NO | NO |
| TJU_CMC_MD2.ID02433.5p-miR | TJU_CMC_MD2.ID02433.hairpin | YES | YES | NO | YES | NO | NO | NO | NO |
| TJU_CMC_MD2.ID02434.3p-miR | TJU_CMC_MD2.ID02434.hairpin | YES | NO | NO | NO | NO | NO | NO | NO |
| TJU_CMC_MD2.ID02434.5p-miR | TJU_CMC_MD2.ID02434.hairpin | YES | YES | YES | YES | NO | NO | NO | NO |
| TJU_CMC_MD2.ID02435.5p-miR | TJU_CMC_MD2.ID02435.hairpin | YES | YES | YES | YES | YES | NO | NO | NO |
| TJU_CMC_MD2.ID02436.3p-miR | TJU_CMC_MD2.ID02436.hairpin | YES | NO | NO | NO | NO | NO | NO | NO |
| TJU_CMC_MD2.ID02437.3p-miR | TJU_CMC_MD2.ID02437.hairpin | YES | NO | NO | NO | NO | NO | NO | NO |
| TJU_CMC_MD2.ID02438.5p-miR | TJU_CMC_MD2.ID02438.hairpin | YES | YES | YES | YES | YES | YES | NO | NO |
| TJU_CMC_MD2.ID02439.5p-miR | TJU_CMC_MD2.ID02439.hairpin | YES | YES | YES | NO | NO | NO | NO | NO |
| TJU_CMC_MD2.ID02440.3p-miR | TJU_CMC_MD2.ID02440.hairpin | YES | NO | NO | NO | NO | NO | NO | NO |
| TJU_CMC_MD2.ID02441.5p-miR | TJU_CMC_MD2.ID02441.hairpin | YES | YES | YES | NO | NO | NO | NO | NO |
| TJU_CMC_MD2.ID02442.5p-miR | TJU_CMC_MD2.ID02442.hairpin | YES | YES | YES | YES | YES | YES | NO | NO |
| TJU_CMC_MD2.ID02443.3p-miR | TJU_CMC_MD2.ID02443.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02444.5p-miR | TJU_CMC_MD2.ID02444.hairpin | YES | NO | NO | NO | NO | NO | NO | NO |
| TJU_CMC_MD2.ID02445.3p-miR | TJU_CMC_MD2.ID02445.hairpin | YES | NO | NO | NO | NO | NO | NO | NO |
| TJU_CMC_MD2.ID02446.5p-miR | TJU_CMC_MD2.ID02446.hairpin | YES | YES | YES | YES | NO | NO | NO | NO |
| TJU_CMC_MD2.ID02447.5p-miR | TJU_CMC_MD2.ID02447.hairpin | YES | YES | YES | YES | NO | NO | NO | NO |
| TJU_CMC_MD2.ID02448.5p-miR | TJU_CMC_MD2.ID02448.hairpin | YES | YES | YES | NO | NO | NO | NO | NO |
| TJU_CMC_MD2.ID02449.3p-miR | TJU_CMC_MD2.ID02449.hairpin | YES | NO | NO | NO | NO | NO | NO | NO |
| TJU_CMC_MD2.ID02450.3p-miR | TJU_CMC_MD2.ID02450.hairpin | YES | NO | NO | NO | NO | NO | NO | NO |
| TJU_CMC_MD2.ID02451.5p-miR | TJU_CMC_MD2.ID02451.hairpin | YES | NO | YES | YES | NO | NO | NO | NO |
| TJU_CMC_MD2.ID02452.3p-miR | TJU_CMC_MD2.ID02452.hairpin | YES | NO | NO | NO | NO | NO | NO | NO |
| TJU_CMC_MD2.ID02453.3p-miR | TJU_CMC_MD2.ID02453.hairpin | YES | NO | NO | NO | NO | NO | NO | NO |
| TJU_CMC_MD2.ID02453.5p-miR | TJU_CMC_MD2.ID02453.hairpin | YES | YES | YES | YES | NO | NO | NO | NO |
| TJU_CMC_MD2.ID02454.5p-miR | TJU_CMC_MD2.ID02454.hairpin | YES | YES | YES | YES | NO | NO | NO | NO |
| TJU_CMC_MD2.ID02455.3p-miR | TJU_CMC_MD2.ID02455.hairpin | YES | NO | NO | NO | NO | NO | NO | NO |
| TJU_CMC_MD2.ID02456.3p-miR | TJU_CMC_MD2.ID02456.hairpin | YES | NO | NO | NO | NO | NO | NO | NO |
| TJU_CMC_MD2.ID02457.3p-miR | TJU_CMC_MD2.ID02457.hairpin | YES | NO | NO | NO | NO | NO | NO | NO |
| TJU_CMC_MD2.ID02458.3p-miR | TJU_CMC_MD2.ID02458.hairpin | YES | NO | NO | NO | NO | NO | NO | NO |
| TJU_CMC_MD2.ID02459.5p-miR | TJU_CMC_MD2.ID02459.hairpin | YES | NO | YES | YES | YES | NO | NO | NO |
| TJU_CMC_MD2.ID02460.5p-miR | TJU_CMC_MD2.ID02460.hairpin | YES | YES | NO | YES | YES | NO | NO | NO |
| TJU_CMC_MD2.ID02461.5p-miR | TJU_CMC_MD2.ID02461.hairpin | YES | YES | YES | YES | YES | NO | NO | NO |
| TJU_CMC_MD2.ID02462.5p-miR | TJU_CMC_MD2.ID02462.hairpin | YES | YES | YES | YES | YES | NO | NO | NO |
| TJU_CMC_MD2.ID02463.3p-miR | TJU_CMC_MD2.ID02463.hairpin | YES | NO | NO | NO | NO | NO | NO | NO |
| TJU_CMC_MD2.ID02464.5p-miR | TJU_CMC_MD2.ID02464.hairpin | YES | YES | YES | YES | NO | NO | NO | NO |
| TJU_CMC_MD2.ID02465.3p-miR | TJU_CMC_MD2.ID02465.hairpin | YES | NO | NO | NO | NO | NO | NO | NO |
| TJU_CMC_MD2.ID02466.3p-miR | TJU_CMC_MD2.ID02466.hairpin | YES | NO | NO | NO | NO | NO | NO | NO |
| TJU_CMC_MD2.ID02467.3p-miR | TJU_CMC_MD2.ID02467.hairpin | YES | NO | NO | NO | NO | NO | NO | NO |
| TJU_CMC_MD2.ID02468.5p-miR | TJU_CMC_MD2.ID02468.hairpin | YES | NO | YES | NO | YES | NO | NO | NO |
| TJU_CMC_MD2.ID02469.3p-miR | TJU_CMC_MD2.ID02469.hairpin | YES | NO | NO | NO | NO | NO | NO | NO |
| TJU_CMC_MD2.ID02470.3p-miR | TJU_CMC_MD2.ID02470.hairpin | YES | NO | NO | NO | NO | NO | NO | NO |
| TJU_CMC_MD2.ID02471.3p-miR | TJU_CMC_MD2.ID02471.hairpin | YES | NO | NO | NO | NO | NO | NO | NO |
| TJU_CMC_MD2.ID02472.3p-miR | TJU_CMC_MD2.ID02472.hairpin | YES | NO | NO | NO | NO | NO | NO | NO |
| TJU_CMC_MD2.ID02473.3p-miR | TJU_CMC_MD2.ID02473.hairpin | YES | NO | NO | NO | NO | NO | NO | NO |
| TJU_CMC_MD2.ID02474.3p-miR | TJU_CMC_MD2.ID02474.hairpin | YES | NO | NO | NO | NO | NO | NO | NO |
| TJU_CMC_MD2.ID02475.5p-miR | TJU_CMC_MD2.ID02475.hairpin | YES | YES | YES | YES | NO | NO | NO | NO |
| TJU_CMC_MD2.ID02476.3p-miR | TJU_CMC_MD2.ID02476.hairpin | YES | NO | NO | NO | NO | NO | NO | NO |
| TJU_CMC_MD2.ID02477.3p-miR | TJU_CMC_MD2.ID02477.hairpin | YES | NO | NO | NO | NO | NO | NO | NO |
| TJU_CMC_MD2.ID02478.3p-miR | TJU_CMC_MD2.ID02478.hairpin | YES | NO | NO | NO | NO | NO | NO | NO |
| TJU_CMC_MD2.ID02479.3p-miR | TJU_CMC_MD2.ID02479.hairpin | YES | NO | NO | NO | NO | NO | NO | NO |
| TJU_CMC_MD2.ID02480.5p-miR | TJU_CMC_MD2.ID02480.hairpin | YES | YES | YES | YES | NO | NO | NO | NO |
| TJU_CMC_MD2.ID02481.5p-miR | TJU_CMC_MD2.ID02481.hairpin | YES | YES | NO | YES | YES | NO | NO | NO |
| TJU_CMC_MD2.ID02482.3p-miR | TJU_CMC_MD2.ID02482.hairpin | YES | NO | NO | NO | NO | NO | NO | NO |
| TJU_CMC_MD2.ID02483.3p-miR | TJU_CMC_MD2.ID02483.hairpin | YES | NO | NO | NO | NO | NO | NO | NO |
| TJU_CMC_MD2.ID02484.3p-miR | TJU_CMC_MD2.ID02484.hairpin | YES | NO | NO | NO | NO | NO | NO | NO |
| TJU_CMC_MD2.ID02485.5p-miR | TJU_CMC_MD2.ID02485.hairpin | YES | NO | YES | NO | NO | NO | NO | NO |
| TJU_CMC_MD2.ID02486.3p-miR | TJU_CMC_MD2.ID02486.hairpin | YES | NO | NO | NO | NO | NO | NO | NO |
| TJU_CMC_MD2.ID02487.5p-miR | TJU_CMC_MD2.ID02487.hairpin | YES | YES | NO | NO | NO | NO | NO | NO |
| TJU_CMC_MD2.ID02488.3p-miR | TJU_CMC_MD2.ID02488.hairpin | YES | NO | NO | NO | NO | NO | NO | NO |
| TJU_CMC_MD2.ID02488.5p-miR | TJU_CMC_MD2.ID02488.hairpin | YES | YES | YES | NO | NO | NO | NO | NO |
| TJU_CMC_MD2.ID02489.3p-miR | TJU_CMC_MD2.ID02489.hairpin | YES | NO | NO | NO | NO | NO | NO | NO |
| TJU_CMC_MD2.ID02490.5p-miR | TJU_CMC_MD2.ID02490.hairpin | YES | YES | YES | YES | NO | NO | NO | NO |
| TJU_CMC_MD2.ID02491.3p-miR | TJU_CMC_MD2.ID02491.hairpin | YES | NO | NO | NO | NO | NO | NO | NO |
| TJU_CMC_MD2.ID02491.5p-miR | TJU_CMC_MD2.ID02491.hairpin | YES | YES | YES | NO | YES | NO | NO | NO |
| TJU_CMC_MD2.ID02492.3p-miR | TJU_CMC_MD2.ID02492.hairpin | YES | NO | NO | NO | NO | NO | NO | NO |
| TJU_CMC_MD2.ID02493.3p-miR | TJU_CMC_MD2.ID02493.hairpin | YES | NO | NO | NO | NO | NO | NO | NO |
| TJU_CMC_MD2.ID02494.3p-miR | TJU_CMC_MD2.ID02494.hairpin | YES | NO | NO | NO | NO | NO | NO | NO |
| TJU_CMC_MD2.ID02495.3p-miR | TJU_CMC_MD2.ID02495.hairpin | YES | NO | NO | NO | NO | NO | NO | NO |
| TJU_CMC_MD2.ID02496.5p-miR | TJU_CMC_MD2.ID02496.hairpin | YES | YES | YES | NO | NO | NO | NO | NO |
| TJU_CMC_MD2.ID02497.3p-miR | TJU_CMC_MD2.ID02497.hairpin | YES | NO | NO | NO | NO | NO | NO | NO |
| TJU_CMC_MD2.ID02498.5p-miR | TJU_CMC_MD2.ID02498.hairpin | YES | YES | YES | YES | NO | NO | NO | NO |
| TJU_CMC_MD2.ID02499.3p-miR | TJU_CMC_MD2.ID02499.hairpin | YES | NO | NO | NO | NO | NO | NO | NO |
| TJU_CMC_MD2.ID02500.3p-miR | TJU_CMC_MD2.ID02500.hairpin | YES | NO | NO | NO | NO | NO | NO | NO |
| TJU_CMC_MD2.ID02501.3p-miR | TJU_CMC_MD2.ID02501.hairpin | YES | NO | NO | NO | NO | NO | NO | NO |
| TJU_CMC_MD2.ID02502.3p-miR | TJU_CMC_MD2.ID02502.hairpin | YES | NO | NO | NO | NO | NO | NO | NO |
| TJU_CMC_MD2.ID02503.3p-miR | TJU_CMC_MD2.ID02503.hairpin | YES | NO | NO | NO | NO | NO | NO | NO |
| TJU_CMC_MD2.ID02504.5p-miR | TJU_CMC_MD2.ID02504.hairpin | YES | YES | YES | YES | NO | NO | NO | NO |
| TJU_CMC_MD2.ID02505.5p-miR | TJU_CMC_MD2.ID02505.hairpin | YES | NO | NO | NO | NO | NO | NO | NO |
| TJU_CMC_MD2.ID02506.3p-miR | TJU_CMC_MD2.ID02506.hairpin | YES | NO | NO | NO | NO | NO | NO | NO |
| TJU_CMC_MD2.ID02507.3p-miR | TJU_CMC_MD2.ID02507.hairpin | YES | NO | NO | NO | NO | NO | NO | NO |
| TJU_CMC_MD2.ID02508.5p-miR | TJU_CMC_MD2.ID02508.hairpin | YES | YES | YES | YES | YES | NO | NO | NO |
| TJU_CMC_MD2.ID02509.3p-miR | TJU_CMC_MD2.ID02509.hairpin | YES | NO | NO | NO | NO | NO | NO | NO |
| TJU_CMC_MD2.ID02510.3p-miR | TJU_CMC_MD2.ID02510.hairpin | YES | NO | NO | NO | NO | NO | NO | NO |
| TJU_CMC_MD2.ID02510.5p-miR | TJU_CMC_MD2.ID02510.hairpin | YES | YES | NO | NO | NO | NO | NO | NO |
| TJU_CMC_MD2.ID02511.3p-miR | TJU_CMC_MD2.ID02511.hairpin | YES | NO | NO | NO | NO | NO | NO | NO |
| TJU_CMC_MD2.ID02512.3p-miR | TJU_CMC_MD2.ID02512.hairpin | YES | NO | NO | NO | NO | NO | NO | NO |
| TJU_CMC_MD2.ID02513.5p-miR | TJU_CMC_MD2.ID02513.hairpin | YES | NO | NO | NO | NO | NO | NO | NO |
| TJU_CMC_MD2.ID02514.3p-miR | TJU_CMC_MD2.ID02514.hairpin | YES | NO | NO | NO | NO | NO | NO | NO |

TABLE 7-continued

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02514.5p-miR | TJU_CMC_MD2.ID02514.hairpin | YES | NO | NO | NO | NO | NO | NO | NO |
| TJU_CMC_MD2.ID02515.3p-miR | TJU_CMC_MD2.ID02515.hairpin | YES | NO | NO | NO | NO | NO | NO | NO |
| TJU_CMC_MD2.ID02516.3p-miR | TJU_CMC_MD2.ID02516.hairpin | YES | NO | NO | NO | NO | NO | NO | NO |
| TJU_CMC_MD2.ID02517.3p-miR | TJU_CMC_MD2.ID02517.hairpin | YES | NO | NO | NO | NO | NO | NO | NO |
| TJU_CMC_MD2.ID02518.3p-miR | TJU_CMC_MD2.ID02518.hairpin | YES | NO | NO | NO | NO | NO | NO | NO |
| TJU_CMC_MD2.ID02519.3p-miR | TJU_CMC_MD2.ID02519.hairpin | YES | YES | YES | YES | NO | NO | NO | NO |
| TJU_CMC_MD2.ID02520.5p-miR | TJU_CMC_MD2.ID02520.hairpin | YES | YES | NO | NO | YES | NO | NO | NO |
| TJU_CMC_MD2.ID02521.5p-miR | TJU_CMC_MD2.ID02521.hairpin | YES | YES | YES | NO | NO | NO | NO | NO |
| TJU_CMC_MD2.ID02522.3p-miR | TJU_CMC_MD2.ID02522.hairpin | YES | NO | NO | NO | NO | NO | NO | NO |
| TJU_CMC_MD2.ID02523.3p-miR | TJU_CMC_MD2.ID02523.hairpin | YES | NO | NO | NO | NO | NO | NO | NO |
| TJU_CMC_MD2.ID02524.5p-miR | TJU_CMC_MD2.ID02524.hairpin | YES | YES | YES | YES | NO | NO | NO | NO |
| TJU_CMC_MD2.ID02525.5p-miR | TJU_CMC_MD2.ID02525.hairpin | YES | YES | YES | YES | NO | NO | NO | NO |
| TJU_CMC_MD2.ID02526.3p-miR | TJU_CMC_MD2.ID02526.hairpin | YES | NO | NO | NO | NO | NO | NO | NO |
| TJU_CMC_MD2.ID02527.5p-miR | TJU_CMC_MD2.ID02527.hairpin | YES | YES | NO | NO | NO | NO | NO | NO |
| TJU_CMC_MD2.ID02528.3p-miR | TJU_CMC_MD2.ID02528.hairpin | YES | NO | NO | NO | NO | NO | NO | NO |
| TJU_CMC_MD2.ID02528.5p-miR | TJU_CMC_MD2.ID02528.hairpin | YES | YES | YES | YES | YES | NO | NO | NO |
| TJU_CMC_MD2.ID02529.5p-miR | TJU_CMC_MD2.ID02529.hairpin | YES | YES | NO | NO | NO | NO | NO | NO |
| TJU_CMC_MD2.ID02530.5p-miR | TJU_CMC_MD2.ID02530.hairpin | YES | NO | NO | YES | NO | NO | NO | NO |
| TJU_CMC_MD2.ID02531.3p-miR | TJU_CMC_MD2.ID02531.hairpin | YES | NO | NO | NO | NO | NO | NO | NO |
| TJU_CMC_MD2.ID02532.3p-miR | TJU_CMC_MD2.ID02532.hairpin | YES | NO | NO | NO | NO | NO | NO | NO |
| TJU_CMC_MD2.ID02533.3p-miR | TJU_CMC_MD2.ID02533.hairpin | YES | NO | NO | NO | NO | NO | NO | NO |
| TJU_CMC_MD2.ID02534.5p-miR | TJU_CMC_MD2.ID02534.hairpin | YES | NO | YES | NO | NO | NO | NO | NO |
| TJU_CMC_MD2.ID02535.3p-miR | TJU_CMC_MD2.ID02535.hairpin | YES | NO | NO | NO | NO | NO | NO | NO |
| TJU_CMC_MD2.ID02536.5p-miR | TJU_CMC_MD2.ID02536.hairpin | YES | YES | YES | YES | NO | YES | NO | NO |
| TJU_CMC_MD2.ID02537.5p-miR | TJU_CMC_MD2.ID02537.hairpin | YES | YES | NO | NO | NO | NO | NO | NO |
| TJU_CMC_MD2.ID02538.3p-miR | TJU_CMC_MD2.ID02538.hairpin | YES | NO | NO | NO | NO | NO | NO | NO |
| TJU_CMC_MD2.ID02539.3p-miR | TJU_CMC_MD2.ID02539.hairpin | YES | NO | NO | NO | NO | NO | NO | NO |
| TJU_CMC_MD2.ID02540.3p-miR | TJU_CMC_MD2.ID02540.hairpin | YES | NO | NO | NO | NO | NO | NO | NO |
| TJU_CMC_MD2.ID02541.5p-miR | TJU_CMC_MD2.ID02541.hairpin | YES | YES | YES | YES | YES | NO | NO | NO |
| TJU_CMC_MD2.ID02542.5p-miR | TJU_CMC_MD2.ID02542.hairpin | YES | YES | YES | YES | YES | NO | NO | NO |
| TJU_CMC_MD2.ID02543.3p-miR | TJU_CMC_MD2.ID02543.hairpin | YES | NO | NO | NO | NO | NO | NO | NO |
| TJU_CMC_MD2.ID02544.5p-miR | TJU_CMC_MD2.ID02544.hairpin | YES | YES | YES | YES | NO | NO | NO | NO |
| TJU_CMC_MD2.ID02545.3p-miR | TJU_CMC_MD2.ID02545.hairpin | YES | NO | NO | NO | NO | NO | NO | NO |
| TJU_CMC_MD2.ID02545.5p-miR | TJU_CMC_MD2.ID02545.hairpin | YES | NO | NO | NO | NO | NO | NO | NO |
| TJU_CMC_MD2.ID02546.5p-miR | TJU_CMC_MD2.ID02546.hairpin | YES | NO | YES | NO | NO | NO | NO | NO |
| TJU_CMC_MD2.ID02547.5p-miR | TJU_CMC_MD2.ID02547.hairpin | YES | YES | YES | NO | NO | NO | NO | NO |
| TJU_CMC_MD2.ID02548.5p-miR | TJU_CMC_MD2.ID02548.hairpin | YES | NO | NO | NO | NO | NO | NO | NO |
| TJU_CMC_MD2.ID02549.3p-miR | TJU_CMC_MD2.ID02549.hairpin | YES | NO | NO | NO | NO | NO | NO | NO |
| TJU_CMC_MD2.ID02550.3p-miR | TJU_CMC_MD2.ID02550.hairpin | YES | NO | NO | NO | NO | NO | NO | NO |
| TJU_CMC_MD2.ID02551.3p-miR | TJU_CMC_MD2.ID02551.hairpin | YES | YES | YES | YES | NO | NO | NO | NO |
| TJU_CMC_MD2.ID02552.3p-miR | TJU_CMC_MD2.ID02552.hairpin | YES | NO | NO | NO | NO | NO | NO | NO |
| TJU_CMC_MD2.ID02553.3p-miR | TJU_CMC_MD2.ID02553.hairpin | YES | NO | NO | NO | NO | NO | NO | NO |
| TJU_CMC_MD2.ID02554.3p-miR | TJU_CMC_MD2.ID02554.hairpin | YES | NO | NO | NO | NO | NO | NO | NO |
| TJU_CMC_MD2.ID02555.5p-miR | TJU_CMC_MD2.ID02555.hairpin | YES | NO | NO | NO | NO | NO | NO | NO |
| TJU_CMC_MD2.ID02556.3p-miR | TJU_CMC_MD2.ID02556.hairpin | YES | NO | NO | NO | NO | NO | NO | NO |
| TJU_CMC_MD2.ID02556.5p-miR | TJU_CMC_MD2.ID02556.hairpin | YES | NO | YES | YES | NO | NO | NO | NO |
| TJU_CMC_MD2.ID02557.3p-miR | TJU_CMC_MD2.ID02557.hairpin | YES | NO | NO | NO | NO | NO | NO | NO |
| TJU_CMC_MD2.ID02558.3p-miR | TJU_CMC_MD2.ID02558.hairpin | YES | NO | NO | NO | NO | NO | NO | NO |
| TJU_CMC_MD2.ID02559.5p-miR | TJU_CMC_MD2.ID02559.hairpin | YES | NO | NO | NO | NO | NO | NO | NO |
| TJU_CMC_MD2.ID02560.3p-miR | TJU_CMC_MD2.ID02560.hairpin | YES | YES | YES | YES | YES | NO | NO | NO |
| TJU_CMC_MD2.ID02561.5p-miR | TJU_CMC_MD2.ID02561.hairpin | YES | YES | YES | YES | YES | NO | NO | NO |
| TJU_CMC_MD2.ID02562.3p-miR | TJU_CMC_MD2.ID02562.hairpin | YES | NO | NO | NO | NO | NO | NO | NO |
| TJU_CMC_MD2.ID02563.3p-miR | TJU_CMC_MD2.ID02563.hairpin | YES | NO | NO | NO | NO | NO | NO | NO |
| TJU_CMC_MD2.ID02564.3p-miR | TJU_CMC_MD2.ID02564.hairpin | YES | NO | NO | NO | NO | NO | NO | NO |
| TJU_CMC_MD2.ID02565.3p-miR | TJU_CMC_MD2.ID02565.hairpin | YES | NO | NO | NO | NO | NO | NO | NO |
| TJU_CMC_MD2.ID02565.5p-miR | TJU_CMC_MD2.ID02565.hairpin | YES | NO | YES | YES | YES | NO | NO | NO |
| TJU_CMC_MD2.ID02566.3p-miR | TJU_CMC_MD2.ID02566.hairpin | YES | NO | NO | NO | NO | NO | NO | NO |
| TJU_CMC_MD2.ID02567.3p-miR | TJU_CMC_MD2.ID02567.hairpin | YES | NO | NO | NO | NO | NO | NO | NO |
| TJU_CMC_MD2.ID02568.3p-miR | TJU_CMC_MD2.ID02568.hairpin | YES | NO | NO | NO | NO | NO | NO | NO |
| TJU_CMC_MD2.ID02569.3p-miR | TJU_CMC_MD2.ID02569.hairpin | YES | NO | NO | NO | NO | NO | NO | NO |
| TJU_CMC_MD2.ID02570.3p-miR | TJU_CMC_MD2.ID02570.hairpin | YES | NO | NO | NO | NO | NO | NO | NO |
| TJU_CMC_MD2.ID02571.5p-miR | TJU_CMC_MD2.ID02571.hairpin | YES | YES | YES | YES | NO | NO | NO | NO |
| TJU_CMC_MD2.ID02572.5p-miR | TJU_CMC_MD2.ID02572.hairpin | YES | YES | NO | NO | NO | NO | NO | NO |
| TJU_CMC_MD2.ID02573.5p-miR | TJU_CMC_MD2.ID02573.hairpin | YES | NO | NO | NO | NO | NO | NO | NO |
| TJU_CMC_MD2.ID02574.3p-miR | TJU_CMC_MD2.ID02574.hairpin | YES | NO | NO | NO | NO | NO | NO | NO |
| TJU_CMC_MD2.ID02575.3p-miR | TJU_CMC_MD2.ID02575.hairpin | YES | NO | NO | NO | NO | NO | NO | NO |
| TJU_CMC_MD2.ID02576.5p-miR | TJU_CMC_MD2.ID02576.hairpin | YES | YES | YES | YES | YES | NO | NO | NO |
| TJU_CMC_MD2.ID02577.3p-miR | TJU_CMC_MD2.ID02577.hairpin | YES | NO | NO | NO | NO | NO | NO | NO |
| TJU_CMC_MD2.ID02578.3p-miR | TJU_CMC_MD2.ID02578.hairpin | YES | NO | NO | NO | NO | NO | NO | NO |
| TJU_CMC_MD2.ID02579.3p-miR | TJU_CMC_MD2.ID02579.hairpin | YES | NO | NO | NO | NO | NO | NO | NO |
| TJU_CMC_MD2.ID02579.5p-miR | TJU_CMC_MD2.ID02579.hairpin | YES | NO | YES | NO | YES | NO | NO | NO |
| TJU_CMC_MD2.ID02580.3p-miR | TJU_CMC_MD2.ID02580.hairpin | YES | NO | NO | NO | NO | NO | NO | NO |
| TJU_CMC_MD2.ID02581.5p-miR | TJU_CMC_MD2.ID02581.hairpin | YES | YES | YES | YES | NO | NO | NO | NO |
| TJU_CMC_MD2.ID02582.3p-miR | TJU_CMC_MD2.ID02582.hairpin | YES | NO | NO | NO | NO | NO | NO | NO |
| TJU_CMC_MD2.ID02583.5p-miR | TJU_CMC_MD2.ID02583.hairpin | YES | YES | YES | YES | YES | NO | NO | NO |

TABLE 7-continued

Conservation properties across the examined model organisms for the novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02584.3p-miR | TJU_CMC_MD2.ID02584.hairpin | YES | NO | NO | NO | NO | NO | NO | NO |
| TJU_CMC_MD2.ID02585.5p-miR | TJU_CMC_MD2.ID02585.hairpin | YES | NO | NO | NO | NO | NO | NO | NO |
| TJU_CMC_MD2.ID02586.3p-miR | TJU_CMC_MD2.ID02586.hairpin | YES | NO | NO | NO | NO | NO | NO | NO |
| TJU_CMC_MD2.ID02587.3p-miR | TJU_CMC_MD2.ID02587.hairpin | YES | NO | NO | NO | NO | NO | NO | NO |
| TJU_CMC_MD2.ID02588.3p-miR | TJU_CMC_MD2.ID02588.hairpin | YES | NO | NO | NO | NO | NO | NO | NO |
| TJU_CMC_MD2.ID02589.5p-miR | TJU_CMC_MD2.ID02589.hairpin | YES | YES | YES | YES | NO | NO | NO | NO |
| TJU_CMC_MD2.ID02590.3p-miR | TJU_CMC_MD2.ID02590.hairpin | YES | NO | NO | NO | NO | NO | NO | NO |
| TJU_CMC_MD2.ID02591.5p-miR | TJU_CMC_MD2.ID02591.hairpin | YES | NO | YES | YES | NO | NO | NO | NO |
| TJU_CMC_MD2.ID02592.5p-miR | TJU_CMC_MD2.ID02592.hairpin | YES | NO | NO | NO | NO | NO | NO | NO |
| TJU_CMC_MD2.ID02593.5p-miR | TJU_CMC_MD2.ID02593.hairpin | YES | YES | NO | YES | NO | NO | NO | NO |
| TJU_CMC_MD2.ID02594.3p-miR | TJU_CMC_MD2.ID02594.hairpin | YES | NO | NO | NO | NO | NO | NO | NO |
| TJU_CMC_MD2.ID02595.5p-miR | TJU_CMC_MD2.ID02595.hairpin | YES | NO | YES | NO | NO | NO | NO | NO |
| TJU_CMC_MD2.ID02596.5p-miR | TJU_CMC_MD2.ID02596.hairpin | YES | YES | YES | YES | NO | NO | NO | NO |
| TJU_CMC_MD2.ID02597.3p-miR | TJU_CMC_MD2.ID02597.hairpin | YES | NO | NO | NO | NO | NO | NO | NO |
| TJU_CMC_MD2.ID02598.3p-miR | TJU_CMC_MD2.ID02598.hairpin | YES | NO | NO | NO | NO | NO | NO | NO |
| TJU_CMC_MD2.ID02599.3p-miR | TJU_CMC_MD2.ID02599.hairpin | YES | NO | NO | NO | NO | NO | NO | NO |
| TJU_CMC_MD2.ID02600.3p-miR | TJU_CMC_MD2.ID02600.hairpin | YES | NO | NO | NO | NO | NO | NO | NO |
| TJU_CMC_MD2.ID02601.5p-miR | TJU_CMC_MD2.ID02601.hairpin | YES | NO | YES | NO | NO | NO | NO | NO |
| TJU_CMC_MD2.ID02602.5p-miR | TJU_CMC_MD2.ID02602.hairpin | YES | YES | NO | YES | NO | NO | NO | NO |
| TJU_CMC_MD2.ID02603.3p-miR | TJU_CMC_MD2.ID02603.hairpin | YES | NO | NO | NO | NO | NO | NO | NO |
| TJU_CMC_MD2.ID02604.3p-miR | TJU_CMC_MD2.ID02604.hairpin | YES | YES | NO | YES | YES | NO | NO | NO |
| TJU_CMC_MD2.ID02604.5p-miR | TJU_CMC_MD2.ID02604.hairpin | YES | YES | YES | YES | YES | NO | NO | NO |
| TJU_CMC_MD2.ID02605.3p-miR | TJU_CMC_MD2.ID02605.hairpin | YES | YES | YES | YES | YES | NO | NO | NO |
| TJU_CMC_MD2.ID02606.5p-miR | TJU_CMC_MD2.ID02606.hairpin | YES | YES | YES | YES | YES | NO | NO | NO |
| TJU_CMC_MD2.ID02607.3p-miR | TJU_CMC_MD2.ID02607.hairpin | YES | NO | NO | NO | NO | NO | NO | NO |
| TJU_CMC_MD2.ID02608.5p-miR | TJU_CMC_MD2.ID02608.hairpin | YES | YES | YES | YES | NO | NO | NO | NO |
| TJU_CMC_MD2.ID02609.3p-miR | TJU_CMC_MD2.ID02609.hairpin | YES | NO | NO | NO | NO | NO | NO | NO |
| TJU_CMC_MD2.ID02610.3p-miR | TJU_CMC_MD2.ID02610.hairpin | YES | NO | NO | NO | NO | NO | NO | NO |
| TJU_CMC_MD2.ID02611.3p-miR | TJU_CMC_MD2.ID02611.hairpin | YES | NO | NO | NO | NO | NO | NO | NO |
| TJU_CMC_MD2.ID02612.5p-miR | TJU_CMC_MD2.ID02612.hairpin | YES | NO | NO | NO | NO | NO | NO | NO |
| TJU_CMC_MD2.ID02613.3p-miR | TJU_CMC_MD2.ID02613.hairpin | YES | NO | NO | NO | NO | NO | NO | NO |
| TJU_CMC_MD2.ID02614.3p-miR | TJU_CMC_MD2.ID02614.hairpin | YES | NO | NO | NO | NO | NO | NO | NO |
| TJU_CMC_MD2.ID02615.5p-miR | TJU_CMC_MD2.ID02615.hairpin | YES | NO | YES | YES | NO | NO | NO | NO |
| TJU_CMC_MD2.ID02616.5p-miR | TJU_CMC_MD2.ID02616.hairpin | YES | YES | YES | YES | YES | NO | NO | NO |
| TJU_CMC_MD2.ID02617.5p-miR | TJU_CMC_MD2.ID02617.hairpin | YES | NO | NO | NO | NO | NO | NO | NO |
| TJU_CMC_MD2.ID02618.3p-miR | TJU_CMC_MD2.ID02618.hairpin | YES | NO | NO | NO | NO | NO | NO | NO |
| TJU_CMC_MD2.ID02619.5p-miR | TJU_CMC_MD2.ID02619.hairpin | YES | YES | YES | YES | NO | NO | NO | NO |
| TJU_CMC_MD2.ID02620.5p-miR | TJU_CMC_MD2.ID02620.hairpin | YES | YES | YES | YES | NO | NO | NO | NO |
| TJU_CMC_MD2.ID02621.3p-miR | TJU_CMC_MD2.ID02621.hairpin | YES | NO | NO | NO | NO | NO | NO | NO |
| TJU_CMC_MD2.ID02622.3p-miR | TJU_CMC_MD2.ID02622.hairpin | YES | NO | NO | NO | NO | NO | NO | NO |
| TJU_CMC_MD2.ID02623.3p-miR | TJU_CMC_MD2.ID02623.hairpin | YES | NO | NO | NO | NO | NO | NO | NO |
| TJU_CMC_MD2.ID02624.3p-miR | TJU_CMC_MD2.ID02624.hairpin | YES | NO | NO | NO | NO | NO | NO | NO |
| TJU_CMC_MD2.ID02625.5p-miR | TJU_CMC_MD2.ID02625.hairpin | YES | YES | YES | NO | NO | NO | NO | NO |
| TJU_CMC_MD2.ID02626.5p-miR | TJU_CMC_MD2.ID02626.hairpin | YES | YES | YES | YES | NO | YES | NO | NO |
| TJU_CMC_MD2.ID02627.5p-miR | TJU_CMC_MD2.ID02627.hairpin | YES | YES | YES | YES | YES | NO | NO | NO |
| TJU_CMC_MD2.ID02628.5p-miR | TJU_CMC_MD2.ID02628.hairpin | YES | YES | YES | YES | NO | NO | NO | NO |
| TJU_CMC_MD2.ID02629.3p-miR | TJU_CMC_MD2.ID02629.hairpin | YES | YES | YES | YES | NO | NO | NO | NO |
| TJU_CMC_MD2.ID02629.5p-miR | TJU_CMC_MD2.ID02629.hairpin | YES | YES | YES | YES | NO | NO | NO | NO |
| TJU_CMC_MD2.ID02630.3p-miR | TJU_CMC_MD2.ID02630.hairpin | YES | NO | NO | NO | NO | NO | NO | NO |
| TJU_CMC_MD2.ID02631.5p-miR | TJU_CMC_MD2.ID02631.hairpin | YES | NO | YES | NO | NO | NO | NO | NO |
| TJU_CMC_MD2.ID02632.5p-miR | TJU_CMC_MD2.ID02632.hairpin | YES | YES | YES | NO | NO | NO | NO | NO |
| TJU_CMC_MD2.ID02633.3p-miR | TJU_CMC_MD2.ID02633.hairpin | YES | YES | YES | YES | NO | NO | NO | NO |
| TJU_CMC_MD2.ID02634.3p-miR | TJU_CMC_MD2.ID02634.hairpin | YES | NO | NO | NO | NO | NO | NO | NO |
| TJU_CMC_MD2.ID02635.5p-miR | TJU_CMC_MD2.ID02635.hairpin | YES | YES | YES | YES | NO | NO | NO | NO |
| TJU_CMC_MD2.ID02636.5p-miR | TJU_CMC_MD2.ID02636.hairpin | YES | YES | YES | YES | YES | NO | NO | NO |
| TJU_CMC_MD2.ID02637.3p-miR | TJU_CMC_MD2.ID02637.hairpin | YES | NO | NO | NO | NO | NO | NO | NO |
| TJU_CMC_MD2.ID02638.3p-miR | TJU_CMC_MD2.ID02638.hairpin | YES | NO | NO | NO | NO | NO | NO | NO |
| TJU_CMC_MD2.ID02638.5p-miR | TJU_CMC_MD2.ID02638.hairpin | YES | YES | YES | NO | NO | NO | NO | NO |
| TJU_CMC_MD2.ID02639.5p-miR | TJU_CMC_MD2.ID02639.hairpin | YES | YES | YES | YES | NO | NO | NO | NO |
| TJU_CMC_MD2.ID02640.3p-miR | TJU_CMC_MD2.ID02640.hairpin | YES | NO | NO | NO | NO | NO | NO | NO |
| TJU_CMC_MD2.ID02641.5p-miR | TJU_CMC_MD2.ID02641.hairpin | YES | YES | YES | YES | YES | NO | NO | NO |
| TJU_CMC_MD2.ID02642.3p-miR | TJU_CMC_MD2.ID02642.hairpin | YES | NO | NO | NO | NO | NO | NO | NO |
| TJU_CMC_MD2.ID02642.5p-miR | TJU_CMC_MD2.ID02642.hairpin | YES | YES | YES | YES | YES | NO | NO | NO |
| TJU_CMC_MD2.ID02643.3p-miR | TJU_CMC_MD2.ID02643.hairpin | YES | NO | NO | NO | NO | NO | NO | NO |
| TJU_CMC_MD2.ID02644.3p-miR | TJU_CMC_MD2.ID02644.hairpin | YES | NO | NO | NO | NO | NO | NO | NO |
| TJU_CMC_MD2.ID02645.5p-miR | TJU_CMC_MD2.ID02645.hairpin | YES | YES | NO | YES | YES | NO | NO | NO |
| TJU_CMC_MD2.ID02646.3p-miR | TJU_CMC_MD2.ID02646.hairpin | YES | NO | NO | NO | NO | NO | NO | NO |
| TJU_CMC_MD2.ID02647.3p-miR | TJU_CMC_MD2.ID02647.hairpin | YES | NO | NO | NO | NO | NO | NO | NO |
| TJU_CMC_MD2.ID02648.5p-miR | TJU_CMC_MD2.ID02648.hairpin | YES | YES | YES | NO | NO | NO | NO | NO |
| TJU_CMC_MD2.ID02649.5p-miR | TJU_CMC_MD2.ID02649.hairpin | YES | NO | YES | YES | NO | NO | NO | NO |
| TJU_CMC_MD2.ID02650.3p-miR | TJU_CMC_MD2.ID02650.hairpin | YES | YES | YES | YES | NO | NO | NO | NO |
| TJU_CMC_MD2.ID02651.5p-miR | TJU_CMC_MD2.ID02651.hairpin | YES | YES | NO | NO | NO | NO | NO | NO |
| TJU_CMC_MD2.ID02652.5p-miR | TJU_CMC_MD2.ID02652.hairpin | YES | YES | YES | NO | NO | NO | NO | NO |
| TJU_CMC_MD2.ID02653.3p-miR | TJU_CMC_MD2.ID02653.hairpin | YES | NO | NO | NO | NO | NO | NO | NO |
| TJU_CMC_MD2.ID02654.3p-miR | TJU_CMC_MD2.ID02654.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02655.3p-miR | TJU_CMC_MD2.ID02655.hairpin | YES | NO | NO | NO | NO | NO | NO | NO |
| TJU_CMC_MD2.ID02656.5p-miR | TJU_CMC_MD2.ID02656.hairpin | YES | YES | YES | YES | YES | NO | NO | NO |
| TJU_CMC_MD2.ID02657.5p-miR | TJU_CMC_MD2.ID02657.hairpin | YES | YES | NO | NO | NO | NO | NO | NO |
| TJU_CMC_MD2.ID02658.5p-miR | TJU_CMC_MD2.ID02658.hairpin | YES | YES | YES | YES | YES | NO | NO | NO |
| TJU_CMC_MD2.ID02659.3p-miR | TJU_CMC_MD2.ID02659.hairpin | YES | NO | NO | NO | NO | NO | NO | NO |
| TJU_CMC_MD2.ID02660.3p-miR | TJU_CMC_MD2.ID02660.hairpin | YES | NO | NO | NO | NO | NO | NO | NO |
| TJU_CMC_MD2.ID02661.5p-miR | TJU_CMC_MD2.ID02661.hairpin | YES | NO | NO | YES | NO | NO | NO | NO |
| TJU_CMC_MD2.ID02662.5p-miR | TJU_CMC_MD2.ID02662.hairpin | YES | YES | YES | YES | YES | NO | NO | NO |
| TJU_CMC_MD2.ID02663.5p-miR | TJU_CMC_MD2.ID02663.hairpin | YES | YES | YES | YES | YES | NO | NO | NO |
| TJU_CMC_MD2.ID02664.5p-miR | TJU_CMC_MD2.ID02664.hairpin | YES | YES | YES | YES | YES | NO | NO | NO |
| TJU_CMC_MD2.ID02665.3p-miR | TJU_CMC_MD2.ID02665.hairpin | YES | NO | NO | NO | NO | NO | NO | NO |
| TJU_CMC_MD2.ID02666.5p-miR | TJU_CMC_MD2.ID02666.hairpin | YES | YES | YES | YES | YES | NO | NO | NO |
| TJU_CMC_MD2.ID02667.5p-miR | TJU_CMC_MD2.ID02667.hairpin | YES | YES | YES | YES | YES | NO | NO | NO |
| TJU_CMC_MD2.ID02668.5p-miR | TJU_CMC_MD2.ID02668.hairpin | YES | YES | YES | NO | NO | NO | NO | NO |
| TJU_CMC_MD2.ID02669.5p-miR | TJU_CMC_MD2.ID02669.hairpin | YES | YES | YES | YES | NO | NO | NO | NO |
| TJU_CMC_MD2.ID02670.3p-miR | TJU_CMC_MD2.ID02670.hairpin | YES | NO | NO | NO | NO | NO | NO | NO |
| TJU_CMC_MD2.ID02670.5p-miR | TJU_CMC_MD2.ID02670.hairpin | YES | NO | YES | NO | YES | NO | NO | NO |
| TJU_CMC_MD2.ID02671.5p-miR | TJU_CMC_MD2.ID02671.hairpin | YES | NO | NO | NO | NO | NO | NO | NO |
| TJU_CMC_MD2.ID02672.5p-miR | TJU_CMC_MD2.ID02672.hairpin | YES | YES | YES | NO | NO | NO | NO | NO |
| TJU_CMC_MD2.ID02673.5p-miR | TJU_CMC_MD2.ID02673.hairpin | YES | YES | YES | YES | YES | NO | NO | NO |
| TJU_CMC_MD2.ID02674.3p-miR | TJU_CMC_MD2.ID02674.hairpin | YES | NO | NO | NO | NO | NO | NO | NO |
| TJU_CMC_MD2.ID02675.3p-miR | TJU_CMC_MD2.ID02675.hairpin | YES | NO | NO | NO | NO | NO | NO | NO |
| TJU_CMC_MD2.ID02676.5p-miR | TJU_CMC_MD2.ID02676.hairpin | YES | NO | NO | NO | NO | NO | NO | NO |
| TJU_CMC_MD2.ID02677.5p-miR | TJU_CMC_MD2.ID02677.hairpin | YES | YES | YES | YES | YES | NO | NO | NO |
| TJU_CMC_MD2.ID02678.3p-miR | TJU_CMC_MD2.ID02678.hairpin | YES | NO | NO | NO | NO | NO | NO | NO |
| TJU_CMC_MD2.ID02679.3p-miR | TJU_CMC_MD2.ID02679.hairpin | YES | NO | NO | NO | NO | NO | NO | NO |
| TJU_CMC_MD2.ID02680.3p-miR | TJU_CMC_MD2.ID02680.hairpin | YES | NO | NO | NO | NO | NO | NO | NO |
| TJU_CMC_MD2.ID02681.3p-miR | TJU_CMC_MD2.ID02681.hairpin | YES | NO | NO | NO | NO | NO | NO | NO |
| TJU_CMC_MD2.ID02682.5p-miR | TJU_CMC_MD2.ID02682.hairpin | YES | YES | YES | NO | YES | NO | NO | NO |
| TJU_CMC_MD2.ID02683.3p-miR | TJU_CMC_MD2.ID02683.hairpin | YES | NO | NO | NO | NO | NO | NO | NO |
| TJU_CMC_MD2.ID02683.5p-miR | TJU_CMC_MD2.ID02683.hairpin | YES | YES | YES | NO | NO | NO | NO | NO |
| TJU_CMC_MD2.ID02684.5p-miR | TJU_CMC_MD2.ID02684.hairpin | YES | YES | YES | NO | NO | NO | NO | NO |
| TJU_CMC_MD2.ID02685.3p-miR | TJU_CMC_MD2.ID02685.hairpin | YES | NO | NO | NO | NO | NO | NO | NO |
| TJU_CMC_MD2.ID02686.5p-miR | TJU_CMC_MD2.ID02686.hairpin | YES | NO | NO | YES | NO | YES | NO | NO |
| TJU_CMC_MD2.ID02687.3p-miR | TJU_CMC_MD2.ID02687.hairpin | YES | NO | NO | NO | NO | NO | NO | NO |
| TJU_CMC_MD2.ID02687.5p-miR | TJU_CMC_MD2.ID02687.hairpin | YES | YES | YES | YES | NO | NO | NO | NO |
| TJU_CMC_MD2.ID02688.5p-miR | TJU_CMC_MD2.ID02688.hairpin | YES | YES | YES | YES | YES | NO | NO | NO |
| TJU_CMC_MD2.ID02689.3p-miR | TJU_CMC_MD2.ID02689.hairpin | YES | NO | NO | NO | NO | NO | NO | NO |
| TJU_CMC_MD2.ID02690.3p-miR | TJU_CMC_MD2.ID02690.hairpin | YES | NO | NO | NO | NO | NO | NO | NO |
| TJU_CMC_MD2.ID02690.5p-miR | TJU_CMC_MD2.ID02690.hairpin | YES | YES | YES | YES | NO | NO | NO | NO |
| TJU_CMC_MD2.ID02691.5p-miR | TJU_CMC_MD2.ID02691.hairpin | YES | YES | YES | YES | YES | YES | NO | NO |
| TJU_CMC_MD2.ID02692.3p-miR | TJU_CMC_MD2.ID02692.hairpin | YES | NO | NO | NO | NO | NO | NO | NO |
| TJU_CMC_MD2.ID02692.5p-miR | TJU_CMC_MD2.ID02692.hairpin | YES | YES | YES | YES | YES | NO | NO | NO |
| TJU_CMC_MD2.ID02693.3p-miR | TJU_CMC_MD2.ID02693.hairpin | YES | NO | NO | NO | NO | NO | NO | NO |
| TJU_CMC_MD2.ID02694.3p-miR | TJU_CMC_MD2.ID02694.hairpin | YES | NO | NO | NO | NO | NO | NO | NO |
| TJU_CMC_MD2.ID02695.3p-miR | TJU_CMC_MD2.ID02695.hairpin | YES | NO | NO | NO | NO | NO | NO | NO |
| TJU_CMC_MD2.ID02696.5p-miR | TJU_CMC_MD2.ID02696.hairpin | YES | YES | YES | YES | YES | NO | NO | NO |
| TJU_CMC_MD2.ID02697.3p-miR | TJU_CMC_MD2.ID02697.hairpin | YES | NO | NO | NO | NO | NO | NO | NO |
| TJU_CMC_MD2.ID02698.3p-miR | TJU_CMC_MD2.ID02698.hairpin | YES | NO | NO | NO | NO | NO | NO | NO |
| TJU_CMC_MD2.ID02699.5p-miR | TJU_CMC_MD2.ID02699.hairpin | YES | YES | NO | NO | NO | NO | NO | NO |
| TJU_CMC_MD2.ID02700.3p-miR | TJU_CMC_MD2.ID02700.hairpin | YES | NO | NO | NO | NO | NO | NO | NO |
| TJU_CMC_MD2.ID02700.5p-miR | TJU_CMC_MD2.ID02700.hairpin | YES | YES | YES | YES | YES | YES | NO | NO |
| TJU_CMC_MD2.ID02701.5p-miR | TJU_CMC_MD2.ID02701.hairpin | YES | YES | YES | YES | NO | NO | NO | NO |
| TJU_CMC_MD2.ID02702.3p-miR | TJU_CMC_MD2.ID02702.hairpin | YES | NO | NO | NO | NO | NO | NO | NO |
| TJU_CMC_MD2.ID02703.3p-miR | TJU_CMC_MD2.ID02703.hairpin | YES | NO | NO | NO | NO | NO | NO | NO |
| TJU_CMC_MD2.ID02704.3p-miR | TJU_CMC_MD2.ID02704.hairpin | YES | NO | NO | NO | NO | NO | NO | NO |
| TJU_CMC_MD2.ID02704.5p-miR | TJU_CMC_MD2.ID02704.hairpin | YES | YES | YES | YES | NO | NO | NO | NO |
| TJU_CMC_MD2.ID02705.3p-miR | TJU_CMC_MD2.ID02705.hairpin | YES | NO | NO | NO | NO | NO | NO | NO |
| TJU_CMC_MD2.ID02706.5p-miR | TJU_CMC_MD2.ID02706.hairpin | YES | YES | YES | NO | YES | NO | NO | NO |
| TJU_CMC_MD2.ID02707.3p-miR | TJU_CMC_MD2.ID02707.hairpin | YES | NO | NO | NO | NO | NO | NO | NO |
| TJU_CMC_MD2.ID02708.5p-miR | TJU_CMC_MD2.ID02708.hairpin | YES | YES | YES | YES | YES | NO | NO | NO |
| TJU_CMC_MD2.ID02709.3p-miR | TJU_CMC_MD2.ID02709.hairpin | YES | NO | NO | NO | NO | NO | NO | NO |
| TJU_CMC_MD2.ID02710.3p-miR | TJU_CMC_MD2.ID02710.hairpin | YES | NO | NO | NO | NO | NO | NO | NO |
| TJU_CMC_MD2.ID02711.3p-miR | TJU_CMC_MD2.ID02711.hairpin | YES | YES | NO | NO | NO | NO | NO | NO |
| TJU_CMC_MD2.ID02712.3p-miR | TJU_CMC_MD2.ID02712.hairpin | YES | YES | YES | YES | YES | NO | NO | NO |
| TJU_CMC_MD2.ID02712.5p-miR | TJU_CMC_MD2.ID02712.hairpin | YES | YES | YES | YES | NO | NO | NO | NO |
| TJU_CMC_MD2.ID02713.3p-miR | TJU_CMC_MD2.ID02713.hairpin | YES | NO | NO | NO | NO | NO | NO | NO |
| TJU_CMC_MD2.ID02713.5p-miR | TJU_CMC_MD2.ID02713.hairpin | YES | YES | YES | YES | NO | NO | NO | NO |
| TJU_CMC_MD2.ID02714.5p-miR | TJU_CMC_MD2.ID02714.hairpin | YES | YES | YES | YES | YES | NO | NO | NO |
| TJU_CMC_MD2.ID02715.3p-miR | TJU_CMC_MD2.ID02715.hairpin | YES | NO | NO | NO | NO | NO | NO | NO |
| TJU_CMC_MD2.ID02716.5p-miR | TJU_CMC_MD2.ID02716.hairpin | YES | YES | YES | YES | YES | NO | NO | NO |
| TJU_CMC_MD2.ID02717.5p-miR | TJU_CMC_MD2.ID02717.hairpin | YES | YES | YES | YES | YES | NO | NO | NO |
| TJU_CMC_MD2.ID02718.3p-miR | TJU_CMC_MD2.ID02718.hairpin | YES | NO | NO | NO | NO | NO | NO | NO |
| TJU_CMC_MD2.ID02719.3p-miR | TJU_CMC_MD2.ID02719.hairpin | YES | YES | YES | NO | YES | NO | NO | NO |
| TJU_CMC_MD2.ID02720.3p-miR | TJU_CMC_MD2.ID02720.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02721.5p-miR | TJU_CMC_MD2.ID02721.hairpin | YES | YES | YES | YES | NO | NO | NO | NO |
| TJU_CMC_MD2.ID02722.3p-miR | TJU_CMC_MD2.ID02722.hairpin | YES | NO | NO | NO | NO | NO | NO | NO |
| TJU_CMC_MD2.ID02723.3p-miR | TJU_CMC_MD2.ID02723.hairpin | YES | NO | NO | NO | NO | NO | NO | NO |
| TJU_CMC_MD2.ID02724.5p-miR | TJU_CMC_MD2.ID02724.hairpin | YES | NO | YES | YES | NO | NO | NO | NO |
| TJU_CMC_MD2.ID02725.3p-miR | TJU_CMC_MD2.ID02725.hairpin | YES | NO | NO | NO | NO | NO | NO | NO |
| TJU_CMC_MD2.ID02726.3p-miR | TJU_CMC_MD2.ID02726.hairpin | YES | NO | NO | NO | NO | NO | NO | NO |
| TJU_CMC_MD2.ID02727.5p-miR | TJU_CMC_MD2.ID02727.hairpin | YES | YES | NO | YES | NO | NO | NO | NO |
| TJU_CMC_MD2.ID02728.5p-miR | TJU_CMC_MD2.ID02728.hairpin | YES | NO | YES | YES | NO | NO | NO | NO |
| TJU_CMC_MD2.ID02729.5p-miR | TJU_CMC_MD2.ID02729.hairpin | YES | YES | YES | YES | NO | NO | NO | NO |
| TJU_CMC_MD2.ID02730.5p-miR | TJU_CMC_MD2.ID02730.hairpin | YES | YES | YES | NO | YES | NO | NO | NO |
| TJU_CMC_MD2.ID02731.3p-miR | TJU_CMC_MD2.ID02731.hairpin | YES | NO | NO | NO | NO | NO | NO | NO |
| TJU_CMC_MD2.ID02732.3p-miR | TJU_CMC_MD2.ID02732.hairpin | YES | NO | NO | NO | NO | NO | NO | NO |
| TJU_CMC_MD2.ID02733.5p-miR | TJU_CMC_MD2.ID02733.hairpin | YES | YES | YES | YES | YES | YES | NO | NO |
| TJU_CMC_MD2.ID02734.3p-miR | TJU_CMC_MD2.ID02734.hairpin | YES | NO | NO | NO | NO | NO | NO | NO |
| TJU_CMC_MD2.ID02735.3p-miR | TJU_CMC_MD2.ID02735.hairpin | YES | NO | NO | NO | NO | NO | NO | NO |
| TJU_CMC_MD2.ID02736.5p-miR | TJU_CMC_MD2.ID02736.hairpin | YES | YES | YES | YES | YES | YES | NO | NO |
| TJU_CMC_MD2.ID02737.3p-miR | TJU_CMC_MD2.ID02737.hairpin | YES | NO | NO | NO | NO | NO | NO | NO |
| TJU_CMC_MD2.ID02738.3p-miR | TJU_CMC_MD2.ID02738.hairpin | YES | NO | NO | NO | NO | NO | NO | NO |
| TJU_CMC_MD2.ID02739.5p-miR | TJU_CMC_MD2.ID02739.hairpin | YES | YES | YES | YES | YES | NO | NO | NO |
| TJU_CMC_MD2.ID02740.3p-miR | TJU_CMC_MD2.ID02740.hairpin | YES | NO | NO | NO | NO | NO | NO | NO |
| TJU_CMC_MD2.ID02741.3p-miR | TJU_CMC_MD2.ID02741.hairpin | YES | NO | NO | NO | NO | NO | NO | NO |
| TJU_CMC_MD2.ID02742.5p-miR | TJU_CMC_MD2.ID02742.hairpin | YES | NO | NO | NO | YES | NO | NO | NO |
| TJU_CMC_MD2.ID02743.5p-miR | TJU_CMC_MD2.ID02743.hairpin | YES | YES | YES | NO | NO | NO | NO | NO |
| TJU_CMC_MD2.ID02744.3p-miR | TJU_CMC_MD2.ID02744.hairpin | YES | NO | NO | NO | NO | NO | NO | NO |
| TJU_CMC_MD2.ID02745.3p-miR | TJU_CMC_MD2.ID02745.hairpin | YES | NO | NO | NO | NO | NO | NO | NO |
| TJU_CMC_MD2.ID02746.5p-miR | TJU_CMC_MD2.ID02746.hairpin | YES | YES | YES | YES | NO | NO | NO | NO |
| TJU_CMC_MD2.ID02747.5p-miR | TJU_CMC_MD2.ID02747.hairpin | YES | YES | YES | YES | NO | NO | NO | NO |
| TJU_CMC_MD2.ID02748.3p-miR | TJU_CMC_MD2.ID02748.hairpin | YES | NO | NO | NO | NO | NO | NO | NO |
| TJU_CMC_MD2.ID02749.5p-miR | TJU_CMC_MD2.ID02749.hairpin | YES | YES | YES | YES | NO | NO | NO | NO |
| TJU_CMC_MD2.ID02750.3p-miR | TJU_CMC_MD2.ID02750.hairpin | YES | NO | NO | NO | NO | NO | NO | NO |
| TJU_CMC_MD2.ID02751.3p-miR | TJU_CMC_MD2.ID02751.hairpin | YES | NO | NO | NO | NO | NO | NO | NO |
| TJU_CMC_MD2.ID02752.3p-miR | TJU_CMC_MD2.ID02752.hairpin | YES | NO | NO | NO | NO | NO | NO | NO |
| TJU_CMC_MD2.ID02753.3p-miR | TJU_CMC_MD2.ID02753.hairpin | YES | YES | YES | NO | YES | NO | NO | NO |
| TJU_CMC_MD2.ID02753.5p-miR | TJU_CMC_MD2.ID02753.hairpin | YES | YES | YES | YES | NO | NO | NO | NO |
| TJU_CMC_MD2.ID02754.5p-miR | TJU_CMC_MD2.ID02754.hairpin | YES | YES | YES | YES | YES | NO | NO | NO |
| TJU_CMC_MD2.ID02755.3p-miR | TJU_CMC_MD2.ID02755.hairpin | YES | NO | NO | NO | NO | NO | NO | NO |
| TJU_CMC_MD2.ID02756.3p-miR | TJU_CMC_MD2.ID02756.hairpin | YES | NO | NO | NO | NO | NO | NO | NO |
| TJU_CMC_MD2.ID02757.3p-miR | TJU_CMC_MD2.ID02757.hairpin | YES | NO | NO | NO | NO | NO | NO | NO |
| TJU_CMC_MD2.ID02758.3p-miR | TJU_CMC_MD2.ID02758.hairpin | YES | NO | NO | NO | NO | NO | NO | NO |
| TJU_CMC_MD2.ID02759.3p-miR | TJU_CMC_MD2.ID02759.hairpin | YES | NO | NO | NO | NO | NO | NO | NO |
| TJU_CMC_MD2.ID02759.5p-miR | TJU_CMC_MD2.ID02759.hairpin | YES | YES | NO | NO | NO | NO | NO | NO |
| TJU_CMC_MD2.ID02760.3p-miR | TJU_CMC_MD2.ID02760.hairpin | YES | NO | NO | NO | NO | NO | NO | NO |
| TJU_CMC_MD2.ID02761.3p-miR | TJU_CMC_MD2.ID02761.hairpin | YES | NO | NO | NO | NO | NO | NO | NO |
| TJU_CMC_MD2.ID02762.5p-miR | TJU_CMC_MD2.ID02762.hairpin | YES | YES | NO | NO | NO | NO | NO | NO |
| TJU_CMC_MD2.ID02763.3p-miR | TJU_CMC_MD2.ID02763.hairpin | YES | NO | NO | NO | NO | NO | NO | NO |
| TJU_CMC_MD2.ID02764.5p-miR | TJU_CMC_MD2.ID02764.hairpin | YES | NO | NO | NO | NO | NO | NO | NO |
| TJU_CMC_MD2.ID02765.3p-miR | TJU_CMC_MD2.ID02765.hairpin | YES | NO | NO | NO | NO | NO | NO | NO |
| TJU_CMC_MD2.ID02766.3p-miR | TJU_CMC_MD2.ID02766.hairpin | YES | NO | NO | NO | NO | NO | NO | NO |
| TJU_CMC_MD2.ID02767.3p-miR | TJU_CMC_MD2.ID02767.hairpin | YES | NO | NO | NO | NO | NO | NO | NO |
| TJU_CMC_MD2.ID02768.3p-miR | TJU_CMC_MD2.ID02768.hairpin | YES | NO | NO | NO | NO | NO | NO | NO |
| TJU_CMC_MD2.ID02769.5p-miR | TJU_CMC_MD2.ID02769.hairpin | YES | YES | YES | NO | NO | NO | NO | NO |
| TJU_CMC_MD2.ID02770.5p-miR | TJU_CMC_MD2.ID02770.hairpin | YES | YES | NO | NO | NO | YES | NO | NO |
| TJU_CMC_MD2.ID02771.3p-miR | TJU_CMC_MD2.ID02771.hairpin | YES | NO | NO | NO | NO | NO | NO | NO |
| TJU_CMC_MD2.ID02772.3p-miR | TJU_CMC_MD2.ID02772.hairpin | YES | NO | NO | NO | NO | NO | NO | NO |
| TJU_CMC_MD2.ID02773.3p-miR | TJU_CMC_MD2.ID02773.hairpin | YES | NO | NO | NO | NO | NO | NO | NO |
| TJU_CMC_MD2.ID02774.5p-miR | TJU_CMC_MD2.ID02774.hairpin | YES | YES | YES | YES | YES | NO | NO | NO |
| TJU_CMC_MD2.ID02775.5p-miR | TJU_CMC_MD2.ID02775.hairpin | YES | YES | YES | YES | YES | NO | NO | NO |
| TJU_CMC_MD2.ID02776.5p-miR | TJU_CMC_MD2.ID02776.hairpin | YES | YES | YES | YES | NO | NO | NO | NO |
| TJU_CMC_MD2.ID02777.3p-miR | TJU_CMC_MD2.ID02777.hairpin | YES | NO | NO | NO | NO | NO | NO | NO |
| TJU_CMC_MD2.ID02778.3p-miR | TJU_CMC_MD2.ID02778.hairpin | YES | NO | NO | NO | NO | NO | NO | NO |
| TJU_CMC_MD2.ID02779.3p-miR | TJU_CMC_MD2.ID02779.hairpin | YES | NO | NO | NO | NO | NO | NO | NO |
| TJU_CMC_MD2.ID02780.3p-miR | TJU_CMC_MD2.ID02780.hairpin | YES | NO | NO | NO | NO | NO | NO | NO |
| TJU_CMC_MD2.ID02781.3p-miR | TJU_CMC_MD2.ID02781.hairpin | YES | NO | NO | NO | NO | NO | NO | NO |
| TJU_CMC_MD2.ID02782.5p-miR | TJU_CMC_MD2.ID02782.hairpin | YES | YES | YES | YES | YES | NO | NO | NO |
| TJU_CMC_MD2.ID02783.5p-miR | TJU_CMC_MD2.ID02783.hairpin | YES | YES | YES | YES | YES | NO | NO | NO |
| TJU_CMC_MD2.ID02784.3p-miR | TJU_CMC_MD2.ID02784.hairpin | YES | NO | NO | NO | NO | NO | NO | NO |
| TJU_CMC_MD2.ID02785.3p-miR | TJU_CMC_MD2.ID02785.hairpin | YES | NO | NO | NO | NO | NO | NO | NO |
| TJU_CMC_MD2.ID02786.5p-miR | TJU_CMC_MD2.ID02786.hairpin | YES | YES | NO | YES | NO | NO | NO | NO |
| TJU_CMC_MD2.ID02787.5p-miR | TJU_CMC_MD2.ID02787.hairpin | YES | YES | YES | NO | YES | NO | NO | NO |
| TJU_CMC_MD2.ID02788.3p-miR | TJU_CMC_MD2.ID02788.hairpin | YES | NO | NO | NO | NO | NO | NO | NO |
| TJU_CMC_MD2.ID02789.5p-miR | TJU_CMC_MD2.ID02789.hairpin | YES | YES | NO | YES | NO | NO | NO | NO |
| TJU_CMC_MD2.ID02790.5p-miR | TJU_CMC_MD2.ID02790.hairpin | YES | YES | YES | YES | YES | NO | NO | NO |
| TJU_CMC_MD2.ID02791.5p-miR | TJU_CMC_MD2.ID02791.hairpin | YES | YES | YES | NO | NO | NO | NO | NO |
| TJU_CMC_MD2.ID02792.3p-miR | TJU_CMC_MD2.ID02792.hairpin | YES | NO | NO | NO | NO | NO | NO | NO |
| TJU_CMC_MD2.ID02793.3p-miR | TJU_CMC_MD2.ID02793.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02794.3p-miR | TJU_CMC_MD2.ID02794.hairpin | YES | NO | NO | NO | NO | NO | NO | NO |
| TJU_CMC_MD2.ID02795.3p-miR | TJU_CMC_MD2.ID02795.hairpin | YES | NO | NO | NO | NO | NO | NO | NO |
| TJU_CMC_MD2.ID02795.5p-miR | TJU_CMC_MD2.ID02795.hairpin | YES | YES | YES | NO | NO | NO | NO | NO |
| TJU_CMC_MD2.ID02796.3p-miR | TJU_CMC_MD2.ID02796.hairpin | YES | YES | YES | YES | NO | NO | NO | NO |
| TJU_CMC_MD2.ID02797.3p-miR | TJU_CMC_MD2.ID02797.hairpin | YES | NO | NO | NO | NO | NO | NO | NO |
| TJU_CMC_MD2.ID02798.3p-miR | TJU_CMC_MD2.ID02798.hairpin | YES | NO | NO | NO | NO | NO | NO | NO |
| TJU_CMC_MD2.ID02799.5p-miR | TJU_CMC_MD2.ID02799.hairpin | YES | NO | YES | YES | NO | YES | NO | NO |
| TJU_CMC_MD2.ID02800.3p-miR | TJU_CMC_MD2.ID02800.hairpin | YES | NO | NO | NO | NO | NO | NO | NO |
| TJU_CMC_MD2.ID02801.3p-miR | TJU_CMC_MD2.ID02801.hairpin | YES | NO | NO | NO | NO | NO | NO | NO |
| TJU_CMC_MD2.ID02802.3p-miR | TJU_CMC_MD2.ID02802.hairpin | YES | NO | NO | NO | NO | NO | NO | NO |
| TJU_CMC_MD2.ID02803.5p-miR | TJU_CMC_MD2.ID02803.hairpin | YES | YES | NO | NO | NO | NO | NO | NO |
| TJU_CMC_MD2.ID02804.5p-miR | TJU_CMC_MD2.ID02804.hairpin | YES | YES | YES | YES | YES | NO | NO | NO |
| TJU_CMC_MD2.ID02805.5p-miR | TJU_CMC_MD2.ID02805.hairpin | YES | YES | YES | NO | NO | YES | NO | NO |
| TJU_CMC_MD2.ID02806.3p-miR | TJU_CMC_MD2.ID02806.hairpin | YES | NO | NO | NO | NO | NO | NO | NO |
| TJU_CMC_MD2.ID02807.3p-miR | TJU_CMC_MD2.ID02807.hairpin | YES | NO | NO | NO | NO | NO | NO | NO |
| TJU_CMC_MD2.ID02808.3p-miR | TJU_CMC_MD2.ID02808.hairpin | YES | NO | NO | NO | NO | NO | NO | NO |
| TJU_CMC_MD2.ID02808.5p-miR | TJU_CMC_MD2.ID02808.hairpin | YES | YES | YES | YES | YES | NO | NO | NO |
| TJU_CMC_MD2.ID02809.3p-miR | TJU_CMC_MD2.ID02809.hairpin | YES | NO | NO | NO | NO | NO | NO | NO |
| TJU_CMC_MD2.ID02810.5p-miR | TJU_CMC_MD2.ID02810.hairpin | YES | YES | YES | YES | YES | NO | NO | NO |
| TJU_CMC_MD2.ID02811.5p-miR | TJU_CMC_MD2.ID02811.hairpin | YES | NO | YES | NO | NO | NO | NO | NO |
| TJU_CMC_MD2.ID02812.3p-miR | TJU_CMC_MD2.ID02812.hairpin | YES | NO | NO | NO | NO | NO | NO | NO |
| TJU_CMC_MD2.ID02813.3p-miR | TJU_CMC_MD2.ID02813.hairpin | YES | NO | NO | NO | NO | NO | NO | NO |
| TJU_CMC_MD2.ID02814.5p-miR | TJU_CMC_MD2.ID02814.hairpin | YES | YES | YES | NO | YES | NO | NO | NO |
| TJU_CMC_MD2.ID02815.3p-miR | TJU_CMC_MD2.ID02815.hairpin | YES | NO | NO | NO | NO | NO | NO | NO |
| TJU_CMC_MD2.ID02816.3p-miR | TJU_CMC_MD2.ID02816.hairpin | YES | NO | NO | NO | NO | NO | NO | NO |
| TJU_CMC_MD2.ID02817.3p-miR | TJU_CMC_MD2.ID02817.hairpin | YES | YES | YES | NO | YES | YES | NO | NO |
| TJU_CMC_MD2.ID02817.5p-miR | TJU_CMC_MD2.ID02817.hairpin | YES | YES | YES | NO | YES | YES | NO | NO |
| TJU_CMC_MD2.ID02818.5p-miR | TJU_CMC_MD2.ID02818.hairpin | YES | YES | NO | YES | NO | NO | NO | NO |
| TJU_CMC_MD2.ID02819.5p-miR | TJU_CMC_MD2.ID02819.hairpin | YES | NO | YES | NO | YES | NO | NO | NO |
| TJU_CMC_MD2.ID02820.3p-miR | TJU_CMC_MD2.ID02820.hairpin | YES | NO | NO | NO | NO | NO | NO | NO |
| TJU_CMC_MD2.ID02821.3p-miR | TJU_CMC_MD2.ID02821.hairpin | YES | NO | NO | NO | NO | NO | NO | NO |
| TJU_CMC_MD2.ID02821.5p-miR | TJU_CMC_MD2.ID02821.hairpin | YES | YES | YES | NO | NO | NO | NO | NO |
| TJU_CMC_MD2.ID02822.5p-miR | TJU_CMC_MD2.ID02822.hairpin | YES | YES | YES | YES | NO | NO | NO | NO |
| TJU_CMC_MD2.ID02823.3p-miR | TJU_CMC_MD2.ID02823.hairpin | YES | NO | NO | NO | NO | NO | NO | NO |
| TJU_CMC_MD2.ID02824.3p-miR | TJU_CMC_MD2.ID02824.hairpin | YES | NO | NO | NO | NO | NO | NO | NO |
| TJU_CMC_MD2.ID02825.3p-miR | TJU_CMC_MD2.ID02825.hairpin | YES | NO | NO | NO | NO | NO | NO | NO |
| TJU_CMC_MD2.ID02826.3p-miR | TJU_CMC_MD2.ID02826.hairpin | YES | NO | NO | NO | NO | NO | NO | NO |
| TJU_CMC_MD2.ID02827.3p-miR | TJU_CMC_MD2.ID02827.hairpin | YES | NO | NO | NO | NO | NO | NO | NO |
| TJU_CMC_MD2.ID02828.3p-miR | TJU_CMC_MD2.ID02828.hairpin | YES | NO | NO | NO | NO | NO | NO | NO |
| TJU_CMC_MD2.ID02829.5p-miR | TJU_CMC_MD2.ID02829.hairpin | YES | YES | NO | YES | YES | NO | NO | NO |
| TJU_CMC_MD2.ID02830.3p-miR | TJU_CMC_MD2.ID02830.hairpin | YES | NO | NO | NO | NO | NO | NO | NO |
| TJU_CMC_MD2.ID02831.3p-miR | TJU_CMC_MD2.ID02831.hairpin | YES | NO | NO | NO | NO | NO | NO | NO |
| TJU_CMC_MD2.ID02831.5p-miR | TJU_CMC_MD2.ID02831.hairpin | YES | YES | NO | NO | NO | NO | NO | NO |
| TJU_CMC_MD2.ID02832.3p-miR | TJU_CMC_MD2.ID02832.hairpin | YES | NO | NO | NO | NO | NO | NO | NO |
| TJU_CMC_MD2.ID02833.5p-miR | TJU_CMC_MD2.ID02833.hairpin | YES | YES | YES | YES | YES | NO | NO | NO |
| TJU_CMC_MD2.ID02834.3p-miR | TJU_CMC_MD2.ID02834.hairpin | YES | NO | NO | NO | NO | NO | NO | NO |
| TJU_CMC_MD2.ID02835.3p-miR | TJU_CMC_MD2.ID02835.hairpin | YES | YES | YES | YES | YES | NO | NO | NO |
| TJU_CMC_MD2.ID02835.5p-miR | TJU_CMC_MD2.ID02835.hairpin | YES | NO | YES | YES | YES | NO | NO | NO |
| TJU_CMC_MD2.ID02836.3p-miR | TJU_CMC_MD2.ID02836.hairpin | YES | NO | NO | NO | NO | NO | NO | NO |
| TJU_CMC_MD2.ID02837.5p-miR | TJU_CMC_MD2.ID02837.hairpin | YES | YES | NO | YES | NO | NO | NO | NO |
| TJU_CMC_MD2.ID02838.5p-miR | TJU_CMC_MD2.ID02838.hairpin | YES | YES | YES | NO | YES | NO | NO | NO |
| TJU_CMC_MD2.ID02839.3p-miR | TJU_CMC_MD2.ID02839.hairpin | YES | NO | NO | NO | NO | NO | NO | NO |
| TJU_CMC_MD2.ID02840.3p-miR | TJU_CMC_MD2.ID02840.hairpin | YES | NO | NO | NO | NO | NO | NO | NO |
| TJU_CMC_MD2.ID02841.5p-miR | TJU_CMC_MD2.ID02841.hairpin | YES | NO | NO | NO | NO | NO | NO | NO |
| TJU_CMC_MD2.ID02842.5p-miR | TJU_CMC_MD2.ID02842.hairpin | YES | YES | NO | YES | NO | NO | NO | NO |
| TJU_CMC_MD2.ID02843.5p-miR | TJU_CMC_MD2.ID02843.hairpin | YES | YES | YES | YES | NO | NO | NO | NO |
| TJU_CMC_MD2.ID02844.5p-miR | TJU_CMC_MD2.ID02844.hairpin | YES | YES | YES | YES | YES | NO | NO | NO |
| TJU_CMC_MD2.ID02845.5p-miR | TJU_CMC_MD2.ID02845.hairpin | YES | YES | YES | YES | YES | NO | NO | NO |
| TJU_CMC_MD2.ID02846.3p-miR | TJU_CMC_MD2.ID02846.hairpin | YES | NO | NO | NO | NO | NO | NO | NO |
| TJU_CMC_MD2.ID02847.5p-miR | TJU_CMC_MD2.ID02847.hairpin | YES | NO | NO | NO | NO | NO | NO | NO |
| TJU_CMC_MD2.ID02848.3p-miR | TJU_CMC_MD2.ID02848.hairpin | YES | NO | NO | NO | NO | NO | NO | NO |
| TJU_CMC_MD2.ID02849.5p-miR | TJU_CMC_MD2.ID02849.hairpin | YES | YES | NO | NO | NO | NO | NO | NO |
| TJU_CMC_MD2.ID02850.3p-miR | TJU_CMC_MD2.ID02850.hairpin | YES | NO | NO | NO | NO | NO | NO | NO |
| TJU_CMC_MD2.ID02851.5p-miR | TJU_CMC_MD2.ID02851.hairpin | YES | NO | YES | NO | NO | NO | NO | NO |
| TJU_CMC_MD2.ID02852.5p-miR | TJU_CMC_MD2.ID02852.hairpin | YES | NO | YES | NO | NO | NO | NO | NO |
| TJU_CMC_MD2.ID02853.3p-miR | TJU_CMC_MD2.ID02853.hairpin | YES | NO | NO | NO | NO | NO | NO | NO |
| TJU_CMC_MD2.ID02854.5p-miR | TJU_CMC_MD2.ID02854.hairpin | YES | YES | YES | YES | NO | NO | NO | NO |
| TJU_CMC_MD2.ID02855.5p-miR | TJU_CMC_MD2.ID02855.hairpin | YES | YES | YES | NO | YES | NO | NO | NO |
| TJU_CMC_MD2.ID02856.5p-miR | TJU_CMC_MD2.ID02856.hairpin | YES | YES | YES | YES | YES | NO | NO | NO |
| TJU_CMC_MD2.ID02857.3p-miR | TJU_CMC_MD2.ID02857.hairpin | YES | NO | NO | NO | NO | NO | NO | NO |
| TJU_CMC_MD2.ID02858.3p-miR | TJU_CMC_MD2.ID02858.hairpin | YES | NO | NO | NO | NO | NO | NO | NO |
| TJU_CMC_MD2.ID02859.3p-miR | TJU_CMC_MD2.ID02859.hairpin | YES | NO | NO | NO | NO | NO | NO | NO |
| TJU_CMC_MD2.ID02860.5p-miR | TJU_CMC_MD2.ID02860.hairpin | YES | NO | NO | YES | NO | NO | NO | NO |
| TJU_CMC_MD2.ID02861.3p-miR | TJU_CMC_MD2.ID02861.hairpin | YES | NO | NO | NO | NO | NO | NO | NO |
| TJU_CMC_MD2.ID02862.3p-miR | TJU_CMC_MD2.ID02862.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02863.3p-miR | TJU_CMC_MD2.ID02863.hairpin | YES | YES | YES | NO | NO | NO | NO | NO |
| TJU_CMC_MD2.ID02864.5p-miR | TJU_CMC_MD2.ID02864.hairpin | YES | YES | YES | YES | YES | NO | NO | NO |
| TJU_CMC_MD2.ID02865.5p-miR | TJU_CMC_MD2.ID02865.hairpin | YES | YES | YES | YES | YES | NO | NO | NO |
| TJU_CMC_MD2.ID02866.5p-miR | TJU_CMC_MD2.ID02866.hairpin | YES | YES | NO | NO | NO | NO | NO | NO |
| TJU_CMC_MD2.ID02867.3p-miR | TJU_CMC_MD2.ID02867.hairpin | YES | NO | NO | NO | NO | NO | NO | NO |
| TJU_CMC_MD2.ID02868.3p-miR | TJU_CMC_MD2.ID02868.hairpin | YES | NO | NO | NO | NO | NO | NO | NO |
| TJU_CMC_MD2.ID02869.3p-miR | TJU_CMC_MD2.ID02869.hairpin | YES | NO | NO | NO | NO | NO | NO | NO |
| TJU_CMC_MD2.ID02870.3p-miR | TJU_CMC_MD2.ID02870.hairpin | YES | YES | YES | YES | NO | NO | NO | NO |
| TJU_CMC_MD2.ID02871.5p-miR | TJU_CMC_MD2.ID02871.hairpin | YES | YES | YES | NO | NO | NO | NO | NO |
| TJU_CMC_MD2.ID02872.3p-miR | TJU_CMC_MD2.ID02872.hairpin | YES | NO | NO | NO | NO | NO | NO | NO |
| TJU_CMC_MD2.ID02873.3p-miR | TJU_CMC_MD2.ID02873.hairpin | YES | NO | NO | NO | NO | NO | NO | NO |
| TJU_CMC_MD2.ID02874.5p-miR | TJU_CMC_MD2.ID02874.hairpin | YES | YES | YES | NO | YES | NO | NO | NO |
| TJU_CMC_MD2.ID02875.5p-miR | TJU_CMC_MD2.ID02875.hairpin | YES | YES | YES | YES | YES | NO | NO | NO |
| TJU_CMC_MD2.ID02876.3p-miR | TJU_CMC_MD2.ID02876.hairpin | YES | NO | YES | NO | YES | NO | NO | NO |
| TJU_CMC_MD2.ID02876.5p-miR | TJU_CMC_MD2.ID02876.hairpin | YES | NO | YES | NO | YES | NO | NO | NO |
| TJU_CMC_MD2.ID02877.5p-miR | TJU_CMC_MD2.ID02877.hairpin | YES | YES | YES | YES | NO | NO | NO | NO |
| TJU_CMC_MD2.ID02878.3p-miR | TJU_CMC_MD2.ID02878.hairpin | YES | YES | YES | YES | YES | NO | NO | NO |
| TJU_CMC_MD2.ID02878.5p-miR | TJU_CMC_MD2.ID02878.hairpin | YES | YES | YES | YES | YES | NO | NO | NO |
| TJU_CMC_MD2.ID02879.3p-miR | TJU_CMC_MD2.ID02879.hairpin | YES | NO | NO | NO | NO | NO | NO | NO |
| TJU_CMC_MD2.ID02880.3p-miR | TJU_CMC_MD2.ID02880.hairpin | YES | NO | NO | NO | NO | NO | NO | NO |
| TJU_CMC_MD2.ID02881.3p-miR | TJU_CMC_MD2.ID02881.hairpin | YES | NO | NO | NO | NO | NO | NO | NO |
| TJU_CMC_MD2.ID02882.3p-miR | TJU_CMC_MD2.ID02882.hairpin | YES | NO | NO | NO | NO | NO | NO | NO |
| TJU_CMC_MD2.ID02883.3p-miR | TJU_CMC_MD2.ID02883.hairpin | YES | NO | NO | NO | NO | NO | NO | NO |
| TJU_CMC_MD2.ID02884.3p-miR | TJU_CMC_MD2.ID02884.hairpin | YES | NO | NO | NO | NO | NO | NO | NO |
| TJU_CMC_MD2.ID02885.3p-miR | TJU_CMC_MD2.ID02885.hairpin | YES | NO | NO | NO | NO | NO | NO | NO |
| TJU_CMC_MD2.ID02886.5p-miR | TJU_CMC_MD2.ID02886.hairpin | YES | YES | YES | YES | YES | NO | NO | NO |
| TJU_CMC_MD2.ID02887.3p-miR | TJU_CMC_MD2.ID02887.hairpin | YES | NO | NO | NO | NO | NO | NO | NO |
| TJU_CMC_MD2.ID02888.5p-miR | TJU_CMC_MD2.ID02888.hairpin | YES | YES | YES | YES | YES | NO | NO | NO |
| TJU_CMC_MD2.ID02889.3p-miR | TJU_CMC_MD2.ID02889.hairpin | YES | NO | NO | NO | NO | NO | NO | NO |
| TJU_CMC_MD2.ID02890.3p-miR | TJU_CMC_MD2.ID02890.hairpin | YES | NO | NO | NO | NO | NO | NO | NO |
| TJU_CMC_MD2.ID02890.5p-miR | TJU_CMC_MD2.ID02890.hairpin | YES | YES | YES | NO | NO | NO | NO | NO |
| TJU_CMC_MD2.ID02891.3p-miR | TJU_CMC_MD2.ID02891.hairpin | YES | NO | NO | NO | NO | NO | NO | NO |
| TJU_CMC_MD2.ID02892.3p-miR | TJU_CMC_MD2.ID02892.hairpin | YES | NO | NO | NO | NO | NO | NO | NO |
| TJU_CMC_MD2.ID02893.5p-miR | TJU_CMC_MD2.ID02893.hairpin | YES | YES | YES | NO | NO | NO | NO | NO |
| TJU_CMC_MD2.ID02894.3p-miR | TJU_CMC_MD2.ID02894.hairpin | YES | NO | NO | NO | NO | NO | NO | NO |
| TJU_CMC_MD2.ID02895.3p-miR | TJU_CMC_MD2.ID02895.hairpin | YES | NO | NO | NO | NO | NO | NO | NO |
| TJU_CMC_MD2.ID02896.5p-miR | TJU_CMC_MD2.ID02896.hairpin | YES | YES | NO | NO | NO | NO | NO | NO |
| TJU_CMC_MD2.ID02897.3p-miR | TJU_CMC_MD2.ID02897.hairpin | YES | NO | NO | NO | NO | NO | NO | NO |
| TJU_CMC_MD2.ID02898.3p-miR | TJU_CMC_MD2.ID02898.hairpin | YES | NO | NO | NO | NO | NO | NO | NO |
| TJU_CMC_MD2.ID02899.3p-miR | TJU_CMC_MD2.ID02899.hairpin | YES | NO | NO | NO | NO | NO | NO | NO |
| TJU_CMC_MD2.ID02900.5p-miR | TJU_CMC_MD2.ID02900.hairpin | YES | YES | YES | NO | YES | NO | NO | NO |
| TJU_CMC_MD2.ID02901.3p-miR | TJU_CMC_MD2.ID02901.hairpin | YES | NO | NO | NO | NO | NO | NO | NO |
| TJU_CMC_MD2.ID02902.5p-miR | TJU_CMC_MD2.ID02902.hairpin | YES | YES | NO | NO | NO | NO | NO | NO |
| TJU_CMC_MD2.ID02903.3p-miR | TJU_CMC_MD2.ID02903.hairpin | YES | NO | NO | NO | NO | NO | NO | NO |
| TJU_CMC_MD2.ID02904.5p-miR | TJU_CMC_MD2.ID02904.hairpin | YES | YES | YES | NO | NO | NO | NO | NO |
| TJU_CMC_MD2.ID02905.3p-miR | TJU_CMC_MD2.ID02905.hairpin | YES | NO | NO | NO | NO | NO | NO | NO |
| TJU_CMC_MD2.ID02906.3p-miR | TJU_CMC_MD2.ID02906.hairpin | YES | NO | NO | NO | NO | NO | NO | NO |
| TJU_CMC_MD2.ID02907.3p-miR | TJU_CMC_MD2.ID02907.hairpin | YES | NO | NO | NO | NO | NO | NO | NO |
| TJU_CMC_MD2.ID02908.3p-miR | TJU_CMC_MD2.ID02908.hairpin | YES | NO | NO | NO | NO | NO | NO | NO |
| TJU_CMC_MD2.ID02909.5p-miR | TJU_CMC_MD2.ID02909.hairpin | YES | YES | YES | YES | YES | NO | NO | NO |
| TJU_CMC_MD2.ID02910.5p-miR | TJU_CMC_MD2.ID02910.hairpin | YES | YES | YES | YES | NO | NO | NO | NO |
| TJU_CMC_MD2.ID02911.5p-miR | TJU_CMC_MD2.ID02911.hairpin | YES | YES | YES | YES | NO | NO | NO | NO |
| TJU_CMC_MD2.ID02912.3p-miR | TJU_CMC_MD2.ID02912.hairpin | YES | NO | NO | NO | NO | NO | NO | NO |
| TJU_CMC_MD2.ID02912.5p-miR | TJU_CMC_MD2.ID02912.hairpin | YES | YES | YES | YES | NO | NO | NO | NO |
| TJU_CMC_MD2.ID02913.5p-miR | TJU_CMC_MD2.ID02913.hairpin | YES | NO | NO | NO | NO | NO | NO | NO |
| TJU_CMC_MD2.ID02914.3p-miR | TJU_CMC_MD2.ID02914.hairpin | YES | NO | NO | NO | NO | NO | NO | NO |
| TJU_CMC_MD2.ID02915.3p-miR | TJU_CMC_MD2.ID02915.hairpin | YES | NO | NO | NO | NO | NO | NO | NO |
| TJU_CMC_MD2.ID02916.5p-miR | TJU_CMC_MD2.ID02916.hairpin | YES | YES | YES | YES | YES | NO | NO | NO |
| TJU_CMC_MD2.ID02917.3p-miR | TJU_CMC_MD2.ID02917.hairpin | YES | NO | NO | NO | NO | NO | NO | NO |
| TJU_CMC_MD2.ID02918.5p-miR | TJU_CMC_MD2.ID02918.hairpin | YES | YES | NO | NO | NO | NO | NO | NO |
| TJU_CMC_MD2.ID02919.5p-miR | TJU_CMC_MD2.ID02919.hairpin | YES | YES | NO | NO | YES | NO | NO | NO |
| TJU_CMC_MD2.ID02920.3p-miR | TJU_CMC_MD2.ID02920.hairpin | YES | NO | NO | NO | NO | NO | NO | NO |
| TJU_CMC_MD2.ID02921.3p-miR | TJU_CMC_MD2.ID02921.hairpin | YES | NO | NO | NO | NO | NO | NO | NO |
| TJU_CMC_MD2.ID02921.5p-miR | TJU_CMC_MD2.ID02921.hairpin | YES | YES | YES | YES | YES | NO | NO | NO |
| TJU_CMC_MD2.ID02922.3p-miR | TJU_CMC_MD2.ID02922.hairpin | YES | NO | NO | NO | NO | NO | NO | NO |
| TJU_CMC_MD2.ID02923.5p-miR | TJU_CMC_MD2.ID02923.hairpin | YES | YES | YES | YES | YES | NO | NO | NO |
| TJU_CMC_MD2.ID02924.3p-miR | TJU_CMC_MD2.ID02924.hairpin | YES | NO | NO | NO | NO | NO | NO | NO |
| TJU_CMC_MD2.ID02925.3p-miR | TJU_CMC_MD2.ID02925.hairpin | YES | NO | NO | NO | NO | NO | NO | NO |
| TJU_CMC_MD2.ID02926.5p-miR | TJU_CMC_MD2.ID02926.hairpin | YES | YES | NO | NO | NO | NO | NO | NO |
| TJU_CMC_MD2.ID02927.5p-miR | TJU_CMC_MD2.ID02927.hairpin | YES | NO | YES | NO | NO | NO | NO | NO |
| TJU_CMC_MD2.ID02928.3p-miR | TJU_CMC_MD2.ID02928.hairpin | YES | NO | NO | NO | NO | NO | NO | NO |
| TJU_CMC_MD2.ID02929.3p-miR | TJU_CMC_MD2.ID02929.hairpin | YES | NO | NO | NO | NO | NO | NO | NO |
| TJU_CMC_MD2.ID02930.3p-miR | TJU_CMC_MD2.ID02930.hairpin | YES | NO | NO | NO | NO | NO | NO | NO |
| TJU_CMC_MD2.ID02931.3p-miR | TJU_CMC_MD2.ID02931.hairpin | YES | NO | NO | NO | NO | NO | NO | NO |
| TJU_CMC_MD2.ID02931.5p-miR | TJU_CMC_MD2.ID02931.hairpin | YES | YES | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID02932.5p-miR | TJU_CMC_MD2.ID02932.hairpin | YES | YES | NO | NO | NO | NO | NO | NO |
| TJU_CMC_MD2.ID02933.5p-miR | TJU_CMC_MD2.ID02933.hairpin | YES | NO | NO | NO | NO | NO | NO | NO |
| TJU_CMC_MD2.ID02934.5p-miR | TJU_CMC_MD2.ID02934.hairpin | YES | YES | YES | NO | YES | NO | NO | NO |
| TJU_CMC_MD2.ID02935.3p-miR | TJU_CMC_MD2.ID02935.hairpin | YES | NO | NO | NO | NO | NO | NO | NO |
| TJU_CMC_MD2.ID02936.5p-miR | TJU_CMC_MD2.ID02936.hairpin | YES | NO | YES | NO | NO | NO | NO | NO |
| TJU_CMC_MD2.ID02937.5p-miR | TJU_CMC_MD2.ID02937.hairpin | YES | YES | YES | YES | NO | NO | NO | NO |
| TJU_CMC_MD2.ID02938.3p-miR | TJU_CMC_MD2.ID02938.hairpin | YES | NO | NO | NO | NO | NO | NO | NO |
| TJU_CMC_MD2.ID02939.5p-miR | TJU_CMC_MD2.ID02939.hairpin | YES | YES | YES | YES | YES | NO | NO | NO |
| TJU_CMC_MD2.ID02940.3p-miR | TJU_CMC_MD2.ID02940.hairpin | YES | NO | NO | NO | NO | NO | NO | NO |
| TJU_CMC_MD2.ID02941.3p-miR | TJU_CMC_MD2.ID02941.hairpin | YES | NO | NO | NO | NO | NO | NO | NO |
| TJU_CMC_MD2.ID02942.5p-miR | TJU_CMC_MD2.ID02942.hairpin | YES | YES | NO | NO | NO | NO | NO | NO |
| TJU_CMC_MD2.ID02943.5p-miR | TJU_CMC_MD2.ID02943.hairpin | YES | YES | YES | YES | NO | NO | NO | NO |
| TJU_CMC_MD2.ID02944.5p-miR | TJU_CMC_MD2.ID02944.hairpin | YES | NO | YES | YES | YES | NO | NO | NO |
| TJU_CMC_MD2.ID02945.3p-miR | TJU_CMC_MD2.ID02945.hairpin | YES | NO | NO | NO | NO | NO | NO | NO |
| TJU_CMC_MD2.ID02945.5p-miR | TJU_CMC_MD2.ID02945.hairpin | YES | YES | YES | NO | NO | NO | NO | NO |
| TJU_CMC_MD2.ID02946.5p-miR | TJU_CMC_MD2.ID02946.hairpin | YES | YES | YES | NO | NO | NO | NO | NO |
| TJU_CMC_MD2.ID02947.3p-miR | TJU_CMC_MD2.ID02947.hairpin | YES | NO | NO | NO | NO | NO | NO | NO |
| TJU_CMC_MD2.ID02948.5p-miR | TJU_CMC_MD2.ID02948.hairpin | YES | YES | NO | NO | NO | YES | NO | NO |
| TJU_CMC_MD2.ID02949.3p-miR | TJU_CMC_MD2.ID02949.hairpin | YES | NO | NO | NO | NO | NO | NO | NO |
| TJU_CMC_MD2.ID02950.3p-miR | TJU_CMC_MD2.ID02950.hairpin | YES | NO | NO | NO | NO | NO | NO | NO |
| TJU_CMC_MD2.ID02951.3p-miR | TJU_CMC_MD2.ID02951.hairpin | YES | NO | NO | NO | NO | NO | NO | NO |
| TJU_CMC_MD2.ID02952.3p-miR | TJU_CMC_MD2.ID02952.hairpin | YES | NO | NO | NO | NO | NO | NO | NO |
| TJU_CMC_MD2.ID02953.5p-miR | TJU_CMC_MD2.ID02953.hairpin | YES | YES | YES | YES | YES | NO | NO | NO |
| TJU_CMC_MD2.ID02954.3p-miR | TJU_CMC_MD2.ID02954.hairpin | YES | NO | NO | NO | NO | NO | NO | NO |
| TJU_CMC_MD2.ID02955.3p-miR | TJU_CMC_MD2.ID02955.hairpin | YES | NO | NO | NO | NO | NO | NO | NO |
| TJU_CMC_MD2.ID02956.5p-miR | TJU_CMC_MD2.ID02956.hairpin | YES | NO | NO | NO | NO | NO | NO | NO |
| TJU_CMC_MD2.ID02957.5p-miR | TJU_CMC_MD2.ID02957.hairpin | YES | YES | YES | YES | NO | NO | NO | NO |
| TJU_CMC_MD2.ID02958.3p-miR | TJU_CMC_MD2.ID02958.hairpin | YES | NO | NO | NO | NO | NO | NO | NO |
| TJU_CMC_MD2.ID02959.3p-miR | TJU_CMC_MD2.ID02959.hairpin | YES | NO | NO | NO | NO | NO | NO | NO |
| TJU_CMC_MD2.ID02960.3p-miR | TJU_CMC_MD2.ID02960.hairpin | YES | NO | NO | NO | NO | NO | NO | NO |
| TJU_CMC_MD2.ID02961.5p-miR | TJU_CMC_MD2.ID02961.hairpin | YES | YES | YES | YES | NO | NO | NO | NO |
| TJU_CMC_MD2.ID02962.3p-miR | TJU_CMC_MD2.ID02962.hairpin | YES | NO | NO | NO | NO | NO | NO | NO |
| TJU_CMC_MD2.ID02963.5p-miR | TJU_CMC_MD2.ID02963.hairpin | YES | YES | YES | NO | NO | NO | NO | NO |
| TJU_CMC_MD2.ID02964.3p-miR | TJU_CMC_MD2.ID02964.hairpin | YES | NO | NO | NO | NO | NO | NO | NO |
| TJU_CMC_MD2.ID02965.5p-miR | TJU_CMC_MD2.ID02965.hairpin | YES | NO | NO | NO | NO | NO | NO | NO |
| TJU_CMC_MD2.ID02966.5p-miR | TJU_CMC_MD2.ID02966.hairpin | YES | YES | YES | YES | YES | NO | NO | NO |
| TJU_CMC_MD2.ID02967.3p-miR | TJU_CMC_MD2.ID02967.hairpin | YES | NO | NO | NO | NO | NO | NO | NO |
| TJU_CMC_MD2.ID02968.3p-miR | TJU_CMC_MD2.ID02968.hairpin | YES | NO | NO | NO | NO | NO | NO | NO |
| TJU_CMC_MD2.ID02969.3p-miR | TJU_CMC_MD2.ID02969.hairpin | YES | NO | NO | NO | NO | NO | NO | NO |
| TJU_CMC_MD2.ID02970.5p-miR | TJU_CMC_MD2.ID02970.hairpin | YES | YES | YES | YES | YES | NO | NO | NO |
| TJU_CMC_MD2.ID02971.3p-miR | TJU_CMC_MD2.ID02971.hairpin | YES | NO | NO | NO | NO | NO | NO | NO |
| TJU_CMC_MD2.ID02972.5p-miR | TJU_CMC_MD2.ID02972.hairpin | YES | YES | YES | YES | NO | NO | NO | NO |
| TJU_CMC_MD2.ID02973.3p-miR | TJU_CMC_MD2.ID02973.hairpin | YES | NO | NO | NO | NO | NO | NO | NO |
| TJU_CMC_MD2.ID02974.3p-miR | TJU_CMC_MD2.ID02974.hairpin | YES | NO | NO | NO | NO | NO | NO | NO |
| TJU_CMC_MD2.ID02975.3p-miR | TJU_CMC_MD2.ID02975.hairpin | YES | NO | NO | NO | NO | NO | NO | NO |
| TJU_CMC_MD2.ID02976.5p-miR | TJU_CMC_MD2.ID02976.hairpin | YES | YES | NO | YES | NO | NO | NO | NO |
| TJU_CMC_MD2.ID02977.3p-miR | TJU_CMC_MD2.ID02977.hairpin | YES | NO | NO | NO | NO | NO | NO | NO |
| TJU_CMC_MD2.ID02978.3p-miR | TJU_CMC_MD2.ID02978.hairpin | YES | NO | NO | NO | NO | NO | NO | NO |
| TJU_CMC_MD2.ID02979.5p-miR | TJU_CMC_MD2.ID02979.hairpin | YES | YES | NO | NO | NO | NO | NO | NO |
| TJU_CMC_MD2.ID02980.3p-miR | TJU_CMC_MD2.ID02980.hairpin | YES | NO | NO | NO | NO | NO | NO | NO |
| TJU_CMC_MD2.ID02981.3p-miR | TJU_CMC_MD2.ID02981.hairpin | YES | NO | NO | NO | NO | NO | NO | NO |
| TJU_CMC_MD2.ID02982.3p-miR | TJU_CMC_MD2.ID02982.hairpin | YES | NO | NO | NO | NO | NO | NO | NO |
| TJU_CMC_MD2.ID02983.3p-miR | TJU_CMC_MD2.ID02983.hairpin | YES | NO | NO | NO | NO | NO | NO | NO |
| TJU_CMC_MD2.ID02984.3p-miR | TJU_CMC_MD2.ID02984.hairpin | YES | NO | NO | NO | NO | NO | NO | NO |
| TJU_CMC_MD2.ID02985.3p-miR | TJU_CMC_MD2.ID02985.hairpin | YES | NO | NO | NO | NO | NO | NO | NO |
| TJU_CMC_MD2.ID02986.5p-miR | TJU_CMC_MD2.ID02986.hairpin | YES | YES | YES | YES | NO | NO | NO | NO |
| TJU_CMC_MD2.ID02987.5p-miR | TJU_CMC_MD2.ID02987.hairpin | YES | YES | YES | YES | YES | NO | NO | NO |
| TJU_CMC_MD2.ID02988.5p-miR | TJU_CMC_MD2.ID02988.hairpin | YES | YES | YES | NO | NO | NO | NO | NO |
| TJU_CMC_MD2.ID02989.3p-miR | TJU_CMC_MD2.ID02989.hairpin | YES | NO | NO | NO | NO | NO | NO | NO |
| TJU_CMC_MD2.ID02990.3p-miR | TJU_CMC_MD2.ID02990.hairpin | YES | NO | NO | NO | NO | NO | NO | NO |
| TJU_CMC_MD2.ID02991.3p-miR | TJU_CMC_MD2.ID02991.hairpin | YES | NO | NO | NO | NO | NO | NO | NO |
| TJU_CMC_MD2.ID02992.5p-miR | TJU_CMC_MD2.ID02992.hairpin | YES | YES | NO | YES | NO | NO | NO | NO |
| TJU_CMC_MD2.ID02993.5p-miR | TJU_CMC_MD2.ID02993.hairpin | YES | YES | YES | YES | YES | NO | NO | NO |
| TJU_CMC_MD2.ID02994.3p-miR | TJU_CMC_MD2.ID02994.hairpin | YES | NO | NO | NO | NO | NO | NO | NO |
| TJU_CMC_MD2.ID02995.3p-miR | TJU_CMC_MD2.ID02995.hairpin | YES | NO | NO | NO | NO | NO | NO | NO |
| TJU_CMC_MD2.ID02996.5p-miR | TJU_CMC_MD2.ID02996.hairpin | YES | YES | YES | YES | NO | NO | NO | NO |
| TJU_CMC_MD2.ID02997.5p-miR | TJU_CMC_MD2.ID02997.hairpin | YES | YES | NO | NO | NO | NO | NO | NO |
| TJU_CMC_MD2.ID02998.3p-miR | TJU_CMC_MD2.ID02998.hairpin | YES | NO | NO | NO | NO | NO | NO | NO |
| TJU_CMC_MD2.ID02999.5p-miR | TJU_CMC_MD2.ID02999.hairpin | YES | YES | NO | YES | NO | NO | NO | NO |
| TJU_CMC_MD2.ID03000.5p-miR | TJU_CMC_MD2.ID03000.hairpin | YES | YES | YES | YES | NO | NO | NO | NO |
| TJU_CMC_MD2.ID03001.3p-miR | TJU_CMC_MD2.ID03001.hairpin | YES | NO | NO | NO | NO | NO | NO | NO |
| TJU_CMC_MD2.ID03002.5p-miR | TJU_CMC_MD2.ID03002.hairpin | YES | YES | YES | YES | YES | NO | NO | NO |
| TJU_CMC_MD2.ID03003.5p-miR | TJU_CMC_MD2.ID03003.hairpin | YES | YES | YES | NO | YES | NO | NO | NO |
| TJU_CMC_MD2.ID03004.3p-miR | TJU_CMC_MD2.ID03004.hairpin | YES | NO | NO | NO | NO | NO | NO | NO |
| TJU_CMC_MD2.ID03005.3p-miR | TJU_CMC_MD2.ID03005.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03006.5p-miR | TJU_CMC_MD2.ID03006.hairpin | YES | YES | YES | YES | NO | NO | NO | NO |
| TJU_CMC_MD2.ID03007.5p-miR | TJU_CMC_MD2.ID03007.hairpin | YES | YES | YES | YES | NO | NO | NO | NO |
| TJU_CMC_MD2.ID03008.5p-miR | TJU_CMC_MD2.ID03008.hairpin | YES | YES | YES | NO | NO | YES | NO | NO |
| TJU_CMC_MD2.ID03009.3p-miR | TJU_CMC_MD2.ID03009.hairpin | YES | NO | NO | NO | NO | NO | NO | NO |
| TJU_CMC_MD2.ID03010.5p-miR | TJU_CMC_MD2.ID03010.hairpin | YES | NO | NO | NO | NO | NO | NO | NO |
| TJU_CMC_MD2.ID03011.5p-miR | TJU_CMC_MD2.ID03011.hairpin | YES | NO | NO | NO | NO | NO | NO | NO |
| TJU_CMC_MD2.ID03012.3p-miR | TJU_CMC_MD2.ID03012.hairpin | YES | NO | NO | NO | NO | NO | NO | NO |
| TJU_CMC_MD2.ID03013.5p-miR | TJU_CMC_MD2.ID03013.hairpin | YES | NO | YES | NO | NO | NO | NO | NO |
| TJU_CMC_MD2.ID03014.3p-miR | TJU_CMC_MD2.ID03014.hairpin | YES | NO | NO | NO | NO | NO | NO | NO |
| TJU_CMC_MD2.ID03015.3p-miR | TJU_CMC_MD2.ID03015.hairpin | YES | NO | NO | NO | NO | NO | NO | NO |
| TJU_CMC_MD2.ID03016.3p-miR | TJU_CMC_MD2.ID03016.hairpin | YES | NO | NO | NO | NO | NO | NO | NO |
| TJU_CMC_MD2.ID03017.5p-miR | TJU_CMC_MD2.ID03017.hairpin | YES | YES | NO | NO | NO | NO | NO | NO |
| TJU_CMC_MD2.ID03018.3p-miR | TJU_CMC_MD2.ID03018.hairpin | YES | NO | NO | NO | NO | NO | NO | NO |
| TJU_CMC_MD2.ID03019.5p-miR | TJU_CMC_MD2.ID03019.hairpin | YES | YES | YES | YES | NO | NO | NO | NO |
| TJU_CMC_MD2.ID03020.3p-miR | TJU_CMC_MD2.ID03020.hairpin | YES | YES | YES | YES | NO | NO | NO | NO |
| TJU_CMC_MD2.ID03021.5p-miR | TJU_CMC_MD2.ID03021.hairpin | YES | NO | YES | YES | NO | NO | NO | NO |
| TJU_CMC_MD2.ID03022.3p-miR | TJU_CMC_MD2.ID03022.hairpin | YES | NO | NO | NO | NO | NO | NO | NO |
| TJU_CMC_MD2.ID03023.3p-miR | TJU_CMC_MD2.ID03023.hairpin | YES | NO | NO | NO | NO | NO | NO | NO |
| TJU_CMC_MD2.ID03024.5p-miR | TJU_CMC_MD2.ID03024.hairpin | YES | NO | YES | NO | NO | NO | NO | NO |
| TJU_CMC_MD2.ID03025.5p-miR | TJU_CMC_MD2.ID03025.hairpin | YES | YES | YES | YES | NO | NO | NO | NO |
| TJU_CMC_MD2.ID03026.5p-miR | TJU_CMC_MD2.ID03026.hairpin | YES | YES | YES | YES | YES | YES | NO | NO |
| TJU_CMC_MD2.ID03027.3p-miR | TJU_CMC_MD2.ID03027.hairpin | YES | NO | NO | NO | NO | NO | NO | NO |
| TJU_CMC_MD2.ID03028.3p-miR | TJU_CMC_MD2.ID03028.hairpin | YES | NO | NO | NO | NO | NO | NO | NO |
| TJU_CMC_MD2.ID03029.3p-miR | TJU_CMC_MD2.ID03029.hairpin | YES | NO | NO | NO | NO | NO | NO | NO |
| TJU_CMC_MD2.ID03030.3p-miR | TJU_CMC_MD2.ID03030.hairpin | YES | NO | NO | NO | NO | NO | NO | NO |
| TJU_CMC_MD2.ID03031.5p-miR | TJU_CMC_MD2.ID03031.hairpin | YES | YES | YES | YES | YES | NO | NO | NO |
| TJU_CMC_MD2.ID03032.3p-miR | TJU_CMC_MD2.ID03032.hairpin | YES | NO | NO | NO | NO | NO | NO | NO |
| TJU_CMC_MD2.ID03033.3p-miR | TJU_CMC_MD2.ID03033.hairpin | YES | NO | NO | NO | NO | NO | NO | NO |
| TJU_CMC_MD2.ID03034.5p-miR | TJU_CMC_MD2.ID03034.hairpin | YES | NO | NO | NO | NO | NO | NO | NO |
| TJU_CMC_MD2.ID03035.3p-miR | TJU_CMC_MD2.ID03035.hairpin | YES | NO | NO | NO | NO | NO | NO | NO |
| TJU_CMC_MD2.ID03036.3p-miR | TJU_CMC_MD2.ID03036.hairpin | YES | YES | YES | YES | YES | NO | NO | NO |
| TJU_CMC_MD2.ID03037.3p-miR | TJU_CMC_MD2.ID03037.hairpin | YES | YES | YES | YES | YES | NO | NO | NO |
| TJU_CMC_MD2.ID03038.3p-miR | TJU_CMC_MD2.ID03038.hairpin | YES | NO | NO | NO | NO | NO | NO | NO |
| TJU_CMC_MD2.ID03039.3p-miR | TJU_CMC_MD2.ID03039.hairpin | YES | NO | NO | NO | NO | NO | NO | NO |
| TJU_CMC_MD2.ID03040.3p-miR | TJU_CMC_MD2.ID03040.hairpin | YES | NO | NO | NO | NO | NO | NO | NO |
| TJU_CMC_MD2.ID03041.3p-miR | TJU_CMC_MD2.ID03041.hairpin | YES | NO | NO | NO | NO | NO | NO | NO |
| TJU_CMC_MD2.ID03042.5p-miR | TJU_CMC_MD2.ID03042.hairpin | YES | NO | NO | NO | NO | NO | NO | NO |
| TJU_CMC_MD2.ID03043.5p-miR | TJU_CMC_MD2.ID03043.hairpin | YES | YES | NO | NO | NO | NO | NO | NO |
| TJU_CMC_MD2.ID03044.3p-miR | TJU_CMC_MD2.ID03044.hairpin | YES | NO | NO | NO | NO | NO | NO | NO |
| TJU_CMC_MD2.ID03045.3p-miR | TJU_CMC_MD2.ID03045.hairpin | YES | NO | NO | NO | NO | NO | NO | NO |
| TJU_CMC_MD2.ID03046.5p-miR | TJU_CMC_MD2.ID03046.hairpin | YES | YES | YES | YES | NO | NO | NO | NO |
| TJU_CMC_MD2.ID03047.3p-miR | TJU_CMC_MD2.ID03047.hairpin | YES | NO | NO | NO | NO | NO | NO | NO |
| TJU_CMC_MD2.ID03048.3p-miR | TJU_CMC_MD2.ID03048.hairpin | YES | NO | NO | NO | NO | NO | NO | NO |
| TJU_CMC_MD2.ID03049.5p-miR | TJU_CMC_MD2.ID03049.hairpin | YES | YES | YES | YES | YES | NO | NO | NO |
| TJU_CMC_MD2.ID03050.3p-miR | TJU_CMC_MD2.ID03050.hairpin | YES | YES | YES | YES | YES | YES | NO | NO |
| TJU_CMC_MD2.ID03051.3p-miR | TJU_CMC_MD2.ID03051.hairpin | YES | NO | NO | NO | NO | NO | NO | NO |
| TJU_CMC_MD2.ID03052.5p-miR | TJU_CMC_MD2.ID03052.hairpin | YES | NO | NO | NO | NO | NO | NO | NO |
| TJU_CMC_MD2.ID03053.3p-miR | TJU_CMC_MD2.ID03053.hairpin | YES | NO | NO | NO | NO | NO | NO | NO |
| TJU_CMC_MD2.ID03054.3p-miR | TJU_CMC_MD2.ID03054.hairpin | YES | NO | NO | NO | NO | NO | NO | NO |
| TJU_CMC_MD2.ID03055.5p-miR | TJU_CMC_MD2.ID03055.hairpin | YES | YES | YES | YES | NO | NO | NO | NO |
| TJU_CMC_MD2.ID03056.3p-miR | TJU_CMC_MD2.ID03056.hairpin | YES | NO | NO | NO | NO | NO | NO | NO |
| TJU_CMC_MD2.ID03057.3p-miR | TJU_CMC_MD2.ID03057.hairpin | YES | NO | NO | NO | NO | NO | NO | NO |
| TJU_CMC_MD2.ID03058.3p-miR | TJU_CMC_MD2.ID03058.hairpin | YES | NO | NO | NO | NO | NO | NO | NO |
| TJU_CMC_MD2.ID03059.3p-miR | TJU_CMC_MD2.ID03059.hairpin | YES | NO | NO | NO | NO | NO | NO | NO |
| TJU_CMC_MD2.ID03060.3p-miR | TJU_CMC_MD2.ID03060.hairpin | YES | NO | NO | NO | NO | NO | NO | NO |
| TJU_CMC_MD2.ID03061.3p-miR | TJU_CMC_MD2.ID03061.hairpin | YES | YES | YES | YES | YES | NO | NO | NO |
| TJU_CMC_MD2.ID03061.5p-miR | TJU_CMC_MD2.ID03061.hairpin | YES | YES | YES | YES | YES | NO | NO | NO |
| TJU_CMC_MD2.ID03062.3p-miR | TJU_CMC_MD2.ID03062.hairpin | YES | NO | NO | NO | NO | NO | NO | NO |
| TJU_CMC_MD2.ID03063.3p-miR | TJU_CMC_MD2.ID03063.hairpin | YES | NO | NO | NO | NO | NO | NO | NO |
| TJU_CMC_MD2.ID03063.5p-miR | TJU_CMC_MD2.ID03063.hairpin | YES | YES | YES | YES | YES | NO | NO | NO |
| TJU_CMC_MD2.ID03064.3p-miR | TJU_CMC_MD2.ID03064.hairpin | YES | NO | NO | NO | NO | NO | NO | NO |
| TJU_CMC_MD2.ID03065.3p-miR | TJU_CMC_MD2.ID03065.hairpin | YES | NO | NO | NO | NO | NO | NO | NO |
| TJU_CMC_MD2.ID03066.3p-miR | TJU_CMC_MD2.ID03066.hairpin | YES | YES | NO | NO | NO | NO | NO | NO |
| TJU_CMC_MD2.ID03066.5p-miR | TJU_CMC_MD2.ID03066.hairpin | YES | YES | YES | YES | NO | NO | NO | NO |
| TJU_CMC_MD2.ID03067.5p-miR | TJU_CMC_MD2.ID03067.hairpin | YES | YES | YES | YES | NO | NO | NO | NO |
| TJU_CMC_MD2.ID03068.3p-miR | TJU_CMC_MD2.ID03068.hairpin | YES | NO | NO | NO | NO | NO | NO | NO |
| TJU_CMC_MD2.ID03069.5p-miR | TJU_CMC_MD2.ID03069.hairpin | YES | NO | YES | YES | NO | YES | NO | NO |
| TJU_CMC_MD2.ID03070.3p-miR | TJU_CMC_MD2.ID03070.hairpin | YES | NO | NO | NO | NO | NO | NO | NO |
| TJU_CMC_MD2.ID03071.3p-miR | TJU_CMC_MD2.ID03071.hairpin | YES | NO | NO | NO | NO | NO | NO | NO |
| TJU_CMC_MD2.ID03072.5p-miR | TJU_CMC_MD2.ID03072.hairpin | YES | YES | YES | YES | NO | NO | NO | NO |
| TJU_CMC_MD2.ID03073.3p-miR | TJU_CMC_MD2.ID03073.hairpin | YES | YES | NO | YES | NO | NO | NO | NO |
| TJU_CMC_MD2.ID03074.5p-miR | TJU_CMC_MD2.ID03074.hairpin | YES | YES | YES | YES | YES | NO | NO | NO |
| TJU_CMC_MD2.ID03075.5p-miR | TJU_CMC_MD2.ID03075.hairpin | YES | YES | YES | YES | YES | NO | NO | NO |
| TJU_CMC_MD2.ID03076.5p-miR | TJU_CMC_MD2.ID03076.hairpin | YES | NO | NO | YES | NO | NO | NO | NO |
| TJU_CMC_MD2.ID03077.3p-miR | TJU_CMC_MD2.ID03077.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03078.3p-miR | TJU_CMC_MD2.ID03078.hairpin | YES | NO | NO | NO | NO | NO | NO | NO |
| TJU_CMC_MD2.ID03079.5p-miR | TJU_CMC_MD2.ID03079.hairpin | YES | YES | YES | YES | YES | NO | NO | NO |
| TJU_CMC_MD2.ID03080.5p-miR | TJU_CMC_MD2.ID03080.hairpin | YES | YES | YES | NO | NO | YES | NO | NO |
| TJU_CMC_MD2.ID03081.5p-miR | TJU_CMC_MD2.ID03081.hairpin | YES | YES | YES | YES | YES | NO | NO | NO |
| TJU_CMC_MD2.ID03082.3p-miR | TJU_CMC_MD2.ID03082.hairpin | YES | NO | NO | NO | NO | NO | NO | NO |
| TJU_CMC_MD2.ID03083.5p-miR | TJU_CMC_MD2.ID03083.hairpin | YES | YES | YES | YES | YES | NO | NO | NO |
| TJU_CMC_MD2.ID03084.3p-miR | TJU_CMC_MD2.ID03084.hairpin | YES | NO | NO | NO | NO | NO | NO | NO |
| TJU_CMC_MD2.ID03085.3p-miR | TJU_CMC_MD2.ID03085.hairpin | YES | YES | YES | NO | NO | NO | NO | NO |
| TJU_CMC_MD2.ID03086.5p-miR | TJU_CMC_MD2.ID03086.hairpin | YES | YES | YES | YES | NO | NO | NO | NO |
| TJU_CMC_MD2.ID03087.3p-miR | TJU_CMC_MD2.ID03087.hairpin | YES | NO | NO | NO | NO | NO | NO | NO |
| TJU_CMC_MD2.ID03088.3p-miR | TJU_CMC_MD2.ID03088.hairpin | YES | NO | NO | NO | NO | NO | NO | NO |
| TJU_CMC_MD2.ID03089.5p-miR | TJU_CMC_MD2.ID03089.hairpin | YES | YES | YES | YES | NO | NO | NO | NO |
| TJU_CMC_MD2.ID03090.3p-miR | TJU_CMC_MD2.ID03090.hairpin | YES | NO | NO | NO | NO | NO | NO | NO |
| TJU_CMC_MD2.ID03091.5p-miR | TJU_CMC_MD2.ID03091.hairpin | YES | YES | NO | NO | NO | NO | NO | NO |
| TJU_CMC_MD2.ID03092.3p-miR | TJU_CMC_MD2.ID03092.hairpin | YES | NO | NO | NO | NO | NO | NO | NO |
| TJU_CMC_MD2.ID03093.3p-miR | TJU_CMC_MD2.ID03093.hairpin | YES | NO | NO | NO | NO | NO | NO | NO |
| TJU_CMC_MD2.ID03093.5p-miR | TJU_CMC_MD2.ID03093.hairpin | YES | YES | YES | YES | NO | NO | NO | NO |
| TJU_CMC_MD2.ID03094.3p-miR | TJU_CMC_MD2.ID03094.hairpin | YES | NO | NO | NO | NO | NO | NO | NO |
| TJU_CMC_MD2.ID03094.5p-miR | TJU_CMC_MD2.ID03094.hairpin | YES | YES | YES | YES | YES | NO | NO | NO |
| TJU_CMC_MD2.ID03095.3p-miR | TJU_CMC_MD2.ID03095.hairpin | YES | YES | YES | YES | YES | NO | NO | NO |
| TJU_CMC_MD2.ID03095.5p-miR | TJU_CMC_MD2.ID03095.hairpin | YES | NO | NO | NO | NO | NO | NO | NO |
| TJU_CMC_MD2.ID03096.5p-miR | TJU_CMC_MD2.ID03096.hairpin | YES | YES | YES | NO | NO | NO | NO | NO |
| TJU_CMC_MD2.ID03097.3p-miR | TJU_CMC_MD2.ID03097.hairpin | YES | NO | NO | NO | NO | NO | NO | NO |
| TJU_CMC_MD2.ID03098.3p-miR | TJU_CMC_MD2.ID03098.hairpin | YES | NO | NO | NO | NO | NO | NO | NO |
| TJU_CMC_MD2.ID03099.3p-miR | TJU_CMC_MD2.ID03099.hairpin | YES | NO | NO | NO | NO | NO | NO | NO |
| TJU_CMC_MD2.ID03100.3p-miR | TJU_CMC_MD2.ID03100.hairpin | YES | NO | NO | NO | NO | NO | NO | NO |
| TJU_CMC_MD2.ID03101.3p-miR | TJU_CMC_MD2.ID03101.hairpin | YES | NO | NO | NO | NO | NO | NO | NO |
| TJU_CMC_MD2.ID03102.5p-miR | TJU_CMC_MD2.ID03102.hairpin | YES | NO | NO | NO | NO | NO | NO | NO |
| TJU_CMC_MD2.ID03103.3p-miR | TJU_CMC_MD2.ID03103.hairpin | YES | NO | NO | NO | NO | NO | NO | NO |
| TJU_CMC_MD2.ID03104.3p-miR | TJU_CMC_MD2.ID03104.hairpin | YES | NO | NO | NO | NO | NO | NO | NO |
| TJU_CMC_MD2.ID03105.3p-miR | TJU_CMC_MD2.ID03105.hairpin | YES | NO | NO | NO | NO | NO | NO | NO |
| TJU_CMC_MD2.ID03106.3p-miR | TJU_CMC_MD2.ID03106.hairpin | YES | NO | NO | NO | NO | NO | NO | NO |
| TJU_CMC_MD2.ID03107.3p-miR | TJU_CMC_MD2.ID03107.hairpin | YES | NO | NO | NO | NO | NO | NO | NO |
| TJU_CMC_MD2.ID03108.5p-miR | TJU_CMC_MD2.ID03108.hairpin | YES | YES | YES | NO | NO | YES | NO | NO |
| TJU_CMC_MD2.ID03109.3p-miR | TJU_CMC_MD2.ID03109.hairpin | YES | YES | YES | YES | YES | NO | NO | NO |
| TJU_CMC_MD2.ID03109.5p-miR | TJU_CMC_MD2.ID03109.hairpin | YES | YES | YES | YES | YES | NO | NO | NO |
| TJU_CMC_MD2.ID03110.3p-miR | TJU_CMC_MD2.ID03110.hairpin | YES | NO | NO | NO | NO | NO | NO | NO |
| TJU_CMC_MD2.ID03111.5p-miR | TJU_CMC_MD2.ID03111.hairpin | YES | YES | NO | NO | NO | NO | NO | NO |
| TJU_CMC_MD2.ID03112.5p-miR | TJU_CMC_MD2.ID03112.hairpin | YES | YES | YES | NO | NO | NO | NO | NO |
| TJU_CMC_MD2.ID03113.3p-miR | TJU_CMC_MD2.ID03113.hairpin | YES | NO | NO | NO | NO | NO | NO | NO |
| TJU_CMC_MD2.ID03114.3p-miR | TJU_CMC_MD2.ID03114.hairpin | YES | YES | YES | NO | YES | NO | NO | NO |
| TJU_CMC_MD2.ID03115.5p-miR | TJU_CMC_MD2.ID03115.hairpin | YES | YES | YES | YES | YES | YES | NO | NO |
| TJU_CMC_MD2.ID03116.3p-miR | TJU_CMC_MD2.ID03116.hairpin | YES | NO | NO | NO | NO | NO | NO | NO |
| TJU_CMC_MD2.ID03117.3p-miR | TJU_CMC_MD2.ID03117.hairpin | YES | NO | NO | NO | NO | NO | NO | NO |
| TJU_CMC_MD2.ID03118.3p-miR | TJU_CMC_MD2.ID03118.hairpin | YES | NO | NO | NO | NO | NO | NO | NO |
| TJU_CMC_MD2.ID03119.5p-miR | TJU_CMC_MD2.ID03119.hairpin | YES | YES | YES | YES | YES | NO | NO | NO |
| TJU_CMC_MD2.ID03120.3p-miR | TJU_CMC_MD2.ID03120.hairpin | YES | NO | NO | NO | NO | NO | NO | NO |
| TJU_CMC_MD2.ID03121.3p-miR | TJU_CMC_MD2.ID03121.hairpin | YES | NO | NO | NO | NO | NO | NO | NO |
| TJU_CMC_MD2.ID03122.3p-miR | TJU_CMC_MD2.ID03122.hairpin | YES | NO | NO | NO | NO | NO | NO | NO |
| TJU_CMC_MD2.ID03123.5p-miR | TJU_CMC_MD2.ID03123.hairpin | YES | YES | YES | YES | YES | NO | NO | NO |
| TJU_CMC_MD2.ID03124.3p-miR | TJU_CMC_MD2.ID03124.hairpin | YES | NO | NO | NO | NO | NO | NO | NO |
| TJU_CMC_MD2.ID03125.3p-miR | TJU_CMC_MD2.ID03125.hairpin | YES | NO | NO | NO | NO | NO | NO | NO |
| TJU_CMC_MD2.ID03126.5p-miR | TJU_CMC_MD2.ID03126.hairpin | YES | YES | YES | YES | YES | NO | NO | NO |
| TJU_CMC_MD2.ID03127.5p-miR | TJU_CMC_MD2.ID03127.hairpin | YES | YES | YES | YES | YES | NO | NO | NO |
| TJU_CMC_MD2.ID03128.5p-miR | TJU_CMC_MD2.ID03128.hairpin | YES | YES | YES | YES | YES | NO | NO | NO |
| TJU_CMC_MD2.ID03129.3p-miR | TJU_CMC_MD2.ID03129.hairpin | YES | NO | NO | NO | NO | NO | NO | NO |
| TJU_CMC_MD2.ID03130.5p-miR | TJU_CMC_MD2.ID03130.hairpin | YES | YES | YES | YES | NO | NO | NO | NO |
| TJU_CMC_MD2.ID03131.3p-miR | TJU_CMC_MD2.ID03131.hairpin | YES | NO | NO | NO | NO | NO | NO | NO |
| TJU_CMC_MD2.ID03132.5p-miR | TJU_CMC_MD2.ID03132.hairpin | YES | YES | YES | NO | YES | NO | NO | NO |
| TJU_CMC_MD2.ID03133.3p-miR | TJU_CMC_MD2.ID03133.hairpin | YES | NO | NO | NO | NO | NO | NO | NO |
| TJU_CMC_MD2.ID03134.3p-miR | TJU_CMC_MD2.ID03134.hairpin | YES | NO | NO | NO | NO | NO | NO | NO |
| TJU_CMC_MD2.ID03135.5p-miR | TJU_CMC_MD2.ID03135.hairpin | YES | YES | YES | YES | NO | NO | NO | NO |
| TJU_CMC_MD2.ID03136.3p-miR | TJU_CMC_MD2.ID03136.hairpin | YES | NO | NO | NO | NO | NO | NO | NO |
| TJU_CMC_MD2.ID03137.5p-miR | TJU_CMC_MD2.ID03137.hairpin | YES | NO | YES | NO | NO | NO | NO | NO |
| TJU_CMC_MD2.ID03138.3p-miR | TJU_CMC_MD2.ID03138.hairpin | YES | NO | NO | NO | NO | NO | NO | NO |
| TJU_CMC_MD2.ID03138.5p-miR | TJU_CMC_MD2.ID03138.hairpin | YES | YES | YES | YES | YES | YES | NO | NO |
| TJU_CMC_MD2.ID03139.5p-miR | TJU_CMC_MD2.ID03139.hairpin | YES | YES | YES | YES | NO | NO | NO | NO |
| TJU_CMC_MD2.ID03140.3p-miR | TJU_CMC_MD2.ID03140.hairpin | YES | NO | NO | NO | NO | NO | NO | NO |
| TJU_CMC_MD2.ID03141.3p-miR | TJU_CMC_MD2.ID03141.hairpin | YES | NO | NO | NO | NO | NO | NO | NO |
| TJU_CMC_MD2.ID03141.5p-miR | TJU_CMC_MD2.ID03141.hairpin | YES | NO | NO | YES | NO | NO | NO | NO |
| TJU_CMC_MD2.ID03142.5p-miR | TJU_CMC_MD2.ID03142.hairpin | YES | NO | NO | NO | NO | NO | NO | NO |
| TJU_CMC_MD2.ID03143.3p-miR | TJU_CMC_MD2.ID03143.hairpin | YES | NO | NO | NO | NO | NO | NO | NO |
| TJU_CMC_MD2.ID03144.5p-miR | TJU_CMC_MD2.ID03144.hairpin | YES | NO | NO | NO | NO | NO | NO | NO |
| TJU_CMC_MD2.ID03145.5p-miR | TJU_CMC_MD2.ID03145.hairpin | YES | YES | NO | YES | NO | NO | NO | NO |
| TJU_CMC_MD2.ID03146.5p-miR | TJU_CMC_MD2.ID03146.hairpin | YES | YES | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03147.5p-miR | TJU_CMC_MD2.ID03147.hairpin | YES | YES | YES | YES | NO | NO | NO | NO |
| TJU_CMC_MD2.ID03148.3p-miR | TJU_CMC_MD2.ID03148.hairpin | YES | NO | NO | NO | NO | NO | NO | NO |
| TJU_CMC_MD2.ID03149.5p-miR | TJU_CMC_MD2.ID03149.hairpin | YES | YES | YES | NO | NO | NO | NO | NO |
| TJU_CMC_MD2.ID03150.3p-miR | TJU_CMC_MD2.ID03150.hairpin | YES | NO | NO | NO | NO | NO | NO | NO |
| TJU_CMC_MD2.ID03151.3p-miR | TJU_CMC_MD2.ID03151.hairpin | YES | NO | NO | NO | NO | NO | NO | NO |
| TJU_CMC_MD2.ID03152.3p-miR | TJU_CMC_MD2.ID03152.hairpin | YES | NO | NO | NO | NO | NO | NO | NO |
| TJU_CMC_MD2.ID03153.3p-miR | TJU_CMC_MD2.ID03153.hairpin | YES | NO | NO | NO | NO | NO | NO | NO |
| TJU_CMC_MD2.ID03154.3p-miR | TJU_CMC_MD2.ID03154.hairpin | YES | NO | NO | NO | NO | NO | NO | NO |
| TJU_CMC_MD2.ID03155.3p-miR | TJU_CMC_MD2.ID03155.hairpin | YES | NO | NO | NO | NO | NO | NO | NO |
| TJU_CMC_MD2.ID03156.5p-miR | TJU_CMC_MD2.ID03156.hairpin | YES | YES | YES | YES | NO | NO | NO | NO |
| TJU_CMC_MD2.ID03157.5p-miR | TJU_CMC_MD2.ID03157.hairpin | YES | NO | YES | YES | NO | NO | NO | NO |
| TJU_CMC_MD2.ID03158.5p-miR | TJU_CMC_MD2.ID03158.hairpin | YES | YES | YES | YES | YES | NO | NO | NO |
| TJU_CMC_MD2.ID03159.3p-miR | TJU_CMC_MD2.ID03159.hairpin | YES | NO | NO | NO | NO | NO | NO | NO |
| TJU_CMC_MD2.ID03159.5p-miR | TJU_CMC_MD2.ID03159.hairpin | YES | YES | NO | NO | NO | NO | NO | NO |
| TJU_CMC_MD2.ID03160.5p-miR | TJU_CMC_MD2.ID03160.hairpin | YES | YES | YES | YES | YES | NO | NO | NO |
| TJU_CMC_MD2.ID03161.3p-miR | TJU_CMC_MD2.ID03161.hairpin | YES | NO | NO | NO | NO | NO | NO | NO |
| TJU_CMC_MD2.ID03162.3p-miR | TJU_CMC_MD2.ID03162.hairpin | YES | YES | YES | YES | YES | NO | NO | NO |
| TJU_CMC_MD2.ID03163.3p-miR | TJU_CMC_MD2.ID03163.hairpin | YES | NO | NO | NO | NO | NO | NO | NO |
| TJU_CMC_MD2.ID03164.3p-miR | TJU_CMC_MD2.ID03164.hairpin | YES | NO | NO | NO | NO | NO | NO | NO |
| TJU_CMC_MD2.ID03165.5p-miR | TJU_CMC_MD2.ID03165.hairpin | YES | YES | NO | YES | NO | NO | NO | NO |
| TJU_CMC_MD2.ID03166.5p-miR | TJU_CMC_MD2.ID03166.hairpin | YES | YES | NO | YES | NO | NO | NO | NO |
| TJU_CMC_MD2.ID03167.3p-miR | TJU_CMC_MD2.ID03167.hairpin | YES | NO | NO | NO | NO | NO | NO | NO |
| TJU_CMC_MD2.ID03168.3p-miR | TJU_CMC_MD2.ID03168.hairpin | YES | NO | NO | NO | NO | NO | NO | NO |
| TJU_CMC_MD2.ID03169.5p-miR | TJU_CMC_MD2.ID03169.hairpin | YES | YES | YES | YES | YES | NO | NO | NO |
| TJU_CMC_MD2.ID03170.3p-miR | TJU_CMC_MD2.ID03170.hairpin | YES | YES | YES | YES | YES | NO | NO | NO |
| TJU_CMC_MD2.ID03170.5p-miR | TJU_CMC_MD2.ID03170.hairpin | YES | YES | YES | YES | YES | NO | NO | NO |
| TJU_CMC_MD2.ID03171.5p-miR | TJU_CMC_MD2.ID03171.hairpin | YES | YES | YES | NO | NO | NO | NO | NO |
| TJU_CMC_MD2.ID03172.3p-miR | TJU_CMC_MD2.ID03172.hairpin | YES | NO | NO | NO | NO | NO | NO | NO |
| TJU_CMC_MD2.ID03173.3p-miR | TJU_CMC_MD2.ID03173.hairpin | YES | NO | NO | NO | NO | NO | NO | NO |
| TJU_CMC_MD2.ID03174.5p-miR | TJU_CMC_MD2.ID03174.hairpin | YES | YES | NO | NO | NO | NO | NO | NO |
| TJU_CMC_MD2.ID03175.3p-miR | TJU_CMC_MD2.ID03175.hairpin | YES | NO | NO | NO | NO | NO | NO | NO |
| TJU_CMC_MD2.ID03176.5p-miR | TJU_CMC_MD2.ID03176.hairpin | YES | YES | YES | YES | NO | NO | NO | NO |
| TJU_CMC_MD2.ID03177.5p-miR | TJU_CMC_MD2.ID03177.hairpin | YES | YES | NO | YES | NO | NO | NO | NO |
| TJU_CMC_MD2.ID03178.5p-miR | TJU_CMC_MD2.ID03178.hairpin | YES | NO | YES | YES | YES | NO | NO | NO |
| TJU_CMC_MD2.ID03179.5p-miR | TJU_CMC_MD2.ID03179.hairpin | YES | YES | YES | YES | NO | NO | NO | NO |
| TJU_CMC_MD2.ID03180.5p-miR | TJU_CMC_MD2.ID03180.hairpin | YES | YES | YES | YES | NO | NO | NO | NO |
| TJU_CMC_MD2.ID03181.3p-miR | TJU_CMC_MD2.ID03181.hairpin | YES | NO | NO | NO | NO | NO | NO | NO |
| TJU_CMC_MD2.ID03182.3p-miR | TJU_CMC_MD2.ID03182.hairpin | YES | NO | NO | NO | NO | NO | NO | NO |
| TJU_CMC_MD2.ID03183.3p-miR | TJU_CMC_MD2.ID03183.hairpin | YES | NO | NO | NO | NO | NO | NO | NO |
| TJU_CMC_MD2.ID03184.3p-miR | TJU_CMC_MD2.ID03184.hairpin | YES | NO | NO | NO | NO | NO | NO | NO |
| TJU_CMC_MD2.ID03185.5p-miR | TJU_CMC_MD2.ID03185.hairpin | YES | YES | YES | YES | YES | NO | NO | NO |
| TJU_CMC_MD2.ID03186.3p-miR | TJU_CMC_MD2.ID03186.hairpin | YES | NO | NO | NO | NO | NO | NO | NO |
| TJU_CMC_MD2.ID03187.3p-miR | TJU_CMC_MD2.ID03187.hairpin | YES | NO | NO | NO | NO | NO | NO | NO |
| TJU_CMC_MD2.ID03188.3p-miR | TJU_CMC_MD2.ID03188.hairpin | YES | NO | NO | NO | NO | NO | NO | NO |
| TJU_CMC_MD2.ID03188.5p-miR | TJU_CMC_MD2.ID03188.hairpin | YES | YES | YES | YES | NO | NO | NO | NO |
| TJU_CMC_MD2.ID03189.3p-miR | TJU_CMC_MD2.ID03189.hairpin | YES | NO | NO | NO | NO | NO | NO | NO |
| TJU_CMC_MD2.ID03190.5p-miR | TJU_CMC_MD2.ID03190.hairpin | YES | NO | YES | YES | NO | NO | NO | NO |
| TJU_CMC_MD2.ID03191.3p-miR | TJU_CMC_MD2.ID03191.hairpin | YES | NO | NO | NO | NO | NO | NO | NO |
| TJU_CMC_MD2.ID03192.5p-miR | TJU_CMC_MD2.ID03192.hairpin | YES | NO | YES | YES | NO | NO | NO | NO |
| TJU_CMC_MD2.ID03193.3p-miR | TJU_CMC_MD2.ID03193.hairpin | YES | NO | NO | NO | NO | NO | NO | NO |
| TJU_CMC_MD2.ID03194.3p-miR | TJU_CMC_MD2.ID03194.hairpin | YES | NO | NO | NO | NO | NO | NO | NO |
| TJU_CMC_MD2.ID03195.3p-miR | TJU_CMC_MD2.ID03195.hairpin | YES | NO | NO | NO | NO | NO | NO | NO |
| TJU_CMC_MD2.ID03196.3p-miR | TJU_CMC_MD2.ID03196.hairpin | YES | NO | NO | NO | NO | NO | NO | NO |
| TJU_CMC_MD2.ID03197.5p-miR | TJU_CMC_MD2.ID03197.hairpin | YES | YES | YES | NO | YES | NO | NO | NO |
| TJU_CMC_MD2.ID03198.3p-miR | TJU_CMC_MD2.ID03198.hairpin | YES | NO | NO | NO | NO | NO | NO | NO |
| TJU_CMC_MD2.ID03199.5p-miR | TJU_CMC_MD2.ID03199.hairpin | YES | YES | YES | YES | NO | NO | NO | NO |
| TJU_CMC_MD2.ID03200.3p-miR | TJU_CMC_MD2.ID03200.hairpin | YES | NO | NO | NO | NO | NO | NO | NO |
| TJU_CMC_MD2.ID03201.3p-miR | TJU_CMC_MD2.ID03201.hairpin | YES | NO | NO | NO | NO | NO | NO | NO |
| TJU_CMC_MD2.ID03202.3p-miR | TJU_CMC_MD2.ID03202.hairpin | YES | NO | NO | NO | NO | NO | NO | NO |
| TJU_CMC_MD2.ID03203.3p-miR | TJU_CMC_MD2.ID03203.hairpin | YES | NO | NO | NO | NO | NO | NO | NO |
| TJU_CMC_MD2.ID03204.3p-miR | TJU_CMC_MD2.ID03204.hairpin | YES | NO | NO | NO | NO | NO | NO | NO |
| TJU_CMC_MD2.ID03205.3p-miR | TJU_CMC_MD2.ID03205.hairpin | YES | NO | NO | NO | NO | NO | NO | NO |
| TJU_CMC_MD2.ID03206.5p-miR | TJU_CMC_MD2.ID03206.hairpin | YES | YES | NO | YES | NO | NO | NO | NO |
| TJU_CMC_MD2.ID03207.3p-miR | TJU_CMC_MD2.ID03207.hairpin | YES | NO | NO | NO | NO | NO | NO | NO |
| TJU_CMC_MD2.ID03208.5p-miR | TJU_CMC_MD2.ID03208.hairpin | YES | YES | YES | NO | YES | NO | NO | NO |
| TJU_CMC_MD2.ID03209.5p-miR | TJU_CMC_MD2.ID03209.hairpin | YES | YES | NO | YES | NO | NO | NO | NO |
| TJU_CMC_MD2.ID03210.5p-miR | TJU_CMC_MD2.ID03210.hairpin | YES | NO | YES | NO | YES | NO | NO | NO |
| TJU_CMC_MD2.ID03211.3p-miR | TJU_CMC_MD2.ID03211.hairpin | YES | NO | NO | NO | NO | NO | NO | NO |
| TJU_CMC_MD2.ID03212.5p-miR | TJU_CMC_MD2.ID03212.hairpin | YES | NO | NO | NO | NO | NO | NO | NO |
| TJU_CMC_MD2.ID03213.5p-miR | TJU_CMC_MD2.ID03213.hairpin | YES | YES | YES | YES | NO | NO | NO | NO |
| TJU_CMC_MD2.ID03214.3p-miR | TJU_CMC_MD2.ID03214.hairpin | YES | NO | NO | NO | NO | NO | NO | NO |
| TJU_CMC_MD2.ID03215.3p-miR | TJU_CMC_MD2.ID03215.hairpin | YES | NO | NO | NO | NO | NO | NO | NO |
| TJU_CMC_MD2.ID03216.3p-miR | TJU_CMC_MD2.ID03216.hairpin | YES | NO | NO | NO | NO | NO | NO | NO |
| TJU_CMC_MD2.ID03217.5p-miR | TJU_CMC_MD2.ID03217.hairpin | YES | YES | YES | YES | YES | NO | NO | NO |
| TJU_CMC_MD2.ID03218.3p-miR | TJU_CMC_MD2.ID03218.hairpin | YES | NO | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03219.3p-miR | TJU_CMC_MD2.ID03219.hairpin | YES | NO | NO | NO | NO | NO | NO | NO |
| TJU_CMC_MD2.ID03220.3p-miR | TJU_CMC_MD2.ID03220.hairpin | YES | NO | NO | NO | NO | NO | NO | NO |
| TJU_CMC_MD2.ID03221.5p-miR | TJU_CMC_MD2.ID03221.hairpin | YES | NO | NO | NO | NO | NO | NO | NO |
| TJU_CMC_MD2.ID03222.5p-miR | TJU_CMC_MD2.ID03222.hairpin | YES | YES | NO | YES | NO | NO | NO | NO |
| TJU_CMC_MD2.ID03223.5p-miR | TJU_CMC_MD2.ID03223.hairpin | YES | YES | YES | YES | NO | NO | NO | NO |
| TJU_CMC_MD2.ID03224.5p-miR | TJU_CMC_MD2.ID03224.hairpin | YES | YES | NO | NO | NO | NO | NO | NO |
| TJU_CMC_MD2.ID03225.3p-miR | TJU_CMC_MD2.ID03225.hairpin | YES | NO | NO | NO | NO | NO | NO | NO |
| TJU_CMC_MD2.ID03226.3p-miR | TJU_CMC_MD2.ID03226.hairpin | YES | NO | NO | NO | NO | NO | NO | NO |
| TJU_CMC_MD2.ID03227.3p-miR | TJU_CMC_MD2.ID03227.hairpin | YES | NO | NO | NO | NO | NO | NO | NO |
| TJU_CMC_MD2.ID03228.5p-miR | TJU_CMC_MD2.ID03228.hairpin | YES | NO | YES | NO | YES | NO | NO | NO |
| TJU_CMC_MD2.ID03229.5p-miR | TJU_CMC_MD2.ID03229.hairpin | YES | NO | YES | YES | NO | NO | NO | NO |
| TJU_CMC_MD2.ID03230.5p-miR | TJU_CMC_MD2.ID03230.hairpin | YES | YES | YES | YES | YES | NO | NO | NO |
| TJU_CMC_MD2.ID03231.5p-miR | TJU_CMC_MD2.ID03231.hairpin | YES | YES | YES | YES | YES | NO | NO | NO |
| TJU_CMC_MD2.ID03232.3p-miR | TJU_CMC_MD2.ID03232.hairpin | YES | NO | NO | NO | NO | NO | NO | NO |
| TJU_CMC_MD2.ID03233.5p-miR | TJU_CMC_MD2.ID03233.hairpin | YES | YES | NO | NO | NO | NO | NO | NO |
| TJU_CMC_MD2.ID03234.5p-miR | TJU_CMC_MD2.ID03234.hairpin | YES | YES | YES | YES | YES | YES | NO | NO |
| TJU_CMC_MD2.ID03235.3p-miR | TJU_CMC_MD2.ID03235.hairpin | YES | NO | NO | NO | NO | NO | NO | NO |
| TJU_CMC_MD2.ID03236.3p-miR | TJU_CMC_MD2.ID03236.hairpin | YES | YES | YES | YES | YES | NO | NO | NO |
| TJU_CMC_MD2.ID03236.5p-miR | TJU_CMC_MD2.ID03236.hairpin | YES | YES | YES | NO | NO | NO | NO | NO |
| TJU_CMC_MD2.ID03237.3p-miR | TJU_CMC_MD2.ID03237.hairpin | YES | NO | NO | NO | NO | NO | NO | NO |
| TJU_CMC_MD2.ID03238.3p-miR | TJU_CMC_MD2.ID03238.hairpin | YES | NO | NO | NO | NO | NO | NO | NO |
| TJU_CMC_MD2.ID03239.5p-miR | TJU_CMC_MD2.ID03239.hairpin | YES | NO | YES | NO | NO | NO | NO | NO |
| TJU_CMC_MD2.ID03240.3p-miR | TJU_CMC_MD2.ID03240.hairpin | YES | NO | NO | NO | NO | NO | NO | NO |
| TJU_CMC_MD2.ID03241.5p-miR | TJU_CMC_MD2.ID03241.hairpin | YES | YES | YES | YES | NO | NO | NO | NO |
| TJU_CMC_MD2.ID03242.5p-miR | TJU_CMC_MD2.ID03242.hairpin | YES | YES | YES | YES | YES | NO | NO | NO |
| TJU_CMC_MD2.ID03243.3p-miR | TJU_CMC_MD2.ID03243.hairpin | YES | NO | NO | NO | NO | NO | NO | NO |
| TJU_CMC_MD2.ID03244.3p-miR | TJU_CMC_MD2.ID03244.hairpin | YES | NO | NO | NO | NO | NO | NO | NO |
| TJU_CMC_MD2.ID03244.5p-miR | TJU_CMC_MD2.ID03244.hairpin | YES | NO | NO | NO | NO | NO | NO | NO |
| TJU_CMC_MD2.ID03245.5p-miR | TJU_CMC_MD2.ID03245.hairpin | YES | NO | NO | NO | NO | NO | NO | NO |
| TJU_CMC_MD2.ID03246.3p-miR | TJU_CMC_MD2.ID03246.hairpin | YES | NO | NO | NO | NO | NO | NO | NO |
| TJU_CMC_MD2.ID03247.3p-miR | TJU_CMC_MD2.ID03247.hairpin | YES | NO | NO | NO | NO | NO | NO | NO |
| TJU_CMC_MD2.ID03248.3p-miR | TJU_CMC_MD2.ID03248.hairpin | YES | NO | NO | NO | NO | NO | NO | NO |
| TJU_CMC_MD2.ID03249.3p-miR | TJU_CMC_MD2.ID03249.hairpin | YES | NO | NO | NO | NO | NO | NO | NO |
| TJU_CMC_MD2.ID03250.5p-miR | TJU_CMC_MD2.ID03250.hairpin | YES | YES | YES | NO | YES | NO | NO | NO |
| TJU_CMC_MD2.ID03251.5p-miR | TJU_CMC_MD2.ID03251.hairpin | YES | YES | YES | YES | NO | NO | NO | NO |
| TJU_CMC_MD2.ID03252.5p-miR | TJU_CMC_MD2.ID03252.hairpin | YES | YES | YES | NO | YES | NO | NO | NO |
| TJU_CMC_MD2.ID03253.3p-miR | TJU_CMC_MD2.ID03253.hairpin | YES | NO | NO | NO | NO | NO | NO | NO |
| TJU_CMC_MD2.ID03254.5p-miR | TJU_CMC_MD2.ID03254.hairpin | YES | YES | YES | YES | YES | NO | NO | NO |
| TJU_CMC_MD2.ID03255.5p-miR | TJU_CMC_MD2.ID03255.hairpin | YES | YES | YES | NO | YES | NO | NO | NO |
| TJU_CMC_MD2.ID03256.3p-miR | TJU_CMC_MD2.ID03256.hairpin | YES | NO | NO | NO | NO | NO | NO | NO |
| TJU_CMC_MD2.ID03257.3p-miR | TJU_CMC_MD2.ID03257.hairpin | YES | NO | NO | NO | NO | NO | NO | NO |
| TJU_CMC_MD2.ID03258.5p-miR | TJU_CMC_MD2.ID03258.hairpin | YES | YES | YES | YES | YES | YES | NO | NO |
| TJU_CMC_MD2.ID03259.3p-miR | TJU_CMC_MD2.ID03259.hairpin | YES | NO | NO | NO | NO | NO | NO | NO |
| TJU_CMC_MD2.ID03260.3p-miR | TJU_CMC_MD2.ID03260.hairpin | YES | NO | NO | NO | NO | NO | NO | NO |
| TJU_CMC_MD2.ID03261.5p-miR | TJU_CMC_MD2.ID03261.hairpin | YES | YES | NO | YES | NO | NO | NO | NO |
| TJU_CMC_MD2.ID03262.5p-miR | TJU_CMC_MD2.ID03262.hairpin | YES | YES | YES | YES | YES | NO | NO | NO |
| TJU_CMC_MD2.ID03263.3p-miR | TJU_CMC_MD2.ID03263.hairpin | YES | NO | NO | NO | NO | NO | NO | NO |
| TJU_CMC_MD2.ID03263.5p-miR | TJU_CMC_MD2.ID03263.hairpin | YES | YES | NO | NO | NO | NO | NO | NO |
| TJU_CMC_MD2.ID03264.3p-miR | TJU_CMC_MD2.ID03264.hairpin | YES | NO | NO | NO | NO | NO | NO | NO |
| TJU_CMC_MD2.ID03265.3p-miR | TJU_CMC_MD2.ID03265.hairpin | YES | NO | NO | NO | NO | NO | NO | NO |
| TJU_CMC_MD2.ID03266.5p-miR | TJU_CMC_MD2.ID03266.hairpin | YES | YES | YES | NO | NO | NO | NO | NO |
| TJU_CMC_MD2.ID03267.3p-miR | TJU_CMC_MD2.ID03267.hairpin | YES | NO | NO | NO | NO | NO | NO | NO |
| TJU_CMC_MD2.ID03268.3p-miR | TJU_CMC_MD2.ID03268.hairpin | YES | NO | NO | NO | NO | NO | NO | NO |
| TJU_CMC_MD2.ID03269.3p-miR | TJU_CMC_MD2.ID03269.hairpin | YES | NO | YES | NO | NO | NO | NO | NO |
| TJU_CMC_MD2.ID03270.3p-miR | TJU_CMC_MD2.ID03270.hairpin | YES | NO | NO | NO | NO | NO | NO | NO |
| TJU_CMC_MD2.ID03271.5p-miR | TJU_CMC_MD2.ID03271.hairpin | YES | NO | NO | NO | NO | NO | NO | NO |
| TJU_CMC_MD2.ID03272.5p-miR | TJU_CMC_MD2.ID03272.hairpin | YES | YES | YES | NO | NO | NO | NO | NO |
| TJU_CMC_MD2.ID03273.3p-miR | TJU_CMC_MD2.ID03273.hairpin | YES | NO | NO | NO | NO | NO | NO | NO |
| TJU_CMC_MD2.ID03274.3p-miR | TJU_CMC_MD2.ID03274.hairpin | YES | NO | NO | NO | NO | NO | NO | NO |
| TJU_CMC_MD2.ID03275.5p-miR | TJU_CMC_MD2.ID03275.hairpin | YES | YES | NO | YES | NO | NO | NO | NO |
| TJU_CMC_MD2.ID03276.5p-miR | TJU_CMC_MD2.ID03276.hairpin | YES | YES | NO | NO | NO | NO | NO | NO |
| TJU_CMC_MD2.ID03277.5p-miR | TJU_CMC_MD2.ID03277.hairpin | YES | YES | YES | YES | NO | NO | NO | NO |
| TJU_CMC_MD2.ID03278.3p-miR | TJU_CMC_MD2.ID03278.hairpin | YES | NO | NO | NO | NO | NO | NO | NO |
| TJU_CMC_MD2.ID03279.3p-miR | TJU_CMC_MD2.ID03279.hairpin | YES | NO | NO | NO | NO | NO | NO | NO |
| TJU_CMC_MD2.ID03279.5p-miR | TJU_CMC_MD2.ID03279.hairpin | YES | YES | NO | YES | NO | NO | NO | NO |
| TJU_CMC_MD2.ID03280.3p-miR | TJU_CMC_MD2.ID03280.hairpin | YES | NO | NO | NO | NO | NO | NO | NO |
| TJU_CMC_MD2.ID03281.3p-miR | TJU_CMC_MD2.ID03281.hairpin | YES | NO | NO | NO | NO | NO | NO | NO |
| TJU_CMC_MD2.ID03282.3p-miR | TJU_CMC_MD2.ID03282.hairpin | YES | NO | NO | NO | NO | NO | NO | NO |
| TJU_CMC_MD2.ID03283.5p-miR | TJU_CMC_MD2.ID03283.hairpin | YES | YES | NO | NO | NO | NO | NO | NO |
| TJU_CMC_MD2.ID03284.3p-miR | TJU_CMC_MD2.ID03284.hairpin | YES | NO | NO | NO | NO | NO | NO | NO |
| TJU_CMC_MD2.ID03285.3p-miR | TJU_CMC_MD2.ID03285.hairpin | YES | NO | NO | NO | NO | NO | NO | NO |
| TJU_CMC_MD2.ID03286.5p-miR | TJU_CMC_MD2.ID03286.hairpin | YES | YES | YES | NO | YES | YES | NO | NO |
| TJU_CMC_MD2.ID03287.3p-miR | TJU_CMC_MD2.ID03287.hairpin | YES | NO | NO | NO | NO | NO | NO | NO |
| TJU_CMC_MD2.ID03288.5p-miR | TJU_CMC_MD2.ID03288.hairpin | YES | NO | YES | NO | NO | NO | NO | NO |
| TJU_CMC_MD2.ID03289.5p-miR | TJU_CMC_MD2.ID03289.hairpin | YES | YES | YES | YES | YES | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03290.3p-miR | TJU_CMC_MD2.ID03290.hairpin | YES | NO | NO | NO | NO | NO | NO | NO |
| TJU_CMC_MD2.ID03291.3p-miR | TJU_CMC_MD2.ID03291.hairpin | YES | NO | NO | NO | NO | NO | NO | NO |
| TJU_CMC_MD2.ID03292.3p-miR | TJU_CMC_MD2.ID03292.hairpin | YES | NO | NO | NO | NO | NO | NO | NO |
| TJU_CMC_MD2.ID03293.3p-miR | TJU_CMC_MD2.ID03293.hairpin | YES | NO | NO | NO | NO | NO | NO | NO |
| TJU_CMC_MD2.ID03294.5p-miR | TJU_CMC_MD2.ID03294.hairpin | YES | YES | YES | NO | YES | NO | NO | NO |
| TJU_CMC_MD2.ID03295.3p-miR | TJU_CMC_MD2.ID03295.hairpin | YES | NO | NO | NO | NO | NO | NO | NO |
| TJU_CMC_MD2.ID03296.3p-miR | TJU_CMC_MD2.ID03296.hairpin | YES | YES | YES | NO | YES | NO | NO | NO |
| TJU_CMC_MD2.ID03296.5p-miR | TJU_CMC_MD2.ID03296.hairpin | YES | YES | YES | NO | NO | NO | NO | NO |
| TJU_CMC_MD2.ID03297.3p-miR | TJU_CMC_MD2.ID03297.hairpin | YES | NO | NO | NO | NO | NO | NO | NO |
| TJU_CMC_MD2.ID03298.3p-miR | TJU_CMC_MD2.ID03298.hairpin | YES | NO | NO | NO | NO | NO | NO | NO |
| TJU_CMC_MD2.ID03299.5p-miR | TJU_CMC_MD2.ID03299.hairpin | YES | YES | YES | YES | YES | YES | NO | NO |
| TJU_CMC_MD2.ID03300.5p-miR | TJU_CMC_MD2.ID03300.hairpin | YES | YES | YES | YES | YES | YES | NO | NO |
| TJU_CMC_MD2.ID03301.3p-miR | TJU_CMC_MD2.ID03301.hairpin | YES | NO | NO | NO | NO | NO | NO | NO |
| TJU_CMC_MD2.ID03302.3p-miR | TJU_CMC_MD2.ID03302.hairpin | YES | NO | NO | NO | NO | NO | NO | NO |
| TJU_CMC_MD2.ID03303.3p-miR | TJU_CMC_MD2.ID03303.hairpin | YES | NO | NO | NO | NO | NO | NO | NO |
| TJU_CMC_MD2.ID03304.3p-miR | TJU_CMC_MD2.ID03304.hairpin | YES | YES | YES | NO | NO | NO | NO | NO |
| TJU_CMC_MD2.ID03305.5p-miR | TJU_CMC_MD2.ID03305.hairpin | YES | YES | YES | YES | NO | NO | NO | NO |
| TJU_CMC_MD2.ID03306.3p-miR | TJU_CMC_MD2.ID03306.hairpin | YES | NO | NO | NO | NO | NO | NO | NO |
| TJU_CMC_MD2.ID03307.3p-miR | TJU_CMC_MD2.ID03307.hairpin | YES | NO | NO | NO | NO | NO | NO | NO |
| TJU_CMC_MD2.ID03308.3p-miR | TJU_CMC_MD2.ID03308.hairpin | YES | NO | NO | NO | NO | NO | NO | NO |
| TJU_CMC_MD2.ID03309.5p-miR | TJU_CMC_MD2.ID03309.hairpin | YES | YES | YES | YES | NO | NO | NO | NO |
| TJU_CMC_MD2.ID03310.5p-miR | TJU_CMC_MD2.ID03310.hairpin | YES | NO | YES | NO | NO | NO | NO | NO |
| TJU_CMC_MD2.ID03311.5p-miR | TJU_CMC_MD2.ID03311.hairpin | YES | YES | NO | NO | NO | NO | NO | NO |
| TJU_CMC_MD2.ID03312.5p-miR | TJU_CMC_MD2.ID03312.hairpin | YES | NO | NO | YES | YES | NO | NO | NO |
| TJU_CMC_MD2.ID03313.3p-miR | TJU_CMC_MD2.ID03313.hairpin | YES | NO | NO | NO | NO | NO | NO | NO |
| TJU_CMC_MD2.ID03314.5p-miR | TJU_CMC_MD2.ID03314.hairpin | YES | YES | YES | YES | YES | NO | NO | NO |
| TJU_CMC_MD2.ID03315.3p-miR | TJU_CMC_MD2.ID03315.hairpin | YES | NO | NO | NO | NO | NO | NO | NO |
| TJU_CMC_MD2.ID03316.3p-miR | TJU_CMC_MD2.ID03316.hairpin | YES | NO | NO | NO | NO | NO | NO | NO |
| TJU_CMC_MD2.ID03317.3p-miR | TJU_CMC_MD2.ID03317.hairpin | YES | NO | NO | NO | NO | NO | NO | NO |
| TJU_CMC_MD2.ID03318.3p-miR | TJU_CMC_MD2.ID03318.hairpin | YES | NO | NO | NO | NO | NO | NO | NO |
| TJU_CMC_MD2.ID03319.3p-miR | TJU_CMC_MD2.ID03319.hairpin | YES | NO | NO | NO | NO | NO | NO | NO |
| TJU_CMC_MD2.ID03320.3p-miR | TJU_CMC_MD2.ID03320.hairpin | YES | NO | NO | NO | NO | NO | NO | NO |
| TJU_CMC_MD2.ID03321.3p-miR | TJU_CMC_MD2.ID03321.hairpin | YES | NO | NO | NO | NO | NO | NO | NO |
| TJU_CMC_MD2.ID03322.3p-miR | TJU_CMC_MD2.ID03322.hairpin | YES | NO | NO | NO | NO | NO | NO | NO |
| TJU_CMC_MD2.ID03323.5p-miR | TJU_CMC_MD2.ID03323.hairpin | YES | YES | YES | YES | NO | NO | NO | NO |
| TJU_CMC_MD2.ID03324.3p-miR | TJU_CMC_MD2.ID03324.hairpin | YES | NO | NO | NO | NO | NO | NO | NO |
| TJU_CMC_MD2.ID03325.5p-miR | TJU_CMC_MD2.ID03325.hairpin | YES | YES | YES | YES | NO | NO | NO | NO |
| TJU_CMC_MD2.ID03326.3p-miR | TJU_CMC_MD2.ID03326.hairpin | YES | NO | NO | NO | NO | NO | NO | NO |
| TJU_CMC_MD2.ID03327.3p-miR | TJU_CMC_MD2.ID03327.hairpin | YES | YES | YES | YES | YES | YES | NO | NO |
| TJU_CMC_MD2.ID03328.5p-miR | TJU_CMC_MD2.ID03328.hairpin | YES | YES | YES | YES | YES | NO | NO | NO |
| TJU_CMC_MD2.ID03329.3p-miR | TJU_CMC_MD2.ID03329.hairpin | YES | NO | NO | NO | NO | NO | NO | NO |
| TJU_CMC_MD2.ID03330.3p-miR | TJU_CMC_MD2.ID03330.hairpin | YES | NO | NO | NO | NO | NO | NO | NO |
| TJU_CMC_MD2.ID03331.3p-miR | TJU_CMC_MD2.ID03331.hairpin | YES | NO | NO | NO | NO | NO | NO | NO |
| TJU_CMC_MD2.ID03332.3p-miR | TJU_CMC_MD2.ID03332.hairpin | YES | NO | NO | NO | NO | NO | NO | NO |
| TJU_CMC_MD2.ID03333.3p-miR | TJU_CMC_MD2.ID03333.hairpin | YES | NO | NO | NO | NO | NO | NO | NO |
| TJU_CMC_MD2.ID03334.5p-miR | TJU_CMC_MD2.ID03334.hairpin | YES | YES | YES | NO | YES | NO | NO | NO |
| TJU_CMC_MD2.ID03335.3p-miR | TJU_CMC_MD2.ID03335.hairpin | YES | NO | NO | NO | NO | NO | NO | NO |
| TJU_CMC_MD2.ID03336.5p-miR | TJU_CMC_MD2.ID03336.hairpin | YES | YES | NO | YES | NO | NO | NO | NO |
| TJU_CMC_MD2.ID03337.3p-miR | TJU_CMC_MD2.ID03337.hairpin | YES | NO | NO | NO | NO | NO | NO | NO |
| TJU_CMC_MD2.ID03338.5p-miR | TJU_CMC_MD2.ID03338.hairpin | YES | YES | NO | YES | NO | NO | NO | NO |
| TJU_CMC_MD2.ID03339.5p-miR | TJU_CMC_MD2.ID03339.hairpin | YES | YES | NO | NO | NO | NO | NO | NO |
| TJU_CMC_MD2.ID03340.3p-miR | TJU_CMC_MD2.ID03340.hairpin | YES | NO | NO | NO | NO | NO | NO | NO |
| TJU_CMC_MD2.ID03340.5p-miR | TJU_CMC_MD2.ID03340.hairpin | YES | YES | YES | NO | NO | NO | NO | NO |
| TJU_CMC_MD2.ID03341.5p-miR | TJU_CMC_MD2.ID03341.hairpin | YES | YES | YES | YES | YES | NO | NO | NO |
| TJU_CMC_MD2.ID03342.3p-miR | TJU_CMC_MD2.ID03342.hairpin | YES | NO | NO | NO | NO | NO | NO | NO |
| TJU_CMC_MD2.ID03343.3p-miR | TJU_CMC_MD2.ID03343.hairpin | YES | NO | NO | NO | NO | NO | NO | NO |
| TJU_CMC_MD2.ID03344.3p-miR | TJU_CMC_MD2.ID03344.hairpin | YES | NO | NO | NO | NO | NO | NO | NO |
| TJU_CMC_MD2.ID03345.5p-miR | TJU_CMC_MD2.ID03345.hairpin | YES | NO | YES | NO | NO | NO | NO | NO |
| TJU_CMC_MD2.ID03346.3p-miR | TJU_CMC_MD2.ID03346.hairpin | YES | NO | NO | NO | NO | NO | NO | NO |
| TJU_CMC_MD2.ID03347.5p-miR | TJU_CMC_MD2.ID03347.hairpin | YES | YES | NO | NO | NO | NO | NO | NO |
| TJU_CMC_MD2.ID03348.3p-miR | TJU_CMC_MD2.ID03348.hairpin | YES | NO | NO | NO | NO | NO | NO | NO |
| TJU_CMC_MD2.ID03349.3p-miR | TJU_CMC_MD2.ID03349.hairpin | YES | NO | NO | NO | NO | NO | NO | NO |
| TJU_CMC_MD2.ID03350.5p-miR | TJU_CMC_MD2.ID03350.hairpin | YES | YES | YES | NO | NO | NO | NO | NO |
| TJU_CMC_MD2.ID03351.5p-miR | TJU_CMC_MD2.ID03351.hairpin | YES | YES | YES | YES | YES | NO | NO | NO |
| TJU_CMC_MD2.ID03352.3p-miR | TJU_CMC_MD2.ID03352.hairpin | YES | NO | YES | NO | YES | NO | NO | NO |
| TJU_CMC_MD2.ID03353.5p-miR | TJU_CMC_MD2.ID03353.hairpin | YES | YES | YES | YES | YES | NO | NO | NO |
| TJU_CMC_MD2.ID03354.5p-miR | TJU_CMC_MD2.ID03354.hairpin | YES | NO | NO | NO | NO | NO | NO | NO |
| TJU_CMC_MD2.ID03355.5p-miR | TJU_CMC_MD2.ID03355.hairpin | YES | YES | NO | YES | YES | NO | NO | NO |
| TJU_CMC_MD2.ID03356.5p-miR | TJU_CMC_MD2.ID03356.hairpin | YES | NO | YES | NO | YES | NO | NO | NO |
| TJU_CMC_MD2.ID03357.3p-miR | TJU_CMC_MD2.ID03357.hairpin | YES | NO | NO | NO | NO | NO | NO | NO |
| TJU_CMC_MD2.ID03358.3p-miR | TJU_CMC_MD2.ID03358.hairpin | YES | NO | NO | NO | NO | NO | NO | NO |
| TJU_CMC_MD2.ID03359.5p-miR | TJU_CMC_MD2.ID03359.hairpin | YES | NO | NO | NO | NO | NO | NO | NO |
| TJU_CMC_MD2.ID03360.3p-miR | TJU_CMC_MD2.ID03360.hairpin | YES | NO | NO | NO | NO | NO | NO | NO |
| TJU_CMC_MD2.ID03361.5p-miR | TJU_CMC_MD2.ID03361.hairpin | YES | YES | YES | YES | NO | NO | NO | NO |
| TJU_CMC_MD2.ID03362.5p-miR | TJU_CMC_MD2.ID03362.hairpin | YES | YES | NO | NO | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03363.5p-miR | TJU_CMC_MD2.ID03363.hairpin | YES | NO | YES | YES | NO | NO | NO | NO |
| TJU_CMC_MD2.ID03364.3p-miR | TJU_CMC_MD2.ID03364.hairpin | YES | NO | NO | NO | NO | NO | NO | NO |
| TJU_CMC_MD2.ID03365.5p-miR | TJU_CMC_MD2.ID03365.hairpin | YES | YES | YES | NO | NO | NO | NO | NO |
| TJU_CMC_MD2.ID03366.3p-miR | TJU_CMC_MD2.ID03366.hairpin | YES | NO | NO | NO | NO | NO | NO | NO |
| TJU_CMC_MD2.ID03367.5p-miR | TJU_CMC_MD2.ID03367.hairpin | YES | NO | NO | NO | NO | NO | NO | NO |
| TJU_CMC_MD2.ID03368.3p-miR | TJU_CMC_MD2.ID03368.hairpin | YES | NO | NO | NO | NO | NO | NO | NO |
| TJU_CMC_MD2.ID03369.3p-miR | TJU_CMC_MD2.ID03369.hairpin | YES | NO | NO | NO | NO | NO | NO | NO |
| TJU_CMC_MD2.ID03370.5p-miR | TJU_CMC_MD2.ID03370.hairpin | YES | YES | NO | YES | NO | NO | NO | NO |
| TJU_CMC_MD2.ID03371.3p-miR | TJU_CMC_MD2.ID03371.hairpin | YES | NO | NO | NO | NO | NO | NO | NO |
| TJU_CMC_MD2.ID03372.3p-miR | TJU_CMC_MD2.ID03372.hairpin | YES | NO | NO | NO | NO | NO | NO | NO |
| TJU_CMC_MD2.ID03373.3p-miR | TJU_CMC_MD2.ID03373.hairpin | YES | NO | NO | NO | NO | NO | NO | NO |
| TJU_CMC_MD2.ID03374.3p-miR | TJU_CMC_MD2.ID03374.hairpin | YES | NO | NO | NO | NO | NO | NO | NO |
| TJU_CMC_MD2.ID03375.5p-miR | TJU_CMC_MD2.ID03375.hairpin | YES | YES | YES | NO | YES | NO | NO | NO |
| TJU_CMC_MD2.ID03376.3p-miR | TJU_CMC_MD2.ID03376.hairpin | YES | NO | NO | NO | NO | NO | NO | NO |
| TJU_CMC_MD2.ID03377.3p-miR | TJU_CMC_MD2.ID03377.hairpin | YES | NO | NO | NO | NO | NO | NO | NO |
| TJU_CMC_MD2.ID03378.3p-miR | TJU_CMC_MD2.ID03378.hairpin | YES | NO | NO | NO | NO | NO | NO | NO |
| TJU_CMC_MD2.ID03379.3p-miR | TJU_CMC_MD2.ID03379.hairpin | YES | NO | NO | NO | NO | NO | NO | NO |
| TJU_CMC_MD2.ID03380.3p-miR | TJU_CMC_MD2.ID03380.hairpin | YES | NO | NO | NO | NO | NO | NO | NO |
| TJU_CMC_MD2.ID03381.3p-miR | TJU_CMC_MD2.ID03381.hairpin | YES | NO | NO | NO | NO | NO | NO | NO |
| TJU_CMC_MD2.ID03381.5p-miR | TJU_CMC_MD2.ID03381.hairpin | YES | YES | YES | NO | YES | NO | NO | NO |
| TJU_CMC_MD2.ID03382.3p-miR | TJU_CMC_MD2.ID03382.hairpin | YES | NO | NO | NO | NO | NO | NO | NO |
| TJU_CMC_MD2.ID03383.3p-miR | TJU_CMC_MD2.ID03383.hairpin | YES | NO | NO | NO | NO | NO | NO | NO |
| TJU_CMC_MD2.ID03384.3p-miR | TJU_CMC_MD2.ID03384.hairpin | YES | NO | NO | NO | NO | NO | NO | NO |
| TJU_CMC_MD2.ID03385.3p-miR | TJU_CMC_MD2.ID03385.hairpin | YES | NO | NO | NO | NO | NO | NO | NO |
| TJU_CMC_MD2.ID03386.5p-miR | TJU_CMC_MD2.ID03386.hairpin | YES | YES | YES | YES | NO | NO | NO | NO |
| TJU_CMC_MD2.ID03387.3p-miR | TJU_CMC_MD2.ID03387.hairpin | YES | NO | NO | NO | NO | NO | NO | NO |
| TJU_CMC_MD2.ID03388.5p-miR | TJU_CMC_MD2.ID03388.hairpin | YES | YES | NO | NO | NO | NO | NO | NO |
| TJU_CMC_MD2.ID03389.3p-miR | TJU_CMC_MD2.ID03389.hairpin | YES | NO | NO | NO | NO | NO | NO | NO |
| TJU_CMC_MD2.ID03390.3p-miR | TJU_CMC_MD2.ID03390.hairpin | YES | NO | NO | NO | NO | NO | NO | NO |
| TJU_CMC_MD2.ID03391.5p-miR | TJU_CMC_MD2.ID03391.hairpin | YES | YES | NO | NO | NO | NO | NO | NO |
| TJU_CMC_MD2.ID03392.3p-miR | TJU_CMC_MD2.ID03392.hairpin | YES | NO | NO | NO | NO | NO | NO | NO |
| TJU_CMC_MD2.ID03393.3p-miR | TJU_CMC_MD2.ID03393.hairpin | YES | NO | NO | NO | NO | NO | NO | NO |
| TJU_CMC_MD2.ID03394.3p-miR | TJU_CMC_MD2.ID03394.hairpin | YES | NO | NO | NO | NO | NO | NO | NO |
| TJU_CMC_MD2.ID03395.3p-miR | TJU_CMC_MD2.ID03395.hairpin | YES | NO | NO | NO | NO | NO | NO | NO |
| TJU_CMC_MD2.ID03396.5p-miR | TJU_CMC_MD2.ID03396.hairpin | YES | NO | YES | NO | NO | NO | NO | NO |
| TJU_CMC_MD2.ID03397.3p-miR | TJU_CMC_MD2.ID03397.hairpin | YES | NO | NO | NO | NO | NO | NO | NO |
| TJU_CMC_MD2.ID03398.5p-miR | TJU_CMC_MD2.ID03398.hairpin | YES | YES | YES | YES | NO | NO | NO | NO |
| TJU_CMC_MD2.ID03399.5p-miR | TJU_CMC_MD2.ID03399.hairpin | YES | NO | NO | YES | NO | NO | NO | NO |
| TJU_CMC_MD2.ID03400.3p-miR | TJU_CMC_MD2.ID03400.hairpin | YES | NO | NO | NO | NO | NO | NO | NO |
| TJU_CMC_MD2.ID03402.5p-miR | TJU_CMC_MD2.ID03402.hairpin | YES | YES | YES | NO | NO | NO | NO | NO |
| TJU_CMC_MD2.ID03403.5p-miR | TJU_CMC_MD2.ID03403.hairpin | YES | NO | YES | NO | NO | NO | NO | NO |
| TJU_CMC_MD2.ID03404.5p-miR | TJU_CMC_MD2.ID03404.hairpin | YES | NO | YES | YES | NO | NO | NO | NO |
| TJU_CMC_MD2.ID03405.3p-miR | TJU_CMC_MD2.ID03405.hairpin | YES | NO | NO | NO | NO | NO | NO | NO |
| TJU_CMC_MD2.ID03406.5p-miR | TJU_CMC_MD2.ID03406.hairpin | YES | YES | NO | NO | NO | NO | NO | NO |
| TJU_CMC_MD2.ID03407.3p-miR | TJU_CMC_MD2.ID03407.hairpin | YES | NO | NO | NO | NO | NO | NO | NO |
| TJU_CMC_MD2.ID03408.3p-miR | TJU_CMC_MD2.ID03408.hairpin | YES | NO | NO | NO | NO | NO | NO | NO |
| TJU_CMC_MD2.ID03409.3p-miR | TJU_CMC_MD2.ID03409.hairpin | YES | NO | NO | NO | NO | NO | NO | NO |
| TJU_CMC_MD2.ID03409.5p-miR | TJU_CMC_MD2.ID03409.hairpin | YES | NO | NO | NO | NO | NO | NO | NO |
| TJU_CMC_MD2.ID03410.5p-miR | TJU_CMC_MD2.ID03410.hairpin | YES | YES | YES | YES | YES | NO | NO | NO |
| TJU_CMC_MD2.ID03411.3p-miR | TJU_CMC_MD2.ID03411.hairpin | YES | NO | NO | NO | NO | NO | NO | NO |
| TJU_CMC_MD2.ID03412.5p-miR | TJU_CMC_MD2.ID03412.hairpin | YES | YES | YES | YES | YES | NO | NO | NO |
| TJU_CMC_MD2.ID03413.5p-miR | TJU_CMC_MD2.ID03413.hairpin | YES | YES | YES | YES | YES | NO | NO | NO |
| TJU_CMC_MD2.ID03414.3p-miR | TJU_CMC_MD2.ID03414.hairpin | YES | NO | NO | NO | NO | NO | NO | NO |
| TJU_CMC_MD2.ID03415.5p-miR | TJU_CMC_MD2.ID03415.hairpin | YES | YES | YES | YES | YES | NO | NO | NO |
| TJU_CMC_MD2.ID03416.5p-miR | TJU_CMC_MD2.ID03416.hairpin | YES | YES | YES | YES | NO | NO | NO | NO |
| TJU_CMC_MD2.ID03417.5p-miR | TJU_CMC_MD2.ID03417.hairpin | YES | YES | YES | YES | YES | NO | NO | NO |
| TJU_CMC_MD2.ID03418.3p-miR | TJU_CMC_MD2.ID03418.hairpin | YES | NO | NO | NO | NO | NO | NO | NO |
| TJU_CMC_MD2.ID03419.5p-miR | TJU_CMC_MD2.ID03419.hairpin | YES | YES | NO | YES | NO | NO | NO | NO |
| TJU_CMC_MD2.ID03420.3p-miR | TJU_CMC_MD2.ID03420.hairpin | YES | NO | NO | NO | NO | NO | NO | NO |
| TJU_CMC_MD2.ID03421.5p-miR | TJU_CMC_MD2.ID03421.hairpin | YES | YES | YES | YES | NO | NO | NO | NO |
| TJU_CMC_MD2.ID03422.3p-miR | TJU_CMC_MD2.ID03422.hairpin | YES | NO | NO | NO | NO | NO | NO | NO |
| TJU_CMC_MD2.ID03423.5p-miR | TJU_CMC_MD2.ID03423.hairpin | YES | NO | NO | NO | NO | NO | NO | NO |
| TJU_CMC_MD2.ID03424.3p-miR | TJU_CMC_MD2.ID03424.hairpin | YES | NO | YES | NO | NO | NO | NO | NO |
| TJU_CMC_MD2.ID03425.5p-miR | TJU_CMC_MD2.ID03425.hairpin | YES | NO | YES | YES | NO | NO | NO | NO |
| TJU_CMC_MD2.ID03426.5p-miR | TJU_CMC_MD2.ID03426.hairpin | YES | YES | NO | NO | NO | NO | NO | NO |
| TJU_CMC_MD2.ID03427.3p-miR | TJU_CMC_MD2.ID03427.hairpin | YES | NO | NO | NO | NO | NO | NO | NO |
| TJU_CMC_MD2.ID03428.5p-miR | TJU_CMC_MD2.ID03428.hairpin | YES | NO | YES | YES | YES | NO | NO | NO |
| TJU_CMC_MD2.ID03429.3p-miR | TJU_CMC_MD2.ID03429.hairpin | YES | NO | NO | NO | NO | NO | NO | NO |
| TJU_CMC_MD2.ID03430.3p-miR | TJU_CMC_MD2.ID03430.hairpin | YES | NO | NO | NO | NO | NO | NO | NO |
| TJU_CMC_MD2.ID03431.5p-miR | TJU_CMC_MD2.ID03431.hairpin | YES | YES | YES | YES | YES | NO | NO | NO |
| TJU_CMC_MD2.ID03432.3p-miR | TJU_CMC_MD2.ID03432.hairpin | YES | NO | NO | NO | NO | NO | NO | NO |
| TJU_CMC_MD2.ID03433.3p-miR | TJU_CMC_MD2.ID03433.hairpin | YES | NO | NO | NO | NO | NO | NO | NO |
| TJU_CMC_MD2.ID03434.5p-miR | TJU_CMC_MD2.ID03434.hairpin | YES | YES | YES | YES | YES | YES | NO | NO |
| TJU_CMC_MD2.ID03435.3p-miR | TJU_CMC_MD2.ID03435.hairpin | YES | NO | NO | NO | NO | NO | NO | NO |
| TJU_CMC_MD2.ID03436.5p-miR | TJU_CMC_MD2.ID03436.hairpin | YES | NO | YES | YES | NO | NO | NO | NO |

TABLE 7-continued

Conservation properties across the examined model organisms for the
novel miRNA:hairpin combinations identified using the miRDeep2 method

| Novel miRNA ID | Hairpin ID | Hu | Ch | Go | Or | Ma | Mo | Dr | Wo |
|---|---|---|---|---|---|---|---|---|---|
| TJU_CMC_MD2.ID03437.5p-miR | TJU_CMC_MD2.ID03437.hairpin | YES | YES | YES | YES | YES | NO | NO | NO |
| TJU_CMC_MD2.ID03438.5p-miR | TJU_CMC_MD2.ID03438.hairpin | YES | YES | YES | YES | YES | NO | NO | NO |
| TJU_CMC_MD2.ID03439.5p-miR | TJU_CMC_MD2.ID03439.hairpin | YES | YES | YES | YES | YES | NO | NO | NO |
| TJU_CMC_MD2.ID03440.5p-miR | TJU_CMC_MD2.ID03440.hairpin | YES | YES | NO | YES | NO | NO | NO | NO |
| TJU_CMC_MD2.ID03441.3p-miR | TJU_CMC_MD2.ID03441.hairpin | YES | NO | NO | NO | NO | NO | NO | NO |
| TJU_CMC_MD2.ID03442.3p-miR | TJU_CMC_MD2.ID03442.hairpin | YES | NO | NO | NO | NO | NO | NO | NO |
| TJU_CMC_MD2.ID03443.3p-miR | TJU_CMC_MD2.ID03443.hairpin | YES | YES | YES | YES | YES | NO | NO | NO |
| TJU_CMC_MD2.ID03444.3p-miR | TJU_CMC_MD2.ID03444.hairpin | YES | NO | NO | NO | NO | NO | NO | NO |
| TJU_CMC_MD2.ID03444.5p-miR | TJU_CMC_MD2.ID03444.hairpin | YES | YES | NO | YES | NO | NO | NO | NO |
| TJU_CMC_MD2.ID03445.3p-miR | TJU_CMC_MD2.ID03445.hairpin | YES | YES | YES | YES | NO | NO | NO | NO |
| TJU_CMC_MD2.ID03446.3p-miR | TJU_CMC_MD2.ID03446.hairpin | YES | NO | NO | NO | NO | NO | NO | NO |
| TJU_CMC_MD2.ID03447.3p-miR | TJU_CMC_MD2.ID03447.hairpin | YES | NO | NO | NO | NO | NO | NO | NO |
| TJU_CMC_MD2.ID03448.3p-miR | TJU_CMC_MD2.ID03448.hairpin | YES | NO | NO | NO | NO | NO | NO | NO |
| TJU_CMC_MD2.ID03449.3p-miR | TJU_CMC_MD2.ID03449.hairpin | YES | NO | NO | NO | NO | NO | NO | NO |
| TJU_CMC_MD2.ID03450.5p-miR | TJU_CMC_MD2.ID03450.hairpin | YES | YES | YES | NO | YES | NO | NO | NO |
| TJU_CMC_MD2.ID03451.3p-miR | TJU_CMC_MD2.ID03451.hairpin | YES | NO | NO | NO | NO | NO | NO | NO |
| TJU_CMC_MD2.ID03452.5p-miR | TJU_CMC_MD2.ID03452.hairpin | YES | NO | YES | YES | YES | NO | NO | NO |
| TJU_CMC_MD2.ID03453.3p-miR | TJU_CMC_MD2.ID03453.hairpin | YES | NO | NO | NO | NO | NO | NO | NO |
| TJU_CMC_MD2.ID03454.3p-miR | TJU_CMC_MD2.ID03454.hairpin | YES | YES | YES | YES | NO | YES | NO | NO |
| TJU_CMC_MD2.ID03455.5p-miR | TJU_CMC_MD2.ID03455.hairpin | YES | YES | YES | YES | YES | YES | NO | NO |
| TJU_CMC_MD2.ID03456.5p-miR | TJU_CMC_MD2.ID03456.hairpin | YES | YES | YES | YES | YES | YES | NO | NO |
| TJU_CMC_MD2.ID03457.3p-miR | TJU_CMC_MD2.ID03457.hairpin | YES | NO | NO | NO | NO | NO | NO | NO |
| TJU_CMC_MD2.ID03458.5p-miR | TJU_CMC_MD2.ID03458.hairpin | YES | YES | YES | YES | NO | NO | NO | NO |
| TJU_CMC_MD2.ID03459.3p-miR | TJU_CMC_MD2.ID03459.hairpin | YES | NO | NO | NO | NO | NO | NO | NO |
| TJU_CMC_MD2.ID03459.5p-miR | TJU_CMC_MD2.ID03459.hairpin | YES | NO | YES | NO | NO | NO | NO | NO |
| TJU_CMC_MD2.ID03460.3p-miR | TJU_CMC_MD2.ID03460.hairpin | YES | NO | NO | NO | NO | NO | NO | NO |
| TJU_CMC_MD2.ID03461.3p-miR | TJU_CMC_MD2.ID03461.hairpin | YES | NO | NO | NO | NO | NO | NO | NO |
| TJU_CMC_MD2.ID03462.5p-miR | TJU_CMC_MD2.ID03462.hairpin | YES | NO | NO | YES | NO | NO | NO | NO |
| TJU_CMC_MD2.ID03463.3p-miR | TJU_CMC_MD2.ID03463.hairpin | YES | NO | NO | NO | NO | NO | NO | NO |
| TJU_CMC_MD2.ID03464.3p-miR | TJU_CMC_MD2.ID03464.hairpin | YES | NO | NO | NO | NO | NO | NO | NO |
| TJU_CMC_MD2.ID03465.3p-miR | TJU_CMC_MD2.ID03465.hairpin | YES | NO | NO | NO | NO | NO | NO | NO |
| TJU_CMC_MD2.ID03466.3p-miR | TJU_CMC_MD2.ID03466.hairpin | YES | YES | YES | YES | YES | YES | NO | NO |
| TJU_CMC_MD2.ID03467.5p-miR | TJU_CMC_MD2.ID03467.hairpin | YES | NO | YES | YES | YES | NO | NO | NO |
| TJU_CMC_MD2.ID03468.3p-miR | TJU_CMC_MD2.ID03468.hairpin | YES | NO | NO | NO | NO | NO | NO | NO |
| TJU_CMC_MD2.ID03469.5p-miR | TJU_CMC_MD2.ID03469.hairpin | YES | NO | NO | YES | YES | NO | NO | NO |
| TJU_CMC_MD2.ID03470.5p-miR | TJU_CMC_MD2.ID03470.hairpin | YES | YES | YES | YES | YES | NO | NO | NO |
| TJU_CMC_MD2.ID03471.3p-miR | TJU_CMC_MD2.ID03471.hairpin | YES | NO | NO | NO | NO | NO | NO | NO |
| TJU_CMC_MD2.ID03472.3p-miR | TJU_CMC_MD2.ID03472.hairpin | YES | YES | YES | YES | NO | NO | NO | NO |
| TJU_CMC_MD2.ID03473.3p-miR | TJU_CMC_MD2.ID03473.hairpin | YES | YES | YES | YES | YES | NO | NO | NO |
| TJU_CMC_MD2.ID03474.3p-miR | TJU_CMC_MD2.ID03474.hairpin | YES | NO | NO | NO | NO | NO | NO | NO |
| TJU_CMC_MD2.ID03475.5p-miR | TJU_CMC_MD2.ID03475.hairpin | YES | YES | YES | YES | YES | NO | NO | NO |
| TJU_CMC_MD2.ID03476.3p-miR | TJU_CMC_MD2.ID03476.hairpin | YES | NO | NO | NO | NO | NO | NO | NO |
| TJU_CMC_MD2.ID03477.3p-miR | TJU_CMC_MD2.ID03477.hairpin | YES | NO | NO | NO | NO | NO | NO | NO |
| TJU_CMC_MD2.ID03478.3p-miR | TJU_CMC_MD2.ID03478.hairpin | YES | NO | NO | NO | NO | NO | NO | NO |
| TJU_CMC_MD2.ID03479.3p-miR | TJU_CMC_MD2.ID03479.hairpin | YES | NO | NO | NO | NO | NO | NO | NO |
| TJU_CMC_MD2.ID03480.3p-miR | TJU_CMC_MD2.ID03480.hairpin | YES | NO | NO | NO | NO | NO | NO | NO |
| TJU_CMC_MD2.ID03481.3p-miR | TJU_CMC_MD2.ID03481.hairpin | YES | NO | NO | NO | NO | NO | NO | NO |
| TJU_CMC_MD2.ID03481.5p-miR | TJU_CMC_MD2.ID03481.hairpin | YES | NO | YES | NO | NO | NO | NO | NO |
| TJU_CMC_MD2.ID03482.3p-miR | TJU_CMC_MD2.ID03482.hairpin | YES | NO | NO | NO | NO | NO | NO | NO |
| TJU_CMC_MD2.ID03483.3p-miR | TJU_CMC_MD2.ID03483.hairpin | YES | NO | NO | NO | NO | NO | NO | NO |
| TJU_CMC_MD2.ID03484.3p-miR | TJU_CMC_MD2.ID03484.hairpin | YES | NO | NO | NO | NO | NO | NO | NO |
| TJU_CMC_MD2.ID03485.5p-miR | TJU_CMC_MD2.ID03485.hairpin | YES | YES | YES | YES | NO | NO | NO | NO |
| TJU_CMC_MD2.ID03486.3p-miR | TJU_CMC_MD2.ID03486.hairpin | YES | NO | NO | NO | NO | NO | NO | NO |
| TJU_CMC_MD2.ID03487.3p-miR | TJU_CMC_MD2.ID03487.hairpin | YES | NO | NO | NO | NO | NO | NO | NO |
| TJU_CMC_MD2.ID03488.3p-miR | TJU_CMC_MD2.ID03488.hairpin | YES | NO | NO | NO | NO | NO | NO | NO |
| TJU_CMC_MD2.ID03489.3p-miR | TJU_CMC_MD2.ID03489.hairpin | YES | NO | NO | NO | NO | NO | NO | NO |
| TJU_CMC_MD2.ID03489.5p-miR | TJU_CMC_MD2.ID03489.hairpin | YES | NO | YES | NO | YES | NO | NO | NO |
| TJU_CMC_MD2.ID03490.3p-miR | TJU_CMC_MD2.ID03490.hairpin | YES | NO | NO | NO | NO | NO | NO | NO |
| TJU_CMC_MD2.ID03491.3p-miR | TJU_CMC_MD2.ID03491.hairpin | YES | NO | NO | NO | NO | NO | NO | NO |
| TJU_CMC_MD2.ID03492.5p-miR | TJU_CMC_MD2.ID03492.hairpin | YES | NO | NO | NO | YES | NO | NO | NO |
| TJU_CMC_MD2.ID03493.3p-miR | TJU_CMC_MD2.ID03493.hairpin | YES | NO | NO | NO | NO | NO | NO | NO |
| TJU_CMC_MD2.ID03494.5p-miR | TJU_CMC_MD2.ID03494.hairpin | YES | YES | NO | NO | NO | NO | NO | NO |
| TJU_CMC_MD2.ID03495.5p-miR | TJU_CMC_MD2.ID03495.hairpin | YES | YES | NO | NO | NO | NO | NO | NO |

Example 3. Tissue Specificity of the Novel miRNAs Described Herein

An additional property of the novel miRNAs described herein is that they are for the most part specific to the tissue in which they were discovered. This finding indicates that these novel miRNAs can be used to form distinguishing "signatures" with application to diagnostic and/or prognostic activities. Their participation in such distinguishing signatures directly implicates these sequences in molecular mechanisms that are currently either unknown or poorly understood: as such, some of these sequences can be eventually used to design appropriate therapeutics that are relevant for the corresponding tissue and tissue-state.

As an example, the inventors focused on the 3,707 novel miRNAs listed in Table 2 that they discovered using the miRDeep2 method and for each pair of tissues they computed the number of novel miRNAs that are in common. The following Table 8 shows the results of this computation:

sequences can be used to design appropriate therapeutics that are relevant for the corresponding tissue and tissue-state.

TABLE 8

Number of novel miRNAs described herein that are in common for each pair of tissues

| Number of Samples | | B-cells | Brain | Breast | CD3+ Lympho-cytes | Fibro-blasts | Gastric Tissue | Lymphoblastoid cell lines (LCLs) | Pancreas | Platelets | Peripheral Blood Mononuclear Cells (PBMC) | Prostate | Serum | Skin |
|---|---|---|---|---|---|---|---|---|---|---|---|---|---|---|
| 37 | B-cells | 317 | 100 | 116 | 15 | 91 | 57 | 118 | 149 | 176 | 88 | 94 | 166 | 30 |
| 24 | Brain | 100 | 455 | 104 | 14 | 115 | 59 | 98 | 160 | 204 | 210 | 146 | 166 | 25 |
| 604 | Breast | 116 | 104 | 432 | 12 | 91 | 56 | 122 | 125 | 115 | 95 | 87 | 142 | 34 |
| 1 | CD3+ Lymphocytes | 15 | 14 | 12 | 18 | 12 | 13 | 14 | 14 | 18 | 12 | 15 | 17 | 7 |
| 4 | Fibroblasts | 91 | 115 | 91 | 12 | 260 | 61 | 75 | 150 | 149 | 96 | 117 | 116 | 22 |
| 25 | Gastric Tissue | 57 | 59 | 56 | 13 | 61 | 136 | 47 | 79 | 70 | 57 | 66 | 62 | 16 |
| 488 | LCLs | 118 | 98 | 122 | 14 | 75 | 47 | 268 | 99 | 127 | 86 | 75 | 122 | 32 |
| 12 | Pancreas | 149 | 160 | 125 | 14 | 150 | 79 | 99 | 527 | 199 | 152 | 151 | 178 | 26 |
| 15 | Platelets | 176 | 204 | 115 | 18 | 149 | 70 | 127 | 199 | 633 | 377 | 155 | 354 | 21 |
| 18 | PBMC | 88 | 210 | 95 | 12 | 96 | 57 | 86 | 152 | 377 | 881 | 123 | 288 | 12 |
| 10 | Prostate | 94 | 146 | 87 | 15 | 117 | 66 | 75 | 151 | 155 | 123 | 273 | 134 | 20 |
| 24 | Serum | 166 | 166 | 142 | 17 | 116 | 62 | 122 | 178 | 354 | 288 | 134 | 698 | 21 |
| 63 | Skin | 30 | 25 | 34 | 7 | 22 | 16 | 32 | 26 | 21 | 12 | 20 | 21 | 48 |

The Jaccard coefficients are also computed for each pair above and shown in Table 9. The lower the Jaccard coefficient is when comparing the novel miRNAs discovered in two tissues types, the higher the number of novel miRNAs that are present in one of the two tissue types but not the other tissue type.

This Example shows that differentially expressed isomiRs listed in Table 3 can be used to separate individuals with platelet antigen hyper-reactivity vs. hypo-reactivity. Platelets derived from 10 healthy male individuals were tested for their aggregation properties in response to the PAR1-AP, PAR4-AP, anti-CD9, ADP, and CRP antigens. The individu-

TABLE 9

Jaccard coefficients for each pair of tissues based on the number of novel miRNAs described herein that are in common shown in Table 8 above

| | B-cells | Brain | Breast | CD3+ Lymphocytes | Fibro-blasts | Gastric Tissue | LCLs | Pancreas | Platelets | PBMC | Prostate | Serum | Skin |
|---|---|---|---|---|---|---|---|---|---|---|---|---|---|
| B-cells | 1 | 0.1488 | 0.1833 | 0.0469 | 0.1872 | 0.1439 | 0.2527 | 0.2144 | 0.2274 | 0.0793 | 0.1895 | 0.1955 | 0.0896 |
| Brain | 0.1488 | 1 | 0.1328 | 0.0305 | 0.1917 | 0.1109 | 0.1568 | 0.1946 | 0.2308 | 0.1865 | 0.2509 | 0.1682 | 0.0523 |
| Breast | 0.1833 | 0.1328 | 1 | 0.0274 | 0.1514 | 0.1094 | 0.2111 | 0.1499 | 0.1211 | 0.078 | 0.1408 | 0.1437 | 0.0762 |
| CD3+ Lymphocytes | 0.0469 | 0.0305 | 0.0274 | 1 | 0.0451 | 0.0922 | 0.0515 | 0.0264 | 0.0284 | 0.0135 | 0.0543 | 0.0243 | 0.1186 |
| Fibroblasts | 0.1872 | 0.1917 | 0.1514 | 0.0451 | 1 | 0.1821 | 0.1656 | 0.2355 | 0.2003 | 0.0919 | 0.2812 | 0.1378 | 0.0769 |
| Gastric Tissue | 0.1439 | 0.1109 | 0.1094 | 0.0922 | 0.1821 | 1 | 0.1317 | 0.1353 | 0.1001 | 0.0594 | 0.1924 | 0.0803 | 0.0952 |
| LCLs | 0.2527 | 0.1568 | 0.2111 | 0.0515 | 0.1656 | 0.1317 | 1 | 0.1422 | 0.1641 | 0.0809 | 0.1609 | 0.1445 | 0.1127 |
| Pancreas | 0.2144 | 0.1946 | 0.1499 | 0.0264 | 0.2355 | 0.1353 | 0.1422 | 1 | 0.2071 | 0.121 | 0.2327 | 0.17 | 0.0474 |
| Platelets | 0.2274 | 0.2308 | 0.1211 | 0.0284 | 0.2003 | 0.1001 | 0.1641 | 0.2071 | 1 | 0.3316 | 0.2064 | 0.3623 | 0.0318 |
| PBMC | 0.0793 | 0.1865 | 0.078 | 0.0135 | 0.0919 | 0.0594 | 0.0809 | 0.121 | 0.3316 | 1 | 0.1193 | 0.2231 | 0.0131 |
| Prostate | 0.1895 | 0.2509 | 0.1408 | 0.0543 | 0.2812 | 0.1924 | 0.1609 | 0.2327 | 0.2064 | 0.1193 | 1 | 0.1601 | 0.0664 |
| Serum | 0.1955 | 0.1682 | 0.1437 | 0.0243 | 0.1378 | 0.0803 | 0.1445 | 0.17 | 0.3623 | 0.2231 | 0.1601 | 1 | 0.029 |
| Skin | 0.0896 | 0.0523 | 0.0762 | 0.1186 | 0.0769 | 0.0952 | 0.1127 | 0.0474 | 0.0318 | 0.0131 | 0.0664 | 0.029 | 1 |

Figure 3:
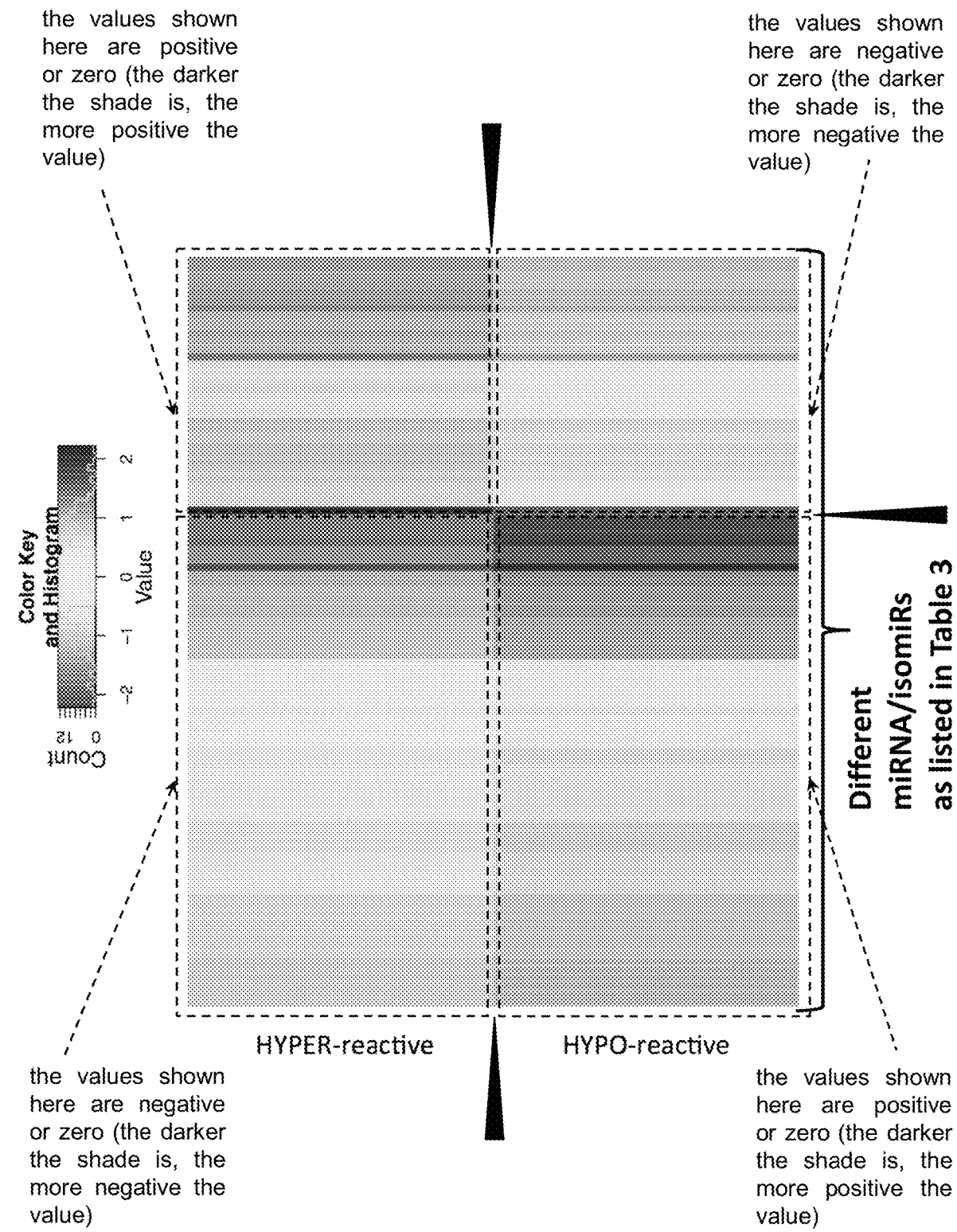
FIG. 3 is a heatmap showing that the two groups of individuals with platelet antigen hyper-reactivity or hypo-reactivity have distinct miRNA/isomiR expression profiles.

Example 4. Exemplary Applications of the isomiRs in Patient Segmentation or Diagnosis In Examples 4-7 below, the isomiRs as listed in Table 3 are found to exhibit different expression behavior between two states of the same tissue, between same-gender members of two different human populations, etc. These examples show that isomiRs, just like miRNAs, can be used to form distinguishing "signatures" with application to diagnostic and/or prognostic activities. Their participation in such distinguishing signatures directly implicates these sequences in molecular mechanisms that are currently either unknown or poorly understood: as such, some of these als were split into two groups ("hyper-reactive" and "hypo-reactive") based on their response to the antigens and time to clot. Short RNA sequencing was used to profile the short RNA populations of the platelets from all 10 individuals and isomiR expression was examined across the hyper-reactive and hypo-reactive group. Differential expression of isomiRs was calculated using the DESeq2 algorithm. An isomiR is considered to be differentially expressed if it had a mean expression of at least 50 sequenced reads, a log 2-change in expression of ≥0.58 or ≤−0.58, and a p-Value ≤0.05. FIG. 3 shows a heatmap that summarizes the results of Table 10 shown below: each row in the heatmap corresponds to a different isomiR as listed in Table 3. FIG. 3 shows that the two groups of individuals with platelet antigen hyper-reactivity or hypo-reactivity have distinct isomiR expression profiles. Since this is a gray-scale image, a two dashed lines was used to separate the drawing in quadrants. The upper left quadrant includes miRNAs/isomiRs that are more abundant in hyper-reactive than in hypo-reactive individuals. The upper right quadrant includes miRNAs/isomiRs that are less abundant in hypo-reactive than in hyper-reactive individuals. The lower left quadrant includes miRNAs/isomiRs that are less abundant in hyper-reactive than in hypo-reactive individuals. The lower right quadrant includes miRNAs/isomiRs that are more abundant in hypo-reactive than in hyper-reactive individuals.

Table 10 below shows the fold-change of the miRNAs and isomiRs in the two groups of individuals with platelet antigen hyper-reactivity or hypo-reactivity that are depicted in the heatmap of FIG. 3. The actual miRNA and corresponding SEQ ID NOs. can be identified in Table 3 according to the "miRNA ID" listed in Table 10.

TABLE 10

Differential expression of isomiR or miRNA in individuals with platelet antigen hyper-reactivity vs. hypo-reactivity

| miRNA ID | Is it a miRNA or an isomiR? | Chromo-some | Strand | IsomiR Start | IsomiR End | log2FoldChange of HYPO-reactive / HYPER-reactive |
|---|---|---|---|---|---|---|
| ID = MIMAT0016844; hsa-miR-4295 | isomiR | 10 | + | 114393939 | 114393960 | 1.693050804 |
| ID = MIMAT0000098; hsa-miR-100-5p | isomiR | 11 | − | 122022982 | 122023004 | 1.823802128 |
| ID = MIMAT0000098; hsa-miR-100-5p | mirBase | 11 | − | 122022983 | 122023004 | 1.814040075 |
| ID = MIMAT0019774; hsa-miR-4687-5p | isomiR | 11 | + | 3877303 | 3877322 | −1.208797144 |
| ID = MIMAT0000267; hsa-miR-210-3p | isomiR | 11 | − | 568113 | 568133 | −1.050732203 |
| ID = MIMAT0014982; hsa-miR-3120-3p | isomiR | 1 | + | 172107998 | 172108019 | 0.975239935 |
| ID = MIMAT0000256; hsa-miR-181a-5p | mirBase | 1 | − | 198828237 | 198828259 | 1.174507982 |
| ID = MIMAT0000681; hsa-miR-29c-3p | isomiR | 1 | − | 207975209 | 207975231 | 0.536818398 |
| ID = MIMAT0017991; hsa-miR-3613-3p | isomiR | 13 | − | 50570564 | 50570585 | 1.608621193 |
| ID = MIMAT0000772; hsa-miR-345-5p | isomiR | 14 | + | 100774213 | 100774232 | −0.840570448 |
| ID = MIMAT0000772; hsa-miR-345-5p | isomiR | 14 | + | 100774213 | 100774233 | −0.614388579 |
| ID = MIMAT0004604; hsa-miR-127-5p | isomiR | 14 | + | 101349338 | 101349358 | −1.307212535 |
| ID = MIMAT0000722; hsa-miR-370-3p | isomiR | 14 | + | 101377523 | 101377543 | −0.973765428 |
| ID = MIMAT0002178; hsa-miR-487a-3p | mirBase | 14 | + | 101518831 | 101518852 | 1.069025151 |
| ID = MIMAT0000447; hsa-miR-134-5p | mirBase | 14 | + | 101521031 | 101521052 | 0.709528735 |
| ID = MIMAT0000447; hsa-miR-134-5p | isomiR | 14 | + | 101521031 | 101521053 | 0.860800629 |
| ID = MIMAT0002176; hsa-miR-485-3p | isomiR | 14 | + | 101521800 | 101521822 | 1.844384975 |
| ID = MIMAT0015050; hsa-miR-323b-3p | isomiR | 14 | + | 101522605 | 101522626 | −1.480187879 |
| ID = MIMAT0000452; hsa-miR-154-5p | mirBase | 14 | + | 101526106 | 101526127 | 0.750616377 |
| ID = MIMAT0000453; hsa-miR-154-3p | mirBase | 14 | + | 101526142 | 101526163 | 1.920772298 |
| ID = MIMAT0000730; hsa-miR-377-3p | isomiR | 14 | + | 101528431 | 101528451 | 2.220079064 |
| ID = MIMAT0000730; hsa-miR-377-3p | mirBase | 14 | + | 101528431 | 101528452 | 1.234206271 |
| ID = MIMAT0001639; hsa-miR-409-3p | isomiR | 14 | + | 101531684 | 101531705 | 1.008026114 |
| ID = MIMAT0015054; hsa-miR-3177-3p | isomiR | 16 | + | 1785039 | 1785060 | −1.070825052 |
| ID = MIMAT0003301; hsa-miR-33b-5p | mirBase | 17 | − | 17717211 | 17717230 | −0.8778958 |
| ID = MIMAT0000433; hsa-miR-142-5p | isomiR | 17 | − | 56408647 | 56408666 | −0.679403276 |
| ID = MIMAT0002820; hsa-miR-497-5p | isomiR | 17 | − | 6921297 | 6921318 | −1.022619012 |
| ID = MIMAT0002820; hsa-miR-497-5p | mirBase | 17 | − | 6921298 | 6921318 | −1.103842786 |
| ID = MIMAT0000763; hsa-miR-338-3p | isomiR | 17 | − | 79099686 | 79099707 | 0.755685679 |
| ID = MIMAT0000763; hsa-miR-338-3p | isomiR | 17 | − | 79099686 | 79099708 | 0.585798504 |
| ID = MIMAT0000763; hsa-miR-R-338-3p | mirBase | 17 | − | 79099687 | 79099708 | 0.637201072 |
| ID = MIMAT0000078; hsa-miR-23a-3p | isomiR | 19 | − | 13947406 | 13947427 | 0.92049045 |
| ID = MIMAT0000078; hsa-miR-23a-3p | isomiR | 19 | − | 13947407 | 13947427 | 1.139296411 |
| ID = MIMAT0000078; hsa-miR-23a-3p | isomiR | 19 | − | 13947407 | 13947429 | 0.605379042 |
| ID = MIMAT0000078; hsa-miR-23a-3p | isomiR | 19 | − | 13947408 | 13947429 | 0.545064371 |
| ID = MIMAT0000258; hsa-miR-181c-5p | isomiR | 19 | + | 13985539 | 13985561 | 0.599867208 |
| ID = MIMAT0000258; hsa-miR-181c-5p | isomiR | 19 | + | 13985539 | 13985562 | 0.643018885 |
| ID = MIMAT0000255; hsa-miR-34a-5p | isomiR | 1 | − | 9211793 | 9211815 | −1.144365962 |
| ID = MIMAT0000255; hsa-miR-34a-5p | mirBase | 1 | − | 9211794 | 9211815 | −0.940567745 |
| ID = MIMAT0003311; hsa-miR-641 | isomiR | 19 | − | 40788511 | 40788534 | 1.173498381 |
| ID = MIMAT0019880; hsa-miR-4746-5p | mirBase | 19 | + | 4445984 | 4446006 | −1.081673049 |
| ID = MIMAT0000689; hsa-miR-99b-5p | isomiR | 19 | + | 52195871 | 52195890 | 1.288028476 |
| ID = MIMAT0000689; hsa-miR-99b-5p | isomiR | 19 | + | 52195871 | 52195891 | 0.942329444 |
| ID = MIMAT0000689; hsa-miR-99b-5p | mirBase | 19 | + | 52195871 | 52195892 | 1.168595698 |
| ID = MIMAT0000689; hsa-miR-99b-5p | isomiR | 19 | + | 52195871 | 52195893 | 1.273940998 |
| ID = MIMAT0004935; hsa-miR-935 | isomiR | 19 | + | 54485618 | 54485638 | −1.290340375 |
| ID = MIMAT0016888; hsa-miR-4326 | isomiR | 20 | + | 61918170 | 61918192 | −2.189171494 |
| ID = MIMAT0000424; hsa-miR-128-3p | isomiR | 2 | + | 136423017 | 136423037 | 1.008351354 |
| ID = MIMAT0022726; hsa-miR-1306-5p | isomiR | 22 | + | 20073595 | 20073615 | −0.687810261 |
| ID = MIMAT0004502; hsa-miR-28-3p | mirBase | 3 | + | 188406622 | 188406643 | 0.805567557 |
| ID = MIMAT0004502; hsa-miR-28-3p | isomiR | 3 | + | 188406622 | 188406644 | 0.98178236 |
| ID = MIMAT0003241; hsa-miR-576-5p | mirBase | 4 | + | 110409869 | 110409890 | 0.702664876 |
| ID = MIMAT0003241; hsa-miR-576-5p | isomiR | 4 | + | 110409869 | 110409892 | 0.918510564 |
| ID = MIMAT0003239; hsa-miR-574-3p | isomiR | 4 | + | 38869714 | 38869734 | −0.905946749 |
| ID = MIMAT0003239; hsa-miR-574-3p | isomiR | 4 | + | 38869714 | 38869735 | −0.716936715 |
| ID = MIMAT0003239; hsa-miR-574-3p | isomiR | 4 | + | 38869714 | 38869736 | −0.907113522 |
| ID = MIMAT0003239; hsa-miR-574-3p | isomiR | 4 | + | 38869715 | 38869734 | −1.143751103 |

TABLE 10-continued

Differential expression of isomiR or miRNA in individuals with platelet antigen hyper-reactivity vs. hypo-reactivity

| miRNA ID | Is it a miRNA or an isomiR? | Chromo-some | Strand | IsomiR Start | IsomiR End | log2FoldChange of HYPO-reactive / HYPER-reactive |
|---|---|---|---|---|---|---|
| ID = MIMAT0003239; hsa-miR-574-3p | isomiR | 4 | + | 38869715 | 38869735 | −0.800015321 |
| ID = MIMAT0003239; hsa-miR-574-3p | isomiR | 4 | + | 38869715 | 38869736 | −0.684840113 |
| ID = MIMAT0004601; hsa-miR-145-3p | mirBase | 5 | + | 148810262 | 148810283 | 0.903088739 |
| ID = MIMAT0000449; hsa-miR-146a-5p | isomiR | 5 | + | 159912380 | 159912401 | 0.787529544 |
| ID = MIMAT0000449; hsa-miR-146a-5p | isomiR | 5 | + | 159912380 | 159912402 | 0.77307406 |
| ID = MIMAT0000449; hsa-miR-146a-5p | isomiR | 5 | + | 159912381 | 159912401 | 0.657010583 |
| ID = MIMAT0004702; hsa-miR-339-3p | isomiR | 7 | − | 1062592 | 1062611 | −0.777037637 |
| ID = MIMAT0000764; hsa-miR-339-5p | isomiR | 7 | − | 1062625 | 1062647 | −0.781301482 |
| ID = MIMAT0000765; hsa-miR-335-5p | isomiR | 7 | + | 130135967 | 130135988 | 0.53296691 |
| ID = MIMAT0000765; hsa-miR-335-5p | mirBase | 7 | + | 130135967 | 130135989 | 0.582659429 |
| ID = MIMAT0000086; hsa-miR-29a-3p | isomiR | 7 | − | 130561506 | 130561528 | 0.563158034 |
| ID = MIMAT0004672; hsa-miR-106b-3p | mirBase | 7 | − | 99691625 | 99691646 | −0.774615259 |
| ID = MIMAT0004672; hsa-miR-106b-3p | isomiR | 7 | − | 99691625 | 99691647 | −1.206525491 |
| ID = MIMAT0000420; hsa-miR-30b-5p | isomiR | 8 | − | 135812811 | 135812834 | 0.656327955 |
| ID = MIMAT0000420; hsa-miR-30b-5p | isomiR | 8 | − | 135812812 | 135812834 | 0.59271139 |
| ID = MIMAT0027604; hsa-miR-6852-5p | isomiR | 9 | − | 35710711 | 35710733 | −0.978676086 |
| ID = MIMAT0027604; hsa-miR-6852-5p | isomiR | 9 | − | 35710712 | 35710733 | −0.623346064 |
| ID = MIMAT0027604; hsa-miR-6852-5p | mirBase | 9 | − | 35710713 | 35710733 | −0.608678796 |
| ID = MIMAT0000099_1; hsa-miR-101-3p | isomiR | 9 | + | 4850347 | 4850368 | 1.057868333 |
| ID = MIMAT0000418; hsa-miR-23b-3p | isomiR | 9 | + | 97847547 | 97847568 | 0.759475648 |
| ID = MIMAT0000418; hsa-miR-23b-3p | isomiR | 9 | + | 97847547 | 97847569 | 0.596830114 |
| ID = MIMAT0000418; hsa-miR-23b-3p | isomiR | 9 | + | 97847547 | 97847570 | 0.670886728 |
| ID = MIMAT0000418; hsa-miR-23b-3p | isomiR | 9 | + | 97847549 | 97847568 | 1.160734587 |
| ID = MIMAT0000418; hsa-miR-23b-3p | isomiR | 9 | + | 97847549 | 97847569 | 1.014775501 |
| ID = MIMAT0000418; hsa-miR-2313-3p | isomiR | 9 | + | 97847549 | 97847570 | 1.28609021 |
| ID = MIMAT0022709; hsa-miR-652-5p | isomiR | X | + | 109298576 | 109298595 | 0.967684929 |
| ID = MIMAT0000707; hsa-miR-363-3p | isomiR | X | − | 133303411 | 133303433 | 0.631364682 |
| ID = MIMAT0003389; hsa-miR-542-3p | isomiR | X | − | 133675393 | 133675415 | 1.304170278 |
| ID = MIMAT0000096; hsa-miR-98-5p | isomiR | X | − | 53583259 | 53583281 | 0.693686608 |
| ID = MIMAT0019919; hsa-miR-4767 | isomiR | X | + | 7065909 | 7065931 | −1.260816811 |
| ID = MIMAT0000727; hsa-miR-374a-5p | isomiR | X | − | 73507158 | 73507181 | 1.387909088 |
| ID = MIMAT0000727; hsa-miR-374a-5p | isomiR | X | − | 73507159 | 73507180 | 0.80294068 |
| ID = MIMAT0000727; hsa-miR-374a-5p | isomiR | X | − | 73507159 | 73507181 | 0.58382585 |

Example 5. Differential Expression of isomiRs Across Populations by Ethnicity

This Example is drawn from the analysis of the deep sequencing data of 482 lymphoblastoid cell line (LCL) samples from the Geuvadis RNA deep-sequencing project, where its information is accessible online at http://www.geuvadis.org/web/geuvadis/RNAseq-project. In particular, the inventors focused and analyzed the 452 unique samples among the collection of 482 datasets (the remaining samples are technical replicates). The 452 samples represent five human populations: Utah Residents with Northern and Western European ancestry (CEU, 87 subjects), Finnish from Finland (FIN, 93 subjects), British in England and Scotland (GBR, 94 subjects), Toscani Italians (TSI, 89 subjects), and Yoruban Africans from the city of Ibadan (YRI, 89 subjects).

Figure 4:
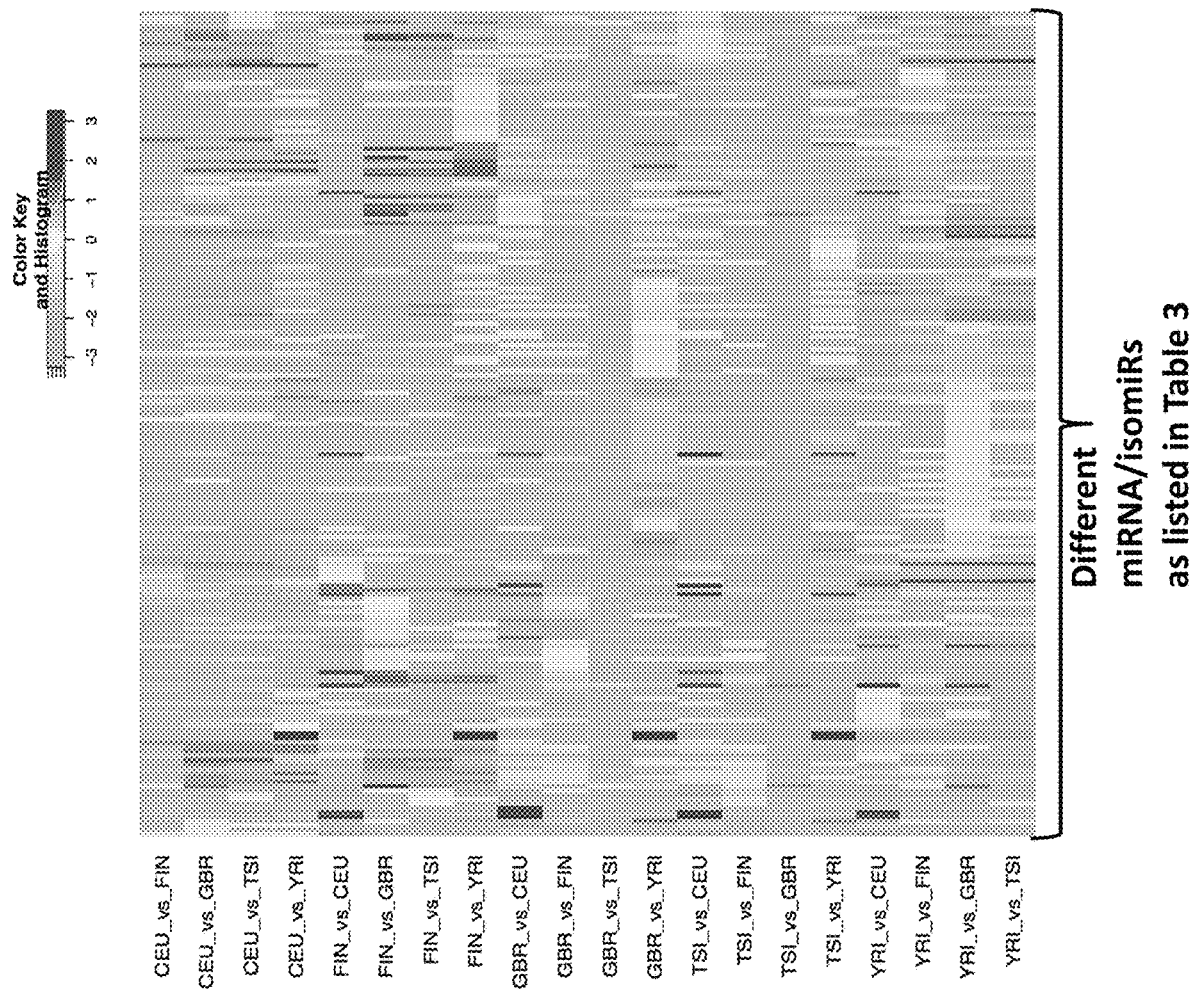
FIG. 4 is a heatmap showing differential expression of novel isomiRs across human populations by ethnicities.

Using samples from both genders, the inventors identified differentially expressed isomiRs separately for each pair of populations. FIG. 4 shows the resulting heatmap for the identified isomiRs listed in Table 3. Cells shown as white correspond to cases that did not reach statistical significance for the corresponding combination of miRNA/isomiR and population-pair. The color intensity scale is logarithmic (log 2 base). For all statistically significant combinations the associated FDR value is ≤0.05. This example shows that miRNAs and isomiRs can be used in principle to distinguish among human populations. Thus, combinations of isomiRs and miRNAs can be used to form distinguishing "signatures" with application to diagnostic and/or prognostic activities. Their participation in such distinguishing signatures directly implicates these sequences in molecular mechanisms that are currently either unknown or poorly understood: as such, some of these sequences can be eventually used to design appropriate therapeutics that are relevant for the corresponding tissue and tissue-state.

Example 6. Differential Expression of isomiRs Across Populations by Gender

Like in Example 5, this Example is drawn from the analysis of the deep sequencing data of 482 LCL samples from the Geuvadis RNA deep-sequencing project, where its information is accessible online at http://www.geuvadis.org/web/geuvadis/RNAseq-project. In particular, the inventors focused and analyzed the 452 unique samples among the collection of 482 datasets (the remaining samples are technical replicates). The 452 samples represent five human populations: Utah Residents with Northern and Western European ancestry (CEU, 87 subjects), Finnish from Finland (FIN, 93 subjects), British in England and Scotland (GBR, 94 subjects), Toscani Italians (TSI, 89 subjects), and Yoruban Africans from the city of Ibadan (YRI, 89 subjects).

Figure 5A:
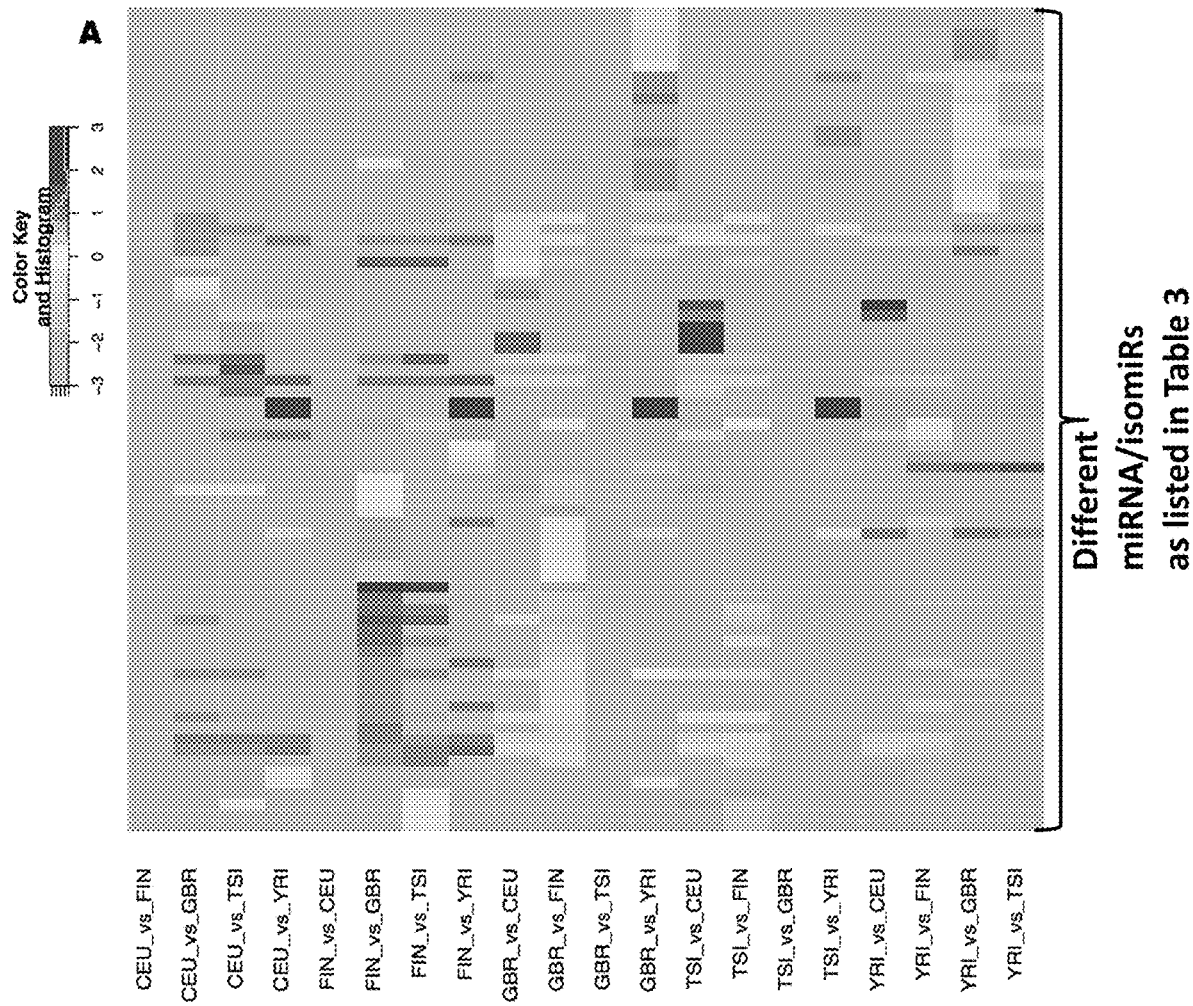
FIGS. 5A-5B is a heatmap showing differential expression of novel isomiRs across human populations by ethnicities and gender.
Figure 5B:
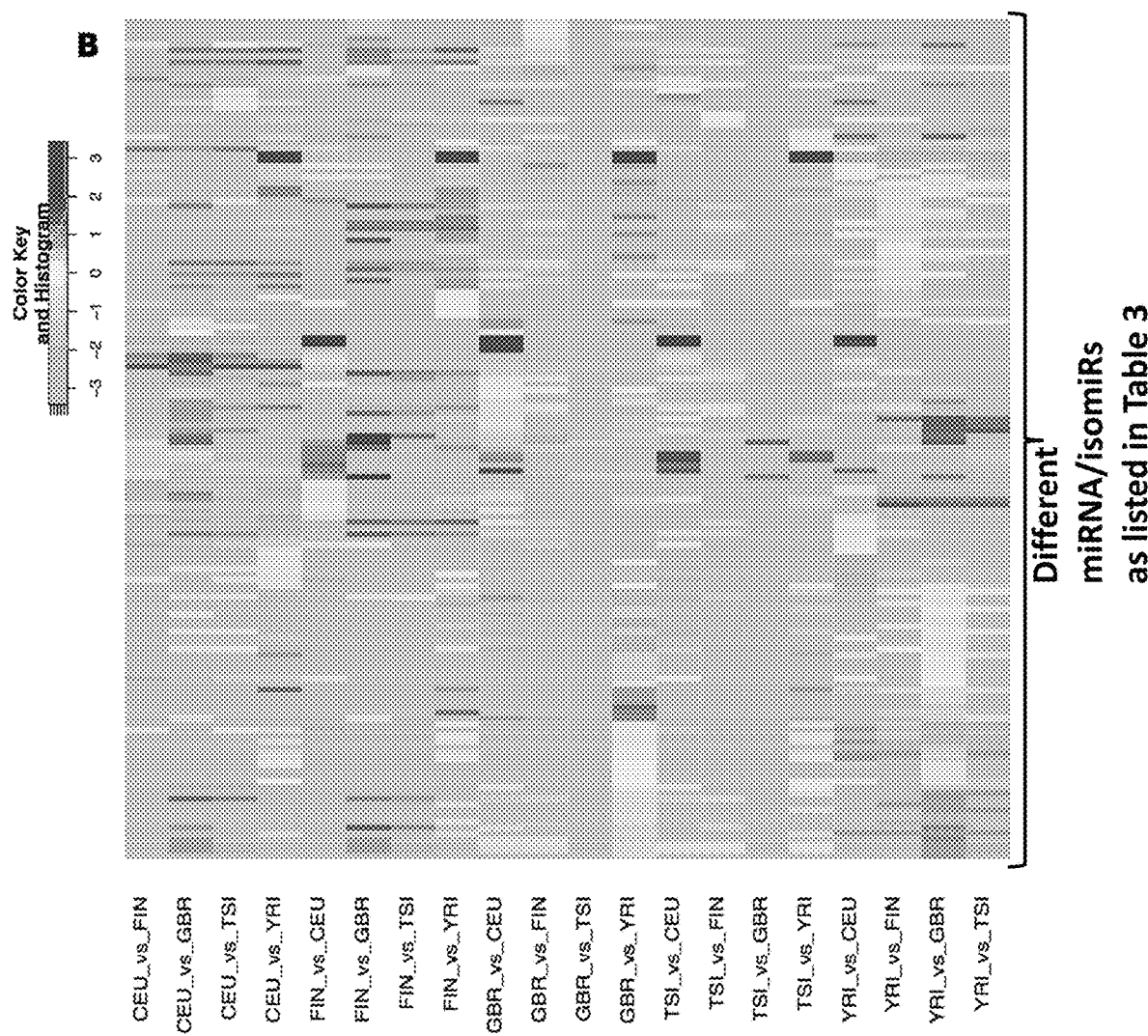

Using samples of the same gender, the inventors identified differentially expressed isomiRs separately for each pair of populations. FIGS. 5A-5B show the resulting heatmap for the isomiRs (identified in Table 3) in male samples and female samples, respectively. Cells shown as white correspond to cases that did not reach statistical significance for the corresponding combination of miRNA/isomiR and population-pair. The color intensity scale is logarithmic (log 2 base). For all statistically significant combinations the associated FDR value is ≤0.05. This example shows that miRNAs and isomiRs have different expression profiles among populations when only males are considered vs. when only females are considered. This shows the presence of different miRNAs/isomiRs and/or different expression patterns between females and males and thus the potential presence of differences in the underlying molecular mechanisms for the corresponding tissue and tissue-state.

Example 7. Differential Expression of Novel miRNAs by Disease States

There are three collections of novel miRNA sequences: (1) novel miRNAs that were discovered using the inventors' developed method as described in Example 1 (as listed in Table 11 below, they are prefixed by "TJU_CMC" only, e.g. TJU_CMC.ID02768.5p-miR); (2) novel miRNAs that were discovered using the miRDeep2 method and listed in Table 11 below, they are prefixed by "TJU_CMC.MD2" i.e. TJU_CMC_MD2.ID01023.3p-miR); and (3) isomiRs from miRNA loci that are in Rel. 20 of the miRBase repository and listed in Table 12 below, they are prefixed by "NovelMiR_KnownLoci" e.g. NovelMiR_KnownLoci_ID0001566).

The inventors processed numerous samples from different tissues and tissue states and sought to determine instances of miRNAs from each of these categories that were differentially expressed between pairs of states of the same tissue. A novel miRNA/isomiR is considered to be differentially expressed if it has a mean expression of at least 50 sequenced reads, a log 2-change in expression between the compared states of ≥0.58 or ≤−0.58, and a p-Value ≤0.05.

Using samples from different disease states, the inventors identified differentially expressed novel miRNAs that were either discovered using their own developed method (prefixed by "TJU_CMC" only, e.g. TJU_CMC.ID02768.5p-miR) or discovered using the miRDeep2 method (prefixed by "TJU_CMC.MD2" i.e. TJU_CMC_MD2.ID01023.3p-miR). As stated above, a miRNA is considered to be differentially expressed if it had a mean expression of at least 50 sequenced reads, a log 2-change in expression between the compared states of ≥0.58 or ≤−0.58, and a p-Value ≤0.05.

Examples 7-8 show that these novel sequences (either novel miRNAs or novel isomiRs from previously reported loci) can be used to form distinguishing "signatures" with application to diagnostic and/or prognostic activities. Again, their very participation in such distinguishing signatures directly implicates these sequences in molecular mechanisms that currently are either unknown or poorly understood: as such, some of these sequences could be eventually used to design appropriate therapeutics that are relevant for the corresponding tissue and tissue-state.

Table 11 below shows the fold-change of the miRNAs in pairs of the same tissue of different states. Abbreviations: TCGA=The Cancer Genome Atlas; PBMC=Peripheral Blood Mononuclear Cells; GEO=Gene Expression Omnibus. The actual miRNA or isomiR sequences and corresponding SEQ ID NOs. can be identified in Tables 1-2 according to the "Name" listed in Table 11.

TABLE 11

Differential expression of miRNAs in tissues of various disease states

| Name | Log2 fold change of Set A/Set B | p-Val | Sets Compared (A/B) |
| --- | --- | --- | --- |
| TJU_CMC.ID06653.3p-miR | −5.350055999 | 1.82E−11 | Chronic Lymphocytic Leukemia/Normal B cells |
| TJU_CMC.ID09612.5p-miR | −6.143612864 | 1.62E−09 | Chronic Lymphocytic Leukemia/Normal B cells |
| TJU_CMC.ID02842.5p-miR | 10.61146501 | 1.24E−08 | Chronic Lymphocytic Leukemia/Normal B cells |
| TJU_CMC_MD2.ID02528.3p-miR | −999999 | 1.79E−08 | Chronic Lymphocytic Leukemia/Normal B cells |
| TJU_CMC.ID09305.5p-miR | −6.666005566 | 6.04E−08 | Chronic Lymphocytic Leukemia/Normal B cells |
| TJU_CMC.ID02503.5p-miR | 10.87508867 | 9.50E−08 | Chronic Lymphocytic Leukemia/Normal B cells |
| TJU_CMC_MD2.ID02528.5p-miR | −999999 | 1.07E−07 | Chronic Lymphocytic Leukemia/Normal B cells |
| TJU_CMC.ID03278.3p-miR | 5.641662569 | 1.40E−07 | Chronic Lymphocytic Leukemia/Normal B cells |
| TJU_CMC.ID04657.3p-miR | −9.866230829 | 1.86E−07 | Chronic Lymphocytic Leukemia/Normal B cells |
| TJU_CMC.ID06600.5p-miR | −8.103688639 | 1.93E−07 | Chronic Lymphocytic Leukemia/Normal B cells |
| TJU_CMC_MD2.ID01860.5p-miR | −999999 | 1.94E−07 | Chronic Lymphocytic Leukemia/Normal B cells |
| TJU_CMC.ID02768.5p-miR | 8.369781246 | 2.13E−07 | Chronic Lymphocytic Leukemia/Normal B cells |
| TJU_CMC_MD2.ID01023.3p-miR | 999999 | 3.16E−07 | Chronic Lymphocytic Leukemia/Normal B cells |
| TJU_CMC.ID03256.3p-miR | −3.917708041 | 2.39E−08 | Hypo-reactive/Hyper-reactive (Platelets) |
| TJU_CMC.ID09799.3p-miR | −4.887841727 | 2.14E−07 | HER2− Breast Cancer/HER2+ Breast Cancer (TCGA) |
| TJU_CMC_MD2.ID00953.5p-miR | −999999 | 8.82E−07 | Chronic Lymphocytic Leukemia/Normal B cells |
| TJU_CMC_MD2.ID01023.5p-miR | 999999 | 8.97E−07 | Chronic Lymphocytic Leukemia/Normal B cells |
| TJU_CMC_MD2.ID00558.3p-miR | −999999 | 1.01E−06 | Chronic Lymphocytic Leukemia/Normal B cells |
| TJU_CMC_MD2.ID02912.5p-miR | 999999 | 1.24E−06 | Chronic Lymphocytic Leukemia/Normal B cells |
| TJU_CMC.ID04299.5p-miR | −5.000995116 | 1.22E−06 | Chronic Lymphocytic Leukemia/Normal B cells |
| TJU_CMC_MD2.ID00258.5p-miR | 8.714626517 | 1.36E−06 | Chronic Lymphocytic Leukemia/Normal B cells |
| TJU_CMC_MD2.ID02465.3p-miR | −8.206164944 | 1.99E−06 | Chronic Lymphocytic Leukemia/Normal B cells |
| TJU_CMC.ID08100.5p-miR | 10.78227313 | 5.45E−07 | Breast Cancer (adenoid/apocrine/atypical/DCIS/IDC/metaplastic)/Normal Breast Tissue (GEO: GSE28884) |
| TJU_CMC_MD2.ID00964.5p-miR | −999999 | 3.18E−06 | Chronic Lymphocytic Leukemia/Normal B cells |
| TJU_CMC.ID05256.5p-miR | −9.115766175 | 3.58E−06 | Chronic Lymphocytic Leukemia/Normal B cells |
| TJU_CMC.ID03524.5p-miR | 7.056227807 | 4.18E−06 | Chronic Lymphocytic Leukemia/Normal B cells |
| TJU_CMC.ID03856.5p-miR | −8.692614532 | 4.12E−06 | Chronic Lymphocytic Leukemia/Normal B cells |
| TJU_CMC.ID03519.3p-miR | 8.82432173 | 4.31E−06 | Chronic Lymphocytic Leukemia/Normal B cells |
| TJU_CMC.ID00299.5p-miR | 4.167117002 | 7.05E−07 | Stage 1 Gastric Cancer/Normal Gastric Tissue |
| TJU_CMC.ID09200.5p-miR | 4.147086478 | 8.81E−07 | Stage 1 Gastric Cancer/Normal Gastric Tissue |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID03504.3p-miR | 6.413198125 | 6.21E−06 | Chronic Lymphocytic Leukemia/Normal B cells |
| TJU_CMC.ID00744.3p-miR | 7.100628383 | 6.80E−06 | Chronic Lymphocytic Leukemia/Normal B cells |
| TJU_CMC.ID00225.3p-miR | 4.242952027 | 1.68E−06 | Stage 1 Gastric Cancer/Normal Gastric Tissue |
| TJU_CMC.ID08731.3p-miR | −5.94141269 | 2.10E−06 | Stage 1 Gastric Cancer/Normal Gastric Tissue |
| TJU_CMC.ID01316.3p-miR | −6.870251682 | 1.52E−05 | Chronic Lymphocytic Leukemia/Normal B cells |
| TJU_CMC.ID03300.5p-miR | 6.702083272 | 1.49E−05 | Chronic Lymphocytic Leukemia/Normal B cells |
| TJU_CMC.ID01494.3p-miR | 5.289938285 | 1.83E−05 | Chronic Lymphocytic Leukemia/Normal B cells |
| TJU_CMC.ID07022.5p-miR | 7.623615595 | 1.58E−05 | Breast Cancer (adenoid/apocrine/atypical/DCIS/IDC/metaplastic)/Normal Breast Tissue (GEO: GSE28884) |
| TJU_CMC.ID03454.5p-miR | 6.77674742 | 2.31E−05 | Chronic Lymphocytic Leukemia/Normal B cells |
| TJU_CMC.ID05541.3p-miR | 5.718371954 | 2.29E−05 | Chronic Lymphocytic Leukemia/Normal B cells |
| TJU_CMC.ID06289.5p-miR | −6.055179931 | 2.34E−05 | Chronic Lymphocytic Leukemia/Normal B cells |
| TJU_CMC.ID08042.5p-miR | −4.371634744 | 2.74E−05 | Chronic Lymphocytic Leukemia/Normal B cells |
| TJU_CMC.ID02508.5p-miR | 5.957071622 | 2.89E−05 | Chronic Lymphocytic Leukemia/Normal B cells |
| TJU_CMC.ID05571.3p-miR | 4.87676621 | 2.94E−05 | Chronic Lymphocytic Leukemia/Normal B cells |
| TJU_CMC.ID02844.3p-miR | 6.131098482 | 3.07E−05 | Chronic Lymphocytic Leukemia/Normal B cells |
| TJU_CMC.ID07466.3p-miR | 5.998317527 | 3.03E−05 | Chronic Lymphocytic Leukemia/Normal B cells |
| TJU_CMC.ID01558.5p-miR | −6.679700391 | 3.49E−05 | Chronic Lymphocytic Leukemia/Normal B cells |
| TJU_CMC.ID01152.5p-miR | 7.246723864 | 3.58E−05 | Chronic Lymphocytic Leukemia/Normal B cells |
| TJU_CMC.ID00581.3p-miR | 5.112712713 | 5.53E−05 | Breast Cancer (adenoid/apocrine/atypical/DCIS/IDC/metaplastic)/Normal Breast Tissue (GEO: GSE28884) |
| TJU_CMC.ID09045.5p-miR | 5.996981054 | 5.01E−05 | Breast Cancer (adenoid/apocrine/atypical/DCIS/IDC/metaplastic)/Normal Breast Tissue (GEO: GSE28884) |
| TJU_CMC.ID08817.5p-miR | −7.040237443 | 4.01E−05 | Chronic Lymphocytic Leukemia/Normal B cells |
| TJU_CMC.ID01743.5p-miR | 5.687787729 | 4.52E−05 | Chronic Lymphocytic Leukemia/Normal B cells |
| TJU_CMC.ID06261.5p-miR | 3.978728907 | 4.80E−05 | Chronic Lymphocytic Leukemia/Normal B cells |
| TJU_CMC.ID06075.5p-miR | 5.198810713 | 5.11E−05 | Chronic Lymphocytic Leukemia/Normal B cells |
| TJU_CMC.ID03003.3p-miR | −5.282487816 | 9.27E−06 | Stage 1 Gastric Cancer/Normal Gastric Tissue |
| TJU_CMC.ID08644.5p-miR | 3.698764073 | 1.02E−05 | Stage 1 Gastric Cancer/Normal Gastric Tissue |
| TJU_CMC.ID09315.5p-miR | 4.202589537 | 9.98E−06 | Stage 1 Gastric Cancer/Normal Gastric Tissue |
| TJU_CMC.ID04909.5p-miR | −5.426714465 | 5.61E−05 | Chronic Lymphocytic Leukemia/Normal B cells |
| TJU_CMC_MD2.ID02721.5p-miR | −6.028345639 | 5.92E−05 | Chronic Lymphocytic Leukemia/Normal B cells |
| TJU_CMC.ID02172.3p-miR | 4.17893251 | 6.33E−05 | Chronic Lymphocytic Leukemia/Normal B cells |
| TJU_CMC.ID03495.5p-miR | −4.565082803 | 6.28E−05 | Chronic Lymphocytic Leukemia/Normal B cells |
| TJU_CMC.ID06967.3p-miR | −6.51771449 | 7.17E−05 | Chronic Lymphocytic Leukemia/Normal B cells |
| TJU_CMC.ID04559.5p-miR | 5.435199575 | 7.57E−05 | Chronic Lymphocytic Leukemia/Normal B cells |
| TJU_CMC.ID01232.3p-miR | 6.558455622 | 0.000110459 | Breast Cancer (adenoid/apocrine/atypical/DCIS/IDC/metaplastic)/Normal Breast Tissue (GEO: GSE28884) |
| TJU_CMC.ID09362.5p-miR | 8.068986534 | 0.000122719 | Breast Cancer (adenoid/apocrine/atypical/DCIS/IDC/metaplastic)/Normal Breast Tissue (GEO: GSE28884) |
| TJU_CMC.ID05136.3p-miR | −6.462794459 | 7.96E−05 | Chronic Lymphocytic Leukemia/Normal B cells |
| TJU_CMC.ID09211.5p-miR | −6.096317714 | 8.22E−05 | Chronic Lymphocytic Leukemia/Normal B cells |
| TJU_CMC_MD2.ID01436.3p-miR | −6.844516944 | 9.18E−05 | Chronic Lymphocytic Leukemia/Normal B cells |
| TJU_CMC.ID05232.3p-miR | 5.269136783 | 9.66E−05 | Chronic Lymphocytic Leukemia/Normal B cells |
| TJU_CMC.ID08857.5p-miR | −5.185841009 | 0.000101318 | Chronic Lymphocytic Leukemia/Normal B cells |
| TJU_CMC.ID04776.3p-miR | −5.968840199 | 0.000108755 | Chronic Lymphocytic Leukemia/Normal B cells |
| TJU_CMC.ID03322.5p-miR | 3.62089628 | 1.74E−05 | Stage 1 Gastric Cancer/Normal Gastric Tissue |
| TJU_CMC.ID05498.3p-miR | −5.923985039 | 0.00012389 | Chronic Lymphocytic Leukemia/Normal B cells |
| TJU_CMC.ID09556.5p-miR | 4.358490643 | 0.000128181 | Chronic Lymphocytic Leukemia/Normal B cells |
| TJU_CMC.ID05794.5p-miR | −7.275302525 | 0.000129705 | Chronic Lymphocytic Leukemia/Normal B cells |
| TJU_CMC.ID01160.3p-miR | 9.981234895 | 0.000134237 | Chronic Lymphocytic Leukemia/Normal B cells |
| TJU_CMC.ID09464.5p-miR | 6.954848435 | 0.000193258 | Breast Cancer (adenoid/apocrine/atypical/DCIS/IDC/metaplastic)/Normal Breast Tissue (GEO: GSE28884) |
| TJU_CMC.ID06420.5p-miR | 999999 | 0.000146696 | Chronic Lymphocytic Leukemia/Normal B cells |
| TJU_CMC.ID00602.3p-miR | −5.398215307 | 1.51E−04 | Chronic Lymphocytic Leukemia/Normal B cells |
| TJU_CMC.ID05591.5p-miR | −5.202141235 | 0.000150691 | Chronic Lymphocytic Leukemia/Normal B cells |
| TJU_CMC.ID03158.5p-miR | −5.18709673 | 0.000154642 | Chronic Lymphocytic Leukemia/Normal B cells |
| TJU_CMC_MD2.ID00326.5p-miR | 7.22768428 | 0.000249828 | Breast Cancer (adenoid/apocrine/atypical/DCIS/IDC/metaplastic)/Normal Breast Tissue (GEO: GSE28884) |
| TJU_CMC.ID03778.3p-miR | −3.575821691 | 2.81E−05 | Stage 1 Gastric Cancer/Normal Gastric Tissue |
| TJU_CMC.ID08027.5p-miR | −4.38644661 | 0.0001772 | Chronic Lymphocytic Leukemia/Normal B cells |
| TJU_CMC.ID08731.3p-miR | −5.399172552 | 5.44E−06 | Gastric Cancer (All Stages)/Normal Gastric Tissue |
| TJU_CMC.ID01135.3p-miR | 2.930131702 | 3.31E−05 | Stage 1 Gastric Cancer/Normal Gastric Tissue |
| TJU_CMC.ID08946.3p-miR | 5.279650918 | 0.000208462 | Chronic Lymphocytic Leukemia/Normal B cells |
| TJU_CMC.ID09118.5p-miR | 6.714196096 | 0.000218512 | Chronic Lymphocytic Leukemia/Normal B cells |
| TJU_CMC_MD2.ID03494.5p-miR | 4.14958141 | 0.000220218 | Chronic Lymphocytic Leukemia/Normal B cells |
| TJU_CMC.ID06656.5p-miR | 3.336125897 | 5.06E−05 | Stage 1 Gastric Cancer/Normal Gastric Tissue |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID05992.3p-miR | 5.78174404 | 5.26E−05 | Stage 1 Gastric Cancer/Normal Gastric Tissue |
| TJU_CMC.ID07790.5p-miR | −3.836018874 | 5.10E−05 | Stage 1 Gastric Cancer/Normal Gastric Tissue |
| TJU_CMC.ID08272.3p-miR | 4.113667399 | 4.77E−05 | Stage 1 Gastric Cancer/Normal Gastric Tissue |
| TJU_CMC.ID06876.5p-miR | 4.690963487 | 0.000271606 | Chronic Lymphocytic Leukemia/Normal B cells |
| TJU_CMC.ID08177.5p-miR | 5.155337948 | 0.000289999 | Chronic Lymphocytic Leukemia/Normal B cells |
| TJU_CMC.ID08261.5p-miR | 4.640781533 | 0.000296545 | Chronic Lymphocytic Leukemia/Normal B cells |
| TJU_CMC.ID04632.3p-miR | 7.838923587 | 0.00029972 | Chronic Lymphocytic Leukemia/Normal B cells |
| TJU_CMC.ID01563.5p-miR | 4.858443966 | 0.000303636 | Chronic Lymphocytic Leukemia/Normal B cells |
| TJU_CMC.ID04558.3p-miR | −5.709826486 | 0.00030917 | Chronic Lymphocytic Leukemia/Normal B cells |
| TJU_CMC.ID04581.5p-miR | −6.24534738 | 0.000309428 | Chronic Lymphocytic Leukemia/Normal B cells |
| TJU_CMC.ID01077.5p-miR | −5.111571124 | 0.000317661 | Chronic Lymphocytic Leukemia/Normal B cells |
| TJU_CMC.ID06657.3p-miR | 4.787416739 | 0.000325 | Chronic Lymphocytic Leukemia/Normal B cells |
| TJU_CMC.ID05096.5p-miR | 6.230029943 | 0.000341974 | Chronic Lymphocytic Leukemia/Normal B cells |
| TJU_CMC.ID06065.3p-miR | −5.558341447 | 0.000343083 | Chronic Lymphocytic Leukemia/Normal B cells |
| TJU_CMC.ID09115.5p-miR | 4.779747152 | 7.19E−05 | Stage 1 Gastric Cancer/Normal Gastric Tissue |
| TJU_CMC.ID05175.5p-miR | −1.378776682 | 0.000201196 | PR− Breast Cancer/PR+ Breast Cancer (TCGA) |
| TJU_CMC.ID02914.3p-miR | 4.169060369 | 8.69E−05 | Stage 1 Gastric Cancer/Normal Gastric Tissue |
| TJU_CMC.ID02650.5p-miR | 4.66315875 | 0.000449771 | Chronic Lymphocytic Leukemia/Normal B cells |
| TJU_CMC.ID09493.5p-miR | −5.34762686 | 0.000456447 | Chronic Lymphocytic Leukemia/Normal B cells |
| TJU_CMC.ID05918.3p-miR | 5.145167112 | 0.000511849 | Chronic Lymphocytic Leukemia/Normal B cells |
| TJU_CMC.ID07047.3p-miR | −5.580371457 | 0.000524814 | Chronic Lymphocytic Leukemia/Normal B cells |
| TJU_CMC.ID01631.5p-miR | 4.195376808 | 0.000545762 | Chronic Lymphocytic Leukemia/Normal B cells |
| TJU_CMC.ID02628.3p-miR | 5.277749364 | 0.000543955 | Chronic Lymphocytic Leukemia/Normal B cells |
| TJU_CMC.ID07634.3p-miR | 5.49736396 | 0.000602502 | Chronic Lymphocytic Leukemia/Normal B cells |
| TJU_CMC.ID02766.3p-miR | −3.543069652 | 0.00062563 | Chronic Lymphocytic Leukemia/Normal B cells |
| TJU_CMC.ID00395.3p-miR | 5.213282626 | 0.000646725 | Chronic Lymphocytic Leukemia/Normal B cells |
| TJU_CMC.ID03304.3p-miR | −5.166631344 | 0.000651137 | Chronic Lymphocytic Leukemia/Normal B cells |
| TJU_CMC.ID01362.5p-miR | 4.410814146 | 0.000668225 | Chronic Lymphocytic Leukemia/Normal B cells |
| TJU_CMC.ID05001.3p-miR | 4.203854064 | 0.00068091 | Chronic Lymphocytic Leukemia/Normal B cells |
| TJU_CMC.ID01606.3p-miR | 6.338522361 | 0.000124339 | Stage 1 Gastric Cancer/Normal Gastric Tissue |
| TJU_CMC.ID04661.5p-miR | 3.449210388 | 0.000146579 | Stage 1 Gastric Cancer/Normal Gastric Tissue |
| TJU_CMC.ID09327.3p-miR | −5.04132634 | 0.000774951 | Chronic Lymphocytic Leukemia/Normal B cells |
| TJU_CMC.ID05693.5p-miR | −3.875915893 | 0.000798401 | Chronic Lymphocytic Leukemia/Normal B cells |
| TJU_CMC.ID06834.3p-miR | −2.587635697 | 0.000835388 | Chronic Lymphocytic Leukemia/Normal B cells |
| TJU_CMC.ID00711.5p-miR | 6.255640602 | 0.0008649 | Chronic Lymphocytic Leukemia/Normal B cells |
| TJU_CMC.ID04683.5p-miR | 2.781068193 | 0.000178069 | Stage 1 Gastric Cancer/Normal Gastric Tissue |
| TJU_CMC.ID08301.3p-miR | 4.376235733 | 0.000886208 | Chronic Lymphocytic Leukemia/Normal B cells |
| TJU_CMC.ID05046.5p-miR | −4.905172311 | 0.000896889 | Chronic Lymphocytic Leukemia/Normal B cells |
| TJU_CMC.ID06865.5p-miR | −3.999286886 | 0.000926659 | Chronic Lymphocytic Leukemia/Normal B cells |
| TJU_CMC.ID08236.3p-miR | 4.960820226 | 0.000937113 | Chronic Lymphocytic Leukemia/Normal B cells |
| TJU_CMC.ID03885.3p-miR | 4.25503448 | 0.000950814 | Chronic Lymphocytic Leukemia/Normal B cells |
| TJU_CMC.ID04994.5p-miR | −4.640194729 | 0.000954192 | Chronic Lymphocytic Leukemia/Normal B cells |
| TJU_CMC.ID00522.5p-miR | −4.153838602 | 0.000967384 | Chronic Lymphocytic Leukemia/Normal B cells |
| TJU_CMC.ID01739.3p-miR | 4.398158234 | 0.000987773 | Chronic Lymphocytic Leukemia/Normal B cells |
| TJU_CMC.ID08957.5p-miR | −4.550746438 | 0.00105123 | Chronic Lymphocytic Leukemia/Normal B cells |
| TJU_CMC.ID02282.3p-miR | −4.167884941 | 0.001077348 | Chronic Lymphocytic Leukemia/Normal B cells |
| TJU_CMC.ID06539.3p-miR | 3.25231861 | 0.000215381 | Stage 1 Gastric Cancer/Normal Gastric Tissue |
| TJU_CMC.ID01852.5p-miR | 4.280188721 | 0.001138706 | Chronic Lymphocytic Leukemia/Normal B cells |
| TJU_CMC.ID03898.3p-miR | 6.209813253 | 0.001142411 | Chronic Lymphocytic Leukemia/Normal B cells |
| TJU_CMC.ID08652.5p-miR | −3.632869643 | 0.001147199 | Chronic Lymphocytic Leukemia/Normal B cells |
| TJU_CMC.ID08763.5p-miR | 3.130267045 | 0.000234446 | Stage 1 Gastric Cancer/Normal Gastric Tissue |
| TJU_CMC.ID08292.3p-miR | −4.550226948 | 0.001253063 | Chronic Lymphocytic Leukemia/Normal B cells |
| TJU_CMC.ID08520.5p-miR | 6.374585156 | 0.001261675 | Chronic Lymphocytic Leukemia/Normal B cells |
| TJU_CMC.ID00107.3p-miR | −3.863162301 | 0.000271664 | Stage 1 Gastric Cancer/Normal Gastric Tissue |
| TJU_CMC.ID04757.3p-miR | 5.379247431 | 5.82E−06 | PBMC Scleroderma Patients/PBMC Control Individuals |
| TJU_CMC.ID06916.5p-miR | −4.342335935 | 0.001362215 | Chronic Lymphocytic Leukemia/Normal B cells |
| TJU_CMC.ID07737.3p-miR | 3.089872089 | 0.000285267 | Stage 1 Gastric Cancer/Normal Gastric Tissue |
| TJU_CMC.ID09230.3p-miR | −3.135381546 | 0.000292281 | Stage 1 Gastric Cancer/Normal Gastric Tissue |
| TJU_CMC.ID06765.5p-miR | 4.568486219 | 0.000301392 | Stage 1 Gastric Cancer/Normal Gastric Tissue |
| TJU_CMC.ID09799.3p-miR | 3.785717025 | 0.000309793 | Stage 1 Gastric Cancer/Normal Gastric Tissue |
| TJU_CMC.ID00020.3p-miR | 4.687645247 | 0.001406275 | Chronic Lymphocytic Leukemia/Normal B cells |
| TJU_CMC.ID01975.3p-miR | 3.961680472 | 0.001446071 | Chronic Lymphocytic Leukemia/Normal B cells |
| TJU_CMC.ID09306.3p-miR | −5.136399176 | 0.001488952 | Chronic Lymphocytic Leukemia/Normal B cells |
| TJU_CMC.ID06325.3p-miR | 3.524257076 | 0.000356331 | Stage 1 Gastric Cancer/Normal Gastric Tissue |
| TJU_CMC.ID06673.3p-miR | −3.813753745 | 0.000352979 | Stage 1 Gastric Cancer/Normal Gastric Tissue |
| TJU_CMC.ID01131.5p-miR | −4.519895228 | 0.001519536 | Chronic Lymphocytic Leukemia/Normal B cells |
| TJU_CMC.ID06092.3p-miR | 3.862574726 | 0.001518102 | Chronic Lymphocytic Leukemia/Normal B cells |
| TJU_CMC.ID03353.3p-miR | −4.160245232 | 0.001573503 | Chronic Lymphocytic Leukemia/Normal B cells |
| TJU_CMC.ID07866.3p-miR | 5.214946608 | 0.001576663 | Chronic Lymphocytic Leukemia/Normal B cells |
| TJU_CMC.ID03982.5p-miR | −4.102714902 | 0.001635801 | Chronic Lymphocytic Leukemia/Normal B cells |
| TJU_CMC.ID00141.3p-miR | 3.825644909 | 0.001653643 | Chronic Lymphocytic Leukemia/Normal B cells |
| TJU_CMC.ID00055.3p-miR | 6.007583643 | 0.001698155 | Chronic Lymphocytic Leukemia/Normal B cells |
| TJU_CMC.ID02091.5p-miR | −4.262258924 | 0.001695972 | Chronic Lymphocytic Leukemia/Normal B cells |
| TJU_CMC.ID00442.3p-miR | 4.627278196 | 0.001815043 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID04345.3p-miR | 3.993726787 | 0.001845504 | Chronic Lymphocytic Leukemia/Normal B cells |
| TJU_CMC.ID04197.5p-miR | 4.026699918 | 0.001925506 | Chronic Lymphocytic Leukemia/Normal B cells |
| TJU_CMC.ID07695.3p-miR | 3.844254186 | 0.001942029 | Chronic Lymphocytic Leukemia/Normal B cells |
| TJU_CMC_MD2.ID01416.3p-miR | −4.356600708 | 0.00195735 | Chronic Lymphocytic Leukemia/Normal B cells |
| TJU_CMC.ID05727.5p-miR | 4.587677454 | 0.002022729 | Chronic Lymphocytic Leukemia/Normal B cells |
| TJU_CMC.ID03098.3p-miR | 5.656770601 | 0.002044575 | Chronic Lymphocytic Leukemia/Normal B cells |
| TJU_CMC.ID02066.3p-miR | 3.561817067 | 0.00213419 | Chronic Lymphocytic Leukemia/Normal B cells |
| TJU_CMC.ID05175.5p-miR | −1.185922549 | 0.001482037 | ER− Breast Cancer/ER+ Breast Cancer (TCGA) |
| TJU_CMC.ID00403.3p-miR | 3.756954798 | 0.002198099 | Chronic Lymphocytic Leukemia/Normal B cells |
| TJU_CMC.ID08111.5p-miR | −3.807724286 | 0.002214865 | Chronic Lymphocytic Leukemia/Normal B cells |
| TJU_CMC.ID00506.3p-miR | 5.164155584 | 0.002253642 | Chronic Lymphocytic Leukemia/Normal B cells |
| TJU_CMC.ID00730.5p-miR | 5.330307488 | 0.002250791 | Chronic Lymphocytic Leukemia/Normal B cells |
| TJU_CMC.ID05115.5p-miR | −4.453529341 | 0.002252647 | Chronic Lymphocytic Leukemia/Normal B cells |
| TJU_CMC.ID06844.3p-miR | 3.978840637 | 0.002267126 | Chronic Lymphocytic Leukemia/Normal B cells |
| TJU_CMC.ID01478.3p-miR | 3.972503878 | 0.002290871 | Chronic Lymphocytic Leukemia/Normal B cells |
| TJU_CMC.ID02970.3p-miR | 2.931980044 | 0.000514428 | Stage 1 Gastric Cancer/Normal Gastric Tissue |
| TJU_CMC.ID07009.3p-miR | 3.839672259 | 0.002356424 | Chronic Lymphocytic Leukemia/Normal B cells |
| TJU_CMC.ID02773.3p-miR | 4.518529043 | 0.002394422 | Chronic Lymphocytic Leukemia/Normal B cells |
| TJU_CMC.ID02905.3p-miR | −3.68657312 | 0.002434754 | Chronic Lymphocytic Leukemia/Normal B cells |
| TJU_CMC.ID08831.3p-miR | 4.054510317 | 0.002463378 | Chronic Lymphocytic Leukemia/Normal B cells |
| TJU_CMC.ID05841.5p-miR | −3.957415667 | 0.002498411 | Chronic Lymphocytic Leukemia/Normal B cells |
| TJU_CMC_MD2.ID02050.5p-miR | −5.234003958 | 0.002482054 | Chronic Lymphocytic Leukemia/Normal B cells |
| TJU_CMC.ID07824.5p-miR | 4.60201983 | 2.45E−05 | PBMC Scleroderma Patients/PBMC Control Individuals |
| TJU_CMC.ID02554.5p-miR | 4.555190677 | 0.00252341 | Chronic Lymphocytic Leukemia/Normal B cells |
| TJU_CMC.ID03893.3p-miR | 3.593847173 | 0.004045668 | Breast Cancer (adenoid/apocrine/atypical/DCIS/IDC/metaplastic)/Normal Breast Tissue (GEO: GSE28884) |
| TJU_CMC_MD2.ID02126.3p-miR | 1.451827053 | 0.001782406 | ER− Breast Cancer/ER+ Breast Cancer (TCGA) |
| TJU_CMC.ID06433.3p-miR | 4.295307413 | 0.00273945 | Chronic Lymphocytic Leukemia/Normal B cells |
| TJU_CMC.ID06390.5p-miR | 3.991012698 | 0.002755294 | Chronic Lymphocytic Leukemia/Normal B cells |
| TJU_CMC.ID03823.5p-miR | 3.879328689 | 0.002812429 | Chronic Lymphocytic Leukemia/Normal B cells |
| TJU_CMC.ID06009.3p-miR | −3.989755274 | 0.002830427 | Chronic Lymphocytic Leukemia/Normal B cells |
| TJU_CMC.ID03653.5p-miR | 4.883752181 | 0.002923736 | Chronic Lymphocytic Leukemia/Normal B cells |
| TJU_CMC.ID07934.5p-miR | −4.078319656 | 0.002929015 | Chronic Lymphocytic Leukemia/Normal B cells |
| TJU_CMC.ID03131.3p-miR | 3.751722034 | 0.00300768 | Chronic Lymphocytic Leukemia/Normal B cells |
| TJU_CMC.ID03972.3p-miR | 3.784569846 | 0.003032851 | Chronic Lymphocytic Leukemia/Normal B cells |
| TJU_CMC.ID02000.5p-miR | 5.392634372 | 0.003143169 | Chronic Lymphocytic Leukemia/Normal B cells |
| TJU_CMC.ID02154.3p-miR | −4.396251781 | 0.003146609 | Chronic Lymphocytic Leukemia/Normal B cells |
| TJU_CMC.ID06554.3p-miR | 4.387798596 | 0.003139251 | Chronic Lymphocytic Leukemia/Normal B cells |
| TJU_CMC.ID07572.3p-miR | −3.915312372 | 0.00320242 | Chronic Lymphocytic Leukemia/Normal B cells |
| TJU_CMC.ID08486.5p-miR | −3.887475153 | 0.003232179 | Chronic Lymphocytic Leukemia/Normal B cells |
| TJU_CMC.ID09605.3p-miR | −4.158036816 | 0.003226871 | Chronic Lymphocytic Leukemia/Normal B cells |
| TJU_CMC.ID03066.3p-miR | −1.599224259 | 0.001625123 | PR− Breast Cancer/PR+ Breast Cancer (TCGA) |
| TJU_CMC_MD2.ID00088.5p-miR | −4.093459824 | 0.003338064 | Chronic Lymphocytic Leukemia/Normal B cells |
| TJU_CMC.ID01339.5p-miR | 3.170500627 | 0.000694131 | Stage 1 Gastric Cancer/Normal Gastric Tissue |
| TJU_CMC.ID02355.3p-miR | −4.222175444 | 0.003602964 | Chronic Lymphocytic Leukemia/Normal B cells |
| TJU_CMC.ID07153.5p-miR | 3.740413618 | 0.003588639 | Chronic Lymphocytic Leukemia/Normal B cells |
| TJU_CMC.ID08371.3p-miR | −3.873087387 | 0.003590353 | Chronic Lymphocytic Leukemia/Normal B cells |
| TJU_CMC.ID06215.3p-miR | 3.702159521 | 0.003651192 | Chronic Lymphocytic Leukemia/Normal B cells |
| TJU_CMC.ID03548.3p-miR | 5.023324428 | 0.003714428 | Chronic Lymphocytic Leukemia/Normal B cells |
| TJU_CMC.ID08211.3p-miR | −4.705342525 | 0.003717942 | Chronic Lymphocytic Leukemia/Normal B cells |
| TJU_CMC.ID04133.5p-miR | −1.657029037 | 0.00248944 | ER− Breast Cancer/ER+ Breast Cancer (TCGA) |
| TJU_CMC.ID02903.5p-miR | −4.144824332 | 0.003739725 | Chronic Lymphocytic Leukemia/Normal B cells |
| TJU_CMC.ID05770.3p-miR | 6.865129325 | 0.003793287 | Chronic Lymphocytic Leukemia/Normal B cells |
| TJU_CMC.ID08135.3p-miR | 4.153903665 | 0.003946667 | Chronic Lymphocytic Leukemia/Normal B cells |
| TJU_CMC.ID00684.3p-miR | 6.195031347 | 0.004034179 | Chronic Lymphocytic Leukemia/Normal B cells |
| TJU_CMC.ID08434.5p-miR | −3.741904172 | 0.004018306 | Chronic Lymphocytic Leukemia/Normal B cells |
| TJU_CMC.ID01093.3p-miR | −3.207971266 | 0.000808878 | Stage 1 Gastric Cancer/Normal Gastric Tissue |
| TJU_CMC.ID01019.3p-miR | −3.947784983 | 0.00414436 | Chronic Lymphocytic Leukemia/Normal B cells |
| TJU_CMC.ID04387.5p-miR | −3.518005909 | 0.004170622 | Chronic Lymphocytic Leukemia/Normal B cells |
| TJU_CMC.ID02329.5p-miR | 3.875903033 | 0.004198355 | Chronic Lymphocytic Leukemia/Normal B cells |
| TJU_CMC.ID00051.5p-miR | 3.736006102 | 0.004367628 | Chronic Lymphocytic Leukemia/Normal B cells |
| TJU_CMC.ID01767.3p-miR | 5.538641135 | 0.004377749 | Chronic Lymphocytic Leukemia/Normal B cells |
| TJU_CMC.ID05633.3p-miR | 5.02784088 | 0.004264183 | Chronic Lymphocytic Leukemia/Normal B cells |
| TJU_CMC.ID05673.5p-miR | −3.764399583 | 0.004329739 | Chronic Lymphocytic Leukemia/Normal B cells |
| TJU_CMC.ID06451.5p-miR | 3.771384312 | 0.00427519 | Chronic Lymphocytic Leukemia/Normal B cells |
| TJU_CMC.ID06926.3p-miR | −4.135406749 | 0.004289928 | Chronic Lymphocytic Leukemia/Normal B cells |
| TJU_CMC_MD2.ID02125.3p-miR | −3.886256183 | 0.004382399 | Chronic Lymphocytic Leukemia/Normal B cells |
| TJU_CMC.ID02796.5p-miR | 4.182424269 | 0.004407616 | Chronic Lymphocytic Leukemia/Normal B cells |
| TJU_CMC.ID02785.3p-miR | 4.324652154 | 0.004614631 | Chronic Lymphocytic Leukemia/Normal B cells |
| TJU_CMC.ID07294.3p-miR | −3.510999533 | 0.004639479 | Chronic Lymphocytic Leukemia/Normal B cells |
| TJU_CMC.ID07864.5p-miR | −3.662633681 | 5.35E−05 | Gastric Cancer (All Stages)/Normal Gastric Tissue |
| TJU_CMC.ID08927.5p-miR | −3.731813089 | 0.000868055 | Stage 1 Gastric Cancer/Normal Gastric Tissue |
| TJU_CMC.ID02027.3p-miR | −5.340729298 | 0.004736291 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
| --- | --- | --- | --- |
| TJU_CMC.ID08389.5p-miR | 3.373648505 | 0.000893978 | Stage 1 Gastric Cancer/Normal Gastric Tissue |
| TJU_CMC.ID09745.3p-miR | −3.76806725 | 0.00476875 | Chronic Lymphocytic Leukemia/Normal B cells |
| TJU_CMC.ID04996.5p-miR | −5.907575247 | 0.004992966 | Chronic Lymphocytic Leukemia/Normal B cells |
| TJU_CMC.ID03448.5p-miR | 3.305828171 | 0.001003754 | Stage 1 Gastric Cancer/Normal Gastric Tissue |
| TJU_CMC.ID06731.3p-miR | −2.627421791 | 0.001010748 | Stage 1 Gastric Cancer/Normal Gastric Tissue |
| TJU_CMC.ID09120.3p-miR | −2.799361236 | 0.001005158 | Stage 1 Gastric Cancer/Normal Gastric Tissue |
| TJU_CMC.ID09799.3p-miR | 4.988057257 | 0.000156714 | HER2-type Breast Cancer/Basal-like Breast Cancer (TCGA) |
| TJU_CMC.ID03066.3p-miR | −1.525246872 | 0.003710768 | ER− Breast Cancer/ER+ Breast Cancer (TCGA) |
| TJU_CMC.ID00808.5p-miR | 4.45455467 | 0.005359437 | Chronic Lymphocytic Leukemia/Normal B cells |
| TJU_CMC.ID04999.3p-miR | 4.55163693 | 0.005443038 | Chronic Lymphocytic Leukemia/Normal B cells |
| TJU_CMC.ID04293.5p-miR | −3.975913396 | 0.005473644 | Chronic Lymphocytic Leukemia/Normal B cells |
| TJU_CMC.ID07897.3p-miR | 3.262292955 | 0.005460879 | Chronic Lymphocytic Leukemia/Normal B cells |
| TJU_CMC.ID04734.3p-miR | 3.31390565 | 0.005513998 | Chronic Lymphocytic Leukemia/Normal B cells |
| TJU_CMC.ID09827.5p-miR | −2.428009406 | 0.005517439 | Chronic Lymphocytic Leukemia/Normal B cells |
| TJU_CMC.ID09669.3p-miR | −3.458782703 | 0.005677504 | Chronic Lymphocytic Leukemia/Normal B cells |
| TJU_CMC.ID03560.3p-miR | 999999 | 0.005760813 | Chronic Lymphocytic Leukemia/Normal B cells |
| TJU_CMC_MD2.ID01860.3p-miR | −999999 | 0.005819237 | Chronic Lymphocytic Leukemia/Normal B cells |
| TJU_CMC.ID08066.3p-miR | 4.287744017 | 0.005869927 | Chronic Lymphocytic Leukemia/Normal B cells |
| TJU_CMC.ID06825.3p-miR | −3.522675208 | 0.001127059 | Stage 1 Gastric Cancer/Normal Gastric Tissue |
| TJU_CMC.ID02186.3p-miR | 3.721624573 | 0.006069033 | Chronic Lymphocytic Leukemia/Normal B cells |
| TJU_CMC.ID05680.3p-miR | −3.487688128 | 0.006066361 | Chronic Lymphocytic Leukemia/Normal B cells |
| TJU_CMC.ID03810.3p-miR | 3.615932991 | 0.006213076 | Chronic Lymphocytic Leukemia/Normal B cells |
| TJU_CMC.ID09849.5p-miR | −3.493578587 | 0.006186266 | Chronic Lymphocytic Leukemia/Normal B cells |
| TJU_CMC.ID08219.3p-miR | 4.875280596 | 0.006322887 | Chronic Lymphocytic Leukemia/Normal B cells |
| TJU_CMC.ID01848.5p-miR | −3.750885689 | 0.006378115 | Chronic Lymphocytic Leukemia/Normal B cells |
| TJU_CMC.ID04261.3p-miR | 4.129878547 | 0.006400059 | Chronic Lymphocytic Leukemia/Normal B cells |
| TJU_CMC_MD2.ID01104.3p-miR | −3.925384235 | 0.006412455 | Chronic Lymphocytic Leukemia/Normal B cells |
| TJU_CMC.ID03499.3p-miR | 3.397485958 | 0.006456307 | Chronic Lymphocytic Leukemia/Normal B cells |
| TJU_CMC.ID08877.5p-miR | 4.015540666 | 5.83E−05 | PBMC Scleroderma Patients/PBMC Control Individuals |
| TJU_CMC.ID05581.5p-miR | 4.983456978 | 0.006763951 | Chronic Lymphocytic Leukemia/Normal B cells |
| TJU_CMC.ID06430.5p-miR | −3.425154896 | 0.006796496 | Chronic Lymphocytic Leukemia/Normal B cells |
| TJU_CMC.ID09687.3p-miR | −3.605372058 | 0.006791673 | Chronic Lymphocytic Leukemia/Normal B cells |
| TJU_CMC_MD2.ID02946.5p-miR | −4.006709967 | 0.00669263 | Chronic Lymphocytic Leukemia/Normal B cells |
| TJU_CMC.ID03249.5p-miR | 3.736002726 | 0.006864919 | Chronic Lymphocytic Leukemia/Normal B cells |
| TJU_CMC.ID03497.5p-miR | −2.826827067 | 0.006934821 | Chronic Lymphocytic Leukemia/Normal B cells |
| TJU_CMC.ID01429.5p-miR | 3.845168153 | 0.001272276 | Stage 1 Gastric Cancer/Normal Gastric Tissue |
| TJU_CMC.ID04813.5p-miR | −2.734683848 | 0.001279186 | Stage 1 Gastric Cancer/Normal Gastric Tissue |
| TJU_CMC.ID02519.3p-miR | 6.626008984 | 0.007071927 | Chronic Lymphocytic Leukemia/Normal B cells |
| TJU_CMC.ID07881.5p-miR | −4.645626441 | 0.007132922 | Chronic Lymphocytic Leukemia/Normal B cells |
| TJU_CMC.ID09682.5p-miR | −3.694229362 | 0.007468685 | Chronic Lymphocytic Leukemia/Normal B cells |
| TJU_CMC.ID00644.5p-miR | −3.975809646 | 0.007567406 | Chronic Lymphocytic Leukemia/Normal B cells |
| TJU_CMC.ID07033.5p-miR | 3.38977647 | 0.007574289 | Chronic Lymphocytic Leukemia/Normal B cells |
| TJU_CMC.ID09781.3p-miR | −3.952929903 | 0.007576322 | Chronic Lymphocytic Leukemia/Normal B cells |
| TJU_CMC.ID09464.5p-miR | −1.268418493 | 0.003556504 | PR− Breast Cancer/PR+ Breast Cancer (TCGA) |
| TJU_CMC.ID05902.3p-miR | 3.520306132 | 0.007741627 | Chronic Lymphocytic Leukemia/Normal B cells |
| TJU_CMC.ID00419.3p-miR | −3.22974304 | 0.00777046 | Chronic Lymphocytic Leukemia/Normal B cells |
| TJU_CMC.ID07864.5p-miR | −2.782784628 | 0.00145645 | Stage 1 Gastric Cancer/Normal Gastric Tissue |
| TJU_CMC.ID02392.3p-miR | −3.395999263 | 0.007852482 | Chronic Lymphocytic Leukemia/Normal B cells |
| TJU_CMC.ID08744.3p-miR | 3.823547998 | 0.007842493 | Chronic Lymphocytic Leukemia/Normal B cells |
| TJU_CMC_MD2.ID00802.5p-miR | −3.761374318 | 0.007825048 | Chronic Lymphocytic Leukemia/Normal B cells |
| TJU_CMC.ID05451.5p-miR | −3.601834058 | 0.007958604 | Chronic Lymphocytic Leukemia/Normal B cells |
| TJU_CMC.ID05889.3p-miR | 3.767260997 | 0.00794515 | Chronic Lymphocytic Leukemia/Normal B cells |
| TJU_CMC.ID07409.3p-miR | 3.713000924 | 0.007961062 | Chronic Lymphocytic Leukemia/Normal B cells |
| TJU_CMC.ID07851.5p-miR | −0.848685228 | 0.003847746 | PR− Breast Cancer/PR+ Breast Cancer (TCGA) |
| TJU_CMC.ID05259.5p-miR | 3.238887474 | 0.008207578 | Chronic Lymphocytic Leukemia/Normal B cells |
| TJU_CMC.ID08501.5p-miR | −3.68015595 | 0.008378015 | Chronic Lymphocytic Leukemia/Normal B cells |
| TJU_CMC.ID03695.5p-miR | −3.629989137 | 0.008416202 | Chronic Lymphocytic Leukemia/Normal B cells |
| TJU_CMC_MD2.ID01679.5p-miR | −2.72629129 | 0.001586112 | Stage 1 Gastric Cancer/Normal Gastric Tissue |
| TJU_CMC.ID04861.3p-miR | −3.49968115 | 0.008701215 | Chronic Lymphocytic Leukemia/Normal B cells |
| TJU_CMC.ID04105.5p-miR | 3.465260213 | 0.008745639 | Chronic Lymphocytic Leukemia/Normal B cells |
| TJU_CMC.ID01675.3p-miR | 3.424525025 | 0.008770798 | Chronic Lymphocytic Leukemia/Normal B cells |
| TJU_CMC.ID00858.5p-miR | −2.738680205 | 0.008834193 | Chronic Lymphocytic Leukemia/Normal B cells |
| TJU_CMC.ID00538.3p-miR | −3.58189314 | 0.008891839 | Chronic Lymphocytic Leukemia/Normal B cells |
| TJU_CMC.ID06335.5p-miR | −8.56605621 | 0.008900687 | Chronic Lymphocytic Leukemia/Normal B cells |
| TJU_CMC.ID09270.3p-miR | 3.076343437 | 0.001696361 | Stage 1 Gastric Cancer/Normal Gastric Tissue |
| TJU_CMC.ID01817.3p-miR | −5.905477213 | 0.009056318 | Chronic Lymphocytic Leukemia/Normal B cells |
| TJU_CMC.ID09441.5p-miR | −3.474391593 | 0.009067118 | Chronic Lymphocytic Leukemia/Normal B cells |
| TJU_CMC.ID03485.5p-miR | −3.449134377 | 0.009097675 | Chronic Lymphocytic Leukemia/Normal B cells |
| TJU_CMC.ID09034.5p-miR | 3.336180378 | 0.009309824 | Chronic Lymphocytic Leukemia/Normal B cells |
| TJU_CMC.ID06503.5p-miR | 3.649753645 | 0.009412983 | Chronic Lymphocytic Leukemia/Normal B cells |
| TJU_CMC.ID03683.3p-miR | −3.033501491 | 0.009501326 | Chronic Lymphocytic Leukemia/Normal B cells |
| TJU_CMC_MD2.ID02126.3p-miR | 1.329339479 | 0.004688008 | PR− Breast Cancer/PR+ Breast Cancer (TCGA) |
| TJU_CMC.ID04846.5p-miR | 2.507408703 | 0.009784292 | Chronic Lymphocytic Leukemia/Normal B cells |
| TJU_CMC.ID03615.3p-miR | 4.380853312 | 0.009830812 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID05919.3p-miR | 3.25341944 | 0.009927145 | Chronic Lymphocytic Leukemia/Normal B cells |
| TJU_CMC.ID05362.5p-miR | −3.481303728 | 0.010097837 | Chronic Lymphocytic Leukemia/Normal B cells |
| TJU_CMC.ID08830.3p-miR | 4.348247017 | 0.010090991 | Chronic Lymphocytic Leukemia/Normal B cells |
| TJU_CMC.ID06942.5p-miR | 4.752723586 | 0.010149942 | Chronic Lymphocytic Leukemia/Normal B cells |
| TJU_CMC.ID08906.5p-miR | −7.174478753 | 0.000452493 | MIA PaCa-2 cells/HPNE cells (Pancreas cell lines) |
| TJU_CMC.ID01532.5p-miR | −3.38421841 | 0.010349591 | Chronic Lymphocytic Leukemia/Normal B cells |
| TJU_CMC.ID00590.5p-miR | 2.594449484 | 0.01047864 | Chronic Lymphocytic Leukemia/Normal B cells |
| TJU_CMC.ID04494.5p-miR | −2.928055747 | 0.010485439 | Chronic Lymphocytic Leukemia/Normal B cells |
| TJU_CMC.ID02447.3p-miR | −3.049395422 | 0.002016216 | Stage 1 Gastric Cancer/Normal Gastric Tissue |
| TJU_CMC.ID03129.3p-miR | 3.721639697 | 0.001947997 | Stage 1 Gastric Cancer/Normal Gastric Tissue |
| TJU_CMC.ID04431.3p-miR | 2.421432866 | 0.001984674 | Stage 1 Gastric Cancer/Normal Gastric Tissue |
| TJU_CMC.ID01967.5p-miR | −4.82691252 | 0.010622482 | Chronic Lymphocytic Leukemia/Normal B cells |
| TJU_CMC.ID05791.3p-miR | 4.041554977 | 0.000123848 | PBMC Scleroderma Patients/PBMC Control Individuals |
| TJU_CMC.ID08760.5p-miR | 3.213735394 | 0.010692497 | Chronic Lymphocytic Leukemia/Normal B cells |
| TJU_CMC.ID07726.5p-miR | −3.275093222 | 0.01078539 | Chronic Lymphocytic Leukemia/Normal B cells |
| TJU_CMC.ID06201.5p-miR | 3.243655826 | 0.010829525 | Chronic Lymphocytic Leukemia/Normal B cells |
| TJU_CMC.ID08567.3p-miR | 3.441135965 | 0.010931409 | Chronic Lymphocytic Leukemia/Normal B cells |
| TJU_CMC.ID04355.3p-miR | −7.774051135 | 0.011020162 | Chronic Lymphocytic Leukemia/Normal B cells |
| TJU_CMC.ID04470.5p-miR | −999999 | 0.002097664 | Stage 1 Gastric Cancer/Normal Gastric Tissue |
| TJU_CMC.ID05510.3p-miR | 3.762851965 | 0.002131497 | Stage 1 Gastric Cancer/Normal Gastric Tissue |
| TJU_CMC.ID08188.3p-miR | 3.632361015 | 0.011095653 | Chronic Lymphocytic Leukemia/Normal B cells |
| TJU_CMC.ID05198.3p-miR | 3.606212091 | 0.011215348 | Chronic Lymphocytic Leukemia/Normal B cells |
| TJU_CMC.ID01964.3p-miR | 3.485799512 | 0.011320868 | Chronic Lymphocytic Leukemia/Normal B cells |
| TJU_CMC.ID01548.3p-miR | 4.06463058 | 0.00016661 | PBMC Scleroderma Patients/PBMC Control Individuals |
| TJU_CMC.ID02965.5p-miR | 4.073358618 | 0.000182467 | PBMC Scleroderma Patients/PBMC Control Individuals |
| TJU_CMC.ID04119.3p-miR | 6.354604426 | 0.000151789 | PBMC Scleroderma Patients/PBMC Control Individuals |
| TJU_CMC.ID06401.3p-miR | 2.937429039 | 0.011418415 | Chronic Lymphocytic Leukemia/Normal B cells |
| TJU_CMC.ID00897.3p-miR | 3.242235398 | 0.011701414 | Chronic Lymphocytic Leukemia/Normal B cells |
| TJU_CMC.ID04312.3p-miR | −2.839092601 | 0.002316521 | Stage 1 Gastric Cancer/Normal Gastric Tissue |
| TJU_CMC.ID00367.5p-miR | 3.612335212 | 0.012015975 | Chronic Lymphocytic Leukemia/Normal B cells |
| TJU_CMC.ID03089.5p-miR | 3.871229705 | 0.011982943 | Chronic Lymphocytic Leukemia/Normal B cells |
| TJU_CMC.ID06918.3p-miR | 3.277969503 | 0.012019111 | Chronic Lymphocytic Leukemia/Normal B cells |
| TJU_CMC.ID07026.3p-miR | 3.21069785 | 0.011993843 | Chronic Lymphocytic Leukemia/Normal B cells |
| TJU_CMC.ID08755.5p-miR | −3.474241921 | 0.012057449 | Chronic Lymphocytic Leukemia/Normal B cells |
| TJU_CMC.ID01584.3p-miR | 2.538363808 | 0.012227387 | Chronic Lymphocytic Leukemia/Normal B cells |
| TJU_CMC.ID06706.3p-miR | 3.229974177 | 0.012225456 | Chronic Lymphocytic Leukemia/Normal B cells |
| TJU_CMC_MD2.ID00546.5p-miR | −2.930199773 | 0.012196577 | Chronic Lymphocytic Leukemia/Normal B cells |
| TJU_CMC.ID03479.5p-miR | 5.138235153 | 0.012283946 | Chronic Lymphocytic Leukemia/Normal B cells |
| TJU_CMC.ID05652.3p-miR | −3.801193157 | 0.012410555 | Chronic Lymphocytic Leukemia/Normal B cells |
| TJU_CMC.ID04133.5p-miR | −1.395446103 | 0.006247856 | PR− Breast Cancer/PR+ Breast Cancer (TCGA) |
| TJU_CMC.ID02661.3p-miR | −3.416158149 | 0.012498757 | Chronic Lymphocytic Leukemia/Normal B cells |
| TJU_CMC.ID07851.5p-miR | −0.746966944 | 0.008090463 | ER− Breast Cancer/ER+ Breast Cancer (TCGA) |
| TJU_CMC.ID08923.3p-miR | −3.354714759 | 0.012687656 | Chronic Lymphocytic Leukemia/Normal B cells |
| TJU_CMC.ID00084.5p-miR | 3.251317323 | 0.002568033 | Stage 1 Gastric Cancer/Normal Gastric Tissue |
| TJU_CMC.ID00409.5p-miR | −2.355643659 | 0.002594432 | Stage 1 Gastric Cancer/Normal Gastric Tissue |
| TJU_CMC.ID02895.5p-miR | 3.067023182 | 0.002518555 | Stage 1 Gastric Cancer/Normal Gastric Tissue |
| TJU_CMC.ID03038.3p-miR | −2.406007669 | 0.002497207 | Stage 1 Gastric Cancer/Normal Gastric Tissue |
| TJU_CMC.ID06178.3p-miR | 3.30228222 | 0.012921953 | Chronic Lymphocytic Leukemia/Normal B cells |
| TJU_CMC.ID00712.3p-miR | −2.583984196 | 0.002706236 | Stage 1 Gastric Cancer/Normal Gastric Tissue |
| TJU_CMC.ID00535.5p-miR | 3.272381812 | 0.013317849 | Chronic Lymphocytic Leukemia/Normal B cells |
| TJU_CMC.ID02225.3p-miR | 3.135280669 | 0.013300742 | Chronic Lymphocytic Leukemia/Normal B cells |
| TJU_CMC_MD2.ID02802.3p-miR | −3.361521606 | 0.013277157 | Chronic Lymphocytic Leukemia/Normal B cells |
| TJU_CMC_MD2.ID03407.3p-miR | 5.253149789 | 0.01340197 | Chronic Lymphocytic Leukemia/Normal B cells |
| TJU_CMC.ID06787.5p-miR | 3.365836898 | 0.013537796 | Chronic Lymphocytic Leukemia/Normal B cells |
| TJU_CMC.ID09586.3p-miR | −4.303430541 | 0.013592915 | Chronic Lymphocytic Leukemia/Normal B cells |
| TJU_CMC.ID07029.5p-miR | 2.549642485 | 0.013794616 | Chronic Lymphocytic Leukemia/Normal B cells |
| TJU_CMC.ID03316.5p-miR | −5.594060316 | 0.014229027 | Chronic Lymphocytic Leukemia/Normal B cells |
| TJU_CMC.ID07174.5p-miR | 3.108044351 | 0.014262938 | Chronic Lymphocytic Leukemia/Normal B cells |
| TJU_CMC.ID01826.5p-miR | 4.009674068 | 0.014512746 | Chronic Lymphocytic Leukemia/Normal B cells |
| TJU_CMC.ID03381.5p-miR | −2.022944804 | 0.014523235 | Chronic Lymphocytic Leukemia/Normal B cells |
| TJU_CMC.ID04092.3p-miR | −3.067669024 | 0.014458501 | Chronic Lymphocytic Leukemia/Normal B cells |
| TJU_CMC.ID06103.3p-miR | −3.017564221 | 0.014477798 | Chronic Lymphocytic Leukemia/Normal B cells |
| TJU_CMC.ID09253.3p-miR | −5.174658694 | 0.014509172 | Chronic Lymphocytic Leukemia/Normal B cells |
| TJU_CMC.ID06029.5p-miR | 2.146941799 | 0.002907061 | Stage 1 Gastric Cancer/Normal Gastric Tissue |
| TJU_CMC.ID01099.3p-miR | −2.904791212 | 0.002996927 | Stage 1 Gastric Cancer/Normal Gastric Tissue |
| TJU_CMC.ID03444.5p-miR | 2.306240096 | 0.003077447 | Stage 1 Gastric Cancer/Normal Gastric Tissue |
| TJU_CMC.ID08716.5p-miR | 2.830640101 | 0.003016562 | Stage 1 Gastric Cancer/Normal Gastric Tissue |
| TJU_CMC.ID06167.3p-miR | 5.117000177 | 0.014670432 | Chronic Lymphocytic Leukemia/Normal B cells |
| TJU_CMC.ID03541.5p-miR | 3.480171069 | 0.014845228 | Chronic Lymphocytic Leukemia/Normal B cells |
| TJU_CMC.ID09776.5p-miR | 2.605647153 | 0.015609005 | Breast Cancer (adenoid/apocrine/atypical/DCIS/IDC/metaplastic)/Normal Breast Tissue (GEO: GSE28884) |
| TJU_CMC_MD2.ID00492.5p-miR | −1.885086231 | 0.007448445 | PR− Breast Cancer/PR+ Breast Cancer (TCGA) |
| TJU_CMC.ID06948.3p-miR | 3.09443663 | 0.014984398 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
| --- | --- | --- | --- |
| TJU_CMC.ID06610.5p-miR | 2.508138788 | 0.003182417 | Stage 1 Gastric Cancer/Normal Gastric Tissue |
| TJU_CMC.ID02254.5p-miR | 1.037361726 | 0.00965459 | ER− Breast Cancer/ER+ Breast Cancer (TCGA) |
| TJU_CMC.ID04304.5p-miR | −3.034487907 | 0.015176374 | Chronic Lymphocytic Leukemia/Normal B cells |
| TJU_CMC.ID05336.5p-miR | −3.326587969 | 0.015295193 | Chronic Lymphocytic Leukemia/Normal B cells |
| TJU_CMC.ID06510.3p-miR | −2.961506778 | 0.015296259 | Chronic Lymphocytic Leukemia/Normal B cells |
| TJU_CMC.ID03515.3p-miR | 3.113144145 | 0.015407568 | Chronic Lymphocytic Leukemia/Normal B cells |
| TJU_CMC.ID08821.5p-miR | −8.212551762 | 0.015353105 | Chronic Lymphocytic Leukemia/Normal B cells |
| TJU_CMC.ID09722.3p-miR | −1.147397694 | 0.007755472 | PR− Breast Cancer/PR+ Breast Cancer (TCGA) |
| TJU_CMC.ID07521.3p-miR | 4.000690248 | 0.015505981 | Chronic Lymphocytic Leukemia/Normal B cells |
| TJU_CMC.ID04182.3p-miR | −9.074339415 | 0.015816824 | Chronic Lymphocytic Leukemia/Normal B cells |
| TJU_CMC_MD2.ID00706.5p-miR | −2.872784647 | 0.015913657 | Chronic Lymphocytic Leukemia/Normal B cells |
| TJU_CMC.ID06339.3p-miR | 2.569368917 | 0.003366898 | Stage 1 Gastric Cancer/Normal Gastric Tissue |
| TJU_CMC.ID02375.5p-miR | −3.243638159 | 0.01623186 | Chronic Lymphocytic Leukemia/Normal B cells |
| TJU_CMC.ID04862.5p-miR | 4.27159012 | 0.016239499 | Chronic Lymphocytic Leukemia/Normal B cells |
| TJU_CMC.ID08840.3p-miR | −2.941710453 | 0.016148847 | Chronic Lymphocytic Leukemia/Normal B cells |
| TJU_CMC.ID00700.3p-miR | 2.896017129 | 0.003539638 | Stage 1 Gastric Cancer/Normal Gastric Tissue |
| TJU_CMC.ID08202.5p-miR | 3.891607394 | 0.003500977 | Stage 1 Gastric Cancer/Normal Gastric Tissue |
| TJU_CMC.ID07681.3p-miR | −2.781127573 | 0.016574899 | Chronic Lymphocytic Leukemia/Normal B cells |
| TJU_CMC.ID04643.5p-miR | −2.685076893 | 0.016782143 | Chronic Lymphocytic Leukemia/Normal B cells |
| TJU_CMC.ID02023.5p-miR | 2.749119483 | 0.016983926 | Chronic Lymphocytic Leukemia/Normal B cells |
| TJU_CMC.ID05546.5p-miR | 2.084155351 | 0.003652502 | Stage 1 Gastric Cancer/Normal Gastric Tissue |
| TJU_CMC.ID08362.3p-miR | 2.968005513 | 0.003638234 | Stage 1 Gastric Cancer/Normal Gastric Tissue |
| TJU_CMC.ID07568.5p-miR | 7.428627427 | 0.017073055 | Chronic Lymphocytic Leukemia/Normal B cells |
| TJU_CMC.ID03979.5p-miR | 4.67551264 | 0.017159213 | Chronic Lymphocytic Leukemia/Normal B cells |
| TJU_CMC.ID01151.5p-miR | −3.312262041 | 0.017458394 | Chronic Lymphocytic Leukemia/Normal B cells |
| TJU_CMC.ID03087.3p-miR | 3.038386397 | 0.017407724 | Chronic Lymphocytic Leukemia/Normal B cells |
| TJU_CMC_MD2.ID02715.3p-miR | −3.116026893 | 0.017439889 | Chronic Lymphocytic Leukemia/Normal B cells |
| TJU_CMC.ID01679.3p-miR | −999999 | 0.017623252 | Chronic Lymphocytic Leukemia/Normal B cells |
| TJU_CMC.ID03599.5p-miR | 4.282056224 | 0.017639021 | Chronic Lymphocytic Leukemia/Normal B cells |
| TJU_CMC.ID05141.5p-miR | −2.784882252 | 0.017823221 | Chronic Lymphocytic Leukemia/Normal B cells |
| TJU_CMC.ID06381.5p-miR | −3.383671724 | 0.017801519 | Chronic Lymphocytic Leukemia/Normal B cells |
| TJU_CMC.ID09346.3p-miR | 2.281824718 | 0.01784029 | Chronic Lymphocytic Leukemia/Normal B cells |
| TJU_CMC.ID09080.5p-miR | 3.045680239 | 0.017987293 | Chronic Lymphocytic Leukemia/Normal B cells |
| TJU_CMC.ID01924.5p-miR | 2.622848898 | 0.018307235 | Chronic Lymphocytic Leukemia/Normal B cells |
| TJU_CMC.ID07390.3p-miR | 7.011168408 | 0.018332359 | Chronic Lymphocytic Leukemia/Normal B cells |
| TJU_CMC_MD2.ID02858.3p-miR | −5.832375062 | 0.018415983 | Chronic Lymphocytic Leukemia/Normal B cells |
| TJU_CMC.ID00528.5p-miR | 5.787064141 | 0.01858266 | Chronic Lymphocytic Leukemia/Normal B cells |
| TJU_CMC.ID04082.3p-miR | −2.426940063 | 0.003982178 | Stage 1 Gastric Cancer/Normal Gastric Tissue |
| TJU_CMC.ID04444.3p-miR | 2.741083034 | 0.003953415 | Stage 1 Gastric Cancer/Normal Gastric Tissue |
| TJU_CMC.ID08750.3p-miR | −2.862400301 | 0.00393965 | Stage 1 Gastric Cancer/Normal Gastric Tissue |
| TJU_CMC.ID00637.3p-miR | 6.058184025 | 0.018701103 | Chronic Lymphocytic Leukemia/Normal B cells |
| TJU_CMC.ID02676.5p-miR | −3.39730811 | 0.018730489 | Chronic Lymphocytic Leukemia/Normal B cells |
| TJU_CMC.ID08828.3p-miR | 3.001424354 | 0.018742632 | Chronic Lymphocytic Leukemia/Normal B cells |
| TJU_CMC.ID00970.5p-miR | −4.896585032 | 0.018951843 | Chronic Lymphocytic Leukemia/Normal B cells |
| TJU_CMC.ID05223.5p-miR | 4.613596249 | 0.01898245 | Chronic Lymphocytic Leukemia/Normal B cells |
| TJU_CMC.ID06204.3p-miR | −3.292787893 | 0.01918446 | Chronic Lymphocytic Leukemia/Normal B cells |
| TJU_CMC.ID01953.5p-miR | 6.457921839 | 0.004130506 | Stage 1 Gastric Cancer/Normal Gastric Tissue |
| TJU_CMC.ID08158.3p-miR | 2.719385226 | 0.019780941 | Chronic Lymphocytic Leukemia/Normal B cells |
| TJU_CMC.ID00536.3p-miR | 5.690336637 | 0.019835689 | Chronic Lymphocytic Leukemia/Normal B cells |
| TJU_CMC.ID00672.3p-miR | 3.128585419 | 0.019904416 | Chronic Lymphocytic Leukemia/Normal B cells |
| TJU_CMC.ID00847.3p-miR | 2.327739347 | 0.020065155 | Chronic Lymphocytic Leukemia/Normal B cells |
| TJU_CMC.ID02654.3p-miR | 3.030401524 | 0.020072372 | Chronic Lymphocytic Leukemia/Normal B cells |
| TJU_CMC.ID04467.5p-miR | 3.051362959 | 0.020037318 | Chronic Lymphocytic Leukemia/Normal B cells |
| TJU_CMC.ID07647.3p-miR | −3.261142395 | 0.019998013 | Chronic Lymphocytic Leukemia/Normal B cells |
| TJU_CMC.ID02635.5p-miR | −3.168203988 | 0.020258028 | Chronic Lymphocytic Leukemia/Normal B cells |
| TJU_CMC.ID00862.5p-miR | 2.666454872 | 0.020028583 | Chronic Lymphocytic Leukemia/Normal B cells |
| TJU_CMC.ID06821.5p-miR | −3.105629789 | 0.004269169 | Stage 1 Gastric Cancer/Normal Gastric Tissue |
| TJU_CMC.ID04958.5p-miR | 2.674148083 | 0.020416847 | Chronic Lymphocytic Leukemia/Normal B cells |
| TJU_CMC.ID09041.3p-miR | −6.077795644 | 0.020488339 | Chronic Lymphocytic Leukemia/Normal B cells |
| TJU_CMC.ID07842.5p-miR | 3.255613703 | 0.020621318 | Chronic Lymphocytic Leukemia/Normal B cells |
| TJU_CMC.ID04877.3p-miR | 3.545625034 | 0.020689356 | Chronic Lymphocytic Leukemia/Normal B cells |
| TJU_CMC.ID00795.3p-miR | 2.69704536 | 0.020894454 | Chronic Lymphocytic Leukemia/Normal B cells |
| TJU_CMC.ID08067.3p-miR | −4.163384881 | 0.021285039 | Chronic Lymphocytic Leukemia/Normal B cells |
| TJU_CMC.ID08640.5p-miR | −3.078424476 | 0.021476099 | Chronic Lymphocytic Leukemia/Normal B cells |
| TJU_CMC.ID04299.5p-miR | 2.245847544 | 0.00463289 | Stage 1 Gastric Cancer/Normal Gastric Tissue |
| TJU_CMC.ID04613.3p-miR | 8.376174999 | 0.004594609 | Stage 1 Gastric Cancer/Normal Gastric Tissue |
| TJU_CMC.ID08197.5p-miR | −2.37595939 | 0.004608642 | Stage 1 Gastric Cancer/Normal Gastric Tissue |
| TJU_CMC.ID03014.5p-miR | −3.72049997 | 0.021530771 | Chronic Lymphocytic Leukemia/Normal B cells |
| TJU_CMC.ID01698.5p-miR | −3.897128686 | 0.02165587 | Chronic Lymphocytic Leukemia/Normal B cells |
| TJU_CMC.ID00325.3p-miR | −4.298352365 | 0.021716858 | Chronic Lymphocytic Leukemia/Normal B cells |
| TJU_CMC.ID09179.3p-miR | 3.499124516 | 0.021737413 | Chronic Lymphocytic Leukemia/Normal B cells |
| TJU_CMC.ID05532.5p-miR | −2.800723762 | 0.021866388 | Chronic Lymphocytic Leukemia/Normal B cells |
| TJU_CMC.ID06173.5p-miR | −4.142784796 | 0.021812138 | Chronic Lymphocytic Leukemia/Normal B cells |
| TJU_CMC_MD2.ID02550.3p-miR | 2.839572543 | 0.021923458 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID04190.5p-miR | 4.887393981 | 0.00035747 | PBMC Scleroderma Patients/PBMC Control Individuals |
| TJU_CMC.ID09189.5p-miR | 4.448951859 | 0.022140339 | Chronic Lymphocytic Leukemia/Normal B cells |
| TJU_CMC.ID03233.3p-miR | 2.886399829 | 0.022207984 | Chronic Lymphocytic Leukemia/Normal B cells |
| TJU_CMC.ID01091.3p-miR | 2.682059506 | 0.022422522 | Chronic Lymphocytic Leukemia/Normal B cells |
| TJU_CMC.ID04249.3p-miR | −2.851528998 | 0.022519412 | Chronic Lymphocytic Leukemia/Normal B cells |
| TJU_CMC_MD2.ID02486.3p-miR | 3.565057498 | 0.022456975 | Chronic Lymphocytic Leukemia/Normal B cells |
| TJU_CMC.ID01877.3p-miR | 3.408842979 | 0.022778055 | Chronic Lymphocytic Leukemia/Normal B cells |
| TJU_CMC.ID04106.3p-miR | 2.679758478 | 0.022818898 | Chronic Lymphocytic Leukemia/Normal B cells |
| TJU_CMC.ID00938.5p-miR | −2.537156423 | 0.004921329 | Stage 1 Gastric Cancer/Normal Gastric Tissue |
| TJU_CMC.ID02270.5p-miR | 2.5676745 | 0.023088502 | Chronic Lymphocytic Leukemia/Normal B cells |
| TJU_CMC.ID01138.5p-miR | 2.626576454 | 0.023250686 | Chronic Lymphocytic Leukemia/Normal B cells |
| TJU_CMC.ID05537.5p-miR | −2.279834527 | 0.023422243 | Chronic Lymphocytic Leukemia/Normal B cells |
| TJU_CMC.ID05200.5p-miR | −8.02556359 | 0.00110676 | MIA PaCa-2 cells/HPNE cells (Pancreas cell lines) |
| TJU_CMC.ID01023.5p-miR | 2.395829761 | 0.0050136 | Stage 1 Gastric Cancer/Normal Gastric Tissue |
| TJU_CMC.ID00746.5p-miR | 5.09545691 | 0.023619774 | Chronic Lymphocytic Leukemia/Normal B cells |
| TJU_CMC.ID05806.3p-miR | 2.713678593 | 0.023613813 | Chronic Lymphocytic Leukemia/Normal B cells |
| TJU_CMC_MD2.ID00244.3p-miR | −2.949064286 | 0.023785381 | Chronic Lymphocytic Leukemia/Normal B cells |
| TJU_CMC.ID05479.3p-miR | −2.923242703 | 0.023892528 | Chronic Lymphocytic Leukemia/Normal B cells |
| TJU_CMC.ID01506.3p-miR | −5.501488348 | 0.024039293 | Chronic Lymphocytic Leukemia/Normal B cells |
| TJU_CMC.ID03855.5p-miR | −3.324653343 | 0.024115172 | Chronic Lymphocytic Leukemia/Normal B cells |
| TJU_CMC.ID04136.5p-miR | 2.963836967 | 0.024002725 | Chronic Lymphocytic Leukemia/Normal B cells |
| TJU_CMC.ID06295.3p-miR | −2.621546871 | 0.024139807 | Chronic Lymphocytic Leukemia/Normal B cells |
| TJU_CMC.ID04598.3p-miR | 3.070250447 | 0.024244748 | Chronic Lymphocytic Leukemia/Normal B cells |
| TJU_CMC.ID07317.3p-miR | 5.409734034 | 0.024418766 | Chronic Lymphocytic Leukemia/Normal B cells |
| TJU_CMC.ID00600.3p-miR | −2.957496647 | 0.024937555 | Chronic Lymphocytic Leukemia/Normal B cells |
| TJU_CMC.ID07021.5p-miR | −3.006798222 | 0.024888573 | Chronic Lymphocytic Leukemia/Normal B cells |
| TJU_CMC.ID07249.3p-miR | −2.309085736 | 0.024894649 | Chronic Lymphocytic Leukemia/Normal B cells |
| TJU_CMC.ID08808.5p-miR | −2.876100294 | 0.024654888 | Chronic Lymphocytic Leukemia/Normal B cells |
| TJU_CMC_MD2.ID02793.3p-miR | −2.744299539 | 0.024676699 | Chronic Lymphocytic Leukemia/Normal B cells |
| TJU_CMC.ID03724.3p-miR | 3.168829498 | 0.025598591 | Chronic Lymphocytic Leukemia/Normal B cells |
| TJU_CMC.ID08577.5p-miR | 2.728949814 | 0.025625947 | Chronic Lymphocytic Leukemia/Normal B cells |
| TJU_CMC.ID02213.5p-miR | 4.034035398 | 0.000431332 | PBMC Scleroderma Patients/PBMC Control Individuals |
| TJU_CMC.ID03948.5p-miR | 4.031522549 | 0.00051144 | PBMC Scleroderma Patients/PBMC Control Individuals |
| TJU_CMC.ID05204.5p-miR | 3.534617933 | 0.000461617 | PBMC Scleroderma Patients/PBMC Control Individuals |
| TJU_CMC.ID00474.5p-miR | −3.273098191 | 0.005235566 | Stage 1 Gastric Cancer/Normal Gastric Tissue |
| TJU_CMC.ID03053.3p-miR | 2.264928957 | 0.005317008 | Stage 1 Gastric Cancer/Normal Gastric Tissue |
| TJU_CMC_MD2.ID00590.5p-miR | 3.198726848 | 0.026219482 | Chronic Lymphocytic Leukemia/Normal B cells |
| TJU_CMC.ID03671.3p-miR | 3.335933612 | 0.026339 | Chronic Lymphocytic Leukemia/Normal B cells |
| TJU_CMC.ID01287.3p-miR | 3.090214346 | 0.026553324 | Chronic Lymphocytic Leukemia/Normal B cells |
| TJU_CMC.ID05125.3p-miR | −2.981887028 | 0.026892611 | Chronic Lymphocytic Leukemia/Normal B cells |
| TJU_CMC.ID05191.3p-miR | 2.703208548 | 0.026757187 | Chronic Lymphocytic Leukemia/Normal B cells |
| TJU_CMC_MD2.ID02043.3p-miR | −3.328877283 | 0.026694567 | Chronic Lymphocytic Leukemia/Normal B cells |
| TJU_CMC.ID09116.3p-miR | 2.234253027 | 0.005488804 | Stage 1 Gastric Cancer/Normal Gastric Tissue |
| TJU_CMC.ID05745.5p-miR | 2.793252473 | 0.027209357 | Chronic Lymphocytic Leukemia/Normal B cells |
| TJU_CMC.ID07158.5p-miR | 2.770719295 | 0.027289652 | Chronic Lymphocytic Leukemia/Normal B cells |
| TJU_CMC.ID05776.5p-miR | 2.580231001 | 0.027373375 | Chronic Lymphocytic Leukemia/Normal B cells |
| TJU_CMC.ID04424.5p-miR | 2.049503056 | 0.005607578 | Stage 1 Gastric Cancer/Normal Gastric Tissue |
| TJU_CMC.ID00117.3p-miR | −2.413142856 | 0.005761416 | Stage 1 Gastric Cancer/Normal Gastric Tissue |
| TJU_CMC.ID05823.5p-miR | 4.392611417 | 0.005676082 | Stage 1 Gastric Cancer/Normal Gastric Tissue |
| TJU_CMC.ID03197.3p-miR | 2.924645557 | 0.028182015 | Chronic Lymphocytic Leukemia/Normal B cells |
| TJU_CMC.ID06019.5p-miR | 4.516508691 | 0.000563694 | PBMC Scleroderma Patients/PBMC Control Individuals |
| TJU_CMC_MD2.ID01945.3p-miR | 3.43074861 | 0.028395532 | Chronic Lymphocytic Leukemia/Normal B cells |
| TJU_CMC.ID01483.3p-miR | −4.25712926 | 0.006193215 | Stage 1 Gastric Cancer/Normal Gastric Tissue |
| TJU_CMC.ID06205.3p-miR | −2.958120365 | 0.006137108 | Stage 1 Gastric Cancer/Normal Gastric Tissue |
| TJU_CMC.ID06799.5p-miR | 2.472851563 | 0.028500375 | Chronic Lymphocytic Leukemia/Normal B cells |
| TJU_CMC.ID02016.5p-miR | 3.069788723 | 0.028705269 | Chronic Lymphocytic Leukemia/Normal B cells |
| TJU_CMC.ID02385.3p-miR | 2.522779608 | 0.028683259 | Chronic Lymphocytic Leukemia/Normal B cells |
| TJU_CMC_MD2.ID02695.3p-miR | −5.511362209 | 0.028676056 | Chronic Lymphocytic Leukemia/Normal B cells |
| TJU_CMC.ID00208.3p-miR | 5.264354571 | 0.028857486 | Chronic Lymphocytic Leukemia/Normal B cells |
| TJU_CMC.ID02153.5p-miR | 2.612771596 | 0.029056618 | Chronic Lymphocytic Leukemia/Normal B cells |
| TJU_CMC.ID00531.3p-miR | −2.927976732 | 0.029162333 | Chronic Lymphocytic Leukemia/Normal B cells |
| TJU_CMC.ID04567.3p-miR | 2.430514625 | 0.029164041 | Chronic Lymphocytic Leukemia/Normal B cells |
| TJU_CMC.ID09154.3p-miR | −2.352812441 | 0.029226599 | Chronic Lymphocytic Leukemia/Normal B cells |
| TJU_CMC.ID08726.5p-miR | 2.589983043 | 0.006329591 | Stage 1 Gastric Cancer/Normal Gastric Tissue |
| TJU_CMC.ID00594.3p-miR | 2.698714332 | 0.029666266 | Chronic Lymphocytic Leukemia/Normal B cells |
| TJU_CMC.ID07185.5p-miR | −2.643656815 | 0.029712357 | Chronic Lymphocytic Leukemia/Normal B cells |
| TJU_CMC.ID07652.3p-miR | 2.472825117 | 0.030047125 | Chronic Lymphocytic Leukemia/Normal B cells |
| TJU_CMC.ID02595.3p-miR | −5.860895396 | 0.030268541 | Chronic Lymphocytic Leukemia/Normal B cells |
| TJU_CMC.ID06528.3p-miR | −3.065102364 | 0.030623702 | Chronic Lymphocytic Leukemia/Normal B cells |
| TJU_CMC.ID06108.3p-miR | 2.627764154 | 0.030913846 | Chronic Lymphocytic Leukemia/Normal B cells |
| TJU_CMC.ID09057.5p-miR | 2.493058232 | 0.031093477 | Chronic Lymphocytic Leukemia/Normal B cells |
| TJU_CMC.ID05094.3p-miR | 3.981816007 | 0.031258199 | Chronic Lymphocytic Leukemia/Normal B cells |
| TJU_CMC.ID07930.3p-miR | 2.791865669 | 0.031218091 | Chronic Lymphocytic Leukemia/Normal B cells |
| TJU_CMC.ID07725.3p-miR | 3.11140989 | 0.03151947 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
| --- | --- | --- | --- |
| TJU_CMC.ID01609.3p-miR | 3.034109734 | 0.031724563 | Chronic Lymphocytic Leukemia/Normal B cells |
| TJU_CMC.ID07454.3p-miR | 2.767698905 | 0.031834835 | Chronic Lymphocytic Leukemia/Normal B cells |
| TJU_CMC.ID01683.5p-miR | 2.783748545 | 0.03213857 | Chronic Lymphocytic Leukemia/Normal B cells |
| TJU_CMC.ID02746.3p-miR | 2.740860826 | 0.032318065 | Chronic Lymphocytic Leukemia/Normal B cells |
| TJU_CMC.ID05663.3p-miR | −2.606628114 | 0.032312028 | Chronic Lymphocytic Leukemia/Normal B cells |
| TJU_CMC.ID08849.3p-miR | 2.428322284 | 0.032381642 | Chronic Lymphocytic Leukemia/Normal B cells |
| TJU_CMC.ID03819.3p-miR | −2.959305937 | 0.032487237 | Chronic Lymphocytic Leukemia/Normal B cells |
| TJU_CMC.ID05844.3p-miR | −2.901395389 | 0.032863215 | Chronic Lymphocytic Leukemia/Normal B cells |
| TJU_CMC.ID00123.5p-miR | −2.589222168 | 0.03303298 | Chronic Lymphocytic Leukemia/Normal B cells |
| TJU_CMC.ID05538.5p-miR | −3.518323724 | 0.033311984 | Chronic Lymphocytic Leukemia/Normal B cells |
| TJU_CMC_MD2.ID01155.5p-miR | −4.328614352 | 0.033315366 | Chronic Lymphocytic Leukemia/Normal B cells |
| TJU_CMC.ID05868.3p-miR | 2.381088277 | 0.006854152 | Stage 1 Gastric Cancer/Normal Gastric Tissue |
| TJU_CMC.ID04089.5p-miR | −6.938537055 | 0.033396886 | Chronic Lymphocytic Leukemia/Normal B cells |
| TJU_CMC.ID00604.5p-miR | −2.183178506 | 0.006979761 | Stage 1 Gastric Cancer/Normal Gastric Tissue |
| TJU_CMC.ID05105.3p-miR | −3.748274568 | 0.033879031 | Chronic Lymphocytic Leukemia/Normal B cells |
| TJU_CMC.ID07218.3p-miR | −2.845161695 | 0.03388715 | Chronic Lymphocytic Leukemia/Normal B cells |
| TJU_CMC.ID05399.3p-miR | −5.443303801 | 0.034175132 | Chronic Lymphocytic Leukemia/Normal B cells |
| TJU_CMC_MD2.ID02704.3p-miR | −2.863958791 | 0.034174026 | Chronic Lymphocytic Leukemia/Normal B cells |
| TJU_CMC.ID04691.5p-miR | −2.373867578 | 0.007247164 | Stage 1 Gastric Cancer/Normal Gastric Tissue |
| TJU_CMC.ID08017.3p-miR | −1.960032406 | 0.007208365 | Stage 1 Gastric Cancer/Normal Gastric Tissue |
| TJU_CMC.ID08439.5p-miR | 2.619626927 | 0.028759019 | Breast Cancer (adenoid/apocrine/atypical/DCIS/IDC/metaplastic)/Normal Breast Tissue (GEO: GSE28884) |
| TJU_CMC.ID06040.5p-miR | −2.950733453 | 0.034656982 | Chronic Lymphocytic Leukemia/Normal B cells |
| TJU_CMC.ID06732.5p-miR | −8.486934482 | 0.034845755 | Chronic Lymphocytic Leukemia/Normal B cells |
| TJU_CMC_MD2.ID00235.5p-miR | 2.758952353 | 0.035035243 | Chronic Lymphocytic Leukemia/Normal B cells |
| TJU_CMC.ID01649.3p-miR | 2.2909278 | 0.035157649 | Chronic Lymphocytic Leukemia/Normal B cells |
| TJU_CMC.ID05869.3p-miR | 2.48044966 | 0.035575191 | Chronic Lymphocytic Leukemia/Normal B cells |
| TJU_CMC.ID08031.5p-miR | −3.266960297 | 0.035568557 | Chronic Lymphocytic Leukemia/Normal B cells |
| TJU_CMC.ID09363.5p-miR | 2.109515609 | 0.035580324 | Chronic Lymphocytic Leukemia/Normal B cells |
| TJU_CMC_MD2.ID00891.5p-miR | −3.542326164 | 0.035508611 | Chronic Lymphocytic Leukemia/Normal B cells |
| TJU_CMC.ID00512.3p-miR | −1.585565585 | 0.035922998 | Chronic Lymphocytic Leukemia/Normal B cells |
| TJU_CMC.ID02417.5p-miR | 3.252147992 | 0.03593434 | Chronic Lymphocytic Leukemia/Normal B cells |
| TJU_CMC.ID03110.3p-miR | 3.456131986 | 0.03585254 | Chronic Lymphocytic Leukemia/Normal B cells |
| TJU_CMC.ID09474.5p-miR | −2.926892522 | 0.035840209 | Chronic Lymphocytic Leukemia/Normal B cells |
| TJU_CMC.ID00167.5p-miR | 2.265225917 | 0.036221926 | Chronic Lymphocytic Leukemia/Normal B cells |
| TJU_CMC.ID00269.3p-miR | 3.553813176 | 0.00797452 | Stage 1 Gastric Cancer/Normal Gastric Tissue |
| TJU_CMC.ID01470.5p-miR | −2.412404392 | 0.007746582 | Stage 1 Gastric Cancer/Normal Gastric Tissue |
| TJU_CMC.ID01900.5p-miR | 2.062213287 | 0.007966914 | Stage 1 Gastric Cancer/Normal Gastric Tissue |
| TJU_CMC.ID01910.3p-miR | −2.876806803 | 0.00788604 | Stage 1 Gastric Cancer/Normal Gastric Tissue |
| TJU_CMC.ID02820.5p-miR | 2.137825806 | 0.007948537 | Stage 1 Gastric Cancer/Normal Gastric Tissue |
| TJU_CMC.ID06804.5p-miR | 2.759182496 | 0.007867192 | Stage 1 Gastric Cancer/Normal Gastric Tissue |
| TJU_CMC.ID07941.3p-miR | 3.564568697 | 0.007923931 | Stage 1 Gastric Cancer/Normal Gastric Tissue |
| TJU_CMC.ID08188.3p-miR | −4.859953321 | 0.00780588 | Stage 1 Gastric Cancer/Normal Gastric Tissue |
| TJU_CMC.ID09566.3p-miR | −2.499761469 | 0.007670309 | Stage 1 Gastric Cancer/Normal Gastric Tissue |
| TJU_CMC.ID03020.5p-miR | −2.513997914 | 0.036537429 | Chronic Lymphocytic Leukemia/Normal B cells |
| TJU_CMC.ID02644.5p-miR | 2.924896392 | 0.036574534 | Chronic Lymphocytic Leukemia/Normal B cells |
| TJU_CMC.ID00853.3p-miR | 2.548731231 | 0.008132425 | Stage 1 Gastric Cancer/Normal Gastric Tissue |
| TJU_CMC.ID04896.3p-miR | −2.356304907 | 0.008138933 | Stage 1 Gastric Cancer/Normal Gastric Tissue |
| TJU_CMC.ID04233.3p-miR | 3.02093281 | 0.03676 | Chronic Lymphocytic Leukemia/Normal B cells |
| TJU_CMC.ID00467.3p-miR | 2.471447378 | 0.036877618 | Chronic Lymphocytic Leukemia/Normal B cells |
| TJU_CMC.ID02097.3p-miR | 3.427980707 | 0.008361803 | Stage 1 Gastric Cancer/Normal Gastric Tissue |
| TJU_CMC.ID05571.3p-miR | 2.5736205 | 0.008436838 | Stage 1 Gastric Cancer/Normal Gastric Tissue |
| TJU_CMC.ID09348.3p-miR | −2.540339155 | 0.008667802 | Stage 1 Gastric Cancer/Normal Gastric Tissue |
| TJU_CMC.ID08204.3p-miR | 2.473750463 | 0.038189412 | Chronic Lymphocytic Leukemia/Normal B cells |
| TJU_CMC.ID08793.5p-miR | −2.611932298 | 0.008750634 | Stage 1 Gastric Cancer/Normal Gastric Tissue |
| TJU_CMC.ID01742.3p-miR | −2.456680699 | 0.038466617 | Chronic Lymphocytic Leukemia/Normal B cells |
| TJU_CMC.ID04356.5p-miR | −4.540040887 | 0.03841956 | Chronic Lymphocytic Leukemia/Normal B cells |
| TJU_CMC.ID01789.5p-miR | −1.905920815 | 0.008923227 | Stage 1 Gastric Cancer/Normal Gastric Tissue |
| TJU_CMC.ID04702.3p-miR | 2.428493724 | 0.009016307 | Stage 1 Gastric Cancer/Normal Gastric Tissue |
| TJU_CMC.ID08714.3p-miR | 2.357174319 | 0.008975537 | Stage 1 Gastric Cancer/Normal Gastric Tissue |
| TJU_CMC.ID06000.3p-miR | 2.829086018 | 0.038796939 | Chronic Lymphocytic Leukemia/Normal B cells |
| TJU_CMC.ID03049.3p-miR | 2.690202949 | 0.038943165 | Chronic Lymphocytic Leukemia/Normal B cells |
| TJU_CMC.ID00477.3p-miR | 2.075310793 | 0.009202389 | Stage 1 Gastric Cancer/Normal Gastric Tissue |
| TJU_CMC.ID01538.3p-miR | 1.974172003 | 0.009399986 | Stage 1 Gastric Cancer/Normal Gastric Tissue |
| TJU_CMC.ID08835.3p-miR | −2.678557786 | 0.009422952 | Stage 1 Gastric Cancer/Normal Gastric Tissue |
| TJU_CMC.ID01842.3p-miR | −2.175939651 | 0.009537435 | Stage 1 Gastric Cancer/Normal Gastric Tissue |
| TJU_CMC.ID08812.3p-miR | −2.388382571 | 0.039782219 | Chronic Lymphocytic Leukemia/Normal B cells |
| TJU_CMC.ID07949.5p-miR | 3.302646452 | 0.039894119 | Chronic Lymphocytic Leukemia/Normal B cells |
| TJU_CMC.ID02447.3p-miR | 2.535368209 | 0.040012763 | Chronic Lymphocytic Leukemia/Normal B cells |
| TJU_CMC.ID05372.3p-miR | −3.702075727 | 0.040103443 | Chronic Lymphocytic Leukemia/Normal B cells |
| TJU_CMC_MD2.ID02886.5p-miR | 2.722208909 | 0.040119191 | Chronic Lymphocytic Leukemia/Normal B cells |
| TJU_CMC.ID06513.5p-miR | 2.941490989 | 0.040341719 | Chronic Lymphocytic Leukemia/Normal B cells |
| TJU_CMC.ID02587.3p-miR | −2.853027083 | 0.040483761 | Chronic Lymphocytic Leukemia/Normal B cells |

TABLE 11-continued

Differential expression of miRNAs in tissues of various disease states

| Name | Log2 fold change of Set A/Set B | p-Val | Sets Compared (A/B) |
| --- | --- | --- | --- |
| TJU_CMC.ID05236.5p-miR | 2.255052835 | 0.040457277 | Chronic Lymphocytic Leukemia/Normal B cells |
| TJU_CMC.ID04253.5p-miR | −2.060363535 | 0.009923538 | Stage 1 Gastric Cancer/Normal Gastric Tissue |
| TJU_CMC.ID06838.5p-miR | −1.974424997 | 0.009915512 | Stage 1 Gastric Cancer/Normal Gastric Tissue |
| TJU_CMC.ID09040.5p-miR | 2.89714561 | 0.00981689 | Stage 1 Gastric Cancer/Normal Gastric Tissue |
| TJU_CMC.ID06200.5p-miR | 5.929738732 | 0.041116714 | Chronic Lymphocytic Leukemia/Normal B cells |
| TJU_CMC.ID04313.5p-miR | 2.689009758 | 0.041411831 | Chronic Lymphocytic Leukemia/Normal B cells |
| TJU_CMC.ID07911.3p-miR | −2.762768146 | 0.041579908 | Chronic Lymphocytic Leukemia/Normal B cells |
| TJU_CMC.ID00469.5p-miR | 2.654255133 | 0.041653536 | Chronic Lymphocytic Leukemia/Normal B cells |
| TJU_CMC.ID03307.5p-miR | 2.667635911 | 0.041794598 | Chronic Lymphocytic Leukemia/Normal B cells |
| TJU_CMC.ID03971.5p-miR | −2.331922089 | 0.041708705 | Chronic Lymphocytic Leukemia/Normal B cells |
| TJU_CMC.ID00796.5p-miR | −2.70664484 | 0.010202348 | Stage 1 Gastric Cancer/Normal Gastric Tissue |
| TJU_CMC.ID04948.3p-miR | 2.226044701 | 0.010185066 | Stage 1 Gastric Cancer/Normal Gastric Tissue |
| TJU_CMC.ID03157.3p-miR | −2.674224631 | 0.042826516 | Chronic Lymphocytic Leukemia/Normal B cells |
| TJU_CMC.ID07044.5p-miR | −2.514589588 | 0.042517078 | Chronic Lymphocytic Leukemia/Normal B cells |
| TJU_CMC.ID07513.3p-miR | −2.667481055 | 0.04283258 | Chronic Lymphocytic Leukemia/Normal B cells |
| TJU_CMC.ID09174.5p-miR | −2.073064939 | 0.042602947 | Chronic Lymphocytic Leukemia/Normal B cells |
| TJU_CMC_MD2.ID00448.3p-miR | −2.815676604 | 0.042238491 | Chronic Lymphocytic Leukemia/Normal B cells |
| TJU_CMC_MD2.ID01627.5p-miR | −2.449972503 | 0.042376064 | Chronic Lymphocytic Leukemia/Normal B cells |
| TJU_CMC.ID02925.3p-miR | −2.791352543 | 0.043037206 | Chronic Lymphocytic Leukemia/Normal B cells |
| TJU_CMC.ID08008.3p-miR | 2.552995689 | 0.043247261 | Chronic Lymphocytic Leukemia/Normal B cells |
| TJU_CMC.ID04118.3p-miR | −1.966661969 | 0.010544399 | Stage 1 Gastric Cancer/Normal Gastric Tissue |
| TJU_CMC.ID05018.3p-miR | 1.987601722 | 0.010506792 | Stage 1 Gastric Cancer/Normal Gastric Tissue |
| TJU_CMC.ID05503.5p-miR | 5.113686357 | 0.010521132 | Stage 1 Gastric Cancer/Normal Gastric Tissue |
| TJU_CMC_MD2.ID03086.5p-miR | 2.885461243 | 0.010512505 | Stage 1 Gastric Cancer/Normal Gastric Tissue |
| TJU_CMC.ID01366.5p-miR | −2.560722335 | 0.043676335 | Chronic Lymphocytic Leukemia/Normal B cells |
| TJU_CMC.ID08624.3p-miR | −3.563081204 | 0.043626761 | Chronic Lymphocytic Leukemia/Normal B cells |
| TJU_CMC.ID06421.5p-miR | 2.461360557 | 0.043942278 | Chronic Lymphocytic Leukemia/Normal B cells |
| TJU_CMC.ID05772.5p-miR | 2.493499888 | 0.044083642 | Chronic Lymphocytic Leukemia/Normal B cells |
| TJU_CMC.ID01925.3p-miR | 2.572862146 | 0.044153843 | Chronic Lymphocytic Leukemia/Normal B cells |
| TJU_CMC.ID05711.5p-miR | 2.814087841 | 0.044727116 | Chronic Lymphocytic Leukemia/Normal B cells |
| TJU_CMC.ID01536.3p-miR | −4.105353872 | 0.044982419 | Chronic Lymphocytic Leukemia/Normal B cells |
| TJU_CMC.ID06984.3p-miR | −2.67863973 | 0.045340989 | Chronic Lymphocytic Leukemia/Normal B cells |
| TJU_CMC.ID01926.3p-miR | 5.115238652 | 0.045633062 | Chronic Lymphocytic Leukemia/Normal B cells |
| TJU_CMC.ID04621.5p-miR | 11.43699463 | 0.045793414 | Chronic Lymphocytic Leukemia/Normal B cells |
| TJU_CMC_MD2.ID02236.3p-miR | −2.022691596 | 0.045777842 | Chronic Lymphocytic Leukemia/Normal B cells |
| TJU_CMC.ID00599.3p-miR | 2.745303697 | 0.045982413 | Chronic Lymphocytic Leukemia/Normal B cells |
| TJU_CMC.ID06814.3p-miR | −3.100226571 | 0.046031206 | Chronic Lymphocytic Leukemia/Normal B cells |
| TJU_CMC.ID08511.3p-miR | 2.144631348 | 0.046138461 | Chronic Lymphocytic Leukemia/Normal B cells |
| TJU_CMC.ID05662.5p-miR | 4.003914487 | 0.046965172 | Chronic Lymphocytic Leukemia/Normal B cells |
| TJU_CMC.ID05481.5p-miR | 5.631202084 | 0.047061598 | Chronic Lymphocytic Leukemia/Normal B cells |
| TJU_CMC.ID02239.5p-miR | 1.666720863 | 0.047287595 | Chronic Lymphocytic Leukemia/Normal B cells |
| TJU_CMC.ID03380.5p-miR | 2.74818524 | 0.047370756 | Chronic Lymphocytic Leukemia/Normal B cells |
| TJU_CMC.ID04832.5p-miR | −2.503859524 | 0.047279009 | Chronic Lymphocytic Leukemia/Normal B cells |
| TJU_CMC.ID05861.5p-miR | 2.727277509 | 0.047371096 | Chronic Lymphocytic Leukemia/Normal B cells |
| TJU_CMC.ID02422.3p-miR | 2.133753278 | 0.011528269 | Stage 1 Gastric Cancer/Normal Gastric Tissue |
| TJU_CMC.ID08218.5p-miR | 6.641461595 | 0.047959303 | Chronic Lymphocytic Leukemia/Normal B cells |
| TJU_CMC.ID00473.3p-miR | 1.751557155 | 0.011781402 | Stage 1 Gastric Cancer/Normal Gastric Tissue |
| TJU_CMC.ID04227.5p-miR | 2.545716489 | 0.048385438 | Chronic Lymphocytic Leukemia/Normal B cells |
| TJU_CMC.ID08725.3p-miR | −10.72268832 | 0.048771568 | Chronic Lymphocytic Leukemia/Normal B cells |
| TJU_CMC.ID00431.5p-miR | 2.148214933 | 0.048901953 | Chronic Lymphocytic Leukemia/Normal B cells |
| TJU_CMC.ID01155.3p-miR | −4.671805316 | 0.049206737 | Chronic Lymphocytic Leukemia/Normal B cells |
| TJU_CMC.ID02221.5p-miR | −2.340384796 | 0.049640476 | Chronic Lymphocytic Leukemia/Normal B cells |
| TJU_CMC.ID00234.3p-miR | −3.547988725 | 0.049841816 | Chronic Lymphocytic Leukemia/Normal B cells |
| TJU_CMC.ID06607.3p-miR | 2.424293579 | 0.049864733 | Chronic Lymphocytic Leukemia/Normal B cells |
| TJU_CMC.ID08109.3p-miR | 2.655905187 | 0.049787226 | Chronic Lymphocytic Leukemia/Normal B cells |
| TJU_CMC.ID00215.3p-miR | −1.885337275 | 0.011970371 | Stage 1 Gastric Cancer/Normal Gastric Tissue |
| TJU_CMC.ID05108.3p-miR | 2.582621485 | 0.011935898 | Stage 1 Gastric Cancer/Normal Gastric Tissue |
| TJU_CMC.ID02577.5p-miR | 2.317229523 | 0.012067212 | Stage 1 Gastric Cancer/Normal Gastric Tissue |
| TJU_CMC.ID05561.5p-miR | −1.789531226 | 0.012278689 | Stage 1 Gastric Cancer/Normal Gastric Tissue |
| TJU_CMC.ID07189.5p-miR | 1.716924712 | 0.012380786 | Stage 1 Gastric Cancer/Normal Gastric Tissue |
| TJU_CMC.ID07383.5p-miR | 1.820527264 | 0.012532463 | Stage 1 Gastric Cancer/Normal Gastric Tissue |
| TJU_CMC.ID07957.5p-miR | −1.935121699 | 0.012588246 | Stage 1 Gastric Cancer/Normal Gastric Tissue |
| TJU_CMC.ID07520.3p-miR | −2.783427678 | 0.012704742 | Stage 1 Gastric Cancer/Normal Gastric Tissue |
| TJU_CMC.ID00375.3p-miR | −2.131326172 | 0.013098444 | Stage 1 Gastric Cancer/Normal Gastric Tissue |
| TJU_CMC.ID01864.5p-miR | 1.643025886 | 0.012849988 | Stage 1 Gastric Cancer/Normal Gastric Tissue |
| TJU_CMC.ID04851.3p-miR | 2.241577679 | 0.01310761 | Stage 1 Gastric Cancer/Normal Gastric Tissue |
| TJU_CMC.ID08174.3p-miR | 1.681512554 | 0.013319781 | Stage 1 Gastric Cancer/Normal Gastric Tissue |
| TJU_CMC.ID09722.3p-miR | −0.986418344 | 0.024951349 | ER− Breast Cancer/ER+ Breast Cancer (TCGA) |
| TJU_CMC.ID00579.3p-miR | −3.598339659 | 0.013560547 | Stage 1 Gastric Cancer/Normal Gastric Tissue |
| TJU_CMC.ID02730.5p-miR | −1.818547003 | 0.013562724 | Stage 1 Gastric Cancer/Normal Gastric Tissue |
| TJU_CMC.ID04620.5p-miR | 2.649212636 | 0.013587286 | Stage 1 Gastric Cancer/Normal Gastric Tissue |
| TJU_CMC.ID03538.3p-miR | 2.582017311 | 0.037828562 | Breast Cancer (adenoid/apocrine/atypical/DCIS/IDC/metaplastic)/Normal Breast Tissue (GEO: GSE28884) |

TABLE 11-continued

Differential expression of miRNAs in tissues of various disease states

| Name | Log2 fold change of Set A/Set B | p-Val | Sets Compared (A/B) |
| --- | --- | --- | --- |
| TJU_CMC.ID02628.3p-miR | −2.201026055 | 0.013732821 | Stage 1 Gastric Cancer/Normal Gastric Tissue |
| TJU_CMC.ID07261.5p-miR | 2.189831384 | 0.01389691 | Stage 1 Gastric Cancer/Normal Gastric Tissue |
| TJU_CMC.ID01297.3p-miR | 3.390718513 | 0.000847778 | PBMC Scleroderma Patients/PBMC Control Individuals |
| TJU_CMC.ID00654.5p-miR | 3.454910509 | 0.000915643 | PBMC Scleroderma Patients/PBMC Control Individuals |
| TJU_CMC.ID05313.5p-miR | −3.764364769 | 0.040079878 | Breast Cancer (adenoid/apocrine/atypical/DCIS/IDC/metaplastic)/Normal Breast Tissue (GEO: GSE28884) |
| TJU_CMC.ID00921.3p-miR | −3.350218667 | 0.014497451 | Stage 1 Gastric Cancer/Normal Gastric Tissue |
| TJU_CMC_MD2.ID00492.5p-miR | −1.620933739 | 0.027178806 | ER− Breast Cancer/ER+ Breast Cancer (TCGA) |
| TJU_CMC.ID01025.5p-miR | 2.811768795 | 0.015092124 | Stage 1 Gastric Cancer/Normal Gastric Tissue |
| TJU_CMC.ID05045.3p-miR | 2.405659845 | 0.015056884 | Stage 1 Gastric Cancer/Normal Gastric Tissue |
| TJU_CMC.ID07022.5p-miR | 5.684162776 | 0.015055519 | Stage 1 Gastric Cancer/Normal Gastric Tissue |
| TJU_CMC.ID08442.5p-miR | 2.725006334 | 0.014965452 | Stage 1 Gastric Cancer/Normal Gastric Tissue |
| TJU_CMC.ID04423.3p-miR | −1.725831913 | 0.015145701 | Stage 1 Gastric Cancer/Normal Gastric Tissue |
| TJU_CMC.ID05148.5p-miR | −2.235695907 | 0.015232917 | Stage 1 Gastric Cancer/Normal Gastric Tissue |
| TJU_CMC.ID07709.5p-miR | −2.024192806 | 0.015314902 | Stage 1 Gastric Cancer/Normal Gastric Tissue |
| TJU_CMC_MD2.ID00121.5p-miR | −0.715200567 | 0.028326407 | ER− Breast Cancer/ER+ Breast Cancer (TCGA) |
| TJU_CMC.ID05312.5p-miR | −2.171325441 | 0.016199312 | Stage 1 Gastric Cancer/Normal Gastric Tissue |
| TJU_CMC.ID06773.3p-miR | 2.47772879 | 0.016239106 | Stage 1 Gastric Cancer/Normal Gastric Tissue |
| TJU_CMC.ID08458.3p-miR | −2.453214057 | 0.016075598 | Stage 1 Gastric Cancer/Normal Gastric Tissue |
| TJU_CMC.ID01174.5p-miR | 4.539765114 | 0.016909714 | Stage 1 Gastric Cancer/Normal Gastric Tissue |
| TJU_CMC.ID00909.5p-miR | −2.266728504 | 0.01735875 | Stage 1 Gastric Cancer/Normal Gastric Tissue |
| TJU_CMC.ID03916.3p-miR | 2.045002013 | 0.017418935 | Stage 1 Gastric Cancer/Normal Gastric Tissue |
| TJU_CMC.ID08289.5p-miR | −2.161273244 | 0.017696904 | Stage 1 Gastric Cancer/Normal Gastric Tissue |
| TJU_CMC.ID01819.5p-miR | 2.295373401 | 0.01783452 | Stage 1 Gastric Cancer/Normal Gastric Tissue |
| TJU_CMC.ID08998.3p-miR | −2.005443142 | 0.017866735 | Stage 1 Gastric Cancer/Normal Gastric Tissue |
| TJU_CMC.ID00512.3p-miR | 2.252872227 | 0.018141777 | Stage 1 Gastric Cancer/Normal Gastric Tissue |
| TJU_CMC.ID02102.3p-miR | 2.36718115 | 0.018321663 | Stage 1 Gastric Cancer/Normal Gastric Tissue |
| TJU_CMC.ID04681.3p-miR | −2.176188804 | 0.018286169 | Stage 1 Gastric Cancer/Normal Gastric Tissue |
| TJU_CMC.ID05039.5p-miR | −1.953170666 | 0.018285911 | Stage 1 Gastric Cancer/Normal Gastric Tissue |
| TJU_CMC.ID07345.5p-miR | 1.837615276 | 0.018278214 | Stage 1 Gastric Cancer/Normal Gastric Tissue |
| TJU_CMC.ID07698.3p-miR | 2.310253622 | 0.018146438 | Stage 1 Gastric Cancer/Normal Gastric Tissue |
| TJU_CMC.ID06033.5p-miR | 2.492889092 | 0.018503478 | Stage 1 Gastric Cancer/Normal Gastric Tissue |
| TJU_CMC.ID08663.3p-miR | 2.385002504 | 0.018459247 | Stage 1 Gastric Cancer/Normal Gastric Tissue |
| TJU_CMC.ID01474.3p-miR | 2.175335304 | 0.018752613 | Stage 1 Gastric Cancer/Normal Gastric Tissue |
| TJU_CMC.ID06994.3p-miR | 1.770534605 | 0.019217521 | Stage 1 Gastric Cancer/Normal Gastric Tissue |
| TJU_CMC.ID07215.5p-miR | −2.02153499 | 0.01920981 | Stage 1 Gastric Cancer/Normal Gastric Tissue |
| TJU_CMC.ID02450.5p-miR | 3.074617894 | 0.019501436 | Stage 1 Gastric Cancer/Normal Gastric Tissue |
| TJU_CMC.ID03700.3p-miR | 2.022040445 | 0.019483381 | Stage 1 Gastric Cancer/Normal Gastric Tissue |
| TJU_CMC.ID00543.3p-miR | −2.559793688 | 0.020403857 | Stage 1 Gastric Cancer/Normal Gastric Tissue |
| TJU_CMC.ID04635.5p-miR | −1.768150111 | 0.020050026 | Stage 1 Gastric Cancer/Normal Gastric Tissue |
| TJU_CMC.ID05313.5p-miR | 2.332004891 | 0.020192941 | Stage 1 Gastric Cancer/Normal Gastric Tissue |
| TJU_CMC.ID08825.5p-miR | 2.129189041 | 0.020016639 | Stage 1 Gastric Cancer/Normal Gastric Tissue |
| TJU_CMC.ID02254.5p-miR | 0.846597348 | 0.030022777 | PR− Breast Cancer/PR+ Breast Cancer (TCGA) |
| TJU_CMC.ID06634.3p-miR | 2.793694953 | 0.020783262 | Stage 1 Gastric Cancer/Normal Gastric Tissue |
| TJU_CMC.ID07607.3p-miR | −1.755779331 | 0.020832546 | Stage 1 Gastric Cancer/Normal Gastric Tissue |
| TJU_CMC.ID02033.5p-miR | −2.025781962 | 0.021296034 | Stage 1 Gastric Cancer/Normal Gastric Tissue |
| TJU_CMC.ID09450.3p-miR | 4.075418332 | 0.021239077 | Stage 1 Gastric Cancer/Normal Gastric Tissue |
| TJU_CMC.ID07790.5p-miR | −3.448884632 | 0.000406238 | Gastric Cancer (All Stages)/Normal Gastric Tissue |
| TJU_CMC.ID04803.5p-miR | −1.6802627 | 0.021607623 | Stage 1 Gastric Cancer/Normal Gastric Tissue |
| TJU_CMC.ID01178.5p-miR | 2.113761409 | 0.022144989 | Stage 1 Gastric Cancer/Normal Gastric Tissue |
| TJU_CMC.ID01987.5p-miR | 2.338536342 | 0.02197785 | Stage 1 Gastric Cancer/Normal Gastric Tissue |
| TJU_CMC.ID06322.5p-miR | −2.288854644 | 0.022044522 | Stage 1 Gastric Cancer/Normal Gastric Tissue |
| TJU_CMC.ID06548.3p-miR | −2.35561253 | 0.022687276 | Stage 1 Gastric Cancer/Normal Gastric Tissue |
| TJU_CMC.ID03007.3p-miR | −4.782773106 | 0.023567016 | Stage 1 Gastric Cancer/Normal Gastric Tissue |
| TJU_CMC.ID05203.3p-miR | 1.645460066 | 0.023573626 | Stage 1 Gastric Cancer/Normal Gastric Tissue |
| TJU_CMC.ID02573.5p-miR | 1.910333851 | 0.023943836 | Stage 1 Gastric Cancer/Normal Gastric Tissue |
| TJU_CMC_MD2.ID00121.5p-miR | −0.677750071 | 0.036899736 | PR− Breast Cancer/PR+ Breast Cancer (TCGA) |
| TJU_CMC.ID01756.3p-miR | 1.800767716 | 0.024285856 | Stage 1 Gastric Cancer/Normal Gastric Tissue |
| TJU_CMC.ID04427.3p-miR | 1.777738941 | 0.024584722 | Stage 1 Gastric Cancer/Normal Gastric Tissue |
| TJU_CMC.ID09661.5p-miR | −2.13052798 | 0.024499508 | Stage 1 Gastric Cancer/Normal Gastric Tissue |
| TJU_CMC.ID03290.3p-miR | 1.861979216 | 0.024898137 | Stage 1 Gastric Cancer/Normal Gastric Tissue |
| TJU_CMC.ID04435.5p-miR | 1.901680316 | 0.025033691 | Stage 1 Gastric Cancer/Normal Gastric Tissue |
| TJU_CMC.ID03542.5p-miR | 1.458859282 | 0.025368833 | Stage 1 Gastric Cancer/Normal Gastric Tissue |
| TJU_CMC.ID01979.3p-miR | −2.200462458 | 0.026533005 | Stage 1 Gastric Cancer/Normal Gastric Tissue |
| TJU_CMC.ID02232.3p-miR | 2.820569719 | 0.026297322 | Stage 1 Gastric Cancer/Normal Gastric Tissue |
| TJU_CMC.ID02658.5p-miR | −2.091347003 | 0.025541927 | Stage 1 Gastric Cancer/Normal Gastric Tissue |
| TJU_CMC.ID03781.3p-miR | 3.583905629 | 0.026450254 | Stage 1 Gastric Cancer/Normal Gastric Tissue |
| TJU_CMC.ID05049.5p-miR | −2.160540938 | 0.025854201 | Stage 1 Gastric Cancer/Normal Gastric Tissue |
| TJU_CMC.ID06537.3p-miR | 2.90612632 | 0.025947367 | Stage 1 Gastric Cancer/Normal Gastric Tissue |
| TJU_CMC.ID08597.5p-miR | −1.657859844 | 0.025898359 | Stage 1 Gastric Cancer/Normal Gastric Tissue |
| TJU_CMC.ID09273.3p-miR | 3.49373008 | 0.02566989 | Stage 1 Gastric Cancer/Normal Gastric Tissue |
| TJU_CMC.ID03886.3p-miR | 3.846813383 | 0.027325624 | Stage 1 Gastric Cancer/Normal Gastric Tissue |
| TJU_CMC.ID00362.3p-miR | 2.004690628 | 0.027537299 | Stage 1 Gastric Cancer/Normal Gastric Tissue |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID04015.5p-miR | −1.696789953 | 0.027738226 | Stage 1 Gastric Cancer/Normal Gastric Tissue |
| TJU_CMC.ID04848.3p-miR | 1.504367112 | 0.027970622 | Stage 1 Gastric Cancer/Normal Gastric Tissue |
| TJU_CMC.ID00399.3p-miR | 1.86923165 | 0.028478098 | Stage 1 Gastric Cancer/Normal Gastric Tissue |
| TJU_CMC.ID02696.5p-miR | 3.394279871 | 0.028852121 | Stage 1 Gastric Cancer/Normal Gastric Tissue |
| TJU_CMC.ID03641.5p-miR | −1.537500732 | 0.028218629 | Stage 1 Gastric Cancer/Normal Gastric Tissue |
| TJU_CMC.ID03895.5p-miR | 2.117157524 | 0.028771843 | Stage 1 Gastric Cancer/Normal Gastric Tissue |
| TJU_CMC.ID05169.3p-miR | −2.254702741 | 0.02873992 | Stage 1 Gastric Cancer/Normal Gastric Tissue |
| TJU_CMC.ID07831.3p-miR | 1.857964134 | 0.028906939 | Stage 1 Gastric Cancer/Normal Gastric Tissue |
| TJU_CMC.ID09027.5p-miR | −1.730870257 | 0.028240138 | Stage 1 Gastric Cancer/Normal Gastric Tissue |
| TJU_CMC.ID09251.3p-miR | 2.099237579 | 0.028783856 | Stage 1 Gastric Cancer/Normal Gastric Tissue |
| TJU_CMC.ID00316.5p-miR | 5.391193344 | 0.029285182 | Stage 1 Gastric Cancer/Normal Gastric Tissue |
| TJU_CMC.ID02122.5p-miR | −2.083758565 | 0.02957992 | Stage 1 Gastric Cancer/Normal Gastric Tissue |
| TJU_CMC.ID06120.5p-miR | 10.07874658 | 0.029951987 | Stage 1 Gastric Cancer/Normal Gastric Tissue |
| TJU_CMC.ID02928.3p-miR | 1.439304727 | 0.030421372 | Stage 1 Gastric Cancer/Normal Gastric Tissue |
| TJU_CMC.ID01384.3p-miR | −1.514093873 | 0.030652927 | Stage 1 Gastric Cancer/Normal Gastric Tissue |
| TJU_CMC.ID00657.5p-miR | −1.95472253 | 0.031165954 | Stage 1 Gastric Cancer/Normal Gastric Tissue |
| TJU_CMC.ID06067.5p-miR | 2.020483018 | 0.031338715 | Stage 1 Gastric Cancer/Normal Gastric Tissue |
| TJU_CMC.ID06171.5p-miR | 2.192147142 | 0.031661783 | Stage 1 Gastric Cancer/Normal Gastric Tissue |
| TJU_CMC.ID07621.5p-miR | −1.627568334 | 0.031656234 | Stage 1 Gastric Cancer/Normal Gastric Tissue |
| TJU_CMC.ID01475.5p-miR | −1.650495677 | 0.032045423 | Stage 1 Gastric Cancer/Normal Gastric Tissue |
| TJU_CMC.ID05551.3p-miR | 1.743804934 | 0.031958613 | Stage 1 Gastric Cancer/Normal Gastric Tissue |
| TJU_CMC.ID05497.5p-miR | −1.925503003 | 0.032980165 | Stage 1 Gastric Cancer/Normal Gastric Tissue |
| TJU_CMC.ID06140.3p-miR | −3.695678844 | 0.032857827 | Stage 1 Gastric Cancer/Normal Gastric Tissue |
| TJU_CMC.ID05355.5p-miR | −1.668282195 | 0.033340954 | Stage 1 Gastric Cancer/Normal Gastric Tissue |
| TJU_CMC.ID01897.5p-miR | −1.670761008 | 0.034026544 | Stage 1 Gastric Cancer/Normal Gastric Tissue |
| TJU_CMC.ID07980.3p-miR | 1.947577562 | 0.033775432 | Stage 1 Gastric Cancer/Normal Gastric Tissue |
| TJU_CMC.ID00655.5p-miR | 1.724749947 | 0.034445379 | Stage 1 Gastric Cancer/Normal Gastric Tissue |
| TJU_CMC.ID07746.3p-miR | −1.512560985 | 0.035394075 | Stage 1 Gastric Cancer/Normal Gastric Tissue |
| TJU_CMC.ID00649.3p-miR | −1.417671335 | 0.036131597 | Stage 1 Gastric Cancer/Normal Gastric Tissue |
| TJU_CMC.ID01354.5p-miR | −1.568861306 | 0.036080821 | Stage 1 Gastric Cancer/Normal Gastric Tissue |
| TJU_CMC.ID04796.5p-miR | −2.01546058 | 0.036177296 | Stage 1 Gastric Cancer/Normal Gastric Tissue |
| TJU_CMC.ID05864.5p-miR | −3.573410271 | 0.035660449 | Stage 1 Gastric Cancer/Normal Gastric Tissue |
| TJU_CMC.ID07502.3p-miR | 1.743984055 | 0.035703936 | Stage 1 Gastric Cancer/Normal Gastric Tissue |
| TJU_CMC.ID07611.5p-miR | −1.714093241 | 0.035869892 | Stage 1 Gastric Cancer/Normal Gastric Tissue |
| TJU_CMC.ID01593.3p-miR | 1.605664473 | 0.036412631 | Stage 1 Gastric Cancer/Normal Gastric Tissue |
| TJU_CMC.ID03574.5p-miR | −1.664336846 | 0.036445651 | Stage 1 Gastric Cancer/Normal Gastric Tissue |
| TJU_CMC.ID02897.3p-miR | 1.359871297 | 0.036639227 | Stage 1 Gastric Cancer/Normal Gastric Tissue |
| TJU_CMC.ID00028.5p-miR | 999999 | 0.037217161 | Stage 1 Gastric Cancer/Normal Gastric Tissue |
| TJU_CMC.ID06935.5p-miR | 1.970997085 | 0.037249063 | Stage 1 Gastric Cancer/Normal Gastric Tissue |
| TJU_CMC.ID00529.5p-miR | −1.87499046 | 0.037915223 | Stage 1 Gastric Cancer/Normal Gastric Tissue |
| TJU_CMC.ID03321.3p-miR | 2.510429351 | 0.038074992 | Stage 1 Gastric Cancer/Normal Gastric Tissue |
| TJU_CMC.ID05942.5p-miR | −2.052000935 | 0.0380364 | Stage 1 Gastric Cancer/Normal Gastric Tissue |
| TJU_CMC.ID01056.3p-miR | 2.323343113 | 0.038188637 | Stage 1 Gastric Cancer/Normal Gastric Tissue |
| TJU_CMC.ID02982.3p-miR | 1.827891802 | 0.038229827 | Stage 1 Gastric Cancer/Normal Gastric Tissue |
| TJU_CMC.ID01560.3p-miR | 1.561285467 | 0.038391402 | Stage 1 Gastric Cancer/Normal Gastric Tissue |
| TJU_CMC.ID02513.5p-miR | 1.935460253 | 0.038528593 | Stage 1 Gastric Cancer/Normal Gastric Tissue |
| TJU_CMC.ID01950.5p-miR | −1.740687512 | 0.038938428 | Stage 1 Gastric Cancer/Normal Gastric Tissue |
| TJU_CMC.ID00712.3p-miR | −3.578820565 | 0.000802636 | Gastric Cancer (All Stages)/Normal Gastric Tissue |
| TJU_CMC.ID03003.3p-miR | −4.105448707 | 0.000602992 | Gastric Cancer (All Stages)/Normal Gastric Tissue |
| TJU_CMC_MD2.ID01679.5p-miR | −2.857222319 | 0.000800548 | Gastric Cancer (All Stages)/Normal Gastric Tissue |
| TJU_CMC.ID03818.3p-miR | 2.771556746 | 0.039337222 | Stage 1 Gastric Cancer/Normal Gastric Tissue |
| TJU_CMC.ID04845.5p-miR | −1.862684838 | 0.039680261 | Stage 1 Gastric Cancer/Normal Gastric Tissue |
| TJU_CMC.ID01893.3p-miR | −1.985105144 | 0.039854534 | Stage 1 Gastric Cancer/Normal Gastric Tissue |
| TJU_CMC.ID01219.5p-miR | −1.534319701 | 0.040088793 | Stage 1 Gastric Cancer/Normal Gastric Tissue |
| TJU_CMC.ID04676.3p-miR | −1.8439995 | 0.04021418 | Stage 1 Gastric Cancer/Normal Gastric Tissue |
| TJU_CMC.ID07163.3p-miR | −1.531242371 | 0.040236773 | Stage 1 Gastric Cancer/Normal Gastric Tissue |
| TJU_CMC.ID05587.5p-miR | 1.869978992 | 0.040353167 | Stage 1 Gastric Cancer/Normal Gastric Tissue |
| TJU_CMC.ID07537.5p-miR | −1.872554033 | 0.040625072 | Stage 1 Gastric Cancer/Normal Gastric Tissue |
| TJU_CMC.ID07356.3p-miR | −2.118855359 | 0.041199329 | Stage 1 Gastric Cancer/Normal Gastric Tissue |
| TJU_CMC.ID05439.5p-miR | 1.508153637 | 0.041577774 | Stage 1 Gastric Cancer/Normal Gastric Tissue |
| TJU_CMC.ID06989.3p-miR | 2.006062026 | 0.041594159 | Stage 1 Gastric Cancer/Normal Gastric Tissue |
| TJU_CMC.ID01444.3p-miR | 2.555115061 | 0.046060647 | Stage 1 Gastric Cancer/Normal Gastric Tissue |
| TJU_CMC.ID01479.3p-miR | 2.058604722 | 0.045693455 | Stage 1 Gastric Cancer/Normal Gastric Tissue |
| TJU_CMC.ID01480.3p-miR | 3.687615024 | 0.044941569 | Stage 1 Gastric Cancer/Normal Gastric Tissue |
| TJU_CMC.ID02100.3p-miR | 1.489891693 | 0.045528966 | Stage 1 Gastric Cancer/Normal Gastric Tissue |
| TJU_CMC.ID02150.3p-miR | 1.391882669 | 0.044235737 | Stage 1 Gastric Cancer/Normal Gastric Tissue |
| TJU_CMC.ID02856.5p-miR | −1.504663531 | 0.044931996 | Stage 1 Gastric Cancer/Normal Gastric Tissue |
| TJU_CMC.ID03480.3p-miR | −1.480600601 | 0.045814693 | Stage 1 Gastric Cancer/Normal Gastric Tissue |
| TJU_CMC.ID03814.3p-miR | −2.042242263 | 0.045171368 | Stage 1 Gastric Cancer/Normal Gastric Tissue |
| TJU_CMC.ID03817.3p-miR | 3.621894525 | 0.047175638 | Stage 1 Gastric Cancer/Normal Gastric Tissue |
| TJU_CMC.ID03994.5p-miR | −1.518059123 | 0.045706439 | Stage 1 Gastric Cancer/Normal Gastric Tissue |
| TJU_CMC.ID05164.5p-miR | −1.544533389 | 0.044049298 | Stage 1 Gastric Cancer/Normal Gastric Tissue |
| TJU_CMC.ID05184.3p-miR | 3.267063409 | 0.047372465 | Stage 1 Gastric Cancer/Normal Gastric Tissue |
| TJU_CMC.ID05337.3p-miR | 1.833858164 | 0.043601761 | Stage 1 Gastric Cancer/Normal Gastric Tissue |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID06035.3p-miR | −999999 | 0.042638355 | Stage 1 Gastric Cancer/Normal Gastric Tissue |
| TJU_CMC.ID06232.3p-miR | 3.246545679 | 0.046176078 | Stage 1 Gastric Cancer/Normal Gastric Tissue |
| TJU_CMC.ID06262.5p-miR | 1.698765745 | 0.043332951 | Stage 1 Gastric Cancer/Normal Gastric Tissue |
| TJU_CMC.ID06636.5p-miR | 1.919980395 | 0.04699867 | Stage 1 Gastric Cancer/Normal Gastric Tissue |
| TJU_CMC.ID06724.5p-miR | 2.168014304 | 0.045874228 | Stage 1 Gastric Cancer/Normal Gastric Tissue |
| TJU_CMC.ID07132.3p-miR | −1.721871795 | 0.046320233 | Stage 1 Gastric Cancer/Normal Gastric Tissue |
| TJU_CMC.ID07608.3p-miR | 1.628464608 | 0.04428472 | Stage 1 Gastric Cancer/Normal Gastric Tissue |
| TJU_CMC.ID07932.3p-miR | 2.369370345 | 0.04736313 | Stage 1 Gastric Cancer/Normal Gastric Tissue |
| TJU_CMC.ID08106.5p-miR | 1.786172532 | 0.042705749 | Stage 1 Gastric Cancer/Normal Gastric Tissue |
| TJU_CMC.ID09086.3p-miR | 1.758695636 | 0.042816967 | Stage 1 Gastric Cancer/Normal Gastric Tissue |
| TJU_CMC.ID09269.3p-miR | 2.219421129 | 0.04599574 | Stage 1 Gastric Cancer/Normal Gastric Tissue |
| TJU_CMC.ID09371.5p-miR | 1.896231138 | 0.043158252 | Stage 1 Gastric Cancer/Normal Gastric Tissue |
| TJU_CMC.ID05831.5p-miR | −4.761579292 | 0.048202506 | Stage 1 Gastric Cancer/Normal Gastric Tissue |
| TJU_CMC.ID00767.5p-miR | −2.527150757 | 0.048321 | Stage 1 Gastric Cancer/Normal Gastric Tissue |
| TJU_CMC.ID05812.5p-miR | −2.517265076 | 0.048359017 | Stage 1 Gastric Cancer/Normal Gastric Tissue |
| TJU_CMC.ID06419.5p-miR | −5.793641439 | 0.003012534 | MIA PaCa-2 cells/HPNE cells (Pancreas cell lines) |
| TJU_CMC.ID04247.5p-miR | 4.395280759 | 0.001679836 | PBMC Scleroderma Patients/PBMC Control Individuals |
| TJU_CMC.ID01210.3p-miR | 999999 | 0.049941853 | Stage 1 Gastric Cancer/Normal Gastric Tissue |
| TJU_CMC.ID03472.3p-miR | −1.475216055 | 0.049699193 | Stage 1 Gastric Cancer/Normal Gastric Tissue |
| TJU_CMC.ID03557.5p-miR | 1.533416634 | 0.049795982 | Stage 1 Gastric Cancer/Normal Gastric Tissue |
| TJU_CMC.ID00512.3p-miR | 2.029773173 | 0.002051085 | Gastric Cancer (All Stages)/Normal Gastric Tissue |
| TJU_CMC.ID01099.3p-miR | −3.269626886 | 0.001077378 | Gastric Cancer (All Stages)/Normal Gastric Tissue |
| TJU_CMC.ID02447.3p-miR | −3.138250987 | 0.001684081 | Gastric Cancer (All Stages)/Normal Gastric Tissue |
| TJU_CMC.ID03472.3p-miR | −2.770632211 | 0.002091258 | Gastric Cancer (All Stages)/Normal Gastric Tissue |
| TJU_CMC.ID03778.3p-miR | −2.566149717 | 0.001432757 | Gastric Cancer (All Stages)/Normal Gastric Tissue |
| TJU_CMC.ID04082.3p-miR | −2.292365086 | 0.001517484 | Gastric Cancer (All Stages)/Normal Gastric Tissue |
| TJU_CMC.ID04470.5p-miR | −9.863088018 | 0.001502956 | Gastric Cancer (All Stages)/Normal Gastric Tissue |
| TJU_CMC.ID06821.5p-miR | −3.25417007 | 0.002307217 | Gastric Cancer (All Stages)/Normal Gastric Tissue |
| TJU_CMC.ID06444.3p-miR | 1.653214013 | 0.000185226 | Hypo-reactive/Hyper-reactive (Platelets) |
| TJU_CMC.ID07305.3p-miR | 2.42654381 | 0.0002754 | Hypo-reactive/Hyper-reactive (Platelets) |
| TJU_CMC.ID09231.3p-miR | 2.335032738 | 0.000381281 | Hypo-reactive/Hyper-reactive (Platelets) |
| TJU_CMC.ID09257.3p-miR | 1.774945288 | 0.000320958 | Hypo-reactive/Hyper-reactive (Platelets) |
| TJU_CMC.ID06656.5p-miR | 2.943589432 | 0.002959778 | Gastric Cancer (All Stages)/Normal Gastric Tissue |
| TJU_CMC.ID00543.3p-miR | −2.952746517 | 0.002860035 | Gastric Cancer (All Stages)/Normal Gastric Tissue |
| TJU_CMC.ID03641.5p-miR | −1.737261622 | 0.003077421 | Gastric Cancer (All Stages)/Normal Gastric Tissue |
| TJU_CMC.ID06731.3p-miR | −2.157167272 | 0.002987265 | Gastric Cancer (All Stages)/Normal Gastric Tissue |
| TJU_CMC.ID06081.3p-miR | 1.613609556 | 0.000795092 | Hypo-reactive/Hyper-reactive (Platelets) |
| TJU_CMC.ID07748.3p-miR | 3.632924218 | 0.000734968 | Hypo-reactive/Hyper-reactive (Platelets) |
| TJU_CMC.ID08608.5p-miR | −4.761294513 | 0.000494056 | Hypo-reactive/Hyper-reactive (Platelets) |
| TJU_CMC.ID09409.5p-miR | 2.051129669 | 0.000679156 | Hypo-reactive/Hyper-reactive (Platelets) |
| TJU_CMC.ID01835.5p-miR | 3.18205863 | 0.002083819 | PBMC Scleroderma Patients/PBMC Control Individuals |
| TJU_CMC.ID06439.5p-miR | −1.977866648 | 0.000932038 | Hypo-reactive/Hyper-reactive (Platelets) |
| TJU_CMC.ID04635.5p-miR | −1.934426287 | 0.003545121 | Gastric Cancer (All Stages)/Normal Gastric Tissue |
| TJU_CMC.ID07938.3p-miR | 3.311028792 | 0.002242892 | PBMC Scleroderma Patients/PBMC Control Individuals |
| TJU_CMC.ID05537.5p-miR | 2.641046763 | 0.0026369 | PBMC Scleroderma Patients/PBMC Control Individuals |
| TJU_CMC.ID00225.3p-miR | 3.951746463 | 0.004153786 | Gastric Cancer (All Stages)/Normal Gastric Tissue |
| TJU_CMC.ID01606.3p-miR | 6.346718292 | 0.004046096 | Gastric Cancer (All Stages)/Normal Gastric Tissue |
| TJU_CMC.ID02015.5p-miR | −2.21281534 | 0.004111365 | Gastric Cancer (All Stages)/Normal Gastric Tissue |
| TJU_CMC.ID00641.5p-miR | 2.868879593 | 0.00453698 | Gastric Cancer (All Stages)/Normal Gastric Tissue |
| TJU_CMC.ID01724.5p-miR | 3.457748523 | 0.003316639 | PBMC Scleroderma Patients/PBMC Control Individuals |
| TJU_CMC.ID01869.5p-miR | −999999 | 0.003192327 | PBMC Scleroderma Patients/PBMC Control Individuals |
| TJU_CMC.ID01093.3p-miR | −2.897451699 | 0.004835397 | Gastric Cancer (All Stages)/Normal Gastric Tissue |
| TJU_CMC.ID02648.3p-miR | 2.950522108 | 0.004231351 | PBMC Scleroderma Patients/PBMC Control Individuals |
| TJU_CMC.ID04455.3p-miR | 999999 | 0.004199682 | PBMC Scleroderma Patients/PBMC Control Individuals |
| TJU_CMC.ID06720.3p-miR | 4.543488868 | 0.004329511 | PBMC Scleroderma Patients/PBMC Control Individuals |
| TJU_CMC.ID00955.3p-miR | 6.831164867 | 0.004772912 | PBMC Scleroderma Patients/PBMC Control Individuals |
| TJU_CMC.ID09015.3p-miR | 3.12609034 | 0.00483077 | PBMC Scleroderma Patients/PBMC Control Individuals |
| TJU_CMC.ID00649.3p-miR | −1.82174396 | 0.005864792 | Gastric Cancer (All Stages)/Normal Gastric Tissue |
| TJU_CMC.ID02426.3p-miR | 999999 | 0.00558375 | PBMC Scleroderma Patients/PBMC Control Individuals |
| TJU_CMC.ID01200.5p-miR | 5.20008035 | 0.005742175 | PBMC Scleroderma Patients/PBMC Control Individuals |
| TJU_CMC.ID05623.3p-miR | 2.925825533 | 0.005784479 | PBMC Scleroderma Patients/PBMC Control Individuals |
| TJU_CMC.ID00340.3p-miR | 1.993239112 | 0.001601574 | Hypo-reactive/Hyper-reactive (Platelets) |
| TJU_CMC.ID04683.5p-miR | 2.246604768 | 0.006516713 | Gastric Cancer (All Stages)/Normal Gastric Tissue |
| TJU_CMC.ID00956.5p-miR | −1.644563996 | 0.006872914 | Gastric Cancer (All Stages)/Normal Gastric Tissue |
| TJU_CMC.ID04312.3p-miR | −2.480319042 | 0.007310973 | Gastric Cancer (All Stages)/Normal Gastric Tissue |
| TJU_CMC.ID05355.5p-miR | −1.855768435 | 0.00715091 | Gastric Cancer (All Stages)/Normal Gastric Tissue |
| TJU_CMC.ID05823.5p-miR | 4.284212647 | 0.007316774 | Gastric Cancer (All Stages)/Normal Gastric Tissue |
| TJU_CMC.ID06673.3p-miR | −3.150401134 | 0.007470134 | Gastric Cancer (All Stages)/Normal Gastric Tissue |
| TJU_CMC.ID07039.3p-miR | 3.463613833 | 0.007037041 | Gastric Cancer (All Stages)/Normal Gastric Tissue |
| TJU_CMC.ID06649.3p-miR | −1.934587257 | 0.007616704 | Gastric Cancer (All Stages)/Normal Gastric Tissue |
| TJU_CMC.ID03702.5p-miR | 3.461908651 | 0.006315937 | PBMC Scleroderma Patients/PBMC Control Individuals |
| TJU_CMC.ID08197.5p-miR | −2.348254142 | 0.008018667 | Gastric Cancer (All Stages)/Normal Gastric Tissue |
| TJU_CMC.ID00773.5p-miR | 2.301016376 | 0.008162097 | Gastric Cancer (All Stages)/Normal Gastric Tissue |
| TJU_CMC.ID00912.5p-miR | 1.96238007 | 0.001862198 | Hypo-reactive/Hyper-reactive (Platelets) |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID00409.5p-miR | −1.824781674 | 0.010067209 | Gastric Cancer (All Stages)/Normal Gastric Tissue |
| TJU_CMC.ID02510.3p-miR | −1.939092573 | 0.010071596 | Gastric Cancer (All Stages)/Normal Gastric Tissue |
| TJU_CMC.ID02658.5p-miR | −2.196705585 | 0.009912383 | Gastric Cancer (All Stages)/Normal Gastric Tissue |
| TJU_CMC.ID08835.3p-miR | −2.675705482 | 0.009634574 | Gastric Cancer (All Stages)/Normal Gastric Tissue |
| TJU_CMC_MD2.ID00858.5p-miR | 4.323371122 | 0.010095344 | Gastric Cancer (All Stages)/Normal Gastric Tissue |
| TJU_CMC.ID00299.5p-miR | 3.787100783 | 0.010281539 | Gastric Cancer (All Stages)/Normal Gastric Tissue |
| TJU_CMC.ID05262.3p-miR | 3.427190631 | 0.007094902 | PBMC Scleroderma Patients/PBMC Control Individuals |
| TJU_CMC.ID03383.3p-miR | 3.451124625 | 0.00782853 | PBMC Scleroderma Patients/PBMC Control Individuals |
| TJU_CMC.ID07583.3p-miR | −4.673021177 | 0.007512288 | PBMC Scleroderma Patients/PBMC Control Individuals |
| TJU_CMC.ID08289.5p-miR | −2.373992253 | 0.010900817 | Gastric Cancer (All Stages)/Normal Gastric Tissue |
| TJU_CMC.ID03699.3p-miR | −1.742638842 | 0.011043398 | Gastric Cancer (All Stages)/Normal Gastric Tissue |
| TJU_CMC.ID01788.5p-miR | −999999 | 0.008110928 | PBMC Scleroderma Patients/PBMC Control Individuals |
| TJU_CMC.ID02580.5p-miR | 1.61352745 | 0.002330424 | Hypo-reactive/Hyper-reactive (Platelets) |
| TJU_CMC.ID00747.3p-miR | 1.691988375 | 0.003680397 | Hypo-reactive/Hyper-reactive (Platelets) |
| TJU_CMC.ID01720.5p-miR | 1.714723319 | 0.004129298 | Hypo-reactive/Hyper-reactive (Platelets) |
| TJU_CMC.ID02109.3p-miR | −1.975837467 | 0.004168064 | Hypo-reactive/Hyper-reactive (Platelets) |
| TJU_CMC.ID06436.3p-miR | 1.503891979 | 0.003179432 | Hypo-reactive/Hyper-reactive (Platelets) |
| TJU_CMC.ID07393.3p-miR | −1.619332054 | 0.004050664 | Hypo-reactive/Hyper-reactive (Platelets) |
| TJU_CMC.ID09218.5p-miR | 3.556651643 | 0.003192236 | Hypo-reactive/Hyper-reactive (Platelets) |
| TJU_CMC.ID00341.3p-miR | −1.726729129 | 0.011967311 | Gastric Cancer (All Stages)/Normal Gastric Tissue |
| TJU_CMC.ID09085.5p-miR | 2.437603929 | 0.012499213 | Gastric Cancer (All Stages)/Normal Gastric Tissue |
| TJU_CMC.ID07062.5p-miR | 1.574930362 | 0.00458083 | Hypo-reactive/Hyper-reactive (Platelets) |
| TJU_CMC.ID07941.3p-miR | 2.999225899 | 0.012768627 | Gastric Cancer (All Stages)/Normal Gastric Tissue |
| TJU_CMC.ID00107.3p-miR | −2.229420458 | 0.01311175 | Gastric Cancer (All Stages)/Normal Gastric Tissue |
| TJU_CMC.ID06672.3p-miR | 2.248698546 | 0.004908521 | Hypo-reactive/Hyper-reactive (Platelets) |
| TJU_CMC.ID03038.3p-miR | −1.908413945 | 0.01358092 | Gastric Cancer (All Stages)/Normal Gastric Tissue |
| TJU_CMC.ID03048.5p-miR | −2.237365771 | 0.00617588 | Hypo-reactive/Hyper-reactive (Platelets) |
| TJU_CMC.ID04575.5p-miR | 1.374083779 | 0.005749961 | Hypo-reactive/Hyper-reactive (Platelets) |
| TJU_CMC.ID07579.5p-miR | 1.513417789 | 0.005707046 | Hypo-reactive/Hyper-reactive (Platelets) |
| TJU_CMC.ID00117.3p-miR | −2.013676533 | 0.014763149 | Gastric Cancer (All Stages)/Normal Gastric Tissue |
| TJU_CMC.ID08644.5p-miR | 3.07740616 | 0.014681356 | Gastric Cancer (All Stages)/Normal Gastric Tissue |
| TJU_CMC.ID01789.5p-miR | −1.528641892 | 0.015622037 | Gastric Cancer (All Stages)/Normal Gastric Tissue |
| TJU_CMC.ID04560.3p-miR | 1.926472464 | 0.015686032 | Gastric Cancer (All Stages)/Normal Gastric Tissue |
| TJU_CMC.ID07132.3p-miR | −2.145459446 | 0.015765732 | Gastric Cancer (All Stages)/Normal Gastric Tissue |
| TJU_CMC.ID03166.3p-miR | −1.367271523 | 0.007441783 | Hypo-reactive/Hyper-reactive (Platelets) |
| TJU_CMC.ID06406.3p-miR | 1.503842206 | 0.007351872 | Hypo-reactive/Hyper-reactive (Platelets) |
| TJU_CMC.ID07180.5p-miR | 2.534389089 | 0.007426857 | Hypo-reactive/Hyper-reactive (Platelets) |
| TJU_CMC.ID02391.5p-miR | 2.065765985 | 0.017318452 | Gastric Cancer (All Stages)/Normal Gastric Tissue |
| TJU_CMC.ID09252.5p-miR | 1.45046237 | 0.008429204 | Hypo-reactive/Hyper-reactive (Platelets) |
| TJU_CMC.ID01025.5p-miR | 2.165904826 | 0.023339219 | Gastric Cancer (All Stages)/Normal Gastric Tissue |
| TJU_CMC.ID01304.5p-miR | 3.221546361 | 0.024071294 | Gastric Cancer (All Stages)/Normal Gastric Tissue |
| TJU_CMC.ID01746.5p-miR | −1.583604032 | 0.026592602 | Gastric Cancer (All Stages)/Normal Gastric Tissue |
| TJU_CMC.ID01910.3p-miR | −2.441311954 | 0.018396986 | Gastric Cancer (All Stages)/Normal Gastric Tissue |
| TJU_CMC.ID02033.5p-miR | −1.774828076 | 0.027084114 | Gastric Cancer (All Stages)/Normal Gastric Tissue |
| TJU_CMC.ID02628.3p-miR | −1.787353578 | 0.023789006 | Gastric Cancer (All Stages)/Normal Gastric Tissue |
| TJU_CMC.ID03007.3p-miR | −3.612174848 | 0.019862328 | Gastric Cancer (All Stages)/Normal Gastric Tissue |
| TJU_CMC.ID03895.5p-miR | 1.981250026 | 0.020003969 | Gastric Cancer (All Stages)/Normal Gastric Tissue |
| TJU_CMC.ID04157.3p-miR | −1.717742097 | 0.023237959 | Gastric Cancer (All Stages)/Normal Gastric Tissue |
| TJU_CMC.ID04253.5p-miR | −1.766416339 | 0.020243759 | Gastric Cancer (All Stages)/Normal Gastric Tissue |
| TJU_CMC.ID04299.5p-miR | 1.997983535 | 0.026818988 | Gastric Cancer (All Stages)/Normal Gastric Tissue |
| TJU_CMC.ID04423.3p-miR | −1.306189429 | 0.027161254 | Gastric Cancer (All Stages)/Normal Gastric Tissue |
| TJU_CMC.ID04427.3p-miR | 1.989335741 | 0.023912734 | Gastric Cancer (All Stages)/Normal Gastric Tissue |
| TJU_CMC.ID04609.5p-miR | −1.598892336 | 0.021224882 | Gastric Cancer (All Stages)/Normal Gastric Tissue |
| TJU_CMC.ID04627.3p-miR | −1.738444442 | 0.027126725 | Gastric Cancer (All Stages)/Normal Gastric Tissue |
| TJU_CMC.ID05571.3p-miR | 2.001384289 | 0.027073479 | Gastric Cancer (All Stages)/Normal Gastric Tissue |
| TJU_CMC.ID05587.5p-miR | 1.889486869 | 0.023685507 | Gastric Cancer (All Stages)/Normal Gastric Tissue |
| TJU_CMC.ID05831.5p-miR | −4.315550633 | 0.025696698 | Gastric Cancer (All Stages)/Normal Gastric Tissue |
| TJU_CMC.ID06140.3p-miR | −2.938939032 | 0.018689128 | Gastric Cancer (All Stages)/Normal Gastric Tissue |
| TJU_CMC.ID07032.3p-miR | −2.678233377 | 0.022403467 | Gastric Cancer (All Stages)/Normal Gastric Tissue |
| TJU_CMC.ID07163.3p-miR | −1.551579634 | 0.018813489 | Gastric Cancer (All Stages)/Normal Gastric Tissue |
| TJU_CMC.ID07328.3p-miR | −1.812228701 | 0.018202268 | Gastric Cancer (All Stages)/Normal Gastric Tissue |
| TJU_CMC.ID07621.5p-miR | −1.630123804 | 0.019632235 | Gastric Cancer (All Stages)/Normal Gastric Tissue |
| TJU_CMC.ID07831.3p-miR | 2.22789396 | 0.023659153 | Gastric Cancer (All Stages)/Normal Gastric Tissue |
| TJU_CMC.ID07957.5p-miR | −1.640732883 | 0.022518983 | Gastric Cancer (All Stages)/Normal Gastric Tissue |
| TJU_CMC.ID08188.3p-miR | −2.548460682 | 0.019403294 | Gastric Cancer (All Stages)/Normal Gastric Tissue |
| TJU_CMC.ID08433.5p-miR | 1.837320352 | 0.02452899 | Gastric Cancer (All Stages)/Normal Gastric Tissue |
| TJU_CMC.ID08542.3p-miR | −1.641071987 | 0.020214569 | Gastric Cancer (All Stages)/Normal Gastric Tissue |
| TJU_CMC.ID08726.5p-miR | 2.41129203 | 0.020897802 | Gastric Cancer (All Stages)/Normal Gastric Tissue |
| TJU_CMC.ID08763.5p-miR | 2.352548471 | 0.025146309 | Gastric Cancer (All Stages)/Normal Gastric Tissue |
| TJU_CMC.ID08919.5p-miR | −1.571636109 | 0.025768628 | Gastric Cancer (All Stages)/Normal Gastric Tissue |
| TJU_CMC.ID09200.5p-miR | 3.751805405 | 0.022814355 | Gastric Cancer (All Stages)/Normal Gastric Tissue |
| TJU_CMC.ID09566.3p-miR | −2.039506479 | 0.027493623 | Gastric Cancer (All Stages)/Normal Gastric Tissue |
| TJU_CMC.ID09661.5p-miR | −1.801675613 | 0.019398026 | Gastric Cancer (All Stages)/Normal Gastric Tissue |
| TJU_CMC.ID01161.5p-miR | −1.871147808 | 0.029528949 | Gastric Cancer (All Stages)/Normal Gastric Tissue |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID04906.3p-miR | −1.621951722 | 0.029550075 | Gastric Cancer (All Stages)/Normal Gastric Tissue |
| TJU_CMC.ID05795.3p-miR | 2.58568564 | 0.029598595 | Gastric Cancer (All Stages)/Normal Gastric Tissue |
| TJU_CMC.ID07769.3p-miR | 9.292014054 | 0.028305422 | Gastric Cancer (All Stages)/Normal Gastric Tissue |
| TJU_CMC.ID08178.3p-miR | −1.642677666 | 0.028858406 | Gastric Cancer (All Stages)/Normal Gastric Tissue |
| TJU_CMC.ID03480.3p-miR | −1.545934793 | 0.03021484 | Gastric Cancer (All Stages)/Normal Gastric Tissue |
| TJU_CMC.ID05411.3p-miR | 1.93344821 | 0.031313051 | Gastric Cancer (All Stages)/Normal Gastric Tissue |
| TJU_CMC.ID05815.3p-miR | −1.667436954 | 0.031498296 | Gastric Cancer (All Stages)/Normal Gastric Tissue |
| TJU_CMC.ID02123.5p-miR | −1.748033387 | 0.033136473 | Gastric Cancer (All Stages)/Normal Gastric Tissue |
| TJU_CMC.ID02311.3p-miR | 2.312634562 | 0.03349258 | Gastric Cancer (All Stages)/Normal Gastric Tissue |
| TJU_CMC.ID04010.5p-miR | −2.448628541 | 0.03400175 | Gastric Cancer (All Stages)/Normal Gastric Tissue |
| TJU_CMC.ID05546.5p-miR | 1.629003531 | 0.031926249 | Gastric Cancer (All Stages)/Normal Gastric Tissue |
| TJU_CMC.ID06935.5p-miR | 1.854549293 | 0.033391047 | Gastric Cancer (All Stages)/Normal Gastric Tissue |
| TJU_CMC.ID01479.3p-miR | 1.986409421 | 0.035272638 | Gastric Cancer (All Stages)/Normal Gastric Tissue |
| TJU_CMC_MD2.ID03086.5p-miR | 2.111181769 | 0.035337682 | Gastric Cancer (All Stages)/Normal Gastric Tissue |
| TJU_CMC.ID08761.5p-miR | −4.267548625 | 0.010203613 | PBMC Scleroderma Patients/PBMC Control Individuals |
| TJU_CMC.ID00938.5p-miR | −1.613840774 | 0.040784364 | Gastric Cancer (All Stages)/Normal Gastric Tissue |
| TJU_CMC.ID00977.5p-miR | −1.341670399 | 0.039528803 | Gastric Cancer (All Stages)/Normal Gastric Tissue |
| TJU_CMC.ID00993.3p-miR | 1.970492029 | 0.038198466 | Gastric Cancer (All Stages)/Normal Gastric Tissue |
| TJU_CMC.ID01429.5p-miR | 2.867504225 | 0.036707831 | Gastric Cancer (All Stages)/Normal Gastric Tissue |
| TJU_CMC.ID02586.5p-miR | 999999 | 0.036738061 | Gastric Cancer (All Stages)/Normal Gastric Tissue |
| TJU_CMC.ID03305.5p-miR | −1.609862851 | 0.037390013 | Gastric Cancer (All Stages)/Normal Gastric Tissue |
| TJU_CMC.ID03732.5p-miR | 2.004244641 | 0.040079898 | Gastric Cancer (All Stages)/Normal Gastric Tissue |
| TJU_CMC.ID04015.5p-miR | −1.498719744 | 0.039679831 | Gastric Cancer (All Stages)/Normal Gastric Tissue |
| TJU_CMC.ID04681.3p-miR | −1.63555378 | 0.038292529 | Gastric Cancer (All Stages)/Normal Gastric Tissue |
| TJU_CMC.ID04702.3p-miR | 2.271594216 | 0.039538409 | Gastric Cancer (All Stages)/Normal Gastric Tissue |
| TJU_CMC.ID04813.5p-miR | −1.58255416 | 0.038834773 | Gastric Cancer (All Stages)/Normal Gastric Tissue |
| TJU_CMC.ID05559.5p-miR | −1.375051006 | 0.040184485 | Gastric Cancer (All Stages)/Normal Gastric Tissue |
| TJU_CMC.ID07960.3p-miR | 2.165855447 | 0.038981849 | Gastric Cancer (All Stages)/Normal Gastric Tissue |
| TJU_CMC.ID08674.5p-miR | 1.601114325 | 0.038080565 | Gastric Cancer (All Stages)/Normal Gastric Tissue |
| TJU_CMC.ID09116.3p-miR | 1.968435382 | 0.04000353 | Gastric Cancer (All Stages)/Normal Gastric Tissue |
| TJU_CMC.ID02809.3p-miR | −2.771104044 | 0.041691648 | Gastric Cancer (All Stages)/Normal Gastric Tissue |
| TJU_CMC.ID06403.5p-miR | −1.920068702 | 0.041883968 | Gastric Cancer (All Stages)/Normal Gastric Tissue |
| TJU_CMC.ID03494.5p-miR | 3.95939225 | 0.010418164 | PBMC Scleroderma Patients/PBMC Control Individuals |
| TJU_CMC.ID00900.5p-miR | 1.895343037 | 0.043922464 | Gastric Cancer (All Stages)/Normal Gastric Tissue |
| TJU_CMC.ID01174.5p-miR | 4.633172229 | 0.042653376 | Gastric Cancer (All Stages)/Normal Gastric Tissue |
| TJU_CMC.ID08272.3p-miR | 3.508139003 | 0.043302973 | Gastric Cancer (All Stages)/Normal Gastric Tissue |
| TJU_CMC.ID00815.3p-miR | −1.772489511 | 0.044945986 | Gastric Cancer (All Stages)/Normal Gastric Tissue |
| TJU_CMC.ID07737.3p-miR | 2.504446699 | 0.045000353 | Gastric Cancer (All Stages)/Normal Gastric Tissue |
| TJU_CMC.ID00269.3p-miR | 2.505206495 | 0.046165249 | Gastric Cancer (All Stages)/Normal Gastric Tissue |
| TJU_CMC.ID03292.3p-miR | −1.424577368 | 0.045752924 | Gastric Cancer (All Stages)/Normal Gastric Tissue |
| TJU_CMC.ID08442.5p-miR | 2.030145449 | 0.0470639 | Gastric Cancer (All Stages)/Normal Gastric Tissue |
| TJU_CMC.ID05497.5p-miR | −1.294583047 | 0.048367954 | Gastric Cancer (All Stages)/Normal Gastric Tissue |
| TJU_CMC.ID02249.3p-miR | 1.895760363 | 0.049410912 | Gastric Cancer (All Stages)/Normal Gastric Tissue |
| TJU_CMC.ID09776.5p-miR | 1.489037083 | 0.038181576 | Prostate Cancer/Normal Prostate |
| TJU_CMC_MD2.ID01581.5p-miR | −1.263595505 | 0.039312083 | Hypo-reactive/Hyper-reactive (Platelets) |
| TJU_CMC.ID00009.3p-miR | 1.477830676 | 0.047912781 | Stage 4/Stage 3 (Gastric Cancer) |
| TJU_CMC.ID00052.3p-miR | −1.563173 | 0.012266671 | Hypo-reactive/Hyper-reactive (Platelets) |
| TJU_CMC.ID00084.5p-miR | −2.939458889 | 0.016355399 | Stage 2/Stage 1 (Gastric Cancer) |
| TJU_CMC.ID00195.5p-miR | 1.079999173 | 0.032878597 | Hypo-reactive/Hyper-reactive (Platelets) |
| TJU_CMC.ID00244.3p-miR | 7.100886471 | 0.038288489 | PBMC Scleroderma Patients/PBMC Control Individuals |
| TJU_CMC.ID00247.5p-miR | 1.3472225 | 0.036882313 | Hypo-reactive/Hyper-reactive (Platelets) |
| TJU_CMC.ID00297.3p-miR | 7.738409678 | 0.012633237 | PBMC Scleroderma Patients/PBMC Control Individuals |
| TJU_CMC.ID00314.3p-miR | −3.076506181 | 0.03766979 | Stage 3/Stage 2 (Gastric Cancer) |
| TJU_CMC.ID00348.3p-miR | 1.327956897 | 0.015928599 | Hypo-reactive/Hyper-reactive (Platelets) |
| TJU_CMC.ID00350.3p-miR | 1.885888423 | 0.042088708 | PBMC Scleroderma Patients/PBMC Control Individuals |
| TJU_CMC.ID00362.3p-miR | −2.085240193 | 0.042942951 | Stage 2/Stage 1 (Gastric Cancer) |
| TJU_CMC.ID00380.3p-miR | −999999 | 0.030703538 | MIA PaCa-2 cells/HPNE cells (Pancreas cell lines) |
| TJU_CMC.ID00568.5p-miR | 2.344610964 | 0.01887733 | PBMC Scleroderma Patients/PBMC Control Individuals |
| TJU_CMC.ID00768.5p-miR | 1.193133606 | 0.047495635 | Hypo-reactive/Hyper-reactive (Platelets) |
| TJU_CMC.ID00768.5p-miR | 2.432325887 | 0.018620428 | PBMC Scleroderma Patients/PBMC Control Individuals |
| TJU_CMC.ID00789.3p-miR | 1.181960622 | 0.043194929 | Hypo-reactive/Hyper-reactive (Platelets) |
| TJU_CMC.ID00863.3p-miR | −1.360451143 | 0.01096608 | Hypo-reactive/Hyper-reactive (Platelets) |
| TJU_CMC.ID00894.5p-miR | −2.728939887 | 0.043569208 | PBMC Scleroderma Patients/PBMC Control Individuals |
| TJU_CMC.ID00919.5p-miR | −2.002438715 | 0.033421367 | Prostate Cancer/Normal Prostate |
| TJU_CMC.ID00971.3p-miR | −2.743521401 | 0.028929917 | Stage 2/Stage 1 (Gastric Cancer) |
| TJU_CMC.ID01018.3p-miR | 5.635072153 | 0.022841887 | MIA PaCa-2 cells/HPNE cells (Pancreas cell lines) |
| TJU_CMC.ID01069.3p-miR | 2.605972125 | 0.021994098 | Psoriasis Biopsy/Normal Skin Biopsy |
| TJU_CMC.ID01080.3p-miR | 0.916170345 | 0.015991941 | Hypo-reactive/Hyper-reactive (Platelets) |
| TJU_CMC.ID01085.3p-miR | 1.678188162 | 0.015798823 | Hypo-reactive/Hyper-reactive (Platelets) |
| TJU_CMC.ID01088.3p-miR | 0.979367272 | 0.042853103 | Hypo-reactive/Hyper-reactive (Platelets) |
| TJU_CMC.ID01135.3p-miR | −1.838228767 | 0.01684644 | Stage 2/Stage 1 (Gastric Cancer) |
| TJU_CMC.ID01162.3p-miR | −1.077075181 | 0.048758702 | Hypo-reactive/Hyper-reactive (Platelets) |
| TJU_CMC.ID01261.3p-miR | 4.587419352 | 0.01645577 | PBMC Scleroderma Patients/PBMC Control Individuals |
| TJU_CMC.ID01273.3p-miR | 1.108485397 | 0.025187843 | Hypo-reactive/Hyper-reactive (Platelets) |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID01296.3p-miR | −6.537795507 | 0.030638518 | MIA PaCa-2 cells/HPNE cells (Pancreas cell lines) |
| TJU_CMC.ID01339.5p-miR | −2.919610922 | 0.012677767 | Stage 2/Stage 1 (Gastric Cancer) |
| TJU_CMC.ID01410.3p-miR | 1.564842602 | 0.010625095 | Hypo-reactive/Hyper-reactive (Platelets) |
| TJU_CMC.ID01421.5p-miR | 2.445206236 | 0.038660729 | PBMC Scleroderma Patients/PBMC Control Individuals |
| TJU_CMC.ID01517.5p-miR | 2.510345858 | 0.043562113 | Stage 3/Stage 2 (Gastric Cancer) |
| TJU_CMC.ID01546.3p-miR | 3.849540809 | 0.03881563 | Prostate Cancer/Normal Prostate |
| TJU_CMC.ID01589.5p-miR | 7.52282662 | 0.01203502 | PBMC Scleroderma Patients/PBMC Control Individuals |
| TJU_CMC.ID01637.5p-miR | −0.951688288 | 0.046805673 | Hypo-reactive/Hyper-reactive (Platelets) |
| TJU_CMC.ID01657.5p-miR | 1.200240685 | 0.044669458 | Hypo-reactive/Hyper-reactive (Platelets) |
| TJU_CMC.ID01691.3p-miR | 6.706337157 | 0.048069193 | PBMC Scleroderma Patients/PBMC Control Individuals |
| TJU_CMC.ID01706.5p-miR | 1.143990065 | 0.049962547 | Hypo-reactive/Hyper-reactive (Platelets) |
| TJU_CMC.ID01719.5p-miR | −4.87303582 | 0.022572743 | MIA PaCa-2 cells/HPNE cells (Pancreas cell lines) |
| TJU_CMC.ID01763.5p-miR | −6.573089908 | 0.038624619 | Stage 2/Stage 1 (Gastric Cancer) |
| TJU_CMC.ID01805.5p-miR | −3.499450023 | 0.022188591 | PBMC Scleroderma Patients/PBMC Control Individuals |
| TJU_CMC.ID01806.3p-miR | 4.789701655 | 0.026115412 | Stage 3/Stage 2 (Gastric Cancer) |
| TJU_CMC.ID01864.5p-miR | −2.332814508 | 0.016055 | Stage 3/Stage 2 (Gastric Cancer) |
| TJU_CMC.ID01909.3p-miR | 3.565702913 | 0.014056536 | PBMC Scleroderma Patients/PBMC Control Individuals |
| TJU_CMC.ID01943.5p-miR | −2.212509523 | 0.010809204 | Prostate Cancer/Normal Prostate |
| TJU_CMC.ID01953.5p-miR | −4.342884428 | 0.045146045 | Stage 2/Stage 1 (Gastric Cancer) |
| TJU_CMC.ID02018.5p-miR | −1.781518856 | 0.028018214 | Prostate Cancer/Normal Prostate |
| TJU_CMC.ID02034.5p-miR | −1.555519162 | 0.012591791 | Hypo-reactive/Hyper-reactive (Platelets) |
| TJU_CMC.ID02138.5p-miR | 2.512632326 | 0.032846065 | PBMC Scleroderma Patients/PBMC Control Individuals |
| TJU_CMC.ID02211.5p-miR | −3.428004423 | 0.014486957 | PBMC Scleroderma Patients/PBMC Control Individuals |
| TJU_CMC.ID02258.3p-miR | 7.462523283 | 0.044389508 | Stage 2/Stage 1 (Gastric Cancer) |
| TJU_CMC.ID02289.5p-miR | 4.806026864 | 0.040544693 | MIA PaCa-2 cells/HPNE cells (Pancreas cell lines) |
| TJU_CMC.ID02290.5p-miR | 6.550642842 | 0.041935162 | PBMC Scleroderma Patients/PBMC Control Individuals |
| TJU_CMC.ID02305.3p-miR | 1.215472034 | 0.031476713 | Hypo-reactive/Hyper-reactive (Platelets) |
| TJU_CMC.ID02326.5p-miR | 4.891081095 | 0.027029515 | PBMC Scleroderma Patients/PBMC Control Individuals |
| TJU_CMC.ID02376.5p-miR | 2.889831458 | 0.0367707 | Psoriasis Biopsy/Normal Skin Biopsy |
| TJU_CMC.ID02420.5p-miR | 1.134690166 | 0.024073365 | Psoriasis Biopsy/Normal Skin Biopsy |
| TJU_CMC.ID02453.5p-miR | 2.283757315 | 0.042273906 | PBMC Scleroderma Patients/PBMC Control Individuals |
| TJU_CMC.ID02479.3p-miR | 1.340706073 | 0.022305849 | Hypo-reactive/Hyper-reactive (Platelets) |
| TJU_CMC.ID02495.5p-miR | 3.40896854 | 0.046205988 | PBMC Scleroderma Patients/PBMC Control Individuals |
| TJU_CMC.ID02499.3p-miR | −2.561743968 | 0.048800688 | Stage 2/Stage 1 (Gastric Cancer) |
| TJU_CMC.ID02522.5p-miR | −1.327874509 | 0.020841274 | Hypo-reactive/Hyper-reactive (Platelets) |
| TJU_CMC.ID02561.5p-miR | −2.513059732 | 0.035711835 | Stage 3/Stage 2 (Gastric Cancer) |
| TJU_CMC.ID02629.3p-miR | −999999 | 0.048131214 | MIA PaCa-2 cells/HPNE cells (Pancreas cell lines) |
| TJU_CMC.ID02630.5p-miR | 1.267984776 | 0.012279347 | Hypo-reactive/Hyper-reactive (Platelets) |
| TJU_CMC.ID02641.5p-miR | 3.851807621 | 0.019760885 | Prostate Cancer/Normal Prostate |
| TJU_CMC.ID02702.5p-miR | −0.848362775 | 0.044000798 | Hypo-reactive/Hyper-reactive (Platelets) |
| TJU_CMC.ID02760.3p-miR | 2.015420588 | 0.044677375 | PBMC Scleroderma Patients/PBMC Control Individuals |
| TJU_CMC.ID02819.5p-miR | 1.080945126 | 0.021311897 | Hypo-reactive/Hyper-reactive (Platelets) |
| TJU_CMC.ID02835.3p-miR | −1.268285688 | 0.047845428 | Hypo-reactive/Hyper-reactive (Platelets) |
| TJU_CMC.ID02909.3p-miR | −0.997536853 | 0.019442636 | Hypo-reactive/Hyper-reactive (Platelets) |
| TJU_CMC.ID02914.3p-miR | −2.5089258 | 0.018325608 | Stage 2/Stage 1 (Gastric Cancer) |
| TJU_CMC.ID02928.3p-miR | −1.823624294 | 0.026092911 | Stage 3/Stage 2 (Gastric Cancer) |
| TJU_CMC.ID02936.3p-miR | 2.230440371 | 0.028695444 | PBMC Scleroderma Patients/PBMC Control Individuals |
| TJU_CMC.ID02951.5p-miR | 3.370149449 | 0.017946247 | PBMC Scleroderma Patients/PBMC Control Individuals |
| TJU_CMC.ID02963.3p-miR | 1.346154092 | 0.049843133 | Hypo-reactive/Hyper-reactive (Platelets) |
| TJU_CMC.ID02974.3p-miR | −3.445625017 | 0.025122478 | PBMC Scleroderma Patients/PBMC Control Individuals |
| TJU_CMC.ID02983.5p-miR | 1.475207022 | 0.019934104 | Hypo-reactive/Hyper-reactive (Platelets) |
| TJU_CMC.ID03009.3p-miR | 1.649167015 | 0.02902873 | Hypo-reactive/Hyper-reactive (Platelets) |
| TJU_CMC.ID03046.3p-miR | −1.19936191 | 0.042007511 | Hypo-reactive/Hyper-reactive (Platelets) |
| TJU_CMC.ID03054.3p-miR | −999999 | 0.013013719 | MIA PaCa-2 cells/HPNE cells (Pancreas cell lines) |
| TJU_CMC.ID03078.3p-miR | 1.531824418 | 0.016192411 | Hypo-reactive/Hyper-reactive (Platelets) |
| TJU_CMC.ID03104.5p-miR | 2.23497465 | 0.029259981 | PBMC Scleroderma Patients/PBMC Control Individuals |
| TJU_CMC.ID03128.3p-miR | 1.359735036 | 0.026875852 | Hypo-reactive/Hyper-reactive (Platelets) |
| TJU_CMC.ID03148.5p-miR | 1.363629432 | 0.017882699 | Hypo-reactive/Hyper-reactive (Platelets) |
| TJU_CMC.ID03152.5p-miR | −1.058108022 | 0.043698842 | Hypo-reactive/Hyper-reactive (Platelets) |
| TJU_CMC.ID03322.5p-miR | −2.726379148 | 0.003149937 | Stage 2/Stage 1 (Gastric Cancer) |
| TJU_CMC.ID03328.5p-miR | 7.228105391 | 0.041174743 | Stage 2/Stage 1 (Gastric Cancer) |
| TJU_CMC.ID03395.3p-miR | −999999 | 0.024920128 | Hypo-reactive/Hyper-reactive (Platelets) |
| TJU_CMC.ID03444.5p-miR | −2.425956557 | 0.014239203 | Stage 2/Stage 1 (Gastric Cancer) |
| TJU_CMC.ID03468.3p-miR | −999999 | 0.026548308 | MIA PaCa-2 cells/HPNE cells (Pancreas cell lines) |
| TJU_CMC.ID03469.3p-miR | −999999 | 0.02046219 | MIA PaCa-2 cells/HPNE cells (Pancreas cell lines) |
| TJU_CMC.ID03525.5p-miR | 2.024236382 | 0.043013288 | Hypo-reactive/Hyper-reactive (Platelets) |
| TJU_CMC.ID03547.3p-miR | 1.088942611 | 0.031389761 | Hypo-reactive/Hyper-reactive (Platelets) |
| TJU_CMC.ID03569.5p-miR | −1.783878949 | 0.041663766 | Stage 2/Stage 1 (Gastric Cancer) |
| TJU_CMC.ID03579.3p-miR | 2.339529876 | 0.031743547 | PBMC Scleroderma Patients/PBMC Control Individuals |
| TJU_CMC.ID03586.5p-miR | 1.559085474 | 0.038078855 | Hypo-reactive/Hyper-reactive (Platelets) |
| TJU_CMC.ID03705.5p-miR | 2.314969901 | 0.01268648 | Hypo-reactive/Hyper-reactive (Platelets) |
| TJU_CMC.ID03708.5p-miR | −2.037179611 | 0.043388527 | Stage 3/Stage 2 (Gastric Cancer) |
| TJU_CMC.ID03820.3p-miR | 2.846686172 | 0.022838815 | Stage 2/Stage 1 (Gastric Cancer) |
| TJU_CMC.ID03902.3p-miR | 1.198598227 | 0.039618344 | Hypo-reactive/Hyper-reactive (Platelets) |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID03912.5p-miR | 1.25809572 | 0.027856237 | Hypo-reactive/Hyper-reactive (Platelets) |
| TJU_CMC.ID04075.5p-miR | 2.310361088 | 0.040051908 | PBMC Scleroderma Patients/PBMC Control Individuals |
| TJU_CMC.ID04080.5p-miR | 3.19306214 | 0.028960073 | Hypo-reactive/Hyper-reactive (Platelets) |
| TJU_CMC.ID04092.3p-miR | -4.408668432 | 0.024276182 | PBMC Scleroderma Patients/PBMC Control Individuals |
| TJU_CMC.ID04286.5p-miR | 4.478044918 | 0.027879142 | MIA PaCa-2 cells/HPNE cells (Pancreas cell lines) |
| TJU_CMC.ID04324.5p-miR | -999999 | 0.043530936 | MIA PaCa-2 cells/HPNE cells (Pancreas cell lines) |
| TJU_CMC.ID04342.5p-miR | 1.800326099 | 0.047129364 | Stage 2/Stage 1 (Gastric Cancer) |
| TJU_CMC.ID04424.5p-miR | -2.001146748 | 0.019798024 | Stage 3/Stage 2 (Gastric Cancer) |
| TJU_CMC.ID04572.5p-miR | -1.08873462 | 0.048571828 | Hypo-reactive/Hyper-reactive (Platelets) |
| TJU_CMC.ID04614.5p-miR | 3.732040576 | 0.049558403 | MIA PaCa-2 cells/HPNE cells (Pancreas cell lines) |
| TJU_CMC.ID04617.3p-miR | 2.237425363 | 0.035202753 | Prostate Cancer/Normal Prostate |
| TJU_CMC.ID04630.3p-miR | 1.247278138 | 0.0465399 | HER2-type Breast Cancer/Basal-like Breast Cancer (TCGA) |
| TJU_CMC.ID04668.3p-miR | 3.319215229 | 0.018021822 | PBMC Scleroderma Patients/PBMC Control Individuals |
| TJU_CMC.ID04740.3p-miR | -2.346176139 | 0.043984837 | PBMC Scleroderma Patients/PBMC Control Individuals |
| TJU_CMC.ID04779.3p-miR | 6.486114799 | 0.045280745 | PBMC Scleroderma Patients/PBMC Control Individuals |
| TJU_CMC.ID04788.5p-miR | -999999 | 0.0487335 | MIA PaCa-2 cells/HPNE cells (Pancreas cell lines) |
| TJU_CMC.ID04803.5p-miR | -999999 | 0.043205027 | MIA PaCa-2 cells/HPNE cells (Pancreas cell lines) |
| TJU_CMC.ID04820.3p-miR | 2.452780432 | 0.017802552 | PBMC Scleroderma Patients/PBMC Control Individuals |
| TJU_CMC.ID04842.5p-miR | -2.421514896 | 0.047905247 | Stage 2/Stage 1 (Gastric Cancer) |
| TJU_CMC.ID04865.5p-miR | -999999 | 0.047614773 | MIA PaCa-2 cells/HPNE cells (Pancreas cell lines) |
| TJU_CMC.ID04868.5p-miR | -1.002409588 | 0.025247313 | Hypo-reactive/Hyper-reactive (Platelets) |
| TJU_CMC.ID04928.5p-miR | 1.359874336 | 0.024281153 | Hypo-reactive/Hyper-reactive (Platelets) |
| TJU_CMC.ID04992.3p-miR | 1.741755955 | 0.033510108 | Stage 3/Stage 2 (Gastric Cancer) |
| TJU_CMC.ID05017.5p-miR | -2.266144482 | 0.027216363 | Stage 3/Stage 2 (Gastric Cancer) |
| TJU_CMC.ID05313.5p-miR | -3.770479664 | 0.003877615 | Stage 2/Stage 1 (Gastric Cancer) |
| TJU_CMC.ID05357.3p-miR | 2.339487344 | 0.049616356 | PBMC Scleroderma Patients/PBMC Control Individuals |
| TJU_CMC.ID05397.3p-miR | 1.526453747 | 0.010537367 | Hypo-reactive/Hyper-reactive (Platelets) |
| TJU_CMC.ID05415.3p-miR | -1.455138672 | 0.041024695 | Prostate Cancer/Normal Prostate |
| TJU_CMC.ID05419.5p-miR | 3.086717415 | 0.01653433 | Stage 3/Stage 2 (Gastric Cancer) |
| TJU_CMC.ID05478.5p-miR | 2.6303543 | 0.012681579 | PBMC Scleroderma Patients/PBMC Control Individuals |
| TJU_CMC.ID05499.5p-miR | 2.419491 | 0.014931304 | PBMC Scleroderma Patients/PBMC Control Individuals |
| TJU_CMC.ID05510.3p-miR | -2.538816142 | 0.041195298 | Stage 2/Stage 1 (Gastric Cancer) |
| TJU_CMC.ID05546.5p-miR | 3.2306874 | 0.0184641 | Psoriasis Biopsy/Normal Skin Biopsy |
| TJU_CMC.ID05548.3p-miR | 2.704833671 | 0.034293728 | Psoriasis Biopsy/Normal Skin Biopsy |
| TJU_CMC.ID05639.5p-miR | -1.086178426 | 0.029198929 | Hypo-reactive/Hyper-reactive (Platelets) |
| TJU_CMC.ID05664.5p-miR | -3.396746446 | 0.048216431 | Stage 3/Stage 2 (Gastric Cancer) |
| TJU_CMC.ID05700.5p-miR | -999999 | 0.042411288 | Hypo-reactive/Hyper-reactive (Platelets) |
| TJU_CMC.ID05758.5p-miR | -2.925617594 | 0.017181581 | Stage 3/Stage 2 (Gastric Cancer) |
| TJU_CMC.ID05781.3p-miR | 1.434647567 | 0.019638069 | Hypo-reactive/Hyper-reactive (Platelets) |
| TJU_CMC.ID05857.5p-miR | 1.447991864 | 0.010024548 | Hypo-reactive/Hyper-reactive (Platelets) |
| TJU_CMC.ID05896.3p-miR | 1.235764812 | 0.016312488 | Hypo-reactive/Hyper-reactive (Platelets) |
| TJU_CMC.ID05937.5p-miR | -1.273568266 | 0.040227023 | Hypo-reactive/Hyper-reactive (Platelets) |
| TJU_CMC.ID05970.3p-miR | 2.879521084 | 0.017012637 | PBMC Scleroderma Patients/PBMC Control Individuals |
| TJU_CMC.ID05977.5p-miR | 999999 | 0.046469869 | Stage 2/Stage 1 (Gastric Cancer) |
| TJU_CMC.ID06037.5p-miR | -3.081541785 | 0.030474184 | PBMC Scleroderma Patients/PBMC Control Individuals |
| TJU_CMC.ID06061.5p-miR | 0.94952706 | 0.035513757 | Hypo-reactive/Hyper-reactive (Platelets) |
| TJU_CMC.ID06076.5p-miR | 1.344256788 | 0.029915762 | Hypo-reactive/Hyper-reactive (Platelets) |
| TJU_CMC.ID06115.3p-miR | 3.10982229 | 0.031329725 | Prostate Cancer/Normal Prostate |
| TJU_CMC.ID06117.5p-miR | 4.085677992 | 0.037262132 | Stage 2/Stage 1 (Gastric Cancer) |
| TJU_CMC.ID06146.3p-miR | -1.277339046 | 0.037711719 | Hypo-reactive/Hyper-reactive (Platelets) |
| TJU_CMC.ID06228.3p-miR | -1.444106832 | 0.01997565 | Hypo-reactive/Hyper-reactive (Platelets) |
| TJU_CMC.ID06339.3p-miR | -2.809713442 | 0.008258968 | Stage 2/Stage 1 (Gastric Cancer) |
| TJU_CMC.ID06484.5p-miR | -1.573142702 | 0.049709755 | Prostate Cancer/Normal Prostate |
| TJU_CMC.ID06539.3p-miR | -3.729993502 | 0.000799716 | Stage 2/Stage 1 (Gastric Cancer) |
| TJU_CMC.ID06553.5p-miR | 1.216440491 | 0.017832843 | Hypo-reactive/Hyper-reactive (Platelets) |
| TJU_CMC.ID06610.5p-miR | -2.398369481 | 0.021323249 | Stage 2/Stage 1 (Gastric Cancer) |
| TJU_CMC.ID06620.5p-miR | 4.717528041 | 0.029027538 | MIA PaCa-2 cells/HPNE cells (Pancreas cell lines) |
| TJU_CMC.ID06651.3p-miR | 1.503525114 | 0.029348763 | Hypo-reactive/Hyper-reactive (Platelets) |
| TJU_CMC.ID06672.3p-miR | 2.363876542 | 0.014376798 | PBMC Scleroderma Patients/PBMC Control Individuals |
| TJU_CMC.ID06684.5p-miR | 1.184849137 | 0.012498505 | Hypo-reactive/Hyper-reactive (Platelets) |
| TJU_CMC.ID06736.5p-miR | 1.027632873 | 0.022289989 | Hypo-reactive/Hyper-reactive (Platelets) |
| TJU_CMC.ID06760.3p-miR | 5.719410568 | 0.038997076 | PBMC Scleroderma Patients/PBMC Control Individuals |
| TJU_CMC.ID06765.5p-miR | -2.734935036 | 0.022526889 | Stage 2/Stage 1 (Gastric Cancer) |
| TJU_CMC.ID06798.3p-miR | -999999 | 0.040991372 | MIA PaCa-2 cells/HPNE cells (Pancreas cell lines) |
| TJU_CMC.ID06865.5p-miR | 2.266458461 | 0.049772174 | Psoriasis Biopsy/Normal Skin Biopsy |
| TJU_CMC.ID06987.5p-miR | 1.32602718 | 0.013148506 | Hypo-reactive/Hyper-reactive (Platelets) |
| TJU_CMC.ID07029.5p-miR | 1.025819086 | 0.039590943 | Hypo-reactive/Hyper-reactive (Platelets) |
| TJU_CMC.ID07034.5p-miR | -999999 | 0.026977278 | Prostate Cancer/Normal Prostate |
| TJU_CMC.ID07073.5p-miR | 1.362074466 | 0.025985874 | Hypo-reactive/Hyper-reactive (Platelets) |
| TJU_CMC.ID07118.3p-miR | 1.358192938 | 0.025833509 | Hypo-reactive/Hyper-reactive (Platelets) |
| TJU_CMC.ID07253.3p-miR | 2.141867332 | 0.042181369 | Stage 2/Stage 1 (Gastric Cancer) |
| TJU_CMC.ID07263.3p-miR | -1.422644797 | 0.017719 | Hypo-reactive/Hyper-reactive (Platelets) |
| TJU_CMC.ID07272.3p-miR | 2.336599302 | 0.04398778 | PBMC Scleroderma Patients/PBMC Control Individuals |
| TJU_CMC.ID07373.5p-miR | -9.715672414 | 0.01529549 | PBMC Scleroderma Patients/PBMC Control Individuals |

TABLE 11-continued

Differential expression of miRNAs in tissues of various disease states

| Name | Log2 fold change of Set A/Set B | p-Val | Sets Compared (A/B) |
|---|---|---|---|
| TJU_CMC.ID07383.5p-miR | −3.198512488 | 0.004985778 | Stage 3/Stage 2 (Gastric Cancer) |
| TJU_CMC.ID07421.5p-miR | 2.135062062 | 0.043113573 | Stage 2/Stage 1 (Gastric Cancer) |
| TJU_CMC.ID07469.3p-miR | 1.025498261 | 0.032668928 | Hypo-reactive/Hyper-reactive (Platelets) |
| TJU_CMC.ID07488.5p-miR | 1.195912797 | 0.026248769 | Hypo-reactive/Hyper-reactive (Platelets) |
| TJU_CMC.ID07510.3p-miR | 1.275122876 | 0.035611377 | Hypo-reactive/Hyper-reactive (Platelets) |
| TJU_CMC.ID07519.3p-miR | 3.836738075 | 0.022542145 | Prostate Cancer/Normal Prostate |
| TJU_CMC.ID07559.3p-miR | −1.460592419 | 0.030481404 | Hypo-reactive/Hyper-reactive (Platelets) |
| TJU_CMC.ID07610.5p-miR | 2.552174284 | 0.022439374 | PBMC Scleroderma Patients/PBMC Control Individuals |
| TJU_CMC.ID07769.3p-miR | 999999 | 0.044834717 | Stage 2/Stage 1 (Gastric Cancer) |
| TJU_CMC.ID07801.3p-miR | −1.119418093 | 0.013262881 | Hypo-reactive/Hyper-reactive (Platelets) |
| TJU_CMC.ID07809.5p-miR | −1.107946725 | 0.031809701 | Hypo-reactive/Hyper-reactive (Platelets) |
| TJU_CMC.ID07834.3p-miR | 2.63743159 | 0.041377417 | Stage 3/Stage 2 (Gastric Cancer) |
| TJU_CMC.ID07841.3p-miR | 2.465873748 | 0.027102666 | Psoriasis Biopsy/Normal Skin Biopsy |
| TJU_CMC.ID07861.5p-miR | 0.985777139 | 0.049157741 | Hypo-reactive/Hyper-reactive (Platelets) |
| TJU_CMC.ID07871.3p-miR | 1.397277995 | 0.018354634 | Hypo-reactive/Hyper-reactive (Platelets) |
| TJU_CMC.ID07914.5p-miR | 1.28398237 | 0.049006487 | Hypo-reactive/Hyper-reactive (Platelets) |
| TJU_CMC.ID07954.3p-miR | −3.239335055 | 0.03042949 | PBMC Scleroderma Patients/PBMC Control Individuals |
| TJU_CMC.ID07960.3p-miR | −2.422033216 | 0.022135075 | Prostate Cancer/Normal Prostate |
| TJU_CMC.ID07973.3p-miR | 2.613660743 | 0.018542662 | Hypo-reactive/Hyper-reactive (Platelets) |
| TJU_CMC.ID08019.5p-miR | −1.394101883 | 0.029579628 | Hypo-reactive/Hyper-reactive (Platelets) |
| TJU_CMC.ID08043.3p-miR | 1.951144233 | 0.045679546 | Stage 2/Stage 1 (Gastric Cancer) |
| TJU_CMC.ID08074.3p-miR | 1.194016545 | 0.016403084 | Hypo-reactive/Hyper-reactive (Platelets) |
| TJU_CMC.ID08202.5p-miR | −2.711995889 | 0.039866728 | Stage 2/Stage 1 (Gastric Cancer) |
| TJU_CMC.ID08252.3p-miR | −2.005602975 | 0.031304754 | Stage 3/Stage 2 (Gastric Cancer) |
| TJU_CMC.ID08284.5p-miR | 1.270489064 | 0.036750125 | Hypo-reactive/Hyper-reactive (Platelets) |
| TJU_CMC.ID08389.5p-miR | −2.706964681 | 0.03043225 | Stage 2/Stage 1 (Gastric Cancer) |
| TJU_CMC.ID08391.3p-miR | 4.402016384 | 0.016291452 | PBMC Scleroderma Patients/PBMC Control Individuals |
| TJU_CMC.ID08401.5p-miR | −5.124839457 | 0.017106129 | PBMC Scleroderma Patients/PBMC Control Individuals |
| TJU_CMC.ID08486.5p-miR | −1.294807018 | 0.032293633 | Hypo-reactive/Hyper-reactive (Platelets) |
| TJU_CMC.ID08586.3p-miR | 2.133653292 | 0.047329924 | PBMC Scleroderma Patients/PBMC Control Individuals |
| TJU_CMC.ID08622.3p-miR | −1.266121461 | 0.025040345 | Hypo-reactive/Hyper-reactive (Platelets) |
| TJU_CMC.ID08632.3p-miR | 1.277309014 | 0.019995413 | Hypo-reactive/Hyper-reactive (Platelets) |
| TJU_CMC.ID08687.5p-miR | 1.209697855 | 0.032166429 | Hypo-reactive/Hyper-reactive (Platelets) |
| TJU_CMC.ID08726.5p-miR | 3.241011862 | 0.001321656 | Psoriasis Biopsy/Normal Skin Biopsy |
| TJU_CMC.ID08800.3p-miR | 2.124294119 | 0.024098946 | PBMC Scleroderma Patients/PBMC Control Individuals |
| TJU_CMC.ID08803.3p-miR | 2.325924074 | 0.040336565 | PBMC Scleroderma Patients/PBMC Control Individuals |
| TJU_CMC.ID08842.3p-miR | −1.501463396 | 0.030740633 | Prostate Cancer/Normal Prostate |
| TJU_CMC.ID08880.5p-miR | −3.156695744 | 0.019176545 | PBMC Scleroderma Patients/PBMC Control Individuals |
| TJU_CMC.ID09005.3p-miR | −5.489788623 | 0.012212712 | PBMC Scleroderma Patients/PBMC Control Individuals |
| TJU_CMC.ID09009.3p-miR | 2.705944072 | 0.033944204 | PBMC Scleroderma Patients/PBMC Control Individuals |
| TJU_CMC.ID09016.3p-miR | 4.989971469 | 0.041187184 | MIA PaCa-2 cells/HPNE cells (Pancreas cell lines) |
| TJU_CMC.ID09037.3p-miR | −1.737934328 | 0.030312535 | Prostate Cancer/Normal Prostate |
| TJU_CMC.ID09069.5p-miR | 1.353962462 | 0.045436789 | Hypo-reactive/Hyper-reactive (Platelets) |
| TJU_CMC.ID09079.3p-miR | 2.222284363 | 0.018051479 | Stage 3/Stage 2 (Gastric Cancer) |
| TJU_CMC.ID09120.3p-miR | 2.195852413 | 0.029115755 | Stage 2/Stage 1 (Gastric Cancer) |
| TJU_CMC.ID09230.3p-miR | 2.171964668 | 0.048313984 | Stage 2/Stage 1 (Gastric Cancer) |
| TJU_CMC.ID09232.5p-miR | −4.639075346 | 0.026129589 | PBMC Scleroderma Patients/PBMC Control Individuals |
| TJU_CMC.ID09235.5p-miR | 3.134775183 | 0.008287097 | Stage 3/Stage 2 (Gastric Cancer) |
| TJU_CMC.ID09235.5p-miR | −2.943457352 | 0.044162599 | Stage 4/Stage 3 (Gastric Cancer) |
| TJU_CMC.ID09252.5p-miR | 2.856342709 | 0.024364685 | PBMC Scleroderma Patients/PBMC Control Individuals |
| TJU_CMC.ID09261.5p-miR | 1.736182465 | 0.011353491 | Hypo-reactive/Hyper-reactive (Platelets) |
| TJU_CMC.ID09273.3p-miR | −5.126428551 | 0.005936221 | Stage 2/Stage 1 (Gastric Cancer) |
| TJU_CMC.ID09283.5p-miR | 999999 | 0.038985348 | Stage 3/Stage 2 (Gastric Cancer) |
| TJU_CMC.ID09315.5p-miR | −3.038172331 | 0.006109781 | Stage 2/Stage 1 (Gastric Cancer) |
| TJU_CMC.ID09441.5p-miR | 4.08569959 | 0.025506003 | Prostate Cancer/Normal Prostate |
| TJU_CMC.ID09442.5p-miR | 1.710183562 | 0.03839507 | PBMC Scleroderma Patients/PBMC Control Individuals |
| TJU_CMC.ID09660.3p-miR | 4.907722665 | 0.020611751 | MIA PaCa-2 cells/HPNE cells (Pancreas cell lines) |
| TJU_CMC.ID09753.5p-miR | −6.066785381 | 0.020677688 | MIA PaCa-2 cells/HPNE cells (Pancreas cell lines) |
| TJU_CMC.ID09799.3p-miR | 2.576122738 | 0.040874487 | Psoriasis Biopsy/Normal Skin Biopsy |
| TJU_CMC_MD2.ID00602.3p-miR | 3.794286038 | 0.042507991 | MIA PaCa-2 cells/HPNE cells (Pancreas cell lines) |
| TJU_CMC_MD2.ID00858.5p-miR | 2.538206626 | 0.043510714 | Prostate Cancer/Normal Prostate |
| TJU_CMC_MD2.ID01526.3p-miR | −1.195280658 | 0.049628324 | Hypo-reactive/Hyper-reactive (Platelets) |
| TJU_CMC_MD2.ID01878.5p-miR | 2.011665229 | 0.010441931 | Hypo-reactive/Hyper-reactive (Platelets) |
| TJU_CMC_MD2.ID01959.5p-miR | −1.286480278 | 0.030700595 | Hypo-reactive/Hyper-reactive (Platelets) |
| TJU_CMC_MD2.ID02369.5p-miR | 2.913986759 | 0.046604875 | PBMC Scleroderma Patients/PBMC Control Individuals |
| TJU_CMC_MD2.ID02968.3p-miR | −1.19449432 | 0.038131744 | Hypo-reactive/Hyper-reactive (Platelets) |
| TJU_CMC_MD2.ID03322.3p-miR | −1.191709316 | 0.034506286 | Hypo-reactive/Hyper-reactive (Platelets) |
| TJU_CMC_MD2.ID03345.5p-miR | −1.709921748 | 0.011392242 | Hypo-reactive/Hyper-reactive (Platelets) |
| TJU_CMC_MD2.ID03472.3p-miR | 5.102327203 | 0.029176763 | Stage 2/Stage 1 (Gastric Cancer) |
| TJU_CMC_MD2.ID03495.5p-miR | 2.563610753 | 0.023443767 | PBMC Scleroderma Patients/PBMC Control Individuals |

Example 8. Differential Expression by Disease States for Novel isomiRs Derived from Known miRNA Loci Using samples from different disease states, the inventors identified differentially expressed novel isomiRs (as listed in Table 3) that were identified as arising from known miRNA loci. As stated above, an isomiR is considered to be differentially expressed if it had a mean expression of at least 50 sequenced reads, a log 2-change in expression between the compared states of ≥0.58 or ≤−0.58, and a p-Value ≤0.05.

Table 12 below shows the fold-change of the isomiRs in pairs of the same tissue of different states. Abbreviations: TCGA=The Cancer Genome Atlas; PBMC=Peripheral Blood Mononuclear Cells; GEO=Gene Expression Omnibus. The actual miRNA/isomiR sequences and corresponding SEQ ID NOs. can be identified in Table 3 according to the "Name" listed in Table 12.

Lengthy table referenced here

US11293064-20220405-T00002

Please refer to the end of the specification for access instructions.

Lengthy table referenced here

US11293064-20220405-T00003

Please refer to the end of the specification for access instructions.

Lengthy table referenced here

US11293064-20220405-T00004

Please refer to the end of the specification for access instructions.

Lengthy table referenced here

US11293064-20220405-T00005

Please refer to the end of the specification for access instructions.

REFERENCES

1.—Lim, L. P., et al., Vertebrate microRNA genes. Science (New York, N.Y.), 2003. 299(5612): p. 1540-1540.
2.—Miranda, K. C., et al., A pattern-based method for the identification of MicroRNA binding sites and their corresponding heteroduplexes. Cell, 2006. 126(6): p. 1203-1217.
3.—Rigoutsos, I., et al., Short blocks from the noncoding parts of the human genome have instances within nearly all known genes and relate to biological processes. Proceedings of the National Academy of Sciences of the United States of America, 2006. 103(17): p. 6605-6610.
4.—Griffiths-Jones, S., miRBase: microRNA sequences, targets and gene nomenclature. Nucleic Acids Research, 2006. 34(90001): p. D140-D144.
5.—Bartel, D. P., MicroRNAs: genomics, biogenesis, mechanism, and function. Cell, 2004. 116(2): p. 281-97.
6.—Bartel, D. P., MicroRNAs: target recognition and regulatory functions. Cell, 2009. 136(2): p. 215-33.
7.—Ambros, V., A hierarchy of regulatory genes controls a larva-to-adult developmental switch in *C. elegans*. Cell, 1989. 57(1): p. 49-57.
8.—Ruvkun, G. and J. Giusto, The *Caenorhabditis elegans* heterochronic gene lin-14 encodes a nuclear protein that forms a temporal developmental switch. Nature, 1989. 338(6213): p. 313-9.
9.—Reinhart, B. J., et al., The 21-nucleotide let-7 RNA regulates developmental timing in *Caenorhabditis elegans*. Nature, 2000. 403(6772): p. 901-6.
10.—Chang, S., et al., MicroRNAs act sequentially and asymmetrically to control chemosensory laterality in the nematode. Nature, 2004. 430(7001): p. 785-9.
11.—Johnston, R. J. and O. Hobert, A microRNA controlling left/right neuronal asymmetry in *Caenorhabditis elegans*. Nature, 2003. 426(6968): p. 845-9.
12. [193649]—Brennecke, J. and S. M. Cohen, Towards a complete description of the microRNA complement of animal genomes. Genome Biol, 2003. 4(9): p. 228.
13.—Bartel, D. P., MicroRNAs: genomics, biogenesis, mechanism, and function. Cell, 2004. 116(2): p. 281-297.
14.—Bartel, D. P., MicroRNAs: target recognition and regulatory functions. Cell, 2009. 136(2): p. 215-233.
15.—Rigoutsos, 1., New tricks for animal microRNAS: targeting of amino acid coding regions at conserved and nonconserved sites. Cancer Research, 2009. 69(8): p. 3245-3248.
16.—Lee, R. C., R. L. Feinbaum, and V. Ambros, The *C. elegans* heterochronic gene lin-4 encodes small RNAs with antisense complementarity to lin-14. Cell, 1993. 75(5): p. 843-854.
17.—Wightman, B., I. Ila, and G. Ruvkun, Posttranscriptional regulation of the heterochronic gene lin-14 by lin-4 mediates temporal pattern formation in *C. clegans*. Cell, 1993. 75(5): p. 855-862.
18.—Tay, Y., et al., MicroRNAs to Nanog, Oct4 and Sox2 coding regions modulate embryonic stem cell differentiation. Nature, 2008. 455(7216): p. 1124-1128.
19.—Brodersen, P. and O. Voinnet, Revisiting the principles of microRNA target recognition and mode of action. Nat Rev Mol Cell Biol, 2009. 10(2): p. 141-8.
20. [2757794]—Lal, A., et al., miR-24 Inhibits cell proliferation by targeting E2F2, MYC, and other cell-cycle genes via binding to "seedless" 3'UTR microRNA recognition elements. Mol Cell, 2009. 35(5): p. 610-25.
21.—Rigoutsos, I. and A. Tsirigos, in MicroRNAs in Development and Cancer Molecular Medicine and Medicinal Chemistry Ch. 10, ed. F. J. Slack. Vol. Vol. 1. 2010: Imperial College Press.
22. [3415692]—Xia, Z., et al., Molecular dynamics simulations of Ago silencing complexes reveal a large repertoire of admissible 'seed-less' targets. Sci Rep, 2012. 2: p. 569.
23.—Xia, 1., B. Wightman, and G. Ruvkun, A bulged lin-4/lin-14 RNA duplex is sufficient for *Caenorhabditis elegans* lin-14 temporal gradient formation. Genes Dev, 1996. 10(23): p. 3041-50.
24. [324419]—Vella, M. C., et al., The *C. elegans* microRNA let-7 binds to imperfect let-7 complementary sites from the lin-41 3'UTR. Genes Dev, 2004. 18(2): p. 132-7.
25.—Farh, K. K., et al., The widespread impact of mammalian MicroRNAs on mRNA repression and evolution. Science, 2005. 310(5755): p. 1817-21.

26.—Stark, A., et al., Animal MicroRNAs confer robustness to gene expression and have a significant impact on 3'UTR evolution. Cell, 2005. 123(6): p. 1133-46.
27.—Didiano, D. and O. Hobert, Perfect seed pairing is not a generally reliable predictor for miRNA-target interactions. Nat Struct Mol Biol, 2006. 13(9): p. 849-51.
28. [1924889]—Easow, G., A. A. Teleman, and S. M. Cohen, Isolation of microRNA targets by miRNP immunopurification. RNA, 2007. 13(8): p. 1198-204.
29. [2745094]—Baek, D., et al., The impact of microRNAs on protein output. Nature, 2008. 455(7209): p. 64-71.
30.—Selbach, M., et al., Widespread changes in protein synthesis induced by microRNAs. Nature, 2008. 455 (7209): p. 58-63.
31. [2733940]—Chi, S. W., et al., Argonaute HITS-CLIP decodes microRNA-mRNA interaction maps. Nature, 2009. 460(7254): p. 479-86.
32.—Fabian, M. R., N. Sonenberg, and W. Filipowicz, Regulation of mRNA translation and stability by microRNAs. Annu Rev Biochem, 2010. 79: p. 351-79.
33. [2861495]—Hafner, M., et al., Transcriptome-wide identification of RNA-binding protein and microRNA target sites by PAR-CLIP. Cell, 2010. 141(1): p. 129-41.
34.—Thomas, M., J. Lieberman, and A. Lal, Desperately seeking microRNA targets. Nat Struct Mol Biol, 2010. 17(10): p. 1169-74.
35. [2834287]—Zisoulis, D. G., et al., Comprehensive discovery of endogenous Argonaute binding sites in *Caenorhabditis elegans*. Nat Struct Mol Biol, 2010. 17(2): p. 173-9.
36.—Chi, S. W., G. J. Hannon, and R. B. Darnell, An alternative mode of microRNA target recognition. Nat Struct Mol Biol, 2012. 19(3): p. 321-7.
37. [3266933]—Skalsky, R. L., et al., The viral and cellular microRNA targetome in lymphoblastoid cell lines. PLoS Pathog, 2012. 8(1): p. e1002484.
38.—Calin, G. A., et al., Frequent deletions and down-regulation of micro-RNA genes miR15 and miR16 at 13q14 in chronic lymphocytic leukemia. Proc Natl Acad Sci USA, 2002. 99(24): p. 15524-9.
39.—Calin, G. A. and C. M. Croce, Chronic lymphocytic leukemia: interplay between non-coding RNAs and protein-coding genes. Blood, 2009. 114(23): p. 4761-4770.
40.—Ha, I., B. Wightman, and G. Ruvkun, A bulged lin-4/ lin-14 RNA duplex is sufficient for *Caenorhabditis elegans* lin-14 temporal gradient formation. Genes & Development, 1996. 10(23): p. 3041-3050.
41.—Ruvkun, G., et al., The 21-nucleotide let-7 RNA regulates developmental timing in *Caenorhabditis elegans*. Nature, 2000. 403(6772): p. 901-906.
42.—Didiano, D. and O. Hobert, Molecular architecture of a miRNA-regulated 3' UTR. RNA, 2008. 14(7): p. 1297-1317.
43.—Small, E. M., R. J. A. Frost, and E. N. Olson, MicroRNAs add a new dimension to cardiovascular disease. Circulation, 2010. 121(8): p. 1022-1032.
44.—Small, E. M. and E. N. Olson, Pervasive roles of microRNAs in cardiovascular biology. Nature, 2011. 469 (7330): p. 336-342.
45.—Taganov, K. D., M. P. Boldin, and D. Baltimore, MicroRNAs and immunity: tiny players in a big field. Immunity, 2007. 26(2): p. 133-137.
46.—Perkins, D. O., et al., microRNA expression in the prefrontal cortex of individuals with schizophrenia and schizoaffective disorder. Genome Biology, 2007. 8(2): p. R27.
47.—Liu, X., K. Fortin, and Z. Mourelatos, MicroRNAs: biogenesis and molecular functions. Brain Pathol, 2008. 18(1): p. 113-21.
48.—Wang, Y., et al., MicroRNA: past and present. Front Biosci, 2007. 12: p. 2316-29.
49.—Wang, W.-X., et al., The expression of microRNA miR-107 decreases early in Alzheimer's disease and may accelerate disease progression through regulation of beta-site amyloid precursor protein-cleaving enzyme 1. Journal of Neuroscience, 2008. 28(5): p. 1213-1223.
50.—Wang, W.-X., et al., miR-107 regulates granulin/progranulin with implications for traumatic brain injury and neurodegenerative disease. The American journal of pathology, 2010. 177(1): p. 334-345.
51.—Abelson, J. F., et al., Sequence variants in SLITRK1 are associated with Tourette's syndrome. Science, 2005. 310(5746): p. 317-320.
52. [2859437]—Nelson, P. T., W. X. Wang, and B. W. Rajeev, MicroRNAs (miRNAs) in neurodegenerative diseases. Brain Pathol, 2008. 18(1): p. 130-8.
53.—Hebert, S. S. and B. De Strooper, Alterations of the microRNA network cause neurodegenerative disease. Trends Neurosci, 2009. 32(4): p. 199-206.
54. [2705848]—Ibanez-Ventoso, C. and M. Driscoll, MicroRNAs in *C. elegans* Aging: Molecular Insurance for Robustness? Curr Genomics, 2009. 10(3): p. 144-53.
55. [2928499]—Somel, M., et al., MicroRNA, mRNA, and protein expression link development and aging in human and macaque brain. Genome Res, 2010. 20(9): p. 1207-18.
56.—Mendell, J. T., miRiad roles for the miR-17-92 cluster in development and disease. Cell, 2008. 133(2): p. 217-222.
57.—Vasilescu, C., et al., MicroRNA fingerprints identify miR-150 as a plasma prognostic marker in patients with sepsis. PLoS ONE, 2009. 4(10): p. e7405.
58.—Williams, A. H., et al., MicroRNA-206 delays ALS progression and promotes regeneration of neuromuscular synapses in mice. Science (New York, N.Y.), 2009. 326 (5959): p. 1549-1554.
59.—Esquela-Kerscher, A. and F. J. Slack, Oncomirs—microRNAs with a role in cancer. Nature Reviews Cancer, 2006. 6(4): p. 259-269.
60.—Hammond, S. M., MicroRNAs as tumor suppressors, in Nature Genetics. 2007, Nature Publishing Group. p. 582-583.
61.—Poliseno, L., et al., A coding-independent function of gene and pseudogene mRNAs regulates tumour biology-Supplement. Nature, 2010. 465(7301): p. 1-19.
62.—Ma, L., J. Teruya-Feldstein, and R. A. Weinberg, Tumour invasion and metastasis initiated by microRNA-10b in breast cancer. Nature, 2007. 449(7163): p. 682-688.
63.—Calin, G. A. and C. M. Croce, MicroRNA-cancer connection: the beginning of a new talc. Cancer Research, 2006. 66(15): p. 7390-7394.
64.—Lu, M., et al., An analysis of human microRNA and disease associations. PLoS ONE, 2008. 3(10): p. e3420.
65.—Godshalk, S. E., et al., A Variant in a MicroRNA complementary site in the 3' UTR of the KIT oncogene increases risk of acral melanoma. Oncogene, 2010.
66.—Ryan, B. M., A. I. Robles, and C. C. Harris, Genetic variation in microRNA networks: the implications for cancer research. Nature Reviews Cancer, 2010. 10(6): p. 389-402.
67.—Saey, T., Cancer's little helpers: Tiny pieces of RNA may turn cells to the dark side. Science News, 2010.

68.—Spizzo, R., et al., SnapShot: MicroRNAs in Cancer. Cell, 2009. 137(3): p. 586-586.c1.
69.—Ventura, A. and T. Jacks, MicroRNAs and cancer: novel miRNAs go a long way. Cell, 2009. 136(4): p. 586-591.
70.—Voorhoeve, P. M. and R. Agami, Classifying microRNAs in cancer: The good, the bad and the ugly. Biochimica et Biophysica Acta (BBA)-Reviews on Cancer, 2007. 1775(2): p. 274-282.

It is understood that the foregoing detailed description and examples are illustrative only and are not to be taken as limitations upon the scope of the invention. Various changes and modifications to the disclosed embodiments, which will be apparent to those of skill in the art, may be made without departing from the spirit and scope of the present invention.

Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventor is not entitled to antedate such disclosure by virtue of prior invention or for any other reason. All statements as to the date or representation as to the contents of these documents is based on the information available to the applicants and does not constitute any admission as to the correctness of the dates or contents of these documents.

LENGTHY TABLES

The patent contains a lengthy table section. A copy of the table is available in electronic form from the USPTO web site (https://seqdata.uspto.gov/?pageRequest=docDetail&DocID=US11293064B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11293064B2). An electronic copy of the "Sequence Listing" will also be available from the USPTO upon request and payment of the fee set forth in 37 CFR 1.19(b)(3).

What is claimed is:

1. A method of treating colon cancer in a subject in need thereof, the method comprising:
   a) measuring in a biological sample obtained from a tissue of interest the expression profile of two or more isoforms of one or more miRNAs, wherein the miRNAs are selected from the group consisting of: SEQ ID NOs: 35717, 35716, 42515, 31086, 31085, 40501, 40502, 40500, 29783, 45821, 39673, 39671, 27278, 34326, 46315, 34324, 46025 and 32857 by deep sequencing, and;
   b) computing a difference in the expression profile of the two or more isoforms of one or more miRNAs as compared to the expression profile of the same isoforms in a reference sample by determining differential expression based on a log 2-change in expression of $\geq 0.58$ and $\leq -0.58$,
   c) administering to the subject an anticancer treatment selected from the group consisting of chemotherapy, radiation therapy, surgery, immunotherapy, RNA therapeutics or any combinations thereof.

2. The method of claim 1, wherein the reference sample represents a normal condition of the tissue.

3. The method of claim 1, wherein the tissue of interest is selected from the group consisting of blood and colon.

* * * * *